: US 10,513,523 B2
(45) Date of Patent: Dec. 24, 2019

(12) United States Patent
Ameriks et al.

(54) IMIDAZOPYRAZINES AND PYRAZOLOPYRIMIDINES AND THEIR USE AS AMPA RECEPTOR MODULATORS

(71) Applicant: Janssen Pharmaceutica NV, Beerse (BE)

(72) Inventors: Michael K. Ameriks, San Diego, CA (US); Bradley M. Savall, San Diego, CA (US); Devin M. Swanson, Carlsbad, CA (US); Dongpei Wu, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/569,273

(22) PCT Filed: Apr. 28, 2016

(86) PCT No.: PCT/US2016/029791
§ 371 (c)(1),
(2) Date: Oct. 25, 2017

(87) PCT Pub. No.: WO2016/176457
PCT Pub. Date: Nov. 3, 2016

(65) Prior Publication Data
US 2018/0118751 A1    May 3, 2018

Related U.S. Application Data

(60) Provisional application No. 62/154,310, filed on Apr. 29, 2015.

(51) Int. Cl.
C07D 487/04    (2006.01)
A61P 25/00     (2006.01)
C07D 231/54    (2006.01)
C07D 235/04    (2006.01)
C07D 239/80    (2006.01)
C07D 249/18    (2006.01)
C07D 275/06    (2006.01)
C07D 277/62    (2006.01)

(52) U.S. Cl.
CPC ............ C07D 487/04 (2013.01); A61P 25/00 (2018.01); C07D 231/54 (2013.01); C07D 235/04 (2013.01); C07D 239/80 (2013.01); C07D 249/18 (2013.01); C07D 275/06 (2013.01); C07D 277/62 (2013.01)

(58) Field of Classification Search
CPC .................................................. C07D 487/04
USPC ...................................................... 514/249
See application file for complete search history.

(56) References Cited

U.S. PATENT DOCUMENTS

| 4,370,340 | A  | 1/1983  | Ueda et al. |
| 5,688,809 | A  | 11/1997 | Macor       |
| 5,886,008 | A  | 3/1999  | Macor       |
| 7,842,698 | B2 | 11/2010 | Rueckle     |

FOREIGN PATENT DOCUMENTS

| EP | 869958 | 10/1998 | |
| WO | WO 95/21836 | 8/1995 | |
| WO | WO 2000/01376 | 1/2000 | |
| WO | WO 02/10170 | 2/2002 | |
| WO | WO 2002/14294 | 2/2002 | |
| WO | WO 2007/135529 | 11/2007 | |
| WO | WO 2008/053031 | 5/2008 | |
| WO | WO 2008/113795 | 9/2008 | |
| WO | WO 2008/148832 | 12/2008 | |
| WO | WO-2008148832 A1 * | 12/2008 | ........... C07D 231/54 |
| WO | WO 2010/005528 | 1/2010 | |
| WO | WO 2010/066658 | 6/2010 | |
| WO | WO 2011/056985 | 5/2011 | |
| WO | WO 2011/156245 | 12/2011 | |
| WO | WO 2013/064984 | 5/2013 | |
| WO | WO 2014/085153 | 6/2014 | |
| WO | WO 2014/128585 | 8/2014 | |

OTHER PUBLICATIONS

International Search Report for PCT/US2016/029791 dated Jun. 9, 2016.
Bagshawe, Drug Dev Res. 1995, 34, 220-230.
Berge, et al., "Pharmaceutical Salts", J Pharm Sci., 1977, 66:1-19.
Bertolini, et al., J Med Chem. 1997, 40, 2011-2016.
Bodor, Adv Drug Res. 1984, 13, 224-331.
(Continued)

Primary Examiner — Kahsay Habte
(74) Attorney, Agent, or Firm — Thomas J. Dodd

(57) ABSTRACT

Provided herein are compounds of Formula (I), and pharmaceutically acceptable salts, N-oxides, or solvates thereof, (I)

[Chemical structure showing a bicyclic ring system with substituents $R^1$, $R^2$, $R^3$, $R^4$, $R^5$ and atoms X, Y, N]

Also provided herein are pharmaceutical compositions, comprising compounds of Formula (I), and methods of using compounds of Formula (I).

38 Claims, No Drawings

(56) References Cited

OTHER PUBLICATIONS

Brewer, G. J. (1997). "Isolation and culture of adult rat hippocampal neurons." Journal of Neuroscience Methods 71(2): 143-155.
Chen et al., Bipolar Disord., 13:1-15, 2011.
Cho et al. (2007). "Two families of TARP isoforms that have distinct effects on the kinetic properties of AMPA receptors and synaptic currents." Neuron 55(6): 890-904.
Du et al., J Neurosci 24: 6578-6589, 2004.
Du et al., J Neurosci 28: 68-79, 2008.
Engin and Treit, Behav Pharmacol 18:365-374, 2007.
Fleisher et al., Adv Drug Delivery Rev., 1996, 19, 115-130.
G.D. Considine, ed., Van Nostrand's Encyclopedia of Chemistry, p. 261, $5^{th}$ ed. (2005).
Harrison, Brain 125:1428-1449, 2002.
Heckers and Konradi, Curr Top Behav Neurosci. 4:529-553, 2010.
Kambe, Tohru; Correia, Bruno E.; Niphakis, Micah J.; Cravatt, Benjamin F., Journal of the American Chemical Society (2014), 136(30), 10777-10782.
Lazzaro et al. (2002). "Functional characterization of CP-465,022, a selective, noncompetitive AMPA receptor antagonist." Neuropharmacology 42(2): 143-153.
McNaughton et al., Behav Pharmacol 18: 329-346, 2007.
Nolen and Bloemkolk, Neuropsychobiology, 42 Suppl 1:11-7, 2000.
Robinson et al., J. Med Chem., 1996, 39(1), 10-18.
Paulekuhn, et al., "Trends in Active Pharmaceutical Ingredient Salt Selection based on Analysis of the Orange Book Database", J. Med. Chem., 2007, 50:6665-72.
Pirotte et al., "AMPA receptor positive allosteric modulators: a patent review", Expert Opinion Therapeutic Patents, vol. 23, No. 5, 2013, pp. 615-628.
Schobel et al., Arch Gen Psych, 66:938-946, 2009.
Shan, et al., J Pharm Sci. 1997, 86 (7), 765-767.
Shi et al (2009) "The stoichiometry of AMPA receptors and TARPs varies by neuronal cell type." Neuron 62(5): 633-640.
Small et al, Nat. Rev. Neurosci. 12:585-601, 2011.
Strange et al. (2006). "Functional characterisation of homomeric ionotropic glutamate receptors GluR1-GluR6 in a fluorescence-based high throughput screening assay." Comb Chem High Throughput Screen 9(2): 147-158.
Tomita et al. (2003). "Functional studies and distribution define a family of transmembrane AMPA receptor regulatory proteins." J Cell Biol 161(4): 805-816.2003.
Tregellas et al., Am J Psychiatry 171: 549-556, 2014.
Yeung et al., Hippocampus 23:278-286, 2013.
Yeung et al., Neuropharmacology 62: 155-160, 2012.
International Search Report for PCT/US2016/029780 dated Jun. 14, 2016.
International Search Report for PCT/US2016/029801 dated Oct. 17, 2016.
International Search Report for PCT/US2016/029805 dated Jun. 8, 2016.
Gill and Bredt, Neoropsychopharmacology, 36(1): 362-363 (2011).
Macor et al., "The discovery of a novel and potent benzodiazepine receptor pharmacophore", Bioorganic & Medicinal Chemistry Letters, Pergamon, Amsterdam, NL, vol . 5, No. 20, Oct. 19, 1995 (Oct. 19, 1995), pp. 2397-2402.
Rogawski et al., Epilepsy Currents, 2011, vol. 11(2), pp. 56-63.
Tikhonova et al.,"Virtual screening of organic molecule databases . Design of focused libraries of potential I igands of NMDA and AMPA receptors", Russian Chemical Bulletin, Kluwer Academic Publishers-Plenum Publishers, NE, vol. 53, No. 6, Jun. 1, 2004, pp. 1335-1344.

* cited by examiner

IMIDAZOPYRAZINES AND PYRAZOLOPYRIMIDINES AND THEIR USE AS AMPA RECEPTOR MODULATORS

CROSS REFERENCE TO RELATED APPLICATIONS

This application is the national stage of PCT Application No. PCT/US2016/029791, filed Apr. 28, 2016, which claims priority from U.S. Provisional Application No. 62/154,310 filed Apr. 29, 2015, the entire disclosures of which are hereby incorporated in their entirety.

FIELD OF THE INVENTION

The present invention is related to compounds having AMPA receptor modulating properties, pharmaceutical compositions comprising these compounds, chemical processes for preparing these compounds and their use in the treatment of diseases associated with AMPA receptor activity in animals, in particular humans.

BACKGROUND OF THE INVENTION

Glutamate is the primary excitatory neurotransmitter in mammalian brain. Glutamatergic signaling participates in a wide range of neural functions including learning and memory, long-term potentiation and synaptic plasticity.

Glutamate receptors can be divided into two families. The ionotropic glutamate receptors form ion channels that activate upon binding agonist, opening a pore through the plasma membrane through which cations can flow. The metabotropic glutamate receptors are G-protein-coupled receptors, activating intracellular signal transduction cascades. The ionotropic glutamate receptors can be further subdivided into four sub-families, based upon sequence homology and selectivity to exogenous agonists. These sub-families are the AMPA (α-amino-3-hydroxyl-5-methyl-4-isoxazole-propionic acid), NMDA (N-methyl-D-aspartate), kainate, and delta receptors.

The AMPA subtype of glutamate receptors are glutamate-gated ion channels expressed primarily on postsynaptic membranes of excitatory synapses in the central nervous system. AMPA receptors assemble as tetramers of subunits. Mammals express four AMPA-receptor subunits, called GluA1-GluA4. Each GluA subunit can be expressed in multiple splice variants; the two most prominent splice variants are called flop and flip. GluA subunits freely form functional homo- and hetero-tetramers. The majority of RNA encoding GluA2 subunits is edited post-transcriptionally, altering a genetically-encoded glutamine to arginine. This RNA editing causes AMPA receptors to preferentially form with two GluA2 units, and also prevents calcium entry through the activated receptor.

In their native environment, the pore-forming GluA tetramers directly or indirectly associate with numerous auxiliary proteins which modify the trafficking, localization, gating characteristics, and pharmacology of the AMPA receptor (AMPAR). These auxiliary subunits include cytoskeletal and anchoring proteins, other signaling proteins, and several intracellular and transmembrane proteins with unknown function. The wide variety of proteins which can participate in AMPA receptor complexes vastly increases the ability of a neuron to tune the response characteristics of its synapses.

Transmembrane AMPA Receptor Regulatory Proteins (TARPs) are a fairly recently discovered family of proteins that have been found to associate with and modulate the activity of AMPA receptors. (Gill and Bredt., Neuropsychopharmacology 36(1): 362-363 (2011). Several TARPs exhibit regiospecific expression in the brain, leading to physiological differentiation of the AMPA receptor activity. For example, TARP γ2-dependent AMPA receptors are primarily localized in the cerebellum and cerebral cortex while TARP γ8-dependent AMPA receptors are localized primarily in the hippocampus.

AMPA receptors mediate the majority of fast neurotransmission across synaptic gaps. Thus, inhibition or negative modulation of AMPA receptors is an attractive strategy for therapeutic intervention in CNS disorders characterized by excessive neuronal activity. However, since AMPA receptor activity is so ubiquitous within CNS, general antagonism affects most areas of the CNS resulting in undesired effects, such as ataxia, sedation, and/or dizziness, which are shared by all known general AMPA receptor antagonists.

Epilepsy affects over 50 million people world-wide, with 30-40% of treated patients being resistant to current pharmacotherapies and only about 8% of treated patients being maintained seizure free. Epilepsy is often defined as when a person has two or more unprovoked epileptic seizures. The International League Against Epilepsy (ILAE) defines an epileptic seizure as "a transient occurrence of signs and/or symptoms due to abnormal excessive or synchronous neuronal activity in the brain." Seizures are thought to have a number of underlying causalities which adds to the difficulty in treating epilepsy. Seizures have been divided according to their clinical presentation including generalized seizures (absence, atonic, tonic-clonic (grand mal), and myoclonic), simple and complex partial onset seizures, gelastic seizures, dacrystic seizures, and status epilepticus. Current therapies target a variety of mechanisms including GABAγ-aminobutyric acid) receptor agonism, T-type calcium channel blockers, sodium channel modulators, synaptic vesicle protein SV2A modulation, and inhibition of GABA transaminase. More recently, AMPA receptor antagonists have been investigated for treatment of seizures as well.

AMPA receptor antagonists are known anticonvulsant agents. Typically, AMPA receptor antagonists have very narrow therapeutic dosing windows; the doses needed to obtain anti-convulsant activity are close to or overlap with doses at which undesired effects are observed. (Michael A. Rogawski. "Revisiting AMPA Receptors as an AntiEpileptic Drug Target" Epilepsy Currents 11.2 (2011).) However, certain anticonvulsant agents such as Talampanel ((8R)-7-Acetyl-5-(4-aminophenyl)-8,9-dihydro-8-methyl-7H-1,3-dioxolo[4,5-h][2,3]benzodiazepine), selurampanel (BGG492) (N-[7-isopropyl-6-(2-methyl-2H-pyrazol-3-yl)-2,4-dioxo-1,4-dihydro-2H-qui-nazolin-3-yl]methanesulfonamide), and perampanel (5'-(2-cyanophenyl)-1'-phenyl-2,3'-bipyridinyl-6'(1'H)-one) are general (non-TARP dependent/non-selective) AMPA receptor antagonists. However, such general antagonism affects most areas of the CNS resulting in undesired effects, Glutamate as an excitatory neurotransmitter has been known to induce neurotoxicity by, for example, abnormal excitation of central nerves. Neurotoxicity is an adverse structural or functional change in the nervous system, and can take the form of subtle or gross biochemical changes, axonal degeneration, dendritic pruning or sprouting, loss or rearrangement of synapses, or cell death. Numerous nervous diseases involve a neurotoxic component, including and not limited to cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain and diabetic neuropathy.

Substances showing an antagonistic action to excitatory neurotransmitter receptors are potentially useful for the treatment of the above-mentioned conditions. For example, WO2000001376 suggests that inhibitors of the interaction of glutamate with the AMPA and/or kainate receptor complex could be useful in treating demyelinating disorders such as encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder; for example, CNS lupus erythematodes, polyarteritis nodosa, Sjogren syndrome, sarcoidosis, isolated cerebral vasculitis, etc.

Hippocampus links the limbic system to frontal cortex, thereby linking emotion to cognition (Small et al, Nat. Rev. Neurosci. 12:585-601, 2011). A meta-analysis of post-mortem neuro-pathology studies suggests that hippocampal volume is reduced in volume in patients with mood disorders (Harrison, Brain 125:1428-1449, 2002). Hippocampal neurons are particularly susceptible to stress-related atrophy. Pathological states characterized by excessive activity within hippocampus may be improved by a therapeutic intervention that selectively reduces hippocampal excitability. Modulation of neuronal excitability within hippocampus may provide a therapeutic benefit in mood disorders.

Excess activity in hippocampus has been observed in response to emotionally-charged stimuli in bipolar patients compared to controls (reviewed by Chen et al., Bipolar Disord., 13:1-15, 2011). Chronic treatment with mood stabilizers such as lithium or valproate reduced AMPA receptor surface expression in hippocampus (Du et al., J Neurosci 28: 68-79, 2008). Tricyclic antidepressants can trigger mania in bipolar patients (Nolen and Bloemkolk, Neuropsychobiology, 42 Suppl 1:11-7, 2000); these treatments can increase AMPA receptor surface expression in hippocampus (Du et al., J Neurosci 24: 6578-6589, 2004.)

In Gray's Neuropsychological Theory of Anxiety (2003), septum and hippocampus form a 'behavioral inhibition system' activated during anxiety-provoking conflict situations. A corollary of this theory is that anxiolytic drugs act by suppressing this 'behavioral inhibition system'. Indeed, intrahippocampal micro-infusion of $GABA_A$ agonists is sufficient to replicate their anxiolytic effects (Engin and Treit, Behav Pharmacol 18:365-374, 2007). Traditional anxiolytics with a variety of mechanisms-of-action, including $GABA_A$-receptor antagonists, $5\text{-}HT_{1A}$ receptor antagonists, and SSRIs, suppress brainstem-stimulated theta rhythm within hippocampus (McNaughton et al., Behav Pharmacol 18: 329-346, 2007). Direct injection of inhibitors of neuronal excitability into rodent hippocampus was shown to reduce the hippocampal theta rhythm, and to produce an anxiolytic phenotype. Intrahippocampal administration of ZD7288, an HCN channel inhibitor, slowed brainstem-stimulated theta rhythm in anesthetized rat and also increased the amount of time that rats spent in the open arms of an elevated plus maze (Yeung et al., Hippocampus 23:278-286, 2013). Intrahippocampal administration of phenytoin, a voltage-gated sodium channel inhibitor and anti-convulsant, showed similar effects on brainstem-stimulated theta rhythm frequency in anesthetized rat and was anxiolytic in conscious rat (Yeung et al., Neuropharmacology 62: 155-160, 2012).

Hippocampal overactivity has been observed in patients suffering from schizophrenia (Heckers and Konradi, Curr Top Behav Neurosci. 4:529-553, 2010). The degree of hyperactivity was be positively correlated to the severity of the symptoms (Tregellas et al., Am J Psychiatry 171: 549-556, 2014). Hypermetabolism in hippocampus (esp. CA1 region) correlates with disease progression in at-risk individuals, and with disease severity in patients diagnosed with schizophrenia (Schobel et al., Arch Gen Psych, 66:938-946, 2009). This over-activity, combined with the sensitivity of hippocampal neurons to excitotoxic damage, may lead to the observed decrease in hippocampal volume in schizophrenic patients. Neuroprotection in prodromal and early stages may prevent progressive damage (Kaur and Cadenhead, *Curr Top Behav Neurosci,* 2010).

In view of the clinical importance of AMPA receptors, the identification of compounds that modulate AMPA receptor function represents an attractive avenue into the development of new therapeutic agents. Such compounds are provided herein.

SUMMARY OF THE INVENTION

Provided herein are compounds which are AMPA receptor modulators. In another aspect, provided herein are compounds which modulate certain TARP dependent AMPA receptors. The compounds described herein are suitable for treatment of conditions involving AMPA receptor activity, and for treatment of conditions involving selective modulation of TARP dependent AMPA receptor activity, thereby allowing for treatment of conditions such as, inter alia, abnormal neurotransmission across synaptic gaps, excessive neuronal activity, abnormal excessive or synchronous neuronal activity in the brain, neurotoxicity (e.g., adverse structural or functional changes in the nervous system, subtle or gross biochemical changes, axonal degeneration, dendritic pruning or sprouting, loss or rearrangement of synapses, or cell death), neuronal excitability within hippocampus, neuronal excitotoxicity, hippocampal overactivity, and the like.

The invention is directed to the general and preferred embodiments defined, respectively, by the independent and dependent claims appended hereto, which are incorporated by reference herein. One aspect of this invention concerns compounds of Formula (I):

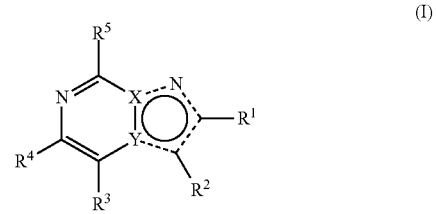

wherein
X is C or N;
Y is C or N; provided that X and Y cannot both be C, and X and Y cannot both be N;
the dotted line (-----) indicates that the referenced bond is a single bond or a double bond;
$R^1$ is selected from the group consisting of: $C_{1-5}$alkyl; $C_{3-7}$cycloalkyl; phenyl optionally substituted with one, two or three members independently selected from halo and —CN; CH₂-phenyl optionally substituted with halo; C(═O)-phenyl, wherein said phenyl is optionally substituted with halo; C(═O)N(CH₃)-phenyl; C(═O) NH-phenyl; C(═O)NH—CH₂-phenyl; C(═O)NH-pyridinyl; C(═O)NH—C₃₋₇cycloalkyl; C(═O)NH—C₁₋₅alkyl; and pyridinyl;

R² is selected from the group consisting of:

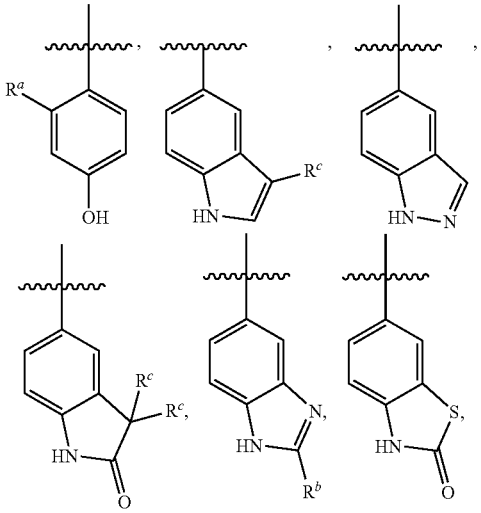

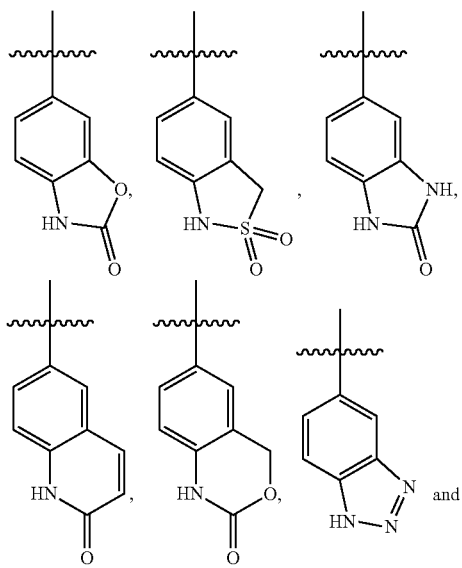

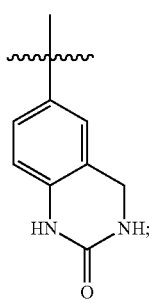

Rᵃ is H or —CH₃;
Rᵇ is H or —NH₂; and
Rᶜ is independently selected from: H and —F;
R³ is selected from the group consisting of: H, ³H, —CH₃ and halo;
R⁴ is selected from the group consisting of: H, —CH₃, or CF₃; and
R⁵ is selected from the group consisting of:
H; halo; —C₁₋₅alkyl; —C₁₋₅alkoxy; —NH₂; —NH(C₁₋₅alkyl); —N(C₁₋₅alkyl)₂; —NH—2-oxopyrrolidin-3-yl; —N(CH₃)cyclopropyl; —N(C₁₋₅alkyl)₂; —SO₂CH₃; —(S═O)CH₃; —OH; —O-cyclopentyl; azetidinyl optionally independently substituted with one or two members selected from the group consisting of: halo, —CH₃, —CF₃, —OCH₃, —SO₂CH₃, —CH₂OH, —OH, and —CN; pyrrolidinyl optionally substituted with a member selected from the group consisting of: —OH, —OCH₃ or —NH—(C═O)CH₃; piperidine optionally independently substituted with one, two, or three members selected from the group consisting of: halo, —OH, —CH₃, —OCH₃, —CH₂F, —CH₂CH₂F, and —NH—(C═O)CH₃; piperazine optionally substituted with —CH₃, —(C═O)CH₃, or —CO₂tBu; morpholine optionally independently substituted with one or two —CH₃, or —CF₃; octadeuteriomorpholin-4-yl; 6-oxa-2-azaspiro[3.3]heptan-2-yl; 3-oxopiperazin-1-yl optionally substituted with one or two —CH₃; 1,1-dioxo-1,4-thiazinan-4-yl; 1,4-dioxa-8-azaspiro[4.5]decan-8-yl; 6-oxa-3-azabicyclo[3.1.1]heptan-3-yl; 5-azaspiro[2.3]hexan-5-yl; diazapanyl optionally substituted with —(C═O)CH₃, 4-oxopiperidin-1-yl; dihydro-2H-pyridinyl optionally substituted with —(C═O)CH₃; dihydro-2H-pyranyl; 4-hydroxyimino-1-piperidyl; and 1,2,6-triazaspiro[2.5]oct-1-en-6-yl;

and pharmaceutically acceptable salts, N-oxides, or solvates of compounds of Formula (I).

Further embodiments are provided by pharmaceutically acceptable prodrugs of compounds of Formula (I), and pharmaceutically active metabolites of compounds of Formula (I).

In certain embodiments, the compounds of Formula (I) are compounds selected from those species described or exemplified in the detailed description below.

In a further aspect, the invention relates to enantiomers and diastereomers of the compounds of Formula (I), as well as their pharmaceutically acceptable salts.

In a further aspect, the invention relates to pharmaceutical compositions, comprising an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the chemical embodiments of the present invention are useful as AMPA receptor modulators. Thus, the invention is directed to a method for modulating AMPA receptor activity, including when such receptor is in a subject, comprising exposing AMPA receptor to an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of compounds of Formula (I).

In another aspect, the invention is directed to a method of treating a subject suffering from, or diagnosed with a disease, disorder, or medical condition mediated by AMPA receptor activity, comprising administering to the subject in need of such treatment an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of compounds of Formula (I). Additional embodiments of methods of treatment are set forth in the detailed description.

In another aspect, the method of studying isotopically labeled compounds in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. For example, an $^{18}F$ or $^{11}C$ labeled compound may be particularly preferred for PET or SPECT studies.

Additional embodiments of this invention include methods of making compounds of Formula (I), pharmaceutically acceptable salts, N-oxides or solvates of compounds of Formula (I), pharmaceutically acceptable prodrugs of compounds of Formula (I), and pharmaceutically active metabolites of Formula (I).

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

In another aspect provided herein are compounds of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA).

In another aspect provided herein are compounds of Formula (IIA), as well as pharmaceutically acceptable salts, N-oxides or solvates of compounds of Formula (IIA), pharmaceutically acceptable prodrugs of compounds of Formula (IIA), and pharmaceutically active metabolites of Formula (IIA).

In another aspect provided herein are compounds of Formula (IIIA), as well as pharmaceutically acceptable salts, N-oxides or solvates of compounds of Formula (IIIA), pharmaceutically acceptable prodrugs of compounds of Formula (IIIA), and pharmaceutically active metabolites of Formula (IIIA).

In a further aspect, provided herein are pharmaceutical compositions, comprising an effective amount of a compound of Formula (IA), Formula (IIA), or Formula (IIIA), as well as pharmaceutically acceptable salts, N-oxides or solvates of compounds of Formula (IA), Formula (IIA), or Formula (IIIA), pharmaceutically acceptable prodrugs of compounds of Formula (IA), Formula (IIA), or Formula (IIIA), and pharmaceutically active metabolites of Formula (IA), Formula (IIA), or Formula (IIIA). In a further aspect, provided herein are compounds of Formula (IA), Formula (IIA), or Formula (IIIA), as well as pharmaceutically acceptable salts, N-oxides or solvates of compounds of Formula (IA), Formula (IIA), or Formula (IIIA), pharmaceutically acceptable prodrugs of compounds of Formula (IA), Formula (IIA), or Formula (IIIA), and pharmaceutically active metabolites of Formula (IA), Formula (IIA), or Formula (IIIA), for the treatment of any condition described herein.

DETAILED DESCRIPTION

In one aspect, provided herein are compounds of Formula (I), and pharmaceutically acceptable salts, N-oxides, or solvates thereof,

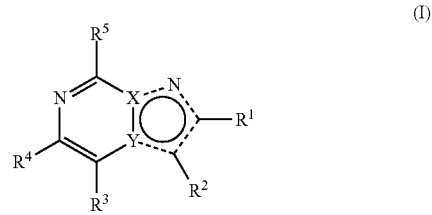

(I)

wherein
X is C or N;
Y is C or N; provided that X and Y cannot both be C, and X and Y cannot both be N;
the dotted line ( ----- ) indicates that the referenced bond is a single bond or a double bond;
$R^1$ is selected from the group consisting of: $C_{1-5}$alkyl; $C_{3-7}$cycloalkyl; phenyl optionally substituted with one, two or three members independently selected from halo and —CN; $CH_2$-phenyl optionally substituted with halo; C(=O)-phenyl, wherein said phenyl is optionally substituted with halo; C(=O)N($CH_3$)-phenyl; C(=O)NH-phenyl; C(=O)NH—$CH_2$-phenyl; C(=O)NH-pyridinyl; C(=O)NH—$C_{3-7}$cycloalkyl; C(=O)NH—$C_{1-5}$alkyl; and pyridinyl;
$R^2$ is selected from the group consisting of:

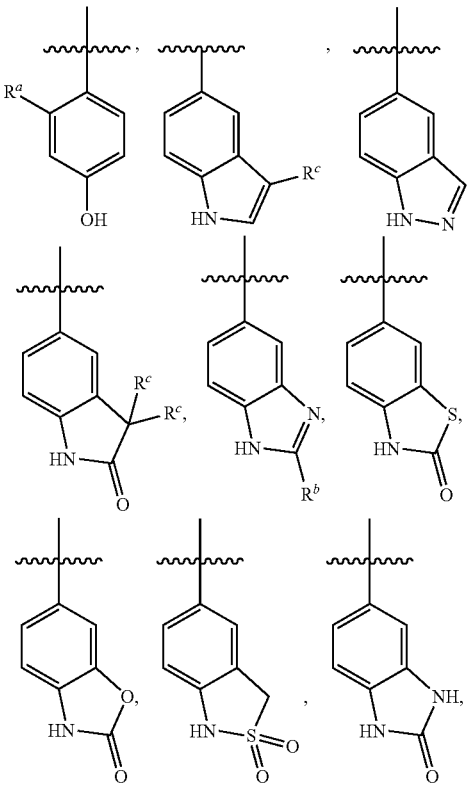

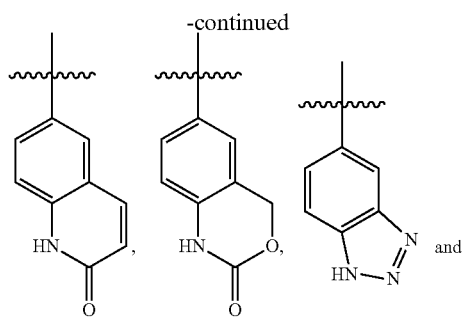

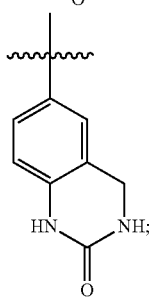

$R^a$ is H or —$CH_3$;
$R^b$ is H or —$NH_2$; and
$R^c$ is independently selected from: H and —F;
$R^3$ is selected from the group consisting of: H, $^3$H, —$CH_3$ and halo;
$R^4$ is H, —$CH_3$, or $CF_3$; and
$R^5$ is selected from the group consisting of:
H; halo; —$C_{1-5}$alkyl; —$C_{1-5}$alkoxy; —$NH_2$; —NH($C_{1-5}$alkyl); —N($C_{1-5}$alkyl)$_2$; —NH— 2-oxopyrrolidin-3-yl; —N($CH_3$)cyclopropyl; —N($C_{1-5}$alkyl)$_2$; —$SO_2CH_3$; —(S=O)$CH_3$; —OH; —O-cyclopentyl; azetidinyl optionally independently substituted with one or two members selected from the group consisting of: halo, —$CH_3$, —$CF_3$, —$OCH_3$, —$SO_2CH_3$, —$CH_2OH$, —OH, and —CN; pyrrolidinyl optionally substituted with —OH, —$OCH_3$ or —NH—(C=O)$CH_3$; piperidine optionally independently substituted with one, two, or three members selected from the group consisting of: halo, —OH, —$CH_3$, —$OCH_3$, —$CH_2F$, —$CH_2CH_2F$, and —NH—(C=O)$CH_3$; piperazine optionally substituted with —$CH_3$, —(C=O)$CH_3$, or —$CO_2tBu$; morpholine optionally independently substituted with one or two —$CH_3$, or —$CF_3$; octadeuteriomorpholin-4-yl; 6-oxa-2-azaspiro[3.3]heptan-2-yl; 3-oxopiperazin-1-yl optionally substituted with one or two —$CH_3$; 1,1-dioxo-1,4-thiazinan-4-yl; 1,4-dioxa-8-azaspiro[4.5]decan-8-yl; 6-oxa-3-azabicyclo[3.1.1]heptan-3-yl; 5-azaspiro[2.3]hexan-5-yl; diazapanyl optionally substituted with —(C=O)$CH_3$; 4-oxopiperidin-1-yl; dihydro-2H-pyridinyl optionally substituted with —(C=O)$CH_3$, dihydro-2H-pyranyl; 4-hydroxyimino-1-piperidyl; and 1,2,6-triazaspiro[2.5]oct-1-en-6-yl.

An additional embodiment of the invention is a compound of Formula (I), and pharmaceutically acceptable salts, N-oxides, or solvates thereof, wherein
X is C or N;
Y is C or N; provided that X and Y cannot both be C, and X and Y cannot both be N;
the dotted line (-----) indicates that the referenced bond is a single bond or a double bond;

$R^1$ is selected from the group consisting of: $C_{1-5}$alkyl; $C_{3-7}$cycloalkyl; phenyl optionally substituted with one, two or three members independently selected from halo and —CN; $CH_2$-phenyl optionally substituted with halo; C(=O)-phenyl, wherein said phenyl is optionally substituted with halo; C(=O)N($CH_3$)-phenyl; C(=O)NH-phenyl; C(=O)NH—$CH_2$-phenyl; C(=O)NH-pyridinyl; C(=O)NH—$C_{3-7}$cycloalkyl; C(=O)NH—$C_{1-5}$alkyl; and pyridinyl;

$R^2$ is selected from the group consisting of:

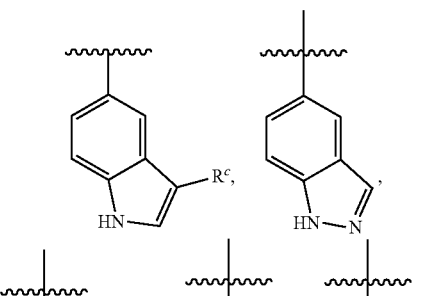

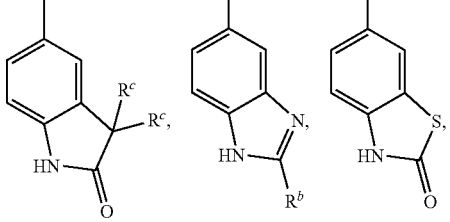

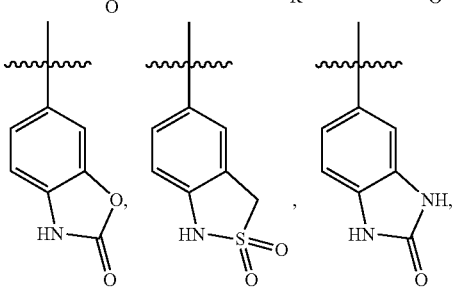

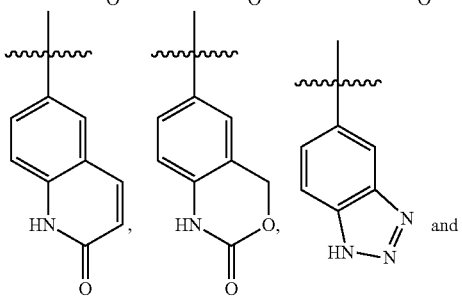

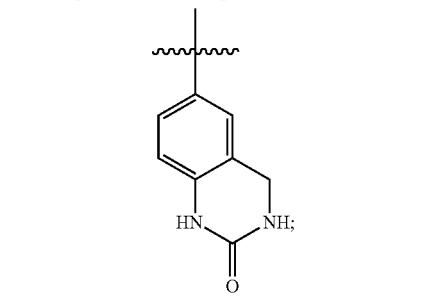

$R^b$ is H or —$NH_2$; and $R^c$ is independently selected from: H and —F;

$R^3$ is selected from the group consisting of: H, $^3H$, —$CH_3$ and halo;

$R^4$ is H, —$CH_3$, or $CF_3$; and $R^5$ is selected from the group consisting of:

H; halo; —$C_{1-5}$alkyl; —$C_{1-5}$alkoxy; —$NH_2$; —NH($C_{1-5}$alkyl); —N($C_{1-5}$alkyl)$_2$; —NH— 2-oxopyrrolidin-3-yl; —N($CH_3$)cyclopropyl; —N($C_{1-5}$alkyl)$_2$; —$SO_2CH_3$; —(S═O)$CH_3$; —OH; —O-cyclopentyl; azetidinyl optionally independently substituted with one or two members selected from the group consisting of: halo, —$CH_3$, —$CF_3$, —$OCH_3$, —$SO_2CH_3$, —$CH_2OH$, —OH, and —CN; pyrrolidinyl optionally substituted with —OH, —$OCH_3$ or —NH—(C═O)$CH_3$; piperidine optionally independently substituted with one, two, or three members selected from the group consisting of: halo, —OH, —$CH_3$, —$OCH_3$, —$CH_2F$, —$CH_2CH_2F$, and —NH—(C═O)$CH_3$; piperazine optionally substituted with —$CH_3$, —(C═O)$CH_3$, or —$CO_2tBu$; morpholine optionally independently substituted with one or two —$CH_3$, or —$CF_3$; octadeuteriomorpholin-4-yl; 6-oxa-2-azaspiro[3.3]heptan-2-yl; 3-oxopiperazin-1-yl optionally substituted with one or two —$CH_3$; 1,1-dioxo-1,4-thiazinan-4-yl; 1,4-dioxa-8-azaspiro[4.5]decan-8-yl; 6-oxa-3-azabicyclo[3.1.1]heptan-3-yl; 5-azaspiro[2.3]hexan-5-yl; diazapanyl optionally substituted with —(C═O)$CH_3$; 4-oxopiperidin-1-yl; dihydro-2H-pyridinyl optionally substituted with —(C═O)$CH_3$, dihydro-2H-pyranyl; 4-hydroxyimino-1-piperidyl; and 1,2,6-triazaspiro[2.5]oct-1-en-6-yl.

An additional embodiment of the invention is a compound of Formula (I), and pharmaceutically acceptable salts, N-oxides, or solvates thereof, having the structure of Formula (II):

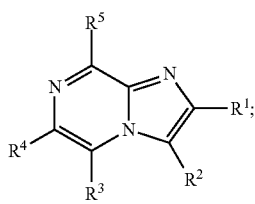

(II)

wherein $R^1$, $R^2$, $R^3$, $R^4$ and $R^5$ are as defined above in Formula (I).

An additional embodiment of the invention is a compound of Formula (I), and pharmaceutically acceptable salts, N-oxides, or solvates thereof, having the structure of Formula (III):

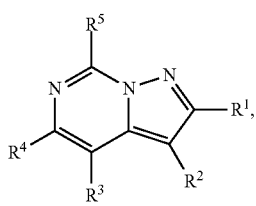

(III)

wherein $R^1$, $R^2$, $R^3$, $R^4$ and $R^5$ are as defined above in Formula (I).

An additional embodiment of the invention is a compound of Formula (I) wherein $R^1$ is —$C_{1-5}$alkyl; $C_{3-7}$cycloalkyl; phenyl optionally substituted with one, two, or three members independently selected from halo and —CN; $CH_2$-phenyl optionally substituted with halo; C(═O)-phenyl, wherein said phenyl is optionally substituted with halo; or pyridinyl.

An additional embodiment of the invention is a compound of Formula (I) wherein $R^1$ is C(═O)N($CH_3$)-phenyl; C(═O)NH-phenyl; C(═O)NH—$CH_2$-phenyl; C(═O)NH-pyridinyl; C(═O)NH—$C_{3-7}$cycloalkyl; or C(═O)NH—$C_{1-5}$alkyl.

An additional embodiment of the invention is a compound of Formula (I) wherein $R^1$ is $C_{1-5}$alkyl, phenyl, or $CH_2$-phenyl, wherein the phenyl rings are independently optionally substituted with one or two substituents selected from halo or —CN.

An additional embodiment of the invention is a compound of Formula (I) wherein $R^1$ is phenyl independently optionally substituted with one or two substituents selected from halo or —CN.

An additional embodiment of the invention is a compound of Formula (I) wherein $R^2$ is selected from the group consisting of:

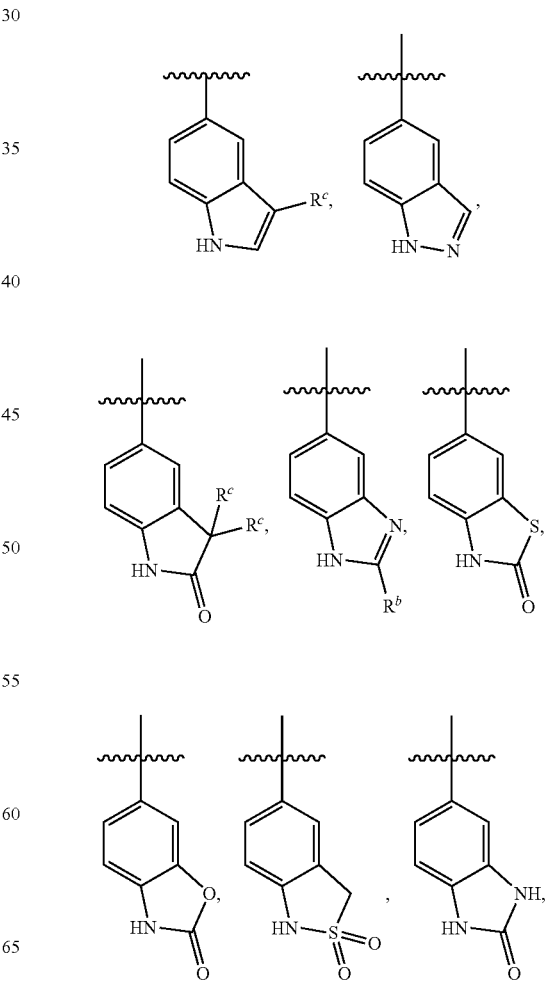

-continued

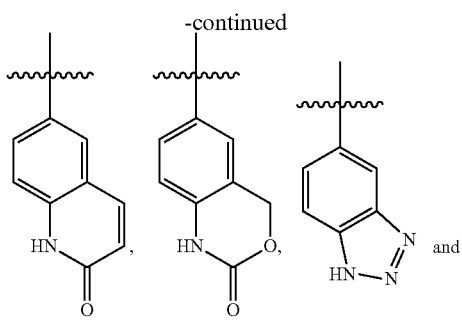

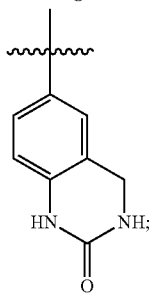

wherein $R^b$ and $R^c$ are as defined above in Formula (I).

An additional embodiment of the invention is a compound of Formula (I) wherein $R^2$ is:

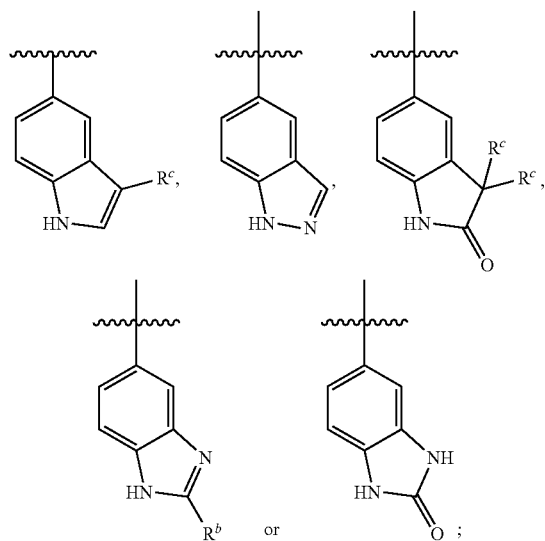

and $R^c$ is independently H or —F.

An additional embodiment of the invention is a compound of Formula (I) wherein $R^2$ is:

-continued and $R^c$ is independently H or —F.

An additional embodiment of the invention is a compound of Formula (I) wherein $R^2$ is:

[structure with $R^c$ groups on indolinone]

and $R^c$ is independently H or —F.

An additional embodiment of the invention is a compound of Formula (I) wherein $R^3$ is H.

An additional embodiment of the invention is a compound of Formula (I) wherein $R^3$ is H, $^3$H, —CH$_3$ or halo.

An additional embodiment of the invention is a compound of Formula (I) wherein $R^3$ is —F, —Cl or —Br.

An additional embodiment of the invention is a compound of Formula (I) wherein $R^3$ is —Br.

An additional embodiment of the invention is a compound of Formula (I) wherein $R^3$ is —CH$_3$.

An additional embodiment of the invention is a compound of Formula (I) wherein $R^3$ and $R^4$ are H.

An additional embodiment of the invention is a compound of Formula (I) wherein $R^5$ is H; halo; —C$_{1-5}$alkyl; —C$_{1-5}$alkoxy; —NH$_2$; —NH(C$_{1-5}$alkyl); —N(C$_{1-5}$alkyl)$_2$; —NH— 2-oxopyrrolidin-3-yl; —N(CH$_3$)cyclopropyl; —N(C$_{1-5}$alkyl)$_2$; —SO$_2$CH$_3$; —(S=O)CH$_3$; —OH; or —O-cyclopentyl.

An additional embodiment of the invention is a compound of Formula (I) wherein $R^5$ is H; halo; —OH; —CH$_3$; —OCH$_3$; —OCH(CH$_3$)$_2$; —NH$_2$; —NH(CH$_3$); —N(CH$_3$)$_2$; —N(CH$_2$CH$_3$)$_2$; —N(CH$_3$)cyclopropyl; —SO$_2$CH$_3$; —(S=O)CH$_3$; or

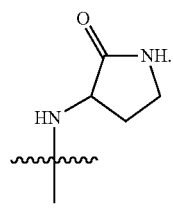 [SMILES: *NC1CCNC1=O]

An additional embodiment of the invention is a compound of Formula (I) wherein $R^5$ is F, —CH$_3$, —(S=O)CH$_3$, —SO$_2$CH$_3$, —NH(CH$_3$), —N(CH$_3$)$_2$, or —OCH$_3$.

An additional embodiment of the invention is a compound of Formula (I) wherein $R^5$ is H; —$C_{1-5}$alkoxy; —NH($C_{1-5}$alkyl); —N($C_{1-5}$alkyl)$_2$; and —O-cyclopentyl.

An additional embodiment of the invention is a compound of Formula (I) wherein $R^5$ is: azetidinyl optionally independently substituted with one or two members selected from the group consisting of: halo, —CH$_3$, —CF$_3$, —OCH$_3$, —SO$_2$CH$_3$, —CH$_2$OH, —OH, and —CN; pyrrolidinyl optionally substituted with —OH, —OCH$_3$ or —NH—(C=O)CH$_3$; piperidine optionally independently substituted with one, two, or three members selected from the group consisting of halo, —OH, —CH$_3$, —OCH$_3$, —CH$_2$F, —CH$_2$CH$_2$F, and —NH—(C=O)CH$_3$; piperazine optionally substituted with —CH$_3$, —(C=O)CH$_3$, or —CO$_2$tBu; morpholine optionally independently substituted with one or two —CH$_3$, or —CF$_3$; octadeuteriomorpholin-4-yl; 6-oxa-2-azaspiro[3.3]heptan-2-yl; 3-oxopiperazin-1-yl optionally substituted with one or two —CH$_3$; 1,1-dioxo-1,4-thiazinan-4-yl; 1,4-dioxa-8-azaspiro[4.5]decan-8-yl; 6-oxa-3-azabicyclo[3.1.1]heptan-3-yl; 5-azaspiro[2.3]hexan-5-yl; diazapanyl optionally substituted with —(C=O)CH$_3$; 4-oxopiperidin-1-yl; dihydro-2H-pyridinyl optionally substituted with —(C=O)CH$_3$; dihydro-2H-pyranyl; 4-hydroxyimino-1-piperidyl; or 1,2,6-triazaspiro[2.5]oct-1-en-6-yl.

An additional embodiment of the invention is a compound of Formula (I) wherein $R^5$ is H.

An additional embodiment of the invention is a compound of Formula (I) wherein $R^5$ is:

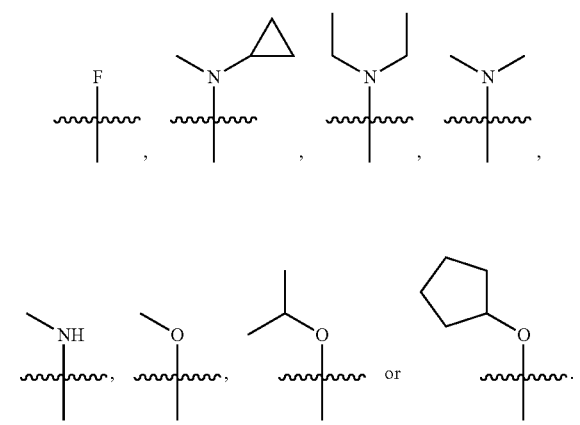

An additional embodiment of the invention is a compound of Formula (I) wherein $R^5$ is

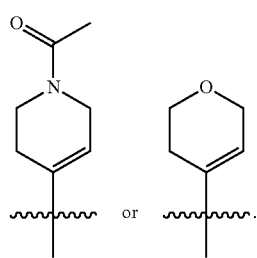

An additional embodiment of the invention is a compound of Formula (I) wherein $R^5$ is:

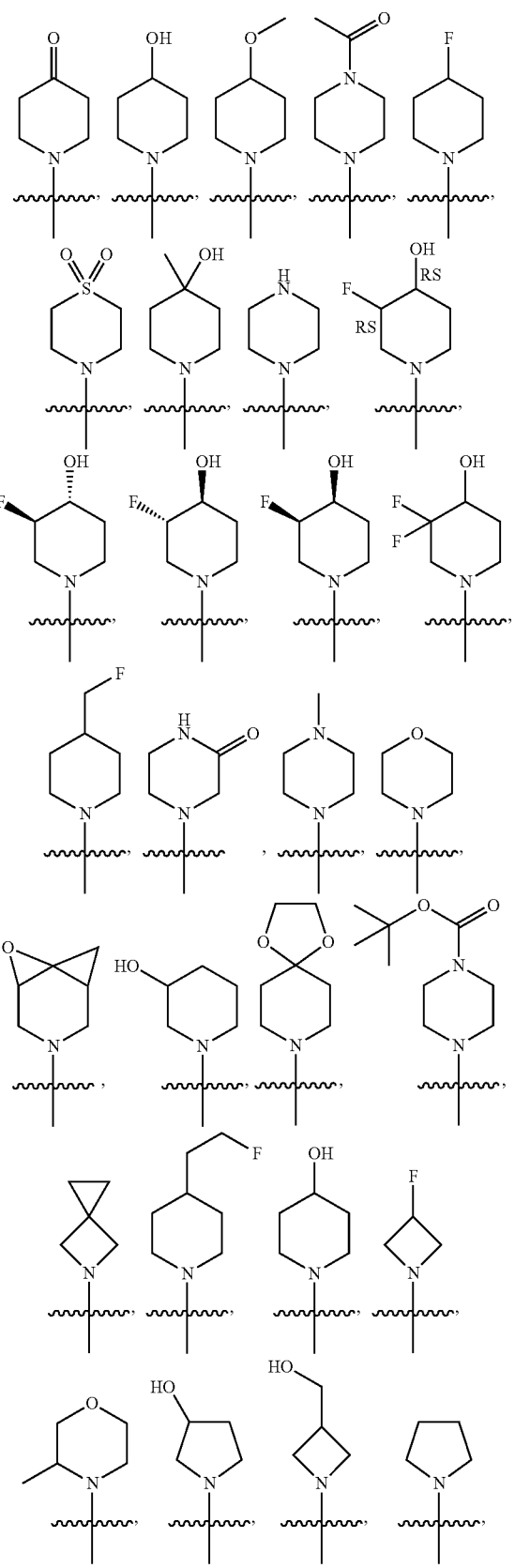

17
-continued

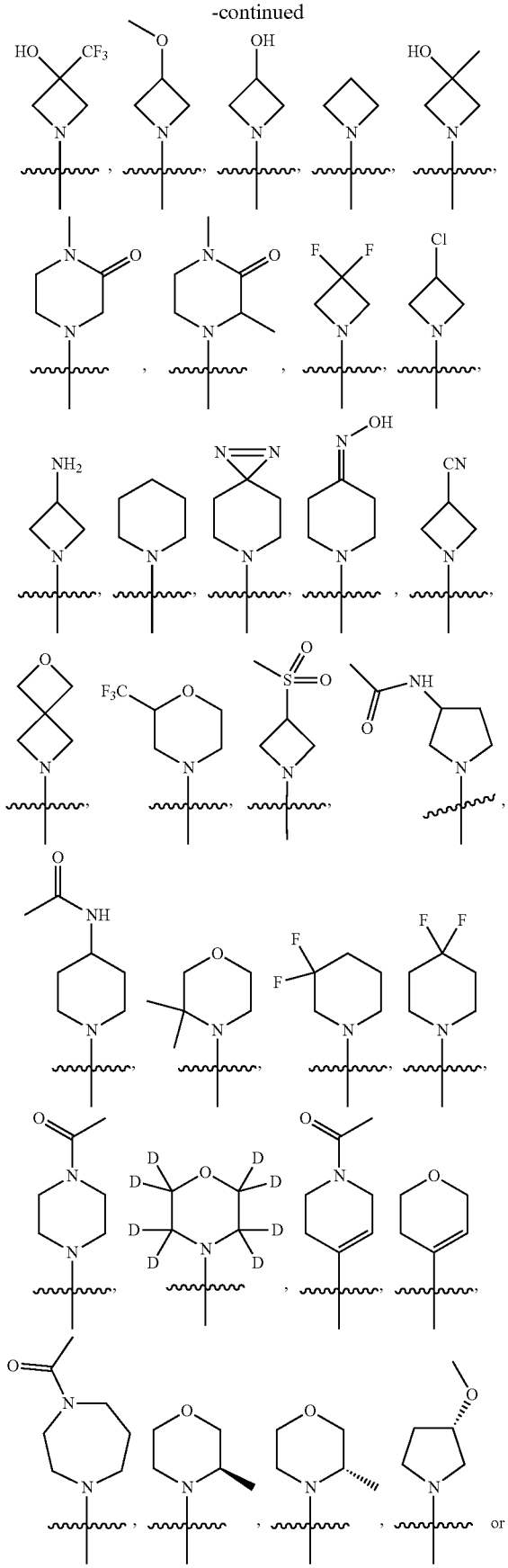

18
-continued

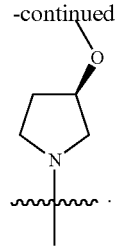

An additional embodiment of the invention is a compound of Formula (I), and pharmaceutically acceptable salts, N-oxides, or solvates thereof, having the structure of Formula (IV):

(IV)

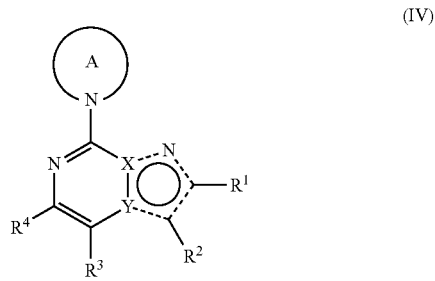

$R^1$, $R^2$, $R^3$ and $R^4$ are as defined in claim 1; and

Ring A is azetidinyl optionally independently substituted with one or two members selected from the group consisting of: halo, —CH₃, —CF₃, —OCH₃, —SO₂CH₃, —CH₂OH, —OH, and —CN; pyrrolidinyl optionally substituted with —OH, —OCH₃ or —NH—(C═O)CH₃; piperidine optionally independently substituted with one, two, or three members selected from the group consisting of: halo, —OH, —CH₃, —OCH₃, —CH₂F, —CH₂CH₂F, and —NH—(C═O)CH₃; piperazine optionally substituted with —CH₃, —(C═O)CH₃, or —CO₂tBu; morpholine optionally independently substituted with one or two —CH₃, or —CF₃; octadeuteriomorpholin-4-yl; 6-oxa-2-azaspiro[3.3]heptan-2-yl; 3-oxopiperazin-1-yl optionally substituted with one or two —CH₃; 1,1-dioxo-1,4-thiazinan-4-yl; 1,4-dioxa-8-azaspiro[4.5]decan-8-yl; 6-oxa-3-azabicyclo[3.1.1]heptan-3-yl; 5-azaspiro[2.3]hexan-5-yl; diazapanyl optionally substituted with —(C═O)CH₃; 4-oxopiperidin-1-yl; dihydro-2H-pyridinyl optionally substituted with —(C═O)CH₃; 4-hydroxyimino-1-piperidyl; or 1,2,6-triazaspiro[2.5]oct-1-en-6-yl.

An additional embodiment of the invention is a compound of Formula (I), having the structure of Formula (IV), wherein Ring A is:

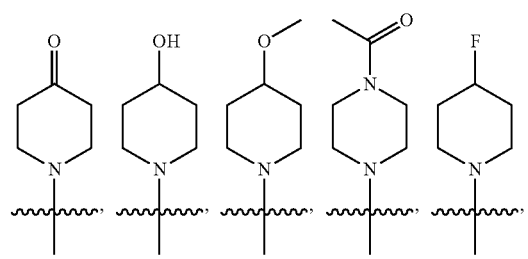

-continued
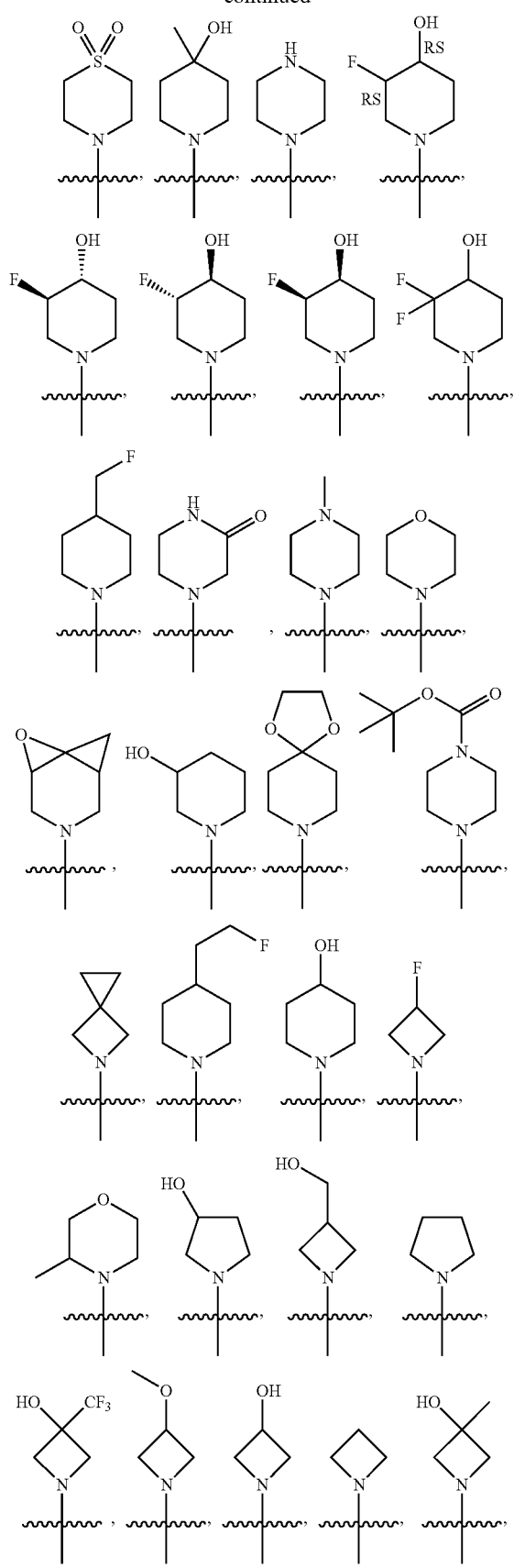
-continued
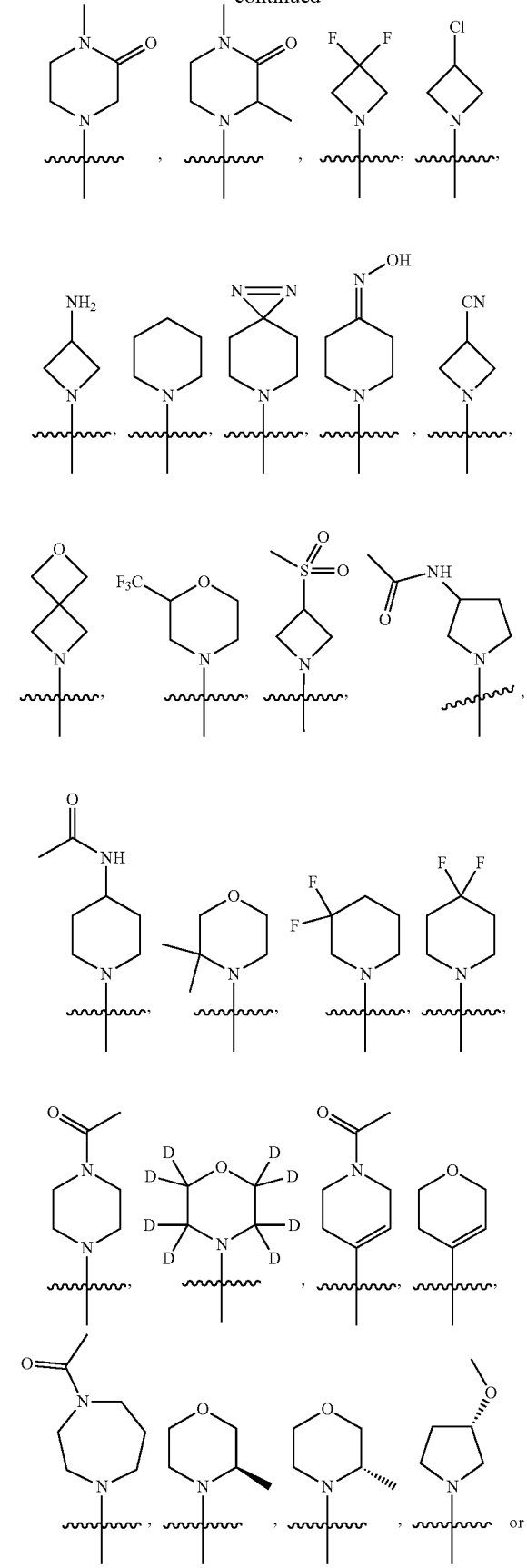

-continued

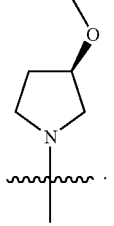

An additional embodiment of the invention is a compound of Formula (I), having the structure of Formula (IV), wherein $R^2$ is

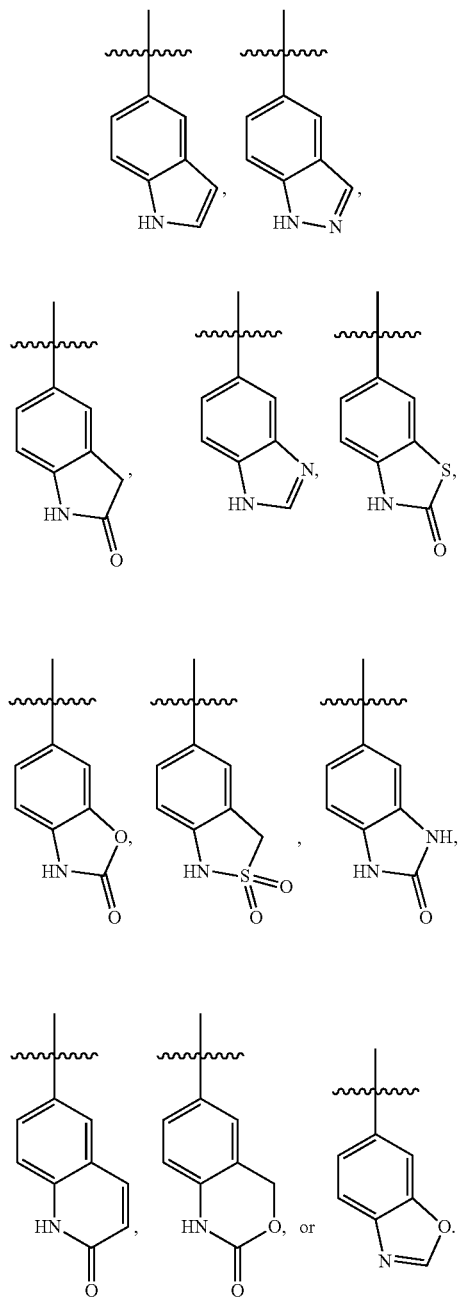

An additional embodiment of the invention is a compound of Formula (I), having the structure of Formula (IA),

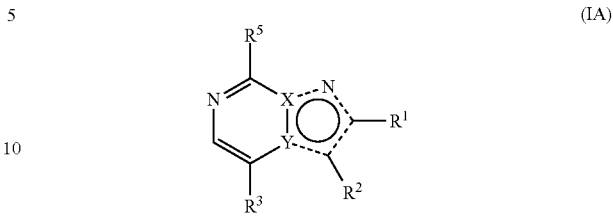

X is C and Y is N;
the dotted line (-----) indicates that the referenced bond is a single bond or a double bond;
$R^1$ is selected from the group consisting of: —CH(CH$_3$)$_2$, —C(CH$_3$)$_3$, 4-fluorophenyl, 3-fluorophenyl, 2-fluorophenyl, 3,4-difluorophenyl, 4-chlorophenyl, 4-cyanophenyl, phenyl, benzyl, and (3-fluorophenyl)methyl;
$R^2$ is selected from the group consisting of:

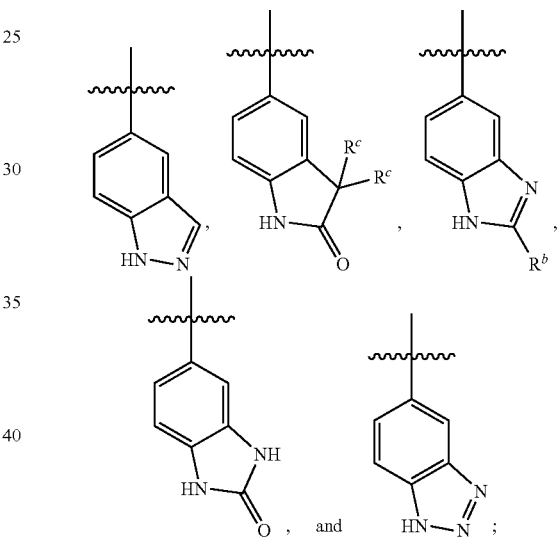

$R^3$ is selected from the group consisting of: H, —CH$_3$ and halo; and
$R^5$ is selected from the group consisting of:
H; halo; —C$_{1-5}$alkyl; —C$_{1-5}$alkoxy; —NH$_2$; —NH(C$_{1-5}$alkyl); —N(C$_{1-5}$alkyl)$_2$; —NH— 2-oxopyrrolidin-3-yl; —N(CH$_3$)cyclopropyl; —N(C$_{1-5}$alkyl)$_2$; —SO$_2$CH$_3$; —(S=O)CH$_3$; —OH; —O— cyclopentyl; azetidinyl optionally independently substituted with one or two members selected from the group consisting of: halo, —CH$_3$, —CF$_3$, —OCH$_3$, —SO$_2$CH$_3$, —CH$_2$OH, —OH, and —CN; pyrrolidinyl optionally substituted with —OH, —OCH$_3$ or —NH—(C=O)CH$_3$; piperidine optionally independently substituted with one, two, or three members selected from the group consisting of: halo, —OH, —CH$_3$, —OCH$_3$, —CH$_2$F, —CH$_2$CH$_2$F, and —NH—(C=O)CH$_3$; piperazine optionally substituted with —CH$_3$, —(C=O)CH$_3$, or —CO$_2$tBu; morpholine optionally independently substituted with one or two —CH$_3$, or —CF$_3$; octadeuteriomorpholin-4-yl; 6-oxa-2-azaspiro[3.3]heptan-2-yl; 3-oxopiperazin-1-yl optionally substituted with one or two —CH₃; 1,1-dioxo-1,4-thiazinan-4-yl; 1,4-dioxa-8-azaspiro[4.5]decan-8-yl; 6-oxa-3-azabicyclo[3.1.1]heptan-3-yl; 5-azaspiro[2.3]hexan-5-yl; diazapanyl optionally substituted with —(C=O)CH₃; 4-oxopiperidin-1-yl; dihydro-2H-pyridinyl optionally substituted with —(C=O)CH₃; dihydro-2H-pyranyl; 4-hydroxyimino-1-piperidyl; and 1,2,6-triazaspiro[2.5]oct-1-en-6-yl.

An additional embodiment of the invention is a compound of Formula (I), and pharmaceutically acceptable salts, N-oxides, or solvates thereof, wherein X is N and Y is C, and having the structure of Formula (IIA):

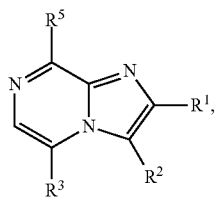

(IIA)

wherein R¹, R², R³, and R⁵ are as defined as above in Formula (IA).

An additional embodiment of the invention is a compound of Formula (I), and pharmaceutically acceptable salts, N-oxides, or solvates thereof, wherein X is N and Y is C, and having the structure of Formula (IIIA):

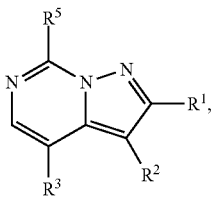

(IIIA)

wherein R¹, R², R³, and R⁵ are as defined as above in Formula (IA).

An additional embodiment of the invention is a compound of Formula (I), and pharmaceutically acceptable salts, N-oxides, or solvates thereof, having the structure of Formula (IA):

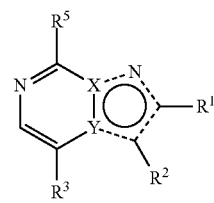

(IA)

X is N and Y is C;

the dotted line (-----) indicates that the referenced bond is a single bond or a double bond;

R¹ is selected from the group consisting of: $C_{1-5}$alkyl; $C_{3-7}$cycloalkyl; and phenyl optionally substituted with one or two halo;

R² is selected from the group consisting of:

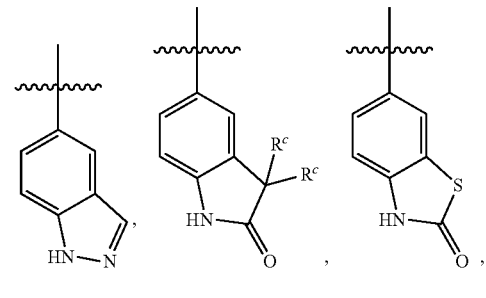

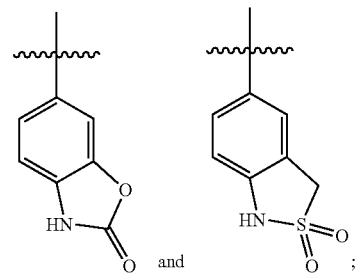

$R^c$ is H;

R³ is selected from the group consisting of: H, —CH₃ and halo; and

R⁵ is selected from the group consisting of:

H; —$C_{1-5}$alkoxy; —NH($C_{1-5}$alkyl); —N($C_{1-5}$alkyl)₂; —O-cyclopentyl; azetidinyl optionally independently substituted with one or two members selected from the group consisting of halo, —CH₃, —OCH₃, —OH, and —CH₂OH; pyrrolidine optionally substituted with —OCH₃; piperidine optionally independently substituted with one or two members selected from halo, —OH, —CH₃, and —OCH₃; piperazine optionally substituted with —(C=O)CH₃; morpholine optionally substituted with —CH₃; 6-oxa-2-azaspiro[3.3]heptan-2-yl; 3-oxopiperazin-1-yl; 1,1-dioxo-1,4-thiazinan-4-yl; and 4-oxopiperidin-1-yl.

A further embodiment of the current invention is a compound as shown below in Table 1.

| Example # | Compound Name |
|---|---|
| 1 | 1-[4-[2-(4-Fluorophenyl)-3-(4-hydroxyphenyl)imidazo[1,2-a]pyrazin-8-yl]piperazin-1-yl]ethanone; |
| 2 | 4-[2-(4-Fluorophenyl)-8-morpholino-imidazo[1,2-a]pyrazin-3-yl]-3-methyl-phenol; |

| Example # | Compound Name |
|---|---|
| 3 | tert-Butyl 4-[2-(4-fluorophenyl)-3-(4-hydroxyphenyl)imidazo[1,2-a]pyrazin-8-yl]piperazine-1-carboxylate; |
| 4 | 4-[2-(3-Fluorophenyl)-8-morpholino-imidazo[1,2-a]pyrazin-3-yl]phenol; |
| 5 | 4-[2-(4-Fluorophenyl)-8-piperazin-1-yl-imidazo[1,2-a]pyrazin-3-yl]phenol; |
| 6 | 4-[2-(4-Fluorophenyl)-8-(4-methylpiperazin-1-yl)imidazo[1,2-a]pyrazin-3-yl]phenol; |
| 7 | 4-[2-(4-Fluorophenyl)-8-(6-oxa-2-azaspiro[3;3]heptan-2-yl)imidazo[1,2-a]pyrazin-3-yl]phenol; |
| 8 | 5-[2-(4-Fluorophenyl)-8-morpholino-imidazo[1,2-a]pyrazin-3-yl]indolin-2-one; |
| 9 | 4-[2-(4-Fluorophenyl)-8-(1-piperidyl)imidazo[1,2-a]pyrazin-3-yl]phenol; |
| 10 | 4-[2-(4-Fluorophenyl)-3-(1H-indazol-5-yl)imidazo[1,2-a]pyrazin-8-yl]morpholine; |
| 11 | 5-[2-(4-Fluorophenyl)-8-morpholino-imidazo[1,2-a]pyrazin-3-yl]-1,3-dihydrobenzimidazol-2-one; |
| 12 | 5-[8-(4-Acetylpiperazin-1-yl)-2-(4-fluorophenyl)imidazo[1,2-a]pyrazin-3-yl]indolin-2-one; |
| 13 | 1-[4-[2-(4-Fluorophenyl)-3-(1H-indazol-5-yl)imidazo[1,2-a]pyrazin-8-yl]piperazin-1-yl]ethanone; |
| 14 | 5-[8-(4-Acetylpiperazin-1-yl)-2-(4-fluorophenyl)imidazo[1,2-a]pyrazin-3-yl]-1,3-dihydrobenzimidazol-2-one; |
| 15 | 4-(2-Benzyl-8-morpholino-imidazo[1,2-a]pyrazin-3-yl)phenol; |
| 16 | 4-[2-(4-Fluorophenyl)-3-(1H-indol-5-yl)imidazo[1,2-a]pyrazin-8-yl]morpholine; |
| 17 | 5-[8-(4-Acetylpiperazin-1-yl)-2-benzyl-imidazo[1,2-a]pyrazin-3-yl]indolin-2-one; |
| 18 | 1-[4-[2-Benzyl-3-(1H-indazol-5-yl)imidazo[1,2-a]pyrazin-8-yl]piperazin-1-yl]ethanone; |
| 19 | 5-[8-(4-Acetylpiperazin-1-yl)-2-benzyl-imidazo[1,2-a]pyrazin-3-yl]-1,3-dihydrobenzimidazol-2-one; |
| 20 | 5-(2-Benzyl-8-morpholino-imidazo[1,2-a]pyrazin-3-yl)indolin-2-one; |
| 21 | 4-[2-Benzyl-3-(1H-indazol-5-yl)imidazo[1,2-a]pyrazin-8-yl]morpholine; |
| 22 | 5-(2-Benzyl-8-morpholino-imidazo[1,2-a]pyrazin-3-yl)-1,3-dihydrobenzimidazol-2-one; |
| 23 | 1-[4-[2-Benzyl-3-(4-hydroxyphenyl)imidazo[1,2-a]pyrazin-8-yl]piperazin-1-yl]ethanone; |
| 24 | 5-[2-(4-Fluorophenyl)-8-(6-oxa-2-azaspiro[3;3]heptan-2-yl)imidazo[1,2-a]pyrazin-3-yl]indolin-2-one; |
| 25 | 2-[2-(4-Fluorophenyl)-3-(1H-indazol-5-yl)imidazo[1,2-a]pyrazin-8-yl]-6-oxa-2-azaspiro[3;3]heptane; |
| 26 | 5-[2-(4-Fluorophenyl)-8-(6-oxa-2-azaspiro[3;3]heptan-2-yl)imidazo[1,2-a]pyrazin-3-yl]-1,3-dihydrobenzimidazol-2-one; |
| 27 | 4-[2-(4-Fluorophenyl)-3-(4-hydroxyphenyl)imidazo[1,2-a]pyrazin-8-yl]piperazin-2-one; |
| 28 | 4-[8-(4,4-Difluoro-1-piperidyl)-2-(4-fluorophenyl)imidazo[1,2-a]pyrazin-3-yl]phenol; |
| 29 | 4-[8-(3,3-Difluoro-1-piperidyl)-2-(4-fluorophenyl)imidazo[1,2-a]pyrazin-3-yl]phenol; |
| 30 | 4-[3-(1H-Benzotriazol-5-yl)-2-(4-fluorophenyl)imidazo[1,2-a]pyrazin-8-yl]morpholine; |
| 31 | 4-[3-(1H-Benzimidazol-5-yl)-2-(4-fluorophenyl)imidazo[1,2-a]pyrazin-8-yl]morpholine; |
| 32 | 5-[2-(4-Fluorophenyl)-8-(3-oxopiperazin-1-yl)imidazo[1,2-a]pyrazin-3-yl]indolin-2-one; |
| 33 | 4-[2-(4-Fluorophenyl)-3-(1H-indazol-5-yl)imidazo[1,2-a]pyrazin-8-yl]piperazin-2-one; |
| 34 | 5-[2-(4-Fluorophenyl)-8-(3-oxopiperazin-1-yl)imidazo[1,2-a]pyrazin-3-yl]-1,3-dihydrobenzimidazol-2-one; |
| 35 | 5-[2-(3,4-Difluorophenyl)-8-morpholino-imidazo[1,2-a]pyrazin-3-yl]indolin-2-one; |
| 36 | tert-Butyl 4-[2-benzyl-3-(2-oxoindolin-5-yl)imidazo[1,2-a]pyrazin-8-yl]piperazine-1-carboxylate; |
| 37 | 5-[2-(4-Fluorophenyl)-8-(4-hydroxy-1-piperidyl)imidazo[1,2-a]pyrazin-3-yl]indolin-2-one; |
| 38 | 5-[2-Benzyl-8-(3-oxopiperazin-1-yl)imidazo[1,2-a]pyrazin-3-yl]indolin-2-one; |
| 39 | 5-[2-(4-Fluorophenyl)-8-(3-methylmorpholin-4-yl)imidazo[1,2-a]pyrazin-3-yl]indolin-2-one; |
| 40 | 5-[2-(4-Fluorophenyl)-8-[(2-oxopyrrolidin-3-yl)amino]imidazo[1,2-a]pyrazin-3-yl]indolin-2-one; |
| 41 | 5-[2-(4-Fluorophenyl)-8-(3-hydroxypyrrolidin-1-yl)imidazo[1,2-a]pyrazin-3-yl]indolin-2-one; |
| 42 | 5-[2-(4-Fluorophenyl)-8-[2-(trifluoromethyl)morpholin-4-yl]imidazo[1,2-a]pyrazin-3-yl]indolin-2-one; |
| 43 | 5-[2-(4-Fluorophenyl)-8-[(3S)-3-methylmorpholin-4-yl]imidazo[1,2-a]pyrazin-3-yl]indolin-2-one; |

-continued

| Example # | Compound Name |
|---|---|
| 44 | 5-[2-(4-Fluorophenyl)-8-[(3R)-3-methylmorpholin-4-yl]imidazo[1,2-a]pyrazin-3-yl]indolin-2-one; |
| 45 | 5-[2-(4-Fluorophenyl)-8-pyrrolidin-1-yl-imidazo[1,2-a]pyrazin-3-yl]indolin-2-one; |
| 46 | 5-[8-[Cyclopropyl(methyl)amino]-2-(4-fluorophenyl)imidazo[1,2-a]pyrazin-3-yl]indolin-2-one; |
| 47 | 5-[8-(1,1-Dioxo-1,4-thiazinan-4-yl)-2-(4-fluorophenyl)imidazo[1,2-a]pyrazin-3-yl]indolin-2-one; |
| 48 | (R*)-5-[2-(4-Fluorophenyl)-8-[2-(trifluoromethyl)morpholin-4-yl]imidazo[1,2-a]pyrazin-3-yl]indolin-2-one; |
| 49 | (S*)-5-[2-(4-Fluorophenyl)-8-[2-(trifluoromethyl)morpholin-4-yl]imidazo[1,2-a]pyrazin-3-yl]indolin-2-one; |
| 50 | 5-[8-(3,3-Dimethylmorpholin-4-yl)-2-(4-fluorophenyl)imidazo[1,2-a]pyrazin-3-yl]indolin-2-one; |
| 51 | 5-[8-(Diethylamino)-2-(4-fluorophenyl)imidazo[1,2-a]pyrazin-3-yl]indolin-2-one; |
| 52 | (R*)-5-[2-(4-Fluorophenyl)-8-(3-hydroxypyrrolidin-1-yl)imidazo[1,2-a]pyrazin-3-yl]indolin-2-one; |
| 53 | (S*)-5-[2-(4-Fluorophenyl)-8-(3-hydroxypyrrolidin-1-yl)imidazo[1,2-a]pyrazin-3-yl]indolin-2-one; |
| 54 | 5-[2-(4-Fluorophenyl)-8-(3-hydroxy-1-piperidyl)imidazo[1,2-a]pyrazin-3-yl]indolin-2-one; |
| 55 | 5-[8-(1,4-Dioxa-8-azaspiro[4;5]decan-8-yl)-2-(4-fluorophenyl)imidazo[1,2-a]pyrazin-3-yl]indolin-2-one; |
| 56 | 5-(2-Cyclohexyl-8-morpholino-imidazo[1,2-a]pyrazin-3-yl)indolin-2-one; |
| 57 | 5-(2-Cyclopentyl-8-morpholino-imidazo[1,2-a]pyrazin-3-yl)indolin-2-one; |
| 58 | 5-[8-(Azetidin-1-yl)-2-(4-fluorophenyl)imidazo[1,2-a]pyrazin-3-yl]indolin-2-one; |
| 59 | 5-[8-(3-Fluoroazetidin-1-yl)-2-(4-fluorophenyl)imidazo[1,2-a]pyrazin-3-yl]indolin-2-one; |
| 60 | 5-[8-(3,3-Difluoroazetidin-1-yl)-2-(4-fluorophenyl)imidazo[1,2-a]pyrazin-3-yl]indolin-2-one; |
| 61 | 5-[8-(3-Chloroazetidin-1-yl)-2-(4-fluorophenyl)imidazo[1,2-a]pyrazin-3-yl]indolin-2-one; |
| 62 | 5-[2-(4-Fluorophenyl)-8-(3-methylsulfonylazetidin-1-yl)imidazo[1,2-a]pyrazin-3-yl]indolin-2-one; |
| 63 | 5-[2-(4-Fluorophenyl)-8-(2,2,3,3,5,5,6,6-octadeuteriomorpholin-4-yl)imidazo[1,2-a]pyrazin-3-yl]indolin-2-one; |
| 64 | 5-[2-(4-Fluorophenyl)-8-[3-(hydroxymethyl)azetidin-1-yl]imidazo[1,2-a]pyrazin-3-yl]indolin-2-one; |
| 65 | 5-(8-Morpholino-2-phenyl-imidazo[1,2-a]pyrazin-3-yl)indolin-2-one; |
| 66 | 1-[2-(4-Fluorophenyl)-3-(2-oxoindolin-5-yl)imidazo[1,2-a]pyrazin-8-yl]azetidine-3-carbonitrile; |
| 67 | 5-[2-(4-Fluorophenyl)-8-(3-hydroxy-3-methyl-azetidin-1-yl)imidazo[1,2-a]pyrazin-3-yl]indolin-2-one; |
| 68 | 5-[2-(4-Fluorophenyl)-8-(4-hydroxy-4-methyl-1-piperidyl)imidazo[1,2-a]pyrazin-3-yl]indolin-2-one; |
| 69 | 5-[2-(4-Fluorophenyl)-8-[3-hydroxy-3-(trifluoromethyl)azetidin-1-yl]imidazo[1,2-a]pyrazin-3-yl]indolin-2-one; |
| 70 | (trans)-5-[8-(3-Fluoro-4-hydroxy-1-piperidyl)-2-(4-fluorophenyl)imidazo[1,2-a]pyrazin-3-yl]indolin-2-one; |
| 71 | 5-[8-(3,3-Difluoro-4-hydroxy-1-piperidyl)-2-(4-fluorophenyl)imidazo[1,2-a]pyrazin-3-yl]indolin-2-one; |
| 72 | 5-[2-(4-Fluorophenyl)-8-(4-methoxy-1-piperidyl)imidazo[1,2-a]pyrazin-3-yl]indolin-2-one; |
| 73 | (cis)-5-[8-(3-Fluoro-4-hydroxy-1-piperidyl)-2-(4-fluorophenyl)imidazo[1,2-a]pyrazin-3-yl]indolin-2-one; |
| 74 | 5-[2-(4-Fluorophenyl)-8-(4-fluoro-1-piperidyl)imidazo[1,2-a]pyrazin-3-yl]indolin-2-one; |
| 75 | 5-[8-(4-Fluoro-1-piperidyl)-2-phenyl-imidazo[1,2-a]pyrazin-3-yl]indolin-2-one; |
| 76 | 5-[8-[4-(Fluoromethyl)-1-piperidyl]-2-phenyl-imidazo[1,2-a]pyrazin-3-yl]indolin-2-one; |
| 77 | 5-[8-[4-(2-Fluoroethyl)-1-piperidyl]-2-phenyl-imidazo[1,2-a]pyrazin-3-yl]indolin-2-one; |
| 78 | 5-[8-(3-Methoxyazetidin-1-yl)-2-phenyl-imidazo[1,2-a]pyrazin-3-yl]indolin-2-one; |
| 79 | 5-[8-(6-Oxa-3-azabicyclo[3;1;1]heptan-3-yl)-2-phenyl-imidazo[1,2-a]pyrazin-3-yl]indolin-2-one; |
| 80 | 5-[8-(5-Azaspiro[2;3]hexan-5-yl)-2-phenyl-imidazo[1,2-a]pyrazin-3-yl]indolin-2-one; |
| 81 | 5-[8-(3-Fluoroazetidin-1-yl)-2-phenyl-imidazo[1,2-a]pyrazin-3-yl]indolin-2-one; |
| 82 | 5-[5-Chloro-2-(4-fluorophenyl)-8-morpholino-imidazo[1,2-a]pyrazin-3-yl]-1,3-dihydrobenzimidazol-2-one; |

-continued

| Example # | Compound Name |
|---|---|
| 83 | 4-[2-(4-Fluorophenyl)-8-morpholino-imidazo[1,2-a]pyrazin-3-yl]-phenol; |
| 84 | 4-[2-(2-Fluorophenyl)-8-morpholino-imidazo[1,2-a]pyrazin-3-yl]phenol; |
| 85 | 4-(2-Cyclohexyl-8-morpholino-imidazo[1,2-a]pyrazin-3-yl)phenol; |
| 86 | 5-(2-tert-Butyl-8-morpholino-imidazo[1,2-a]pyrazin-3-yl)indolin-2-one; |
| 87 | 5-[8-Amino-2-(4-fluorophenyl)imidazo[1,2-a]pyrazin-3-yl]-1,3-dihydrobenzimidazol-2-one; |
| 88 | 5-[2-tert-Butyl-8-(4-hydroxy-1-pipendyl)imidazo[1,2-a]pyrazin-3-yl]indolin-2-one; |
| 89 | 5-[8-(3-Fluoroazetidin-1-yl)-2-(4-pyridyl)imidazo[1,2-a]pyrazin-3-yl]indolin-2-one; |
| 90 | 5-(2-Cyclobutyl-8-morpholino-imidazo[1,2-a]pyrazin-3-yl)indolin-2-one; |
| 91 | 5-(2-Cyclopropyl-8-morpholino-imidazo[1,2-a]pyrazin-3-yl)indolin-2-one; |
| 92 | 1-[4-[2-(4-Chlorophenyl)-3-(4-hydroxyphenyl)imidazo[1,2-a]pyrazin-8-yl]-1,4-diazepan-1-yl]ethanone; |
| 93 | N-[1-[2-(4-Chlorophenyl)-3-(4-hydroxyphenyl)imidazo[1,2-a]pyrazin-8-yl]-4-pipendyl]acetamide; |
| 94 | 1-[4-[2-(4-Chlorophenyl)-3-(4-hydroxyphenyl)imidazo[1,2-a]pyrazin-8-yl]piperazin-1-yl]ethanone; |
| 95 | 4-[3-(4-Hydroxyphenyl)-8-morpholino-imidazo[1,2-a]pyrazin-2-yl]benzonitrile; |
| 96 | 4-[2-[(3-Fluorophenyl)methyl]-8-morpholino-imidazo[1,2-a]pyrazin-3-yl]phenol; |
| 97 | 4-[3-(1H-Indazol-5-yl)-8-morpholino-imidazo[1,2-a]pyrazin-2-yl]benzonitrile; |
| 98 | N-[(3S)-1-[2-(4-Fluorophenyl)-3-(2-oxo-1,3-dihydrobenzimidazol-5-yl)imidazo[1,2-a]pyrazin-8-yl]pyrrolidin-3-yl]acetamide; |
| 99 | 5-[2-(4-Fluorophenyl)-8-methoxy-imidazo[1,2-a]pyrazin-3-yl]-1,3-dihydrobenzimidazol-2-one; |
| 100 | N-[(3R)-1-[2-(4-Fluorophenyl)-3-(2-oxo-1,3-dihydrobenzimidazol-5-yl)imidazo[1,2-a]pyrazin-8-yl]pyrrolidin-3-yl]acetamide; |
| 101 | 5-[8-(Dimethylamino)-2-(4-fluorophenyl)imidazo[1,2-a]pyrazin-3-yl]-1,3-dihydrobenzimidazol-2-one; |
| 102 | 4-[8-Morpholino-3-(2-oxoindolin-5-yl)imidazo[1,2-a]pyrazin-2-yl]benzonitrile; |
| 103 | 4-[8-(4-Acetylpiperazin-1-yl)-3-(1H-indazol-5-yl)imidazo[1,2-a]pyrazin-2-yl]benzonitrile; |
| 104 | 5-[2-(4-Fluorophenyl)-8-(methylamino)imidazo[1,2-a]pyrazin-3-yl]-1,3-dihydrobenzimidazol-2-one; |
| 105 | 4-[8-Morpholino-3-(2-oxo-1,3-dihydrobenzimidazol-5-yl)imidazo[1,2-a]pyrazin-2-yl]benzonitrile; |
| 106 | 4-[8-(4-Acetylpiperazin-1-yl)-3-(2-oxo-1,3-dihydrobenzimidazol-5-yl)imidazo[1,2-a]pyrazin-2-yl]benzonitrile; |
| 107 | 4-[8-(4-Acetylpiperazin-1-yl)-3-(2-oxoindolin-5-yl)imidazo[1,2-a]pyrazin-2-yl]benzonitrile; |
| 108 | 5-(2-(4-Fluorophenyl)-8-(2-oxa-6-azaspiro[3;3]heptan-6-yl)imidazo[1,2-a]pyrazin-3-yl)-1,3-dihydrobenzo[c]isothiazole 2,2-dioxide; |
| 109 | 5-(2-(4-Fluorophenyl)-8-(4-oxopiperidin-1-yl)imidazo[1,2-a]pyrazin-3-yl)indolin-2-one; |
| 110 | 5-(8-(4-Methyl-3-oxopiperazin-1-yl)-2-phenylimidazo[1,2-a]pyrazin-3-yl)indolin-2-one; |
| 111 | 5-(8-(2,4-Dimethyl-3-oxopiperazin-1-yl)-2-phenylimidazo[1,2-a]pyrazin-3-yl)indolin-2-one; |
| 112 | tert-Butyl 4-(2-benzyl-5-bromo-3-(2-oxoindolin-5-yl)imidazo[1,2-a]pyrazin-8-yl)piperazine-1-carboxylate; |
| 113 | 5-(8-(4-Acetylpiperazin-1-yl)-2-benzyl-5-bromoimidazo[1,2-a]pyrazin-3-yl)indolin-2-one; |
| 114 | 5-(8-(4-Acetylpiperazin-1-yl)-2-benzyl-5-methylimidazo[1,2-a]pyrazin-3-yl)indolin-2-one |
| 115 | 5-[8-(4-Acetylpiperazin-1-yl)-2-(4-fluorophenyl)imidazo[1,2-a]pyrazin-3-yl]indolin-2-one |
| 116 | 6-(2-(4-Fluorophenyl)-8-morpholinoimidazo[1,2-a]pyrazin-3-yl)benzo[d]oxazol-2(3H)-one; |
| 117 | 5-[2-(4-Fluorophenyl)-8-morpholino-imidazo[1,2-a]pyrazin-3-yl]-1,3-dihydro-2,1-benzothiazole 2,2-dioxide; |
| 118 | 6-[2-(4-Fluorophenyl)-8-morpholino-imidazo[1,2-a]pyrazin-3-yl]-3H-1,3-benzothiazol-2-one; |
| 119 | 1-[3-(2,2-Dioxo-1,3-dihydro-2,1-benzothiazol-5-yl)-2-(4-fluorophenyl)imidazo[1,2-a]pyrazin-8-yl]piperidin-4-ol |
| 120 | 6-[2-(4-Fluorophenyl)-8-morpholino-imidazo[1,2-a]pyrazin-3-yl]-3,4-dihydro-1H-quinazolin-2-one; |
| 121 | 5-[2-(4-Fluorophenyl)-8-morpholino-imidazo[1,2-a]pyrazin-3-yl]-1H-benzimidazol-2-amine; |
| 122 | 3-Fluoro-5-[2-(4-fluorophenyl)-8-morpholino-imidazo[1,2-a]pyrazin-3-yl]indolin-2-one; |
| 123 | 4-[3-(3-Fluoro-1H-indol-5-yl)-2-(4-fluorophenyl)imidazo[1,2-a]pyrazin-8-yl]morpholine; |

| Example # | Compound Name |
|---|---|
| 124 | 6-[2-(4-Fluorophenyl)-8-morpholino-imidazo[1,2-a]pyrazin-3-yl]-1,4-dihydro-3,1-benzoxazin-2-one; |
| 125 | 6-[2-(4-Fluorophenyl)-8-morpholino-imidazo[1,2-a]pyrazin-3-yl]-1H-quinolin-2-one; |
| 126 | 4-[2-(4-Fluorophenyl)-8-pyrrolidin-1-yl-imidazo[1,2-a]pyrazin-3-yl]phenol; |
| 127 | 5-[2-(4-Fluorophenyl)-8-methylsulfonyl-imidazo[1,2-a]pyrazin-3-yl]indolin-2-one; |
| 128 | 5-[2-(4-Fluorophenyl)-8-methylsulfinyl-imidazo[1,2-a]pyrazin-3-yl]indolin-2-one; |
| 129 | 5-[2-(4-Fluorophenyl)-8-isopropoxy-imidazo[1,2-a]pyrazin-3-yl]indolin-2-one; |
| 130 | 1-[4-[2-(4-Fluorophenyl)-3-(4-hydroxyphenyl)imidazo[1,2-a]pyrazin-8-yl]-3,6-dihydro-2H-pyridin-1-yl]ethanone; |
| 131 | 5-(8-(3,6-Dihydro-2H-pyran-4-yl)-2-phenylimidazo[1,2-a]pyrazin-3-yl)indolin-2-one; |
| 132 | 5-[8-Fluoro-2-(4-fluorophenyl)imidazo[1,2-a]pyrazin-3-yl]indolin-2-one; |
| 133 | 5-[2-(4-Fluorophenyl)-8-methyl-imidazo[1,2-a]pyrazin-3-yl]indolin-2-one |
| 134 | 5-(2-Phenylimidazo[1,2-a]pyrazin-3-yl)indolin-2-one; |
| 135 | 5-(2-(4-Fluorophenyl)imidazo[1,2-a]pyrazin-3-yl)indolin-2-one; |
| 136 | 3,3-Difluoro-5-[2-(4-fluorophenyl)-8-morpholino-imidazo[1,2-a]pyrazin-3-yl]indolin-2-one; |
| 137 | 8-Morpholino-3-(2-oxoindolin-5-yl)-N-phenylimidazo[1,2-a]pyrazine-2-carboxamide; |
| 138 | 3-(4-Hydroxyphenyl)-8-morpholino-N-phenyl-imidazo[1,2-a]pyrazine-2-carboxamide; |
| 139 | N-Benzyl-8-morpholino-3-(2-oxo-1,3-dihydrobenzimidazol-5-yl)imidazo[1,2-a]pyrazine-2-carboxamide; |
| 140 | 8-Morpholino-3-(2-oxo-1,3-dihydrobenzimidazol-5-yl)-N-phenyl-imidazo[1,2-a]pyrazine-2-carboxamide; |
| 141 | 5-[8-(Dimethylamino)-2-(4-fluorophenyl)imidazo[1,2-a]pyrazin-3-yl]indolin-2-one; |
| 142 | N-Benzyl-8-morpholino-3-(2-oxoindolin-5-yl)imidazo[1,2-a]pyrazine-2-carboxamide |
| 143 | 3-(2-Oxoindolin-5-yl)-8-(3-oxopiperazin-1-yl)-N-phenyl-imidazo[1,2-a]pyrazine-2-carboxamide; |
| 144 | 8-(Dimethylamino)-3-(2-oxoindolin-5-yl)-N-phenyl-imidazo[1,2-a]pyrazine-2-carboxamide; |
| 145 | N-Methyl-8-morpholino-3-(2-oxo-1,3-dihydrobenzimidazol-5-yl)-N-phenyl-imidazo[1,2-a]pyrazine-2-carboxamide; |
| 146 | N-Cyclopropyl-8-morpholino-3-(2-oxo-1,3-dihydrobenzimidazol-5-yl)imidazo[1,2-a]pyrazine-2-carboxamide; |
| 147 | 8-Morpholino-3-(2-oxo-1,3-dihydrobenzimidazol-5-yl)-N-(4-pyridyl)imidazo[1,2-a]pyrazine-2-carboxamide |
| 148 | 3-(4-Hydroxyphenyl)-8-morpholino-N-propyl-imidazo[1,2-a]pyrazine-2-carboxamide |
| 149 | 8-Morpholino-3-(2-oxoindolin-5-yl)-N-phenylimidazo[1,2-a]pyrazine-2-carboxamide; |
| 150 | N-[(3S)-1-[2-(4-Fluorophenyl)-3-(2-oxoindolin-5-yl)imidazo[1,2-a]pyrazin-8-yl]pyrrolidin-3-yl]acetamide; |
| 151 | [3-(4-Hydroxyphenyl)-8-morpholino-imidazo[1,2-a]pyrazin-2-yl]-phenyl-methanone; |
| 152 | 5-[2-Benzoyl-8-(dimethylamino)imidazo[1,2-a]pyrazin-3-yl]indolin-2-one; |
| 153 | 5-(2-Benzoyl-8-morpholino-imidazo[1,2-a]pyrazin-3-yl)indolin-2-one; |
| 154 | 5-[2-Benzoyl-8-(4-hydroxy-1-piperidyl)imidazo[1,2-a]pyrazin-3-yl]indolin-2-one; |
| 155 | 5-[2-(4-Fluorophenyl)-8-(4-hydroxyimino-1-piperidyl)imidazo[1,2-a]pyrazin-3-yl]indolin-2-one; |
| 156 | 6-(2-Benzoyl-8-morpholino-imidazo[1,2-a]pyrazin-3-yl)-3H-1,3-benzoxazol-2-one; |
| 157 | 5-[2-Benzoyl-8-(1,1-dioxo-1,4-thiazinan-4-yl)imidazo[1,2-a]pyrazin-3-yl]indolin-2-one; |
| 158 | 5-[8-(4-Acetylpiperazin-1-yl)-2-benzoyl-imidazo[1,2-a]pyrazin-3-yl]indolin-2-one; |
| 159 | [3-(2,2-Dioxo-1,3-dihydro-2,1-benzothiazol-5-yl)-8-morpholino-imidazo[1,2-a]pyrazin-2-yl]-phenyl-methanone; |
| 160 | 5-[2-Benzoyl-8-(methylamino)imidazo[1,2-a]pyrazin-3-yl]indolin-2-one; |
| 161 | 5-(5-Fluoro-2-(4-fluorophenyl)-8-morpholinoimidazo[1,2-a]pyrazin-3-yl)indolin-2-one |
| 162 | 5-[5-Fluoro-2-(4-fluorophenyl)-8-morpholino-imidazo[1,2-a]pyrazin-3-yl]-1,3-dihydrobenzimidazol-2-one |
| 163 | 5-[5-Chloro-2-(4-fluorophenyl)-8-morpholino-imidazo[1,2-a]pyrazin-3-yl]indolin-2-one; |
| 164 | 5-[2-(4-Fluorophenyl)-7-morpholino-pyrazolo[1,5-c]pyrimidin-3-yl]indolin-2-one; |

| Example # | Compound Name |
|---|---|
| 165 | 5-(2-tert-Butylpyrazolo[1,5-c]pyrimidin-3-yl)indolin-2-one; |
| 166 | 5-[2-(4-Fluorophenyl)-7-(4-hydroxy-1-piperidyl)pyrazolo[1,5-c]pyrimidin-3-yl]indolin-2-one; |
| 167 | 5-[2-(4-Fluorophenyl)-8-(methylamino)imidazo[1,2-a]pyrazin-3-yl]indolin-2-one; |
| 168 | 5-[2-(4-Fluorophenyl)-7-(3-oxopiperazin-1-yl)pyrazolo[1,5-c]pyrimidin-3-yl]indolin-2-one; |
| 169 | 5-[7-(Dimethylamino)-2-(4-fluorophenyl)pyrazolo[1,5-c]pyrimidin-3-yl]indolin-2-one; |
| 170 | 5-[7-(1,1-Dioxo-1,4-thiazinan-4-yl)-2-(4-fluorophenyl)pyrazolo[1,5-c]pyrimidin-3-yl]indolin-2-one; |
| 171 | 5-[2-(4-Fluorophenyl)-7-(methylamino)pyrazolo[1,5-c]pyrimidin-3-yl]indolin-2-one; |
| 172 | 5-[7-(4-Acetylpiperazin-1-yl)-2-(4-fluorophenyl)pyrazolo[1,5-c]pyrimidin-3-yl]indolin-2-one; |
| 173 | 6-[2-(4-Fluorophenyl)-7-morpholino-pyrazolo[1,5-c]pyrimidin-3-yl]-3H-1,3-benzoxazol-2-one; |
| 174 | 5-[2-(4-Fluorophenyl)-7-(4-oxo-1-piperidyl)pyrazolo[1,5-c]pyrimidin-3-yl]indolin-2-one; |
| 175 | 5-[2-(4-Fluorophenyl)pyrazolo[1,5-c]pyrimidin-3-yl]indolin-2-one; |
| 176 | 5-[7-(3,3-Difluoroazetidin-1-yl)-2-(4-fluorophenyl)pyrazolo[1,5-c]pyrimidin-3-yl]indolin-2-one; |
| 177 | 5-[2-(4-Fluorophenyl)-7-(3-methylmorpholin-4-yl)pyrazolo[1,5-c]pyrimidin-3-yl]indolin-2-one; |
| 178 | 5-[2-(4-Fluorophenyl)-7-morpholino-pyrazolo[1,5-c]pyrimidin-3-yl]-1,3-dihydro-2,1-benzothiazole 2,2-dioxide; |
| 179 | 5-[2-(4-Fluorophenyl)-7-(3-hydroxyazetidin-1-yl)pyrazolo[1,5-c]pyrimidin-3-yl]indolin-2-one; |
| 180 | 5-[2-(4-Fluorophenyl)-7-[3-(hydroxymethyl)azetidin-1-yl]pyrazolo[1,5-c]pyrimidin-3-yl]indolin-2-one; |
| 181 | 5-[2-tert-Butyl-7-(4-hydroxy-1-piperidyl)pyrazolo[1,5-c]pyrimidin-3-yl]indolin-2-one; |
| 182 | 5-(2-tert-Butyl-7-morpholino-pyrazolo[1,5-c]pyrimidin-3-yl)indolin-2-one; |
| 183 | 5-[2-tert-Butyl-7-(3,3-difluoroazetidin-1-yl)pyrazolo[1,5-c]pyrimidin-3-yl]indolin-2-one; |
| 184 | 5-[2-(4-Fluorophenyl)-7-(3-hydroxy-3-methyl-azetidin-1-yl)pyrazolo[1,5-c]pyrimidin-3-yl]indolin-2-one; |
| 185 | 5-(2-(4-Fluorophenyl)-8-(1,2,6-triazaspiro[2;5]oct-1-en-6-yl)imidazo[1,2-a]pyrazin-3-yl)indolin-2-one; |
| 186 | 5-[2-(4-Fluorophenyl)-7-(4-hydroxy-4-methyl-1-piperidyl)pyrazolo[1,5-c]pyrimidin-3-yl]indolin-2-one; |
| 187 | 5-[7-(4-Hydroxy-1-piperidyl)-2-phenyl-pyrazolo[1,5-c]pyrimidin-3-yl]indolin-2-one; |
| 188 | 5-[7-(4-Fluoro-1-piperidyl)-2-phenyl-pyrazolo[1,5-c]pyrimidin-3-yl]indolin-2-one; |
| 189 | 5-[7-(4-Methoxy-1-piperidyl)-2-phenyl-pyrazolo[1,5-c]pyrimidin-3-yl]indolin-2-one; |
| 190 | 5-[2-(4-Fluorophenyl)-7-(4-fluoro-1-piperidyl)pyrazolo[1,5-c]pyrimidin-3-yl]indolin-2-one; |
| 191 | 5-[7-(3-Methoxyazetidin-1-yl)-2-phenyl-pyrazolo[1,5-c]pyrimidin-3-yl]indolin-2-one; |
| 192 | 5-[7-(Cyclopentoxy)-2-phenyl-pyrazolo[1,5-c]pyrimidin-3-yl]indolin-2-one; |
| 193 | trans-5-[7-(3-Fluoro-4-hydroxy-1-piperidyl)-2-phenyl-pyrazolo[1,5-c]pyrimidin-3-yl]indolin-2-one; |
| 194 | 5-(7-Isopropoxy-2-phenyl-pyrazolo[1,5-c]pyrimidin-3-yl)indolin-2-one; |
| 195 | 5-[2-Cyclopentyl-7-(3-methoxyazetidin-1-yl)pyrazolo[1,5-c]pyrimidin-3-yl]indolin-2-one |
| 196 | 5-[2-Cyclopentyl-7-(3-fluoroazetidin-1-yl)pyrazolo[1,5-c]pyrimidin-3-yl]indolin-2-one; |
| 197 | 5-[7-[(3S)-3-Methoxypyrrolidin-1-yl]-2-phenyl-pyrazolo[1,5-c]pyrimidin-3-yl]indolin-2-one; |
| 198 | 5-(5-Methyl-7-morpholino-2-phenyl-pyrazolo[1,5-c]pyrimidin-3-yl)indolin-2-one; |
| 199 | 5-[2-tert-Butyl-7-(6-oxa-2-azaspiro[3;3]heptan-2-yl)pyrazolo[1,5-c]pyrimidin-3-yl]indolin-2-one; |
| 200 | 5-[7-(3-Fluoroazetidin-1-yl)-2-phenyl-pyrazolo[1,5-c]pyrimidin-3-yl]indolin-2-one; |
| 201 | 5-(7-Morpholino-2-phenyl-pyrazolo[1,5-c]pyrimidin-3-yl)indolin-2-one; |
| 202 | 5-[7-[(3R)-3-Methoxypyrrolidin-1-yl]-2-phenyl-pyrazolo[1,5-c]pyrimidin-3-yl]indolin-2-one; |
| 203 | 5-(2-Cyclopentyl-7-morpholino-pyrazolo[1,5-c]pyrimidin-3-yl)indolin-2-one; |
| 204 | (cis)-5-[7-(3-Fluoro-4-hydroxy-1-piperidyl)-2-phenyl-pyrazolo[1,5-c]pyrimidin-3-yl]indolin-2-one |

-continued

| Example # | Compound Name |
|---|---|
| 205 | 5-[2-Cyclopentyl-7-(3-hydroxyazetidin-1-yl)pyrazolo[1,5-c]pyrimidin-3-yl]indolin-2-one; |
| 206 | 5-(7-Methoxy-2-phenyl-pyrazolo[1,5-c]pyrimidin-3-yl)indolin-2-one; |
| 207 | 5-(4-Bromo-7-morpholino-2-phenyl-pyrazolo[1,5-c]pyrimidin-3-yl)indolin-2-one; |
| 208 | 5-(4-Methyl-7-morpholino-2-phenyl-pyrazolo[1,5-c]pyrimidin-3-yl)indolin-2-one; |
| 209 | 4-[3-(1H-Indazol-5-yl)-8-(3-oxopiperazin-1-yl)imidazo[1,2-a]pyrazin-2-yl]benzonitrile; |
| 210 | 4-[3-(2-Oxoindolin-5-yl)-8-(3-oxopiperazin-1-yl)imidazo[1,2-a]pyrazin-2-yl]benzonitrile; |
| 211 | 4-[3-(2-Oxo-1,3-dihydrobenzimidazol-5-yl)-8-(3-oxopiperazin-1-yl)imidazo[1,2-a]pyrazin-2-yl]benzonitrile; |
| 212 | 4-[3-(1H-Indazol-5-yl)-4-methyl-2-phenyl-pyrazolo[1,5-c]pyrimidin-7-yl]morpholine; |
| 213 | 6-[7-(4-Methoxy-1-piperidyl)-2-phenyl-pyrazolo[1,5-c]pyrimidin-3-yl]-3H-1,3-benzothiazol-2-one; |
| 214 | N-Cyclohexyl-8-morpholino-3-(2-oxo-1,3-dihydrobenzimidazol-5-yl)imidazo[1,2-a]pyrazine-2-carboxamide; |
| 215 | 5-[8-(4-Hydroxy-1-piperidyl)-2-(4-pyridyl)imidazo[1,2-a]pyrazin-3-yl]indolin-2-one; |
| 216 | 6-[2-Cyclopropyl-6-(trifluoromethyl)imidazo[1,2-a]pyrazin-3-yl]-3H-1,3-benzothiazol-2-one; |
| 217 | 5-[2-Benzoyl-8-(methylamino)imidazo[1,2-a]pyrazin-3-yl]indolin-2-one; |
| 218 | 5-[2-Phenyl-6-(trifluoromethyl)imidazo[1,2-a]pyrazin-3-yl]indolin-2-one; |
| 219 | 5-[2-Cyclopropyl-6-(trifluoromethyl)imidazo[1,2-a]pyrazin-3-yl]indolin-2-one; |
| 220 | 5-[2-tert-Butyl-8-(4-oxo-1-piperidyl)imidazo[1,2-a]pyrazin-3-yl]indolin-2-one; |
| 221 | 8-Morpholino-3-(2-oxo-1,3-dihydrobenzimidazol-5-yl)-N-(2-pyridyl)imidazo[1,2-a]pyrazine-2-carboxamide; |
| 222 | 5-[2-Phenyl-5-(trifluoromethyl)pyrazolo[1,5-c]pyrimidin-3-yl]indolin-2-one; |
| 223 | 6-[2-Phenyl-5-(trifluoromethyl)pyrazolo[1,5-c]pyrimidin-3-yl]-3H-1,3-benzoxazol-2-one; |
| 224 | 6-[2-phenyl-5-(trifluoromethyl)pyrazolo[1,5-c]pyrimidin-3-yl]-3H-1,3-benzothiazol-2-one; |
| 225 | 5-[2-tert-Butyl-5-(trifluoromethyl)pyrazolo[1,5-c]pyrimidin-3-yl]indolin-2-one; |
| 226 | 5-[2-Cyclobutyl-5-(trifluoromethyl)pyrazolo[1,5-c]pyrimidin-3-yl]indolin-2-one; |
| 227 | 5-[2-Isopropyl-5-(trifluoromethyl)pyrazolo[1,5-c]pyrimidin-3-yl]indolin-2-one; |
| 228 | 5-[2-Cyclopropyl-5-(trifluoromethyl)pyrazolo[1,5-c]pyrimidin-3-yl]indolin-2-one; |
| 229 | 6-[2-Cyclobutyl-5-(trifluoromethyl)pyrazolo[1,5-c]pyrimidin-3-yl]-3H-1,3-benzothiazol-2-one; |
| 230 | 6-[2-Cyclopropyl-5-(trifluoromethyl)pyrazolo[1,5-c]pyrimidin-3-yl]-3H-1,3-benzothiazol-2-one; |
| 231 | 6-[2-Isopropyl-5-(trifluoromethyl)pyrazolo[1,5-c]pyrimidin-3-yl]-3H-1,3-benzothiazol-2-one; |
| 232 | 6-[2-tert-Butyl-5-(trifluoromethyl)pyrazolo[1,5-c]pyrimidin-3-yl]-3H-1,3-benzothiazol-2-one; |
| 233 | 4-[3-(1H-Indazol-5-yl)-2-phenyl-pyrazolo[1,5-c]pyrimidin-7-yl]morpholine; |
| 234 | 3-(1H-Indazol-5-yl)-7-(4-methoxy-1-piperidyl)-2-phenyl-pyrazolo[1,5-c]pyrimidine; |
| 235 | 5-(4-Fluoro-2-isopropyl-7-morpholino-pyrazolo[1,5-c]pyrimidin-3-yl)indolin-2-one; |
| 236 | 4-[4-Fluoro-3-(1H-indazol-5-yl)-2-isopropyl-pyrazolo[1,5-c]pyrimidin-7-yl]morpholine; |
| 237 | 3-(1H-indazol-5-yl)-2-isopropyl-7-(4-methoxy-1-piperidyl)pyrazolo[1,5-c]pyrimidine; |
| 238 | 4-[3-(1H-Indazol-5-yl)-2-isopropyl-pyrazolo[1,5-c]pyrimidin-7-yl]morpholine; |
| 239 | 4-[3-(1H-Indazol-5-yl)-2-isopropyl-4-methyl-pyrazolo[1,5-c]pyrimidin-7-yl]morpholine; |
| 240 | 6-(2-Isopropyl-7-morpholino-pyrazolo[1,5-c]pyrimidin-3-yl)-3H-1,3-benzothiazol-2-one; |
| 241 | 6-[2-Isopropyl-7-(4-methoxy-1-piperidyl)pyrazolo[1,5-c]pyrimidin-3-yl]-3H-1,3-benzothiazol-2-one; |
| 242 | 6-(7-Morpholino-2-phenyl-pyrazolo[1,5-c]pyrimidin-3-yl)-3H-1,3-benzothiazol-2-one; |
| 243 | 6-(2-Isopropyl-4-methyl-7-morpholino-pyrazolo[1,5-c]pyrimidin-3-yl)-3H-1,3-benzothiazol-2-one; |
| 244 | 5-(2-Isopropyl-4-methyl-7-morpholino-pyrazolo[1,5-c]pyrimidin-3-yl)indolin-2-one; |

| Example # | Compound Name |
|---|---|
| 245 | 6-[2-Phenyl-6-(trifluoromethyl)imidazo[1,2-a]pyrazin-3-yl]-3H-1,3-benzothiazol-2-one; |
| 246 | 5-[2-Benzoyl-8-(3-oxopiperazin-1-yl)imidazo[1,2-a]pyrazin-3-yl]indolin-2-one; |
| 247 | 5-[2-(4-Fluorophenyl)-8-methoxy-imidazo[1,2-a]pyrazin-3-yl]indolin-2-one; |
| 248 | 5-[8-Amino-2-(4-fluorophenyl)imidazo[1,2-a]pyrazin-3-yl]indolin-2-one; |
| 249 | 5-[2-(4-fluorophenyl)-8-hydroxy-imidazo[1,2-a]pyrazin-3-yl]-1,3-dihydrobenzimidazol-2-one; and |
| 250 | N-[(3R)-1-[2-(4-fluorophenyl)-3-(2-oxoindolin-5-yl)imidazo[1,2-a]pyrazin-8-yl]pyrrolidin-3-yl]acetamide; | and pharmaceutically acceptable salts, N-oxides, or solvates thereof.

An additional embodiment of the invention is a pharmaceutical composition comprising:

(A) an effective amount of at least one compound of Formula (I):

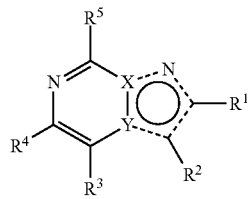

wherein

X is C or N;

Y is C or N; provided that X and Y cannot both be C, and X and Y cannot both be N;

the dotted line (-----) indicates that the referenced bond is a single bond or a double bond;

$R^1$ is selected from the group consisting of: $C_{1-5}$alkyl; $C_{3-7}$cycloalkyl; phenyl optionally substituted with one, two or three members independently selected from halo and —CN; $CH_2$-phenyl optionally substituted with halo; C(=O)-phenyl, wherein said phenyl is optionally substituted with halo; C(=O)N($CH_3$)-phenyl; C(=O)NH-phenyl; C(=O)NH—$CH_2$-phenyl; C(=O)NH-pyridinyl; C(=O)NH—$C_{3-7}$cycloalkyl; C(=O)NH—$C_{1-5}$alkyl; and pyridinyl;

$R^2$ is:

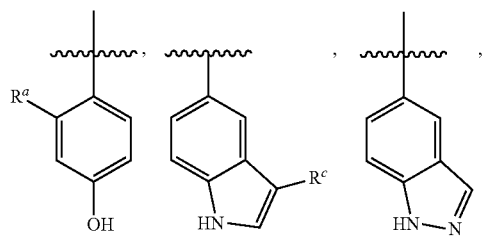

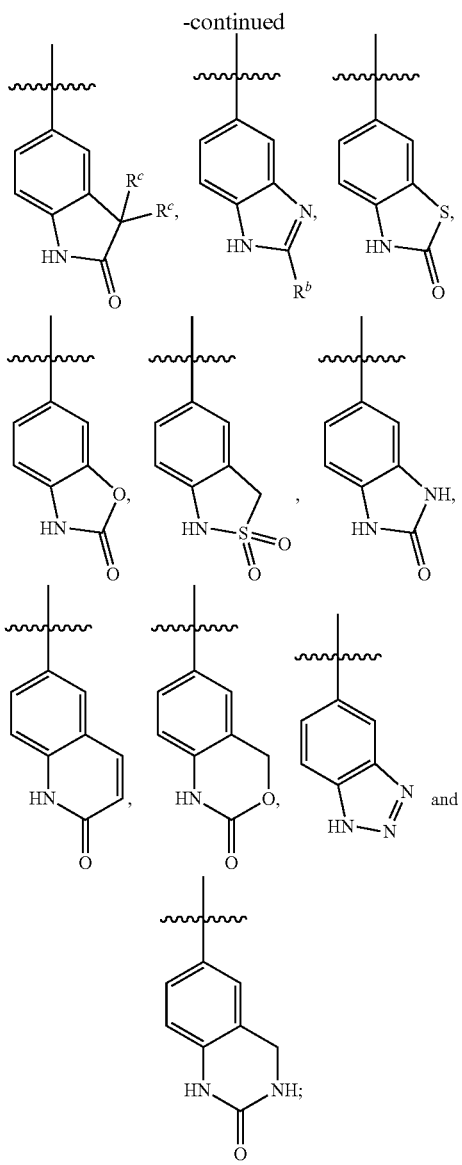

$R^a$ is H or —$CH_3$;
$R^b$ is H or —$NH_2$;
$R^c$ is independently selected from: H and —F;
$R^3$ is selected from the group consisting of: H, $^3$H, —$CH_3$ and halo;
$R^4$ is H, —$CH_3$, or $CF_3$; and $R^5$ is selected from the group consisting of:
H; halo; —$C_{1-5}$alkyl; —$C_{1-5}$alkoxy; —$NH_2$; —NH($C_{1-5}$alkyl); —N($C_{1-5}$alkyl)$_2$; —NH—2-oxopyrrolidin-3-yl; —N(CH$_3$)cyclopropyl; —N($C_{1-5}$alkyl)$_2$; —SO$_2$CH$_3$; —(S═O)CH$_3$; —OH; —O-cyclopentyl; azetidinyl optionally independently substituted with one or two halo, —CH$_3$, —CF$_3$, —OCH$_3$, —SO$_2$CH$_3$, —CH$_2$OH, —OH, and —CN; pyrrolidinyl optionally substituted with —OH, —OCH$_3$ or —NH—(C═O)CH$_3$; piperidine optionally independently substituted with one, two, or three halo, —OH, —CH$_3$, —OCH$_3$, —CH$_2$F, —CH$_2$CH$_2$F, and —NH—(C═O)CH$_3$; piperazine optionally substituted with —CH$_3$, —(C═O)CH$_3$, or —CO$_2$tBu; morpholine optionally independently substituted with one or two —CH$_3$, or —CF$_3$; octadeuteriomorpholin-4-yl; 6-oxa-2-azaspiro[3.3]heptan-2-yl; 3-oxopiperazin-1-yl optionally substituted with one or two —CH$_3$; 1,1-dioxo-1,4-thiazinan-4-yl; 1,4-dioxa-8-azaspiro[4.5]decan-8-yl; 6-oxa-3-azabicyclo[3.1.1]heptan-3-yl; 5-azaspiro[2.3]hexan-5-yl; diazapanyl optionally substituted with —(C═O)CH$_3$, 4-oxopiperidin-1-yl; dihydro-2H-pyridinyl optionally substituted with —(C═O)CH$_3$; dihydro-2H-pyranyl; 4-hydroxyimino-1-piperidyl; and 1,2,6-triazaspiro[2.5]oct-1-en-6-yl;

and pharmaceutically acceptable salts, N-oxides or solvates of compounds of Formula (I);

and (B) at least one pharmaceutically acceptable excipient.

An additional embodiment of the invention is a pharmaceutical composition comprising and effective amount of at least one compound of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA); and at least one pharmaceutically acceptable excipient.

An additional embodiment of the invention is a pharmaceutical composition comprising and effective amount of at least one compound of Formula (IIA), as well as pharmaceutically acceptable salts, N-oxides or solvates of compounds of Formula (IIA), pharmaceutically acceptable prodrugs of compounds of Formula (IIA), and pharmaceutically active metabolites of Formula (IIA); and at least one pharmaceutically acceptable excipient.

An additional embodiment of the invention is a pharmaceutical composition comprising and effective amount of at least one compound of Formula (IIIA), as well as pharmaceutically acceptable salts, N-oxides or solvates of compounds of Formula (IIIA), pharmaceutically acceptable prodrugs of compounds of Formula (IIIA), and pharmaceutically active metabolites of Formula (IIIA); and at least one pharmaceutically acceptable excipient.

An additional embodiment of the invention is a pharmaceutical composition comprising and effective amount of at least one compound in Table 1, as well as pharmaceutically acceptable salts, N-oxides or solvates of compounds of Table 1, pharmaceutically acceptable prodrugs of compounds of Table 1, and pharmaceutically active metabolites of Table 1; and at least one pharmaceutically acceptable excipient.

An additional embodiment of the invention is a pharmaceutical composition comprising and effective amount of at least one compound in Table 2, as well as pharmaceutically acceptable salts, N-oxides or solvates of compounds of Table 2, pharmaceutically acceptable prodrugs of compounds of Table 2, and pharmaceutically active metabolites of Table 2; and at least one pharmaceutically acceptable excipient.

Also within the scope of the invention are enantiomers and diastereomers of the compounds of Formula (I) (as well as Formula (II), Formula (III), Formula (IV), Formula (IA), Formula (IIA) and Formula (IIIA)). Also within the scope of the invention are the pharmaceutically acceptable salts, N-oxides or solvates of the compounds of Formula (I) (as well as Formula (II), Formula (III), Formula (IV), Formula (IA), Formula (IIA) and Formula (IIIA)). Also within the scope of the invention are the pharmaceutically acceptable prodrugs of compounds of Formula (I) (as well as Formula (II), Formula (III), Formula (IV), Formula (IA), Formula (IIA) and Formula (IIIA)), and pharmaceutically active metabolites of the compounds of Formula (I) (as well as Formula (II), Formula (III), Formula (IV), Formula (IA), Formula (IIA) and Formula (IIIA)).

Also within the scope of the invention are isotopic variations of compounds of Formula (I) (as well as Formula (II), Formula (III), Formula (IV), Formula (IA), Formula (IIA) and Formula (IIIA)), such as, e.g., deuterated compounds of Formula (I). Also within the scope of the invention are the pharmaceutically acceptable salts, N-oxides or solvates of the isotopic variations of the compounds of Formula (I) (as well as Formula (II), Formula (III), Formula (IV), Formula (IA), Formula (IIA) and Formula (IIIA)). Also within the scope of the invention are the pharmaceutically acceptable prodrugs of the isotopic variations of the compounds of Formula (I) (as well as Formula (II), Formula (III), Formula (IV), Formula (IA), Formula (IIA) and Formula (IIIA)), and pharmaceutically active metabolites of the isotopic variations of the compounds of Formula (I) (as well as Formula (II), Formula (III), Formula (IV), Formula (IA), Formula (IIA) and Formula (IIIA)).

An additional embodiment of the invention is a method of treating a subject suffering from or diagnosed with a disease, disorder, or medical condition mediated by AMPA receptor activity, comprising administering to a subject in need of such treatment an effective amount of at least one compound selected from compounds of Formula (I):

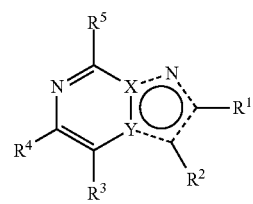

(I)

wherein
X is C or N;
Y is C or N; provided that X and Y cannot both be C, and X and Y cannot both be N;
the dotted line (-----) indicates that the referenced bond is a single bond or a double bond;
$R^1$ is selected from the group consisting of: $C_{1-5}$alkyl; $C_{3-7}$cycloalkyl; phenyl optionally substituted with one, two or three members independently selected from halo and —CN; CH$_2$-phenyl optionally substituted with halo; C(═O)-phenyl, wherein said phenyl is optionally substituted with halo; C(═O)N(CH$_3$)-phenyl; C(═O)

NH-phenyl; C(=O)NH—CH₂-phenyl; C(=O)NH-pyridinyl; C(=O)NH—C₃₋₇cycloalkyl; C(=O)NH—C₁₋₅alkyl; and pyridinyl;

R² is:

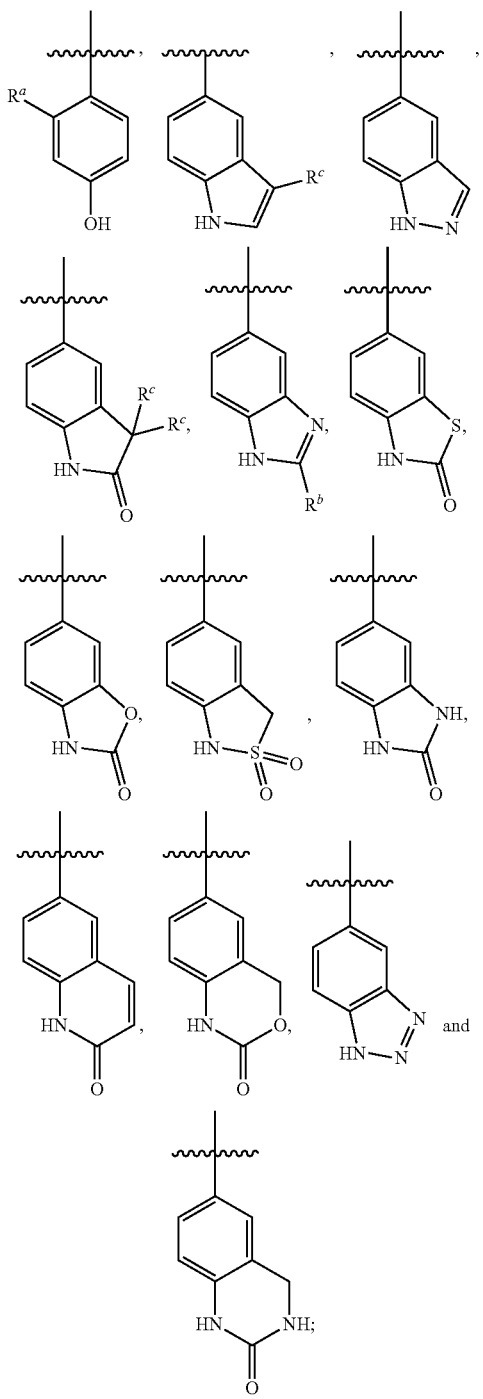

Rᵃ is H or —CH₃;
Rᵇ is H or —NH₂;
Rᶜ is independently selected from: H and —F;
R³ is selected from the group consisting of: H, ³H, —CH₃ and halo;

R⁴ is H, —CH₃, or CF₃; and
R⁵ is selected from the group consisting of:
H; halo; —C₁₋₅alkyl; —C₁₋₅alkoxy; —NH₂; —NH(C₁₋₅alkyl); —N(C₁₋₅alkyl)₂; —NH—2-oxopyrrolidin-3-yl; —N(CH₃)cyclopropyl; —N(C₁₋₅alkyl)₂; —SO₂CH₃; —(S=O)CH₃; —OH; —O-cyclopentyl; azetidinyl optionally independently substituted with one or two halo, —CH₃, —CF₃, —OCH₃, —SO₂CH₃, —CH₂OH, —OH, and —CN; pyrrolidinyl optionally substituted with —OH, —OCH₃ or —NH—(C=O)CH₃; piperidine optionally independently substituted with one, two, or three halo, —OH, —CH₃, —OCH₃, —CH₂F, —CH₂CH₂F, and —NH—(C=O)CH₃; piperazine optionally substituted with —CH₃, —(C=O)CH₃, or —CO₂tBu; morpholine optionally independently substituted with one or two —CH₃, or —CF₃; octadeuteriomorpholin-4-yl; 6-oxa-2-azaspiro[3.3]heptan-2-yl; 3-oxopiperazin-1-yl optionally substituted with one or two —CH₃; 1,1-dioxo-1,4-thiazinan-4-yl; 1,4-dioxa-8-azaspiro[4.5]decan-8-yl; 6-oxa-3-azabicyclo[3.1.1]heptan-3-yl; 5-azaspiro[2.3]hexan-5-yl; diazapanyl optionally substituted with —(C=O)CH₃, 4-oxopiperidin-1-yl; dihydro-2H-pyridinyl optionally substituted with —(C=O)CH₃; dihydro-2H-pyranyl; 4-hydroxyimino-1-piperidyl; and 1,2,6-triazaspiro[2.5]oct-1-en-6-yl;

and pharmaceutically acceptable salts, N-oxides, or solvates thereof, to a subject in need thereof.

The AMPA subtype of glutamate receptors are glutamate-gated ion channels expressed primarily on postsynaptic membranes of excitatory synapses in the central nervous system. AMPA receptors assemble as tetramers of subunits. Mammals express four AMPA-receptor subunits, called GluA1-GluA4. In their native environment, the pore-forming GluA tetramers directly or indirectly associate with numerous auxiliary proteins. The wide variety of proteins which can participate in AMPA receptor complexes vastly increases the ability of a neuron to tune the response characteristics of its synapses.

AMPA receptors mediate the majority of fast neurotransmission across synaptic gaps. However, since AMPA receptor activity is so ubiquitous within CNS, general antagonism affects most areas of the CNS resulting in undesired effects, such as ataxia, sedation, and/or dizziness, which are shared by all known general AMPA receptor antagonists.

In order to circumvent the problems with side-effects noted above, it is hereby proposed that selective modulation of TARP γ8-associated AMPA receptor complexes provides effective therapeutic agents which also avoid or reduce the side-effects associated with the administration of non-selective AMPA receptor modulators. TARP γ8 is primarily expressed in the hippocampus and the cortex, while TARP γ2 is primarily expressed in the cerebellum. In one aspect, selective modulation of TARP γ8 potentially avoids modulation of TARP γ2-associated AMPA receptor complexes, which are more prevalent in the cerebellum, thereby reducing side effects associated with general (non-TARP dependent/non-selective) AMPA antagonism.

For instance, selective modulation of TARP γ8-associated AMPA receptor complexes is contemplated as an effective anti-seizure/anti-epileptic therapeutic with reduced the side effects (e.g. sedation, ataxis, and/or dizziness) associated with general (non-TARP dependent/non-selective) AMPA antagonists. Similarly, reduction of hippocampal over-excitability, using selective modulation of TARP γ8-associated AMPA receptor complexes may lead to normalization of the symptoms of schizophrenia, and it may protect against the subsequent decline in hippocampal volume. In a further instance, selectively attenuating hippocampal excitability, via selective modulation of TARP γ8-associated AMPA receptor complexes, could provide therapeutic benefit to patients with bipolar disorder. Likewise, selective modulation of TARP γ8-associated AMPA receptor complexes within the hippocampus may provide an effective anxiolytic.

Accordingly, provided herein are compounds which are selective modulators of TARP γ8-associated AMPA receptor complexes. Compounds which are selective modulators of TARP γ8-associated AMPA receptor complexes ameliorate and/or eliminate the side effects (e.g. sedation, ataxis, and/or dizziness) of general (non-TARP dependent/non-selective) AMPA receptor modulators.

In some embodiments, provided herein are compounds which selectively modulate the activity of complexes comprising GluA1 receptors associated with the protein TARP γ8.

In one embodiment, selective modulation of TARP γ8-associated AMPA receptor complexes refers to selective antagonism of TARP γ8-associated AMPA receptor complexes. In another embodiment, selective modulation of TARP γ8-associated AMPA receptor complexes refers to selective partial inhibition of TARP γ8-associated AMPA receptor complexes. In a further embodiment, selective antagonism of TARP γ8-associated AMPA receptor complexes refers to negative allosteric modulation of TARP γ8-associated AMPA receptor complexes.

The invention relates to methods of using the compounds described herein to treat subjects diagnosed with or suffering from a disease, disorder, or condition mediated by AMPA receptor activity. These methods are accomplished by administering to the subject a compound of the invention. In some embodiments, the compounds described herein are selective for modulation of TARP γ8 associated AMPA receptor complexes.

An AMPA receptor mediated disease, disorder or condition includes and is not limited to cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain, diabetic neuropathy, encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder (for example, CNS lupus erythematodes, polyarteritis nodosa, Sjogren syndrome, sarcoidosis, isolated cerebral vasculitis, etc.), schizophrenia, depression, and bipolar disorder. In some embodiments, the AMPA mediated disease, disorder or condition is depression, anxiety disorders, anxious depression, post traumatic stress disorder, epilepsy, schizophrenia, prodromal schizophrenia, or a cognitive disorder.

In one group of embodiments, an AMPA receptor mediated disease, disorder or condition is a condition related to hippocampal hyperexcitability. In one embodiment, provided herein are methods to selectively dampen hippocampal activity in the brain comprising administration of compounds described herein to a subject in need thereof. In one embodiment, provided herein are methods for the treatment of an AMPA receptor mediated disease, disorder or condition which is depression comprising administration of compounds described herein to a subject in need thereof. As used herein, depression includes and is not limited to major depression, psychotic depression, persistent depressive disorder, post-partum depression, seasonal affective disorder, depression which is resistant to other anti-depressants, manic-depression associated with bipolar disorder, post traumatic stress disorder, and the like. In another embodiment, provided herein are methods for the treatment of an AMPA receptor mediated disease, disorder or condition which is post traumatic stress disorder (PTSD) comprising administration of compounds described herein to a subject in need thereof. In another embodiment, provided herein are methods for the treatment of an AMPA receptor mediated disease, disorder or condition which is epilepsy, schizophrenia, or prodromal schizophrenia comprising administration of compounds described herein to a subject in need thereof. In yet another embodiment, provided herein are methods for the treatment of an AMPA receptor mediated disease, disorder or condition which is a cognitive disorder comprising administration of compounds described herein to a subject in need thereof. As used herein, cognitive disorder includes and is not limited to mild cognitive impairment, amnesia, dementia, delirium, cognitive impairment associated with anxiety disorders, mood disorders, psychotic disorders and the like.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

Certain Definitions

As used herein, the terms "including", "containing" and "comprising" are used herein in their open, non-limiting sense.

The term "alkyl" refers to a straight- or branched-chain alkyl group having from 1 to 12 carbon atoms in the chain. In some embodiments, an alkyl group is a $C_{1-6}$alkyl group. In some embodiments, an alkyl group is a $C_{1-5}$alkyl group. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "haloalkyl" refers to a straight- or branched-chain alkyl group having from 1 to 12 carbon atoms in the chain and having at least one of the hydrogens replaced with a halogen. In some embodiments, a haloalkyl group is a $C_{1-6}$haloalkyl group. In some embodiments, a haloalkyl group is a $C_{1-5}$haloalkyl group. One exemplary substitutent is fluoro. Preferred substituted alkyl groups of the invention include trihalogenated alkyl groups such as trifluoromethyl groups. Haloalkyl includes and is not limited to —$CF_3$, —$CH_2F$, —$CHF_2$, —$CH_2Cl$, —$CH_2$—$CF_3$, and the like.

The term "cycloalkyl" refers to monocyclic, non-aromatic hydrocarbon groups having from 3 to 8 carbon atoms. Examples of cycloalkyl groups include, for example, cyclopropyl, cyclobutyl, cyclopentyl, cyclohexyl, and the like.

The term "heterocycloalkyl" refers to a monocyclic, fused, or spiro polycyclic ring structure that is saturated or partially saturated and has from 4 to 7 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

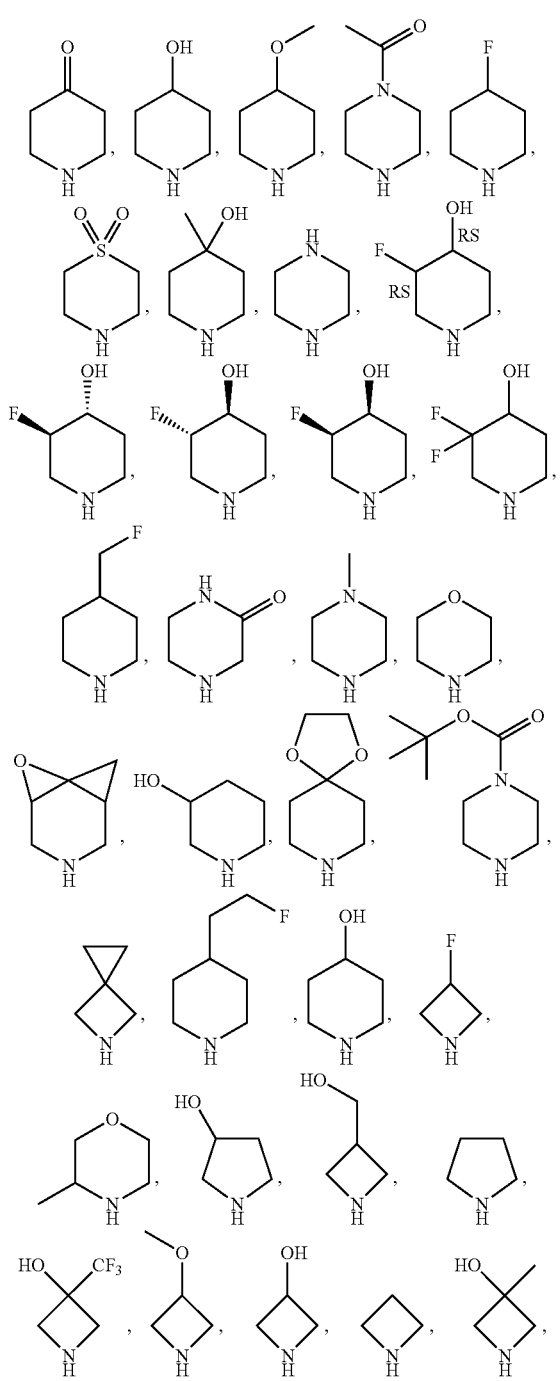
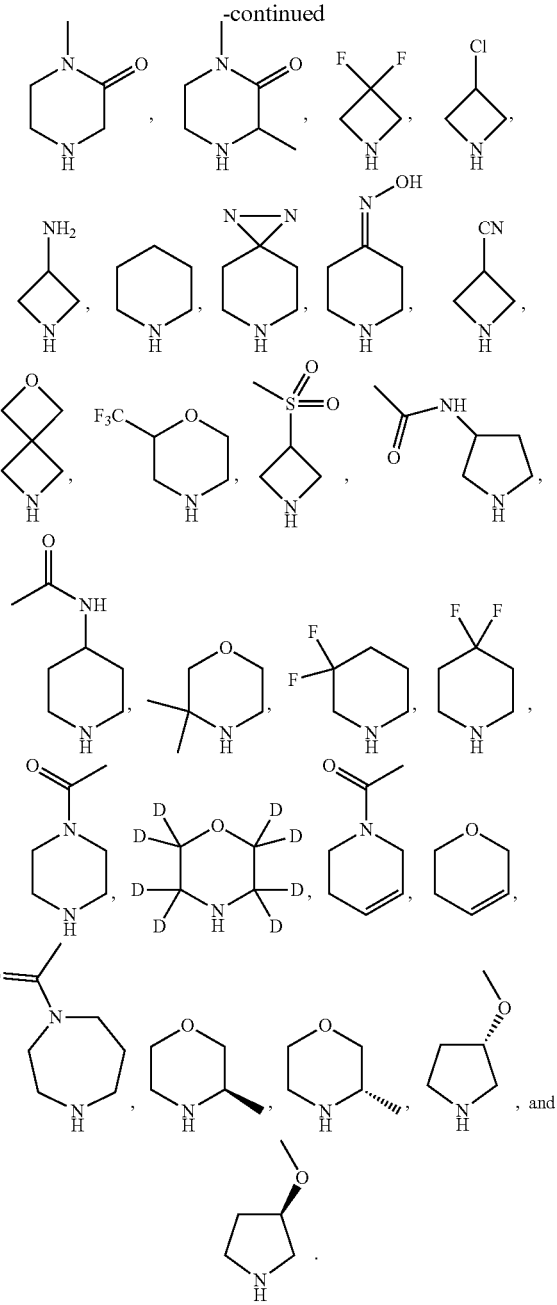

The term "alkoxy" includes a straight chain or branched alkyl group with a terminal oxygen linking the alkyl group to the rest of the molecule. In some embodiments, an alkoxy group is a $C_{1-6}$alkoxy group. In some embodiments, an alkoxy group is a $C_{1-5}$alkoxy group. Alkoxy includes methoxy, ethoxy, propoxy, isopropoxy, butoxy, t-butoxy, pentoxy and so on.

The term "haloalkoxy" includes a straight chain or branched alkyl group with a terminal oxygen linking the alkyl group to the rest of the molecule and having at least one of the hydrogens replaced with a halogen. In some embodiments, a haloalkoxy group is a $C_{1-6}$haloalkoxy group. In some embodiments, a haloalkoxy group is a $C_{1-5}$haloalkoxy group. Haloalkoxy includes and is not limited to —$OCF_3$, —$OCH_2F$, —$OCHF_2$, —$OCH_2Cl$, —O—$CH_2$—$CF_3$, and the like.

The term "thiophenyl" and "thienyl" are used interchangeably.

The term "halogen" represents chlorine, fluorine, bromine, or iodine. The term "halo" represents chloro, fluoro, bromo, or iodo.

The term "benzyl" and —CH$_2$-phenyl are used interchangeably

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

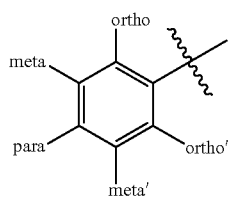

When referring to substituents on a pyridyl group, the terms "para", "meta", and "ortho" refer to the placement of a substituent relative to the point of attachment of the pyridyl ring. For example the structure below is described as 3-pyridyl with the X$^1$ substituent in the ortho position, the X$^2$ substituent in the meta position, and X$^3$ substituent in the para position:

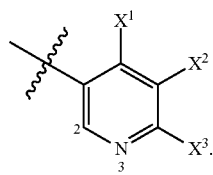

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, 5th ed. (2005), describing, inter alia, buffer solutions and how the concentrations of the buffer constituents relate to the pH of the buffer. For example, a buffered solution is obtained by adding MgSO$_4$ and NaHCO$_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers." Isomers that differ in the arrangement of their atoms in space are termed "."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the acid- and nitro-forms of phenyl nitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enatiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

Compounds of the invention may also exist as "rotamers," that is, conformational isomers that occur when the rotation leading to different conformations is hindered, resulting a rotational energy barrier to be overcome to convert from one conformational isomer to another.

The symbols ━ and ▬ are used as meaning the same spatial arrangement in chemical structures shown herein. Analogously, the symbols ⁞⁞⁞⁞ and ┈┈ are used as meaning the same spatial arrangement in chemical structures shown herein.

A wavy line "∿" indicates the point of attachment to the rest of the molecule.

Additionally, any formula given herein is intended to refer also to hydrates, solvates, and polymorphs of such compounds, and mixtures thereof, even if such forms are not listed explicitly. Certain compounds of Formula (I) (as well as Formula (II), Formula (III), Formula (IV), Formula (IA), Formula (IIA) and Formula (IIIA)), or pharmaceutically acceptable salts of Formula (I) (as well as Formula (II), Formula (III), Formula (IV), Formula (IA), Formula (IIA) and Formula (IIIA)) may be obtained as solvates. Solvates include those formed from the interaction or complexation of compounds of the invention with one or more solvents, either in solution or as a solid or crystalline form. In some embodiments, the solvent is water and the solvates are hydrates. In addition, certain crystalline forms of compounds of Formula (I) (as well as Formula (II), Formula (III), Formula (IV), Formula (IA), Formula (IIA) and Formula (IIIA)) or pharmaceutically acceptable salts of compounds of Formula (I) (as well as Formula (II), Formula (III), Formula (IV), Formula (IA), Formula (IIA) and Formula (IIIA)) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH(s), R—COOH$_{(sol)}$, and R—COO$^-_{(sol)}$. In this example, R—COOH(s) refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium or tritium (i.e., $^{2}H$, $^{3}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^3$, $R^4$, $R^5$, $R^{5a}$, X, Y, PG, and $Hal^1$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^3$, $R^4$, $R^5$, $R^{5a}$, X, Y, PG, and $Hal^1$, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The invention includes also pharmaceutically acceptable salts of the compounds of Formula (I) (as well as Formula (II), Formula (III), Formula (IV), Formula (IA), Formula (IIA) and Formula (IIIA)), preferably of those described above and of the specific compounds exemplified herein, and methods of treatment using such salts.

The term "pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

A "pharmaceutically acceptable salt" is intended to mean a salt of a free acid or base of compounds represented by Formula (I) (as well as Formula (II), Formula (III), Formula (IV), Formula (IA), Formula (IIA) and Formula (IIIA)) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of*

*Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) (as well as Formula (II), Formula (III), Formula (IV), Formula (IA), Formula (IIA) and Formula (IIIA)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I) (as well as Formula (II), Formula (III), Formula (IV), Formula (IA), Formula (IIA) and Formula (IIIA)) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) (as well as Formula (II), Formula (III), Formula (IV), Formula (IA), Formula (IIA) and Formula (IIIA)) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of Formula (I) (as well as Formula (II), Formula (III), Formula (IV), Formula (IA), Formula (IIA) and Formula (IIIA)), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I) (as well as Formula (II), Formula (III), Formula (IV), Formula (IA), Formula (IIA) and Formula (IIIA)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I) (as well as Formula (II), Formula (III), Formula (IV), Formula (IA), Formula (IIA) and Formula (IIIA)). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) (as well as Formula (II), Formula (III), Formula (IV), Formula (IA), Formula (IIA) and Formula (IIIA)) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) (as well as Formula (II), Formula (III), Formula (IV), Formula (IA), Formula (IIA) and Formula (IIIA)), which may also be used in the methods of the invention. A "pharmaceutically active metabolite" means a pharmacologically active product of metabolism in the body of a compound of Formula (I) (as well as Formula (II), Formula (III), Formula (IV), Formula (IA), Formula (IIA) and Formula (IIIA)) (as applicable) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) (as well as Formula (II), Formula (III), Formula (IV), Formula (IA), Formula (IIA) and Formula (IIIA)) and their pharmaceutically acceptable salts, pharmaceutically acceptable prodrugs, and pharmaceutically active metabolites of the present invention are useful as modulators of the AMPA receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the AMPA receptor expression or activity, and "activators" are compounds that increase, activate, facilitate, sensitize, or up-regulate AMPA receptor expression or activity.

The term "pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

The term "subject" includes humans. The terms "human," "patient," and "subject" are used interchangeably herein.

The term "treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 10 mg to about 2.5 g/day.

"Compounds of the present invention," and equivalent expressions, are meant to embrace compounds of the Formula (I) as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. The additional active ingredients may be coadministered separately with a compound of the invention or included with such an agent in a pharmaceutical composition according to the invention. In an exemplary embodiment, additional active ingredients are those that are known or discovered to be effective in the treatment of conditions, disorders, or diseases mediated by orexin activity, such as another orexin modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The compounds of the invention are used, alone or in combination with one or more additional active ingredients, to formulate pharmaceutical compositions of the invention. A pharmaceutical composition of the invention comprises: (a) an effective amount of at least one compound in accordance with the invention; and (b) a pharmaceutically acceptable excipient.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 .mu.g/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I), as well as Formulas (IA)-(IB). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations

TABLE 2

Abbreviations and acronyms used herein include the following.

| Term | Acronym/Abbreviation |
|---|---|
| Acetic anhydride | $Ac_2O$ |
| Acetonitrile | ACN, MeCN |
| Acetic acid | AcOH |
| Azobisisobutyronitirile | AIBN |
| 1,1'-Azobis(cyclohexanecarbonitrile | ABCN |
| 2,2'-Bis(diphenylphosphino)-1,1'-binaphthyl | BINAP |
| tert-Butylcarbamoyl | BOC |

TABLE 2-continued

| Abbreviations and acronyms used herein include the following. | |
|---|---|
| Term | Acronym/Abbreviation |
| (Benzotriazol-1-yloxy)tris(dimethylamino)phosphonium hexafluorophosphate | BOP |
| 1,1'-Carbonyldiimidazole | CDI |
| Diatomaceous Earth | Celite 545, Celite ® |
| (Diethylamino)sulfur trifluoride | DAST |
| Dichlorethane | DCE |
| 1,8-Diazabicyclo[5.4.0]undec-7-ene | DBU |
| Methylene chloride, dichloromethane | DCM |
| Bis(2-methoxyethyl)aminosulfur trifluoride | Deoxo-Fluor ® |
| Diisopropyl azodicarboxylate | DIAD |
| N,N-Diisopropylethylamine | DIPEA, DIEA, Hunig's base |
| Dimethylacetamide | DMA |
| N,N-Dimethylformamide | DMF |
| Dimethyl sulfoxide | DMSO |
| Deutero-dimethyl sulfoxide | DMSO-$d_6$ |
| Diphenylphosphino ferrocene | dppf |
| Di-tert-butylphosphino ferrocene | dtbpf |
| Electrospray Ionisation | ESI |
| Ethyl Acetate | EtOAc, or EA, or AcOEt |
| Ethanol | EtOH |
| Flash Column Chromatography | FCC |
| 1-[Bis(dimethylamino)methylene]-1H-1,2,3-triazolo[4,5-b]pyridinium 3-oxid hexafluorophosphate | HATU |
| Acetic Acid | HOAc |
| 1-Hydroxy-benzotriazole | HOBt |
| High-pressure liquid chromatography | HPLC |
| Isopropyl Alcohol | IPA |
| Lithium hexamethyldisilylazide | LHMDS |
| meta-Chloroperoxybenzoic acid | mCPBA or MCPBA |
| Deteromethanol | MeOD-$d_4$ |
| Methanol | MeOH |
| Sodium tert-butoxide | NaOtBu |
| N-Bromosuccinimide | NBS |
| Tetrakis(triphenylphosphine)palladium(0) | Pd(PPh$_3$)$_4$ |
| Palladium(II) acetate | Pd(OAc)$_2$ |
| Tris(dibenzylideneacetone(dipalladium (0) | Pd$_2$(dba)$_3$ |
| [1,1'-Bis(diphenylphosphino)ferrocene]dichloropalladium(II), complex with dichloromethane | Pd(dppf)Cl$_2$•CH$_2$Cl$_2$ |
| [1,1'-Bis(di-tert-butylphosphino)ferrocene]dichloropalladium(II) | PdCl$_2$(dtbpf) |
| Palladium(II)bis(triphenylphosphine) dichloride, bis(triphenylphosphine)palladium(II) dichloride | PdCl$_2$(PPh$_3$)$_2$ |
| Phosphorous oxychloride | POCl$_3$ |
| Triphenylphosphine | PPh$_3$ |
| Precipitate | ppt |
| Pyridinium tribromide | Py$^+$Br$_3^-$ |
| Room temperature | rt |
| N-Chloromethyl-N-fluorotriethylenediammonium bis(tetrafluoroborate) | Selectfluor ® |
| 2-(TriMethsilyl)-ethoxyMethyl chloride | SEM-Cl |
| [2-(Trimethylsilyl)ethoxy]methyl acetal | SEM |
| Supercritical Fluid Chromatography | SFC |
| Thionyl chloride | SOCl$_2$ |
| Nucleophilic Aromatic Substitution | S$_N$Ar |
| Tetrabutylammonium fluoride | TBAF |
| Triethyl amine | TEA |
| Trifluoroacetic acid | TFA |
| Trifluoroacetic anhydride | TFAA |
| Tetrahydrofuran | THF |
| Tetrahydropyran | THP |

PREPARATIVE EXAMPLES

Exemplary compounds useful in methods of the invention will now be described by reference to the illustrative synthetic schemes for their general preparation below and the specific examples to follow.

SCHEME A

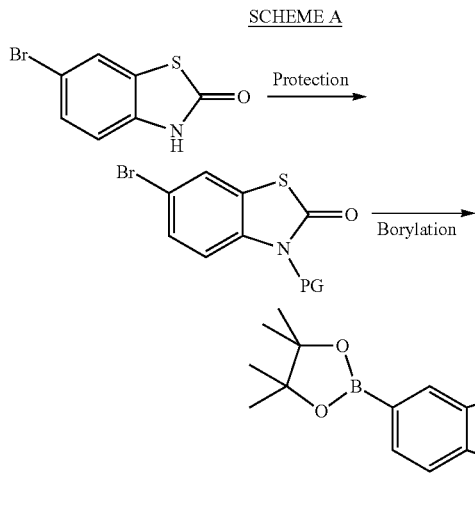

According to SCHEME A, a compound such as 5-bromo-1-(tetrahydro-2H-pyran-2-yl)-1)-1H-indazole, or 6-bromo-3-((2-(trimethylsilyl)ethoxy)methyl)benzo[d]thiazol-2(3H)-one, is reacted with bis-pinacol boronate, a base such as potassium acetate, a palladium catalyst such as Pd(dppf)Cl$_2$·CH$_2$Cl$_2$, Pd$_2$(dba)$_3$, and the like, 60-90° C., for a period of about 12-18 h, to provide a 4,4,5,5-tetramethyl-1,3,2-dioxaborolan-2-yl compound.

In a similar fashion, 5-bromo-1,3-dihydro-benzo[c]isothiazole 2,2-dioxide is borylated with bis(pinacolato)diborane, potassium acetate, a palladium catalyst such as PdCl$_2$(dt-bpf), in a solvent such as DMF, at a temperature of about 95° C., for a period of about 16 h, to provide 5-(4,4,5,5-tetramethyl-1,3,2-dioxaborolan-2-yl)-1,3-dihydrobenzo[c]isothiazole 2,2-dioxide.

SCHEME B

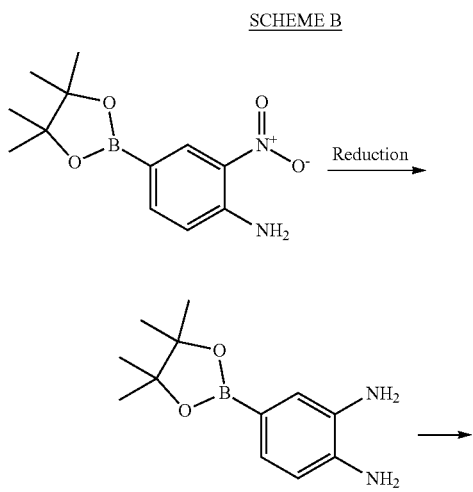

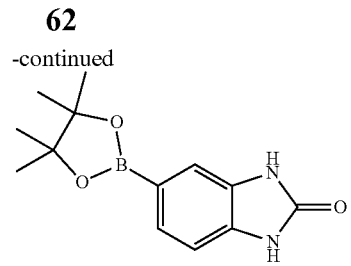

According to SCHEME B, 2-nitro-4-(4,4,5,5-tetramethyl-1,3,2-dioxaborolan-2-yl)aniline is reduced, under hydrogenation conditions, to provide 4-(4,4,5,5-tetramethyl-1,3,2-dioxaborolan-2-yl)benzene-1,2-diamine. 4-(4,4,4,5,5-Tetramethyl-1,3,2-dioxaborolan-2-yl)benzene-1,2-diamine is reacted with 1,1'-carbonyldiimidazole (CDI), in a solvent such as EtOAc, at a temperature of about 23° C., for a period of about 16 h, to provide 5-(4,4,5,5-tetramethyl-1,3,2-dioxaborolan-2-yl)-1,3-dihydro-2H-benzo[d]imidazol-2-one.

SCHEME C

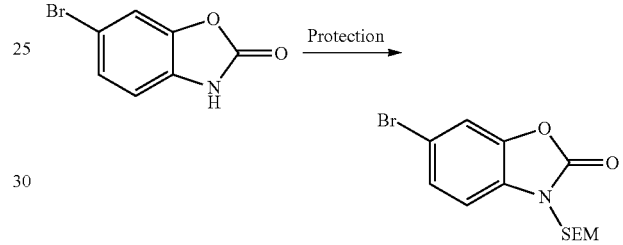

According to SCHEME C, 6-bromo-1,3-benzoxazol-2(3H)-one is protected with a suitable nitrogen protecting group such as SEM ((trimethylsilyl)ethoxy)methyl), under conditions known to one skilled in the art to provide 6-bromo-3-((2-(trimethylsilyl)ethoxy)methyl)benzo[d]oxazol-2(3H)-one.

SCHEME D

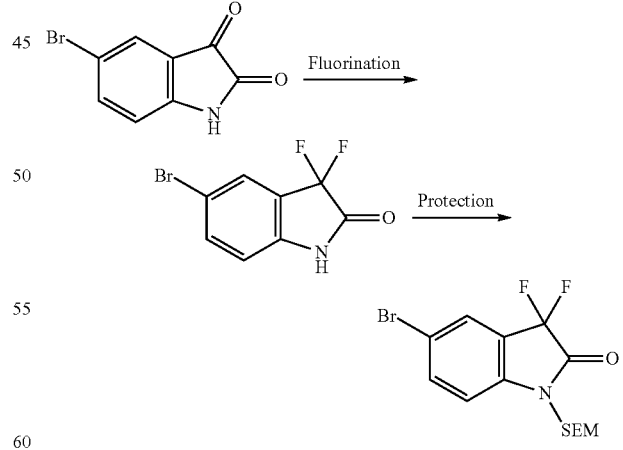

According to SCHEME D, 5-bromoindoline-2,3-dione is fluorinated with a fluorinating agent such as diethylaminosulfur trifluoride (DAST), and the like, in a solvent such as DCM, for a period of about 5 h, to provide 5-bromo-3,3-difluoroindolin-2-one. 5-Bromo-3,3-difluoroindolin-2-one is protected with a suitable nitrogen protecting group such as SEM, employing conditions previously described, to provide 5-bromo-3,3-difluoro-1-((2-(trimethylsilyl)ethoxy)methyl)indolin-2-one.

SCHEME E

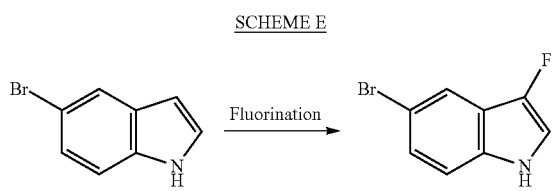 [SMILES: Brc1ccc2[nH]ccc2c1 ; Fc1c[nH]c2ccc(Br)cc12]

According to SCHEME E, 5-bromoindole is fluorinated with a fluorinating agent such as 1-chloromethyl-4-fluoro-1,4-diazoniabicyclo[2.2.2]octane bis(tetrafluoroborate) (Selectfluor®), in a solvent mixture such as ACN/pyridine, to provide 5-bromo-3-fluoro-1H-indole.

SCHEME F

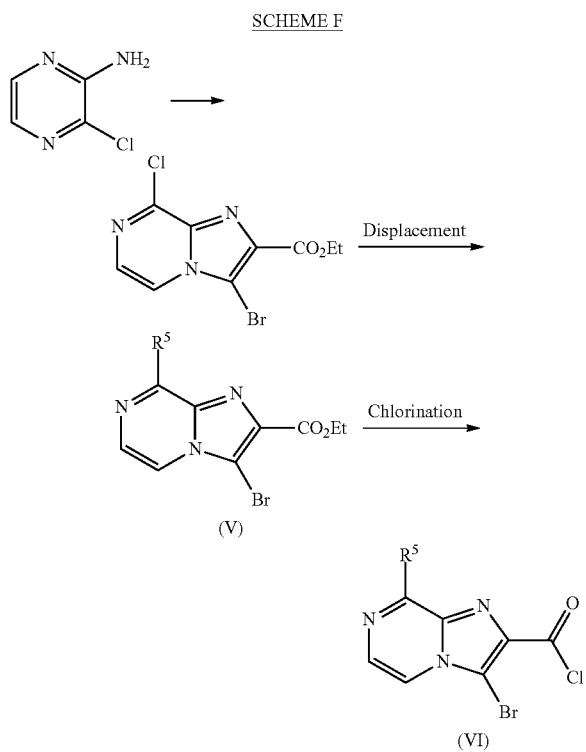

According to SCHEME F, 2-amino-3-chloropyrazine is reacted with ethyl 3-bromo-2-oxopropanoate in dimethoxyethane, at rt, for a period of about 16 h, to provide ethyl 8-chloroimidazo[1,2-a]pyrazine-2-carboxylate. Ethyl 8-chloroimidazo[1,2-a]pyrazine-2-carboxylate is brominated under conditions known to one skilled in the art, to provide ethyl 3-bromo-8-chloroimidazo[1,2-a]pyrazine-2-carboxylate. Ethyl 3-bromo-8-chloroimidazo[1,2-a]pyrazine-2-carboxylate is reacted with —N($C_{1-5}$alkyl)$_2$, heterocycloalkylamine such as morpholine or 3-oxopiperazin-1-yl, and the like to provide a compound of formula (V). A compound of formula (V), where $R^5$ is morpholine, 3-oxopiperazin-1-yl, —N($C_{1-5}$alkyl)$_2$, and the like, is saponified to the acid, followed by conversion of the acid to the acid chloride, to provide an acid chloride compound of formula (VI).

SCHEME G

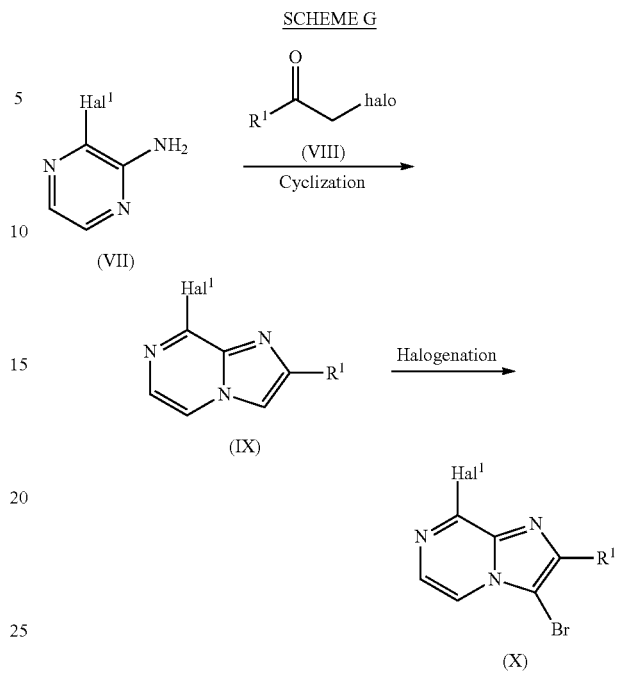

According to SCHEME G, a compound of formula (VII), where $Hal^1$ is —Cl, is reacted with a compound of formula (VIII), where $R^1$ is —$C_{1-5}$alkyl, phenyl, phenyl substituted with one or two halo groups, —$CH_2$-phenyl optionally substituted, or —$C_{3-7}$cycloalkyl, in a solvent such as propionitrile, and the like, at a temperature ranging from 80-120° C., followed by treatment with diethylaniline, at a temperature of 120° C., for a period of about 24 h, to provide a substituted imidazo[1,2-a]pyrazine compound of formula (IX). A commercially available or synthetically accessible substituted imidazo[1,2-a]pyrazine compound of formula (IX) is treated with a brominating reagent such as N-bromosuccinimide (NBS), with our without a suitable catalyst such as AIBN, ABCN, and the like, in a suitable solvent such as DCM, carbon tetrachloride, and the like, to provide a compound of formula (X).

A compound of formula (IX), where $Hal^1$ is —Cl, can undergo an $S_NAr$ reaction with KF, and 18-crown-6, in a solvent such as ACN, and the like, at a temperature of about 150° C., employing microwave heating, to provide a compound of formula (IX), where $Hal^1$ is —F.

SCHEME H

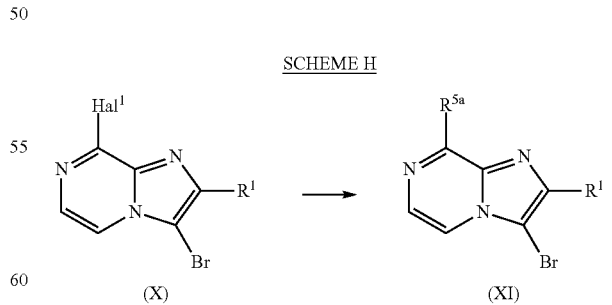

According to SCHEME H, a compound of formula (X) is reacted in an $S_NAr$ (nucleophilic aromatic substitution) reaction with a suitably substituted 3-8 membered heterocycloalkyl ring (fused, bridged, spirocyclic, monocyclic or bicyclic), —NH—$C_{3-7}$cycloalkyl, $NH_2$($C_{1-5}$alkyl), $NHC_{3-}$ 7cycloalkyl($C_{1-5}$alkyl), or NH($C_{1-5}$alkyl)$_2$, in the presence of a suitable base such as trimethylamine (TEA), sodium tert-butoxide (NaO-tBu), NaH, $K_2CO_3$, and the like, in a suitable solvent such as ACN, THF, DMF, and the like, employing conventional heating, at a temperature ranging from 50 to 80° C., to provide a compound of formula (XI), where $R^{5a}$ is a suitably substituted 3-8 membered heterocycloalkyl ring (fused, bridged, spirocyclic, monocyclic or bicyclic), —NH—$C_{3-7}$cycloalkyl, —N($CH_3$)$C_{3-7}$cycloalkyl, —NH($C_{1-5}$alkyl), or —N($C_{1-5}$alkyl)$_2$.

A compound of formula (X) is reacted with ammonia, in a sealed tube, at a temperature of about 100° C., for a period of about 16 h, to provide a compound of formula (XI), where $R^{5a}$ is $NH_2$.

A compound of formula (X) is reacted with sodium thiomethoxide, in a solvent such as DMF, at a temperature ranging from 0° C. to rt, to provide a compound of formula (XI), where $R^{5a}$ is —$SCH_3$. Oxidation of a compound of formula (XI), where $R^{5a}$ is —$SCH_3$, is achieved with an oxidizing agent such as mCPBA, and the like, in a suitable solvent such as DCM, for a period of about 1-3 h, to provide a compound of formula (XI), where $R^{5a}$ is —$SO_2CH_3$.

A compound of formula (XI), where $R^{5a}$ is piperazin-2-one is further alkylated with an alkylating agent such as iodomethane, an appropriate base such as NaH, and the like, in a solvent such as dioxane, to provide a compound of formula (XI), where $R^{5a}$ is 1-methylpiperazin-2-one or 1,3-dimethylpiperazin-2-one.

A compound of formula (X), where $Hal^1$ is —Cl, and $R^1$ is phenyl, or phenyl substituted with halo and $Hal^1$ is —Br, is reacted in a Suzuki cross coupling reaction, under conditions previously described, with 1-N-boc-4-(4,4,5,5-tetramethyl-[1,3,2]dioxaborolan-2-yl)-3,6-dihydro-2H-pyridine, 2-(3,6-dihydro-2H-pyran-4-yl)-4,4,5,5-tetramethyl-1,3,2-dioxaborolane, methylboronic acid, and the like.

SCHEME I

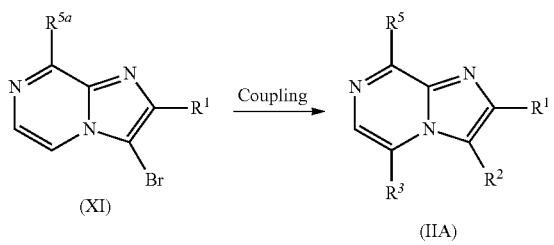

According to SCHEME I, a compound of formula (XI), is coupled under Suzuki reaction conditions, known to one skilled in the art, with a commercially available or synthetically accessible suitably substituted aryl or heteroaryl boronic acid or boronic ester, in the presence of a palladium catalyst such as Pd(PPh$_3$)$_4$, PdCl$_2$(dppf)-CH$_2$Cl$_2$, PdCl$_2$(dtbpf), and the like, a suitable base such a Na$_2$CO$_3$, potassium phosphate, and the like, in a solvent such as dioxane, water, or a mixture thereof, employing conventional or microwave heating, at a temperature such as 110° C., to provide a compound of Formula (IIA), where $R^2$ is 4-hydroxyphenyl, 3-methyl-phenol, 1H-indazol-5-yl, 1,3-dihydrobenzimidazol-2-one, indolin-2-one, 1H-indol-5-yl, 1H-benzotriazol-5-yl, or 1H-benzimidazol-5-yl, and $R^3$ is H. A deprotection step is necessary where the $R^2$ moiety is protected with a nitrogen protecting group such as SEM, to provide a compound of Formula (IIA).

A compound of Formula (IIA) where $R^5$ is —$SO_2CH_3$, is reacted with pyrrolidine, and N-ethyl-N-isopropyl-propan-2-amine, in a solvent such as ACN, to provide a compound of Formula (IIA) where $R^5$ is pyrrolidine.

A compound of Formula (IIA), where $R^5$ is 4-oxopiperidin-1-yl, comes from the deprotection of 1,4-dioxa-8-azaspiro[4.5]decan-8-yl, employing methods known to one skilled in the art. In a preferred method, HCl in dioxane, at 55° C. is employed.

A compound of Formula (IIA) is further brominated, under conditions previously described, to provide a compound of Formula (IIA), where $R^3$ is —Br.

A bromo compound of formula (IIA), where $R^3$ is —Br, under a metal mediated cross-coupling reaction with an alkyl boronic acid, such as methylboronic acid, in the presence of a palladium catalyst such as Pd(OAc)$_2$, and the like, a phosphine ligand such as Ph$_3$P, and the like, a base such as Na$_2$CO$_3$, K$_2$CO$_3$, and the like, in a suitable solvent such as 1,4-dioxane, DMF, and the like at temperatures ranging from room temperature to 90° C., for a period of 4 h, to provide a compound of Formula (IIA), where $R^3$ is —$CH_3$.

A compound of Formula (IIA), where $R^5$ is a nitrogen heterocycloalkyl such as piperazine substituted with —$CO_2$tBu, is deprotected under conditions known to one skilled in the art to provide a compound of Formula (IIA), where $R^5$ is piperazine. In a preferred method, the acid is TFA, and the solvent is DCM.

Acylation of a compound of Formula (IIA), where $R^5$ is a nitrogen heterocycloalkyl such as piperazine, is accomplished in a solvent such as DCM, and the like, a base such as TEA, an acylating agent such as Ac$_2$O, to provide a compound of Formula (IIA), where $R^5$ is a nitrogen heterocycloalkyl such as piperazine substituted with —(C=O)CH$_3$.

A compound of formula (XI), where $R^{5a}$ is, —CH$_3$, or 3,6-dihydro-2H-pyran-4-yl, is subsequently reacted in a second coupling reaction, under conditions previously described, with 5-(4,4,5,5-tetramethyl[1,3,2]dioxaborolan-2-yl)indolin-2-one, and the like, to provide a compound of Formula (IA), where $R^2$ is indolin-2-one.

SCHEME J

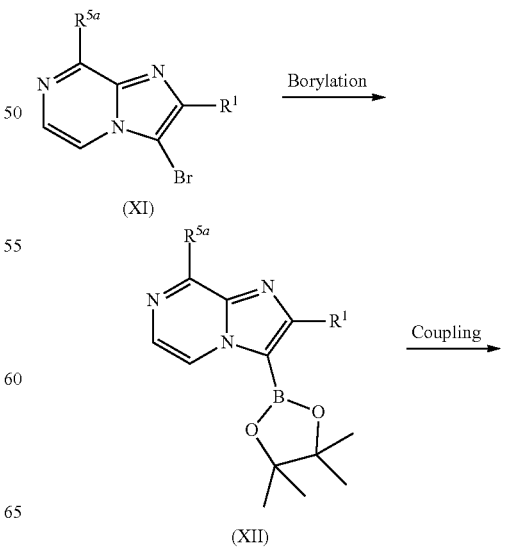

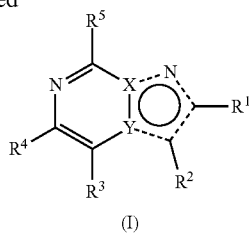

(I)

According to SCHEME J, a compound of formula (XI), where $R^1$ is —$C_{1-5}$alkyl, phenyl, phenyl substituted with 1-2 halo, —$CH_2$-phenyl, or —$C_{3-7}$cycloalkyl, $R^{5a}$ is a suitably substituted 3-8 membered heterocycloalkyl ring (fused, bridged, spirocyclic, monocyclic or bicyclic), —NH—$C_{3-7}$cycloalkyl, $NH_2(C_{1-5}$alkyl), or —NH($C_{1-5}$alkyl)$_2$, is treated with 2-isoproxy-4,4,5,5-tetramethyl-1,3,2-dioxaborolane in the presence of a base, such as n-BuLi, and the like, in a suitable solvent such as THF, dioxane, and the like, at a temperature ranging from −70 to 23° C., for a period of about 1-4 h, to provide a compound of formula (XII). A compound of formula (XII) is coupled under Suzuki reaction conditions, as previously described, with an appropriately substituted commercially available or synthetically accessible halo substituted compound such as indole, indazole, benzimidazolone, benzo[d]thiazol-2(3H)-one, indolinone, 1,3-dihydrobenzo[c]isothiazole 2,2-dioxide, 3,4-dihydroquinazolin-2(1H)-one, 1H-benzo[d]imidazol-2-amine, quinolin-2(1H)-one, 1,4-dihydro-2H-benzo[d][1,3]oxazin-2-one, and the like, to provide a compound of Formula (I), where X is C and Y is N.

A compound of Formula (I), where X is C, Y is N, and $R^5$ is halo, is reacted with an alcohol such as isopropanol, and the like, a base such as NaH, and the like, to provide a compound of Formula (I), where $R^5$ is —$C_{1-5}$alkoxy.

A compound of Formula (I), where X is C, Y is N, and $R^2$ is 3-fluoro-1H-indol-5-yl, is reacted with pyridinium tribromide, in acetic acid/water, to provide a compound of Formula (I), where $R^2$ is 3-Fluoro-indolin-2-one.

SCHEME K

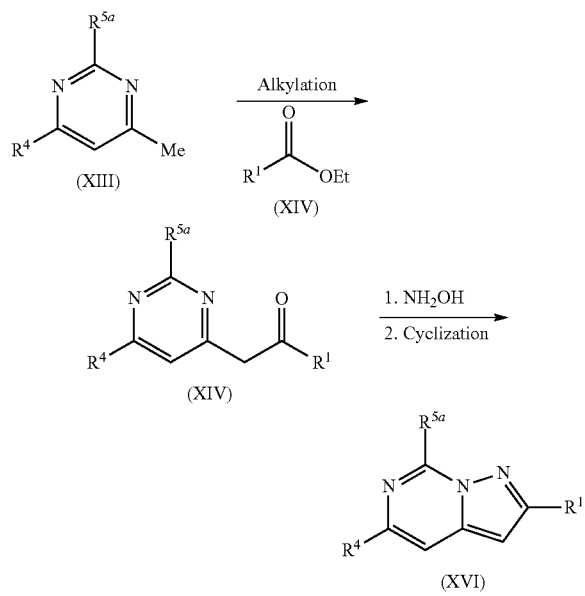

According to SCHEME K, a compound of formula (XIII), where $R^4$ is H, —$CH_3$, —$CF_3$, and $R^{5a}$ is H, or —$SCH_3$, is reacted with a compound of formula (XIV), where $R^1$ is phenyl, phenyl substituted with halo, —$C_{1-5}$alkyl, —$C_{3-7}$cycloalkyl, in the presence of a base such as lithium hexamethyldisilazide (LHMDS), and the like, in a solvent such as THF, and the like, to provide a compound of formula (XIV). A compound of formula (XVI), is prepared from a compound of formula (XIV) in two steps. A compound of formula (XIV) is reacted with hydroxylamine hydrochloride, and a base such as NaOH, in a solvent such as MeOH, and the like, at reflux temperatures, to provide the oxime compound of formula (XV). The oxime compound of formula (XV) is subsequently cyclized with trifluoroacetic anhydride (TFAA), at a temperature of about 0° C., followed by trimethylamine (TEA), at rt, for a period of about 2 h, followed by the addition of FeCl$_2$, at a temperature of about 80° C. for a period of about 8 h, to provide a compound of formula (XVI), where $R^4$ is H, —$CH_3$, or —$CF_3$, $R^{5a}$ is H, or —$SCH_3$ and $R^1$ is phenyl, phenyl substituted with halo, —$C_{1-5}$alkyl, or —$C_{3-7}$cycloalkyl.

SCHEME L

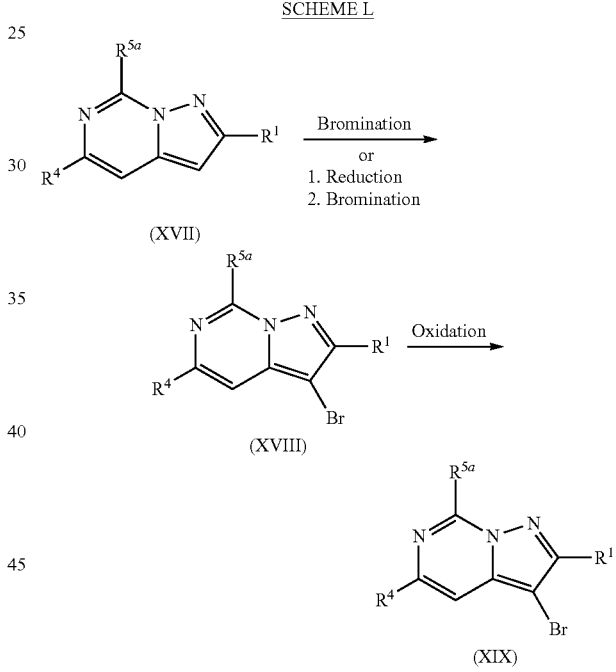

According to SCHEME L, a compound of formula (XVII), where $R^4$ is H, —$CH_3$, or —$CF_3$, and $R^{5a}$ is —$SCH_3$, is brominated with a brominating agent such as n-bromosuccinimide (NBS), and the like, in a suitable solvent such as acetonitrile, and the like, at temperatures ranging from 0-30° C., for a period of 12-18 h to provide a compound of formula (XVIII). A compound of formula (XVII), is oxidized with an oxidizing agent such as meta-chloroperoxybenzoic acid (mCPBA), and the like, in a suitable solvent such as DCM, for a period of about 1-3 h, to provide a compound of formula (XIX), where $R^{5a}$ is —$SO_2CH_3$.

In an alternate method, a compound of formula (XVIII), where $R^{5a}$ is H, is prepared in two steps from a compound of formula (XVII). Removal of the —$SCH_3$, is achieved under reducing conditions such as Pd/C, in the presence of triethylsilane, at a temperature ranging from 0° C. to rt, for a period of about 5 h. Subsequent bromination, employing conditions previously described, provides a compound of formula (XVIII), where $R^{5a}$ is H.

SCHEME M

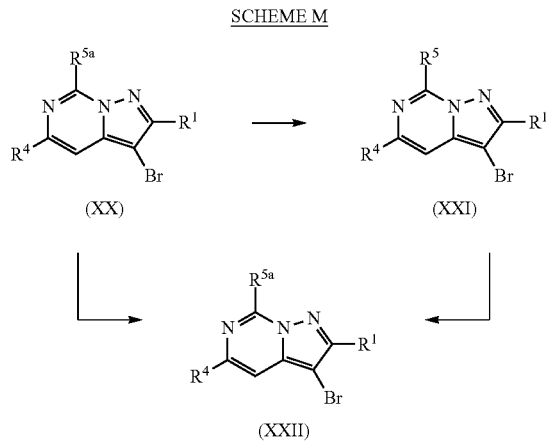

According to SCHEME M, a compound of formula (XX), where $R^1$ is —$C_{1-5}$alkyl, phenyl, or phenyl substituted with halo, $R^4$ is H or —$CH_3$, and $R^{5a}$ is —$SO_2CH_3$, is reacted in an $S_NAr$ (nucleophilic aromatic substitution) reaction with a suitably substituted 3-8 membered heterocycloalkyl ring (fused, bridged, spirocyclic, monocyclic or bicyclic), in a solvent such as DMA, and the like, employing conventional heating, at a temperature ranging from 50 to 100° C., to provide a compound of formula (XXI), where $R^5$ is a suitably substituted 3-8 membered heterocycloalkyl ring (fused, bridged, spirocyclic, monocyclic or bicyclic).

A compound of formula (XX), where $R^1$ is —$C_{1-5}$alkyl, phenyl, or phenyl substituted with halo, $R^4$ is H or —$CH_3$, and $R^{5a}$ is —$SO_2CH_3$, is reacted with sodium isopropoxide, in a solvent such as THF, and the like, for a period of about 10 h, to provide a compound of formula (XXII), where $R^{5a}$ is —OH. Subsequent reaction with an alcohol such as methanol, propan-2-ol, cyclopentanol, and the like, $PPh_3$, diisopropyl azodicarboxylate (DIAD), in a solvent such as THF, and the like, for a period of about 10 h, provides a compound of formula (XXI), where $R^5$ is —$C_{1-5}$alkoxy or —O—$C_{3-7}$cycloalkyl.

SCHEME N

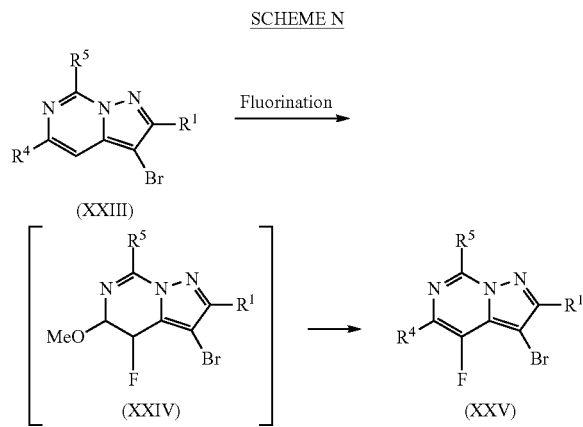

According to SCHEME N, a compound of formula (XXIII), where $R^1$ is $C_{1-5}$alkyl, $R^4$ is H, and $R^5$ is morpholine, is fluorinated under conditions known to one skilled in the art, for example, with an electrophilic fluorinating agent such as Selectfluor®, and the like, in a suitable solvent such as MeOH, and the like, at temperatures ranging from 0-30° C., for a period of 1-4 h to provide an intermediate compound of formula (XXIV). The intermediate compound of formula (XXIV) is heated in a suitable solvent such as DMF, DMA, and the like, at a temperature of about 100° C., for a period of 12-18 h to provide a compound of formula (XXV).

SCHEME O

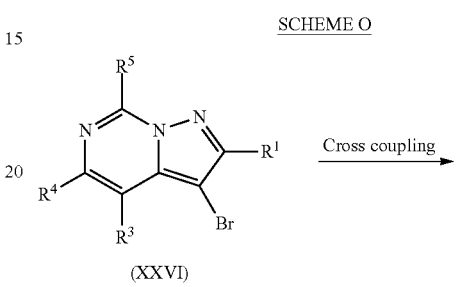

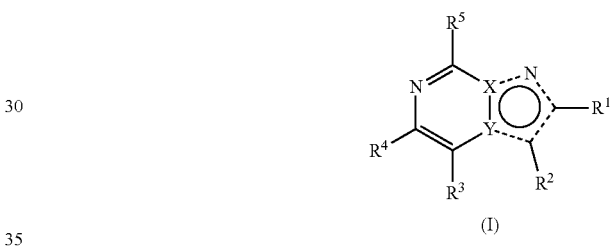

According to SCHEME O, a commercially available or synthetically accessible compound of formula (XXVI) (which encompasses intermediate compounds of formulas (XVIII), (XXI), and (XXV)), where $R^1$ is $C_{1-5}$alkyl, $C_{3-7}$cycloalkyl, phenyl optionally substituted with one or two halo, $R^3$ is H or F, $R^4$ is H, —$CH_3$, or —$CF_3$, and $R^5$ is H, —$C_{1-5}$alkoxy, —O—$C_{3-7}$cycloalkyl, suitably substituted 3-8 membered heterocycloalkyl ring (fused, bridged, spirocyclic, monocyclic or bicyclic), —NH($C_{1-5}$alkyl), —N($C_{1-5}$alkyl)$_2$, is reacted in a Suzuki cross coupling reaction with commercially available or synthetically accessible boronic acids or esters such as those described in SCHEME A and SCHEME B, and the like, a base such as $NaHCO_3$, a palladium catalyst such as $PdCl_2$(dtbpf), and the like, in a solvent such as dioxane, water, or a mixture thereof, at a temperature of about 100-120° C., provides a compound of Formula (I) where X is N, Y is C. A compound of Formula (I) is brominated, under conditions previously described, to provide an intermediate compound where $R^3$ is —Br, and subsequent coupling with a palladium catalyst such as $Pd(PPh_3)_4$, a base such as $Cs_2CO_3$, and trimethylboroxine, provides a compound of Formula (I), where X is N, Y is C, and $R^3$ is —$CH_3$.

A compound of Formula (I), where X is N, Y is C, and $R^3$ is —Br, is reacted with tetramethyltin, LiCl, and a palladium catalyst such as $Pd(PPh_3)_2Cl_2$, in a solvent such as DMF, at a temperature of about 120° C., for a period of about 6 h, to provide a compound of Formula (I), where X is N, Y is C, and $R^3$ is —$CH_3$.

SCHEME P

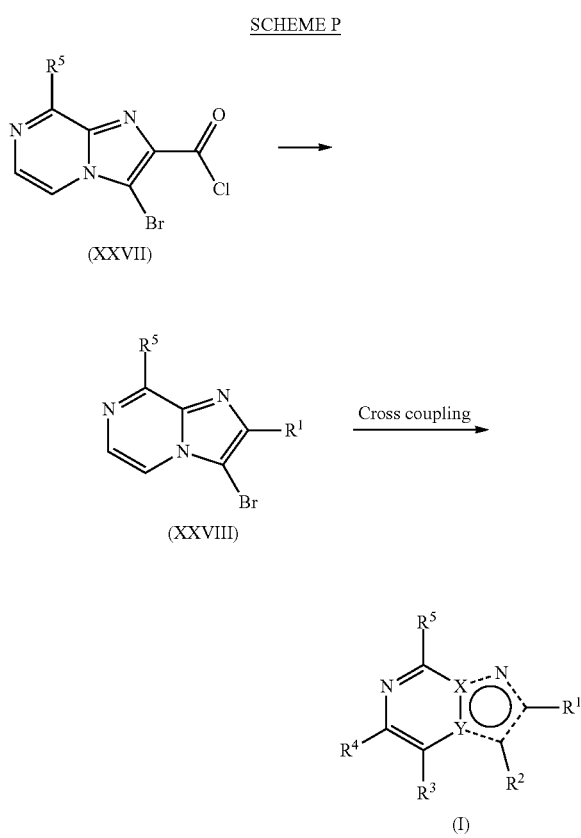

According to SCHEME P, an acid chloride compound of formula (XXVII), is reacted with $NH_2$-phenyl, $—NH_2—CH_2$phenyl, $—NH_2—C_{3-7}$cycloalkyl, $—NH_2$-pyridyl, $—NH(C_{1-5}$alkyl$)_2$, or $—NH(C_{1-5}$alkyl)phenyl, a base such DIPEA, in a solvent such as DCM, and the like, to provide a compound of formula (XXVIII). Subsequent coupling of a compound of formula (XXVIII) under conditions previously described, provides a compound of Formula (I), where X is C, Y is N, and $R^1$ is C(=O)N(CH$_3$)-phenyl; C(=O)NH-phenyl; C(=O)NH—CH$_2$-phenyl; C(=O)NH-pyridinyl; C(=O)NH—C$_{3-7}$cycloalkyl; C(=O)NH—C$_{1-5}$alkyl.

SCHEME Q

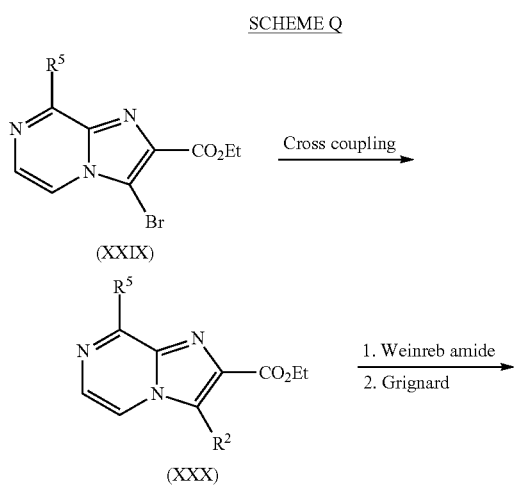

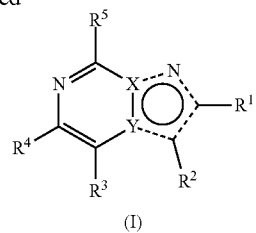

(I)

According to SCHEME Q, a compound of formula (XXIX), is reacted in a cross coupling reaction, as previously described in the SCHEMES above, to provide a compound of formula (XXX), where $R^5$ is morpholinyl, $—N(C_{1-5}$alkyl$)_2$, 4-hydroxy-1-piperidinyl, 1,1-dioxo-1,4-thiazinan-4-yl, or 4-acetylpiperazin-1-yl, $R^2$ is indolin-2-one, 2,2-dioxo-1,3-dihydro-2,1-benzothiazol-5-yl, 1,3-benzoxazol-2-one, or 4-hydroxyphenyl. A compound of Formula (I), is prepared in two steps from a compound of formula (XXX). In a first step, conversion of a compound of formula (XXX) to the corresponding Weinreb amide, under conditions known to one skilled in the art, followed by a second step, in a Grignard reaction with a suitably substituted aryl magnesium bromide, provides a compound of Formula (I), where X is C, Y is N, and $R^1$ is —(C=O)phenyl, wherein the phenyl is optionally substituted with halo.

Compounds of Formula (I) may be converted to their corresponding salts using methods known to one of ordinary skill in the art. For example, an amine of Formula (I) is treated with trifluoroacetic acid, HCl, or citric acid in a solvent such as Et$_2$O, CH$_2$Cl$_2$, THF, CH$_3$OH, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at rt (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via 1/16" PTFE (PolyTetraFluoroEthylene) tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

An Agilent HPLC with an Xterra Prep RP18 column (5 μM, 30×100 or 50×150 mm) or an XBridge $^{18}C$ OBD column (5 μM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

A Shimadzu LC-8A Series HPLC with an Inertsil ODS-3 column (3 μm, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min.

or

A Shimadzu LC-8A Series HPLC with an XBridge C18 OBD column (5 μm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

A Gilson HPLC with an XBridge C18 column (5 μm, 100×50 mm), mobile phase of 5-99% ACN in 20 mM $NH_4OH$ over 10 min and then hold at 99 ACN for 2 min, at a flow rate of 80 mL/min.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100-150 bar with a flow rate ranging from 40-60 mL/min. The column was heated to 35-40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, Mass.) or ACD/Name Version 10.01 (Advanced Chemistry).

Compounds designated as R* or S* are enantiopure compounds where the absolute configuration was not determined.

EXAMPLES

Chemical names were generated using ChemDraw Ultra 12.0 (CambridgeSoft Corp., Cambridge, Mass.) or ACD/Name Version 10.01 (Advanced Chemistry). A prefix of (R/S*) indicates that the compound(s) is/are single enantiomers; however the stereochemistry shown is arbitrary and the absolute stereochemistry has not been determined.

Intermediate 1: 2-(4-Fluorophenyl)-7-(methylthio)pyrazolo[1,5-c]pyrimidine

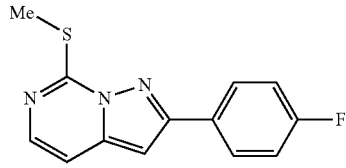 [SMILES: CSc1nccc2cc(-c3ccc(F)cc3)nn12]

Step A: 1-(4-Fluorophenyl)-2-(2-(methylthio)pyrimidin-4-yl)ethanone

A solution 4-methyl-2-(methylthio)pyrimidine (3.0 mL, 2.01 mmol) and ethyl 4-fluorobenzoate (6.1 mL, 42.0 mmol) in THF (60 mL) at 23° C. was treated with 1.0 M solution of LHMDS in THF (42 mL, 42.0 mmol). The reaction warmed to 45° C. for 15 h. The mixture was diluted with water and extracted with EtOAc. The combined organics were dried ($MgSO_4$), filtered, concentrated under reduced pressure. Purification ($SiO_2$, EtOAc/heptane gradient 0 to 10%) afforded the title compound (5.6 g, 85%).

Step B: 1-(4-Fluorophenyl)-2-(2-(methylthio)pyrimidin-4-yl)ethanone oxime

A solution of 1-(4-fluorophenyl)-2-(2-(methylthio)pyrimidin-4-yl)ethanone (7.3 g, 27.8 mmol) in MeOH (85 mL) was treated with hydroxylamine hydrochloride (9.7 g, 140 mmol) and 3 M NaOH (55 mL, 140 mmol). The reaction mixture was refluxed for 2 h. The mixture was diluted with water and extracted with EtOAc. The combined organics were dried ($MgSO_4$), filtered, concentrated under reduced pressure. Purification ($SiO_2$, EtOAc/heptane gradient 0 to 50%) afforded the title compound (7.9 g, 50%).

Step C: 2-(4-Fluorophenyl)-7-(methylthio)pyrazolo[1,5-c]pyrimidine

A solution of 1-(4-fluorophenyl)-2-(2-(methylthio)pyrimidin-4-yl)ethanone oxime (3.9 g, 13.9 mmol) at 0° C. was treated with TFAA (1.94 mL, 13.9 mmol) then triethylamine (3.9 mL, 27.8 mmol). The reaction was warmed to 23° C. over 1.5 h. FeCl$_2$ was added, and the reaction mixture was heated at 80° C. for 8 h. The reaction was concentrated under reduced pressure. Purification (SiO$_2$, EtOAc/heptane gradient 0 to 15%) afforded the title compound (3.7 g, 53%). MS (ESI): mass calcd. for C$_{13}$H$_{10}$FN$_3$S, 259.3; m/z found, 260.0 [M+H]$^+$.

Intermediate 2: 2-(tert-butyl)pyrazolo[1,5-c]pyrimidine

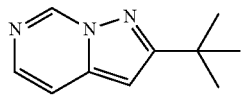

The title compound was prepared in a manner analogous to Intermediate 1.

Intermediate 3: 2-(tert-Butyl)-7-(methylthio)pyrazolo[1,5-c]pyrimidine

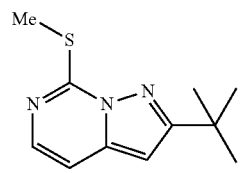

The title compound was prepared in a manner analogous to Intermediate 1. MS (ESI): mass calcd. for C$_{11}$H$_{15}$N$_3$S, 221.3; m/z found, 222.0 [M+H]$^+$.

Intermediate 4: 7-(Methylthio)-2-phenylpyrazolo[1,5-c]pyrimidine

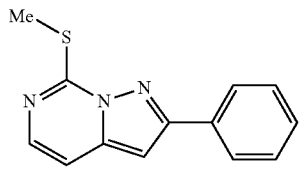 [SMILES: CSc1nccc2cc(-c3ccccc3)nn12]

The title compound was prepared in a manner analogous to Intermediate 1. MS (ESI): mass calcd. for C$_{13}$H$_{11}$N$_3$S, 241.3; m/z found, 242.0 [M+H]$^+$.

Intermediate 5: 5-Methyl-7-(methylthio)-2-phenylpyrazolo[1,5-c]pyrimidine

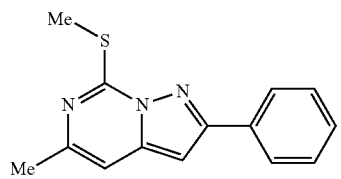 [SMILES: CSc1nc(C)cc2cc(-c3ccccc3)nn12]

The title compound was prepared in a manner analogous to Intermediate 1, using 4,6-dimethylpyrimidine. MS (ESI): mass calcd. for C$_{14}$H$_{13}$BrN$_3$S, 255.3; m/z found, 256.0 [M+H]$^+$.

Intermediate 6: 2-Phenyl-5-(trifluoromethyl)pyrazolo[1,5-c]pyrimidine

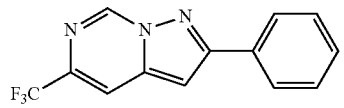

The title compound was prepared in a manner analogous to Intermediate 1, using 4-methyl-6-(trifluoromethyl)-pyrimidine. MS (ESI): mass calcd. for C$_{13}$H$_8$F$_3$N$_3$, 263.2; m/z found, 264.0 [M+H]$^+$.

Intermediate 7: 2-Cyclobutyl-7-(methylthio)-5-(trifluoromethyl)pyrazolo[1,5-c]pyrimidine

The title compound was prepared in a manner analogous to Intermediate 1. MS (ESI): mass calcd. for C$_{12}$H$_{12}$F$_3$N$_3$S, 287.3; m/z found, 288.0 [M+H]$^+$.

Intermediate 8: 2-Isopropyl-7-(methylthio)-5-(trifluoromethyl)pyrazolo[1,5-c]pyrimidine

The title compound was prepared in a manner analogous to Intermediate 1. MS (ESI): mass calcd. for C$_{11}$H$_{12}$F$_3$N$_3$S, 275.3; m/z found, 276.0 [M+H]$^+$.

Intermediate 9: 2-Cyclopropyl-7-(methylthio)-5-(trifluoromethyl)pyrazolo[1,5-c]pyrimidine

The title compound was prepared in a manner analogous to Intermediate 1. MS (ESI): mass calcd. for $C_{11}H_{10}F_3N_3S$, 273.3; m/z found, 274.0 $[M+H]^+$.

Intermediate 10: 3-Bromo-2-(4-fluorophenyl)-7-(methylthio)pyrazolo[1,5-c]pyrimidine

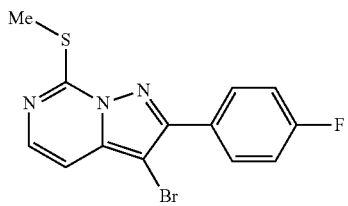 [SMILES: CSc1nccc2c(Br)c(-c3ccc(F)cc3)nn12]

A solution of 2-(4-fluorophenyl)-7-(methylthio)pyrazolo [1,5-c]pyrimidine (Intermediate 1, 2.6 g, 10.1 mmol) in ACN, at 0° C. was treated with n-bromosuccinimide (NBS) (1.9 g, 10.6 mmol). The reaction mixture was stirred at 23° C. for 12 h. NaHCO$_3$ was added and the mixture extracted with EtOAc. The combined organics were dried (MgSO$_4$), filtered, concentrated under reduced pressure. Purification (SiO$_2$, EtOAc/heptane gradient 0 to 10%) afforded the title compound (3.5 g, 82%). MS (ESI): mass calcd. for $C_{13}H_{19}BrFN_3S$, 338.2; m/z found, 340.0 $[M+H]^+$.

Intermediate 11: 3-Bromo-2-(tert-butyl)-5-(trifluoromethyl)pyrazolo[1,5-c]pyrimidine

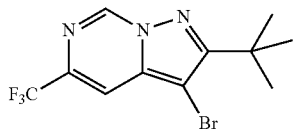 [SMILES: CC(C)(C)c1nn2cnc(C(F)(F)F)cc2c1Br]

Step A: 2-(tert-Butyl)-7-(methylthio)-5-(trifluoromethyl)pyrazolo[1,5-c]pyrimidine The title compound was prepared in a manner analogous to Intermediate 1 using 4-methyl-2-(methylthio)-6-(trifluoromethyl)pyrimidine. MS (ESI): mass calcd. for $C_{12}H_{14}F_3N_3S$, 289.3; m/z found, 290.0 $[M+H]^+$.

Step B: 2-(tert-Butyl)-5-(trifluoromethyl)pyrazolo[1,5-c]pyrimidine

A cooled solution (0° C.) of 2-(tert-butyl)-7-(methylthio)-5-(trifluoromethyl)pyrazolo[1,5-c]pyrimidine (500 mg. 1.7 mmol) in THF was treated first with Pd/C (37 mg, catalytic) followed by the dropwise addition of triethylsilane. The reaction mixture was stirred at 0° C. for 30 min and then 23° C. for 4.5 h. The crude mixture was filtered through a pad of Celite®. The filtrate was concentrated under reduced pressure. Purification (FCC, SiO$_2$, EtOAc in heptane from 0/100 to 5/95) afforded the title compound (155 mg, 36%).

Step C: 3-Bromo-2-(tert-butyl)-5-(trifluoromethyl)pyrazolo[1,5-c]pyrimidine

The title compound was prepared in a manner analogous to Intermediate 14. MS (ESI): mass calcd. for $C_{11}H_{11}BrF_3N_3$, 322.1; m/z found, 324.0 $[M+H]^+$.

Intermediate 12: 3-Bromo-2-cyclobutyl-5-(trifluoromethyl)pyrazolo[1,5-c]pyrimidine

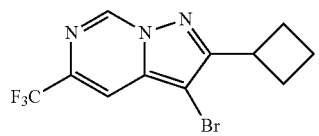 [SMILES: FC(F)(F)c1cc2c(Br)c(C3CCC3)nn2cn1]

The title compound was prepared in a manner analogous to Intermediate 11 starting from 2-cyclobutyl-7-(methylthio)-5-(trifluoromethyl)pyrazolo[1,5-c]pyrimidine (Intermediate 7). MS (ESI): mass calcd. for $C_{11}H_9BrF_3N_3$, 320.1; m/z found, 321.0 $[M+H]^+$.

Intermediate 13: 3-Bromo-2-isopropyl-5-(trifluoromethyl)pyrazolo[1,5-c]pyrimidine

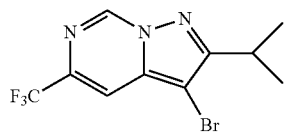

The title compound was prepared in a manner analogous to Intermediate 11 starting from (2-isopropyl-7-(methylthio)-5-(trifluoromethyl)pyrazolo[1,5-c]pyrimidine) Intermediate 8. MS (ESI): mass calcd. for $C_{10}H_9F_3N_3$, 308.1; m/z found, 308.0 $[M+H]^+$.

Intermediate 14: 3-Bromo-2-(4-fluorophenyl)-7-(methylthio)pyrazolo[1,5-c]pyrimidine

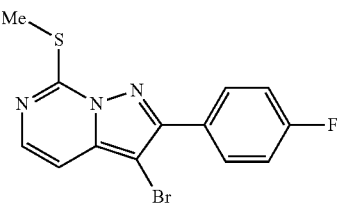 [SMILES: CSc1nccc2c(Br)c(-c3ccc(F)cc3)nn12]

A solution of 2-(4-fluorophenyl)-7-(methylthio)pyrazolo [1,5-c]pyrimidine (Intermediate 1, 2.6 g, 10.1 mmol) in ACN, at 0° C. was treated with n-bromosuccinimide (NBS) (1.9 g, 10.6 mmol). The reaction mixture was stirred at 23° C. for 12 h. NaHCO$_3$ was added and the mixture extracted with EtOAc. The combined organics were dried (MgSO$_4$), filtered, concentrated under reduced pressure. Purification (SiO$_2$, EtOAc/heptane gradient 0 to 10%) afforded the title compound (3.5 g, 82%). MS (ESI): mass calcd. for $C_{13}H_{19}BrFN_3S$, 338.2; m/z found, 340.0 $[M+H]^+$.

Intermediate 15: 3-Bromo-2-cyclopropyl-5-(trifluoromethyl)pyrazolo[1,5-c]pyrimidine

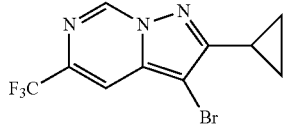 [SMILES: FC(F)(F)c1cc2c(Br)c(C3CC3)nn2cn1]

The title compound was prepared in a manner analogous to Intermediate 14. MS (ESI): mass calcd. for $C_{10}H_7BrF_3N_3$, 306.1; m/z found, 306.0 [M+H]$^+$.

Intermediate 16: 2-(4-Fluorophenyl)-pyrazolo[1,5-c]pyrimidine

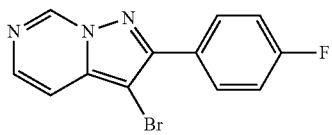 [SMILES: Fc1ccc(-c2nn3cnccc3c2Br)cc1]

The title compound was prepared in a manner analogous to Intermediate 14. MS (ESI): mass calcd. for $C_{12}H_8BrN_3$, 274.1; m/z found, 274.0 [M+H]$^+$.

Intermediate 17: 3-Bromo-2-phenyl-5-(trifluoromethyl)pyrazolo[1,5-c]pyrimidine

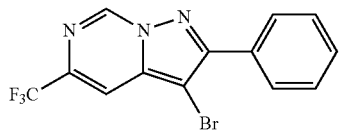 [SMILES: FC(F)(F)c1cc2c(Br)c(-c3ccccc3)nn2cn1]

The title compound was prepared in a manner analogous to Intermediate 14 using 2-phenyl-5-(trifluoromethyl)pyrazolo[1,5-c]pyrimidine (Intermediate 6). MS (ESI): mass calcd. for $C_{13}H_7BrF_3N_3$, 342.1; m/z found, 344.0 [M+H]$^+$.

Intermediate 18: 3-Bromo-2-(4-fluorophenyl)-7-(methylsulfonyl)pyrazolo[1,5-c]pyrimidine

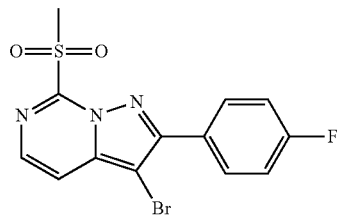 [SMILES: CS(=O)(=O)c1nccc2c(Br)c(-c3ccc(F)cc3)nn12]

A solution of 3-bromo-2-(4-fluorophenyl)-7-(methylthio)pyrazolo[1,5-c]pyrimidine (Intermediate 2, 600 mg, 1.8 mmol) at 0° C. was treated with meta-chloroperoxybenzoic acid (mCPBA) (600 mg, 2.7 mmol). The reaction mixture was stirred at 0° C. for 1 h. The mixture was diluted with NaHCO$_3$ and extracted with EtOAc. The combined organics were dried (MgSO$_4$), filtered, concentrated under reduced pressure to afford the title compound which was used crude in the next step without further purification.

Intermediate 19: 3-Bromo-7-(methylsulfonyl)-2-phenylpyrazolo[1,5-c]pyrimidine

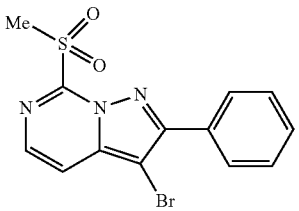 [SMILES: CS(=O)(=O)c1nccc2c(Br)c(-c3ccccc3)nn12]

The title compound was prepared in a manner analogous to Intermediate 18. Step A. MS (ESI): mass calcd. for $C_{13}H_{10}BrN_3O_2S$, 352.2; m/z found, 353.0 [M+H]$^+$.

Intermediate 20: 3-Bromo-5-methyl-7-(methylsulfonyl)-2-phenylpyrazolo[1,5-c]pyrimidine

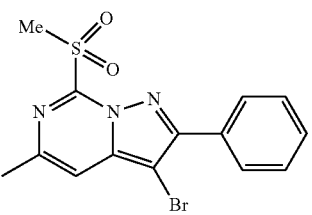 [SMILES: Cc1cc2c(Br)c(-c3ccccc3)nn2c(S(C)(=O)=O)n1]

The title compound was prepared in a manner analogous to Intermediate 18.

Intermediate 21: 4-(3-Bromo-2-(4-fluorophenyl)-pyrazolo[1,5-c]pyrimidin-7-yl)morpholine

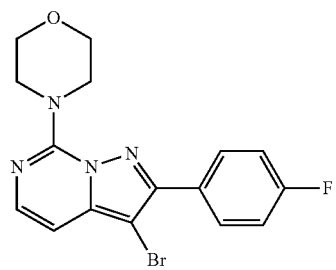 [SMILES: Fc1ccc(-c2nn3c(N4CCOCC4)nccc3c2Br)cc1]

A solution of 3-bromo-2-(4-fluorophenyl)-7-(methylsulfonyl)pyrazolo[1,5-c]pyrimidine (Intermediate 18, 660 mg, 1.8 mmol) in DMA (10 mL) was treated with morpholine (0.8 mL, 8.8 mmol). The reaction mixture was stirred at 100° C. for 16 h. The mixture was diluted with NaHCO$_3$ and extracted with EtOAc. The combined organics were dried (MgSO$_4$), filtered, concentrated under reduced pressure. Purification (SiO$_2$, EtOAc/heptane gradient 0 to 50%) afforded the title compound (440 mg, 65%). MS (ESI): mass calcd. for $C_{16}H_{14}BrFN_4O$, 377.2; m/z found, 378.0 [M+H]$^+$.

Intermediate 22: 4-(3-Bromo-2-phenylpyrazolo[1,5-c]pyrimidin-7-yl)morpholine

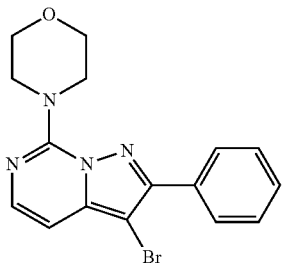 [SMILES: Brc1c(-c2ccccc2)nn2c(N3CCOCC3)nccc12]

The title compound was prepared in a manner analogous to Intermediate 21. MS (ESI): mass calcd. for $C_{16}H_{15}BrN_4O$, 359.2; m/z found, 359.0 [M+H]$^+$.

Intermediate 23: 3-Bromo-7-(4-methoxypiperidin-1-yl)-2-phenylpyrazolo[1,5-c]pyrimidine

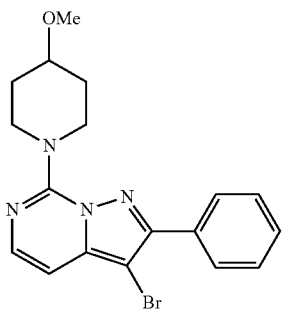 [SMILES: COC1CCN(c2nccc3c(Br)c(-c4ccccc4)nn23)CC1]

The title compound was prepared in a manner analogous to Intermediate 21. MS (ESI): mass calcd. for $C_{18}H_{19}BrN_4O$, 387.3; m/z found, 388.0 [M+H]$^+$.

Intermediate 24: 3-Bromo-2-isopropyl-7-(4-methoxypiperidin-1-yl)pyrazolo[1,5-c]pyrimidine

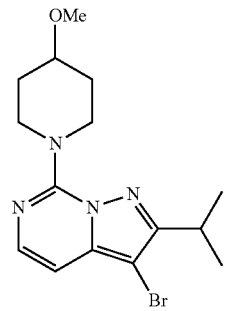 [SMILES: COC1CCN(c2nccc3c(Br)c(C(C)C)nn23)CC1]

The title compound was prepared in a manner analogous to Intermediate 21. MS (ESI): mass calcd. for $C_{18}H_{19}BrN_4O$, 387.3; m/z found, 388.0 [M+H]$^+$.

Intermediate 25: 4-(3-Bromo-2-isopropylpyrazolo[1,5-c]pyrimidin-7-yl)morpholine

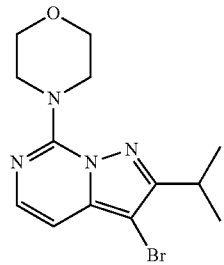 [SMILES: CC(C)c1nn2c(N3CCOCC3)nccc2c1Br]

The title compound was prepared in a manner analogous to Intermediate 21. MS (ESI): mass calcd. for $C_{15}H_{21}BrN_4O$, 353.3; m/z found, 354.0 [M+H]$^+$.

Intermediate 26. 4-(3-Bromo-5-methyl-2-phenylpyrazolo[1,5-c]pyrimidin-7-yl)morpholine

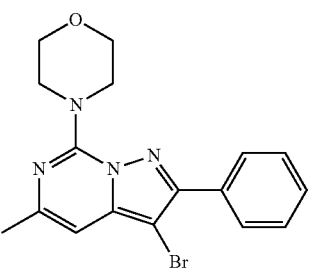 [SMILES: Cc1cc2c(Br)c(-c3ccccc3)nn2c(N2CCOCC2)n1]

The title compound was prepared in a manner analogous to Intermediate 21. [M+H]=374.

Intermediate 27: 4-(3-Bromo-4-fluoro-2-isopropylpyrazolo[1,5-c]pyrimidin-7-yl)morpholine

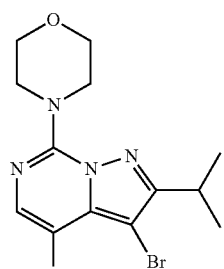

Step A: 4-(3-Bromo-4-fluoro-2-isopropyl-5-methoxy-4,5-dihydropyrazolo[1,5-c]pyrimidin-7-yl)morpholine To a solution of 4-(3-bromo-4-fluoro-2-isopropylpyrazolo[1,5-c]pyrimidin-7-yl)morpholine (Intermediate 25, 440 mg, 1.3 mmol) in methanol (4 mL) was added Selectfluor® (675 mg, 1.75 mmol). The mixture was stirred at 23° C. for 4 h.

The solvent was evaporated under reduced pressure to afford the title compound which was used without purification in the next step.

Step B: 4-(3-Bromo-4-fluoro-2-isopropylpyrazolo[1,5-c]pyrimidin-7-yl)morpholine 4-(3-bromo-4-fluoro-2-isopropyl-5-methoxy-4,5-dihydropyrazolo[1,5-c]pyrimidin-7-yl)morpholine (490 mg, 1.3 mmol) in DMF (5 mL) stirred at 100° C. overnight. The reaction mixture was cooled and diluted with sat NaHCO$_3$. The reaction mixture was extracted with EtOAc. The organic layer was separated, dried (MgSO$_4$), filtered, and concentrated under reduced pressure. Purification (FCC, SiO$_2$, from 32% [25 mM NH$_4$HCO$_3$]-68% [100% MeOH] to 4% [25 mM NH$_4$HCO$_3$]-96% [100% MeOH]) afforded the title compound (7 mg, 1.5% yield). MS (ESI): mass calcd. for C$_{21}$H$_{22}$FN$_5$O$_2$, 395.2; m/z found, 395 [M+H]$^+$. $^1$H NMR (300 MHz, DMSO-d$_6$) δ 10.46 (br s, 1H), 7.59 (d, J=2.0 Hz, 1H), 7.22 (s, 1H), 7.19 (d, J=8.1 Hz, 1H), 6.89 (d, J=7.9 Hz, 1H), 3.80 (s, 8H), 3.53 (s, 2H), 3.24-3.11 (m, 1H), 1.24 (d, J=6.8 Hz, 6H).

Intermediate 28. 3-Bromo-7-(cyclopentyloxy)-2-phenylpyrazolo[1,5-c]pyrimidine

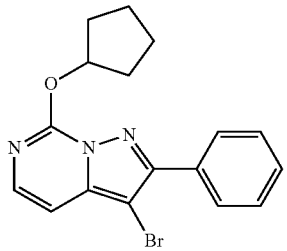 [SMILES: Brc1c(-c2ccccc2)nn2c(OC3CCCC3)nccc12]

Step A: 3-Bromo-2-phenylpyrazolo[1,5-c]pyrimidin-7-ol

To a solution of 3-bromo-7-(methylsulfonyl)-2-phenylpyrazolo[1,5-c]pyrimidine (Intermediate 19, 286 mg, 0.81 mmol) in THF was added sodium isopropoxide (80 mg, 0.98 mmol). The reaction mixture was stirred at 23° C. for 10 h. The reaction mixture was diluted with water and extracted with EtOAc. The combined organics were dried, filtered and concentrated under reduced pressure. Purification (FCC, SiO$_2$, gradient 1-10% EtOAc/heptane) afforded the title compound (100 mg, 45%).

Step B: 3-Bromo-7-(cyclopentyloxy)-2-phenylpyrazolo[1,5-c]pyrimidine

To a solution of 3-bromo-2-phenylpyrazolo[1,5-c]pyrimidin-7-ol (100 mg, 0.34 mmol), cyclopentanol (0.035 mL, 0.38 mmol), and PPh$_3$ (140 mg, 0.52 mmol) in THF (10 mL) was added diisopropyl azodicarboxalate (0.1 mL, 0.52 mmol) by dropwise addition. The reaction mixture stirred at 23° C. for 18 h. The reaction mixture was concentrated under reduced pressure. Purification (FCC, SiO$_2$, EtOAc in Heptane 0/100 to 5/95) afforded the title compound which was used immediately in the next step.

Intermediate 29. 3-Bromo-7-isopropoxy-2-phenylpyrazolo[1,5-c]pyrimidine

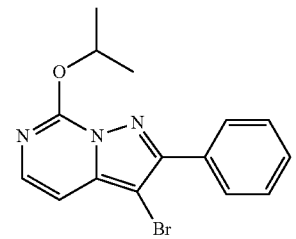 [SMILES: CC(C)Oc1nccc2c(Br)c(-c3ccccc3)nn12]

The title compound was prepared in a manner analogous to Intermediate 28. [M+H]=333

Intermediate 30: 6-(4,4,5,5-Tetramethyl-1,3,2-dioxaborolan-2-yl)-3-((2-(trimethylsilyl)ethoxy)methyl)benzo[d]thiazol-2(3H)-one

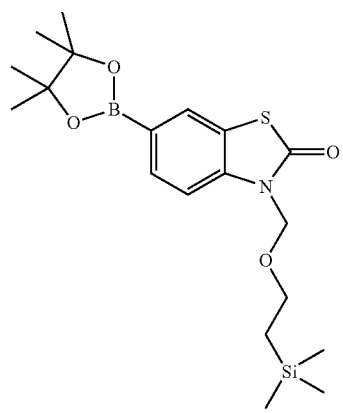 [SMILES: CC1(C)OB(c2ccc3c(c2)sc(=O)n3COCC[Si](C)(C)C)OC1(C)C]

Step A: 6-Bromo-3-((2-(trimethylsilyl)ethoxy)methyl)benzo[d]thiazol-2(3H)-one

To a cooled solution (0° C.) of 6-bromobenzo[d]thiazol-2(3H)-one (1.5 g, 6.5 mmol) in THF (15 mL) was added NaH (60% in oil, 0.31 g, 7.8 mmol)). After 30 minutes, (2-(chloromethoxy)ethyl)trimethylsilane (1.2 mL, 6.5 mmol) was added dropwise. The mixture was stirred for 2 hours at 23° C. The reaction was treated with saturated NaHCO$_3$ and EtOAc and the phases separated. The organic layer was dried (MgSO$_4$), filtered and concentrated under reduced pressure. Purification (FCC, SiO$_2$, EtOAc/Heptane 0/100 to 10/90) afforded the title compound as a brown oil (2.1 g, 53% yield).

Step B: 6-(4,4,5,5-Tetramethyl-1,3,2-dioxaborolan-2-yl)-3-((2-(trimethylsilyl)ethoxy)methyl)benzo[d]thiazol-2(3H)-one To a solution of 6-bromo-3-((2-(trimethylsilyl)ethoxy)methyl)benzo[d]thiazol-2(3H)-one (2.1 g, 5.8 mmol), bis-pinacol boronate (1.8 g, 7.0 mmol) and KOAc (1.1 g, 11.6 mmol) in 1,4-dioxane (30 mL) was added Pd(dppf)Cl$_2$.CH$_2$Cl$_2$ (480 mg, 0.58 mmol) while N$_2$ was bubbled in. The mixture was stirred overnight at 90° C. in a sealed tube.

Intermediate 31: 1-(Tetrahydro-2H-pyran-2-yl)-5-(4,4,5,5-tetramethyl-1,3,2-dioxaborolan-2-yl)-1H-indazole

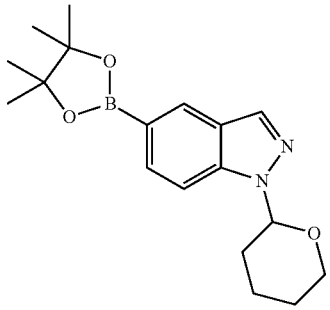 [SMILES: CC1(C)OB(c2ccc3c(cnn3C3CCCCO3)c2)OC1(C)C]

The title compound was prepared in a manner analogous to Intermediate 30, Step B from 5-bromo-1-(tetrahydro-2H-pyran-2-yl)-1H-indazole. MS (ESI): mass calcd. for $C_{18}H_{25}BN_2O_3$, 328.2; m/z found, 329.0 [M+H]$^+$.

Intermediate 32: 5-(4,4,5,5-Tetramethyl-1,3,2-dioxaborolan-2-yl)-1,3-dihydro-2H-benzo[d]imidazol-2-one

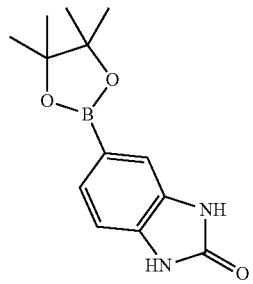 [SMILES: CC1(C)OB(c2ccc3[nH]c(=O)[nH]c3c2)OC1(C)C]

Step A: 4-(4,4,5,5-Tetramethyl-1,3,2-dioxaborolan-2-yl)benzene-1,2-diamine

A solution of 2-nitro-4-(4,4,5,5-tetramethyl-1,3,2-dioxaborolan-2-yl)aniline (4.5 g, 17 mmol) in EtOAc (360 mL) was hydrogenated in a Continuous-flow Hydrogenation Reactor (H-cube®) (1.5 mL/min, 70 mm/30 mm PtO$_2$ 10% cartridge, full H$_2$ mode, 1 cycle). The solution was concentrated in vacuo afford the title compound as a clear oil which was in the next step without further purification.

Step B: 5-(4,4,5,5-Tetramethyl-1,3,2-dioxaborolan-2-yl)-1,3-dihydro-2H-benzo[d]imidazol-2-one To a solution of 4-(4,4,5,5-tetramethyl-1,3,2-dioxaborolan-2-yl)benzene-1,2-diamine (17 mmol) in EtOAc (360 mL) was added 1,1'-carbonyldiimidazole (CDI) (3.0 g, 19 mmol). The resulting mixture was stirred at 23° C. for 16 h. The reaction mixture was diluted with DCM and the resulting white solid was filtered and washed with MeOH to afford the title compound (10.8 g, 63.2%).

Intermediate 33. 5-(4,4,5,5-Tetramethyl-1,3,2-dioxaborolan-2-yl)-1,3-dihydrobenzo[c]isothiazole 2,2-dioxide

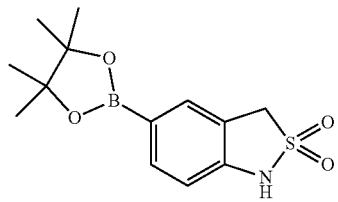 [SMILES: CC1(C)OB(c2ccc3c(c2)CS(=O)(=O)N3)OC1(C)C]

A suspension of 5-bromo-1,3-dihydro-benzo[c]isothiazole 2,2-dioxide (318 mg, 1.28 mmol), bis(pinacolato)diborane (391 mg, 1.54 mmol) and potassium acetate (252 mg, 2.56 mmol) in DMF (2.0 mL) inside a 2 mL microwave vial was purged with N$_2$ then was treated with PdCl$_2$(dtbpf) (47 mg, 0.06 mmol) then the reaction mixture was purged again with nitrogen. The resulting mixture was stirred at 95° C. for 16 h. The reaction mixture was cooled down, diluted with water and extracted with EtOAc, dried (Na$_2$SO$_4$), filtered, concentrated and the crude product Purification (FCC, SiO$_2$, EtOAc/Hexane gradient 0 to 40%) to yield white wax (97 mg, 80%).

Intermediate 34. 5-Bromo-3-fluoro-1H-indole

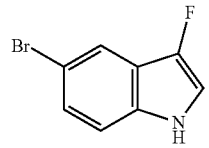

To a solution of 5-bromoindole (500 mg, 2.55 mmol) in CH$_3$CN (5.0 mL)/pyridine (1.5 mL) was added Selectfluor® (813 mg, 2.30 mmol). The reaction mixture was stirred for 16 h. The mixture was diluted with water (50 mL), extracted with EtOAc (50 mL). The combined organics were dried (Na$_2$SO$_4$), filtered, concentrated under reduced pressure to give oil. To the oil was added DCM (2 mL) and formed precipitate. The precipitate was removed by filtration and the DCM solution was purified (FCC, SiO$_2$, 0-30% EtOAc/Hexane) to afford the title compound which was further purified (prep HPLC, Agilent 1100 Series XBridge Prep C18 OBD 5 um, basic conditions (20 mM Ammonium Hydroxide in water/MeCN)) to afford the title compound as an oil (84 mg, 15.4%). $^1$H NMR (500 MHz, CDCl$_3$): δ 7.77 (d, J=1.6 Hz, 1H), 7.62 (s, 1H), 7.30 (dd, J=8.7, 1.9 Hz, 1H), 7.21-7.16 (m, 1H), 6.99 (t, J=2.8 Hz, 1H); $^{19}$F NMR (376 MHz, CDCl$_3$): δ −172.64-−174.96 (m).

Intermediate 35. 6-Bromo-3-((2-(trimethylsilyl)ethoxy)methyl)benzo[d]oxazol-2(3H)-one

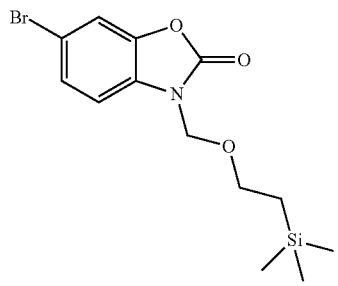 [SMILES: C[Si](C)(C)CCOCn1c(=O)oc2cc(Br)ccc21]

To a solution of 6-bromo-1,3-benzoxazol-2(3H)-one (250 mg, 1.17 mmol) in anhydrous DMF (2 mL) at 0° C. was added NaH (60% dispersion in mineral oil, 51.4 mg, 1.29 mmol) under nitrogen. The reaction mixture was stirred for 20 min. Then the reaction mixture was treated with (2-(chloromethoxy)ethyl)trimethylsilane (0.269 mL, 1.52 mmol) drop wise at 0° C. and the resulting mixture was stirred for 1 h. The reaction mixture was warmed to 23° C., diluted with water (5 mL) and extracted with EtOAc. The combined organics were dried (Na$_2$SO$_4$), filtered, concentrated under reduced pressure. Purification (FCC, SiO$_2$, 0 to 30% EtOAc/Hexane) afforded the title compound (383 mg, 95.3%).

Intermediate 36. 5-Bromo-3,3-difluoro-1-((2-(trimethylsilyl)ethoxy)methyl)indolin-2-one

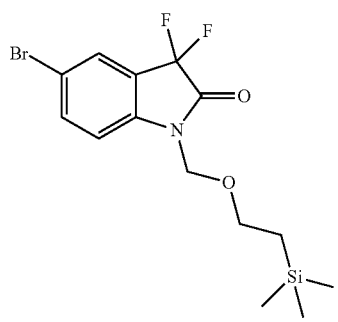 [SMILES: C[Si](C)(C)CCOCN1C(=O)C(F)(F)c2cc(Br)ccc21]

Step A: 5-Bromo-3,3-difluoroindolin-2-one

To a solution of 5-bromoindoline-2,3-dione (1.0 g, 4.42 mmol) in DCM (40 mL) was added DAST (1.83 mL, 13.9 mmol). The reaction mixture was stirred at 23° C. for 5 h. The reaction mixture was cooled to 0° C. and MeOH (15 mL) was added. The reaction mixture was stirred for 15 min, diluted with water, and extracted with DCM (×3). The combined organics were dried (Na$_2$SO$_4$), filtered, concentrated under reduced pressure. Purification (FCC, SiO$_2$, 0 to 50% EtOAc/Hexane) afforded the title compound (0.84 g, 77%). MS (ESI): mass calcd. for C$_8$H$_4$BrF$_2$NO, 246.9; m/z found, 247.9.0 [M+H].

Step B: 5-Bromo-3,3-difluoro-1-((2-(trimethylsilyl)ethoxy)methyl)indolin-2-one

To solution of 5-bromo-3,3-difluoroindolin-2-one (480 mg, 1.94 mmol) in anhydrous DMF (2 mL) at 0° C. was added NaH (60% dispersion in mineral oil, 85.1 mg, 2.13 mmol) under nitrogen. The reaction mixture was stirred for 20 min., then treated with (2-(chloromethoxy)ethyl)trimethylsilane (0.446 mL, 2.52 mmol) drop wise at 0° C. The reaction mixture was stirred for 1 h. The reaction mixture was warmed to 23° C., diluted with water (5 mL) and extracted with EtOAc (3×5 mL). The combined organics were dried (Na$_2$SO$_4$), filtered, concentrated under reduced pressure. Purification (FCC, SiO$_2$, 0 to 30% EtOAc/Hexane) afforded the title compound as a solid (470 mg, 64.2%). $^1$H NMR (400 MHz, CDCl$_3$): δ 7.73 (d, J=1.8 Hz, 1H), 7.70-7.60 (m, 1H), 7.10-6.98 (m, 1H), 5.15 (s, 2H), 3.64-3.53 (m, 2H), 0.99-0.84 (m, 2H), 0.10-0.00 (m, 9H).

Intermediate 37. 3-Bromo-2-phenylimidazo[1,2-a]pyrazine

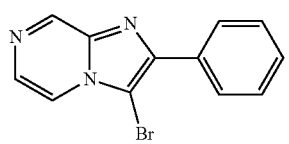 [SMILES: Brc1c(-c2ccccc2)nc2cnccn12]

Step A: 2-Phenylimidazo[1,2-a]pyrazine

To a solution of 8-chloro-2-phenylimidazo[1,2-a]pyrazine (3.00 g, 10.5 mmol) in THF (10.0 mL) was added formic acid (0.633 mL, 15.7 mmol), Et$_3$N (4.36 mL, 31.4 mmol) and Pd(PPh$_3$)$_4$ (604 mg, 0.522 mmol). The reaction mixture was purged with nitrogen then heated in microwave at 110° C. for 2 h. The reaction mixture was cooled then concentrated under reduced. Purification (FCC, SiO$_2$, 0 to 100% EtOAc: DCM) afforded the title compound (0.84 g, 41%). MS (ESI): mass calcd. for C$_{12}$H$_9$N$_3$, 195.2; m/z found, 196.1 [M+H]$^+$.

Step B: 3-Bromo-2-phenylimidazo[1,2-a]pyrazine

To a solution of 2-phenylimidazo[1,2-a]pyrazine (925 mg, 0.474 mmol) in DCM (10 mL) was added NBS (1.01 g, 0.569 mmol). The reaction mixture was stirred at 23° C. for 10 min. The reaction mixture was concentrated under reduced pressure and then suspended in MeOH. The resulting precipitate was filtered and dried via suction then vacuum to yield the title compound as a white solid (1.12 g, 89.2%) that was used in the next step without further purification. MS (ESI): mass calcd. for C$_{12}$H$_8$BrN$_3$, 273.0; m/z found, 274.0 [M+H].

Intermediate 38. 3-Bromo-8-fluoro-2-(4-fluorophenyl)imidazo[1,2-a]pyrazine

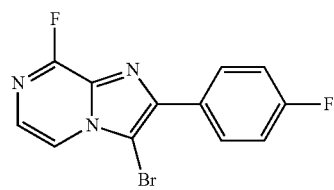 [SMILES: Fc1ccc(-c2nc3c(F)nccn3c2Br)cc1]

Step A: 8-Fluoro-2-(4-fluorophenyl)imidazo[1,2-a]pyrazine

To a solution of 8-chloro-2-(4-fluorophenyl)imidazo[1,2-a]pyridine (250 mg, 1.01 mmol) in acetonitrile (2 mL) was added KF (176 mg, 3.03 mmol) and 18-crown-6 (26.7 mg, 0.101 mmol). The resulting mixture was heated by microwave at 150° C. for 2 h then was heated in oil bath at 120° C. for 60 h. The reaction mixture was diluted with water (5.0 mL), and extracted with EtOAc (3×5 mL). The combined organics were dried (Na$_2$SO$_4$), filtered, concentrated under reduced pressure. Purification (FCC, SiO$_2$, 0 to 40% EtOAc/Hexane) afforded the title compound (100 mg, 42.8%). MS (ESI): mass calcd. for C$_{12}$H$_7$F$_2$N$_3$, 231.2; m/z found, 232.0 [M+H]$^+$. $^1$H NMR (400 MHz, CDCl$_3$) δ 8.04-7.93 (m, 4H), 7.46 (dd, J=4.6, 1.7 Hz, 1H), 7.22-7.10 (m, 2H).

Step B 3-Bromo-8-fluoro-2-(4-fluorophenyl)imidazo[1,2-a]pyrazine

To a solution of 8-fluoro-2-(4-fluorophenyl)imidazo[1,2-a]pyrazine (145 mg, 0.627 mmol) in DCM (10 mL) at 0° C. was added NBS (167 mg, 0.941 mmol). The reaction mixture was stirred at 0° C. for 10 min. The reaction mixture was concentrated under reduced pressure. Purification (FCC, SiO$_2$, 0 to 30% EtOAc/Hexane) afforded the title compound (220 mg, 99.7%) MS (ESI): mass calcd. for C$_{12}$H$_6$BrF$_2$N$_3$, 309.0 m/z found, 309.8 [M+H].

Intermediate 39. 3-Bromo-2-(4-fluorophenyl)-8-(methylthio)imidazo[1,2-a]pyrazine

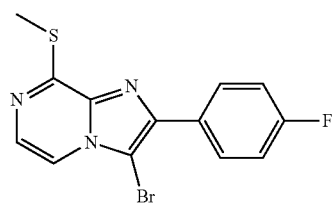 [SMILES: CSc1nccn2c(Br)c(-c3ccc(F)cc3)nc12]

To a solution of 3-bromo-8-chloro-2-(4-fluorophenyl)imidazo[1,2-a]pyrazine (Intermediate 47, 5.10 g, 13.6 mmol) in DMF (50 mL) at 0° C. was added with sodium thiomethoxide (1.39 g, 18.9 mmol). The reaction mixture was stirred at 0° C. for 1 h. The reaction mixture was poured into water (100 mL) and the resulting precipitate was filtered, washed with water and dried to afford the title compound (4.96 g, 93.9%). MS (ESI): mass calcd. for C$_{13}$H$_9$BrFN$_3$S, 337.0 m/z found, 338.0 [M+H]. $^1$H NMR (400 MHz, CDCl$_3$): δ 8.25-8.02 (m, 2H), 7.96-7.70 (m, 2H), 7.17 (t, J=8.7 Hz, 2H), 2.69 (s, 3H).

Intermediate 40: 4-(3-Bromo-2-(4-fluorophenyl)imidazo[1,2-a]pyrazin-8-yl)morpholine

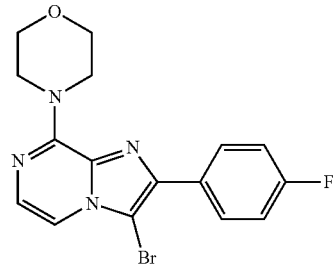 [SMILES: Fc1ccc(-c2nc3c(N4CCOCC4)nccn3c2Br)cc1]

The title compound was prepared in a manner analogous to Example 1, Steps A-D. MS (ESI): mass calcd. for C$_{29}$H$_{29}$FN$_6$O$_3$, 377.2 m/z found, 377.1 [M+H].

Intermediate 41: 6-(3-Bromo-2-(4-fluorophenyl)imidazo[1,2-a]pyrazin-8-yl)-2-oxa-6-azaspiro[3.3]heptane

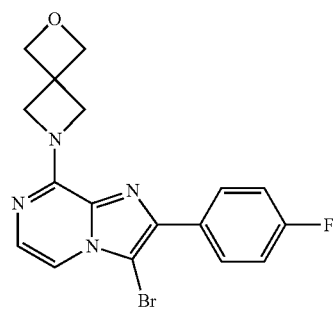 [SMILES: Fc1ccc(-c2nc3c(N4CC5(COC5)C4)nccn3c2Br)cc1]

The title compound was prepared in a manner analogous to Intermediate 40.

Intermediate 42: 4-(2-(4-Fluorophenyl)-3-(4,4,5,5-tetramethyl-1,3,2-dioxaborolan-2-yl)imidazo [1,2-a]pyrazin-8-yl)morpholine

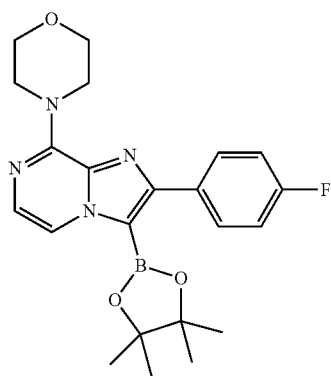 [SMILES: CC1(C)OB(c2c(-c3ccc(F)cc3)nc3c(N4CCOCC4)nccn23)OC1(C)C]

To a solution of 4-(3-bromo-2-(4-fluorophenyl)imidazo[1,2-a]pyrazin-8-yl)morpholine (Intermediate 40, 1.68 g, 4.45 mmol) in anhydrous THF (50 mL) was added 2-isoproxy-4,4,5,5-tetramethyl-1,3,2-dioxaborolane (1.85 mL, 8.90 mmol) under nitrogen. The reaction mixture was cooled to −78° C. and n-BuLi (1.6 M in hexane, 5.6 mL, 8.9 mmol) was added drop wise while maintaining the internal temperature lower than −72° C. The resulting mixture was stirred at −78° C. for 1 h after the addition was complete. The reaction mixture was warmed to 23° C. and stirred for 2 h. The reaction mixture was quenched with water (50 mL) and extracted with EtOAc (3×50 mL). The combined organics were dried (Na$_2$SO$_4$), filtered, concentrated under reduced pressure. Purification (FCC, SiO$_2$, 0 to 40% EtOAc/Hexane) afforded the title compound (980 mg, 51.8%). $^1$H NMR (400 MHz, CDCl$_3$): δ 8.38 (d, J=4.6 Hz, 1H), 8.00 (dd, J=8.8, 5.5 Hz, 2H), 7.44 (d, J=4.6 Hz, 1H), 7.09 (t, J=8.8 Hz, 2H), 4.41-4.14 (m, 4H), 4.05-3.75 (m, 4H), 1.37 (s, 9H).

Intermediate 43: Ethyl 3-bromo-8-chloroimidazo[1,2-a]pyrazine-2-carboxylate

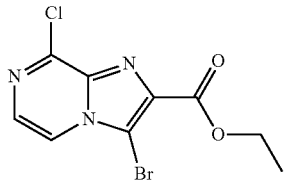 [SMILES: CCOC(=O)c1nc2c(Cl)nccn2c1Br]

Step A: Ethyl 8-chloroimidazo[1,2-a]pyrazine-2-carboxylate

To a solution of 2-amino-3-chloropyrazine (3.5 g, 27.0 mmol) in dimethoxyethane (84 mL) was added ethyl 3-bromo-2-oxopropanoate (4.1 mL, 32.4 mmol). The reaction mixture was stirred at 23° C. for 16 h. The reaction was cooled to 0° C., and the resulting precipitate was filtered, washed with ether, then suspended in EtOH and stirred for 16 h. The reaction mixture was concentrated under reduced pressure to afford the title compound (2.3 g, 38% yield) which was used without further purification in the next step.

Step B: Ethyl 3-bromo-8-chloroimidazo[1,2-a]pyrazine-2-carboxylate

To a solution of ethyl 8-chloroimidazo[1,2-a]pyrazine-2-carboxylate (8.6 g, 38.1 mmol) in DCM (146 mL) at 0° C. was added NBS (7.5 g, 41.9 mmol). The reaction mixture was stirred at 23° C. for 2 h. The reaction mixture was treated with sat. aq. NaHCO$_3$ and the organic layer separated, dried (Na$_2$SO$_4$), filtered, and concentrated under reduced pressure to afford the title compound as a white solid (11.6 g, 74%). MS (ESI): mass calcd. for C$_9$H$_7$BrClN$_3$O$_2$, 302.5; m/z found, 303.0 [M+H]$^+$.

Intermediate 44: Ethyl 8-hydroxyimidazo[1,2-a]pyrazine-2-carboxylate

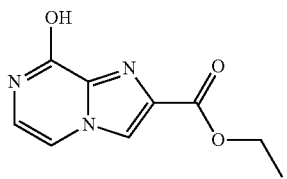

A solution of ethyl 8-chloroimidazo[1,2-a]pyrazine-2-carboxylate (Intermediate 43, product from Step A, 20 g, 89 mmol) in EtOH (367 mL) was stirred at 90° C. for 2 h. The solid was filtered and washed with EtOH to afford the title compound as a white solid (8.5 g, 46%). MS (ESI): mass calcd. for C$_9$H$_9$N$_3$O$_3$ 207.1; m/z found, 208 [M+H]$^+$.

Intermediate 45. 3-Bromo-8-morpholinoimidazo[1,2-a]pyrazine-2-carbonyl chloride

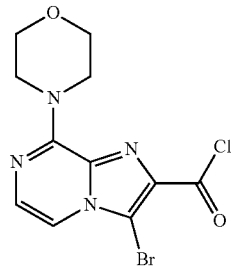 [SMILES: O=C(Cl)c1nc2c(N3CCOCC3)nccn2c1Br]

Step A: Ethyl 3-bromo-8-morpholinoimidazo[1,2-a]pyrazine-2-carboxylate

To a cooled (° C.) solution of ethyl 3-bromo-8-chloroimidazo[1,2-a]pyrazine-2-carboxylate (Intermediate 43, 11.5 g, 37.8 mmol) in CH$_3$CN (50 mL) was added morpholine (3.3 mL, 37.8 mmol) and DIPEA (6.6 mL, 37.8 mmol). The reaction mixture was warmed to 23° C. for 64 h. Sat. aq. NH$_4$Cl was added and the organics were extracted with CH$_2$Cl$_2$. The organic layer was washed with brine, dried (Na$_2$SO$_4$), filtered and concentrated under reduced pressure. The resulting solid was stirred in DCM (20 mL) and DIPE (60 mL). The suspension was cooled to 0° C., filtered and dried under reduced pressure to afford the title compound (13.4 g, 84%).

Step B: 3-Bromo-8-morpholinoimidazo[1,2-a]pyrazine-2-carboxylic acid

To a solution of ethyl 3-bromo-8-morpholinoimidazo[1,2-a]pyrazine-2-carboxylate (3 g, 8.5 mmol) in THF (40 mL) and MeOH (10 mL) was added LiOH (607 mg, 25.3 mmol) in water (40 mL). The reaction mixture was stirred at 23° C. for 1 h. The reaction mixture was concentrated under reduced pressure and the resultant solid was treated with 1N HCl aqueous solution. The resultant white solid was filtered and washed with water, EtOAc and dried under reduced pressure to afford the title compound (2.8 g, 76%).

Step C: 3-Bromo-8-morpholinoimidazo[1,2-a]pyrazine-2-carbonyl chloride

To a cooled (0° C.) solution of 3-bromo-8-morpholinoimidazo[1,2-a]pyrazine-2-carboxylic acid (1.2 g, 3.7 mmol) in DCM (12 mL) and DMF (0.36 mL) at added thionyl chloride (0.4 mL, 5.5 mmol) drop-wise. The reaction mixture was stirred for 3 h at 23° C., and concentrated under reduced pressure. Trituration in Et$_2$O afforded the title compound, which was used crude without further purification (0.95 g, 75%).

Intermediate 46. 3-Bromo-8-morpholino-N-phenylimidazo[1,2-a]pyrazine-2-carboxamide

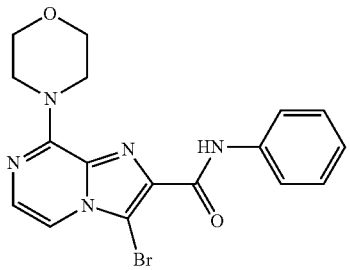 [SMILES: O=C(Nc1ccccc1)c1nc2c(N3CCOCC3)nccn2c1Br]

To a stirred solution of 3-bromo-8-morpholinoimidazo[1,2-a]pyrazine-2-carbonyl chloride (Intermediate 45, 400 mg, 1.2 mmol) and DIPEA (0.3 mL, 1.7 mmol) in DCM (4 mL) was added aniline (0.14 mL, 1.5 mmol). The reaction mixture was stirred at 23° C. for 3 h. The mixture was concentrated under reduced pressure to afford the title compound as a white solid (362 mg, 78%).

Intermediate 47: 3-Bromo-8-chloro-2-(4-fluorophenyl)imidazo[1,2-a]pyrazine

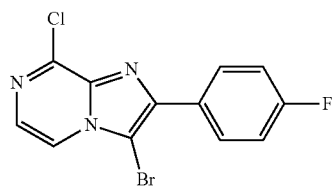 [SMILES: Fc1ccc(-c2nc3c(Cl)nccn3c2Br)cc1]

Step A: 8-Chloro-2-(4-fluorophenyl)imidazo[1,2-a]pyrazine

A suspension of 2-amino-3-chloropyrazine (10.0 g, 77.2 mmol) and 2-chloro-4'-fluoroacetophenone (13.5 g, 77.2 mmol) in propionitrile (30 mL) was heated at 120° C. for 30 min. The reaction mixture was cooled to 80° C., and diethylaniline (12.3 mL, 77.2 mmol) was added. The reaction mixture was refluxed at 120° C. for 23 h. The reaction mixture was cooled to 23° C. and the resulting precipitate was filtered off and dried to afford the title compound as a solid (12.0 g, 80% pure, 50%) that was used without further purification. MS (ESI): mass calcd. for $C_{12}H_7ClFN_3$, 247.0 m/z found, 247.9 [M+H]. $^1$H NMR (400 MHz, CDCl$_3$): δ 8.04 (d, J=4.5 Hz, 1H), 8.02-7.95 (m, 3H), 7.69 (d, J=4.5 Hz, 1H), 7.21-7.12 (m, 2H).

Step B: 3-Bromo-8-chloro-2-(4-fluorophenyl)imidazo[1,2-a]pyrazine

To a suspension of 8-chloro-2-(4-fluorophenyl)imidazo[1,2-a]pyrazine (7.34 g, 70% pure, 2.07 mmol) in DCM (100 mL) at 0° C. was added N-bromosuccinimide (5.54 g, 3.11 mmol). The reaction solution was stirred at 23° C. for 1 h. The reaction solution was concentrated and to the crude residue was added MeOH (75 mL). The resulting mixture was cooled to −5° C. and the resulting precipitate was filtered off, washed with cold MeOH and dried to afford the title compound as a solid (4.70 g, 69.4%). MS (ESI): mass calcd. for $C_{12}H_6BrClFN_3$, 324.9 m/z found, 325.8 [M+H]. $^1$H NMR (400 MHz, CDCl$_3$): δ 8.19-8.11 (m, 2H), 8.08 (d, J=4.6 Hz, 1H), 7.83 (d, J=4.6 Hz, 1H), 7.20 (dd, J=9.0, 8.4 Hz, 2H).

Intermediate 48: 4-(2-(4-Fluorophenyl)-8-(methylsulfonyl)imidazo[1,2-a]pyrazin-3-yl)phenol

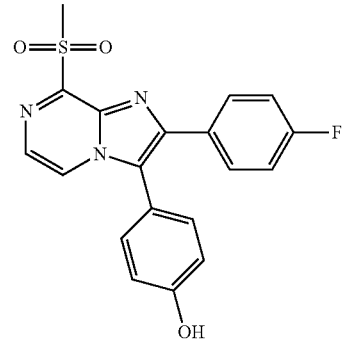 [SMILES: CS(=O)(=O)c1nccn2c(-c3ccc(O)cc3)c(-c3ccc(F)cc3)nc12]

Step A: 3-Bromo-2-(4-fluorophenyl)-8-(methylthio)imidazo[1,2-a]pyrazine

To a solution of 3-bromo-8-chloro-2-(4-fluorophenyl)imidazo[1,2-a]pyrazine (Intermediate 47) in DMF (50 mL) at 0° C. was added with sodium thiomethoxide (1.39 g, 18.9 mmol). The reaction mixture was stirred at 0° C. for 1 h. The reaction mixture was poured into water (100 mL) and the resulting precipitate was filtered, washed with water and dried to afford the title compound (4.96 g, 93.9%). MS (ESI): mass calcd. for $C_{13}H_9BrFN_3S$, 337.0 m/z found, 338.0 [M+H]. $^1$H NMR (400 MHz, CDCl$_3$): δ 8.25-8.02 (m, 2H), 7.96-7.70 (m, 2H), 7.17 (t, J=8.7 Hz, 2H), 2.69 (s, 3H).

Step B: 3-Bromo-2-(4-fluorophenyl)-8-(methylsulfonyl)imidazo[1,2-a]pyrazine To a solution of 3-bromo-2-(4-fluorophenyl)-8-(methylthio)imidazo[1,2-a]pyrazine (2.25 g, 6.65 mmol) in DCM (30 mL) was added mCPBA (4.59 g, 26.6 mmol). The reaction mixture was stirred at room temperature for 1 h. The reaction mixture was diluted with sat. aq. NaHCO$_3$ (50 mL) and extracted with DCM (3×50 mL). The combined organics were dried (Na$_2$SO$_4$), filtered, concentrated under reduced pressure. Purification (FCC, SiO$_2$, 0 to 40% EtOAc/DCM) afforded the title compound (1.67 g, 67.7%). MS (ESI): mass calcd. for $C_{13}H_9BrFN_3O_2S$, 369.0 m/z found, 370.0 [M+H]. $^1$H NMR (400 MHz, CDCl$_3$): δ 8.33 (d, J=4.5 Hz, 1H), 8.27-8.19 (m, 2H), 8.16 (d, J=4.5 Hz, 1H), 7.21 (t, J=8.6 Hz, 2H), 3.62 (s, 3H).

Step C: 4-(2-(4-Fluorophenyl)-8-(methylsulfonyl)imidazo[1,2-a]pyrazin-3-yl)phenol To a solution of 3-bromo-2-(4-fluorophenyl)-8-(methylsulfonyl)imidazo[1,2-a]pyrazine (600 mg, 1.62 mmol), 4-(4,4,5,5-tetramethyl-1,3,2-dioxaborolan-2-yl)phenol (446 mg, 2.03 mmol), potassium phosphate tribasic (860 mg, 4.05 mmol), 1,4-dioxane (8.0 mL), water (2.0 mL) was added PdCl$_2$(dtbpf) (211 mg, 0.324 mmol). The reaction mixture was purged with nitrogen for 1 min. The reaction mixture was heated in microwave at 90° C. for 10 min. The reaction mixture was diluted with water (50 mL, adjusted pH~1 by addition of 1N HCl and extracted with EtOAc (3×50 mL). The combined organics were dried (Na$_2$SO$_4$), filtered, concentrated under reduced pressure. Purification (FCC, SiO$_2$, 0 to 50% EtOAc: DCM) afforded the title compound (272 mg, 43.7%). MS (ESI): mass calcd. for C$_{19}$H$_{14}$FN$_3$O$_3$S, 369.0 m/z found, 383.1 [M+H]. $^1$H NMR (500 MHz, DMSO-d$_6$): δ 10.05 (s, 1H), 8.34 (d, J=4.5 Hz, 1H), 8.01 (d, J=4.5 Hz, 1H), 7.73 (dd, J=8.9, 5.5 Hz, 2H), 7.37 (d, J=8.5 Hz, 2H), 7.25 (t, J=8.9 Hz, 2H), 7.01 (d, J=8.5 Hz, 2H), 3.69 (s, 3H).

Intermediate 49. 1,2,6-Triazaspiro[2.5]oct-1-ene

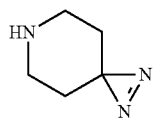

Step A: tert-Butyl 1,2,6-triazaspiro[2.5]oct-1-ene-6-carboxylate

The title compound was prepared according to the procedure in Kambe, Tohru; Correia, Bruno E.; Niphakis, Micah J.; Cravatt, Benjamin F., Journal of the American Chemical Society (2014), 136(30), 10777-10782).

Step B: 1,2,6-Triazaspiro[2.5]oct-1-ene

To a solution of tert-butyl-1,2,6-triazaspiro[2.5]oct-1-ene-6-carboxylate (0.53 g, 2.51 mmol) in 250 mL roundbottom flask covered in aluminum to block out light in formic acid (4 mL) was added 6.0 N HCl (0.84 mL). After 1 hr, the reaction was diluted with MeOH (75 mL) and evaporated. The reaction process was repeated 4 times. The crude solid was used without further purification. MS (ESI): mass calcd. for C$_5$H$_9$N$_3$, 111.1; m/z found, 112.2 [M+H]$^+$.

Example 1: 1-[4-[2-(4-Fluorophenyl)-3-(4-hydroxyphenyl)imidazo[1,2-a]pyrazin-8-yl]piperazin-1-yl]ethanone

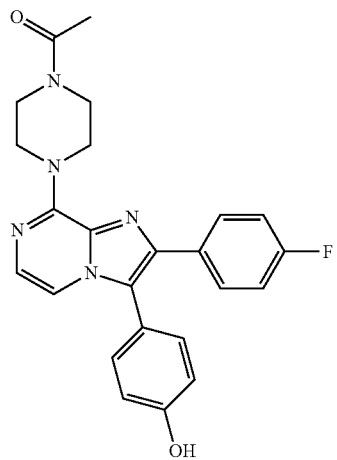 [SMILES: CC(=O)N1CCN(c2nccn3c(-c4ccc(O)cc4)c(-c4ccc(F)cc4)nc23)CC1]

Step A: 8-Chloro-2-(4-fluorophenyl)imidazo[1,2-a]pyrazine

A suspension of 2-amino-3-chloropyrazine (10.0 g, 77.2 mmol) and 2-chloro-4'-fluoroacetophenone (13.5 g, 77.2 mmol) in propionitrile (30 mL) was heated at 120° C. for 30 min. The reaction mixture was cooled to 80° C., and diethylaniline (12.3 mL, 77.2 mmol) was added. The reaction mixture was refluxed at 120° C. for 23 h. The reaction mixture was cooled to 23° C. and the resulting precipitate was filtered off and dried to afford the title compound as a solid (12.0 g, 80% pure, 50%) that was used without further purification. MS (ESI): mass calcd. for C$_{12}$H$_7$ClFN$_3$, 247.0 m/z found, 247.9 [M+H]. $^1$H NMR (400 MHz, CDCl$_3$): δ 8.04 (d, J=4.5 Hz, 1H), 8.02-7.95 (m, 3H), 7.69 (d, J=4.5 Hz, 1H), 7.21-7.12 (m, 2H).

Step B: 3-Bromo-8-chloro-2-(4-fluorophenyl)imidazo[1,2-a]pyrazine

To a suspension of 8-chloro-2-(4-fluorophenyl)imidazo[1,2-a]pyrazine (7.34 g, 70% pure, 2.07 mmol) in DCM (100 mL) at 0° C. was added N-bromosuccinimide (5.54 g, 3.11 mmol). The reaction mixture was stirred at 23° C. for 1 h. The reaction solution was concentrated and to the crude residue was added MeOH (75 mL). The resulting mixture was cooled to ¯5° C. and the resulting precipitate was filtered off, washed with cold MeOH and dried to afford the title compound as a solid (4.70 g, 69.4%). MS (ESI): mass calcd. for C$_{12}$H$_6$BrClFN$_3$, 324.9 m/z found, 325.8 [M+H]. $^1$H NMR (400 MHz, CDCl$_3$): δ 8.19-8.11 (m, 2H), 8.08 (d, J=4.6 Hz, 1H), 7.83 (d, J=4.6 Hz, 1H), 7.20 (dd, J=9.0, 8.4 Hz, 2H).

Step C: tert-Butyl 4-(3-bromo-2-(4-fluorophenyl) imidazo[1,2-a]pyrazin-8-yl)piperazine-1-carboxylate A suspension of 3-bromo-8-chloro-2-(4-fluorophenyl) imidazo[1,2-a]pyrazine (250 mg, 0.766 mmol) in acetonitrile (5 mL) was treated with 1-Boc-piperizine (285 mg, 1.53 mmol) and triethylamine (127 μL, 0.919 mmol). The resulting mixture was refluxed at 80° C. for 16 h. The resulting mixture was cooled to ¯5° C. The resulting precipitate was filtered, washed with cold acetonitrile and dried to afford the title compound as a solid (250 mg, 68.6%). MS (ESI): mass calcd. for C$_{21}$H$_{23}$BrFN$_5$O$_2$, 475.1 m/z found, 476.1 [M+H]. $^1$H NMR (400 MHz, CDCl$_3$): δ 8.15-8.04 (m, 2H), 7.56 (d, J=4.5 Hz, 1H), 7.49 (d, J=4.5 Hz, 1H), 7.21-7.12 (m, 2H), 4.30 (s, 4H), 3.67-3.55 (m, 4H), 1.50 (s, 9H).

Step D: tert-Butyl 4-(2-(4-fluorophenyl)-3-(4-hydroxyphenyl)imidazo[1,2-a]pyrazin-8-yl)piperazine-1-carboxylate A suspension of tert-butyl 4-(3-bromo-2-(4-fluorophenyl) imidazo[1,2-a]pyrazin-8-yl)piperazine-1-carboxylate (52.0 mg, 0.109 mmol), (4-hydroxyphenyl)boronic acid (18.1 mg, 0.131 mmol) in dioxane (1.0 mL) and 1M Na$_2$CO$_3$ (1.0 mL) inside a 2 mL microwave vial was treated with Pd(PPh$_3$)$_4$ (12.6 mg, 0.0109 mmol) and then the reaction mixture was purged with nitrogen then heated in microwave at 110° C. for 10 minutes. The reaction mixture was cooled, diluted with water (5.0 mL), extracted with DCM (3×5 mL), dried (Na$_2$SO$_4$), filtered, and concentrated under reduced pressure. Purification (FCC, SiO$_2$, 0 to 40% EtOAc/Hexane) afforded the title compound a solid (58.0 mg, 84.0%). MS (ESI): mass calcd. for C$_{27}$H$_{28}$FN$_5$O$_3$, 489.2 m/z found, 490.2 [M+H]. $^1$H NMR (400 MHz, CDCl$_3$): δ 7.63 (dd, J=8.9, 5.5 Hz, 2H), 7.34-7.26 (m, 4H), 7.08-6.88 (m, 4H), 5.27 (s, 1H), 4.33 (s, 4H), 3.72-3.57 (m, 4H), 1.51 (s, 9H).

Step E: 3-Bromo-2-(4-fluorophenyl)-8-(piperazin-1-yl)imidazo[1,2-a]pyrazine

A solution of tert-butyl 4-(2-(4-fluorophenyl)-3-(4-hydroxyphenyl)imidazo[1,2-a]pyrazin-8-yl)piperazine-1-carboxylate (58 mg, 0.10 mmol) in DCM (1.0 mL) and TFA (78 µL, 1.0 mmol) was stirred for 5 h. Then the solution was concentrated under reduced pressure to afford the title compound (30 mg, 77%). MS (ESI): mass calcd. for C$_{22}$H$_{20}$FN$_5$O, 389.2 m/z found, 390.2 [M+H]. $^1$H NMR (400 MHz, CDCl$_3$): δ 7.69-7.58 (m, 2H), 7.34-7.29 (m, 1H), 7.26-7.21 (m, 2H), 7.03-6.89 (m, 4H), 4.37 (t, J=5.0 Hz, 4H), 3.13 (t, J=5.0 Hz, 4H).

Step F: 4-(8-(4-Acetylpiperazin-1-yl)-2-(4-fluorophenyl)imidazo[1,2-a]pyrazin-3-yl)phenyl acetate A solution of 3-bromo-2-(4-fluorophenyl)-8-(piperazin-1-yl)imidazo[1,2-a]pyrazine (20 mg, 0.036 mmol) in DCM (1.0 mL) was treated with Ac$_2$O (5.1 µL, 0.054 mmol) and Et$_3$N (15 µL, 0.11 mmol) and the resulting solution was stirred for 3 h. The reaction solution was diluted with saturated sodium bicarbonate solution (5 mL) and extracted with DCM (3×5 mL). The DCM layer was concentrated to give the title compound which was used crude in the next step without further purification.

Step G: 1-[4-[2-(4-Fluorophenyl)-3-(4-hydroxyphenyl)imidazo[1,2-a]pyrazin-8-yl]piperazin-1-yl]ethanone A mixture of 4-(8-(4-acetylpiperazin-1-yl)-2-(4-fluorophenyl)imidazo[1,2-a]pyrazin-3-yl)phenyl acetate (17.0 mg, 0.0359 mmol) in THF (1.0 mL) was treated with 3.0 N NaOH (0.10 mL, 0.30 mmol) and the reaction mixture was stirred for 16 h. The reaction mixture was diluted with water (5 mL) and adjusted pH~6 by addition of 1N HCl. Then the aqueous layer was extracted with EtOAc (3×5 mL), dried (Na$_2$SO$_4$), filtered and concentrated to give a solid (11.0 mg, 71.0% in two steps). MS (ESI): mass calcd. for C$_{24}$H$_{22}$FN$_5$O$_2$, 431.1 m/z found, 432.2 [M+H]. $^1$H NMR (400 MHz, DMSO-d$_6$): δ d 9.95 (s, 1H), 7.67-7.59 (m, 2H), 7.37-7.34 (m, 1H), 7.33-7.30 (m, 1H), 7.27 (d, J=8.6 Hz, 2H), 7.22-7.14 (m, 2H), 7.00-6.93 (m, 2H), 4.28 (d, J=68.3 Hz, 4H), 3.63 (d, J=5.1 Hz, 4H), 2.07 (s, 3H).

Example 2-Example 86 were prepared in a manner analogous to Example 1.

Example 2: 4-[2-(4-Fluorophenyl)-8-morpholino-imidazo[1,2-a]pyrazin-3-yl]-3-methyl-phenol

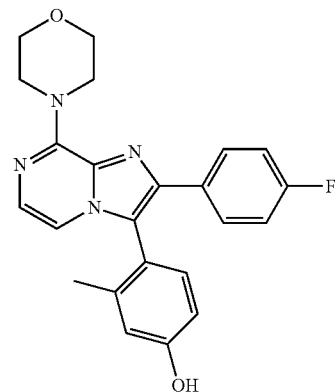 [SMILES: Cc1cc(O)ccc1-c1c(-c2ccc(F)cc2)nc2c(N3CCOCC3)nccn12]

The title compound was prepared in a manner analogous to Example 1. MS (ESI): mass calcd. for C$_{23}$H$_{21}$FN$_4$O$_2$, 404.2; m/z found, 405.2 [M+H]$^+$. $^1$H NMR (400 MHz, CDCl$_3$) δ 7.68-7.57 (m, 2H), 7.31 (d, J=4.5 Hz, 1H), 7.14 (d, J=8.2 Hz, 1H), 7.02-6.92 (m, 3H), 6.89 (d, J=2.5 Hz, 1H), 6.82 (dd, J=8.2, 2.6 Hz, 1H), 5.36 (s, 1H), 4.38 (td, J=4.5, 2.9 Hz, 4H), 3.94 (t, J=4.8 Hz, 4H), 1.95 (s, 3H).

Example 3: tert-Butyl 4-[2-(4-fluorophenyl)-3-(4-hydroxyphenyl)imidazo[1,2-a]pyrazin-8-yl]piperazine-1-carboxylate

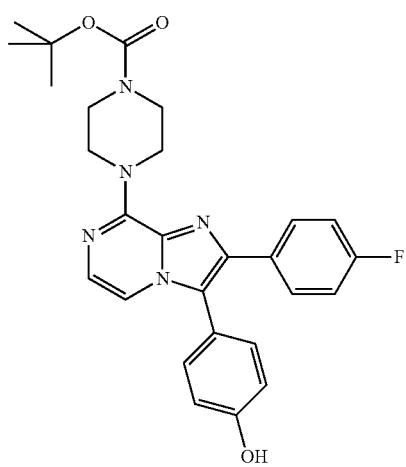 [SMILES: CC(C)(C)OC(=O)N1CCN(c2nccn3c(-c4ccc(O)cc4)c(-c4ccc(F)cc4)nc23)CC1]

The title compound was prepared in a manner analogous to Example 1. MS (ESI): mass calcd. for C$_{27}$H$_{28}$FN$_5$O$_3$, 489.2; m/z found, 490.3 [M+H]$^+$. $^1$H NMR (400 MHz, CDCl$_3$) δ 7.63 (dd, J=8.9, 5.5 Hz, 2H), 7.34-7.26 (m, 4H), 7.08-6.88 (m, 4H), 5.27 (s, 1H), 4.33 (s, 4H), 3.72-3.57 (m, 4H), 1.51 (s, 9H).

Example 4: 4-[2-(3-Fluorophenyl)-8-morpholinoimidazo[1,2-a]pyrazin-3-yl]phenol

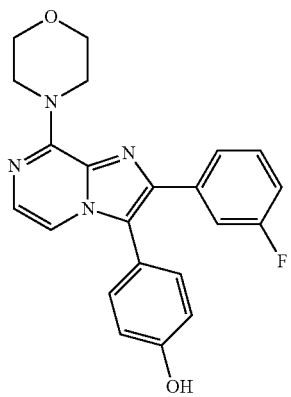 [SMILES: Oc1ccc(-c2c(-c3cccc(F)c3)nc3c(N4CCOCC4)nccn23)cc1]

The title compound was prepared in a manner analogous to Example 1. MS (ESI): mass calcd. for $C_{22}H_{19}FN_4O_2$, 390.1; m/z found, 391.2 [M+H]⁺. ¹H NMR (400 MHz, CDCl₃) δ 7.47-7.35 (m, 2H), 7.33-7.27 (m, 3H), 7.25-7.18 (m, 2H), 7.05-6.97 (m, 2H), 6.94 (td, J=8.5, 2.8 Hz, 1H), 5.09 (s, 1H), 4.37 (t, J=4.7 Hz, 4H), 3.92 (t, J=4.8 Hz, 4H).

Example 5: 4-[2-(4-Fluorophenyl)-8-piperazin-1-yl-imidazo[1,2-a]pyrazin-3-yl]phenol

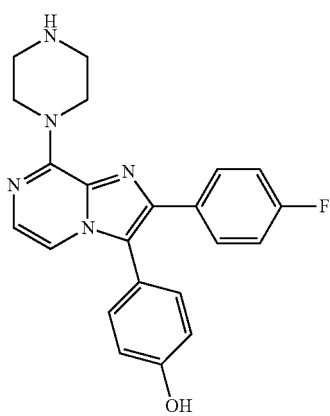 [SMILES: Oc1ccc(-c2c(-c3ccc(F)cc3)nc3c(N4CCNCC4)nccn23)cc1]

The title compound was prepared in a manner analogous to Example 1. MS (ESI): mass calcd. for $C_{22}H_{20}FN_5O$, 389.2; m/z found, 390.2 [M+H]⁺. ¹H NMR (400 MHz, CDCl₃) δ 7.69-7.58 (m, 2H), 7.34-7.29 (m, 1H), 7.26-7.21 (m, 2H), 7.03-6.89 (m, 4H), 4.37 (t, J=5.0 Hz, 4H), 3.13 (t, J=5.0 Hz, 4H).

Example 6: 4-[2-(4-Fluorophenyl)-8-(4-methylpiperazin-1-yl)imidazo[1,2-a]pyrazin-3-yl]phenol

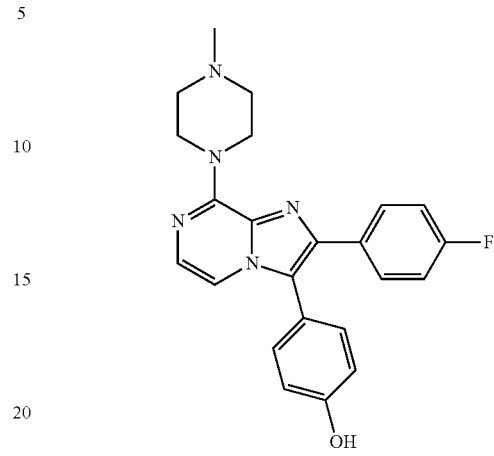

The title compound was prepared in a manner analogous to Example 1. MS (ESI): mass calcd. for $C_{23}H_{22}FN_5O$, 403.2; m/z found, 404.2 [M+H]⁺. ¹H NMR (400 MHz, CDCl₃) δ 7.71-7.55 (m, 2H), 7.24 (dd, J=5.1, 2.2 Hz, 4H), 7.07-6.86 (m, 4H), 4.37 (s, 4H), 2.65 (d, J=4.9 Hz, 4H), 2.38 (dd, J=5.5, 2.7 Hz, 3H).

Example 7: 4-[2-(4-Fluorophenyl)-8-(6-oxa-2-azaspiro[3.3]heptan-2-yl)imidazo[1,2-a]pyrazin-3-yl]phenol

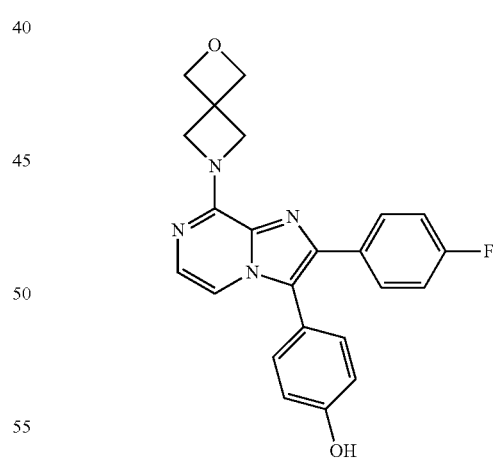

The title compound was prepared in a manner analogous to Example 1. MS (ESI): mass calcd. for $C_{23}H_{19}FN_4O_2$, 402.1; m/z found, 403.2 [M+H]⁺. ¹H NMR (400 MHz, DMSO-d₆) δ 9.94 (s, 1H), 7.63 (dd, J=8.9, 5.6 Hz, 2H), 7.28-7.21 (m, 4H), 7.18 (t, J=8.9 Hz, 2H), 6.95 (d, J=8.6 Hz, 2H), 4.78 (s, 4H), 4.60 (s, 4H).

Example 8: 5-[2-(4-Fluorophenyl)-8-morpholino-imidazo[1,2-a]pyrazin-3-yl]indolin-2-one

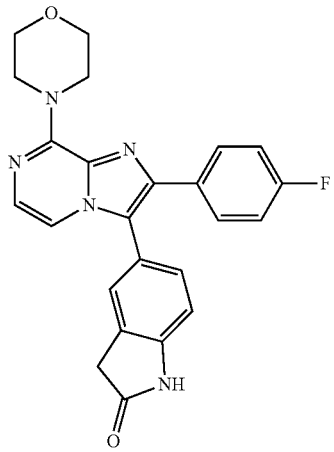 [SMILES: O=C1Cc2cc(-c3c(-c4ccc(F)cc4)nc4c(N5CCOCC5)nccn34)ccc2N1]

The title compound was prepared in a manner analogous to Example 1. MS (ESI): mass calcd. for $C_{24}H_{20}FN_5O_2$, 429.2; m/z found, 430.1 [M+H]$^+$. $^1$H NMR (400 MHz, CDCl$_3$) δ 8.12 (s, 1H), 7.61 (dd, J=8.9, 5.5 Hz, 2H), 7.33 (d, J=4.6 Hz, 1H), 7.26-7.22 (m, 4H), 7.04 (dd, J=7.8, 0.7 Hz, 1H), 6.98 (t, J=8.7 Hz, 2H), 4.37 (t, J=4.8 Hz, 4H), 3.92 (t, J=4.8 Hz, 4H), 3.62 (s, 2H).

Example 9: 4-[2-(4-Fluorophenyl)-8-(1-piperidyl)imidazo[1,2-a]pyrazin-3-yl]phenol

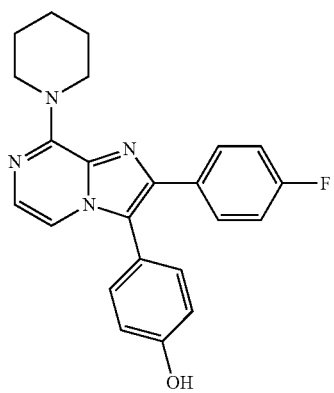 [SMILES: Oc1ccc(-c2c(-c3ccc(F)cc3)nc3c(N4CCCCC4)nccn23)cc1]

The title compound was prepared in a manner analogous to Example 1. MS (ESI): mass calcd. for $C_{23}H_{21}FN_4O$, 388.2; m/z found, 389.2 [M+H]$^+$. $^1$H NMR (400 MHz, CDCl$_3$) δ 7.64 (dd, J=8.9, 5.5 Hz, 2H), 7.32-7.27 (m, 2H), 7.18 (d, J=4.6 Hz, 1H), 7.08-6.89 (m, 4H), 5.61 (s, 1H), 4.30 (s, 4H), 1.76 (s, 6H).

Example 10: 4-[2-(4-Fluorophenyl)-3-(1H-indazol-5-yl)imidazo[1,2-a]pyrazin-8-yl]morpholine

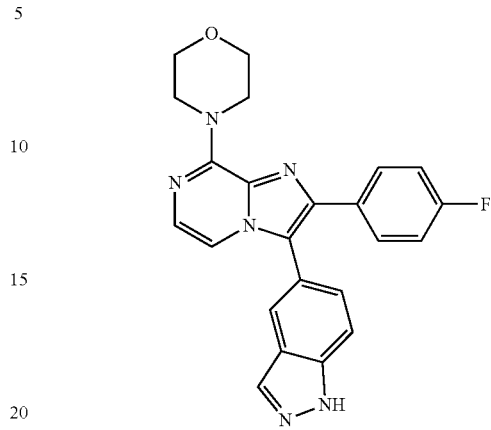

The title compound was prepared in a manner analogous to Example 1. MS (ESI): mass calcd. for $C_{23}H_{19}FN_6O$, 414.2; m/z found, 415.2 [M+H]$^+$. $^1$H NMR (400 MHz, CDCl$_3$) δ 10.25 (s, 1H), 8.16 (d, J=1.1 Hz, 1H), 7.86 (dd, J=1.5, 0.9 Hz, 1H), 7.67 (dt, J=8.6, 1.0 Hz, 1H), 7.63-7.56 (m, 2H), 7.38 (dd, J=8.6, 1.5 Hz, 1H), 7.33 (d, J=4.6 Hz, 1H), 6.94 (t, J=8.8 Hz, 2H), 4.38 (t, J=4.7 Hz, 4H), 3.93 (t, J=4.8 Hz, 4H).

Example 11: 5-[2-(4-Fluorophenyl)-8-morpholino-imidazo[1,2-a]pyrazin-3-yl]-1,3-dihydrobenzimidazol-2-one

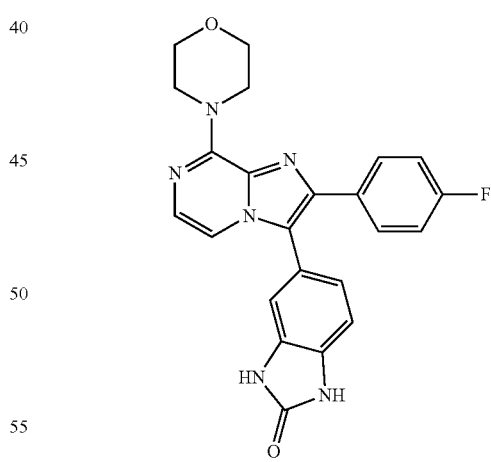

The title compound was prepared in a manner analogous to Example 1. MS (ESI): mass calcd. for $C_{23}H_{19}FN_6O_2$, 430.2; m/z found, 431.1 [M+H]$^+$. $^1$H NMR (400 MHz, DMSO-d$_6$) δ 10.86 (d, J=47.3 Hz, 2H), 7.60 (dd, J=8.7, 5.7 Hz, 2H), 7.35 (q, J=4.6 Hz, 2H), 7.22-7.09 (m, 3H), 7.06-6.88 (m, 2H), 4.26 (t, J=4.6 Hz, 4H), 3.79 (t, J=4.8 Hz, 4H).

Example 12: 5-[8-(4-Acetylpiperazin-1-yl)-2-(4-fluorophenyl)imidazo[1,2-a]pyrazin-3-yl]indolin-2-one

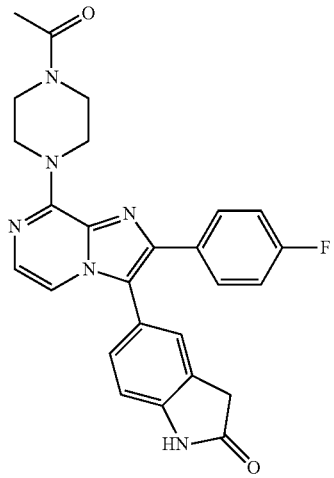 [SMILES: CC(=O)N1CCN(c2nccn3c(-c4ccc5c(c4)CC(=O)N5)c(-c4ccc(F)cc4)nc23)CC1]

The title compound was prepared in a manner analogous to Example 1. MS (ESI): mass calcd. for $C_{26}H_{23}FN_6O_2$, 470.2; m/z found, 471.2 [M+H]$^+$. $^1$H NMR (400 MHz, CDCl$_3$) δ 7.86 (s, 1H), 7.66-7.58 (m, 2H), 7.34 (d, J=4.6 Hz, 1H), 7.26 (s, 3H), 7.08-6.94 (m, 3H), 4.38 (dt, J=42.7, 5.2 Hz, 4H), 3.76 (dt, J=59.4, 5.2 Hz, 4H), 3.62 (s, 2H), 2.19 (s, 3H).

Example 13: 1-[4-[2-(4-Fluorophenyl)-3-(1H-indazol-5-yl)imidazo[1,2-a]pyrazin-8-yl]piperazin-1-yl]ethanone

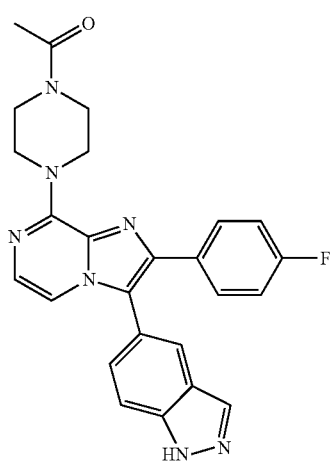 [SMILES: CC(=O)N1CCN(c2nccn3c(-c4ccc5[nH]ncc5c4)c(-c4ccc(F)cc4)nc23)CC1]

The title compound was prepared in a manner analogous to Example 1. MS (ESI): mass calcd. for $C_{25}H_{22}FN_7O$, 455.2; m/z found, 456.2 [M+H]$^+$. $^1$H NMR (400 MHz, CDCl$_3$) δ 10.36 (s, 1H), 8.17 (d, J=1.0 Hz, 1H), 7.86 (dd, J=1.6, 0.9 Hz, 1H), 7.68 (dt, J=8.6, 1.0 Hz, 1H), 7.65-7.56 (m, 2H), 7.38 (dd, J=8.6, 1.5 Hz, 1H), 7.36-7.32 (m, 1H), 7.31-7.27 (m, 1H), 6.95 (t, J=8.7 Hz, 2H), 4.40 (dt, J=44.5, 5.3 Hz, 4H), 3.97-3.62 (m, 4H), 2.20 (s, 3H).

Example 14: 5-[8-(4-Acetylpiperazin-1-yl)-2-(4-fluorophenyl)imidazo[1,2-a]pyrazin-3-yl]-1,3-dihydrobenzimidazol-2-one

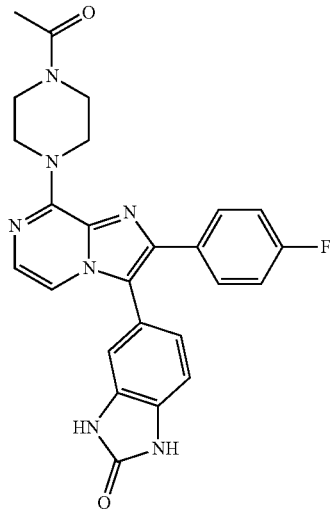 [SMILES: CC(=O)N1CCN(c2nccn3c(-c4ccc5[nH]c(=O)[nH]c5c4)c(-c4ccc(F)cc4)nc23)CC1]

The title compound was prepared in a manner analogous to Example 1. MS (ESI): mass calcd. for $C_{25}H_{22}FN_7O_2$, 471.2; m/z found, 472.2 [M+H]$^+$. $^1$H NMR (400 MHz, DMSO-d$_6$) δ 10.92 (s, 1H), 10.80 (s, 1H), 7.65-7.58 (m, 2H), 7.35 (q, J=4.6 Hz, 2H), 7.23-7.09 (m, 3H), 7.02 (dd, J=8.0, 1.6 Hz, 1H), 6.96 (s, 1H), 4.29 (d, J=67.8 Hz, 4H), 3.64 (d, J=5.2 Hz, 4H), 2.08 (s, 3H).

Example 15: 4-(2-Benzyl-8-morpholino-imidazo[1,2-a]pyrazin-3-yl)phenol

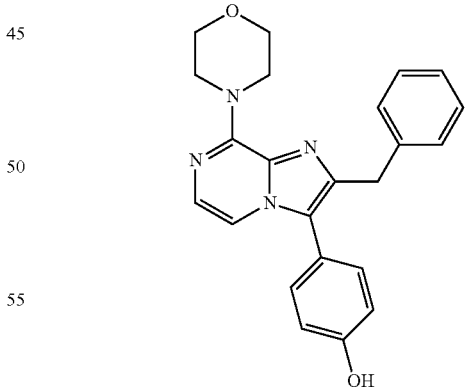

The title compound was prepared in a manner analogous to Example 1. MS (ESI): mass calcd. for $C_{23}H_{22}N_4O_2$, 386.2; m/z found, 387.0 [M+H]$^+$. $^1$H NMR (400 MHz, CDCl$_3$) δ 7.36-7.32 (m, 1H), 7.31-7.28 (m, 1H), 7.25-7.13 (m, 7H), 6.97-6.92 (m, 2H), 5.28 (s, 1H), 4.28 (t, J=4.8 Hz, 4H), 4.07 (s, 2H), 3.88 (t, J=4.8 Hz, 4H).

Example 16: 4-[2-(4-Fluorophenyl)-3-(1H-indol-5-yl)imidazo[1,2-a]pyrazin-8-yl]morpholine

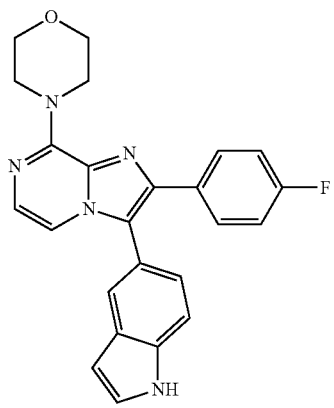 [SMILES: Fc1ccc(-c2nc3c(N4CCOCC4)nccn3c2-c2ccc3[nH]ccc3c2)cc1]

The title compound was prepared in a manner analogous to Example 1. MS (ESI): mass calcd. for $C_{24}H_{20}FN_5O$, 413.2; m/z found, 414.2 [M+H]$^+$. $^1$H NMR (400 MHz, CDCl$_3$) δ 8.44 (s, 1H), 7.70 (dd, J=1.6, 0.8 Hz, 1H), 7.68-7.61 (m, 2H), 7.54 (dt, J=8.3, 0.9 Hz, 1H), 7.34 (dd, J=3.2, 2.4 Hz, 1H), 7.32-7.27 (m, 2H), 7.16 (dd, J=8.3, 1.6 Hz, 1H), 6.92 (t, J=8.8 Hz, 2H), 6.63 (ddd, J=3.1, 2.1, 0.9 Hz, 1H), 4.38 (t, J=4.8 Hz, 4H), 3.93 (t, J=4.8 Hz, 4H).

Example 17: 5-[8-(4-Acetylpiperazin-1-yl)-2-benzyl-imidazo[1,2-a]pyrazin-3-yl]indolin-2-one

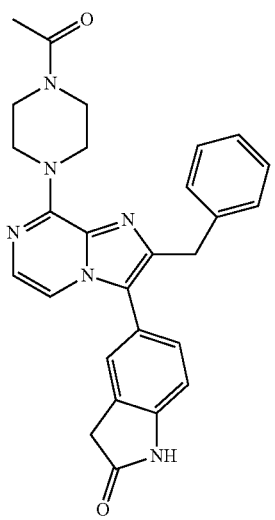 [SMILES: CC(=O)N1CCN(c2nccn3c(-c4ccc5c(c4)CC(=O)N5)c(Cc4ccccc4)nc23)CC1]

The title compound was prepared in a manner analogous to Example 1. MS (ESI): mass calcd. for $C_{27}H_{26}N_6O_2$, 466.2; m/z found, 467.2 [M+H]$^+$. $^1$H NMR (400 MHz, CDCl$_3$) δ 8.63 (s, 1H), 7.38-7.33 (m, 1H), 7.33-7.29 (m, 1H), 7.26-7.15 (m, 7H), 7.01 (dd, J=8.0, 0.6 Hz, 1H), 4.46-4.31 (m, 2H), 4.27 (dd, J=6.2, 4.2 Hz, 2H), 4.09 (s, 2H), 3.90-3.75 (m, 2H), 3.65 (dd, J=6.2, 4.1 Hz, 2H), 3.60 (s, 2H), 2.18 (s, 3H).

Example 18: 1-[4-[2-Benzyl-3-(1H-indazol-5-yl)imidazo[1,2-a]pyrazin-8-yl]piperazin-1-yl]ethanone

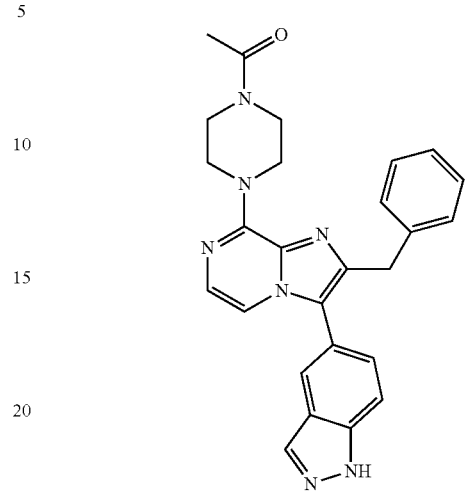

The title compound was prepared in a manner analogous to Example 1. MS (ESI): mass calcd. for $C_{26}H_{25}N_7O$, 451.2; m/z found, 452.2 [M+H]$^+$. $^1$H NMR (400 MHz, CDCl$_3$) δ 10.59 (s, 1H), 8.14 (d, J=1.0 Hz, 1H), 7.74 (dd, J=1.5, 0.9 Hz, 1H), 7.63 (dt, J=8.6, 1.0 Hz, 1H), 7.39-7.33 (m, 2H), 7.33-7.29 (m, 1H), 7.30-7.12 (m, 5H), 4.45-4.23 (m, 4H), 4.19-4.09 (m, 2H), 3.90-3.58 (m, 4H), 2.19 (s, 3H).

Example 19: 5-[8-(4-Acetylpiperazin-1-yl)-2-benzyl-imidazo[1,2-a]pyrazin-3-yl]-1,3-dihydrobenzimidazol-2-one

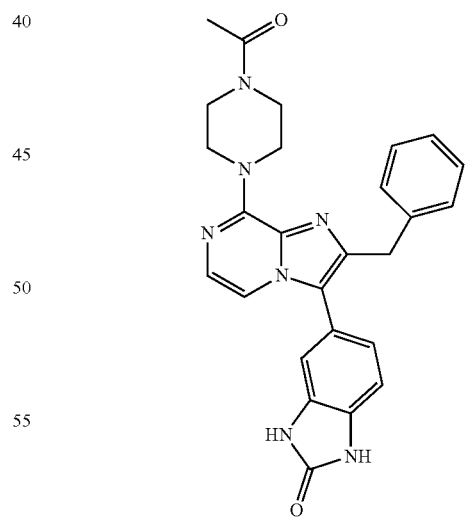

The title compound was prepared in a manner analogous to Example 1. MS (ESI): mass calcd. for $C_{26}H_{25}N_7O_2$, 467.2; m/z found, 468.2 [M+H]$^+$. $^1$H NMR (400 MHz, CDCl$_3$) δ 9.34 (d, J=32.0 Hz, 2H), 7.36 (d, J=4.6 Hz, 1H), 7.29 (d, J=4.6 Hz, 1H), 7.25-7.10 (m, 6H), 7.08-6.98 (m, 2H), 4.30 (dt, J=35.1, 5.0 Hz, 4H), 4.09 (s, 2H), 3.72 (dt, J=63.2, 5.2 Hz, 4H), 2.17 (s, 3H).

Example 20: 5-(2-Benzyl-8-morpholino-imidazo[1,2-a]pyrazin-3-yl)indolin-2-one

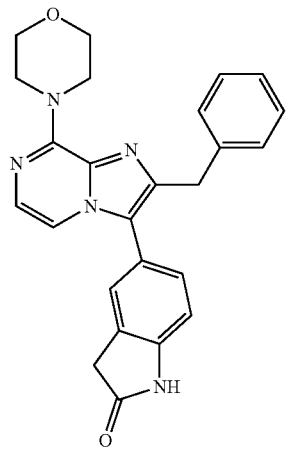 [SMILES: O=C1Cc2cc(-c3c(Cc4ccccc4)nc4c(N5CCOCC5)nccn34)ccc2N1]

The title compound was prepared in a manner analogous to Example 1. MS (ESI): mass calcd. for $C_{25}H_{23}N_5O_2$, 425.2; m/z found, 426.2 [M+H]$^+$. $^1$H NMR (400 MHz, CDCl$_3$) δ 7.77 (d, J=6.7 Hz, 1H), 7.57 (s, 1H), 7.31 (d, J=0.8 Hz, 2H), 7.25-7.11 (m, 6H), 7.01-6.92 (m, 1H), 4.29 (t, J=4.8 Hz, 4H), 4.08 (s, 2H), 3.89 (t, J=4.8 Hz, 4H), 3.58 (s, 2H).

Example 21: 4-[2-Benzyl-3-(1H-indazol-5-yl)imidazo[1,2-a]pyrazin-8-yl]morpholine

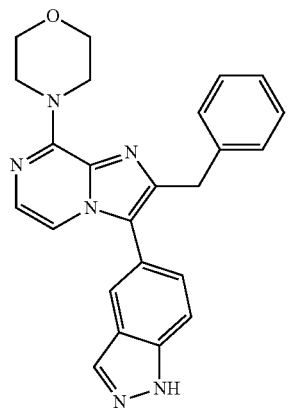 [SMILES: c1ccc(Cc2nc3c(N4CCOCC4)nccn3c2-c2ccc3[nH]ncc3c2)cc1]

The title compound was prepared in a manner analogous to Example 1. MS (ESI): mass calcd. for $C_{24}H_{22}N_6O$, 410.2; m/z found, 411.2 [M+H]$^+$. $^1$H NMR (400 MHz, CDCl$_3$) δ 10.23 (s, 1H), 8.14 (d, J=1.1 Hz, 1H), 7.73 (dd, J=1.5, 0.8 Hz, 1H), 7.62 (dt, J=8.6, 1.0 Hz, 1H), 7.39-7.29 (m, 3H), 7.25-7.12 (m, 5H), 4.31 (t, J=4.8 Hz, 4H), 4.11 (s, 2H), 4.02-3.77 (m, 4H).

Example 22: 5-(2-Benzyl-8-morpholino-imidazo[1,2-a]pyrazin-3-yl)-1,3-dihydrobenzimidazol-2-one

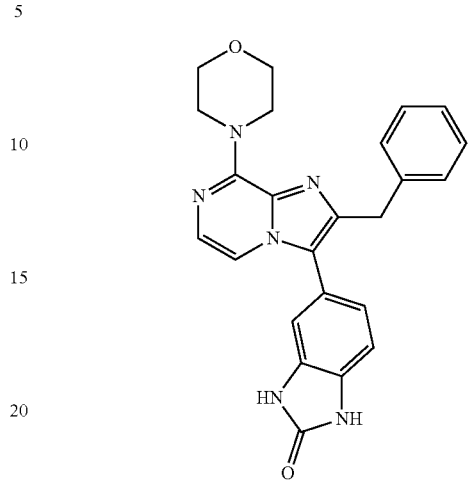

The title compound was prepared in a manner analogous to Example 1. MS (ESI): mass calcd. for $C_{24}H_{22}N_6O_2$ 426.2; m/z found 427.2 [M+H]$^+$. $^1$H NMR (400 MHz, CDCl$_3$) δ 7.36 (d, J=4.6 Hz, 1H), 7.32-7.29 (m, 1H), 7.26-7.11 (m, 6H), 7.06-7.01 (m, 1H), 6.94 (dd, J=1.6, 0.6 Hz, 1H), 4.27 (t, J=4.8 Hz, 4H), 4.09 (s, 2H), 3.89 (t, J=4.8 Hz, 4H), 3.43 (t, J=1.8 Hz, 1H), 1.98 (s, 1H).

Example 23: 1-[4-[2-Benzyl-3-(4-hydroxyphenyl)imidazo[1,2-a]pyrazin-8-yl]piperazin-1-yl]ethanone

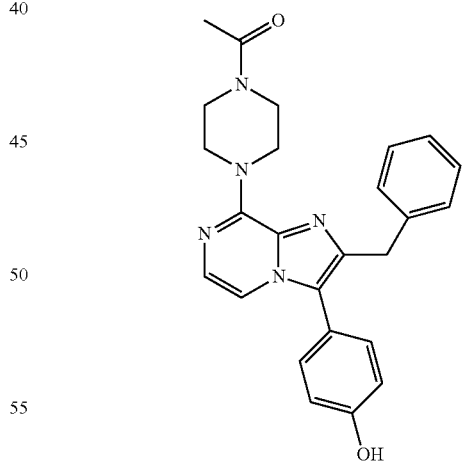

The title compound was prepared in a manner analogous to Example 1. MS (ESI): mass calcd. for $C_{25}H_{25}N_5O_2$, 427.2; m/z found, 428.2 [M+H]$^+$. $^1$H NMR (400 MHz, CDCl$_3$) δ 7.36 (d, J=4.6 Hz, 1H), 7.32-7.28 (m, 1H), 7.26 (s, 7H), 6.96 (d, J=8.5 Hz, 2H), 5.34 (s, 1H), 4.30 (dt, J=37.4, 5.3 Hz, 4H), 4.08 (s, 2H), 3.72 (dt, J=62.0, 5.3 Hz, 4H), 2.17 (s, 3H).

Example 24: 5-[2-(4-Fluorophenyl)-8-(6-oxa-2-azaspiro[3.3]heptan-2-yl)imidazo[1,2-a]pyrazin-3-yl]indolin-2-one

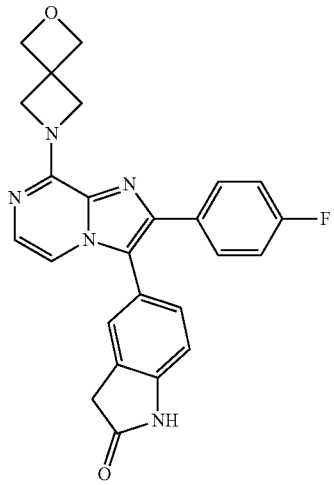 [SMILES: O=C1Cc2cc(-c3c(-c4ccc(F)cc4)nc4c(N5CC6(COC6)C5)nccn34)ccc2N1]

The title compound was prepared in a manner analogous to Example 1. MS (ESI): mass calcd. for $C_{25}H_{20}FN_5O_2$, 441.2; m/z found, 442.1 [M+H]$^+$. $^1$H NMR (400 MHz, CDCl$_3$) δ 7.80 (s, 1H), 7.63 (dd, J=8.9, 5.4 Hz, 2H), 7.28 (m, 3H), 7.17 (d, J=4.7 Hz, 1H), 7.08-6.93 (m, 3H), 4.92 (s, 4H), 4.74 (s, 4H), 3.61 (s, 2H).

Example 25: 2-[2-(4-Fluorophenyl)-3-(1H-indazol-5-yl)imidazo[1,2-a]pyrazin-8-yl]-6-oxa-2-azaspiro[3.3]heptane

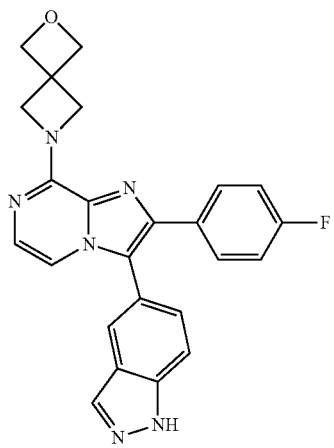 [SMILES: Fc1ccc(-c2nc3c(N4CC5(COC5)C4)nccn3c2-c2ccc3[nH]ncc3c2)cc1]

The title compound was prepared in a manner analogous to Example 1. MS (ESI): mass calcd. for $C_{24}H_{19}FN_6O$, 426.2; m/z found, 427.1 [M+H]$^+$. $^1$H NMR (400 MHz, CDCl$_3$) δ 10.52 (s, 1H), 8.16 (d, J=1.0 Hz, 1H), 7.85 (dd, J=1.5, 0.8 Hz, 1H), 7.71-7.55 (m, 3H), 7.37 (dd, J=8.6, 1.5 Hz, 1H), 7.28 (d, J=4.7 Hz, 1H), 7.19 (d, J=4.7 Hz, 1H), 6.95 (t, J=8.7 Hz, 2H), 4.93 (s, 4H), 4.76 (s, 4H).

Example 26: 5-[2-(4-Fluorophenyl)-8-(6-oxa-2-azaspiro[3.3]heptan-2-yl)imidazo[1,2-a]pyrazin-3-yl]-1,3-dihydrobenzimidazol-2-one

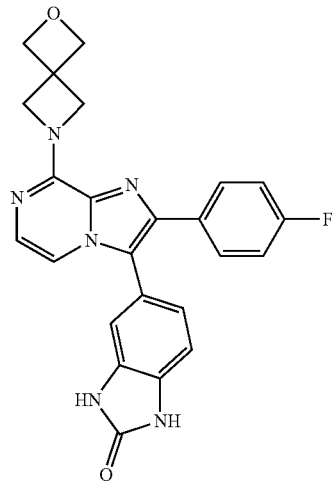 [SMILES: O=c1[nH]c2ccc(-c3c(-c4ccc(F)cc4)nc4c(N5CC6(COC6)C5)nccn34)cc2[nH]1]

The title compound was prepared in a manner analogous to Example 1. MS (ESI): mass calcd. for $C_{24}H_{19}FN_6O_2$, 442.2; m/z found, 443.1 [M+H]$^+$. $^1$H NMR (400 MHz, DMSO-d$_6$) δ 10.90 (s, 1H), 10.78 (d, J=1.8 Hz, 1H), 7.62 (dd, J=8.7, 5.7 Hz, 2H), 7.26 (q, J=4.7 Hz, 2H), 7.17 (t, J=8.9 Hz, 2H), 7.14-7.09 (m, 1H), 7.00 (dd, J=7.9, 1.6 Hz, 1H), 6.94 (d, J=1.5 Hz, 1H), 4.79 (s, 4H), 4.61 (s, 4H).

Example 27: 4-[2-(4-Fluorophenyl)-3-(4-hydroxyphenyl)imidazo[1,2-a]pyrazin-8-yl]piperazin-2-one

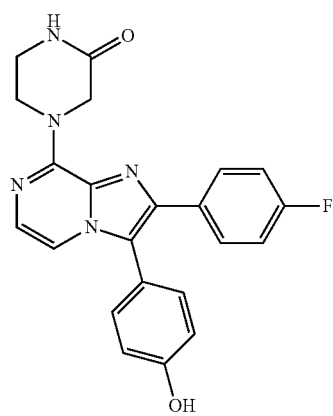 [SMILES: O=C1CN(c2nccn3c(-c4ccc(O)cc4)c(-c4ccc(F)cc4)nc23)CCN1]

The title compound was prepared in a manner analogous to Example 1. MS (ESI): mass calcd. for $C_{22}H_{18}FN_5O_2$, 403.1; m/z found, 404.0 [M+H]$^+$. $^1$H NMR (400 MHz, DMSO-d$_6$) δ 9.96 (s, 1H), 8.11 (s, 1H), 7.67-7.56 (m, 2H), 7.39-7.35 (m, 1H), 7.35-7.31 (m, 1H), 7.27 (d, J=8.5 Hz, 2H), 7.19 (t, J=8.9 Hz, 2H), 6.97 (d, J=8.6 Hz, 2H), 4.71 (s, 2H), 4.52 (s, 2H), 3.45-3.37 (m, 2H).

Example 28: 4-[8-(4,4-Difluoro-1-piperidyl)-2-(4-fluorophenyl)imidazo[1,2-a]pyrazin-3-yl]phenol

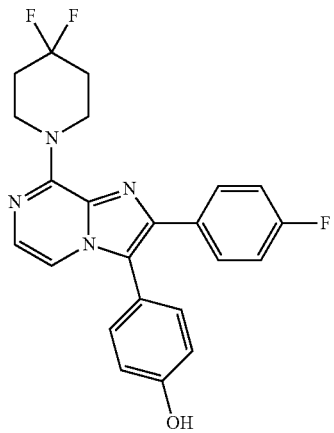 [SMILES: Oc1ccc(-c2c(-c3ccc(F)cc3)nc3c(N4CCC(F)(F)CC4)nccn23)cc1]

The title compound was prepared in a manner analogous to Example 1. MS (ESI): mass calcd. for $C_{23}H_{19}F_3N_4O$, 424.2; m/z found, 425.0 [M+H]$^+$. $^1$H NMR (400 MHz, CDCl$_3$) δ 7.67-7.59 (m, 2H), 7.34-7.31 (m, 1H), 7.31-7.26 (m, 4H), 7.05-6.93 (m, 4H), 4.49 (t, J=5.8 Hz, 4H), 2.15 (dt, J=14.0, 7.7 Hz, 4H).

Example 29: 4-[8-(3,3-Difluoro-1-piperidyl)-2-(4-fluorophenyl)imidazo[1,2-a]pyrazin-3-yl]phenol

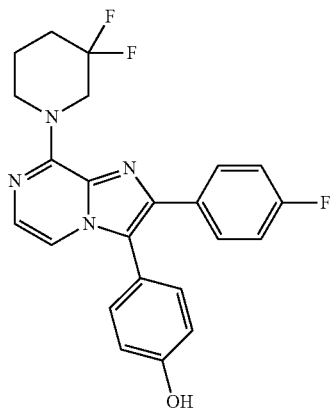 [SMILES: Oc1ccc(-c2c(-c3ccc(F)cc3)nc3c(N4CCCC(F)(F)C4)nccn23)cc1]

The title compound was prepared in a manner analogous to Example 1. MS (ESI): mass calcd. for $C_{23}H_{19}F_3N_4O$, 424.2; m/z found, 425.0 [M+H]$^+$. $^1$H NMR (400 MHz, CDCl$_3$) δ 7.64 (dd, J=8.9, 5.4 Hz, 2H), 7.34-7.30 (m, 1H), 7.30-7.26 (m, 4H), 7.03-6.93 (m, 4H), 4.75 (t, J=11.8 Hz, 2H), 4.28 (t, J=5.2 Hz, 2H), 2.15 (td, J=13.5, 6.8 Hz, 2H), 2.07-1.92 (m, 2H).

Example 30: 4-[3-(1H-Benzotriazol-5-yl)-2-(4-fluorophenyl)imidazo[1,2-a]pyrazin-8-yl]morpholine

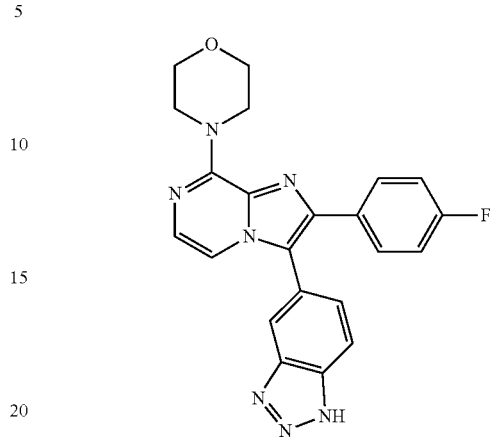

The title compound was prepared in a manner analogous to Example 1. MS (ESI): mass calcd. for $C_{22}H_{18}FN_7O$, 415.2; m/z found, 416.0 [M+H]$^+$. $^1$H NMR (400 MHz, DMSO-d$_6$) δ 8.12 (s, 2H), 7.60-7.51 (m, 2H), 7.46 (d, J=8.7 Hz, 1H), 7.42 (d, J=4.6 Hz, 1H), 7.36 (d, J=4.6 Hz, 1H), 7.21-7.09 (m, 2H), 4.27 (t, J=4.7 Hz, 4H), 3.80 (t, J=4.7 Hz, 4H).

Example 31: 4-[3-(1H-Benzimidazol-5-yl)-2-(4-fluorophenyl)imidazo[1,2-a]pyrazin-8-yl]morpholine

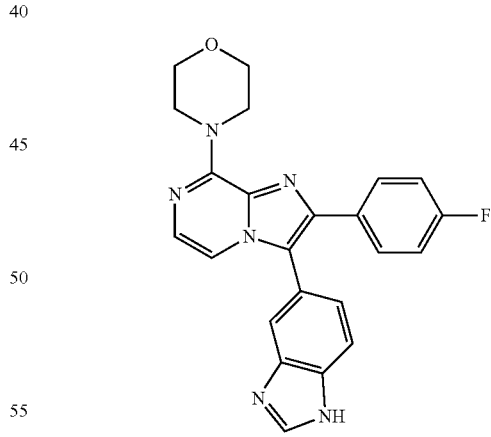

The title compound was prepared in a manner analogous to Example 1. MS (ESI): mass calcd. for $C_{23}H_{19}FN_6O$, 414.2; m/z found, 415.0 [M+H]$^+$. $^1$H NMR (400 MHz, DMSO-d$_6$) δ 12.71 (d, J=35.1 Hz, 1H), 8.37 (s, 1H), 7.86 (d, J=8.3 Hz, 0.5H), 7.77 (s, 0.5H), 7.74 (d, J=8.3 Hz, 0.5H), 7.64 (s, 0.5H), 7.58 (dd, J=8.7, 5.7 Hz, 2H), 7.41-7.29 (m, 2H), 7.24 (t, J=7.5 Hz, 1H), 7.14 (td, J=8.8, 3.3 Hz, 2H), 4.27 (d, J=4.6 Hz, 4H), 3.80 (t, J=4.7 Hz, 4H).

Example 32: 5-[2-(4-Fluorophenyl)-8-(3-oxopiperazin-1-yl)imidazo[1,2-a]pyrazin-3-yl]indolin-2-one

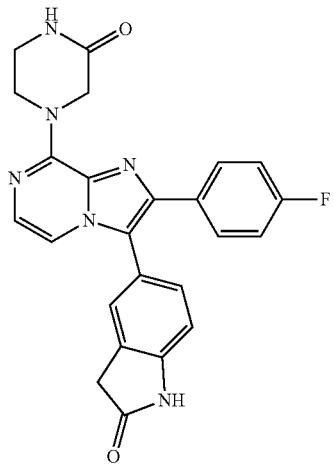 [SMILES: O=C1CN(c2nccn3c(-c4ccc5c(c4)CC(=O)N5)c(-c4ccc(F)cc4)nc23)CCN1]

The title compound was prepared in a manner analogous to Example 1. MS (ESI): mass calcd. for $C_{24}H_{19}FN_6O_2$, 442.2; m/z found, 443.2 [M+H]$^+$. $^1$H NMR (500 MHz, DMSO-d$_6$) δ 10.64 (s, 1H), 8.09 (s, 1H), 7.76-7.52 (m, 2H), 7.39-7.34 (m, 2H), 7.32 (d, J=1.6 Hz, 1H), 7.25 (dd, J=8.0, 1.7 Hz, 1H), 7.19 (t, J=8.9 Hz, 2H), 7.01 (d, J=7.9 Hz, 1H), 4.72 (s, 2H), 4.52 (t, J=5.4 Hz, 2H), 3.70-3.49 (m, 2H), 3.39 (td, J=6.5, 5.8, 2.6 Hz, 2H).

Example 33: 4-[2-(4-Fluorophenyl)-3-(1H-indazol-5-yl)imidazo[1,2-a]pyrazin-8-yl]piperazin-2-one

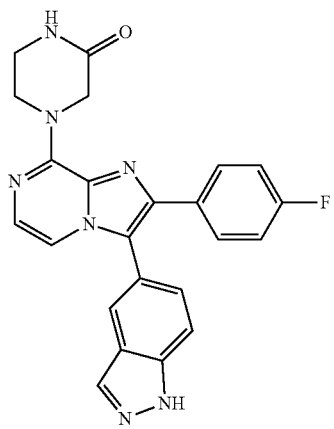 [SMILES: O=C1CN(c2nccn3c(-c4ccc5[nH]ncc5c4)c(-c4ccc(F)cc4)nc23)CCN1]

The title compound was prepared in a manner analogous to Example 1. MS (ESI): mass calcd. for $C_{23}H_{18}FN_7O$, 427.2; m/z found, 428.0 [M+H]$^+$. $^1$H NMR (400 MHz, DMSO-d$_6$) δ 13.36 (s, 1H), 8.19 (s, 1H), 8.11 (s, 1H), 7.95 (s, 1H), 7.76 (d, J=8.6 Hz, 1H), 7.66-7.50 (m, 2H), 7.47-7.29 (m, 3H), 7.15 (t, J=8.9 Hz, 2H), 4.74 (s, 2H), 4.54 (s, 2H), 3.40 (s, 2H), 3.28 (s, 2H).

Example 34: 5-[2-(4-Fluorophenyl)-8-(3-oxopiperazin-1-yl)imidazo[1,2-a]pyrazin-3-yl]-1,3-dihydrobenzimidazol-2-one

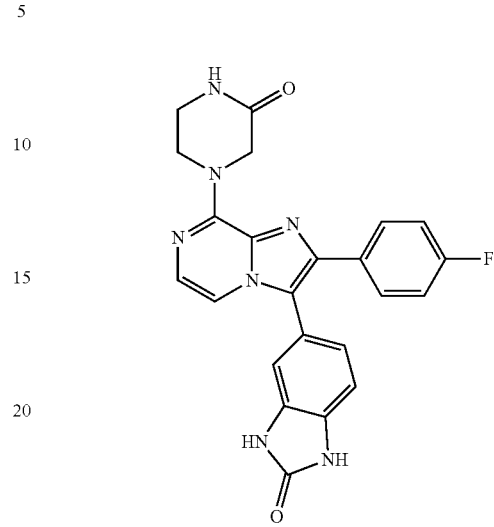

The title compound was prepared in a manner analogous to Example 1. MS (ESI): mass calcd. for $C_{23}H_{18}FN_7O_2$, 443.2; m/z found, 444.2 [M+H]$^+$. $^1$H NMR (400 MHz, DMSO-d$_6$) δ 10.91 (s, 1H), 10.79 (s, 1H), 8.10 (s, 1H), 7.61 (dd, J=8.7, 5.6 Hz, 2H), 7.36 (q, J=4.6 Hz, 2H), 7.23-7.09 (m, 3H), 7.02 (dd, J=7.9, 1.6 Hz, 1H), 6.99-6.87 (m, 1H), 4.72 (s, 2H), 4.52 (s, 2H), 3.39 (d, J=5.3 Hz, 2H).

Example 35: 5-[2-(3,4-Difluorophenyl)-8-morpholino-imidazo[1,2-a]pyrazin-3-yl]indolin-2-one

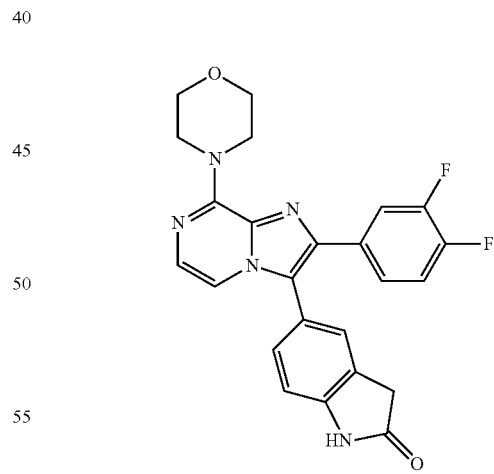

The title compound was prepared in a manner analogous to Example 1. MS (ESI): mass calcd. for $C_{24}H_{19}F_2N_5O_2$, 447.2; m/z found, 447.9 [M+H]$^+$. $^1$H NMR (400 MHz, DMSO-d$_6$) δ 10.67 (s, 1H), 7.66-7.54 (m, 2H), 7.44-7.39 (m, 1H), 7.39-7.31 (m, 3H), 7.30-7.23 (m, 1H), 7.03 (d, J=8.0 Hz, 1H), 4.26 (t, J=4.7 Hz, 4H), 3.79 (t, J=4.7 Hz, 4H), 3.58 (s, 2H).

Example 36: tert-Butyl 4-[2-benzyl-3-(2-oxoindolin-5-yl)imidazo[1,2-a]pyrazin-8-yl]piperazine-1-carboxylate

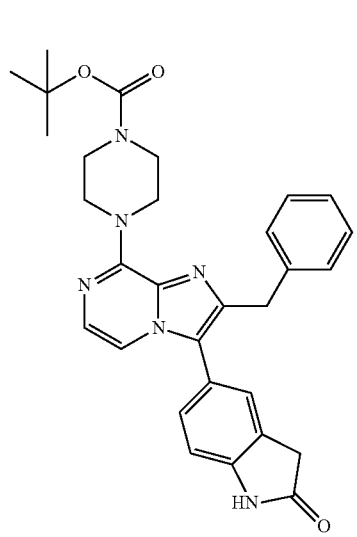 [SMILES: CC(C)(C)OC(=O)N1CCN(c2nccn3c(-c4ccc5c(c4)CC(=O)N5)c(Cc4ccccc4)nc23)CC1]

The title compound was prepared in a manner analogous to Example 1. MS (ESI): mass calcd. for $C_{30}H_{32}N_6O_3$, 524.3; m/z found, 525.0 [M+H]$^+$. $^1$H NMR (400 MHz, DMSO-d$_6$) δ 10.60 (s, 1H), 7.52 (d, J=4.6 Hz, 1H), 7.34 (d, J=4.6 Hz, 1H), 7.30-7.26 (m, 1H), 7.24 (d, J=7.2 Hz, 3H), 7.17 (d, J=7.4 Hz, 3H), 6.98 (d, J=8.0 Hz, 1H), 4.17 (d, J=5.7 Hz, 4H), 4.08-3.98 (m, 2H), 3.56 (s, 2H), 3.46 (d, J=12.1 Hz, 4H), 1.43 (s, 9H).

Example 37: 5-[2-(4-Fluorophenyl)-8-(4-hydroxy-1-piperidyl)imidazo[1,2-a]pyrazin-3-yl]indolin-2-one

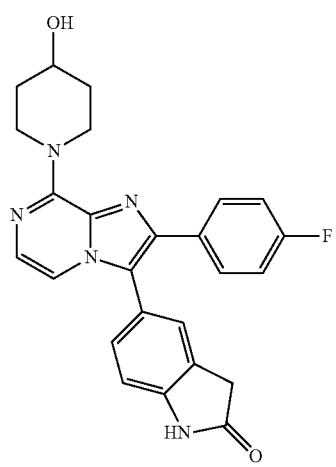 [SMILES: O=C1Cc2cc(-c3c(-c4ccc(F)cc4)nc4c(N5CCC(O)CC5)nccn34)ccc2N1]

The title compound was prepared in a manner analogous to Example 1. MS (ESI): mass calcd. for $C_{25}H_{22}FN_5O_2$, 443.2; m/z found, 443.9 [M+H]$^+$. $^1$H NMR (400 MHz, DMSO-d$_6$) δ 10.64 (s, 1H), 7.62 (dd, J=8.7, 5.7 Hz, 2H), 7.35-7.31 (m, 2H), 7.30-7.27 (m, 1H), 7.26-7.23 (m, 1H), 7.18 (t, J=8.9 Hz, 2H), 7.01 (d, J=8.0 Hz, 1H), 4.94 (d, J=13.1 Hz, 2H), 4.76 (d, J=4.3 Hz, 1H), 3.80 (d, J=4.3 Hz, 1H), 3.64 (t, J=11.5 Hz, 2H), 3.57 (s, 2H), 1.89 (d, J=12.2 Hz, 2H), 1.47 (d, J=9.2 Hz, 2H).

Example 38: 5-[2-Benzyl-8-(3-oxopiperazin-1-yl)imidazo[1,2-a]pyrazin-3-yl]indolin-2-one

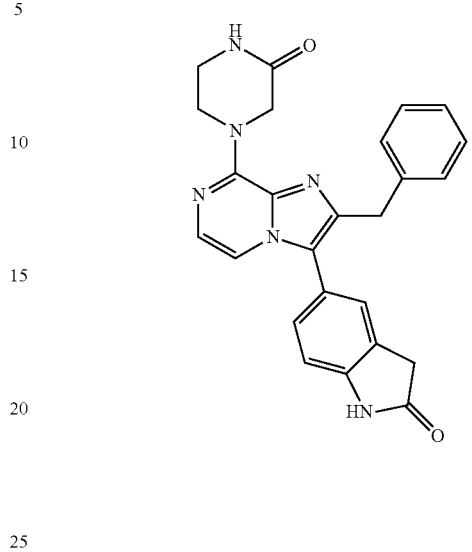

The title compound was prepared in a manner analogous to Example 1. MS (ESI): mass calcd. for $C_{25}H_{22}N_6O_2$, 438.2; m/z found, 439.0 [M+H]$^+$. $^1$H NMR (400 MHz, DMSO-d$_6$) δ 10.59 (s, 1H), 8.06 (s, 1H), 7.53 (d, J=4.6 Hz, 1H), 7.36 (d, J=4.6 Hz, 1H), 7.32-7.21 (m, 4H), 7.21-7.11 (m, 3H), 6.99 (d, J=8.0 Hz, 1H), 4.65 (s, 2H), 4.43 (t, J=5.4 Hz, 2H), 4.06 (s, 2H), 3.56 (s, 2H), 3.34 (s, 2H).

Example 39: 5-[2-(4-Fluorophenyl)-8-(3-methylmorpholin-4-yl)imidazo[1,2-a]pyrazin-3-yl]indolin-2-one The title compound was prepared in a manner analogous to Example 1. MS (ESI): mass calcd. for $C_{25}H_{22}FN_5O_2$, 443.2; m/z found, 444.0 [M+H]$^+$. $^1$H NMR (400 MHz, CDCl$_3$) δ 7.72 (s, 1H), 7.65-7.58 (m, 2H), 7.32 (d, J=4.6 Hz, 1H), 7.28 (d, J=1.6 Hz, 2H), 7.22 (d, J=4.6 Hz, 1H), 7.07-6.91 (m, 3H), 4.12 (d, J=7.1 Hz, 1H), 4.07 (dd, J=11.6, 3.4 Hz, 1H), 3.95-3.88 (m, 2H), 3.87-3.81 (m, 2H), 3.80-3.68 (m, 1H), 3.65-3.52 (m, 2H), 1.44 (d, J=6.8 Hz, 3H).

Example 40: 5-[2-(4-Fluorophenyl)-8-[(2-oxopyrrolidin-3-yl)amino]imidazo[1,2-a]pyrazin-3-yl]indolin-2-one

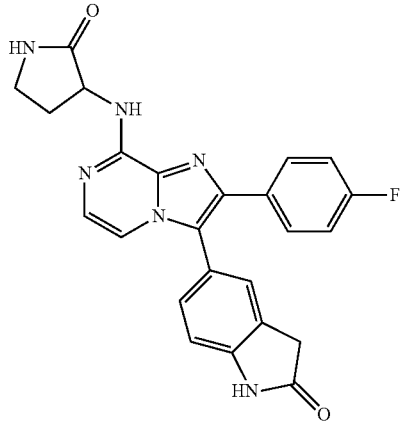 [SMILES: O=C1Cc2cc(-c3c(-c4ccc(F)cc4)nc4c(NC5CCNC5=O)nccn34)ccc2N1]

The title compound was prepared in a manner analogous to Example 1. MS (ESI): mass calcd. for $C_{24}H_{19}FN_6O_2$, 442.2; m/z found, 442.9 [M+H]$^+$. $^1$H NMR (400 MHz, DMSO-d$_6$) δ 10.64 (s, 1H), 7.88 (s, 1H), 7.66 (dd, J=8.7, 5.8 Hz, 2H), 7.54 (d, J=7.9 Hz, 1H), 7.33 (s, 1H), 7.26 (s, 3H), 7.19 (t, J=8.9 Hz, 2H), 7.00 (d, J=8.0 Hz, 1H), 4.81 (d, J=9.3 Hz, 1H), 3.57 (s, 2H), 3.28 (d, J=10.8 Hz, 2H), 2.46 (s, 1H), 2.20 (t, J=11.0 Hz, 1H).

Example 41: 5-[2-(4-Fluorophenyl)-8-(3-hydroxypyrrolidin-1-yl)imidazo[1,2-a]pyrazin-3-yl]indolin-2-one

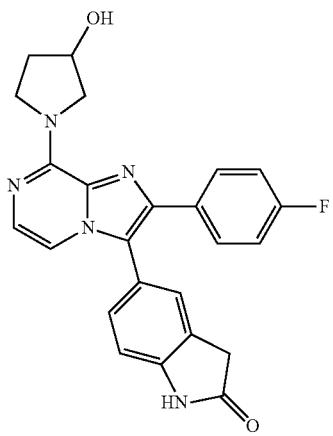 [SMILES: O=C1Cc2cc(-c3c(-c4ccc(F)cc4)nc4c(N5CCC(O)C5)nccn34)ccc2N1]

The title compound was prepared in a manner analogous to Example 1. MS (ESI): mass calcd. for $C_{24}H_{20}FN_5O_2$, 429.2; m/z found, 430.0 [M+H]$^+$. $^1$H NMR (400 MHz, CDCl$_3$) δ 7.91 (s, 1H), 7.63 (dd, J=8.9, 5.4 Hz, 2H), 7.31-7.23 (m, 3H), 7.10 (d, J=4.7 Hz, 1H), 7.06-6.90 (m, 3H), 4.69 (s, 1H), 4.50-4.00 (m, 4H), 3.60 (s, 2H), 2.28-2.08 (m, 2H), 1.80 (s, 1H).

Example 42: 5-[2-(4-Fluorophenyl)-8-[2-(trifluoromethyl)morpholin-4-yl]imidazo[1,2-a]pyrazin-3-yl]indolin-2-one

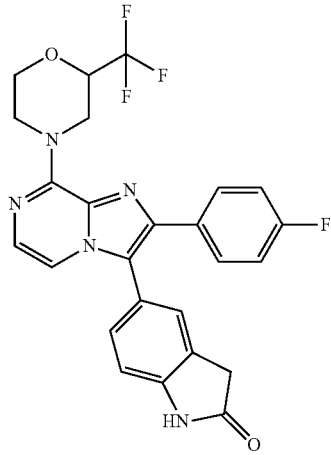 [SMILES: O=C1Cc2cc(-c3c(-c4ccc(F)cc4)nc4c(N5CCOC(C(F)(F)F)C5)nccn34)ccc2N1]

The title compound was prepared in a manner analogous to Example 1. MS (ESI): mass calcd. for $C_{25}H_{19}F_4N_5O_2$, 497.1; m/z found, 497.9 [M+H]$^+$. $^1$H NMR (400 MHz, CDCl$_3$) δ 7.84 (s, 1H), 7.67 (s, 1H), 7.61 (dd, J=8.9, 5.4 Hz, 2H), 7.57-7.44 (m, 1H), 7.35 (d, J=4.6 Hz, 1H), 7.30 (d, J=4.7 Hz, 1H), 7.08-6.93 (m, 3H), 5.56 (dd, J=43.3, 13.5 Hz, 2H), 4.29-4.05 (m, 1H), 3.89 (td, J=11.7, 2.7 Hz, 1H), 3.62 (s, 2H), 3.57-3.25 (m, 3H).

Example 43: 5-[2-(4-Fluorophenyl)-8-[(3S)-3-methylmorpholin-4-yl]imidazo[1,2-a]pyrazin-3-yl]indolin-2-one

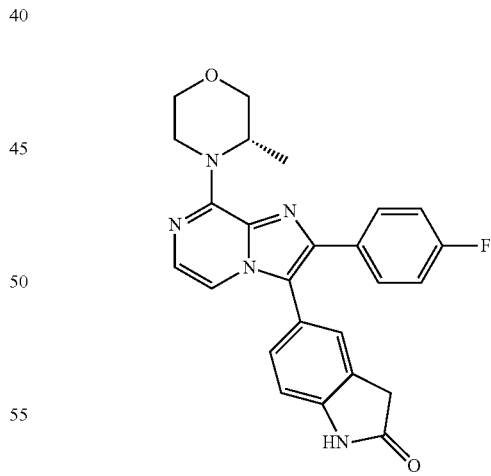

The title compound was prepared in a manner analogous to Example 1. MS (ESI): mass calcd. for $C_{25}H_{22}FN_5O_2$, 443.2; m/z found, 444.2 [M+H]$^+$. $^1$H NMR (500 MHz, DMSO-d$_6$) δ 10.67 (s, 1H), 7.71-7.56 (m, 2H), 7.36 (d, J=4.9 Hz, 1H), 7.34-7.29 (m, 2H), 7.26 (dd, J=8.0, 1.7 Hz, 1H), 7.19 (t, J=8.9 Hz, 2H), 7.03 (d, J=8.0 Hz, 1H), 4.14-3.95 (m, 1H), 3.94-3.72 (m, 2H), 3.72-3.53 (m, 6H), 1.39 (d, J=6.7 Hz, 3H).

Example 44: 5-[2-(4-Fluorophenyl)-8-[(3R)-3-methylmorpholin-4-yl]imidazo[1,2-a]pyrazin-3-yl]indolin-2-one

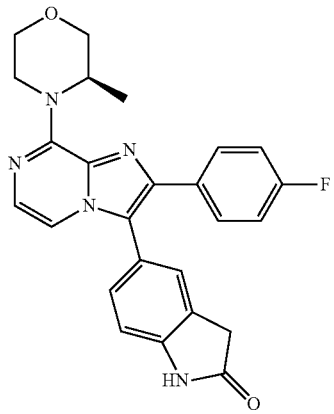 [SMILES: C[C@@H]1COCCN1c1nccn2c(-c3ccc4c(c3)CC(=O)N4)c(-c3ccc(F)cc3)nc12]

The title compound was prepared in a manner analogous to Example 1. MS (ESI): mass calcd. for $C_{25}H_{22}FN_5O_2$, 443.2; m/z found, 443.9 [M+H]$^+$.

Example 45: 5-[2-(4-Fluorophenyl)-8-pyrrolidin-1-yl-imidazo[1,2-a]pyrazin-3-yl]indolin-2-one

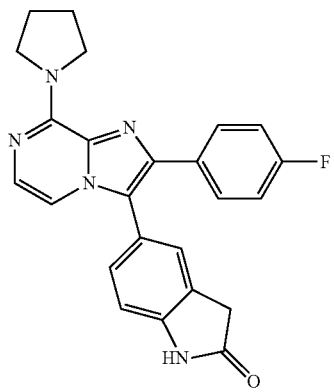 [SMILES: O=C1Cc2cc(-c3c(-c4ccc(F)cc4)nc4c(N5CCCC5)nccn34)ccc2N1]

The title compound was prepared in a manner analogous to Example 1. MS (ESI): mass calcd. for $C_{24}H_{20}FN_5O$, 413.2; m/z found, 414.0 [M+H]$^+$. $^1$H NMR (400 MHz, CDCl$_3$) δ 7.80 (s, 1H), 7.68-7.58 (m, 2H), 7.26 (s, 3H), 7.08 (d, J=4.7 Hz, 1H), 7.05-6.93 (m, 3H), 4.12 (q, J=7.2 Hz, 4H), 3.61 (s, 2H), 2.05 (s, 4H).

Example 46: 5-[8-[Cyclopropyl(methyl)amino]-2-(4-fluorophenyl)imidazo[1,2-a]pyrazin-3-yl]indolin-2-one

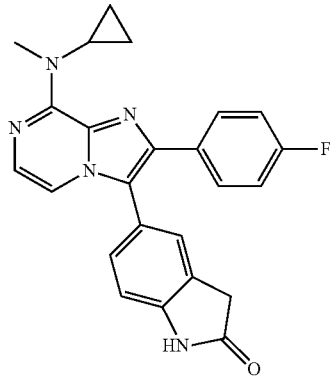 [SMILES: CN(c1nccn2c(-c3ccc4c(c3)CC(=O)N4)c(-c3ccc(F)cc3)nc12)C1CC1]

The title compound was prepared in a manner analogous to Example 1. MS (ESI): mass calcd. for $C_{24}H_{20}FN_5O$, 413.2; m/z found, 414.0 [M+H]$^+$. $^1$H NMR (400 MHz, CDCl$_3$) δ 8.47 (s, 1H), 7.71-7.56 (m, 2H), 7.38 (d, J=4.6 Hz, 1H), 7.33-7.26 (m, 2H), 7.23 (d, J=4.6 Hz, 1H), 7.04 (dd, J=7.7, 0.7 Hz, 1H), 6.97 (t, J=8.8 Hz, 2H), 3.69 (s, 3H), 3.63 (s, 2H), 3.18 (tt, J=7.1, 3.9 Hz, 1H), 1.05-0.90 (m, 2H), 0.83-0.67 (m, 2H).

Example 47: 5-[8-(1,1-Dioxo-1,4-thiazinan-4-yl)-2-(4-fluorophenyl)imidazo[1,2-a]pyrazin-3-yl]indolin-2-one

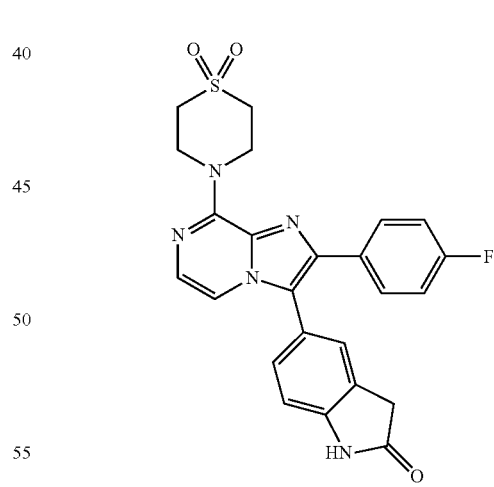

The title compound was prepared in a manner analogous to Example 1. MS (ESI): mass calcd. for $C_{24}H_{20}FN_5O_3S$, 477.1; m/z found, 477.9 [M+H]$^+$. $^1$H NMR (400 MHz, CDCl$_3$) δ 7.67-7.54 (m, 3H), 7.36 (d, J=0.7 Hz, 2H), 7.29 (s, 2H), 7.10-6.93 (m, 3H), 4.90 (s, 4H), 3.62 (s, 2H), 3.21 (t, J=5.1 Hz, 4H).

Example 48: (R*)-5-[2-(4-Fluorophenyl)-8-[2-(trifluoromethyl)morpholin-4-yl]imidazo[1,2-a]pyrazin-3-yl]indolin-2-one

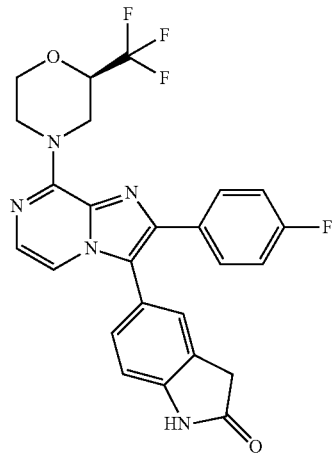 [SMILES: O=C1Cc2cc(-c3c(-c4ccc(F)cc4)nc4c(N5CCO[C@@H](C(F)(F)F)C5)nccn34)ccc2N1]

The title compound was prepared in a manner analogous to Example 1. MS (ESI): mass calcd. for $C_{25}H_{19}F_4N_5O_2$, 497.1; m/z found, 497.9 [M+H]$^+$. Purified by chiral column, absolute configuration is unknown.

Example 49: (S*)-5-[2-(4-Fluorophenyl)-8-[2-(trifluoromethyl)morpholin-4-yl]imidazo[1,2-a]pyrazin-3-yl]indolin-2-one

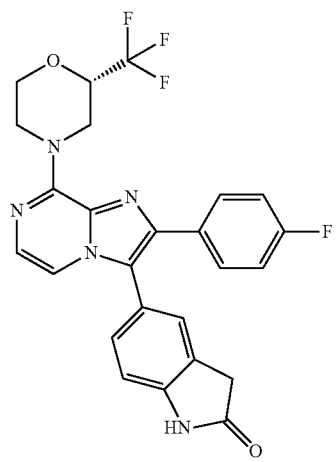 [SMILES: O=C1Cc2cc(-c3c(-c4ccc(F)cc4)nc4c(N5CCO[C@H](C(F)(F)F)C5)nccn34)ccc2N1]

The title compound was prepared in a manner analogous to Example 1. MS (ESI): mass calcd. for $C_{25}H_{19}F_4N_5O_2$, 497.1; m/z found, 497.9 [M+H]$^+$. Purified by chiral column, absolute configuration is unknown.

Example 50: 5-[8-(3,3-Dimethylmorpholin-4-yl)-2-(4-fluorophenyl)imidazo[1,2-a]pyrazin-3-yl]indolin-2-one

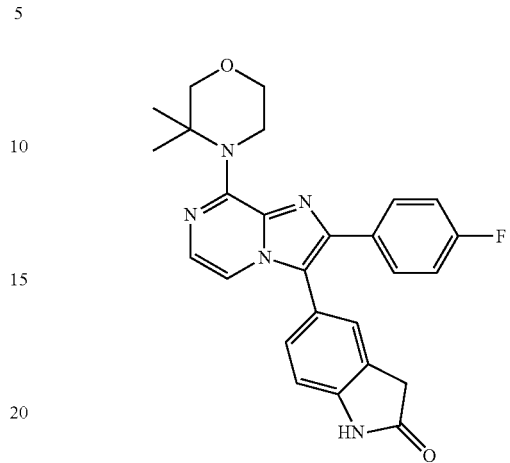

The title compound was prepared in a manner analogous to Example 1. MS (ESI): mass calcd. for $C_{26}H_{24}FN_5O_2$, 457.2; m/z found, 458.0 [M+H]$^+$. $^1$H NMR (500 MHz, CDCl$_3$) δ 8.04 (s, 1H), 7.69-7.58 (m, 2H), 7.40 (d, J=4.5 Hz, 1H), 7.35 (d, J=4.5 Hz, 1H), 7.25 (s, 2H), 7.03 (dd, J=7.8, 0.6 Hz, 1H), 6.97 (t, J=8.7 Hz, 2H), 4.39 (t, J=4.9 Hz, 2H), 4.06 (t, J=4.9 Hz, 2H), 3.62 (s, 2H), 3.56 (s, 2H), 1.58 (s, 6H).

Example 51: 5-[8-(Diethylamino)-2-(4-fluorophenyl)imidazo[1,2-a]pyrazin-3-yl]indolin-2-one

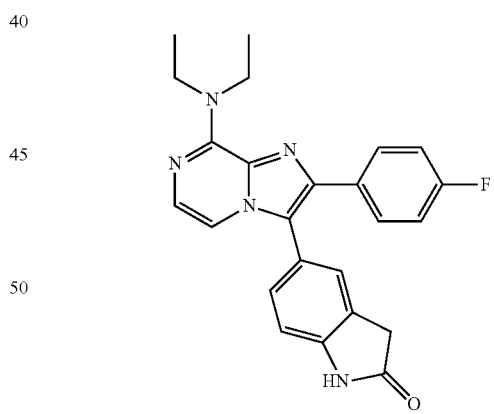

The title compound was prepared in a manner analogous to Example 1. MS (ESI): mass calcd. for $C_{24}H_{22}FN_5O$, 415.2; m/z found, 416.0 [M+H]$^+$. $^1$H NMR (500 MHz, CDCl$_3$) δ 7.70 (s, 1H), 7.63 (dd, J=8.9, 5.5 Hz, 2H), 7.26 (s, 2H), 7.09 (d, J=4.5 Hz, 1H), 7.05-6.91 (m, 3H), 4.13 (d, J=7.0 Hz, 4H), 3.61 (s, 2H), 1.36 (t, J=6.9 Hz, 6H).

Example 52: (R*)-5-[2-(4-Fluorophenyl)-8-(3-hydroxypyrrolidin-1-yl)imidazo[1,2-a]pyrazin-3-yl]indolin-2-one

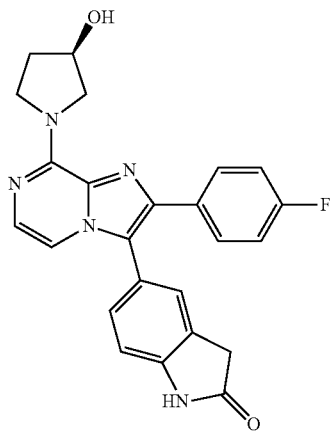 [SMILES: O=C1Cc2cc(-c3c(-c4ccc(F)cc4)nc4c(N5CC[C@@H](O)C5)nccn34)ccc2N1]

The title compound was prepared in a manner analogous to Example 1. MS (ESI): mass calcd. for $C_{24}H_{20}FN_5O_2$, 429.2; m/z found, 430.0 [M+H]$^+$. Purified by chiral column, absolute configuration is unknown.

Example 53: (S*)-5-[2-(4-Fluorophenyl)-8-(3-hydroxypyrrolidin-1-yl)imidazo[1,2-a]pyrazin-3-yl]indolin-2-one

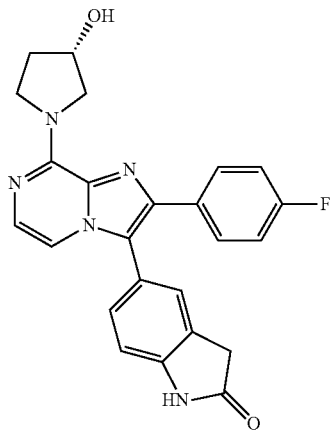

The title compound was prepared in a manner analogous to Example 1. MS (ESI): mass calcd. for $C_{24}H_{20}FN_5O_2$, 429.2; m/z found, 429.9 [M+H]$^+$. Purified by chiral column, absolute configuration is unknown.

Example 54: 5-[2-(4-Fluorophenyl)-8-(3-hydroxy-1-piperidyl)imidazo[1,2-a]pyrazin-3-yl]indolin-2-one

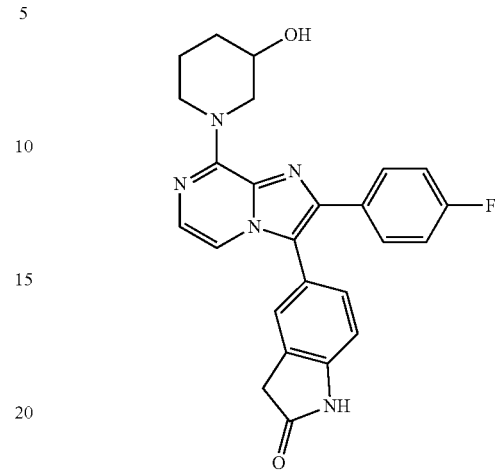

The title compound was prepared in a manner analogous to Example 1. MS (ESI): mass calcd. for $C_{25}H_{22}FN_5O_2$, 443.2; m/z found, 444.2 [M+H]$^+$. $^1$H NMR (400 MHz, DMSO-d$_6$) δ 10.64 (s, 1H), 7.63 (dd, J=8.7, 5.7 Hz, 2H), 7.34-7.24 (m, 3H), 7.24-7.14 (m, 3H), 7.01 (d, J=8.0 Hz, 1H), 5.12 (d, J=13.0 Hz, 2H), 4.94 (d, J=4.4 Hz, 1H), 4.17-3.89 (m, 1H), 3.57 (s, 3H), 1.99 (s, 2H), 1.81 (s, 1H), 1.49 (d, J=9.7 Hz, 2H).

Example 55: 5-[8-(1,4-Dioxa-8-azaspiro[4.5]decan-8-yl)-2-(4-fluorophenyl)imidazo[1,2-a]pyrazin-3-yl]indolin-2-one

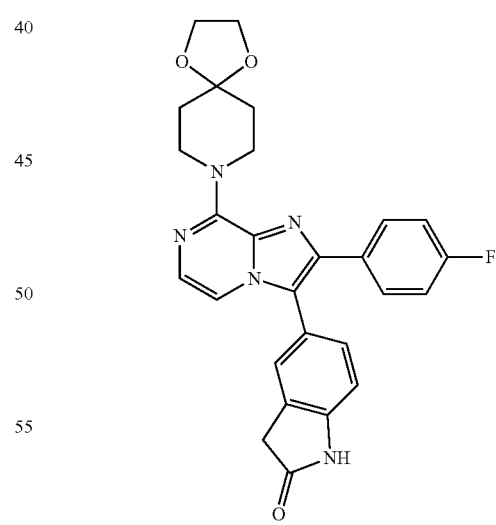

The title compound was prepared in a manner analogous to Example 1. MS (ESI): mass calcd. for $C_{27}H_{24}FN_5O_3$, 485.2; m/z found, 486.2 [M+H]$^+$. $^1$H NMR (400 MHz, CDCl$_3$) δ 7.84 (s, 1H), 7.62 (dd, J=8.9, 5.4 Hz, 2H), 7.31 (d, J=4.6 Hz, 1H), 7.20 (d, J=4.6 Hz, 1H), 7.10-6.85 (m, 3H), 4.47 (t, J=5.5 Hz, 4H), 4.04 (s, 4H), 3.61 (s, 2H), 1.90 (t, J=5.8 Hz, 4H).

Example 56: 5-(2-Cyclohexyl-8-morpholino-imidazo[1,2-a]pyrazin-3-yl)indolin-2-one

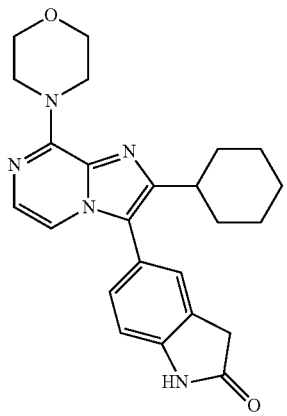 [SMILES: O=C1Cc2cc(-c3c(C4CCCCC4)nc4c(N5CCOCC5)nccn34)ccc2N1]

The title compound was prepared in a manner analogous to Example 1. MS (ESI): mass calcd. for $C_{24}H_{27}N_5O_2$, 417.2; m/z found, 418.2 [M+H]$^+$. $^1$H NMR (500 MHz, DMSO-d$_6$) δ 10.64 (s, 1H), 7.47 (d, J=5.1 Hz, 1H), 7.40 (t, J=3.1 Hz, 1H), 7.30 (s, 1H), 7.28-7.19 (m, 2H), 7.03 (d, J=8.0 Hz, 1H), 4.31 (s, 4H), 3.82 (t, J=4.8 Hz, 4H), 3.59 (s, 2H), 2.78-2.65 (m, 1H), 1.75 (d, J=10.9 Hz, 4H), 1.62 (t, J=12.4 Hz, 3H), 1.25 (t, J=9.2 Hz, 3H).

Example 57: 5-(2-Cyclopentyl-8-morpholino-imidazo[1,2-a]pyrazin-3-yl)indolin-2-one

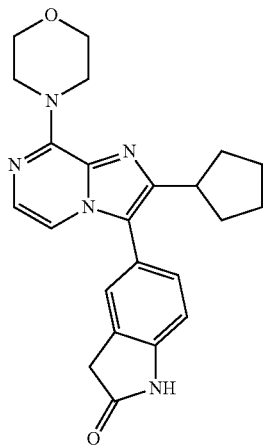 [SMILES: O=C1Cc2cc(-c3c(C4CCCC4)nc4c(N5CCOCC5)nccn34)ccc2N1]

The title compound was prepared in a manner analogous to Example 1. MS (ESI): mass calcd. for $C_{23}H_{25}N_5O_2$, 403.2; m/z found, 404.0 [M+H]$^+$. $^1$H NMR (500 MHz, DMSO-d$_6$) δ 10.64 (s, 1H), 7.50 (d, J=4.9 Hz, 1H), 7.31 (s, 1H), 7.29-7.21 (m, 2H), 7.02 (d, J=7.8 Hz, 1H), 4.30 (br s, 4H), 3.85-3.76 (m, 4H), 3.58 (s, 2H), 3.11 (quin, J=7.9 Hz, 1H), 1.96-1.85 (m, 2H), 1.85-1.72 (m, 4H), 1.65-1.53 (m, 2H)

Example 58: 5-[8-(Azetidin-1-yl)-2-(4-fluorophenyl)imidazo[1,2-a]pyrazin-3-yl]indolin-2-one

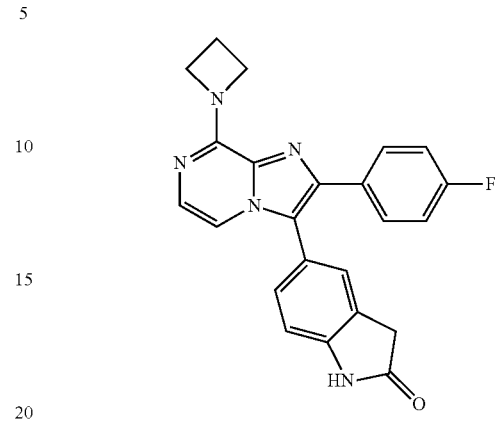

The title compound was prepared in a manner analogous to Example 1. MS (ESI): mass calcd. for $C_{23}H_{18}FN_5O$, 399.1; m/z found, 400.2 [M+H]$^+$. $^1$H NMR (500 MHz, DMSO-d$_6$) δ 10.69 (s, 1H), 7.69-7.57 (m, 2H), 7.31 (d, J=1.7 Hz, 1H), 7.29-7.23 (m, 2H), 7.23-7.14 (m, 3H), 7.02 (d, J=8.0 Hz, 1H), 4.62 (s, 4H), 3.57 (s, 3H), 3.17 (s, 1H).

Example 59: 5-[8-(3-Fluoroazetidin-1-yl)-2-(4-fluorophenyl)imidazo[1,2-a]pyrazin-3-yl]indolin-2-one

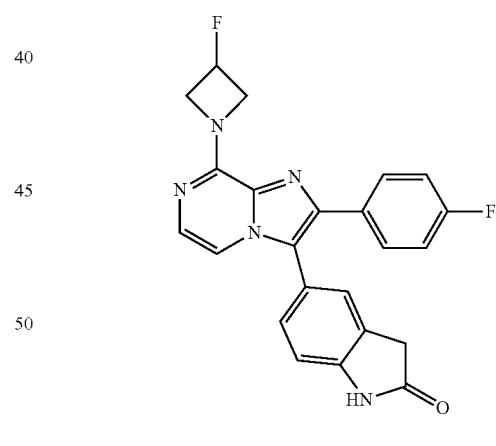

The title compound was prepared in a manner analogous to Example 1. MS (ESI): mass calcd. for $C_{23}H_{17}F_2N_5O$, 417.1; m/z found, 418.2 [M+H]$^+$. $^1$H NMR (500 MHz, DMSO-d$_6$) δ 10.70 (s, 1H), 7.73-7.59 (m, 2H), 7.37 (d, J=5.3 Hz, 1H), 7.33 (d, J=1.7 Hz, 1H), 7.30-7.24 (m, 2H), 7.20 (t, J=8.9 Hz, 2H), 7.03 (d, J=8.0 Hz, 1H), 5.63 (ddd, J=60.2, 5.8, 2.9 Hz, 1H), 5.01 (s, 2H), 4.71 (s, 2H), 3.58 (s, 2H).

Example 60: 5-[8-(3,3-Difluoroazetidin-1-yl)-2-(4-fluorophenyl)imidazo[1,2-a]pyrazin-3-yl]indolin-2-one

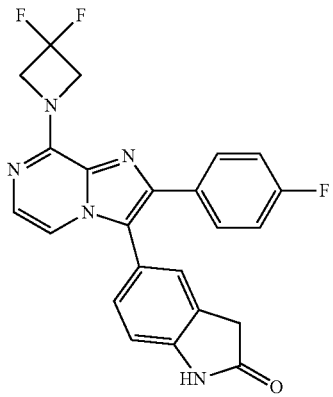 [SMILES: O=C1Cc2cc(-c3c(-c4ccc(F)cc4)nc4c(N5CC(F)(F)C5)nccn34)ccc2N1]

The title compound was prepared in a manner analogous to Example 1. MS (ESI): mass calcd. for $C_{23}H_{16}F_3N_5O$, 435.1; m/z found, 436.2 [M+H]$^+$. $^1$H NMR (500 MHz, DMSO-d$_6$) δ 10.67 (s, 1H), 7.66 (dd, J=8.8, 5.7 Hz, 2H), 7.43 (d, J=4.9 Hz, 1H), 7.40-7.30 (m, 2H), 7.25 (dd, J=8.0, 1.7 Hz, 1H), 7.18 (t, J=8.9 Hz, 2H), 7.02 (d, J=8.0 Hz, 1H), 4.93 (t, J=12.3 Hz, 4H), 3.57 (s, 3H).

Example 61: 5-[8-(3-Chloroazetidin-1-yl)-2-(4-fluorophenyl)imidazo[1,2-a]pyrazin-3-yl]indolin-2-one

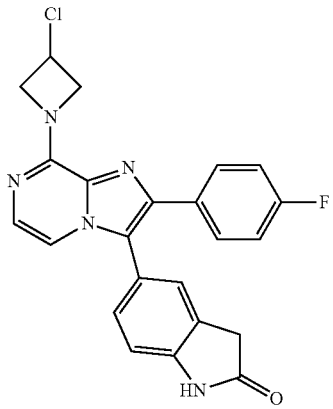 [SMILES: O=C1Cc2cc(-c3c(-c4ccc(F)cc4)nc4c(N5CC(Cl)C5)nccn34)ccc2N1]

The title compound was prepared in a manner analogous to Example 1. MS (ESI): mass calcd. for $C_{23}H_{17}ClFN_5O$, 433.1; m/z found, 434.1 [M+H]$^+$. $^1$H NMR (500 MHz, DMSO-d$_6$) δ 10.68 (s, 1H), 7.70-7.61 (m, 2H), 7.37 (d, J=5.1 Hz, 1H), 7.32 (s, 1H), 7.29 (d, J=5.2 Hz, 1H), 7.26 (dd, J=8.0, 1.7 Hz, 1H), 7.19 (t, J=8.9 Hz, 2H), 7.02 (d, J=8.0 Hz, 1H), 5.30-4.88 (m, 3H), 4.62 (s, 2H), 3.57 (s, 2H).

Example 62: 5-[2-(4-Fluorophenyl)-8-(3-methylsulfonylazetidin-1-yl)imidazo[1,2-a]pyrazin-3-yl]indolin-2-one

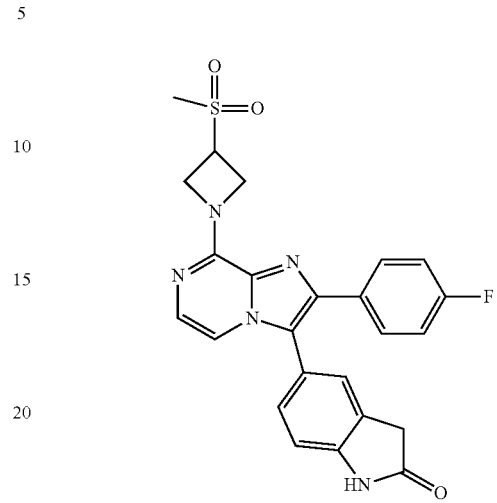

The title compound was prepared in a manner analogous to Example 1. MS (ESI): mass calcd. for $C_{24}H_{20}FN_5O_3S$, 477.1; m/z found, 478.3 [M+H]$^+$. $^1$H NMR (500 MHz, DMSO-d$_6$) δ 10.70 (s, 1H), 7.71-7.64 (m, 2H), 7.38 (d, J=5.3 Hz, 1H), 7.33 (d, J=1.7 Hz, 1H), 7.29 (d, J=5.3 Hz, 1H), 7.26 (d, J=1.7 Hz, 1H), 7.20 (t, J=8.9 Hz, 2H), 7.03 (d, J=8.0 Hz, 1H), 4.87 (d, J=59.9 Hz, 4H), 4.70-4.45 (m, 1H), 3.58 (s, 4H), 3.17 (s, 3H).

Example 63: 5-[2-(4-Fluorophenyl)-8-(2,2,3,3,5,5,6,6-octadeuteriomorpholin-4-yl)imidazo[1,2-a]pyrazin-3-yl]indolin-2-one

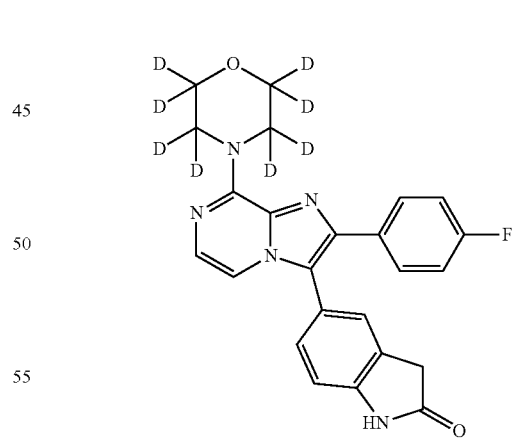

The title compound was prepared in a manner analogous to Example 1. MS (ESI): mass calcd. for $C_{24}H_{20}FN_5O_2$, 437.2; m/z found, 438.2 [M+H]$^+$. $^1$H NMR (500 MHz, DMSO-d$_6$) δ 10.66 (s, 1H), 7.68-7.58 (m, 2H), 7.36 (d, J=4.8 Hz, 1H), 7.32 (d, J=4.8 Hz, 2H), 7.25 (dd, J=8.0, 1.7 Hz, 1H), 7.18 (t, J=8.9 Hz, 2H), 7.02 (d, J=8.0 Hz, 1H), 3.57 (s, 2H).

Example 64: 5-[2-(4-Fluorophenyl)-8-[3-(hydroxymethyl)azetidin-1-yl]imidazo[1,2-a]pyrazin-3-yl]indolin-2-one

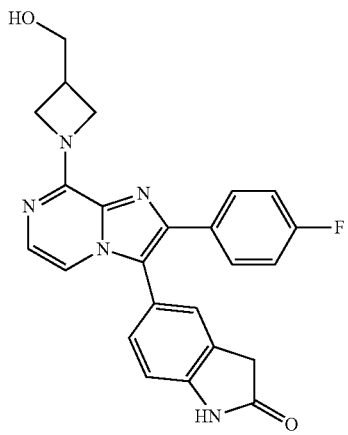 [SMILES: O=C1Cc2cc(-c3c(-c4ccc(F)cc4)nc4c(N5CC(CO)C5)nccn34)ccc2N1]

The title compound was prepared in a manner analogous to Example 1. MS (ESI): mass calcd. for $C_{24}H_{20}FN_5O_2$, 429.2; m/z found, 430.2 [M+H]$^+$. $^1$H NMR (500 MHz, DMSO-d$_6$) δ 10.72 (s, 1H), 7.68-7.60 (m, 2H), 7.33 (d, J=1.7 Hz, 1H), 7.29 (d, J=5.6 Hz, 1H), 7.27 (dd, J=8.0, 1.6 Hz, 1H), 7.24-7.16 (m, 3H), 7.04 (d, J=8.0 Hz, 1H), 3.68 (d, J=5.7 Hz, 2H), 3.58 (s, 2H), 3.35 (m, 4H), 3.03 (d, J=5.9 Hz, 1H).

Example 65: 5-(8-Morpholino-2-phenyl-imidazo[1,2-a]pyrazin-3-yl)indolin-2-one

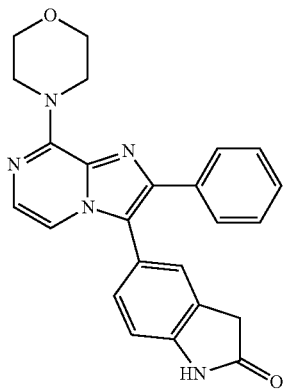 [SMILES: O=C1Cc2cc(-c3c(-c4ccccc4)nc4c(N5CCOCC5)nccn34)ccc2N1]

The title compound was prepared in a manner analogous to Example 1. MS (ESI): mass calcd. for $C_{24}H_{21}N_5O_2$, 411.2; m/z found, 412.2 [M+H]$^+$. $^1$H NMR (500 MHz, DMSO-d$_6$) δ 10.67 (s, 1H), 7.61 (dd, J=8.4, 1.4 Hz, 2H), 7.37 (d, J=4.9 Hz, 1H), 7.36-7.23 (m, 5H), 7.02 (d, J=8.0 Hz, 1H), 4.34 (s, 4H), 3.83 (t, J=4.7 Hz, 4H), 3.57 (s, 2H).

Example 66: 1-[2-(4-Fluorophenyl)-3-(2-oxoindolin-5-yl)imidazo[1,2-a]pyrazin-8-yl]azetidine-3-carbonitrile

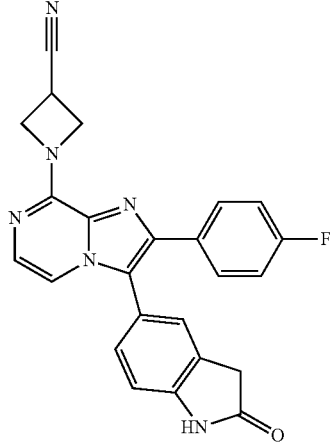 [SMILES: N#CC1CN(c2nccn3c(-c4ccc5c(c4)CC(=O)N5)c(-c4ccc(F)cc4)nc23)C1]

The title compound was prepared in a manner analogous to Example 1. MS (ESI): mass calcd. for $C_{24}H_{17}FN_6O$, 424.1; m/z found, 425.2 [M+H]$^+$. $^1$H NMR (500 MHz, DMSO-d$_6$) δ 10.70 (s, 1H), 7.71-7.60 (m, 2H), 7.39 (d, J=5.3 Hz, 1H), 7.33 (d, J=1.7 Hz, 1H), 7.31-7.24 (m, 2H), 7.20 (t, J=8.9 Hz, 2H), 7.03 (d, J=8.0 Hz, 1H), 4.85 (d, J=60.6 Hz, 4H), 4.23-3.95 (m, 1H), 3.58 (s, 2H).

Example 67: 5-[2-(4-Fluorophenyl)-8-(3-hydroxy-3-methyl-azetidin-1-yl)imidazo[1,2-a]pyrazin-3-yl]indolin-2-one

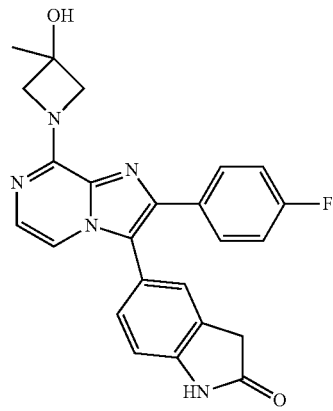 [SMILES: CC1(O)CN(c2nccn3c(-c4ccc5c(c4)CC(=O)N5)c(-c4ccc(F)cc4)nc23)C1]

The title compound was prepared in a manner analogous to Example 1. MS (ESI): mass calcd. for $C_{24}H_{20}FN_5O_2$, 429.2; m/z found, 430.2 [M+H]$^+$. $^1$H NMR (500 MHz, DMSO-d$_6$) δ 10.70 (s, 1H), 7.70-7.59 (m, 2H), 7.35-7.28 (m, 2H), 7.26 (dd, J=8.0, 1.8 Hz, 1H), 7.24-7.16 (m, 3H), 7.04 (d, J=8.0 Hz, 1H), 4.45 (s, 4H), 3.58 (s, 2H), 1.53 (s, 3H).

Example 68: 5-[2-(4-Fluorophenyl)-8-(4-hydroxy-4-methyl-1-piperidyl)imidazo[1,2-a]pyrazin-3-yl]indolin-2-one

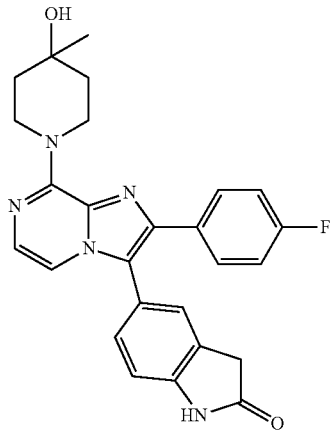 [SMILES: CC1(O)CCN(c2nccn3c(-c4ccc5c(c4)CC(=O)N5)c(-c4ccc(F)cc4)nc23)CC1]

The title compound was prepared in a manner analogous to Example 1. MS (ESI): mass calcd. for $C_{26}H_{24}FN_5O_2$, 457.2; m/z found, 458.2 [M+H]$^+$. $^1$H NMR (500 MHz, DMSO-d$_6$) δ 10.68 (s, 1H), 7.67-7.57 (m, 2H), 7.32 (t, J=2.1 Hz, 2H), 7.28-7.23 (m, 2H), 7.20 (t, J=8.9 Hz, 2H), 7.03 (d, J=8.0 Hz, 1H), 3.82 (s, 4H), 3.58 (s, 2H), 1.68 (s, 4H), 1.20 (s, 3H).

Example 69: 5-[2-(4-Fluorophenyl)-8-[3-hydroxy-3-(trifluoromethyl)azetidin-1-yl]imidazo[1,2-a]pyrazin-3-yl]indolin-2-one

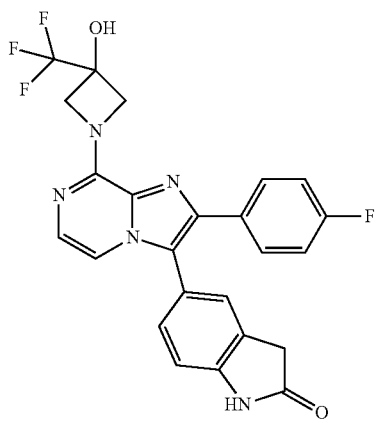 [SMILES: O=C1Cc2cc(-c3c(-c4ccc(F)cc4)nc4c(N5CC(O)(C(F)(F)F)C5)nccn34)ccc2N1]

The title compound was prepared in a manner analogous to Example 1. MS (ESI): mass calcd. for $C_{24}H_{17}F_4N_5O_2$, 483.1; m/z found, 484.1 [M+H]$^+$. $^1$H NMR (500 MHz, DMSO-d$_6$) δ 10.71 (s, 1H), 7.82 (s, 1H), 7.67 (dd, J=8.7, 5.7 Hz, 2H), 7.40 (d, J=5.3 Hz, 1H), 7.33 (d, J=1.7 Hz, 1H), 7.31-7.24 (m, 2H), 7.19 (t, J=8.9 Hz, 2H), 7.04 (d, J=8.0 Hz, 1H), 4.81 (d, J=99.2 Hz, 4H), 3.58 (s, 2H).

Example 70: (trans)-5-[8-(3-Fluoro-4-hydroxy-1-piperidyl)-2-(4-fluorophenyl)imidazo[1,2-a]pyrazin-3-yl]indolin-2-one

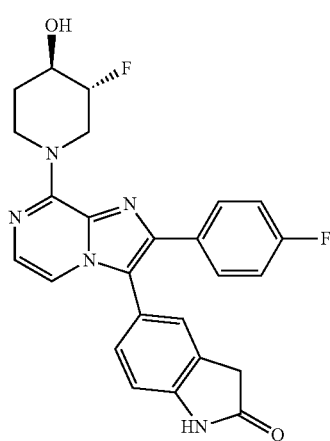 [SMILES: O=C1Cc2cc(-c3c(-c4ccc(F)cc4)nc4c(N5CC[C@@H](O)[C@H](F)C5)nccn34)ccc2N1]

The title compound was prepared in a manner analogous to Example 1. MS (ESI): mass calcd. for $C_{25}H_{21}F_2N_5O_2$, 461.2; m/z found, 462.2 [M+H]$^+$. $^1$H NMR (500 MHz, DMSO-d$_6$) δ 10.67 (s, 1H), 7.67-7.60 (m, 2H), 7.38 (d, J=4.8 Hz, 1H), 7.35-7.29 (m, 2H), 7.29-7.24 (m, 1H), 7.24-7.16 (m, 2H), 7.03 (d, J=8.0 Hz, 1H), 4.86 (t, J=16.3 Hz, 1H), 4.53 (d, J=49.8 Hz, 3H), 4.16-3.81 (m, 3H), 3.17 (s, 2H), 2.14-1.98 (m, 1H), 1.63 (d, J=9.5 Hz, 1H).

Example 71: 5-[8-(3,3-Difluoro-4-hydroxy-1-piperidyl)-2-(4-fluorophenyl)imidazo[1,2-a]pyrazin-3-yl]indolin-2-one

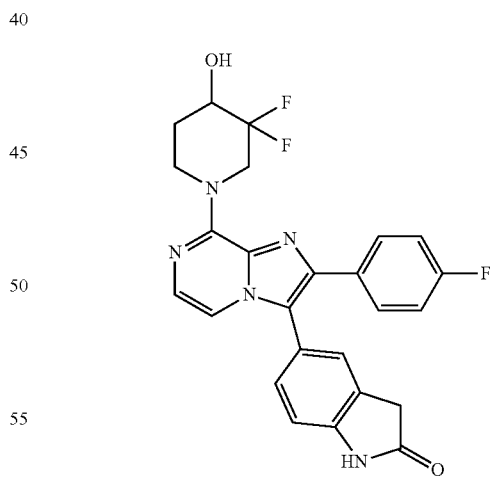

The title compound was prepared in a manner analogous to Example 1. MS (ESI): mass calcd. for $C_{25}H_{20}F_3N_5O_2$, 479.2; m/z found, 480.2 [M+H]$^+$. $^1$H NMR (500 MHz, DMSO-d$_6$) δ 10.65 (s, 1H), 7.71-7.54 (m, 3H), 7.41-7.37 (m, 1H), 7.37-7.31 (m, 2H), 7.26 (dd, J=8.1, 1.8 Hz, 1H), 7.20 (t, J=8.9 Hz, 2H), 7.01 (d, J=8.0 Hz, 1H), 5.06 (s, 1H), 4.78-4.31 (m, 2H), 4.01 (d, J=35.7 Hz, 2H), 3.57 (s, 2H), 1.90 (dd, J=96.0, 8.7 Hz, 2H).

Example 72: 5-[2-(4-Fluorophenyl)-8-(4-methoxy-1-piperidyl)imidazo[1,2-a]pyrazin-3-yl]indolin-2-one

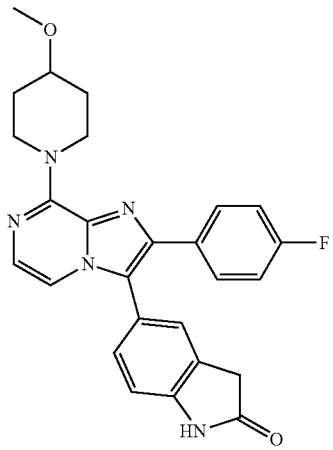 [SMILES: COC1CCN(c2nccn3c(-c4ccc5c(c4)CC(=O)N5)c(-c4ccc(F)cc4)nc23)CC1]

The title compound was prepared in a manner analogous to Example 1. MS (ESI): mass calcd. for $C_{26}H_{24}FN_5O_2$, 457.2; m/z found, 458.2 [M+H]$^+$. $^1$H NMR (500 MHz, DMSO-d$_6$) δ 10.69 (s, 1H), 7.69-7.57 (m, 2H), 7.39-7.31 (m, 2H), 7.29-7.24 (m, 2H), 7.20 (t, J=8.9 Hz, 2H), 7.04 (d, J=8.0 Hz, 1H), 4.73 (s, 2H), 4.05 (s, 2H), 3.58 (s, 2H), 3.32 (s, 3H), 2.17-1.55 (m, 4H).

Example 73: (cis)-5-[8-(3-Fluoro-4-hydroxy-1-piperidyl)-2-(4-fluorophenyl)imidazo[1,2-a]pyrazin-3-yl]indolin-2-one

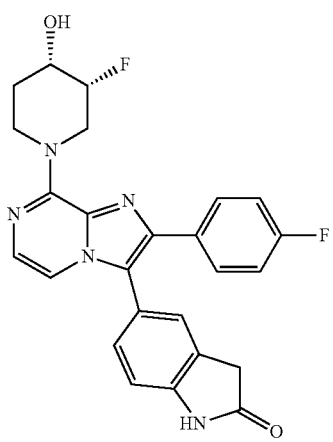 [SMILES: O=C1Cc2cc(-c3c(-c4ccc(F)cc4)nc4c(N5CC[C@H](O)[C@H](F)C5)nccn34)ccc2N1]

The title compound was prepared in a manner analogous to Example 1. MS (ESI): mass calcd. for $C_{25}H_{21}F_2N_5O_2$, 461.2; m/z found, 462.2 [M+H]$^+$. $^1$H NMR (500 MHz, DMSO-d$_6$) δ 10.68 (s, 1H), 7.68-7.58 (m, 2H), 7.37 (d, J=4.9 Hz, 1H), 7.33 (d, J=1.7 Hz, 1H), 7.30 (d, J=4.9 Hz, 1H), 7.27 (dd, J=8.0, 1.7 Hz, 1H), 7.20 (t, J=8.9 Hz, 2H), 7.03 (d, J=8.0 Hz, 1H), 5.51 (s, 1H), 4.83 (d, J=46.9 Hz, 1H), 4.11-3.82 (m, 2H), 3.57 (s, 2H), 3.17 (s, 2H), 1.87 (q, J=7.6, 4.8 Hz, 2H).

Example 74: 5-[2-(4-Fluorophenyl)-8-(4-fluoro-1-piperidyl)imidazo[1,2-a]pyrazin-3-yl]indolin-2-one

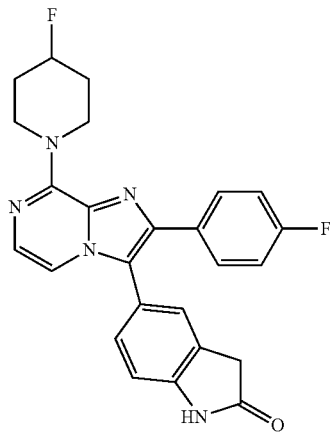 [SMILES: O=C1Cc2cc(-c3c(-c4ccc(F)cc4)nc4c(N5CCC(F)CC5)nccn34)ccc2N1]

The title compound was prepared in a manner analogous to Example 1. MS (ESI): mass calcd. for $C_{25}H_{21}F_2N_5O$, 445.2; m/z found, 446.2 [M+H]$^+$. $^1$H NMR (500 MHz, DMSO-d$_6$) δ 10.68 (s, 1H), 7.68-7.58 (m, 2H), 7.37 (d, J=5.0 Hz, 1H), 7.32 (d, J=1.7 Hz, 1H), 7.30 (d, J=5.0 Hz, 1H), 7.26 (dd, J=7.9, 1.7 Hz, 1H), 7.20 (t, J=8.9 Hz, 2H), 7.03 (d, J=8.0 Hz, 1H), 5.28-4.81 (m, 1H), 4.43 (s, 4H), 3.58 (s, 2H), 2.31-1.75 (m, 4H).

Example 75: 5-[8-(4-Fluoro-1-piperidyl)-2-phenyl-imidazo[1,2-a]pyrazin-3-yl]indolin-2-one

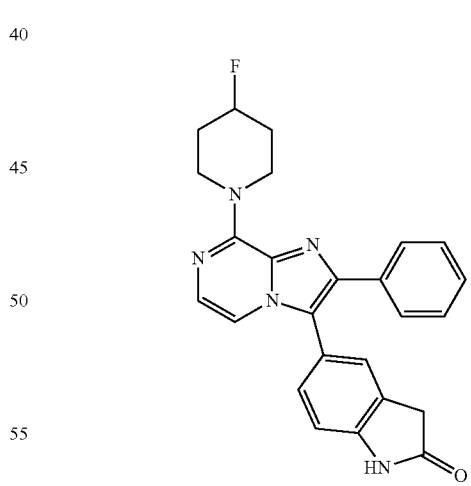

The title compound was prepared in a manner analogous to Example 1. MS (ESI): mass calcd. for $C_{25}H_{22}FN_5O$, 427.2; m/z found, 428.2 [M+H]$^+$. $^1$H NMR (400 MHz, DMSO-d$_6$) δ 10.70 (s, 1H), 7.62 (dd, J=8.3, 1.5 Hz, 3H), 7.50-7.19 (m, 6H), 7.04 (d, J=8.0 Hz, 1H), 5.04 (dt, J=48.4, 3.3 Hz, 1H), 4.47 (s, 4H), 3.59 (s, 2H), 2.32-1.81 (m, 4H).

Example 76: 5-[8-[4-(Fluoromethyl)-1-piperidyl]-2-phenyl-imidazo[1,2-a]pyrazin-3-yl]indolin-2-one

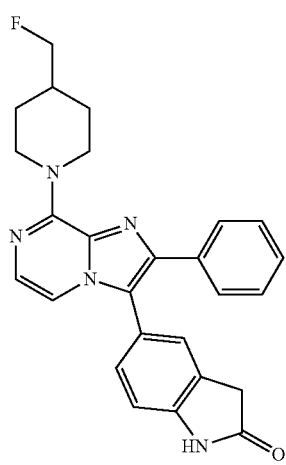 [SMILES: O=C1Cc2cc(-c3c(-c4ccccc4)nc4c(N5CCC(CF)CC5)nccn34)ccc2N1]

The title compound was prepared in a manner analogous to Example 1. MS (ESI): mass calcd. for $C_{26}H_{24}FN_5O$, 441.2; m/z found, 442.2 [M+H]$^+$. $^1$H NMR (400 MHz, DMSO-d$_6$) δ 10.67 (s, 1H), 7.60 (dd, J=8.4, 1.5 Hz, 3H), 7.50-7.16 (m, 6H), 7.02 (d, J=8.0 Hz, 1H), 5.44 (s, 2H), 4.35 (dd, J=47.5, 5.8 Hz, 2H), 3.57 (s, 2H), 3.37 (s, 2H), 2.14 (s, 1H), 1.98-1.29 (m, 4H).

Example 77: 5-[8-[4-(2-Fluoroethyl)-1-piperidyl]-2-phenyl-imidazo[1,2-a]pyrazin-3-yl]indolin-2-one

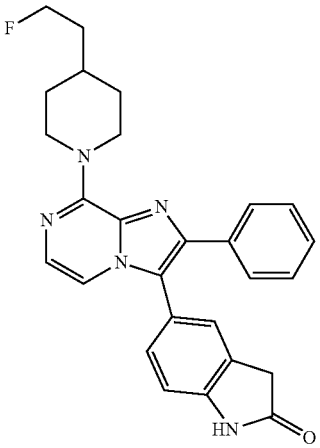 [SMILES: O=C1Cc2cc(-c3c(-c4ccccc4)nc4c(N5CCC(CCF)CC5)nccn34)ccc2N1]

The title compound was prepared in a manner analogous to Example 1. MS (ESI): mass calcd. for $C_{27}H_{26}FN_5O$, 455.2; m/z found, 456.2 [M+H]$^+$. $^1$H NMR (400 MHz, DMSO-d$_6$) δ 10.70 (s, 1H), 7.61 (dd, J=8.3, 1.5 Hz, 2H), 7.47-7.17 (m, 7H), 7.04 (d, J=8.0 Hz, 1H), 5.45 (s, 2H), 4.56 (dt, J=47.5, 6.0 Hz, 2H), 3.59 (s, 2H), 1.95 (d, J=13.4 Hz, 4H), 1.67 (dd, J=26.8, 6.2 Hz, 2H), 1.43 (d, J=12.7 Hz, 3H).

Example 78: 5-[8-(3-Methoxyazetidin-1-yl)-2-phenyl-imidazo[1,2-a]pyrazin-3-yl]indolin-2-one

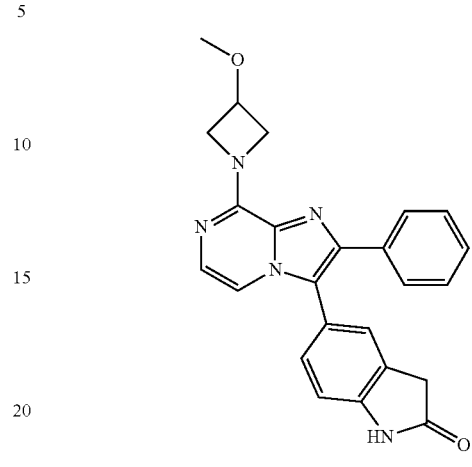

The title compound was prepared in a manner analogous to Example 1. MS (ESI): mass calcd. for $C_{24}H_{21}N_5O_2$, 411.2; m/z found, 412.2 [M+H]$^+$. $^1$H NMR (500 MHz, DMSO-d$_6$) δ 10.69 (s, 1H), 7.63 (dd, J=8.4, 1.5 Hz, 2H), 7.38-7.28 (m, 5H), 7.28-7.20 (m, 2H), 7.03 (d, J=8.0 Hz, 1H), 4.87 (s, 2H), 4.48 (s, 2H), 3.57 (s, 2H), 3.17 (s, 1H), 1.07 (s, 3H).

Example 79: 5-[8-(6-Oxa-3-azabicyclo[3.1.1]heptan-3-yl)-2-phenyl-imidazo[1,2-a]pyrazin-3-yl]indolin-2-one

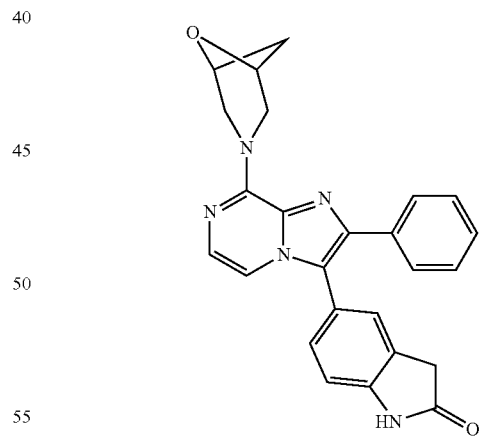

The title compound was prepared in a manner analogous to Example 1. MS (ESI): mass calcd. for $C_{25}H_{21}N_5O_2$, 423.2; m/z found, 424.2 [M+H]$^+$. $^1$H NMR (500 MHz, DMSO-d$_6$) δ 10.71 (s, 1H), 7.64 (dd, J=8.3, 1.4 Hz, 2H), 7.43-7.29 (m, 5H), 7.28 (d, J=5.3 Hz, 2H), 7.05 (d, J=8.0 Hz, 1H), 4.85 (d, J=6.4 Hz, 2H), 4.23 (s, 2H), 3.59 (s, 2H), 3.22 (d, J=7.5 Hz, 1H), 2.03 (d, J=9.1 Hz, 1H), 1.35-1.11 (m, 1H), 1.07 (s, 1H).

Example 80: 5-[8-(5-Azaspiro[2.3]hexan-5-yl)-2-phenyl-imidazo[1,2-a]pyrazin-3-yl]indolin-2-one

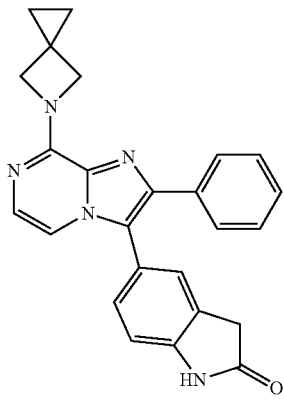 [SMILES: O=C1Cc2cc(-c3c(-c4ccccc4)nc4c(N5CC6(CC6)C5)nccn34)ccc2N1]

The title compound was prepared in a manner analogous to Example 1. MS (ESI): mass calcd. for $C_{25}H_{21}N_5O$, 407.2; m/z found, 408.2 [M+H]$^+$. $^1$H NMR (500 MHz, DMSO-d$_6$) δ 10.68 (s, 1H), 7.75-7.51 (m, 2H), 7.46-7.14 (m, 7H), 7.03 (d, J=8.0 Hz, 1H), 4.70 (s, 2H), 3.58 (s, 2H), 3.17 (s, 2H), 0.80 (s, 4H).

Example 81: 5-[8-(3-Fluoroazetidin-1-yl)-2-phenyl-imidazo[1,2-a]pyrazin-3-yl]indolin-2-one

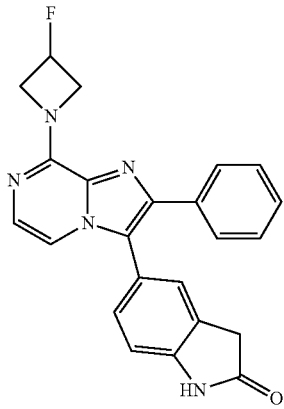 [SMILES: O=C1Cc2cc(-c3c(-c4ccccc4)nc4c(N5CC(F)C5)nccn34)ccc2N1]

The title compound was prepared in a manner analogous to Example 1. MS (ESI): mass calcd. for $C_{23}H_{18}FN_5O$, 399.1; m/z found, 400.2 [M+H]$^+$. $^1$H NMR (400 MHz, DMSO-d$_6$) δ 10.67 (s, 1H), 7.62 (dd, J=8.2, 1.6 Hz, 2H), 7.38-7.33 (m, 2H), 7.33-7.28 (m, 2H), 7.28-7.21 (m, 2H), 7.02 (d, J=7.9 Hz, 1H), 5.73-5.42 (m, 1H), 4.83 (d, J=124.3 Hz, 4H), 3.56 (s, 2H).

Example 82: 5-[5-Chloro-2-(4-fluorophenyl)-8-morpholino-imidazo[1,2-a]pyrazin-3-yl]-1,3-dihydrobenzimidazol-2-one

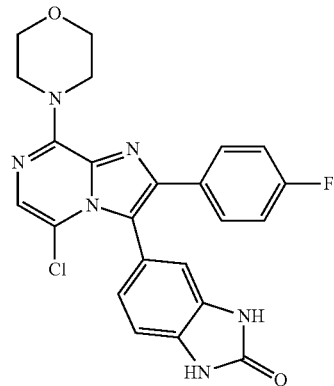 [SMILES: O=c1[nH]c2ccc(-c3c(-c4ccc(F)cc4)nc4c(N5CCOCC5)ncc(Cl)n34)cc2[nH]1]

The title compound was prepared in a manner analogous to Example 1. MS (ESI): mass calcd. for $C_{23}H_{18}ClFN_6O_2$, 464.11 m/z found, 464.9 [M+H]$^+$. $^1$H NMR (600 MHz, DMSO-d$_6$) δ 10.93-10.73 (dd, J=73.3, 2.0 Hz, 2H), 7.52-7.45 (m, 2H), 7.37-7.33 (s, 1H), 7.15-7.07 (m, 2H), 7.06-7.00 (m, 2H), 6.96-6.88 (s, 1H), 4.31-4.11 (t, J=4.8 Hz, 4H), 3.86-3.67 (t, J=4.8 Hz, 4H).

Example 83: 4-[2-(4-Fluorophenyl)-8-morpholino-imidazo[1,2-a]pyrazin-3-yl]-phenol

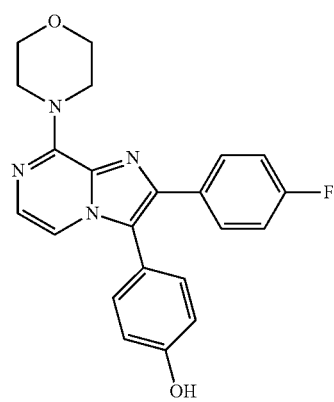 [SMILES: Oc1ccc(-c2c(-c3ccc(F)cc3)nc3c(N4CCOCC4)nccn23)cc1]

The title compound was prepared in a manner analogous to Example 1. MS (ESI): mass calcd. for $C_{22}H_{19}ClFN_4O_2$, 390.42 m/z found, 391.3 [M+H]$^+$. $^1$H NMR (400 MHz, CDCl$_3$) 7.70-7.54 (m, 1H), 7.37-7.29 (m, 1H), 7.27-7.20 (m, 1H), 7.07-6.89 (m, 2H), 6.70-6.50 (s, 1H), 4.46-4.26 (t, J=4.8 Hz, 2H), 3.98-3.87 (m, 2H).

Example 84: 4-[2-(2-Fluorophenyl)-8-morpholino-imidazo[1,2-a]pyrazin-3-yl]phenol

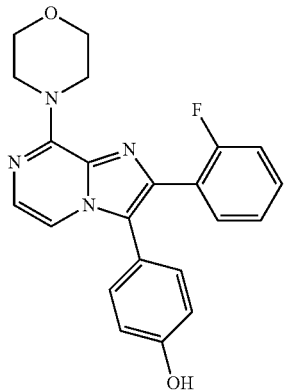 [SMILES: Oc1ccc(-c2c(-c3ccccc3F)nc3c(N4CCOCC4)nccn23)cc1]

The title compound was prepared in a manner analogous to Example 1. MS (ESI): mass calcd. for $C_{22}H_{19}FN_4O_2$, 390.4; m/z found, 391.2 [M+H]$^+$. $^1$H NMR (400 MHz, CDCl$_3$) δ 7.60 (td, J=7.5, 1.8 Hz, 1H), 7.46 (d, J=4.6 Hz, 1H), 7.36 (d, J=4.6 Hz, 1H), 7.33-7.27 (m, 1H), 7.24-7.19 (m, 2H), 7.16 (td, J=7.5, 1.2 Hz, 1H), 6.99 (ddd, J=10.4, 8.2, 1.2 Hz, 1H), 6.93-6.84 (m, 2H), 5.70 (s, 1H), 4.33 (t, J=4.7 Hz, 4H), 3.90 (t, J=4.8 Hz, 4H).

Example 85: 4-(2-Cyclohexyl-8-morpholino-imidazo[1,2-a]pyrazin-3-yl)phenol

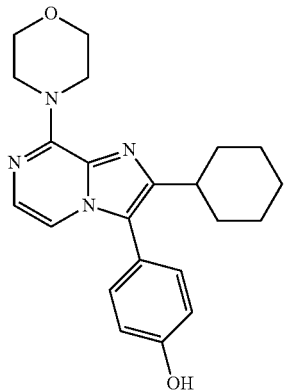 [SMILES: Oc1ccc(-c2c(C3CCCCC3)nc3c(N4CCOCC4)nccn23)cc1]

The title compound was prepared in a manner analogous to Example 1. MS (ESI): mass calcd. for $C_{22}H_{26}N_4O_2$, 378.5; m/z found, 379.2 [M+H]$^+$. $^1$H NMR (400 MHz, CDCl$_3$) δ 7.31-7.28 (m, 1H), 7.26-7.23 (m, 3H), 7.02-6.95 (m, 2H), 5.27 (s, 1H), 4.30 (t, J=4.8 Hz, 4H), 3.90 (t, J=4.8 Hz, 4H), 2.69 (t, J=11.2 Hz, 1H), 1.86-1.63 (m, 6H), 1.29 (s, 4H).

Example 86: 5-(2-tert-Butyl-8-morpholino-imidazo[1,2-a]pyrazin-3-yl)indolin-2-one

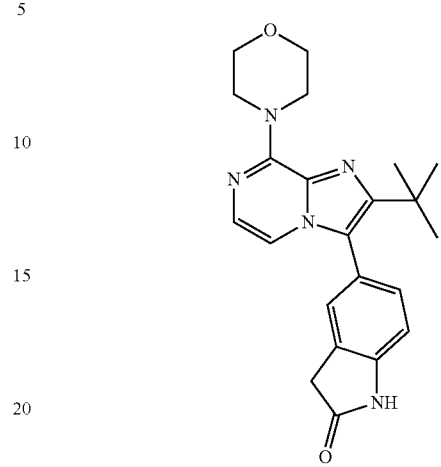

The title compound was prepared in a manner analogous to Example 1. MS (ESI): mass calcd. for $C_{22}H_{25}N_5O_2$, 391.5; m/z found, 392.2 [M+H]$^+$. $^1$H NMR (500 MHz, CDCl$_3$) δ 10.65 (s, 1H), 7.24 (d, J=1.7 Hz, 1H), 7.22-7.17 (m, 2H), 7.06 (d, J=5.1 Hz, 1H), 7.01 (d, J=7.9 Hz, 1H), 4.35 (s, 4H), 3.83 (t, J=4.7 Hz, 4H), 3.58 (d, J=11.1 Hz, 2H), 1.23 (s, 9H).

Example 87: 5-[8-Amino-2-(4-fluorophenyl)imidazo[1,2-a]pyrazin-3-yl]-1,3-dihydrobenzimidazol-2-one

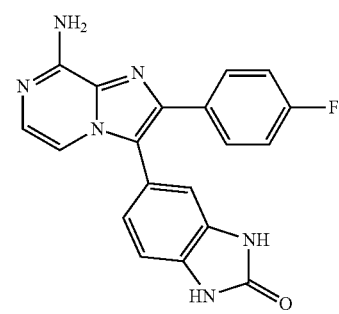 [SMILES: Nc1nccn2c(-c3ccc4[nH]c(=O)[nH]c4c3)c(-c3ccc(F)cc3)nc12]

Step A: 3-Bromo-2-(4-fluorophenyl)imidazo[1,2-a]pyrazin-8-amine

A solution of 3-bromo-8-chloro-2-(4-fluorophenyl)imidazo[1,2-a]pyrazine (Intermediate 47; 500 mg, 1.53 mmol) in isopropanol (1 mL) was treated with ammonia (33% in water, 16.0 mL, 280 mmol) in a sealed tube. The resulting mixture was stirred at 100° C. for 16 h. The reaction mixture was cooled to rt and water was added (20 mL). The resulting precipitate was filtered, washed with water (10 mL) and dried to afford the title compound as a solid (439 mg, 93%). MS (APCI): mass calcd. for $C_{12}H_8BrFN_4$, 306.0 m/z found, 306.9 [M+H]. $^1$H NMR (400 MHz, DMSO-d$_6$) δ 7.16 (br s, 2H) 7.31-7.45 (m, 3H) 7.62 (d, J=4.7 Hz, 1H) 8.04-8.13 (m, 2H).

Step B: 5-[8-Amino-2-(4-fluorophenyl)imidazo[1,2-a]pyrazin-3-yl]-1,3-dihydrobenzimidazol-2-one A suspension of 3-bromo-2-(4-fluorophenyl)imidazo[1,2-a]pyrazin-8-amine (239.0 mg, 0.778 mmol), 2-hydroxybenzimidazole-5-boronic acid pinacol ester (263 mg, 1.010 mmol) in dioxane/ethanol (1:1, 12 mL) and 1M $Na_2CO_3$ (3.89 mL) inside a 20 mL microwave vial was treated with $PdCl_2(PPh_3)_2$ (27.3 mg, 0.0389 mmol) and 2-(dicyclohexylphosphino)biphenyl (cyclohexyl JohnPhos) (16.4 mg, 0.0467 mmol). The reaction mixture was purged with nitrogen then heated in microwave at 130° C. for 15 minutes. The reaction mixture was cooled and concentrated. The crude product was adsorbed on $SiO_2$ and purified (FCC, $SiO_2$, 2 to 10% MeOH/DCM) to afford the title compound as a solid (44 mg, 16%). MS (ESI): mass calcd. for $C_{19}H_{13}FN_6O$, 360.4; m/z found, 361.0 $[M+H]^+$. $^1H$ NMR (400 MHz, DMSO-$d_6$) δ 10.89 (br s, 1H), 10.77 (br s, 1H), 7.65-7.58 (m, 2H), 7.25 (d, J=4.6 Hz, 1H), 7.19 (d, J=4.6 Hz, 1H), 7.20-7.13 (m, 2H), 7.11 (d, J=8.1 Hz, 1H), 7.01 (dd, J=1.5, 8.0 Hz, 1H), 6.98 (s, 2H), 6.95 (d, J=1.2 Hz, 1H).

Example 88: 5-[2-tert-Butyl-8-(4-hydroxy-1-piperidyl)imidazo[1,2-a]pyrazin-3-yl]indolin-2-one

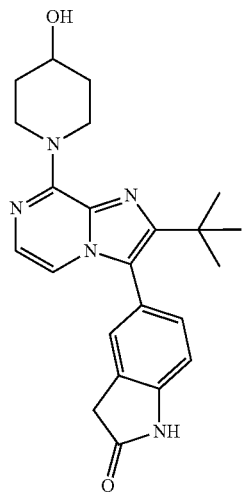 [SMILES: CC(C)(C)c1nc2c(N3CCC(O)CC3)nccn2c1-c1ccc2c(c1)CC(=O)N2]

The title compound was prepared in a manner analogous to Example 1. MS (ESI): mass calcd. for $C_{23}H_{27}N_5O_2$, 405.5; m/z found, 406.0 $[M+H]^+$. $^1H$ NMR (500 MHz, DMSO-$d_6$) δ 10.68 (s, 1H), 7.24 (s, 1H), 7.20 (dd, J=1.4, 8.1 Hz, 1H), 7.11 (d, J=5.5 Hz, 1H), 7.03 (d, J=5.5 Hz, 1H), 7.01 (d, J=8.1 Hz, 1H), 4.70 (br s, 2H), 3.98 (br s, 2H), 3.89 (spt, J=3.9 Hz, 1H), 3.61 (br s, 4H), 2.00-1.92 (m, 2H), 1.65-1.53 (m, 2H), 1.22 (s, 9H).

Example 89: 5-[8-(3-Fluoroazetidin-1-yl)-2-(4-pyridyl)imidazo[1,2-a]pyrazin-3-yl]indolin-2-one

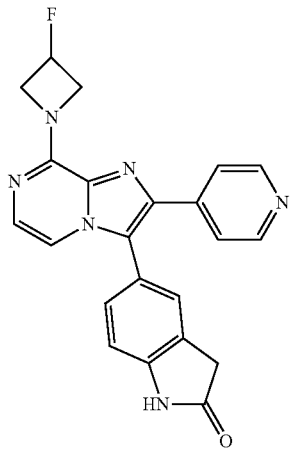 [SMILES: O=C1Cc2cc(-c3c(-c4ccncc4)nc4c(N5CC(F)C5)nccn34)ccc2N1]

The title compound was prepared in a manner analogous to Example 215. MS (ESI): mass calcd. for $C_{22}H_{17}FN_6O$, 400.4; m/z found, 401.0 $[M+H]^+$. $^1H$ NMR (400 MHz, DMSO-$d_6$) δ 10.82 (s, 1H), 8.77 (d, J=6.9 Hz, 2H), 8.05 (d, J=6.7 Hz, 2H), 7.41 (s, 1H), 7.38 (d, J=5.1 Hz, 1H), 7.40-7.35 (m, 1H), 7.32 (d, J=5.3 Hz, 1H), 7.10 (d, J=8.1 Hz, 1H), 5.79-5.52 (m, 1H), 5.15-4.89 (m, 2H), 4.87-4.56 (m, 2H), 3.73 (br s, 1H), 3.60 (s, 2H).

Example 90-Example 98 were prepared in a manner analogous to Example 1.

Example 90: 5-(2-Cyclobutyl-8-morpholino-imidazo[1,2-a]pyrazin-3-yl)indolin-2-one

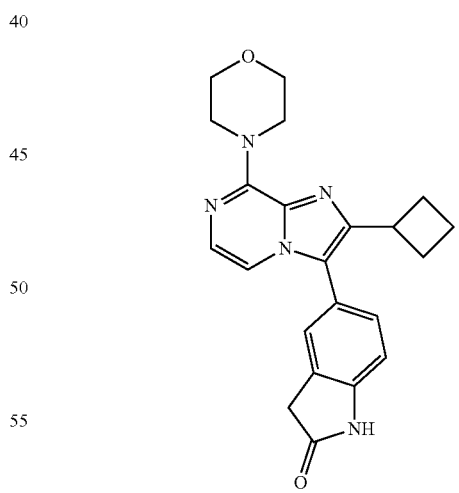

The title compound was prepared in a manner analogous to Example 1. MS (ESI): mass calcd. for $C_{22}H_{23}N_5O_2$, 389.5; m/z found, 390.0 $[M+H]^+$. $^1H$ NMR (500 MHz, DMSO-$d_6$) δ 10.62 (s, 1H), 7.54 (d, J=4.9 Hz, 1H), 7.29 (d, J=4.9 Hz, 1H), 7.27 (s, 1H), 7.22 (d, J=8.1 Hz, 1H), 7.01 (d, J=8.1 Hz, 1H), 4.29 (br s, 4H), 3.87-3.76 (m, 4H), 3.58 (s, 2H), 3.63-3.54 (m, 1H), 3.48 (br s, 1H), 2.40-2.29 (m, 2H), 2.25-2.14 (m, 2H), 2.00-1.89 (m, 1H), 1.90-1.80 (m, 1H).

Example 91: 5-(2-Cyclopropyl-8-morpholino-imidazo[1,2-a]pyrazin-3-yl)indolin-2-one

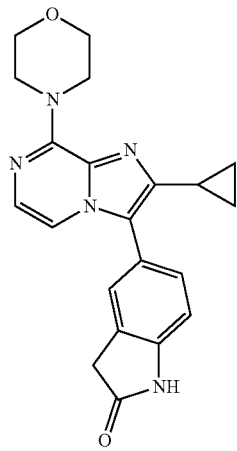 [SMILES: O=C1Cc2cc(-c3c(C4CC4)nc4c(N5CCOCC5)nccn34)ccc2N1]

The title compound was prepared in a manner analogous to Example 1. MS (ESI): mass calcd. for $C_{21}H_{21}N_5O_2$, 375.4; m/z found, 376.0 [M+H]$^+$. $^1$H NMR (500 MHz, DMSO-d$_6$) δ 10.65 (s, 1H), 7.58 (d, J=5.2 Hz, 1H), 7.40 (s, 1H), 7.38 (d, J=8.1 Hz, 1H), 7.26 (d, J=4.9 Hz, 1H), 7.04 (d, J=8.1 Hz, 1H), 4.25 (br s, 4H), 3.82-3.75 (m, 4H), 3.59 (s, 2H), 3.52 (br s, 1H), 2.04-1.92 (m, 1H), 0.99-0.86 (m, 4H).

Example 92: 1-[4-[2-(4-Chlorophenyl)-3-(4-hydroxyphenyl)imidazo[1,2-a]pyrazin-8-yl]-1,4-diazepan-1-yl]ethanone

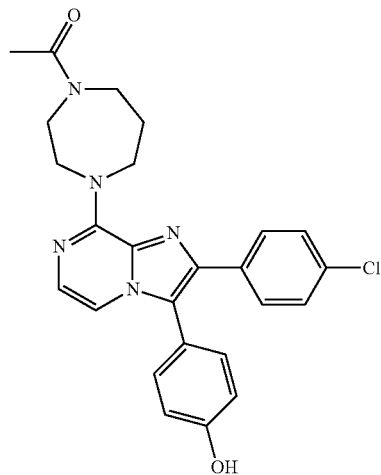 [SMILES: CC(=O)N1CCCN(c2nccn3c(-c4ccc(O)cc4)c(-c4ccc(Cl)cc4)nc23)CC1]

The title compound was prepared in a manner analogous to Example 1. MS (ESI): mass calcd. for $C_{25}H_{24}ClN_5O_2$, 461.2; m/z found, 462.2 [M+H]$^+$. $^1$H NMR (400 MHz, DMSO-d$_6$) δ 9.95 (s, 1H), 7.63-7.54 (m, 2H), 7.43-7.36 (m, 2H), 7.33-7.24 (m, 3H), 7.23-7.20 (m, 1H), 7.00-6.92 (m, 2H), 4.50-4.13 (m, 4H), 3.78-3.73 (m, 1H), 3.73-3.68 (m, 1H), 3.53-3.47 (m, 1H), 3.47-3.41 (m, 1H), 2.02 (s, 1.5H), 2.06-1.96 (m, 1H), 1.92 (s, 1.5H), 1.91-1.83 (m, 1H).

Example 93: N-[1-[2-(4-Chlorophenyl)-3-(4-hydroxyphenyl)imidazo[1,2-a]pyrazin-8-yl]-4-piperidyl]acetamide

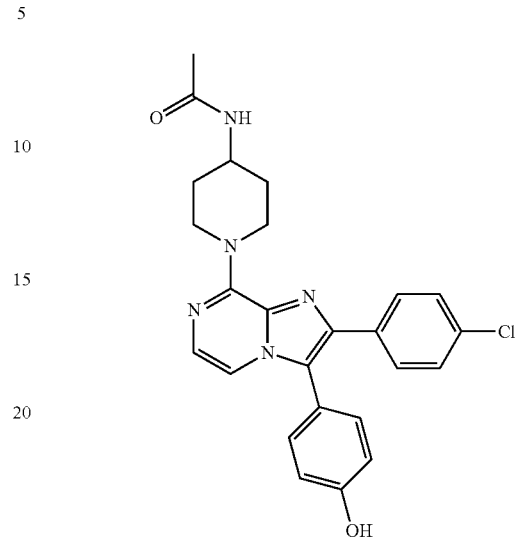

The title compound was prepared in a manner analogous to Example 1. MS (ESI): mass calcd. for $C_{25}H_{24}ClN_5O_2$, 461.2; m/z found, 462.2 [M+H]$^+$. $^1$H NMR (500 MHz, DMSO-d$_6$) δ 9.97 (br s, 1H), 7.82 (d, J=7.8 Hz, 1H), 7.61-7.56 (m, 2H), 7.42-7.38 (m, 2H), 7.33 (d, J=4.6 Hz, 1H), 7.28-7.24 (m, 3H), 6.99-6.94 (m, 2H), 5.26 (br. d, J=13.0 Hz, 2H), 3.96-3.86 (m, 1H), 3.34 (s, 2H), 1.90-1.84 (m, 2H), 1.80 (s, 3H), 1.50-1.39 (m, 2H).

Example 94: 1-[4-[2-(4-Chlorophenyl)-3-(4-hydroxyphenyl)imidazo[1,2-a]pyrazin-8-yl]piperazin-1-yl]ethanone

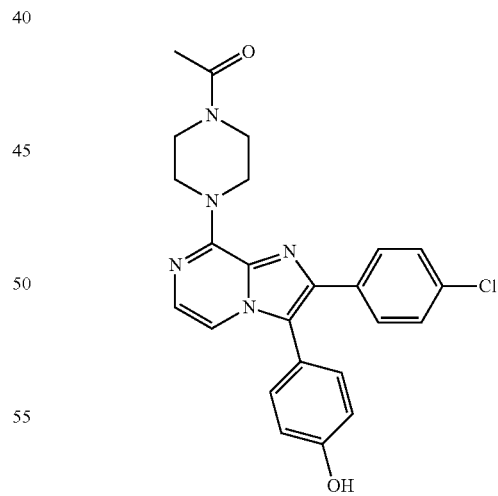

The title compound was prepared in a manner analogous to Example 1. MS (ESI): mass calcd. for $C_{24}H_{22}ClN_5O_2$, 447.1; m/z found, 448.1 [M+H]$^+$. $^1$H NMR (500 MHz, DMSO-d$_6$) δ 10.17-9.74 (m, 1H), 7.62 (d, J=8.7 Hz, 2H), 7.41 (d, J=8.4 Hz, 2H), 7.36 (d, J=4.6 Hz, 1H), 7.32 (d, J=4.6 Hz, 1H), 7.28 (d, J=8.7 Hz, 2H), 6.98 (d, J=8.7 Hz, 2H), 4.42-4.34 (m, 2H), 4.26-4.16 (m, 2H), 3.70-3.57 (m, 4H), 2.08 (s, 3H).

Example 95: 4-[3-(4-Hydroxyphenyl)-8-morpholino-imidazo[1,2-a]pyrazin-2-yl]benzonitrile

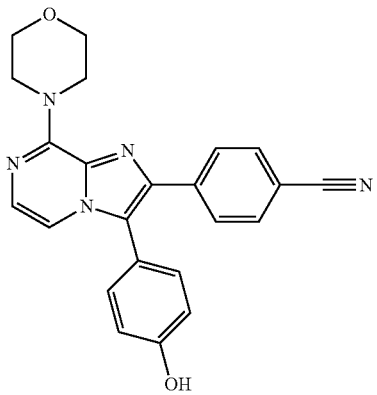 [SMILES: N#Cc1ccc(-c2nc3c(N4CCOCC4)nccn3c2-c2ccc(O)cc2)cc1]

The title compound was prepared in a manner analogous to Example 1. MS (ESI): mass calcd. for $C_{23}H_{19}N_5O_2$, 397.2; m/z found, 398.2 [M+H]$^+$. $^1$H NMR (400 MHz, CDCl$_3$) δ 7.81-7.74 (m, 2H), 7.60-7.54 (m, 2H), 7.34 (d, J=4.6 Hz, 1H), 7.31-7.26 (m, 2H), 7.24 (d, J=4.6 Hz, 1H), 7.06-7.00 (m, 2H), 5.39 (br s, 1H), 4.43-4.33 (m, 4H), 3.99-3.89 (m, 4H).

Example 96: 4-[2-[(3-Fluorophenyl)methyl]-8-morpholino-imidazo[1,2-a]pyrazin-3-yl]phenol

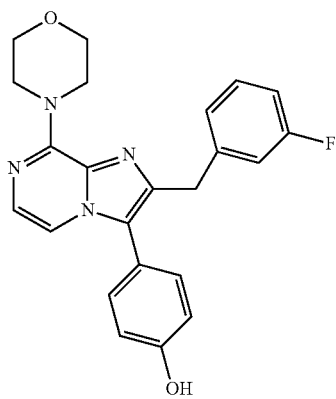 [SMILES: Oc1ccc(-c2c(Cc3cccc(F)c3)nc3c(N4CCOCC4)nccn23)cc1]

The title compound was prepared in a manner analogous to Example 1. MS (ESI): mass calcd. for $C_{23}H_{21}FN_4O_2$, 404.2; m/z found, 405.2 [M+H]$^+$. $^1$H NMR (500 MHz, DMSO-d$_6$) δ 10.16-9.54 (m, 1H), 7.48 (d, J=4.6 Hz, 1H), 7.33 (d, J=4.6 Hz, 1H), 7.30-7.21 (m, 3H), 7.01-6.90 (m, 5H), 4.19-4.12 (m, 4H), 4.04 (s, 2H), 3.79-3.68 (m, 4H).

Example 97: 4-[3-(1H-Indazol-5-yl)-8-morpholino-imidazo[1,2-a]pyrazin-2-yl]benzonitrile

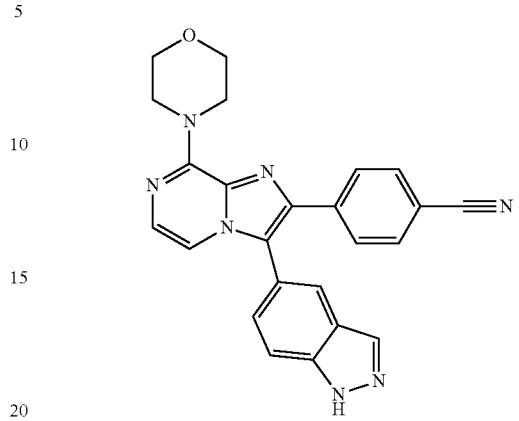

The title compound was prepared in a manner analogous to Example 1. MS (ESI): mass calcd. for $C_{24}H_{19}N_7O$, 421.2; m/z found, 422.2 [M+H]$^+$. $^1$H NMR (400 MHz, DMSO-d$_6$) δ 13.43 (br s, 1H), 8.20 (s, 1H), 7.96 (s, 1H), 7.80-7.67 (m, 5H), 7.41-7.30 (m, 3H), 4.33-4.22 (m, 4H), 3.89-3.69 (m, 4H).

Example 98: N-[(3S)-1-[2-(4-Fluorophenyl)-3-(2-oxo-1,3-dihydrobenzimidazol-5-yl)imidazo[1,2-a]pyrazin-8-yl]pyrrolidin-3-yl]acetamide

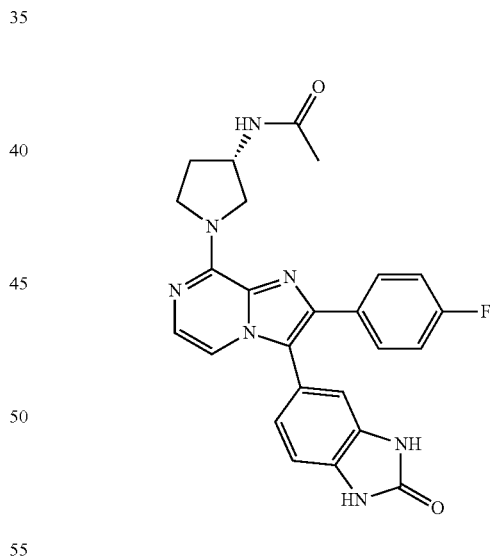

The title compound was prepared in a manner analogous to Example 1. MS (ESI): mass calcd. for $C_{25}H_{22}FN_7O_2$, 471.2; m/z found, 472.2 [M+H]$^+$. $^1$H NMR (400 MHz, DMSO-d$_6$) δ 10.85 (br. s, 2H), 8.20 (d, J=6.5 Hz, 1H), 7.66-7.56 (m, 2H), 7.26 (d, J=4.6 Hz, 1H), 7.20 (d, J=4.6 Hz, 1H), 7.20-7.13 (m, 2H), 7.13 (d, J=8.1 Hz, 1H), 7.00 (dd, J=1.6, 7.9 Hz, 1H), 6.94 (d, J=1.4 Hz, 1H), 4.44-4.33 (m, 1H), 4.06 (br s, 4H), 2.25-2.11 (m, 1H), 1.98-1.86 (m, 1H), 1.83 (s, 3H).

Example 99: 5-[2-(4-Fluorophenyl)-8-methoxy-imidazo[1,2-a]pyrazin-3-yl]-1,3-dihydrobenzimidazol-2-one

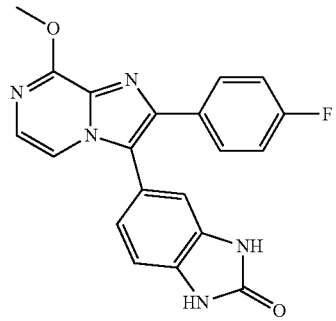 [SMILES: COc1nccn2c(-c3ccc4[nH]c(=O)[nH]c4c3)c(-c3ccc(F)cc3)nc12]

The title compound was prepared in a manner analogous to Example 192. MS (ESI): mass calcd. for $C_{20}H_{14}FN_5O_2$, 375.1; m/z found, 376.1 [M+H]$^+$. $^1$H NMR (400 MHz, DMSO-d$_6$) δ 10.87 (br s, 2H), 7.66 (d, J=4.9 Hz, 1H), 7.65-7.59 (m, 2H), 7.38 (d, J=4.6 Hz, 1H), 7.20-7.14 (m, 2H), 7.13 (d, J=7.9 Hz, 1H), 7.03 (dd, J=1.4, 7.9 Hz, 1H), 6.99 (d, J=1.2 Hz, 1H), 4.08 (s, 3H).

Example 100: N-[(3R)-1-[2-(4-Fluorophenyl)-3-(2-oxo-1,3-dihydrobenzimidazol-5-yl)imidazo[1,2-a]pyrazin-8-yl]pyrrolidin-3-yl]acetamide

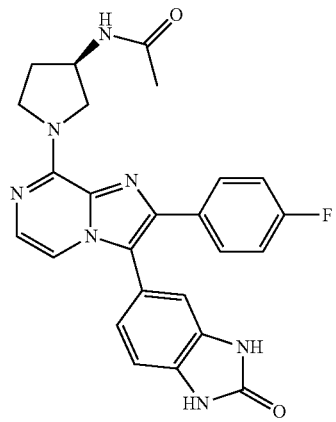 [SMILES: CC(=O)N[C@@H]1CCN(c2nccn3c(-c4ccc5[nH]c(=O)[nH]c5c4)c(-c4ccc(F)cc4)nc23)C1]

The title compound was prepared in a manner analogous to Example 1. MS (ESI): mass calcd. for $C_{25}H_{22}FN_7O_2$, 471.2; m/z found, 472.4 [M+H]$^+$. $^1$H NMR (500 MHz, DMSO-d$_6$) δ 10.83 (br s, 2H), 8.19 (d, J=6.6 Hz, 1H), 7.62 (dd, J=5.8, 8.4 Hz, 2H), 7.26 (d, J=4.6 Hz, 1H), 7.23-7.10 (m, 4H), 6.99 (dd, J=1.0, 7.9 Hz, 1H), 6.94 (s, 1H), 4.44-4.35 (m, 1H), 4.07 (br s, 4H), 2.25-2.13 (m, 1H), 1.98-1.88 (m, 1H), 1.84 (s, 3H).

Example 101: 5-[8-(Dimethylamino)-2-(4-fluorophenyl)imidazo[1,2-a]pyrazin-3-yl]-1,3-dihydrobenzimidazol-2-one

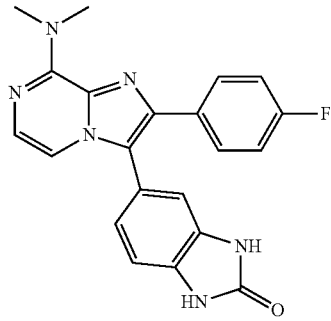 [SMILES: CN(C)c1nccn2c(-c3ccc4[nH]c(=O)[nH]c4c3)c(-c3ccc(F)cc3)nc12]

The title compound was prepared in a manner analogous to Example 1. MS (ESI): mass calcd. for $C_{21}H_{17}FN_6O$, 388.1; m/z found, 389.1 [M+H]$^+$. $^1$H NMR (500 MHz, DMSO-d$_6$) δ 10.84 (br s, 2H), 7.65-7.59 (m, 2H), 7.29 (d, J=4.6 Hz, 1H), 7.25 (d, J=4.6 Hz, 1H), 7.17 (br. t, J=9.0 Hz, 2H), 7.14 (d, J=8.1 Hz, 1H), 7.02 (dd, J=1.3, 7.9 Hz, 1H), 6.96 (d, J=1.2 Hz, 1H), 3.56 (s, 6H).

Example 102: 4-[8-Morpholino-3-(2-oxoindolin-5-yl)imidazo[1,2-a]pyrazin-2-yl]benzonitrile

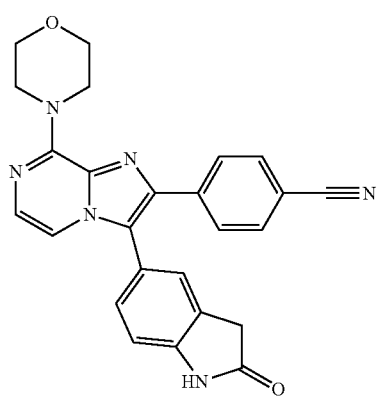 [SMILES: N#Cc1ccc(-c2nc3c(N4CCOCC4)nccn3c2-c2ccc3c(c2)CC(=O)N3)cc1]

The title compound was prepared in a manner analogous to Example 1. MS (ESI): mass calcd. for $C_{25}H_{20}N_6O_2$, 436.2; m/z found, 437.2 [M+H]$^+$. $^1$H NMR (500 MHz, DMSO-d$_6$) δ 10.67 (s, 1H), 7.81-7.78 (m, 2H), 7.78-7.74 (m, 2H), 7.37 (d, J=4.6 Hz, 1H), 7.35-7.30 (m, 2H), 7.26 (d, J=8.1 Hz, 1H), 7.03 (d, J=8.1 Hz, 1H), 4.33-4.19 (m, 4H), 3.85-3.71 (m, 4H), 3.58 (s, 2H).

Example 103: 4-[8-(4-Acetylpiperazin-1-yl)-3-(1H-indazol-5-yl)imidazo[1,2-a]pyrazin-2-yl]benzonitrile

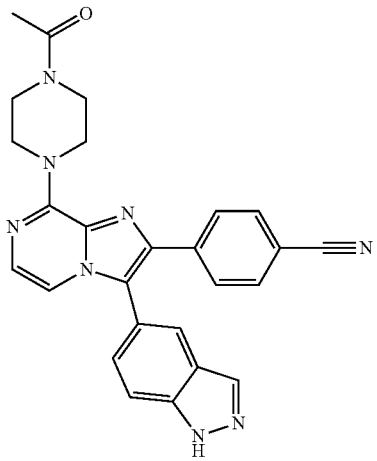 [SMILES: CC(=O)N1CCN(c2nccn3c(-c4ccc5[nH]ncc5c4)c(-c4ccc(C#N)cc4)nc23)CC1]

The title compound was prepared in a manner analogous to Example 1. MS (ESI): mass calcd. for $C_{26}H_{22}N_8O$, 462.2; m/z found, 463.2 [M+H]$^+$. $^1$H NMR (500 MHz, CDCl$_3$) δ 10.67 (br s, 1H), 8.18 (s, 1H), 7.86 (s, 1H), 7.75 (br. d, J=8.7 Hz, 2H), 7.72 (d, J=8.7 Hz, 1H), 7.53 (br. d, J=8.7 Hz, 2H), 7.37 (dd, J=1.3, 8.5 Hz, 1H), 7.35 (d, J=4.6 Hz, 1H), 7.26 (d, J=4.6 Hz, 1H), 4.51-4.43 (m, 2H), 4.40-4.33 (m, 2H), 3.89-3.82 (m, 2H), 3.74-3.67 (m, 2H), 2.21 (s, 3H).

Example 104: 5-[2-(4-Fluorophenyl)-8-(methylamino)imidazo[1,2-a]pyrazin-3-yl]-1,3-dihydrobenzimidazol-2-one

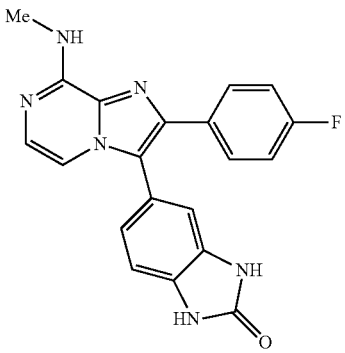 [SMILES: CNc1nccn2c(-c3ccc4[nH]c(=O)[nH]c4c3)c(-c3ccc(F)cc3)nc12]

The title compound was prepared in a manner analogous to Example 1. MS (ESI): mass calcd. for $C_{20}H_{15}FN_6O$, 374.1; m/z found, 375.1 [M+H]$^+$. $^1$H NMR (500 MHz, DMSO-d$_6$) δ 10.85 (br s, 1H), 10.76 (br s, 1H), 7.64-7.58 (m, 2H), 7.52 (q, J=4.5 Hz, 1H), 7.26 (d, J=4.6 Hz, 1H), 7.22 (d, J=4.6 Hz, 1H), 7.16 (br. t, J=9.0 Hz, 2H), 7.11 (d, J=7.8 Hz, 1H), 7.01 (dd, J=1.4, 8.1 Hz, 1H), 6.95 (s, 1H), 2.98 (d, J=4.6 Hz, 3H).

Example 105: 4-[8-Morpholino-3-(2-oxo-1,3-dihydrobenzimidazol-5-yl)imidazo[1,2-a]pyrazin-2-yl]benzonitrile

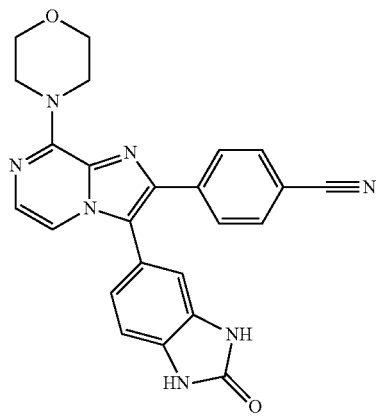 [SMILES: N#Cc1ccc(-c2nc3c(N4CCOCC4)nccn3c2-c2ccc3[nH]c(=O)[nH]c3c2)cc1]

The title compound was prepared in a manner analogous to Example 1. MS (ESI): mass calcd. for $C_{24}H_{19}N_7O_2$, 437.2; m/z found, 438.2 [M+H]$^+$. $^1$H NMR (500 MHz, DMSO-d$_6$) δ 10.93 (br s, 1H), 10.81 (br. s, 1H), 7.78 (d, J=8.4 Hz, 2H), 7.74 (d, J=8.1 Hz, 2H), 7.39-7.31 (m, 2H), 7.14 (d, J=7.8 Hz, 1H), 7.02 (d, J=8.1 Hz, 1H), 6.99 (s, 1H), 4.30-4.23 (m, 4H), 3.82-3.76 (m, 4H).

Example 106: 4-[8-(4-Acetylpiperazin-1-yl)-3-(2-oxo-1,3-dihydrobenzimidazol-5-yl)imidazo[1,2-a]pyrazin-2-yl]benzonitrile

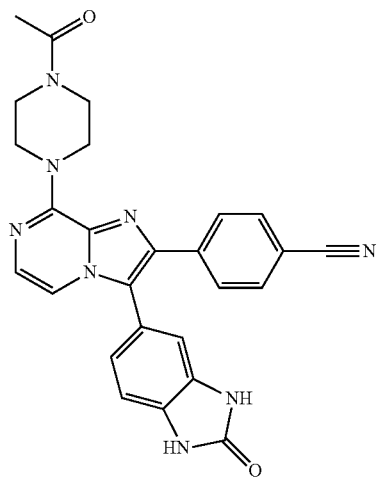 [SMILES: CC(=O)N1CCN(c2nccn3c(-c4ccc5[nH]c(=O)[nH]c5c4)c(-c4ccc(C#N)cc4)nc23)CC1]

The title compound was prepared in a manner analogous to Example 1. MS (ESI): mass calcd. for $C_{26}H_{22}N_8O_2$, 478.2; m/z found, 479.2 [M+H]$^+$. $^1$H NMR (500 MHz, DMSO-d$_6$) δ 10.82 (br s, 2H), 7.79 (d, J=8.4 Hz, 2H), 7.76 (d, J=8.7 Hz, 2H), 7.38-7.33 (m, J=1.4 Hz, 2H), 7.15 (d, J=7.8 Hz, 1H), 7.03 (dd, J=1.3, 7.9 Hz, 1H), 7.00 (s, 1H), 4.42-4.35 (m, 2H), 4.25-4.18 (m, 2H), 3.68-3.61 (m, 4H), 2.08 (s, 3H).

Example 107: 4-[8-(4-Acetylpiperazin-1-yl)-3-(2-oxoindolin-5-yl)imidazo[1,2-a]pyrazin-2-yl]benzonitrile

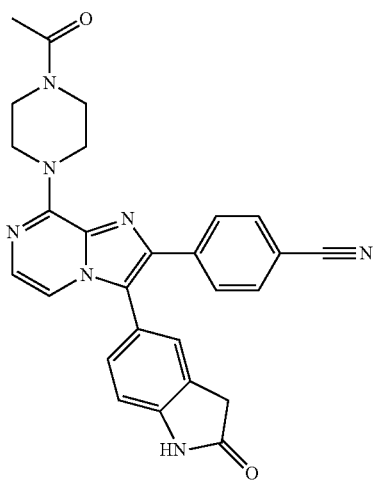 [SMILES: CC(=O)N1CCN(c2nccn3c(-c4ccc5c(c4)CC(=O)N5)c(-c4ccc(C#N)cc4)nc23)CC1]

The title compound was prepared in a manner analogous to Example 1. MS (ESI): mass calcd. for $C_{27}H_{23}N_7O_2$, 477.2; m/z found, 478.2 [M+H]$^+$. $^1$H NMR (500 MHz, CD$_3$OD) δ 7.85 (br. d, J=8.7 Hz, 2H), 7.69 (br. d, J=8.7 Hz, 2H), 7.55 (d, J=5.5 Hz, 1H), 7.38 (s, 1H), 7.35 (d, J=7.8 Hz, 1H), 7.25 (d, J=5.5 Hz, 1H), 7.15 (d, J=7.8 Hz, 1H), 4.67 (br s, 2H), 4.47 (br s, 2H), 3.98-3.88 (m, 4H), 3.65 (s, 2H), 2.21 (s, 3H) (NH CD$_3$OD).

Example 108: 5-(2-(4-Fluorophenyl)-8-(2-oxa-6-azaspiro[3.3]heptan-6-yl)imidazo[1,2-a]pyrazin-3-yl)-1,3-dihydrobenzo[c]isothiazole 2,2-dioxide

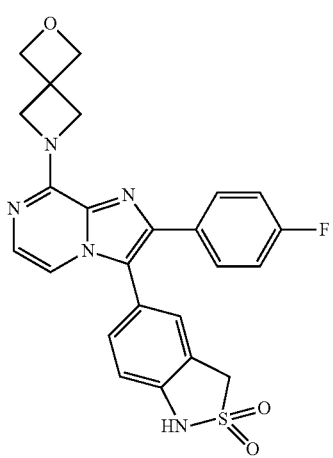 [SMILES: O=S1(=O)Cc2cc(-c3c(-c4ccc(F)cc4)nc4c(N5CC6(COC6)C5)nccn34)ccc2N1]

A suspension of 6-(3-bromo-2-(4-fluorophenyl)imidazo[1,2-a]pyrazin-8-yl)-2-oxa-6-azaspiro[3.3]heptane (Intermediate 41, 38 mg, 0.099 mmol), 5-(4,4,5,5-tetramethyl-1,3,2-dioxaborolan-2-yl)-1,3-dihydrobenzo[c]isothiazole 2,2-dioxide (Intermediate 33, 35 mg, 0.12 mmol) in dioxane (1.0 mL) and 1M Na$_2$CO$_3$ (1.0 mL) inside a 2 mL microwave vial was treated with Pd(PPh$_3$)$_4$ (5.7 mg, 0.0049 mmol) and then the reaction mixture was purged with nitrogen then heated in microwave at 110° C. for 10 minutes. The reaction mixture was cooled down, diluted with water and extracted with EtOAc, dried (Na$_2$SO$_4$), filtered, concentrated and the crude oil Purification (FCC, SiO$_2$, MeOH/DCM gradient 0 to 10% with 0.1% HOAc in DCM) to yield an off-white solid (4.9 mg, 10%). MS (ESI): mass calcd. for $C_{24}H_{20}FN_5O_3S$, 477.1; m/z found, 477.9 [M+H]$^+$. $^1$H NMR (400 MHz, CDCl$_3$) δ 7.66-7.55 (m, 2H), 7.33 (dd, J=8.1, 1.7 Hz, 1H), 7.29 (dd, J=3.1, 1.5 Hz, 2H), 7.15 (d, J=4.7 Hz, 1H), 7.09-6.96 (m, 3H), 4.92 (s, 4H), 4.74 (s, 4H), 4.45 (s, 2H).

Example 109: 5-(2-(4-Fluorophenyl)-8-(4-oxopiperidin-1-yl)imidazo[1,2-a]pyrazin-3-yl)indolin-2-one

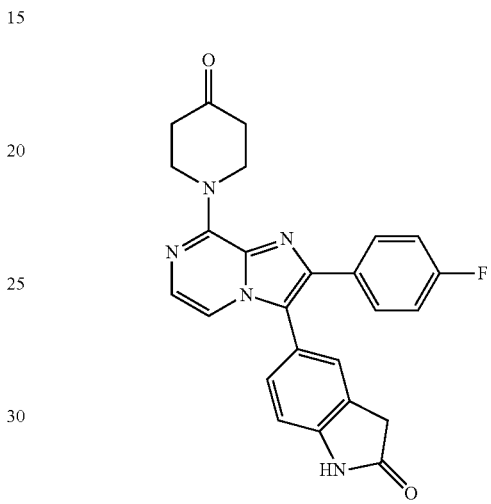

Step A: 5-(2-(4-Fluorophenyl)-8-(1,4-dioxa-8-azaspiro[4.5]decan-8-yl)imidazo[1,2-a]pyrazin-3-yl)indolin-2-one The title compound was prepared in a manner analogous to Example 1.

Step B: 5-(2-(4-Fluorophenyl)-8-(4-oxopiperidin-1-yl)imidazo[1,2-a]pyrazin-3-yl)indolin-2-one A solution of 5-(2-(4-fluorophenyl)-8-(1,4-dioxa-8-azaspiro[4.5]decan-8-yl)imidazo[1,2-a]pyrazin-3-yl)indolin-2-one (90 mg, 0.19 mmol) in dioxane (2.0 mL) and 6.0 M HCl (0.5 mL, 3.0 mmol) was stirred at 55° C. for 1 h. The reaction solution was diluted with saturated sodium bicarbonate solution and extracted with EtOAc, dried (Na$_2$SO$_4$), filtered, concentrated under reduced pressure. Purification (FCC, SiO$_2$, EtOAc/DCM gradient 0 to 50%) afforded the title compound (18.5 mg) as a yellowish solid.

Step C: 5-(2-(4-Fluorophenyl)-8-(4-oxopiperidin-1-yl)imidazo[1,2-a]pyrazin-3-yl)indolin-2-one. HCl Salt 5-(2-(4-Fluorophenyl)-8-(4-oxopiperidin-1-yl)imidazo[1,2-a]pyrazin-3-yl)indolin-2-one was dissolved in DCM (3.0 mL), and 4.0 N HCl in dioxane (1.2 eq, 12.6 μL, 0.05 mmol) was added to make the HCl salt. The solution was concentrated under reduced pressure to afford the title compound as a solid (20 mg, 23%). MS (ESI): mass calcd. for $C_{25}H_{20}FN_5O_2$, 441.2; m/z found, 442.2 [M+H]$^+$. $^1$H NMR (500 MHz, DMSO-d$_6$) δ 10.69 (s, 1H), 7.70-7.59 (m, 2H), 7.41 (d, J=5.0 Hz, 1H), 7.37-7.31 (m, 2H), 7.27 (dd, J=8.0, 1.7 Hz, 1H), 7.20 (t, J=8.9 Hz, 2H), 7.04 (d, J=8.0 Hz, 1H), 4.64 (s, 4H), 3.58 (s, 2H), 2.62 (t, J=6.0 Hz, 4H).

Example 110: 5-(2-(4-fluorophenyl)-8-(4-methyl-3-oxopiperazin-1-yl)imidazo[1,2-a]pyrazin-3-yl)indolin-2-one

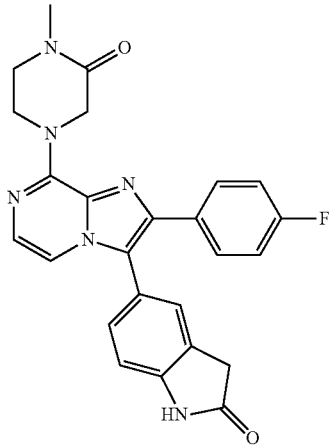 [SMILES: CN1CCN(c2nccn3c(-c4ccc5c(c4)CC(=O)N5)c(-c4ccc(F)cc4)nc23)CC1=O]

Step A: 4-(3-Bromo-2-(4-fluorophenyl)imidazo[1,2-a]pyrazin-8-yl)piperazin-2-one

The title compound was prepared in a manner analogous to Example 1.

Step B: 4-(3-bromo-2-(4-fluorophenyl)imidazo[1,2-a]pyrazin-8-yl)-1-methylpiperazin-2-one To a solution of 4-(3-bromo-2-(4-fluorophenyl)imidazo[1,2-a]pyrazin-8-yl(piperazin-2-one (120 mg, 0.31 mmol) in dioxane (2.0 mL) was added NaH (60% in mineral oil, 36.9 mg, 0.923 mmol) under $N_2$. The reaction mixture was stirred for 5 minutes. To the reaction mixture was added iodomethane (38.1 µL, 0.62 mmol). The reaction mixture was stirred at room temperature for 16 h. To the mixture was added DMF (1.0 mL) and another batch of iodomethane (80 µL, 1.30 mmol). The reaction mixture was stirred for an additional 3 h. The reaction mixture was diluted with water (5.0 mL) and extracted with EtOAc (3×5.0 mL). The combined organics were dried ($Na_2SO_4$), filtered, concentrated under reduced pressure. Purification (FCC, $SiO_2$EtOAc/DCM gradient 0 to 40%) afforded the title compound (40 mg, 32%) white solid. MS (ESI): mass calcd. for $C_{17}H_{15}BrFN_5O$, 403.0; m/z found, 403.8 [M+H]. $^1$H NMR (600 MHz, CDCl$_3$) δ 8.16-8.04 (m, 2H), 7.58 (d, J=4.5 Hz, 1H), 7.50 (d, J=4.6 Hz, 1H), 7.17 (t, J=8.7 Hz, 2H), 4.92 (s, 2H), 4.61 (t, J=5.4 Hz, 2H), 3.55 (t, J=5.4 Hz, 2H), 3.05 (s, 3H).

This reaction also generated 4-(3-bromo-2-(4-fluorophenyl)imidazo[1,2-a]pyrazin-8-yl)-1,3-dimethylpiperazin-2-one as a white solid (32 mg, 25%). MS (ESI): mass calcd. for $C_{18}H_{17}BrFN_5O$, 417.1; m/z found, 417.9 [M+H]. $^1$H NMR (600 MHz, CDCl$_3$) δ 8.21-8.03 (m, 2H), 7.60-7.51 (m, 1H), 7.51-7.43 (m, 1H), 7.17 (t, J=8.7 Hz, 2H), 6.07 (s, 1H), 5.64 (s, 1H), 3.81-3.68 (m, 1H), 3.67-3.52 (m, 1H), 3.29 (ddd, J=11.6, 3.5, 1.7 Hz, 1H), 3.03 (s, 3H), 1.64 (d, J=7.1 Hz, 3H).

Step C: 5-(2-(4-Fluorophenyl)-8-(4-methyl-3-oxopiperazin-1-yl)imidazo[1,2-a]pyrazin-3-yl)indolin-2-one A suspension of 4-(3-bromo-2-phenylimidazo[1,2-a]pyrazin-8-yl)-1-methylpiperazin-2-one (34 mg, 0.084 mmol), 5-(4,4,5,5-tetramethyl-[1,3,2]dioxaborolan-2-yl)indolin-2-one (33 mg, 0.13 mmol) in dioxane (1.0 mL) and 1M $Na_2CO_3$ (0.85 mL) inside a 2 mL microwave vial was treated with Pd(Ph$_3$P)$_4$ (5.0 mg, 0.0042 mmol) and was purged with nitrogen. The reaction mixture was heated under microwave conditions at 110° C. for 10 minutes. The reaction mixture was cooled down, diluted with water and extracted with EtOAc. The combined organics were dried ($Na_2SO_4$), filtered, and concentrated under reduced pressure. Purification (FCC, $SiO_2$, EtOAc/DCM gradient 0 to 40%, then 2M $NH_3$MeOH/DCM 0 to 5%) afforded the title compound as an off-white solid (26.9 mg, 70.1%). MS (ESI): mass calcd. for $C_{25}H_{21}FN_6O_2$, 456.2; m/z found, 456.9 [M+H]$^+$. $^1$H NMR (400 MHz, CDCl$_3$) δ 7.83 (s, 1H), 7.72-7.57 (m, 2H), 7.34 (d, J=4.6 Hz, 1H), 7.29-7.26 (m, 3H), 7.06-7.02 (m, 1H), 6.98 (t, J=8.7 Hz, 2H), 4.96 (s, 2H), 4.66 (t, J=5.4 Hz, 2H), 3.62 (s, 2H), 3.58 (t, J=5.4 Hz, 2H), 3.07 (s, 3H).

Example 111: 5-(8-(2,4-Dimethyl-3-oxopiperazin-1-yl)-2-(4-fluorophenyl)imidazo[1,2-a]pyrazin-3-yl)indolin-2-one

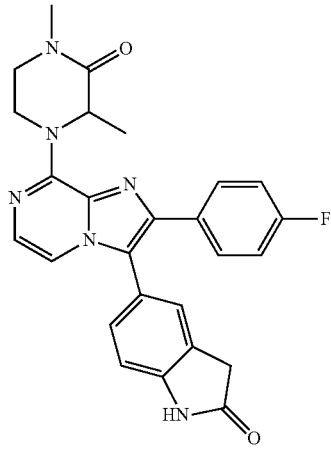 [SMILES: CC1C(=O)N(C)CCN1c1nccn2c(-c3ccc4c(c3)CC(=O)N4)c(-c3ccc(F)cc3)nc12]

The title compound was prepared in a manner analogous to Example 110, substituting 4-(3-bromo-2-(4-fluorophenyl)imidazo[1,2-a]pyrazin-8-yl)-1,3-dimethylpiperazin-2-one (by-product from Example 110, Step A) for 4-(3-bromo-2-phenylimidazo[1,2-a]pyrazin-8-yl)-1-methylpiperazin-2-one in Step B. MS (ESI): mass calcd. for $C_{26}H_{23}FN_6O_2$, 470.2; m/z found, 470.9 [M+H]$^+$. $^1$H NMR (400 MHz, CDCl$_3$) δ 8.74 (s, 1H), 7.72-7.53 (m, 2H), 7.31 (d, J=4.6 Hz, 1H), 7.29-7.24 (m, 2H), 7.22 (d, J=4.6 Hz, 1H), 7.07 (d, J=7.9 Hz, 1H), 6.98 (t, J=8.7 Hz, 2H), 6.15 (d, J=7.8 Hz, 1H), 5.73 (d, J=12.2 Hz, 1H), 3.88-3.55 (m, 4H), 3.32 (ddd, J=11.8, 3.6, 1.7 Hz, 1H), 3.05 (s, 3H), 1.67 (d, J=7.1 Hz, 3H).

Example 112: tert-Butyl 4-(2-benzyl-5-bromo-3-(2-oxoindolin-5-yl)imidazo[1,2-a]pyrazin-8-yl)piperazine-1-carboxylate

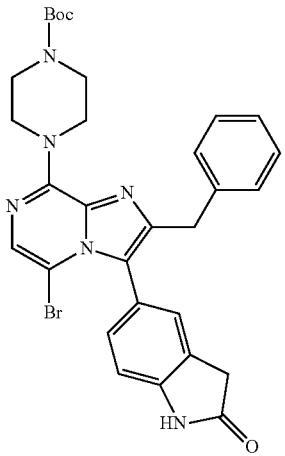 [SMILES: CC(C)(C)OC(=O)N1CCN(c2ncc(Br)n3c(-c4ccc5c(c4)CC(=O)N5)c(Cc4ccccc4)nc23)CC1]

To a solution of tert-butyl 4-[2-benzyl-3-(2-oxoindolin-5-yl)imidazo[1,2-a]pyrazin-8-yl]piperazine-1-carboxylate (Example 36, 133 mg, 0.177 mmol) in DCM (5 mL) was added NBS (31.6 mg, 0.177 mmol). The reaction mixture was stirred at room temperature for 0.5 h. The reaction mixture was diluted with NaHCO$_3$ and extracted with EtOAc. The combined organics were dried (Na$_2$SO$_4$), filtered, concentrated under reduced pressure. Purification (FCC, SiO$_2$EtOAc/hexane gradient 0 to 40%) afforded the title compound (66 mg, 62%). MS (ESI): mass calcd. for C$_{30}$H$_{31}$BrN$_6$O$_3$, 602.2; m/z found, 602.8 [M+H]$^+$. $^1$H NMR (400 MHz, CDCl$_3$) δ 7.84 (s, 1H), 7.33 (s, 1H), 7.24-7.18 (m, 2H), 7.19-7.13 (m, 1H), 7.13-7.08 (m, 3H), 7.08-7.03 (m, 1H), 6.88 (d, J=7.8 Hz, 1H), 4.31-4.17 (m, 4H), 3.90 (s, 2H), 3.72-3.42 (m, 6H), 1.50 (s, 9H).

Example 113: 5-(8-(4-Acetylpiperazin-1-yl)-2-benzyl-5-bromoimidazo[1,2-a]pyrazin-3-yl)indolin-2-one

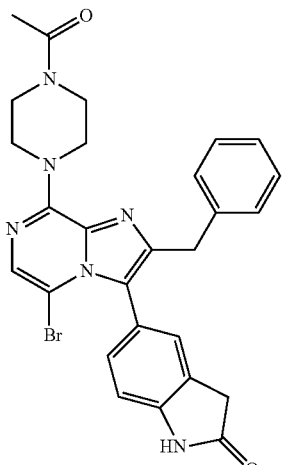

Step A: 5-(2-Benzyl-5-bromo-8-(piperazin-1-yl)imidazo[1,2-a]pyrazin-3-yl)indolin-2-one To a solution of tert-butyl 4-(2-benzyl-5-bromo-3-(2-oxoindolin-5-yl)imidazo[1,2-a]pyrazin-8-yl(piperazine-1-carboxylate (Example 112, 60 mg, 0.10 mmol) in DCM (2.0 mL) was added TFA (0.5 mL). The reaction mixture was stirred at room temperature for 1 h. The reaction mixture was concentrated under reduced pressure to afford the title compound which was used in the next step without further purification.

Step B: 5-(8-(4-Acetylpiperazin-1-yl)-2-benzyl-5-bromoimidazo[1,2-a]pyrazin-3-yl)indolin-2-one To a solution of 5-(2-benzyl-5-bromo-8-(piperazin-1-yl)imidazo[1,2-a]pyrazin-3-yl)indolin-2-one (50 mg, 0.10 mmol) in DCM (3.0 mL) was added with Ac$_2$O (28.2 μL, 0.298 mmol) and Et$_3$N (124 μL, 0.894 mmol). The reaction mixture was stirred for 1 h. The reaction mixture was diluted with sat. aq. NaHCO$_3$ and extracted with DCM. The organics were dried (Na$_2$SO$_4$), filtered, concentrated under reduced pressure. Purification (FCC, SiO$_2$EtOAc/DCM gradient 0 to 50%, then 2M NH$_3$MeOH in DCM/DCM 0 to 10%) afforded the title compound (28 mg, 52%). MS (ESI): mass calcd. for C$_{27}$H$_{25}$BrN$_6$O$_2$, 544.1; m/z found, 544.8 [M+H]$^+$. $^1$H NMR (600 MHz, CDCl$_3$) δ 9.01 (s, 1H), 7.34 (s, 1H), 7.26-7.19 (m, 2H), 7.19-7.14 (m, 1H), 7.14-7.09 (m, 3H), 7.09-7.04 (m, 1H), 6.93 (d, J=7.9 Hz, 1H), 4.36-4.18 (m, 4H), 3.91 (s, 2H), 3.86-3.62 (m, 4H), 3.62-3.52 (m, 2H), 2.18 (s, 3H).

Example 114: 5-(8-(4-Acetylpiperazin-1-yl)-2-benzyl-5-methylimidazo[1,2-a]pyrazin-3-yl)indolin-2-one

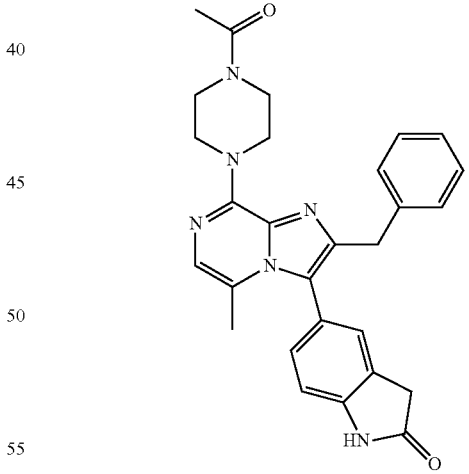

To a solution of 5-(8-(4-acetylpiperazin-1-yl)-2-benzyl-5-bromoimidazo[1,2-a]pyrazin-3-yl)indolin-2-one (Example 113, 8 mg, 0.015 mmol), methylboronic acid (13.2 mg, 0.22 mmol) and Ph$_3$P (0.29 mg, 0.0011 mmol) in dioxane (0.4 mL) and 1M Na$_2$CO$_3$ (0.2 mL) was added with Pd(OAc)$_2$ (0.25 mg, 0.0011 mmol). The reaction mixture was purged with nitrogen then heated in oil bath at 85° C. for 4 h. The reaction mixture was cooled, diluted with water (3.0 mL) and extracted with EtOAc (3×3.0 mL). The combined organics were dried (Na$_2$SO$_4$), filtered, concentrated under reduced pressure. Purification (FCC, SiO$_2$, EtOAc/DCM gradient 0 to 40%, then 2M NH$_3$MeOH/DCM 0 to 5%) to afford (6.6 mg, 29%) as a colorless gel which was further purified (SFC, Stationary phase: Lux 5 um Cellulose-4, 250×21 mm, Mobile phase: 45% MeOH+0.2% TEA, 55% CO$_2$) to afford the title compound (2.1 mg, 30%). MS (ESI): mass calcd. for C$_{28}$H$_{28}$N$_6$O$_2$, 480.2 m/z found, 481.0 [M+H]. $^1$H NMR (400 MHz, CDCl$_3$): δ 7.85 (s, 1H), 7.24-7.18 (m, 2H), 7.17-7.03 (m, 5H), 7.00 (d, J=1.2 Hz, 1H), 6.88 (d, J=7.9 Hz, 1H), 4.17 (dt, J=25.0, 5.3 Hz, 4H), 3.90 (s, 2H), 3.73 (dt, J=61.4, 5.3 Hz, 4H), 3.55 (s, 2H), 2.17 (s, 3H), 1.91 (d, J=1.1 Hz, 3H).

Example 115: 5-[8-(4-Acetylpiperazin-1-yl)-2-(4-fluorophenyl)imidazo[1,2-a]pyrazin-3-yl]indolin-2-one

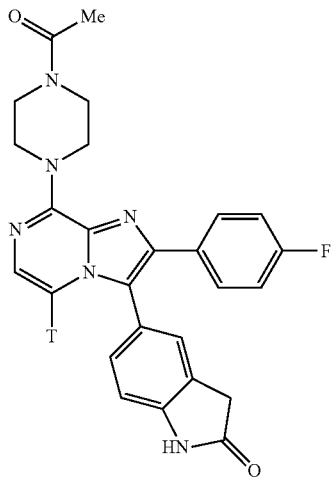

Step A. tert-Butyl 4-(2-(4-fluorophenyl)-3-(2-oxoindolin-5-yl)imidazo[1,2-a]pyrazin-8-yl)piperazine-1-carboxylate The title compound was prepared in a manner analogous to Example 1. MS (ESI): mass calcd. for C$_{29}$H$_{29}$FN$_6$O$_3$, 528.6 m/z found, 529.3 [M+H].

Step B: tert-Butyl 4-(5-bromo-2-(4-fluorophenyl)-3-(2-oxoindolin-5-yl)imidazo[1,2-a]pyrazin-8-yl)piperazine-1-carboxylate To a solution of tert-butyl 4-(2-(4-fluorophenyl)-3-(2-oxoindolin-5-yl)imidazo[1,2-a]pyrazin-8-yl)piperazine-1-carboxylate (47 mg, 0.09 mmol) in DCM (10 mL) was added NBS (18 mg, 0.1 mmol). The reaction mixture was stirred at room temperature for 48 h. The mixture was diluted with NaHCO$_3$ and extracted with EtOAc. The combined organics were dried (Na$_2$SO$_4$), filtered, concentrated under reduced pressure. Purification (FCC, SiO$_2$, EtOAc/hexane gradient 0 to 40%) afforded the title compound (13 mg, 25%).

Step C: 5-(5-Bromo-2-(4-fluorophenyl)-8-(piperazin-1-yl)imidazo[1,2-a]pyrazin-3-yl)indolin-2-one To a solution of tert-butyl 4-(5-bromo-2-(4-fluorophenyl)-3-(2-oxoindolin-5-yl)imidazo[1,2-a]pyrazin-8-yl)piperazine-1-carboxylate (13 mg, 0.04 mmol) in formic acid (0.5. mL) was added of 6.0 N HCl (71 µL). The reaction mixture was stirred for 10 min, then diluted with MeOH. The reaction mixture was concentrated under reduced pressure to afford the title compound (12.4 mg, 99%), which was used crude in the next step without further purification.

Step D: 5-(8-(4-Acetylpiperazin-1-yl)-5-bromo-2-(4-fluorophenyl)imidazo[1,2-a]pyrazin-3-yl)indolin-2-one To a solution of 5-(5-bromo-2-(4-fluorophenyl)-8-(piperazin-1-yl)imidazo[1,2-a]pyrazin-3-yl)indolin-2-one (8.5 mg, 0.02 mmol) in DCM (1 mL) was added Et$_3$N (10 µL, 0.07 mmol), then acetyl chloride (1.6 µL, 0.02 mmol). The reaction mixture was stirred at room temperature for 20 min. The mixture was diluted with NaHCO$_3$ and extracted with EtOAc. The combined organics were dried (Na$_2$SO$_4$), filtered, concentrated under reduced pressure. Purification (FCC, SiO$_2$, EtOAc/hexane gradient 0 to 40%) afforded the title compound (8.5 mg, 72%).

Step E: 5-[8-(4-Acetylpiperazin-1-yl)-2-(4-fluorophenyl)imidazo[1,2-a]pyrazin-3-yl]indolin-2-one To a solution of 5-(8-(4-acetylpiperazin-1-yl)-5-bromo-2-(4-fluorophenyl)imidazo[1,2-a]pyrazin-3-yl)indolin-2-one (4 mg, 0.007 mmol) in EtOH (1 mL) was added Pd/C 10% (5 mg,), and $^3$H$_2$ (tritium) gas (10 Ci). The mixture was stirred for 3 h at room temperature. The reaction mixture was dissolved in ethanol and filtered. The labile tritium was exchanged as the ethanol was removed by rotovap. This was repeated 2 additional times. Purification (HPLC, Capcell C18 column (20×250 mm). Mobile phase: 30% CH$_3$CN, 0.1% TFAFlow: 7 mL/min, U.V.: 278 nm) afforded the title compound (20 µCi).

Example 116: 6-(2-(4-Fluorophenyl)-8-morpholinoimidazo[1,2-a]pyrazin-3-yl)benzo[d]oxazol-2(3H)-one

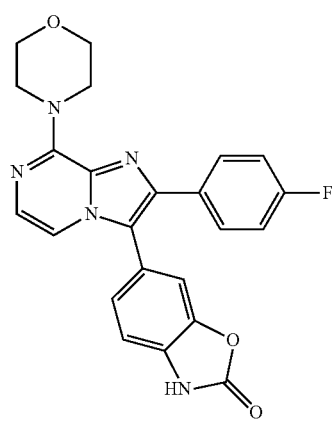 [SMILES: O=c1[nH]c2ccc(-c3c(-c4ccc(F)cc4)nc4c(N5CCOCC5)nccn34)cc2o1]

Step A: 6-(2-(4-Fluorophenyl)-8-morpholinoimidazo[1,2-a]pyrazin-3-yl)-34(2-(trimethylsilyl)ethoxy)methyl)benzo[d]oxazol-2(3H)-one To a solution of 4-(2-(4-fluorophenyl)-3-(4,4,5,5-tetramethyl-1,3,2-dioxaborolan-2-yl)imidazo[1,2-a]pyrazin-8-yl)morpholine (Intermediate 42, 50.0 mg, 0.118 mmol) and 6-bromo-3-((2-(trimethylsilyl)ethoxy)methyl) benzo[d]oxazol-2(3H)-one (Intermediate 35, 81.1 mg, 0.236 mmol) in 1,4-dioxane (1.6 mL) and water (0.4 mL) was added potassium phosphate tribasic (62.5 mg, 0.295 mmol) and 1,1'-bis(di-tert-butylphosphino)ferrocene palladium dichloride (PdCl$_2$(dtbpf)) (15.4 mg, 0.0236 mmol). The reaction mixture was purged with nitrogen for 1 min. then heated at 100° C. for 16 h. The reaction mixture was cooled, diluted with water (5.0 mL), and extracted with EtOAc (3×5 mL). The combined organics were dried (Na$_2$SO$_4$), filtered, concentrated under reduced pressure. Purification (prep HPLC, Agilent 1100 Series XBridge Prep C18 OBD 5 um, basic conditions (20 mM Ammonium Hydroxide in water/MeCN)) afforded the title compound as an oil (30.4 mg, 45.9%). MS (ESI): mass calcd. for C$_{29}$H$_{32}$FN$_5$O$_4$Si, 561.2 m/z found, 562.0 [M+H].

Step B. 6-(2-(4-Fluorophenyl)-8-morpholinoimidazo[1,2-a]pyrazin-3-yl)-3-(hydroxymethyl)benzo[d]oxazol-2(3H)-one To a solution of 6-(2-(4-fluorophenyl)-8-morpholinoimidazo[1,2-a]pyrazin-3-yl)-3-((2-(trimethylsilyl)ethoxy)methyl)benzo[d]oxazol-2(3H)-one (30.0 mg, 0.0534 mmol) in DCM (2 mL) was added with TFA (1 mL). The reaction mixture was stirred at 23° C. for 1 h. The reaction solution was diluted with sat. aq. NaHCO$_3$ (5 mL), and extracted with DCM (3×5 mL). The combined organics were dried (Na$_2$SO$_4$), filtered, concentrated under reduced pressure to afford the title compound (24.4 mg, 99.0%).

Step C: 6-(2-(4-Fluorophenyl)-8-morpholinoimidazo[1,2-a]pyrazin-3-yl)benzo[d]oxazol-2(3H)-one To a solution of 6-(2-(4-fluorophenyl)-8-morpholinoimidazo[1,2-a]pyrazin-3-yl)-3-(hydroxymethyl)benzo[d]oxazol-2(3H)-one (10.0 mg, 0.0217 mmol) in DCM (1.0 mL) was added 2N NH$_3$OH in MeOH (1.0 mL). The reaction mixture was stirred at room temperature for 1 h. The reaction mixture was concentrated under reduced pressure to afford the title compound (9.4 mg, 100%). MS (ESI): mass calcd. for C$_{23}$H$_{18}$FN$_5$O$_3$, 431.1 m/z found, 431.9 [M+H]. $^1$H NMR (400 MHz, CDCl$_3$): δ 7.63-7.53 (m, 2H), 7.35 (d, J=4.6 Hz, 1H), 7.26-7.18 (m, 5H), 6.98 (t, J=8.7 Hz, 2H), 4.37 (t, J=4.8 Hz, 4H), 4.02-3.80 (m, 4H).

Example 117-Example 121 were prepared in a manner analogous to Example 116.

Example 117: 5-[2-(4-Fluorophenyl)-8-morpholino-imidazo[1,2-a]pyrazin-3-yl]-1,3-dihydro-2,1-benzothiazole 2,2-dioxide

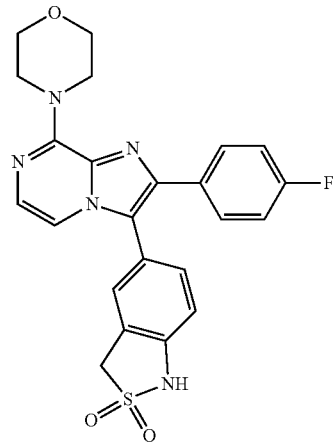 [SMILES: O=S1(=O)Cc2cc(-c3c(-c4ccc(F)cc4)nc4c(N5CCOCC5)nccn34)ccc2N1]

The title compound was prepared in a manner analogous to Example 116. MS (ESI): mass calcd. for C$_{23}$H$_{20}$FN$_5$O$_3$S, 465.1; m/z found, 466.1 [M+H]$^+$. $^1$H NMR (400 MHz, CDCl$_3$) δ 7.65-7.51 (m, 2H), 7.38-7.34 (m, 1H), 7.34-7.28 (m, 2H), 7.23 (d, J=4.6 Hz, 1H), 7.05 (dd, J=8.1, 0.6 Hz, 1H), 7.00 (t, J=8.7 Hz, 2H), 4.46 (s, 2H), 4.37 (t, J=4.7 Hz, 4H), 3.92 (t, J=4.8 Hz, 4H).

Example 118: 6-[2-(4-Fluorophenyl)-8-morpholino-imidazo[1,2-a]pyrazin-3-yl]-3H-1,3-benzothiazol-2-one

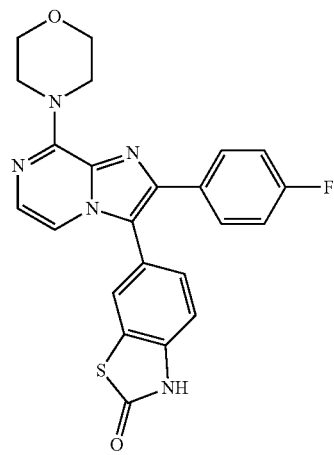 [SMILES: O=c1[nH]c2ccc(-c3c(-c4ccc(F)cc4)nc4c(N5CCOCC5)nccn34)cc2s1]

The title compound was prepared in a manner analogous to Example 116. MS (ESI): mass calcd. for C$_{23}$H$_{18}$FN$_5$O$_2$S, 447.1; m/z found, 447.9 [M+H]$^+$. $^1$H NMR (500 MHz, CDCl$_3$) δ 7.66-7.53 (m, 2H), 7.45 (d, J=1.6 Hz, 1H), 7.35 (d, J=4.5 Hz, 1H), 7.33-7.28 (m, 1H), 7.26 (s, 3H), 6.99 (t, J=8.7 Hz, 2H), 4.37 (t, J=4.7 Hz, 4H), 4.10-3.72 (m, 4H).

Example 119: 1-[3-(2,2-Dioxo-1,3-dihydro-2,1-benzothiazol-5-yl)-2-(4-fluorophenyl)imidazo[1,2-a]pyrazin-8-yl]piperidin-4-ol

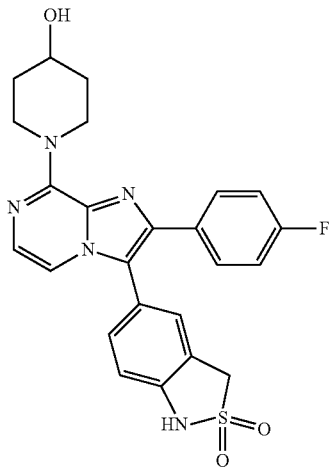 [SMILES: O=S1(=O)Cc2cc(-c3c(-c4ccc(F)cc4)nc4c(N5CCC(O)CC5)nccn34)ccc2N1]

The title compound was prepared in a manner analogous to Example 116. MS (ESI): mass calcd. for $C_{24}H_{22}FN_5O_3S$, 479.1; m/z found, 480.2 [M+H]$^+$. $^1$H NMR (500 MHz, DMSO-d$_6$) δ 10.99 (s, 1H), 7.66-7.58 (m, 2H), 7.42 (d, J=1.7 Hz, 1H), 7.37 (d, J=5.0 Hz, 1H), 7.33 (dd, J=8.2, 1.9 Hz, 1H), 7.27 (d, J=5.0 Hz, 1H), 7.22 (t, J=8.9 Hz, 2H), 7.02 (d, J=8.2 Hz, 1H), 4.82 (s, 2H), 4.71 (s, 1H), 4.64 (s, 2H), 3.88 (s, 3H), 1.94 (s, 2H), 1.57 (d, J=11.9 Hz, 2H).

Example 120: 6-[2-(4-Fluorophenyl)-8-morpholino-imidazo[1,2-a]pyrazin-3-yl]-3,4-dihydro-1H-quinazolin-2-one

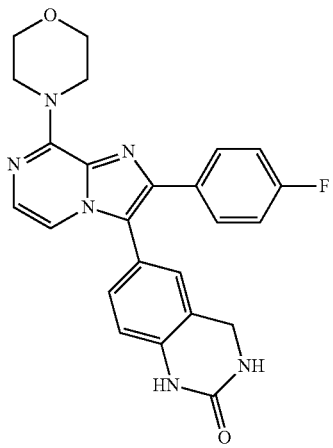 [SMILES: O=C1NCc2cc(-c3c(-c4ccc(F)cc4)nc4c(N5CCOCC5)nccn34)ccc2N1]

The title compound was prepared in a manner analogous to Example 116. MS (ESI): mass calcd. for $C_{24}H_{21}FN_6O_2$, 444.5; m/z found, 445.2 [M+H]$^+$. $^1$H NMR (500 MHz, DMSO-d$_6$) δ 9.32 (d, J=1.5 Hz, 1H), 7.63 (dd, J=8.7, 5.7 Hz, 2H), 7.39 (d, J=4.8 Hz, 1H), 7.32 (d, J=4.8 Hz, 1H), 7.25-7.16 (m, 4H), 6.96 (d, J=8.2 Hz, 2H), 4.37 (s, 2H), 4.30 (s, 4H), 3.81 (t, J=4.7 Hz, 4H).

Example 121: 5-[2-(4-Fluorophenyl)-8-morpholino-imidazo[1,2-a]pyrazin-3-yl]-1H-benzimidazol-2-amine

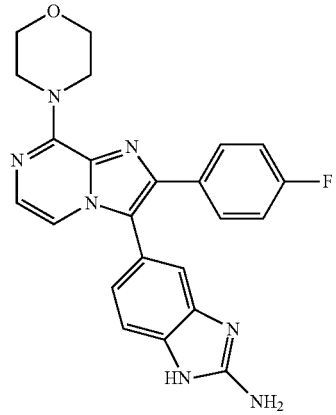 [SMILES: Nc1nc2cc(-c3c(-c4ccc(F)cc4)nc4c(N5CCOCC5)nccn34)ccc2[nH]1]

The title compound was prepared in a manner analogous to Example 116. MS (ESI): mass calcd. for $C_{23}H_{20}FN_7O$, 429.5; m/z found, 430.2 [M+H]$^+$. $^1$H NMR (500 MHz, DMSO-d$_6$) δ 12.70 (d, J=52.1 Hz, 1H), 8.66 (s, 2H), 7.64-7.52 (m, 3H), 7.44 (d, J=1.5 Hz, 1H), 7.40-7.33 (m, 2H), 7.31 (dd, J=8.2, 1.6 Hz, 1H), 7.16 (t, J=8.9 Hz, 2H), 4.27 (t, J=4.5 Hz, 4H), 3.93-3.67 (m, 4H).

Example 122: 4-[3-(3-Fluoro-1H-indol-5-yl)-2-(4-fluorophenyl)imidazo[1,2-a]pyrazin-8-yl]morpholine

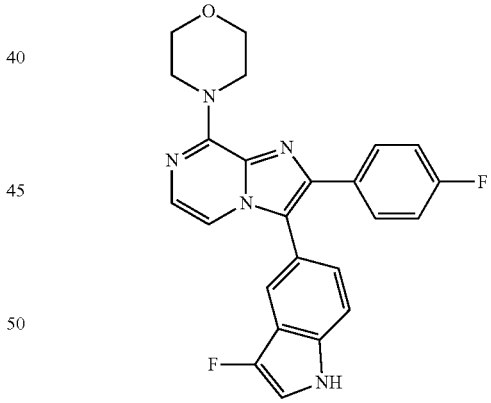

To a solution of 4-(2-(4-fluorophenyl)-3-(4,4,5,5-tetramethyl-1,3,2-dioxaborolan-2-yl)imidazo[1,2-a]pyrazin-8-yl)morpholine (Intermediate 42; 95 mg, 0.224 mmol) and 5-bromo-3-fluoro-1H-indole (Intermediate 34, 72.0 mg, 0.336 mmol) in 1,4-dioxane (1.6 mL) and water (0.4 mL) was added potassium phosphate tribasic (119 mg, 0.561 mmol) and PdCl$_2$(dtbpf) (29.2 mg, 0.0449 mmol). The resulting mixture was purged with nitrogen for 1 min. then heated at 100° C. for 16 h. The reaction mixture was cooled down, diluted with water (5.0 mL), and extracted with EtOAc (3×5 mL). The combined organics were dried (Na₂SO₄), filtered, concentrated under reduced pressure. Purification (prep HPLC, Agilent 1100 Series XBridge Prep C18 OBD 5 um, basic conditions (20 mM Ammonium Hydroxide in water/MeCN)) afforded the title compound (57.4 mg) which was further purified (FCC, SiO₂, 0-30% EtOAc/Hexane) to afford the title compound (38.9 mg, 40.2%). MS (ESI): mass calcd. for $C_{24}H_{19}F_2N_5O$, 431.1 m/z found, 431.9 [M+H]. ¹H NMR (500 MHz, CDCl₃): δ 7.82 (s, 1H), 7.73-7.68 (m, 1H), 7.67-7.57 (m, 2H), 7.46 (dd, J=8.4, 2.3 Hz, 1H), 7.33-7.30 (m, 1H), 7.29-7.27 (m, 1H), 7.18 (dd, J=8.4, 1.6 Hz, 1H), 7.11 (t, J=2.8 Hz, 1H), 6.99-6.87 (m, 2H), 4.38 (t, J=4.7 Hz, 4H), 4.02-3.79 (m, 4H).

Example 123: 3-Fluoro-5-[2-(4-fluorophenyl)-8-morpholino-imidazo[1,2-a]pyrazin-3-yl]indolin-2-one

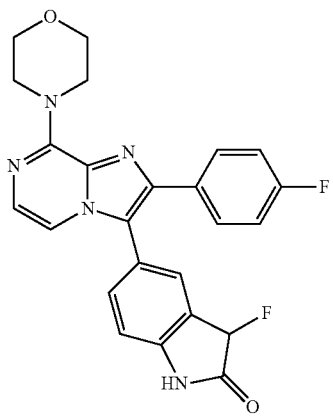 [SMILES: O=C1Nc2ccc(-c3c(-c4ccc(F)cc4)nc4c(N5CCOCC5)nccn34)cc2C1F]

To a solution of 4-(3-(3-fluoro-1H-indol-5-yl)-2-(4-fluorophenyl)imidazo[1,2-a]pyrazin-8-yl)morpholine (Example 122, 17.0 mg, 0.0394 mmol) in AcOH (0.5 mL) and H₂O (0.1 mL) was added a solution of pyridinium tribromide (13.9 mg, 0.0433 mmol) in acetic acid (0.5 mL). The reaction mixture was stirred for 10 min. The reaction mixture was concentrated under reduced pressure and the residue was diluted with 10% Na₂CO₃ (5 mL) and extracted with EtOAc (3×5 mL). The combined organics were dried (Na₂SO₄), filtered, concentrated under reduced pressure. Purification (FCC, SiO₂, 0 to 40% EtOAc: DCM) to afford the title compound (4.6 mg) which was further purified by prep. TLC (EMD Chemicals Inc., 13794-7, PLC Silica glass 60 F254, 0.5 mm with concentrating zone 20×4 cm, 20×20 cm plate, 0 to 40% EtOAc: DCM) to give oil (1.5 mg, 8.5%). MS (ESI): mass calcd. for $C_{24}H_{19}F_2N_5O_2$, 447.2 m/z found, 448.1 [M+H]. ¹H NMR (500 MHz, CDCl₃): δ 7.73 (s, 1H), 7.64-7.56 (m, 2H), 7.52 (s, 1H), 7.42-7.38 (m, 1H), 7.36 (d, J=4.6 Hz, 1H), 7.25 (d, J=4.6 Hz, 1H), 7.05 (dd, J=8.0, 1.3 Hz, 1H), 7.00 (t, J=8.7 Hz, 2H), 5.75 (d, J=50.6 Hz, 1H), 4.38 (t, J=4.8 Hz, 4H), 4.00-3.83 (m, 4H).

Example 124: 6-[2-(4-fluorophenyl)-8-morpholino-imidazo[1,2-a]pyrazin-3-yl]-1,4-dihydro-3,1-benzoxazin-2-one

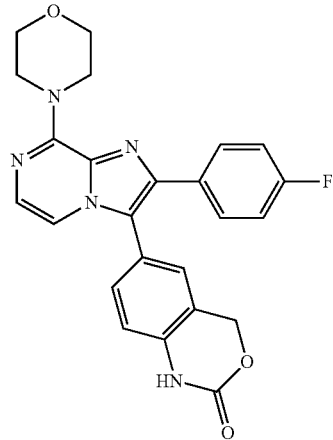 [SMILES: O=C1Nc2ccc(-c3c(-c4ccc(F)cc4)nc4c(N5CCOCC5)nccn34)cc2CO1]

Step A: 4-(2-(4-Fluorophenyl)imidazo[1,2-a]pyrazin-8-yl)morpholine

To a solution of 8-chloro-2-(4-fluorophenyl)imidazo[1,2-a]pyrazine (Example 1, product from Step A, 50.0 mg, 0.202 mmol) in CH₃CN (2.0 mL) was added morpholine (35.2 µL, 0.404 mmol) and triethylamine (33.6 µL, 0.242 mmol). The reaction mixture was heated at 80° C. for 16 h. The reaction mixture was concentrated under reduced pressure. Purification (FCC, SiO₂, 0 to 50% EtOAc/Hexane) afforded the title compound (13.8 mg, 22.9%). MS (ESI): mass calcd. for $C_{16}H_{15}FN_4O$, 298.1 m/z found, 299.2 [M+H]. ¹H NMR (400 MHz, CDCl₃): δ 7.95-7.82 (m, 1H), 7.74-7.67 (s, 1H), 7.56-7.46 (d, J=4.4 Hz, 1H), 7.41-7.32 (d, J=4.5 Hz, 1H), 7.18-7.07 (t, J=8.7 Hz, 1H), 4.38-4.29 (t, J=4.8 Hz, 2H), 3.96-3.85 (t, J=4.8 Hz, 2H).

Step B: 6-[2-(4-Fluorophenyl)-8-morpholino-imidazo[1,2-a]pyrazin-3-yl]-1,4-dihydro-3,1-benzoxazin-2-one To a solution of 4-(2-(4-fluorophenyl)imidazo[1,2-a]pyrazin-8-yl)morpholine (50.0 mg, 0.168 mmol), 6-bromo-1,4-dihydro-2H-3,1-benzoxazin-2-one (76.4 mg, 0.335 mmol), potassium phosphate tribasic (71.2 mg, 0.335 mmol), in DMF (2.0 mL) was added palladium (II) acetate (3.76 mg, 0.0168 mmol) and butyldi-1-adamantylphosphine (6.01 mg, 0.0168 mmol). The reaction mixture was purged with nitrogen for 1 min., and heated at 120° C. for 16 h. The reaction mixture was diluted with water (5 mL) and extracted with EtOAc (3×5 mL). The combined organics were dried (Na₂SO₄), filtered, concentrated under reduced pressure. Purification (FCC, SiO₂, 0 to 40% EtOAc: DCM) afforded the title compound (9.2 mg, 12.3%) which was further purified by prep. TLC (EMD Chemicals Inc., 13794-7, PLC Silica glass 60 F254, 0.5 mm with concentrating zone 20×4 cm, 20×20 cm plate, 0 to 40% EtOAc: DCM) to give oil (1.5 mg, 8.5%). MS (ESI): mass calcd. for $C_{24}H_{20}FN_5O_3$, 445.2 m/z found, 445.9 [M+H]. ¹H NMR (400 MHz, CDCl₃): δ 8.38 (s, 1H), 7.66-7.51 (m, 2H), 7.39-7.30 (m, 2H), 7.23 (d, J=4.6 Hz, 1H), 7.17 (d, J=1.7 Hz, 1H), 7.07-6.93 (m, 3H), 5.38 (s, 2H), 4.36 (t, J=4.7 Hz, 4H), 4.00-3.77 (m, 4H).

Example 125: 6-[2-(4-Fluorophenyl)-8-morpholino-imidazo[1,2-a]pyrazin-3-yl]-1H-quinolin-2-one

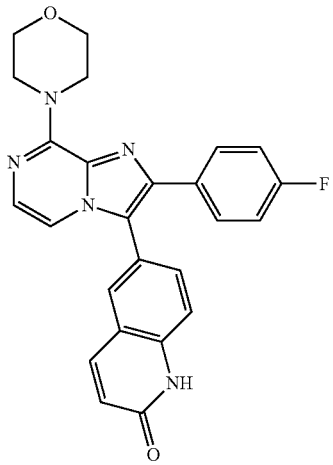 [SMILES: O=c1ccc2cc(-c3c(-c4ccc(F)cc4)nc4c(N5CCOCC5)nccn34)ccc2[nH]1]

The title compound was prepared in a manner analogous to Example 1. MS (ESI): mass calcd. for $C_{25}H_{20}FN_5O_2$, 441.2; m/z found, 442.2 [M+H]$^+$. $^1$H NMR (400 MHz, CDCl$_3$) δ 11.59 (s, 1H), 7.82 (d, J=9.6 Hz, 1H), 7.78-7.70 (m, 1H), 7.65 (d, J=1.4 Hz, 1H), 7.59 (dd, J=8.9, 5.4 Hz, 2H), 7.53 (s, 2H), 7.38-7.33 (m, 1H), 6.97 (t, J=8.7 Hz, 2H), 6.78 (d, J=9.5 Hz, 1H), 4.38 (t, J=4.6 Hz, 4H), 4.05-3.76 (m, 4H).

Example 126: 4-[2-(4-Fluorophenyl)-8-pyrrolidin-1-yl-imidazo[1,2-a]pyrazin-3-yl]phenol

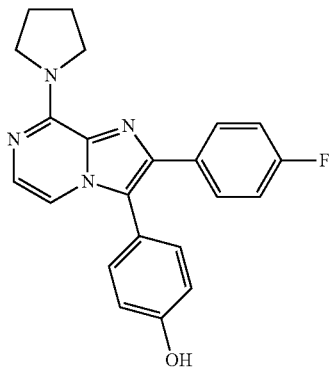 [SMILES: Oc1ccc(-c2c(-c3ccc(F)cc3)nc3c(N4CCCC4)nccn23)cc1]

Step A: 3-Bromo-2-(4-fluorophenyl)-8-(methylthio)imidazo[1,2-a]pyrazine

To a solution of 3-bromo-8-chloro-2-(4-fluorophenyl)imidazo[1,2-a]pyrazine (Intermediate 47) in DMF (50 mL) at 0° C. was added with sodium thiomethoxide (1.39 g, 18.9 mmol). The reaction mixture was stirred at 0° C. for 1 h. The reaction mixture was poured into water (100 mL) and the resulting precipitate was filtered, washed with water and dried to afford the title compound (4.96 g, 93.9%). MS (ESI): mass calcd. for $C_{13}H_9BrFN_3S$, 337.0 m/z found, 338.0 [M+H]. $^1$H NMR (400 MHz, CDCl$_3$): δ 8.25-8.02 (m, 2H), 7.96-7.70 (m, 2H), 7.17 (t, J=8.7 Hz, 2H), 2.69 (s, 3H).

Step B: 3-Bromo-2-(4-fluorophenyl)-8-(methylsulfonyl)imidazo[1,2-a]pyrazine

To a solution of 3-bromo-2-(4-fluorophenyl)-8-(methylthio)imidazo[1,2-a]pyrazine (2.25 g, 6.65 mmol) in DCM (30 mL) was added mCPBA (4.59 g, 26.6 mmol). The reaction mixture was stirred at room temperature for 1 h. The reaction mixture was diluted with sat. aq. NaHCO$_3$ (50 mL) and extracted with DCM (3×50 mL). The combined organics were dried (Na$_2$SO$_4$), filtered, and concentrated under reduced pressure. Purification (FCC, SiO$_2$, 0 to 40% EtOAc/DCM) afforded the title compound (1.67 g, 67.7%). MS (ESI): mass calcd. for $C_{13}H_9BrFN_3O_2S$, 369.0 m/z found, 370.0 [M+H]. $^1$H NMR (400 MHz, CDCl$_3$): δ 8.33 (d, J=4.5 Hz, 1H), 8.27-8.19 (m, 2H), 8.16 (d, J=4.5 Hz, 1H), 7.21 (t, J=8.6 Hz, 2H), 3.62 (s, 3H).

Step C: 4-(2-(4-Fluorophenyl)-8-(methylsulfonyl)imidazo[1,2-a]pyrazin-3-yl)phenol To a solution of 3-bromo-2-(4-fluorophenyl)-8-(methylsulfonyl)imidazo[1,2-a]pyrazine (600 mg, 1.62 mmol), 4-(4,4,5,5-tetramethyl-1,3,2-dioxaborolan-2-yl)phenol (446 mg, 2.03 mmol), potassium phosphate tribasic (860 mg, 4.05 mmol), 1,4-dioxane (8.0 mL), water (2.0 mL) was added PdCl$_2$(dtbpf) (211 mg, 0.324 mmol). The reaction mixture was purged with nitrogen for 1 min. The reaction mixture was heated in microwave at 90° C. for 10 min. The reaction mixture was diluted with water (50 mL, adjusted pH~1 by addition of 1N HCl and extracted with EtOAc (3×50 mL). The combined organics were dried (Na$_2$SO$_4$), filtered, concentrated under reduced pressure. Purification (FCC, SiO$_2$, 0 to 50% EtOAc: DCM) afforded the title compound (272 mg, 43.7%). MS (ESI): mass calcd. for $C_{19}H_{14}FN_3O_3S$, 369.0 m/z found, 383.1 [M+H]. $^1$H NMR (500 MHz, DMSO-d$_6$): δ 10.05 (s, 1H), 8.34 (d, J=4.5 Hz, 1H), 8.01 (d, J=4.5 Hz, 1H), 7.73 (dd, J=8.9, 5.5 Hz, 2H), 7.37 (d, J=8.5 Hz, 2H), 7.25 (t, J=8.9 Hz, 2H), 7.01 (d, J=8.5 Hz, 2H), 3.69 (s, 3H).

Step D: 4-[2-(4-Fluorophenyl)-8-pyrrolidin-1-yl-imidazo[1,2-a]pyrazin-3-yl]phenol To a solution of 4-(2-(4-fluorophenyl)-8-(methylsulfonyl)imidazo[1,2-a]pyrazin-3-yl)phenol (50.0 mg, 0.130 mmol) in CH$_3$CN (1.0 mL) was added pyrrolidine (21.9 µL, 0.261 mmol) and N-ethyl-N-isopropyl-propan-2-amine (34.1 µL, 0.196 mmol). The reaction mixture was refluxed at 90° C. for 16 h. The reaction mixture was cooled, diluted with water (5 mL) and extracted with EtOAc (3×5 mL). The combined organics were dried (Na$_2$SO$_4$), filtered, concentrated under reduced pressure. Purification (FCC, SiO$_2$, 0 to 40% EtOAc: DCM) afforded the title compound (20 mg, 0.053 mmol).

Step E: 4-[2-(4-Fluorophenyl)-8-pyrrolidin-1-yl-imidazo[1,2-a]pyrazin-3-yl]phenol-HCl salt To a solution of 4-[2-(4-fluorophenyl)-8-pyrrolidin-1-yl-imidazo[1,2-a]pyrazin-3-yl]phenol in 10% MeOH in DCM (1 mL) was added 1N HCl (1.2 eq, 0.064 mmol, 64 µL). The reaction mixture was concentrated under reduced pressure to afford the title compound (21.9 mg, 40.9%). MS (ESI): mass calcd. for $C_{22}H_{19}FN_4O$, 374.2.0 m/z found, 375.2 [M+H]. $^1$H NMR (500 MHz, DMSO-d$_6$): δ 10.10 (s, 1H), 7.69-7.60 (m, 2H), 7.31-7.25 (m, 3H), 7.25-7.12 (m, 3H), 7.05-6.97 (m, 2H), 3.34 (s, 4H), 2.08 (dd, J=5.8, 3.0 Hz, 4H).

Example 127-Example 128 were prepared in a manner analogous to Example 126, Steps A-D.

Example 127: 5-[2-(4-Fluorophenyl)-8-methylsulfonyl-imidazo[1,2-a]pyrazin-3-yl]indolin-2-one

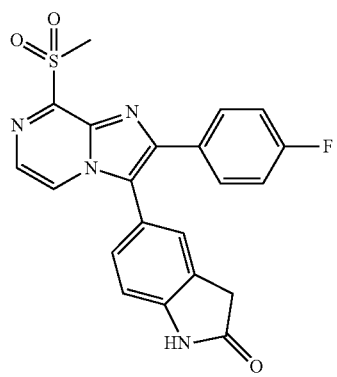 [SMILES: CS(=O)(=O)c1nccn2c(-c3ccc4c(c3)CC(=O)N4)c(-c3ccc(F)cc3)nc12]

The title compound was prepared in a manner analogous to Example 126. MS (ESI): mass calcd. for $C_{21}H_{15}FN_4O_3S$, 422.4; m/z found, 423.1 [M+H]$^+$. $^1$H NMR (500 MHz, CDCl$_3$) δ 8.03 (d, J=4.5 Hz, 1H), 7.97 (d, J=4.5 Hz, 1H), 7.79 (s, 1H), 7.78-7.72 (m, 2H), 7.30 (dd, J=8.0, 1.9 Hz, 1H), 7.27 (s, 1H), 7.10 (d, J=7.8 Hz, 1H), 7.02 (t, J=8.7 Hz, 2H), 3.68 (s, 3H), 3.64 (s, 2H).

Example 128: 5-[2-(4-Fluorophenyl)-8-methylsulfinyl-imidazo[1,2-a]pyrazin-3-yl]indolin-2-one

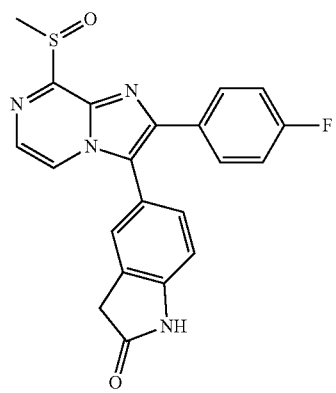 [SMILES: CS(=O)c1nccn2c(-c3ccc4c(c3)CC(=O)N4)c(-c3ccc(F)cc3)nc12]

The title compound was prepared in a manner analogous to Example 126. MS (ESI): mass calcd. for $C_{21}H_{15}FN_4O_2S$, 406.4; m/z found, 407.1 [M+H]$^+$. $^1$H NMR (500 MHz, DMSO-d$_6$) δ 8.06 (d, J=4.5 Hz, 1H), 7.93 (d, J=4.5 Hz, 2H), 7.73-7.63 (m, 2H), 7.32 (dd, J=8.0, 1.7 Hz, 1H), 7.29 (s, 1H), 7.10 (d, J=8.0 Hz, 1H), 7.07-6.99 (m, 2H), 3.63 (s, 2H), 3.28 (s, 3H).

Example 129: 5-[2-(4-Fluorophenyl)-8-isopropoxy-imidazo[1,2-a]pyrazin-3-yl]indolin-2-one

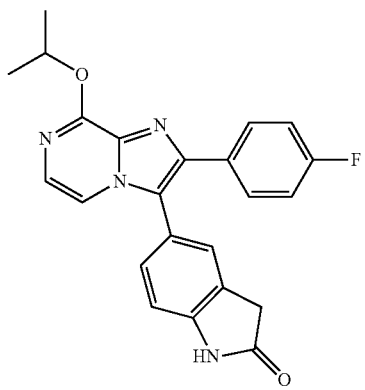 [SMILES: CC(C)Oc1nccn2c(-c3ccc4c(c3)CC(=O)N4)c(-c3ccc(F)cc3)nc12]

Step A. 5-[2-(4-Fluorophenyl)-8-isopropoxy-imidazo[1,2-a]pyrazin-3-yl]indolin-2-one To anhydrous IPA (0.6 mL) added NaH (60% dispersion in mineral oil, 30 mg, 0.75 mmol) slowly under nitrogen. The mixture was stirred for 30 min. then 5-(2-(4-fluorophenyl)-8-(methylsulfonyl)imidazo[1,2-a]pyrazin-3-yl)indolin-2-one (Example 127, 50.0 mg, 0.118 mmol) was added. The resulting mixture was heated at 100° C. for 20 min. The reaction mixture was cooled and diluted water (5 mL), extracted with EtOAc (3×5 mL). The combined organics were dried (Na$_2$SO$_4$), filtered and concentrated under reduced pressure. Purification (FCC, SiO$_2$, 0 to 100% EtOAc/DCM) afforded the title compound (8.2 mg, 0.020 mmol).

Step B. 5-[2-(4-Fluorophenyl)-8-isopropoxy-imidazo[1,2-a]pyrazin-3-yl]indolin-2-one-HCl salt To a solution of 5-[2-(4-fluorophenyl)-8-isopropoxy-imidazo[1,2-a]pyrazin-3-yl]indolin-2-one in 10% MeOH in DCM (2 mL) was added 1N HCl (1.2 eq, 0.025 mmol, 25 µL). The reaction mixture was stirred at room temperature for 0.5 h. The reaction mixture was concentrated under reduced pressure to afford the title compound (9.2 mg, 18%). MS (ESI): mass calcd. for $C_{23}H_{19}FN_4O_2$, 402.1 m/z found, 403.2 [M+H]. $^1$H NMR (500 MHz, DMSO-d$_6$): δ 10.65 (s, 1H), 7.72-7.55 (m, 3H), 7.39 (d, J=4.7 Hz, 1H), 7.34 (d, J=1.8 Hz, 1H), 7.26 (dd, J=8.0, 1.7 Hz, 1H), 7.17 (t, J=8.9 Hz, 2H), 7.01 (d, J=8.0 Hz, 1H), 5.69-5.34 (m, 1H), 3.57 (s, 2H), 1.43 (d, J=6.2 Hz, 6H).

Example 130: 1-[4-[2-(4-Fluorophenyl)-3-(4-hydroxyphenyl)imidazo[1,2-a]pyrazin-8-yl]-3,6-dihydro-2H-pyridin-1-yl]ethanone

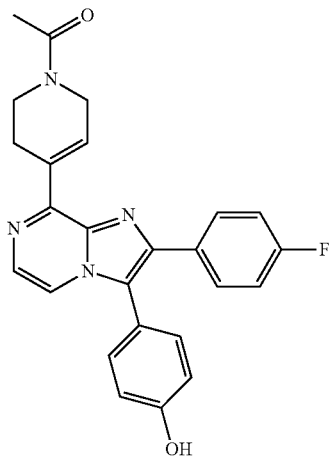 [SMILES: CC(=O)N1CC=C(c2nccn3c(-c4ccc(O)cc4)c(-c4ccc(F)cc4)nc23)CC1]

Step A: tert-Butyl 4-(3-bromo-2-(4-fluorophenyl)imidazo[1,2-a]pyrazin-8-yl)-5,6-dihydropyridine-1(2H)-carboxylate To a solution of 3-bromo-8-chloro-2-(4-fluorophenyl)imidazo[1,2-a]pyrazine (Intermediate 47, 100 mg, 0.306 mmol), 1-N-boc-4-(4,4,5,5-tetramethyl-[1,3,2]dioxaborolan-2-yl)-3,6-dihydro-2H-pyridine (96.6 mg, 0.306 mmol) in dioxane (3.0 mL) and 1M $Na_2CO_3$ (3.0 mL) was added $Pd(Ph_3P)_4$ (17.7 mg, 0.0153 mmol). The reaction mixture was purged with nitrogen then heated in microwave at 110° C. for 10 minutes. The reaction mixture was cooled, diluted with water (5.0 mL), and extracted with EtOAc (3×5 mL). The combined organics were dried ($Na_2SO_4$), filtered, concentrated under reduced pressure. Purification (FCC, $SiO_2$, 0 to 40% EtOAc/Hexane) afforded the title compound (130 mg, 89.7%). MS (ESI): mass calcd. for $C_{22}H_{22}BrFN_4O_2$, 472.1; m/z found 473.1 [M+H]$^+$. $^1$H NMR (400 MHz, CDCl$_3$) δ 8.23-8.11 (m, 3H), 8.03-7.96 (m, 2H), 7.20 (t, J=8.7 Hz, 2H), 4.32 (d, J=2.9 Hz, 2H), 3.70 (s, 2H), 2.87 (s, 2H), 1.51 (s, 9H).

Step B: 3-Bromo-2-(4-fluorophenyl)-8-(1,2,3,6-tetrahydropyridin-4-yl)imidazo[1,2-a]pyrazine A mixture of tert-butyl 4-(3-bromo-2-(4-fluorophenyl)imidazo[1,2-a]pyrazin-8-yl)-5,6-dihydropyridine-1(2H)-carboxylate (130 mg, 0.275 mmol) and 1M HCl ether solution (2.75 mL, 2.75 mmol) was stirred at 23° C. for 16 h. The reaction mixture was concentrated under reduced pressure and used in the next step without further purification. MS (ESI): mass calcd. for $C_{17}H_{14}BrFN_4$, 372.0; m/z found 373.0 [M+H]$^+$.

Step C: 1-(4-(3-Bromo-2-(4-fluorophenyl)imidazo[1,2-a]pyrazin-8-yl)-5,6-dihydropyridin-1(2H)-yl)ethanone To a solution of 3-bromo-2-(4-fluorophenyl)-8-(1,2,3,6-tetrahydropyridin-4-yl)imidazo[1,2-a]pyrazine (102 mg, 0.273 mmol) in DCM (5.0 mL) was added Ac$_2$O (80.0 µL, 0.820 mmol) and Et$_3$N (193 µL, 1.37 mmol). The reaction mixture was stirred at room temperature for 3 h. The reaction mixture was diluted with sat. aq. NaHCO$_3$ (5 mL) and extracted with DCM (3×5 mL). The combined organics were dried (Na$_2$SO$_4$), filtered and concentrated under reduced pressure to afford the title compound (76.3 mg, 67.2%) which was used without further purification in the next step. MS (ESI): mass calcd. for $C_{19}H_{16}BrFN_4O$, 414.0 m/z found, 415.0 [M+H].

Step D: 1-[4-[2-(4-Fluorophenyl)-3-(4-hydroxyphenyl)imidazo[1,2-a]pyrazin-8-yl]-3,6-dihydro-2H-pyridin-1-yl]ethanone To a solution of 1-(4-(3-bromo-2-(4-fluorophenyl)imidazo[1,2-a]pyrazin-8-yl)-5,6-dihydropyridin-1(2H)-yl)ethanone (30.0 mg, 0.0732 mmol), (4-hydroxyphenyl)boronic acid (15.1 mg, 0.110 mmol) in dioxane (1.0 mL) and 1M Na$_2$CO$_3$ (1.0 mL) was added Pd(Ph$_3$P)$_4$ (8.5 mg, 0.0073 mmol). The reaction mixture was purged with nitrogen then heated in microwave at 110° C. for 10 minutes. The reaction mixture was cooled, diluted with water (5.0 mL) and extracted with EtOAc (3×5 mL). The combined organics were dried (Na$_2$SO$_4$), filtered, concentrated under reduced pressure. Purification (FCC, SiO$_2$, 0 to 4% of 2M NH$_3$/MeOH in DCM: DCM) afforded the title compound (15.8 mg, 48.5%). MS (ESI): mass calcd. for $C_{25}H_{21}FN_4O_2$, 428.5; m/z found, 429.1 [M+H]$^+$. $^1$H NMR (400 MHz, CDCl$_3$) δ 8.31-8.18 (m, 1H), 7.85-7.63 (m, 4H), 7.32-7.27 (m, 1H), 7.10-6.93 (m, 5H), 4.47 (dd, J=47.1, 3.0 Hz, 2H), 3.92 (t, J=5.7 Hz, 1H), 3.76 (t, J=5.7 Hz, 1H), 2.96 (d, J=18.8 Hz, 2H), 2.24 (d, J=7.3 Hz, 3H).

Example 131: 5-(8-(3,6-Dihydro-2H-pyran-4-yl)-2-phenylimidazo[1,2-a]pyrazin-3-yl)indolin-2-one

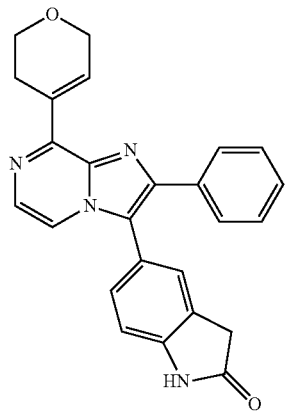

The title compound was prepared in a manner analogous to Example 130. MS (ESI): mass calcd. for $C_{25}H_{20}N_4O_2$, 408.2; m/z found, 409.2 [M+H]$^+$. $^1$H NMR (500 MHz, DMSO-d$_6$) δ 10.67 (s, 1H), 8.37 (dd, J=3.7, 2.2 Hz, 1H), 7.92 (d, J=4.6 Hz, 1H), 7.86 (d, J=4.6 Hz, 1H), 7.74-7.66 (m, 2H), 7.41-7.33 (m, 3H), 7.34-7.24 (m, 2H), 7.03 (d, J=8.0 Hz, 1H), 4.46 (d, J=2.8 Hz, 2H), 3.91 (t, J=5.5 Hz, 2H), 3.58 (s, 2H), 2.74 (s, 2H).

Example 132: 5-[8-Fluoro-2-(4-fluorophenyl)imidazo[1,2-a]pyrazin-3-yl]indolin-2-one

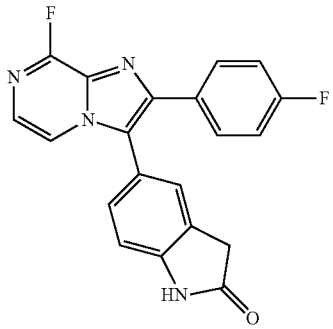 [SMILES: O=C1Cc2cc(-c3c(-c4ccc(F)cc4)nc4c(F)nccn34)ccc2N1]

The title compound was prepared in a manner analogous to Example 1, Step D, using 3-bromo-8-fluoro-2-(4-fluorophenyl)imidazo[1,2-a]pyrazine (Intermediate 38) and 5-(4,4,5,5-tetramethyl-[1,3,2]dioxaborolan-2-yl)indolin-2-one. MS (ESI): mass calcd. for $C_{20}H_{12}F_2N_4O$, 362.3; m/z found, 362.9 [M+H]$^+$. $^1$H NMR (400 MHz, DMSO-d$_6$) δ 7.97 (s, 1H), 7.75 (dd, J=4.7, 2.1 Hz, 1H), 7.72-7.63 (m, 2H), 7.41 (dd, J=4.6, 1.6 Hz, 1H), 7.35-7.28 (m, 2H), 7.07 (d, J=7.9 Hz, 1H), 7.02 (t, J=8.7 Hz, 2H), 3.63 (s, 2H).

Example 133: 5-[2-(4-Fluorophenyl)-8-methyl-imidazo[1,2-a]pyrazin-3-yl]indolin-2-one

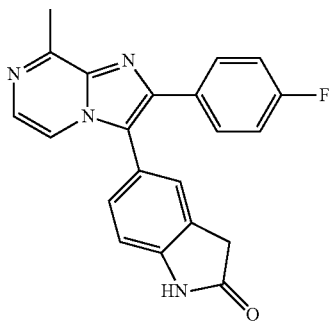 [SMILES: Cc1nccn2c(-c3ccc4c(c3)CC(=O)N4)c(-c3ccc(F)cc3)nc12]

Step A: 3-Bromo-2-(4-fluorophenyl)-8-methylimidazo[1,2-a]pyrazine

To a solution of 3-bromo-8-chloro-2-(4-fluorophenyl)imidazo[1,2-a]pyrazine (Intermediate 47, 250 mg, 0.766 mmol), in dioxane (5.0 mL) was added methylboronic acid (225 mg, 0.306 mmol), PPh$_3$ (20 mg, 0.077 mmol) and Pd(OAc)$_2$ (17 mg, 0.077 mmol). The reaction mixture was purged with nitrogen for 1 min. then heated in at 85° C. for 2 h. The reaction mixture was cooled, filtered and the ppt. was washed with MeOH and DCM. The filtrate was concentrated under reduced pressure. Purification (FCC, SiO$_2$, 0 to 100% EtOAc/Hexane) afforded the title compound (61.5 mg, 26.2%). MS (ESI): mass calcd. for $C_{13}H_9BrFN_3$, 305.0; m/z found 306.0 [M+H]$^+$.

Step B: 5-(2-(4-Fluorophenyl)-8-methylimidazo[1,2-a]pyrazin-3-yl)indolin-2-one

To a solution of 3-bromo-2-(4-fluorophenyl)-8-methylimidazo[1,2-a]pyrazine (60.0 mg, 0.196 mmol), 5-(4,4,5,5-tetramethyl-[1,3,2]dioxaborolan-2-yl)indolin-2-one (76.2 mg, 0.294 mmol) in dioxane (1.1 mL) and 1M Na$_2$CO$_3$ (1.1 mL) was added Pd(Ph$_3$P)$_4$ (11 mg, 0.0098 mmol). The reaction mixture was purged with nitrogen then heated in microwave at 110° C. for 10 minutes. The reaction mixture was cooled, filtered and the ppt. was washed with MeOH and DCM. The filtrate was concentrated under reduced pressure. Purification (FCC, SiO$_2$, 0 to 10% of 2M NH$_3$MeOH in DCM: DCM)) afforded the title compound which was further purified (FCC, SiO$_2$, 0 to 100% EtOAc: DCM) to afford the title compound (20.4 mg, 0.057 mmol).

Step C: 5-(2-(4-Fluorophenyl)-8-methylimidazo[1,2-a]pyrazin-3-yl)indolin-2-one-HCl salt A solution of 5-(2-(4-fluorophenyl)-8-methylimidazo[1,2-a]pyrazin-3-yl)indolin-2-one in 10% MeOH in DCM (3 mL), was treated with 1N HCl (1.2 eq, 0.068 mmol, 68 µL). The reaction mixture was concentrated under reduced pressure to afford the title compound (21.9 mg, 27.5%). MS (ESI): mass calcd. for $C_{21}H_{15}FN_4O$, 358.4; m/z found, 359.2 [M+H]$^+$. $^1$H NMR (500 MHz, DMSO-d$_6$) δ 10.69 (s, 1H), 8.05 (d, J=4.9 Hz, 1H), 7.80 (d, J=4.9 Hz, 1H), 7.70 (dd, J=8.6, 5.7 Hz, 2H), 7.38 (d, J=1.7 Hz, 1H), 7.29 (dd, J=8.0, 1.7 Hz, 1H), 7.22 (t, J=8.9 Hz, 2H), 7.03 (d, J=8.0 Hz, 1H), 3.58 (s, 2H), 2.89 (s, 3H).

Example 134: 5-(2-Phenylimidazo[1,2-a]pyrazin-3-yl)indolin-2-one

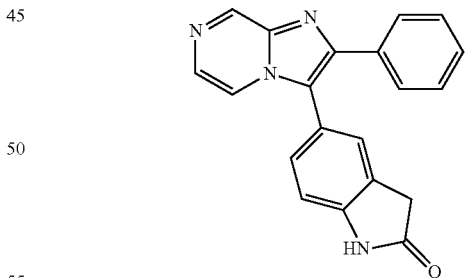

The title compound was prepared in a manner analogous to Example 1, Step D, using 3-bromo-2-phenylimidazo[1,2-a]pyrazine (Intermediate 33) and 5-(4,4,5,5-tetramethyl-[1,3,2]dioxaborolan-2-yl)indolin-2-one. MS (ESI): mass calcd. for $C_{20}H_{14}N_4O$, 326.4; m/z found, 327.2 [M+H]$^+$. $^1$H NMR (500 MHz, DMSO-d$_6$) δ 10.68 (s, 1H), 9.45-9.00 (m, 1H), 8.16 (d, J=4.5 Hz, 1H), 7.92 (dd, J=5.0, 2.3 Hz, 1H), 7.72-7.65 (m, 2H), 7.45-7.25 (m, 5H), 7.03 (d, J=8.0 Hz, 1H), 3.17 (s, 2H).

Example 135: 5-(2-(4-Fluorophenyl)imidazo[1,2-a]pyrazin-3-yl)indolin-2-one

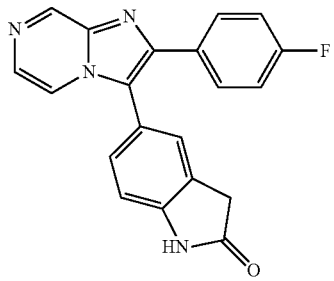 [SMILES: O=C1Cc2cc(-c3c(-c4ccc(F)cc4)nc4cnccn34)ccc2N1]

Step A: 5-(2-(4-Fluorophenyl)-8-(methylthio)imidazo[1,2-a]pyrazin-3-yl)indolin-2-one A mixture of 3-bromo-2-(4-fluorophenyl)-8-(methylthio)imidazo[1,2-a]pyrazine (Intermediate 39, 500 mg, 1.48 mmol), 5-(4,4,5,5-tetramethyl-1,3,2-dioxaborolan-2-yl)indolin-2-one (479 mg, 1.85 mmol), potassium phosphate tribasic (785 mg, 3.70 mmol), 1,4-dioxane (8.0 mL), water (2.0 mL) and PdCl$_2$(dtbpf) (193 mg, 0.296 mmol) in a 20 mL microwave vial was purged with nitrogen for 1 min. The reaction mixture was heated in microwave at 90° C. for 20 min. The reaction mixture was diluted with water (50 mL) and extracted with EtOAc (3×50 mL), dried over Na$_2$SO$_4$, filtered, concentrated under reduced pressure. Purification (FCC, SiO$_2$, 0 to 50% EtOAc: DCM) afforded the title compound (466 mg, 80.6%). MS (ESI): mass calcd. for C$_{21}$H$_{15}$FN$_4$OS, 390.1 m/z found, 391.1 [M+H]. $^1$H NMR (500 MHz, CDCl$_3$): δ 7.91 (s, 1H), 7.67 (td, J=5.6, 3.0 Hz, 3H), 7.57 (d, J=4.6 Hz, 1H), 7.32-7.26 (m, 2H), 7.03 (d, J=8.0 Hz, 1H), 6.99 (t, J=8.7 Hz, 2H), 3.62 (s, 2H), 2.71 (s, 3H).

Step B: 5-(2-(4-Fluorophenyl)imidazo[1,2-a]pyrazin-3-yl)indolin-2-one

A mixture of 5-(2-(4-fluorophenyl)-8-(methylthio)imidazo[1,2-a]pyrazin-3-yl)indolin-2-one (178 mg, 0.456 mmol) and Raney Ni (1.17 g, 13.7 mmol) in EtOH (4 mL) was stirred at 70° C. for 15 minutes. The reaction mixture was cooled and filtered to remove black precipitate. The filtrate was concentrated in vacuo to give 120 mg of brown oil. Purification (reverse phase HPLC, 5-95% ACN in 20 nM NH$_4$OH in water) afforded a yellowish gel (21 mg) which was further dissolved in DCM (2 mL) then 1M HCl in MeOH (1.2 eq, 73 μL, 0.073 mmol) was added and the resulting mixture was concentrated in vacuo to give a yellow solid as the title compound (21 mg, 12%). MS (ESI): mass calcd. for C$_{20}$H$_{13}$FN$_4$O, 344.1; m/z found, 345.1 [M+H]$^+$. $^1$H NMR (400 MHz, CDCl$_3$) δ 9.14 (d, J=1.1 Hz, 1H), 7.92-7.82 (m, 3H), 7.73-7.62 (m, 2H), 7.34-7.28 (m, 2H), 7.12-6.96 (m, 3H), 3.63 (s, 2H).

Example 136: 3,3-Difluoro-5-[2-(4-fluorophenyl)-8-morpholino-imidazo[1,2-a]pyrazin-3-yl]indolin-2-one

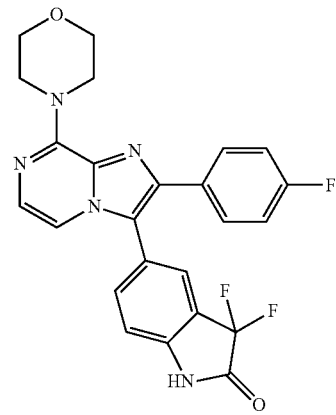 [SMILES: O=C1Nc2ccc(-c3c(-c4ccc(F)cc4)nc4c(N5CCOCC5)nccn34)cc2C1(F)F]

The title compound was prepared in a manner analogous to Example 116, using 4-(2-(4-fluorophenyl)-3-(4,4,5,5-tetramethyl-1,3,2-dioxaborolan-2-yl)imidazo[1,2-a]pyrazin-8-yl)morpholine (Intermediate 37) and 5-bromo-3,3-difluoro-1-((2-(trimethylsilyl)ethoxy)methyl)indolin-2-one (Intermediate 36). MS (ESI): mass calcd. for C$_{24}$H$_{18}$F$_3$N$_5$O$_2$, 465.4; m/z found, 465.9 [M+H]$^+$. $^1$H NMR (400 MHz, CDCl$_3$) δ 7.63 (d, J=1.7 Hz, 1H), 7.62-7.54 (m, 2H), 7.49 (d, J=8.3 Hz, 1H), 7.38 (d, J=4.6 Hz, 1H), 7.25 (d, J=4.6 Hz, 1H), 7.09 (d, J=8.1 Hz, 1H), 7.01 (t, J=8.7 Hz, 2H), 4.37 (t, J=4.8 Hz, 4H), 4.02-3.79 (m, 4H), 3.49 (s, 1H).

Example 137: 8-Morpholino-3-(2-oxoindolin-5-yl)-N-phenylimidazo[1,2-a]pyrazine-2-carboxamide

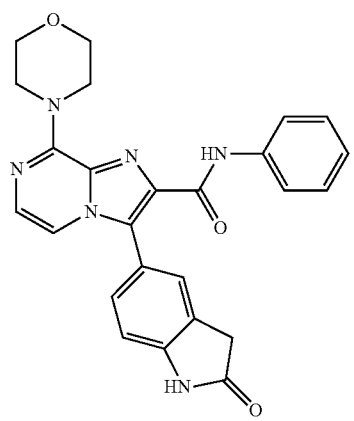 [SMILES: O=C1Cc2cc(-c3c(C(=O)Nc4ccccc4)nc4c(N5CCOCC5)nccn34)ccc2N1]

Step A: 8-Morpholino-3-(2-oxoindolin-5-yl)-N-phenylimidazo[1,2-a]pyrazine-2-carboxamide The title compound was prepared in a manner analogous to Example 1, Step D, using 3-bromo-8-morpholino-N-phenylimidazo[1,2-a]pyrazine-2-carboxamide (Intermediate 45) and 5-(4,4,5,5-tetramethyl-1,3,2-dioxaborolan-2-yl)indolin-2-one.

Step B: 8-Morpholino-3-(2-oxoindolin-5-yl)-N-phenylimidazo[1,2-a]pyrazine-2-carboxamide-HCl salt A solution of 8-morpholino-3-(2-oxoindolin-5-yl)-N-phenylimidazo[1,2-a]pyrazine-2-carboxamide in HCl in isopropanol. The reaction mixture was concentrated under reduced pressure to afford the title compound as a white solid (120 mg, 30%).

Example 138-Example 148 were prepared in a manner analogous to Example 137.

Example 138: 3-(4-Hydroxyphenyl)-8-morpholino-N-phenyl-imidazo[1,2-a]pyrazine-2-carboxamide

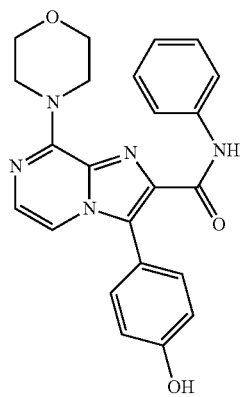 [SMILES: O=C(Nc1ccccc1)c1nc2c(N3CCOCC3)nccn2c1-c1ccc(O)cc1]

The title compound was prepared in a manner analogous to Example 137. MS (ESI): mass calcd. for $C_{23}H_{21}N_5O_3$, 415.2; m/z found, 416.2 [M+H]$^+$. $^1$H NMR (400 MHz, DMSO-d$_6$) δ 10.00 (s, 1H), 9.88 (br s, 1H), 7.72 (br. d, J=7.6 Hz, 2H), 7.46 (d, J=4.6 Hz, 1H), 7.42-7.29 (m, 5H), 7.09 (tt, J=0.9, 7.4 Hz, 1H), 6.96-6.88 (m, 2H), 4.30-4.20 (m, 4H), 3.84-3.74 (m, 4H).

Example 139: N-Benzyl-8-morpholino-3-(2-oxo-1,3-dihydrobenzimidazol-5-yl)imidazo[1,2-a]pyrazine-2-carboxamide

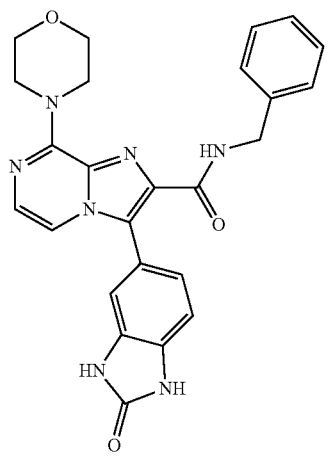 [SMILES: O=C(NCc1ccccc1)c1nc2c(N3CCOCC3)nccn2c1-c1ccc2[nH]c(=O)[nH]c2c1]

The title compound was prepared in a manner analogous to Example 137. MS (ESI): mass calcd. for $C_{25}H_{23}N_7O_3$, 469.2; m/z found, 470.1 [M+H]$^+$. $^1$H NMR (400 MHz, DMSO-d$_6$) δ 10.77 (br s, 2H), 8.92 (t, J=6.4 Hz, 1H), 7.44 (d, J=4.6 Hz, 1H), 7.35 (d, J=4.6 Hz, 1H), 7.28 (d, J=2.1 Hz, 4H), 7.25-7.18 (m, 1H), 7.05 (s, 3H), 4.44 (d, J=6.5 Hz, 2H), 4.28-4.19 (m, 4H), 3.82-3.71 (m, 4H).

Example 140: 8-Morpholino-3-(2-oxo-1,3-dihydrobenzimidazol-5-yl)-N-phenyl-imidazo[1,2-a]pyrazine-2-carboxamide

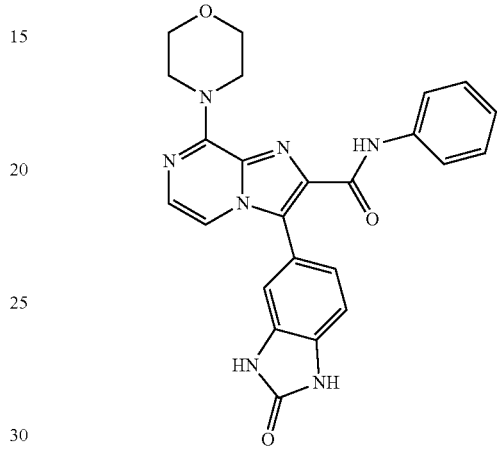

The title compound was prepared in a manner analogous to Example 137. MS (ESI): mass calcd. for $C_{24}H_{21}N_7O_3$, 455.2; m/z found, 455.2 [M+H]$^+$. $^1$H NMR (400 MHz, DMSO-d$_6$) δ 10.80 (br s, 2H), 10.03 (s, 1H), 7.72 (br. d, J=7.6 Hz, 2H), 7.49 (d, J=4.6 Hz, 1H), 7.39 (d, J=4.6 Hz, 1H), 7.33 (br. t, J=7.9 Hz, 2H), 7.14-7.04 (m, 4H), 4.33-4.20 (m, 4H), 3.86-3.73 (m, 4H)

Example 141: 5-[8-(Dimethylamino)-2-(4-fluorophenyl)imidazo[1,2-a]pyrazin-3-yl]indolin-2-one

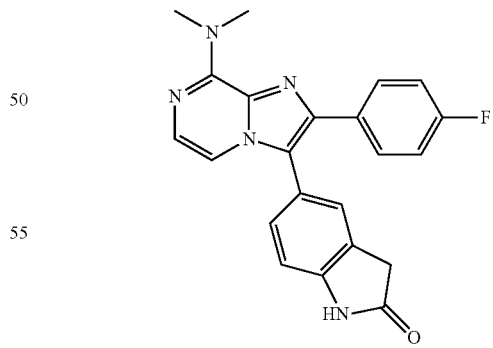

The title compound was prepared in a manner analogous to Example 137. MS (ESI): mass calcd. for $C_{22}H_{18}FN_5O$, 387.1; m/z found, 388.2 [M+H]$^+$. $^1$H NMR (500 MHz, DMSO-d$_6$) δ 10.64 (br s, 1H), 7.67-7.59 (m, 2H), 7.33-7.27 (m, 2H), 7.26-7.20 (m, 2H), 7.16 (br. t, J=8.2 Hz, 2H), 7.00 (d, J=7.5 Hz, 1H), 3.56 (br s, 2H), 3.55 (br s, 6H)

Example 142: N-Benzyl-8-morpholino-3-(2-oxoindolin-5-yl)imidazo[1,2-a]pyrazine-2-carboxamide

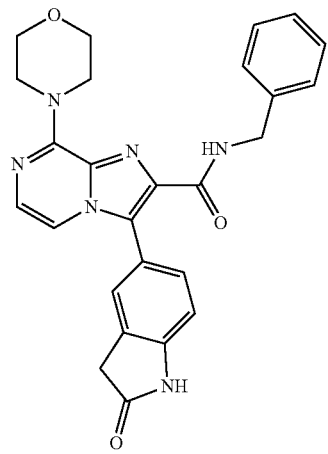 [SMILES: O=C1Cc2cc(-c3c(C(=O)NCc4ccccc4)nc4c(N5CCOCC5)nccn34)ccc2N1]

The title compound was prepared in a manner analogous to Example 137. MS (ESI): mass calcd. for C$_{26}$H$_{24}$N$_6$O$_3$, 468.2; m/z found, 469.1 [M+H]$^+$. $^1$H NMR (400 MHz, DMSO-d$_6$) δ 10.62 (s, 1H), 9.02 (t, J=6.4 Hz, 1H), 7.44 (d, J=4.9 Hz, 1H), 7.38-7.25 (m, 7H), 7.24-7.18 (m, 1H), 6.95 (d, J=8.1 Hz, 1H), 4.45 (d, J=6.2 Hz, 2H), 4.30 (br s, 4H), 3.82-3.76 (m, 4H), 3.55 (s, 2H).

Example 143: 3-(2-Oxoindolin-5-yl)-8-(3-oxopiperazin-1-yl)-N-phenyl-imidazo[1,2-a]pyrazine-2-carboxamide

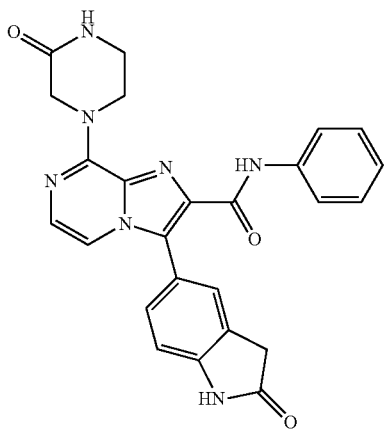 [SMILES: O=C1CN(c2nccn3c(-c4ccc5c(c4)CC(=O)N5)c(C(=O)Nc4ccccc4)nc23)CCN1]

The title compound was prepared in a manner analogous to Example 137. MS (ESI): mass calcd. for C$_{25}$H$_{21}$N$_7$O$_3$, 467.2; m/z found, 468.1 [M+H]$^+$. $^1$H NMR (400 MHz, DMSO-d$_6$) δ 10.61 (s, 1H), 10.07 (s, 1H), 8.15-8.11 (m, 1H), 7.73 (d, J=7.6 Hz, 2H), 7.50 (d, J=4.6 Hz, 1H), 7.43 (d, J=4.6 Hz, 1H), 7.41-7.30 (m, 4H), 7.13-7.06 (m, 1H), 6.98 (d, J=7.9 Hz, 1H), 4.67-4.55 (m, 4H), 3.57 (s, 2H), 3.46-3.40 (m, 2H).

Example 144: 8-(Dimethylamino)-3-(2-oxoindolin-5-yl)-N-phenyl-imidazo[1,2-a]pyrazine-2-carboxamide

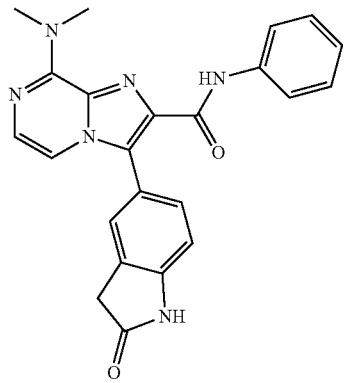 [SMILES: CN(C)c1nccn2c(-c3ccc4c(c3)CC(=O)N4)c(C(=O)Nc3ccccc3)nc12]

The title compound was prepared in a manner analogous to Example 137. MS (ESI): mass calcd. for C$_{23}$H$_{20}$N$_6$O$_2$, 412.2; m/z found, 413.1 [M+H]$^+$. $^1$H NMR (500 MHz, DMSO-d$_6$) δ 10.62 (s, 1H), 10.02 (br s, 1H), 7.73 (d, J=8.1 Hz, 2H), 7.44-7.28 (m, 6H), 7.10 (t, J=7.4 Hz, 1H), 6.99 (d, J=8.1 Hz, 1H), 3.65 (br s, 6H), 3.57 (s, 2H).

Example 145: N-Methyl-8-morpholino-3-(2-oxo-1,3-dihydrobenzimidazol-5-yl)-N-phenyl-imidazo[1,2-a]pyrazine-2-carboxamide

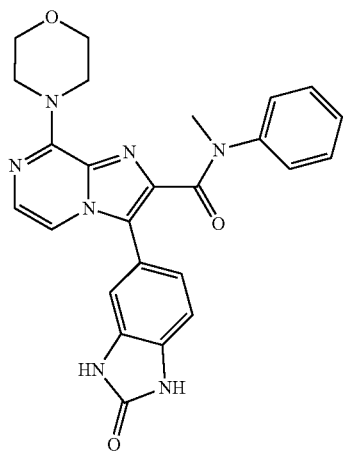 [SMILES: CN(C(=O)c1nc2c(N3CCOCC3)nccn2c1-c1ccc2[nH]c(=O)[nH]c2c1)c1ccccc1]

The title compound was prepared in a manner analogous to Example 137. MS (ESI): mass calcd. for C$_{25}$H$_{23}$N$_7$O$_3$, 469.5; m/z found, 470.0 [M+H]$^+$. $^1$H NMR (400 MHz, DMSO-d$_6$) δ 10.87 (s, 1H), 10.77 (s, 1H), 7.47 (d, J=2.8 Hz, 1H), 7.29 (d, J=4.6 Hz, 1H), 7.25-7.09 (m, 3H), 7.07 (d, J=7.9 Hz, 1H), 7.00-6.86 (m, 4H), 3.91 (br s, 4H), 3.66-3.57 (m, 4H), 3.28 (s, 3H).

Example 146: N-Cyclopropyl-8-morpholino-3-(2-oxo-1,3-dihydrobenzimidazol-5-yl)imidazo[1,2-a]pyrazine-2-carboxamide

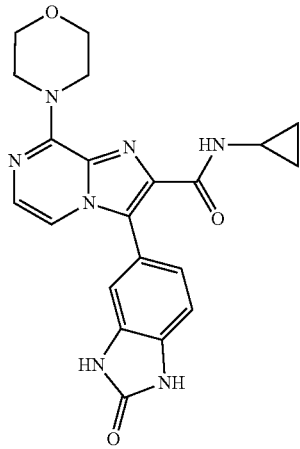 [SMILES: O=C(NC1CC1)c1nc2c(N3CCOCC3)nccn2c1-c1ccc2[nH]c(=O)[nH]c2c1]

The title compound was prepared in a manner analogous to Example 137. MS (ESI): mass calcd. for $C_{21}H_{21}N_7O_3$, 419.4; m/z found, 420.0 [M+H]⁺. ¹H NMR (500 MHz, DMSO-d₆) δ 10.83 (s, 1H), 10.76 (s, 1H), 8.24 (d, J=3.8 Hz, 1H), 7.43 (d, J=4.6 Hz, 1H), 7.34 (d, J=4.6 Hz, 1H), 7.09-7.00 (m, 3H), 4.25-4.16 (m, 4H), 3.81-3.71 (m, 4H), 2.71 (qt, J=3.9, 7.3 Hz, 1H), 0.70-0.63 (m, 2H), 0.62-0.56 (m, 2H).

Example 147: 8-Morpholino-3-(2-oxo-1,3-dihydrobenzimidazol-5-yl)-N-(4-pyridyl)imidazo[1,2-a]pyrazine-2-carboxamide

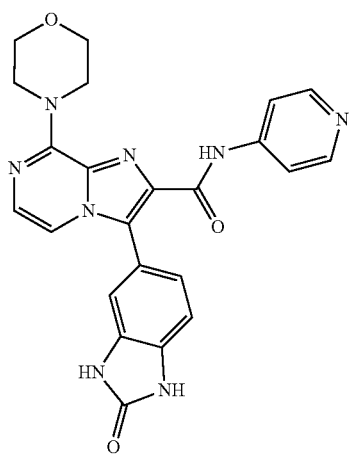 [SMILES: O=C(Nc1ccncc1)c1nc2c(N3CCOCC3)nccn2c1-c1ccc2[nH]c(=O)[nH]c2c1]

The title compound was prepared in a manner analogous to Example 137. MS (ESI): mass calcd. for $C_{23}H_{20}N_8O_3$, 456.5; m/z found, 457.0 [M+H]⁺. ¹H NMR (500 MHz, DMSO-d₆) δ 10.87 (s, 1H), 10.79 (s, 1H), 10.35 (s, 1H), 8.48-8.42 (m, 2H), 7.80-7.74 (m, 2H), 7.50 (d, J=4.6 Hz, 1H), 7.41 (d, J=4.6 Hz, 1H), 7.14-7.06 (m, 3H), 4.31-4.22 (m, 4H), 3.85-3.76 (m, 4H).

Example 148: 3-(4-Hydroxyphenyl)-8-morpholino-N-propyl-imidazo[1,2-a]pyrazine-2-carboxamide

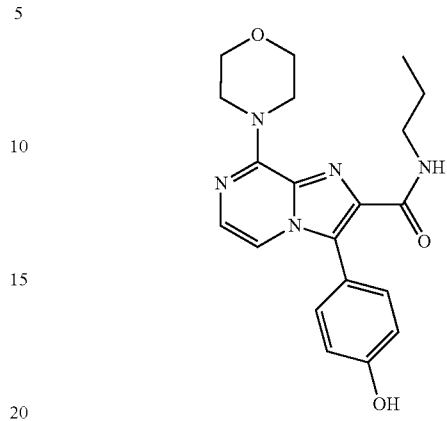

The title compound was prepared in a manner analogous to Example 137. MS (ESI): mass calcd. for $C_{20}H_{23}N_5O_3$, 381.4; m/z found, 382.2 [M+H]⁺. ¹H NMR (500 MHz, DMSO-d₆) δ 9.81 (br s, 1H), 8.29 (t, J=5.3 Hz, 1H), 7.40 (d, J=4.3 Hz, 1H), 7.35 (d, J=4.0 Hz, 1H), 7.32 (d, J=7.8 Hz, 2H), 6.89 (d, J=8.1 Hz, 2H), 4.25-4.18 (m, 4H), 3.80-3.73 (m, 4H), 3.17 (q, J=6.6 Hz, 2H), 1.50 (sxt, J=7.2 Hz, 2H), 0.85 (t, J=7.4 Hz, 3H).

Example 149: 8-Morpholino-3-(2-oxoindolin-5-yl)-N-phenylimidazo[1,2-a]pyrazine-2-carboxamide

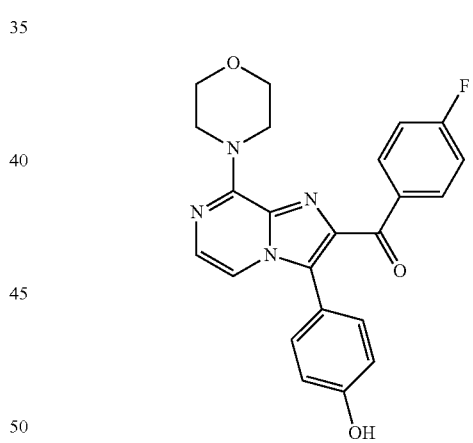

Step A: Ethyl 3-(4-(benzyloxy)phenyl)-8-morpholinoimidazo[1,2-a]pyrazine-2-carboxylate To a solution of ethyl 3-bromo-8-morpholinoimidazo[1,2-a]pyrazine-2-carboxylate (Intermediate 45, Step A, 1.0 g, 2.8 mmol), 2-(4-(benzyloxy)phenyl)-4,4,5,5-tetramethyl-1,3,2-dioxaborolane (1.0 g, 3.4 mmol), PPh₃ (74 mg, 0.28 mmol) and K₂CO₃ (1.5 g, 10.6 mmol) in 1,4-dioxane (24 mL) under nitrogen was added Pd(OAc)₂ (43 mg, 0.19 mmol). The reaction mixture was stirred at 80° C. for 16 h. The reaction mixture was cooled, and filtered through Celite®, and concentrated under reduced pressure. The resulting solid was triturated and filtered to afford the title compound as a yellow solid (1.1 g, 68%).

Step B: 3-(4-(Benzyloxy)phenyl)-N-methoxy-N-methyl-8-morpholinoimidazo[1,2-a]pyrazine-2-carboxamide To a cooled (−78° C.) solution of ethyl 3-(4-(benzyloxy) phenyl)-8-morpholinoimidazo[1,2-a]pyrazine-2-carboxylate (1.1 g, 2.31 mmol) and N-methyl-O-methyl hydroxylamine hydrochloride (405 mg, 4.2.mmol) in DCM (10 mL) under nitrogen at was added methyl magnesium bromide (3.0 M in THF, 4.62 mL, 13.9 mmol). The reaction mixture was stirred at 23° C. for 16 h, then the mixture was cooled at −78° C., and additional methyl magnesium bromide (3.0 M, 4.62 mL, 13.9 mmol) was added. The mixture was stirred at 23° C. for 16 h. Water was added, and the mixture was extracted with EtOAc. The organic layer was separated, dried (Na₂SO₄), filtered and concentrated under reduced pressure. Purification (FCC, SiO₂, EtOAc in heptane 0/100 to 50/50) afforded the title compound as a yellow solid (0.66 g, 61%).

Step C: (3-(4-(Benzyloxy)phenyl)-8-morpholinoimidazo[1,2-a]pyrazin-2-yl)(4-fluorophenyl)methanone To a cooled (0° C.) solution of 3-(4-(benzyloxy)phenyl)-N-methoxy-N-methyl-8-morpholinoimidazo[1,2-a]pyrazine-2-carboxamide (140 mg, 0.3 mmol) in THF (1.6 mL) under nitrogen was added 4-fluorophenyl magnesium bromide (1M in THF, 0.44 mL, 0.44 mmol). The reaction mixture was stirred at 0° C. for 3 h. Water was added and the reaction mixture was extracted with EtOAc. The organic layer was separated, dried (Na₂SO₄), filtered and concentrated under reduced pressure. Purification (FCC, SiO₂, EtOAc in Heptane 0/100 to 40/60) afforded the title compound (50 mg, 33%).

Step D: (4-Fluorophenyl)(3-(4-hydroxyphenyl)-8-morpholinoimidazo[1,2-a]pyrazin-2-yl)methanone To a cooled (−78° C.) solution of (3-(4-(benzyloxy) phenyl)-8-morpholinoimidazo[1,2-a]pyrazin-2-yl)(4-fluorophenyl)methanone (50 mg, 0.10 mmol) in DCM (2 mL) was added boron trichloride (1.0 M in DCM, 0.098 mL, 0.10 mmol). The reaction mixture was stirred at −78° C. for 5 h. Water was added and the reaction mixture was extracted with EtOAc. The organic layer was separated, dried (Na₂SO₄), filtered and concentrated under reduced pressure. Purification (FCC, SiO₂, EtOAc in Heptane 0/100 to 100/0) afforded the title compound which was further purified (reverse phase HPLC, Stationary phase: C18 XBridge 30×100 mm 5 um), Mobile phase: Gradient from 60% 0.1% NH₄CO₃H/NH₄OH pH 9 solution in Water, 40% CH₃CN to 43% 0.1% NH₄CO₃H/NH₄OH pH 9 solution in Water, 57% CH₃CN) to afford the title compound (14 mg, 34% yield).

Example 150-Example 154 were prepared in a manner analogous to Example 149.

Example 150: N-[(3S)-1-[2-(4-Fluorophenyl)-3-(2-oxoindolin-5-yl)imidazo[1,2-a]pyrazin-8-yl]pyrrolidin-3-yl]acetamide

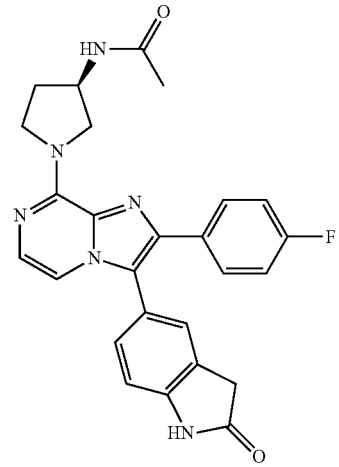 [SMILES: CC(=O)N[C@@H]1CCN(c2nccn3c(-c4ccc5c(c4)CC(=O)N5)c(-c4ccc(F)cc4)nc23)C1]

The title compound was prepared in a manner analogous to Example 149. MS (ESI): mass calcd. for C₂₆H₂₃FN₆O₂, 470.2; m/z found, 471.0 [M+H]⁺. ¹H NMR (500 MHz, DMSO-d₆) δ 10.64 (br s, 1H), 8.19 (d, J=6.1 Hz, 1H), 7.63 (t, J=6.4 Hz, 2H), 7.37-7.10 (m, 6H), 7.00 (d, J=7.8 Hz, 1H), 4.42-4.33 (m, 1H), 4.05 (br s, 4H), 3.57 (br s, 2H), 2.25-2.09 (m, 1H), 1.98-1.87 (m, 1H), 1.82 (s, 3H).

Example 151: [3-(4-Hydroxyphenyl)-8-morpholino-imidazo[1,2-a]pyrazin-2-yl]-phenyl-methanone

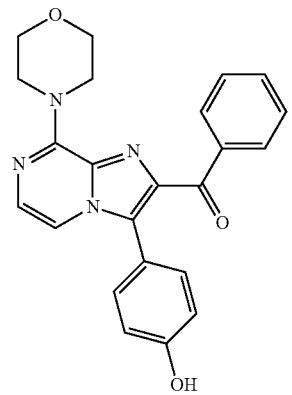 [SMILES: O=C(c1ccccc1)c1nc2c(N3CCOCC3)nccn2c1-c1ccc(O)cc1]

The title compound was prepared in a manner analogous to Example 149. MS (ESI): mass calcd. for C₂₃H₂₀N₄O₃, 400.2; m/z found, 401.2 [M+H]⁺. ¹H NMR (500 MHz, DMSO-d₆) δ 9.87 (s, 1H), 8.06-7.99 (m, 2H), 7.63-7.58 (m, 1H), 7.52-7.46 (m, 3H), 7.42 (d, J=4.6 Hz, 1H), 7.36-7.32 (m, 2H), 6.92-6.87 (m, 2H), 4.26-4.18 (m, 4H), 3.79-3.69 (m, 4H).

Example 152: 5-[2-Benzoyl-8-(dimethylamino)imidazo[1,2-a]pyrazin-3-yl]indolin-2-one

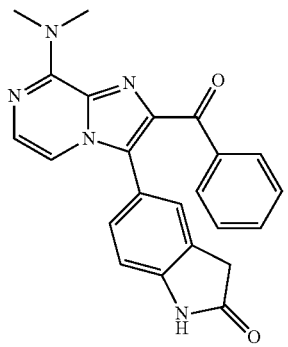 [SMILES: CN(C)c1nccn2c(-c3ccc4c(c3)CC(=O)N4)c(C(=O)c3ccccc3)nc12]

The title compound was prepared in a manner analogous to Example 149. MS (ESI): mass calcd. for $C_{23}H_{19}N_5O_2$, 397.2; m/z found, 398.2 [M+H]$^+$. $^1$H NMR (400 MHz, DMSO-$d_6$) δ 10.70 (s, 1H), 8.10-8.04 (m, 2H), 7.70-7.61 (m, 1H), 7.58-7.47 (m, 3H), 7.38 (s, 1H), 7.35 (d, J=8.1 Hz, 1H), 7.29 (d, J=5.5 Hz, 1H), 6.99 (d, J=7.9 Hz, 1H), 3.68 (br s, 6H), 3.56 (s, 2H).

Example 153: 5-(2-Benzoyl-8-morpholino-imidazo[1,2-a]pyrazin-3-yl)indolin-2-one

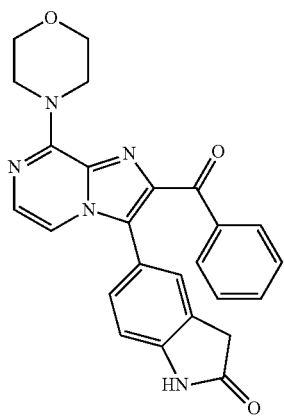 [SMILES: O=C1Cc2cc(-c3c(C(=O)c4ccccc4)nc4c(N5CCOCC5)nccn34)ccc2N1]

The title compound was prepared in a manner analogous to Example 149. MS (ESI): mass calcd. for $C_{25}H_{21}N_5O_3$, 439.2; m/z found, 440.2 [M+H]$^+$. $^1$H NMR (400 MHz, DMSO-$d_6$) δ 10.62 (s, 1H), 8.05 (d, J=7.4 Hz, 2H), 7.66-7.58 (m, J=7.4 Hz, 1H), 7.55-7.46 (m, 3H), 7.42 (d, J=4.9 Hz, 1H), 7.37 (s, 1H), 7.34 (d, J=8.1 Hz, 1H), 6.95 (d, J=8.1 Hz, 1H), 4.28-4.18 (m, 4H), 3.81-3.69 (m, 4H), 3.54 (s, 2H).

Example 154: 5-[2-Benzoyl-8-(4-hydroxy-1-piperidyl)imidazo[1,2-a]pyrazin-3-yl]indolin-2-one

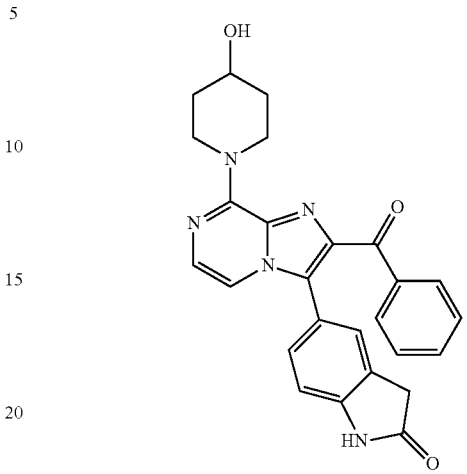

The title compound was prepared in a manner analogous to Example 149. MS (ESI): mass calcd. for $C_{26}H_{23}N_5O_3$, 453.2; m/z found, 454.2 [M+H]$^+$. $^1$H NMR (400 MHz, DMSO-$d_6$+D2O) δ 7.99 (d, J=7.4 Hz, 2H), 7.65-7.57 (m, 1H), 7.53-7.43 (m, 3H), 7.35 (s, 1H), 7.31 (d, J=7.9 Hz, 1H), 7.22 (d, J=4.2 Hz, 1H), 7.00 (d, J=8.1 Hz, 1H), 4.66 (br s, 2H), 3.94-3.77 (m, 3H), 3.53 (s, 2H), 2.01-1.85 (m, 2H), 1.63-1.48 (m, 2H) (OH and NH exchanged).

Example 155: 5-[2-(4-Fluorophenyl)-8-(4-hydroxyimino-1-piperidyl)imidazo[1,2-a]pyrazin-3-yl]indolin-2-one

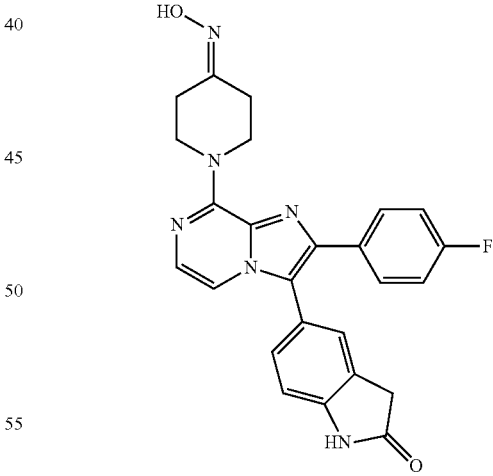

The title compound was prepared in a manner analogous to Example 1, Steps A-D, substituting 1,2,6-triazaspiro[2.5]oct-1-ene for 1-boc-piperizine in Step C, (2-oxoindolin-5-yl)boronic acid for (4-hydroxyphenyl)boronic acid in Step D. This product was a by-product of the reaction Example 185. MS (ESI): mass calcd. for $C_{25}H_{21}FN_6O_2$, 456.5; m/z found, 457.2 [M+H]$^+$. $^1$H NMR (500 MHz, CDCl$_3$) δ 7.73-7.59 (m, 3H), 7.34 (d, J=4.5 Hz, 1H), 7.31-7.26 (m, 2H), 7.24 (d, J=4.6 Hz, 1H), 7.07-6.94 (m, 3H), 6.85 (s, 1H), 4.49 (s, 4H), 3.62 (s, 2H), 2.84 (t, J=6.0 Hz, 2H), 2.56 (t, J=6.0 Hz, 2H).

Example 156-Example 160 were prepared in a manner analogous to Example 149

Example 156: 6-(2-Benzoyl-8-morpholino-imidazo[1,2-a]pyrazin-3-yl)-3H-1,3-benzoxazol-2-one

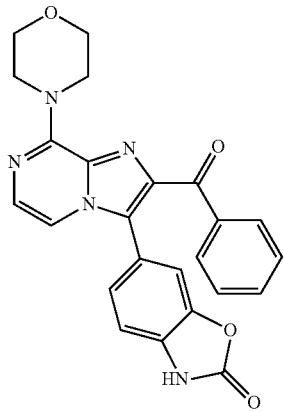 [SMILES: O=C(c1ccccc1)c1nc2c(N3CCOCC3)nccn2c1-c1ccc2[nH]c(=O)oc2c1]

The title compound was prepared in a manner analogous to Example 149. MS (ESI): mass calcd. for $C_{24}H_{19}N_5O_4$, 441.1; m/z found, 442.2 [M+H]$^+$. $^1$H NMR (400 MHz, DMSO-d$_6$) δ 11.92 (s, 1H), 8.09-8.03 (m, 2H), 7.66-7.58 (m, 1H), 7.56-7.47 (m, 4H), 7.43 (d, J=4.6 Hz, 1H), 7.30 (dd, J=1.4, 7.9 Hz, 1H), 7.23 (d, J=7.9 Hz, 1H), 4.29-4.19 (m, 4H), 3.79-3.73 (m, 4H).

Example 157: 5-[2-Benzoyl-8-(1,1-dioxo-1,4-thiazinan-4-yl)imidazo[1,2-a]pyrazin-3-yl]indolin-2-one

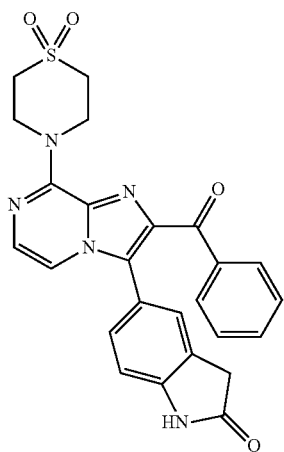 [SMILES: O=C1Cc2cc(-c3c(C(=O)c4ccccc4)nc4c(N5CCS(=O)(=O)CC5)nccn34)ccc2N1]

The title compound was prepared in a manner analogous to Example 149. MS (ESI): mass calcd. for $C_{25}H_{21}N_5O_4S$, 487.1; m/z found, 488.1 [M+H]$^+$. $^1$H NMR (400 MHz, DMSO-d$_6$) δ 10.62 (s, 1H), 8.09-8.04 (m, 2H), 7.62 (d, J=4.6 Hz, 1H), 7.67-7.61 (m, 1H), 7.57-7.50 (m, 2H), 7.48 (d, J=4.9 Hz, 1H), 7.36 (s, 1H), 7.33 (dd, J=1.7, 8.0 Hz, 1H), 6.97 (d, J=8.1 Hz, 1H), 4.67 (br s, 4H), 3.56 (s, 2H), 3.35-3.27 (m, 4H).

Example 158: 5-[8-(4-Acetylpiperazin-1-yl)-2-benzoyl-imidazo[1,2-a]pyrazin-3-yl]indolin-2-one

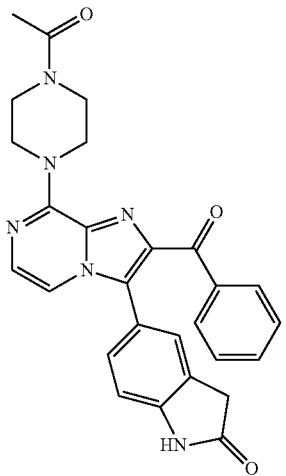 [SMILES: CC(=O)N1CCN(c2nccn3c(-c4ccc5c(c4)CC(=O)N5)c(C(=O)c4ccccc4)nc23)CC1]

The title compound was prepared in a manner analogous to Example 149. MS (ESI): mass calcd. for $C_{27}H_{24}N_6O_3$, 480.2; m/z found, 481.2 [M+H]$^+$. $^1$H NMR (500 MHz, DMSO-d$_6$) δ 10.63 (s, 1H), 8.11-8.03 (m, 2H), 7.67-7.60 (m, 1H), 7.57-7.49 (m, 3H), 7.43 (d, J=4.6 Hz, 1H), 7.37 (s, 1H), 7.34 (br. d, J=8.1 Hz, 1H), 6.96 (d, J=7.8 Hz, 1H), 4.32 (br s, 2H), 4.19 (br s, 2H), 3.64-3.59 (m, 4H), 3.55 (s, 2H), 2.05 (s, 3H).

Example 159: [3-(2,2-Dioxo-1,3-dihydro-2,1-benzothiazol-5-yl)-8-morpholino-imidazo[1,2-a]pyrazin-2-yl]-phenyl-methanone

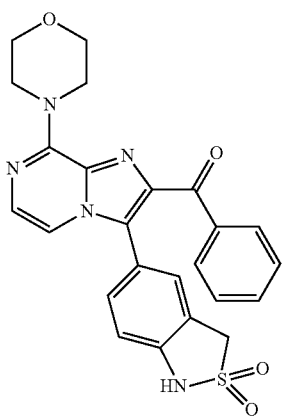

The title compound was prepared in a manner analogous to Example 149. MS (ESI): mass calcd. for $C_{24}H_{21}N_5O_4S$, 475.1; m/z found, 476.2 [M+H]$^+$. $^1$H NMR (500 MHz, DMSO-d$_6$+D2O) δ 8.07-8.03 (m, 2H), 7.65-7.60 (m, 1H), 7.54 (d, J=4.6 Hz, 1H), 7.53-7.48 (m, 2H), 7.46 (d, J=1.2 Hz, 1H), 7.43-7.39 (m, 2H), 6.96 (d, J=8.1 Hz, 1H), 4.60 (s, 2H), 4.26-4.18 (m, 4H), 3.78-3.72 (m, 4H) (NH exchanged).

Example 160: 5-[2-Benzoyl-8-(methylamino)imidazo[1,2-a]pyrazin-3-yl]indolin-2-one

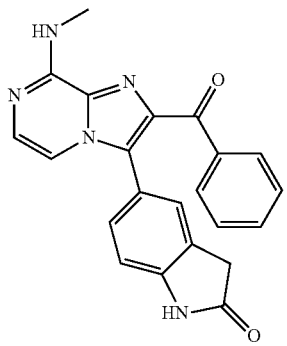 [SMILES: CNc1nccn2c(-c3ccc4c(c3)CC(=O)N4)c(C(=O)c3ccccc3)nc12]

The title compound was prepared in a manner analogous to Example 149. MS (ESI): mass calcd. for $C_{22}H_{17}N_5O_2$, 383.4; m/z found, 384.0 [M+H]$^+$. $^1$H NMR (400 MHz, DMSO-d$_6$) δ 10.66 (s, 1H), 9.41 (br s, 1H), 8.08-8.01 (m, 2H), 7.67-7.61 (m, 1H), 7.55-7.47 (m, 3H), 7.37 (s, 1H), 7.34 (dd, J=1.2, 8.1 Hz, 1H), 7.31 (d, J=5.5 Hz, 1H), 6.97 (d, J=8.1 Hz, 1H), 3.55 (s, 2H), 3.38 (br s, 1H), 3.11 (d, J=4.2 Hz, 3H).

Example 161: 5-(5-Fluoro-2-(4-fluorophenyl)-8-morpholinoimidazo[1,2-a]pyrazin-3-yl)indolin-2-one

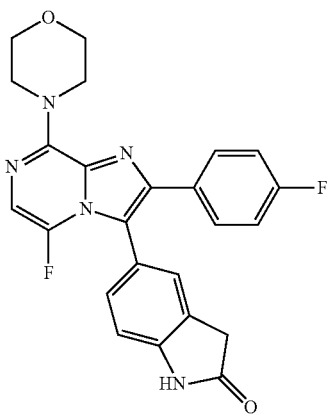 [SMILES: O=C1Cc2cc(-c3c(-c4ccc(F)cc4)nc4c(N5CCOCC5)ncc(F)n34)ccc2N1]

Step A: 4-(5-Fluoro-2-(4-fluorophenyl)imidazo[1,2-a]pyrazin-8-yl)morpholine

To a cooled (−78° C.) solution of 4-(2-(4-fluorophenyl)imidazo[1,2-a]pyrazin-8-yl)morpholine (Example 124, product from Step A, 0.40 g, 1.3 mmol) in acetonitrile (50 mL) was added N-fluorobenzenesulfonimide (0.11 g, 0.34 mmol) in one portion. After 1 hour the reaction was removed from the dry ice bath and stirred for 4 h at rt. The reaction mixture was concentrated under reduced pressure. Purification (FCC, SiO$_2$; Hex:EtOAc) afforded the title compound (0.040 g, 10%). MS (ESI): mass calcd. for $C_{16}H_{14}F_2N_4O$, 316.11 m/z found, 317.0 [M+H]$^+$. $^1$H NMR (500 MHz, CDCl$_3$) δ 8.05-8.00 (m, 1H), 7.95-7.89 (m, 2H), 7.84-7.81 (s, 1H), 7.80-7.75 (m, 1H), 7.66-7.58 (m, 1H), 7.27-7.23 (s, 1H), 7.18-7.10 (m, 2H), 4.23-4.17 (t, J=4.8 Hz, 4H), 3.93-3.88 (t, J=4.8 Hz, 4H).

Step B: 4-(5-Fluoro-2-(4-fluorophenyl)-3-iodoimidazo[1,2-a]pyrazin-8-yl)morpholine To a solution of 4-(5-fluoro-2-(4-fluorophenyl)imidazo[1,2-a]pyrazin-8-yl)morpholine (0.060 g, 0.14 mmol) in TFA (0.5 mL) was added N-iodosuccinimide (0.040 g, 0.18 mmol). The reaction was stirred for 30 min then quenched with ammonium acetate. The resulting solution was extracted with EtOAc (10 mL×3). The organic layers were combined, dried (Na$_2$SO$_4$), and concentrated in vacuo. The resulting solid was triturated with cold acetonitrile to provide the title compound (0.60 mg, 72%). MS (ESI): mass calcd. for $C_{16}H_{13}F_2IN_4O$, 442.01 m/z found, 442.8 [M+H]$^+$.

Step C: 5-(5-Fluoro-2-(4-fluorophenyl)-8-morpholinoimidazo[1,2-a]pyrazin-3-yl)indolin-2-one To a solution of 4-(5-fluoro-2-(4-fluorophenyl)-3-iodoimidazo[1,2-a]pyrazin-8-yl)morpholine (0.050 g, 0.11 mmol), 5-(4,4,5,5-tetramethyl-1,3,2-dioxaborolan-2-yl)indoline-2-one (0.044 g, 0.17 mmol), K$_3$PO$_4$ (0.072 g, 0.34 mmol), in 1.4 dioxane (2.8 mL), and H$_2$O (0.5 mL) was added Pd(dtbpf)Cl$_2$ (0.004 g, 0.0056 mmol). The reaction mixture was heated in a microwave apparatus at 100° C. for 30 min. The reaction was cooled, diluted with DCM, and filtered through Celite®. The organics were dried (Na$_2$SO$_4$), filtered, and concentrated under reduced pressure. Purification (FCC, SiO$_2$; NH$_3$(MeOH):DCM) afforded the title compound (0.010 g, 20%). MS (ESI): mass calcd. for $C_{24}H_{19}F_2N_5O_2$, 447.15 m/z found, 448.0 [M+H]$^+$. $^1$H NMR (500 MHz, CDCl$_3$) δ 7.99-7.92 (s, 1H), 7.57-7.48 (m, 2H), 7.30-7.27 (m, 2H), 7.17-7.13 (d, J=1.1 Hz, 1H), 7.00-6.91 (m, 3H), 4.31-4.13 (t, J=4.8 Hz, 4H), 3.96-3.82 (t, J=4.8 Hz, 4H), 3.64-3.56 (s, 2H).

Example 162-Example 163 were prepared in a manner analogous to Example 161.

Example 162: 5-[5-Fluoro-2-(4-fluorophenyl)-8-morpholino-imidazo[1,2-a]pyrazin-3-yl]-1,3-dihydrobenzimidazol-2-one

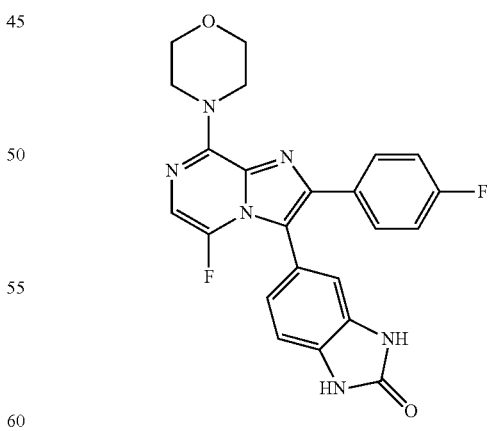

The title compound was prepared in a manner analogous to Example 161. MS (ESI): mass calcd. for $C_{23}H_{18}F_2N_6O_2$, 448.15 m/z found, 449.0 [M+H]$^+$. $^1$H NMR (600 MHz, CDCl$_3$) d 8.55-8.11 (m, 2H), 4.24-4.17 (t, J=4.8 Hz, 4H), 3.94-3.87 (t, J=4.8 Hz, 4H), 6.97-6.90 (m, 2H), 7.17-7.10 (m, 2H), 7.55-7.48 (m, 2H), 7.10-7.01 (m, 2H).

Example 163: 5-[5-Chloro-2-(4-fluorophenyl)-8-morpholino-imidazo[1,2-a]pyrazin-3-yl]indolin-2-one

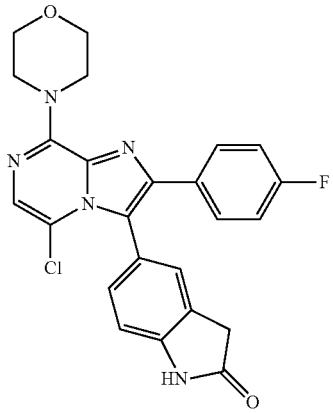 [SMILES: O=C1Cc2cc(-c3c(-c4ccc(F)cc4)nc4c(N5CCOCC5)ncc(Cl)n34)ccc2N1]

The title compound was prepared in a manner analogous to Example 161. MS (ESI): mass calcd. for C$_{24}$H$_{19}$ClFN$_5$O$_2$, 463.12 m/z found, 463.9 [M+H]$^+$. $^1$H NMR (600 MHz, DMSO-d$_6$) δ 10.79-10.47 (s, 1H), 7.55-7.49 (m, 2H), 7.38-7.34 (s, 1H), 7.34-7.25 (m, 2H), 7.16-7.09 (m, 2H), 6.94-6.89 (d, J=7.9 Hz, 1H), 4.25-4.14 (t, J=4.8 Hz, 4H), 4.05-3.92 (s, 1H), 3.81-3.74 (t, J=4.8 Hz, 4H).

Example 164: 5-[2-(4-Fluorophenyl)-7-morpholino-pyrazolo[1,5-c]pyrimidin-3-yl]indolin-2-one

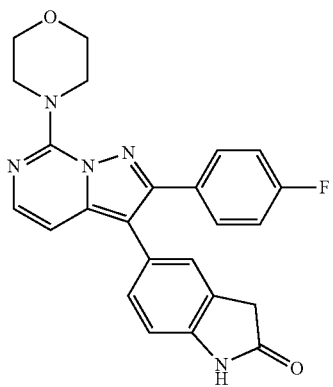 [SMILES: O=C1Cc2cc(-c3c(-c4ccc(F)cc4)nn4c(N5CCOCC5)nccc34)ccc2N1]

To a solution of 4-(3-bromo-2-(4-fluorophenyl)pyrazolo[1,5-c]pyrimidin-7-yl)morpholine (Intermediate 3, 230 mg, 0.61 mmol), 5-(4,4,5,5-tetramethyl-1,3,2-dioxaborolan-2-yl)indolin-2-one (190 mg, 0.73 mmol), NaHCO$_3$ (17 mg, 0.2 mmol) in dioxane (8 mL) and water (2 mL) was added PdCl$_2$(dtbpf) (40 mg, 0.06 mmol). The reaction mixture was stirred at 110° C. for 6 h. The mixture was cooled, then diluted with water and extracted with EtOAc. The combined organics were dried (MgSO$_4$), filtered, concentrated under reduced pressure. Purification (FCC, SiO$_2$, EtOAc/heptane gradient 0 to 50%) afforded the title compound (115 mg, 43%). MS (ESI): mass calcd. for C$_{24}$H$_{20}$FN$_5$O$_2$, 429.2; m/z found, 430.0 [M+H]$^+$. $^1$H NMR (300 MHz, DMSO-d$_6$) δ 10.46 (s, 1H), 7.67-7.56 (m, 3H), 7.24 (t, J=8.9 Hz, 2H), 7.16 (s, 1H), 7.06 (d, J=8.0 Hz, 1H), 6.98 (d, J=6.2 Hz, 1H), 6.87 (d, J=8.0 Hz, 1H), 4.03-3.90 (m, 4H), 3.87-3.75 (m, 4H), 3.49 (s, 2H).

Example 165-Example 184, Example 186-Example 191, Example 193, Example 195-Example 197, Example 199-Example 205, and Example 207-Example 211 were prepared in a manner analogous to Example 164.

Example 165: 5-(2-tert-Butylpyrazolo[1,5-c]pyrimidin-3-yl)indolin-2-one

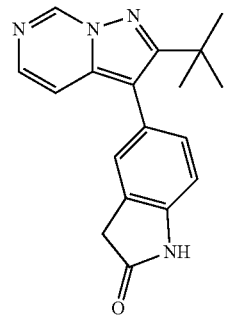 [SMILES: CC(C)(C)c1nn2cnccc2c1-c1ccc2c(c1)CC(=O)N2]

The title compound was prepared in a manner analogous to Example 164. MS (ESI): mass calcd. for C$_{18}$H$_{18}$N$_4$O, 306.1; m/z found, 307.1 [M+H]$^+$. $^1$H NMR (300 MHz, CDCl$_3$) δ 9.18 (s, 1H), 8.10 (br s, 1H), 7.68 (d, J=6.3 Hz, 1H), 7.21-7.14 (m, 2H), 7.00-6.91 (m, 2H), 3.62 (s, 2H), 1.35 (s, 9H).

Example 166: 5-[2-(4-Fluorophenyl)-7-(4-hydroxy-1-piperidyl)pyrazolo[1,5-c]pyrimidin-3-yl]indolin-2-one

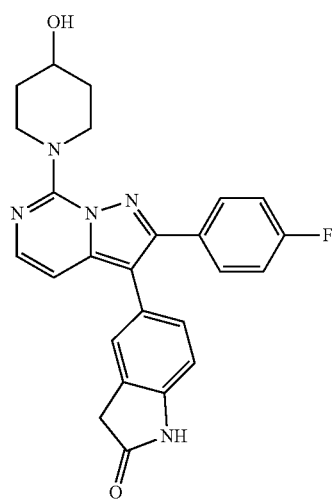 [SMILES: O=C1Cc2cc(-c3c(-c4ccc(F)cc4)nn4c(N5CCC(O)CC5)nccc34)ccc2N1]

The title compound was prepared in a manner analogous to Example 164. MS (ESI): mass calcd. for C$_{25}$H$_{22}$FN$_5$O$_2$, 443.2; m/z found, 444.0 [M+H]$^+$. $^1$H NMR (300 MHz, CDCl$_3$) δ=7.68-7.54 (m, 4H), 7.21-7.12 (m, 2H), 7.04 (t, J=8.7 Hz, 2H), 6.91 (s, 1H), 6.90 (d, J=6.3 Hz, 1H), 4.56 (td, J=4.7, 13.5 Hz, 2H), 4.12-3.98 (m, 1H), 3.69-3.44 (m, 4H), 2.21-2.07 (m, 2H), 1.91-1.74 (m, 2H).

Example 167: 5-[2-(4-Fluorophenyl)-8-(methylamino)imidazo[1,2-a]pyrazin-3-yl]indolin-2-one

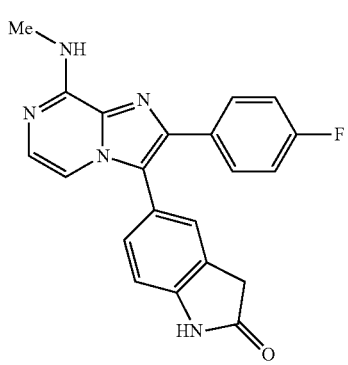 [SMILES: CNc1nccn2c(-c3ccc4c(c3)CC(=O)N4)c(-c3ccc(F)cc3)nc12]

The title compound was prepared in a manner analogous to Example 164. MS (ESI): mass calcd. for $C_{21}H_{16}FN_5O$, 373.1; m/z found, 374.1 [M+H]+. 1H NMR (500 MHz, DMSO-$d_6$) δ 10.62 (s, 1H), 7.77 (br s, 1H), 7.66-7.60 (m, 2H), 7.31 (s, 1H), 7.27 (d, J=4.6 Hz, 1H), 7.25-7.21 (m, 2H), 7.18 (br. t, J=9.0 Hz, 2H), 6.99 (d, J=8.1 Hz, 1H), 3.56 (s, 2H), 3.00 (d, J=4.6 Hz, 3H)

Example 168: 5-[2-(4-Fluorophenyl)-7-(3-oxopiperazin-1-yl)pyrazolo[1,5-c]pyrimidin-3-yl]indolin-2-one

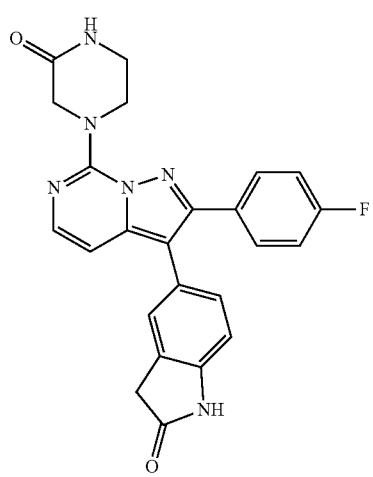 [SMILES: O=C1CN(c2nccc3c(-c4ccc5c(c4)CC(=O)N5)c(-c4ccc(F)cc4)nn23)CCN1]

The title compound was prepared in a manner analogous to Example 164. MS (ESI): mass calcd. for $C_{24}H_{19}FN_6O_2$, 442.2; m/z found, 443.0 [M+H]+. 1H NMR (300 MHz, DMSO-$d_6$) δ 10.48 (s, 1H), 8.09 (br s, 1H), 7.76-7.45 (m, 3H), 7.25 (t, J=8.9 Hz, 2H), 7.16 (s, 1H), 7.06 (d, J=8.2 Hz, 1H), 7.00 (d, J=6.2 Hz, 1H), 6.87 (d, J=8.0 Hz, 1H), 4.48 (s, 2H), 4.22 (br. t, J=4.9 Hz, 2H), 3.50 (s, 2H), 3.43-3.30 (m, 2H)

Example 169: 5-[7-(Dimethylamino)-2-(4-fluorophenyl)pyrazolo[1,5-c]pyrimidin-3-yl]indolin-2-one

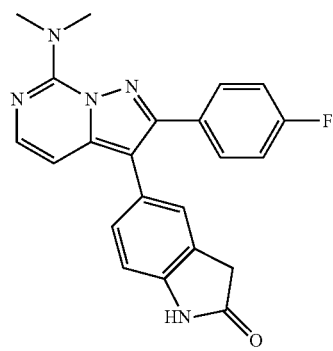 [SMILES: CN(C)c1nccc2c(-c3ccc4c(c3)CC(=O)N4)c(-c3ccc(F)cc3)nn12]

The title compound was prepared in a manner analogous to Example 164. MS (ESI): mass calcd. for $C_{22}H_{18}FN_5O$, 387.1; m/z found, 388.2 [M+H]+. 1H NMR (300 MHz, DMSO-$d_6$) δ 10.47 (s, 1H), 7.64-7.56 (m, 3H), 7.24 (t, J=8.9 Hz, 2H), 7.15 (s, 1H), 7.05 (d, J=8.0 Hz, 1H), 6.91-6.81 (m, 2H), 3.49 (s, 2H), 3.39 (s, 6H).

Example 170: 5-[7-(1,1-Dioxo-1,4-thiazinan-4-yl)-2-(4-fluorophenyl)pyrazolo[1,5-c]pyrimidin-3-yl]indolin-2-one

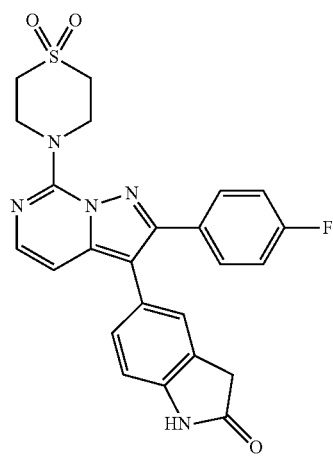 [SMILES: O=C1Cc2cc(-c3c(-c4ccc(F)cc4)nn4c(N5CCS(=O)(=O)CC5)nccc34)ccc2N1]

The title compound was prepared in a manner analogous to Example 164. MS (ESI): mass calcd. for $C_{24}H_{20}FN_5O_3S$, 477.1; m/z found, 478 [M+H]+. 1H NMR (300 MHz, DMSO-$d_6$) δ 10.48 (s, 1H), 7.73-7.55 (m, 3H), 7.25 (t, J=8.8 Hz, 2H), 7.16 (s, 1H), 7.11-7.00 (m, 2H), 6.88 (d, J=8.1 Hz, 1H), 4.46 (br s, 4H), 3.50 (s, 2H), 3.33 (br. s, 4H).

Example 171: 5-[2-(4-Fluorophenyl)-7-(methylamino)pyrazolo[1,5-c]pyrimidin-3-yl]indolin-2-one

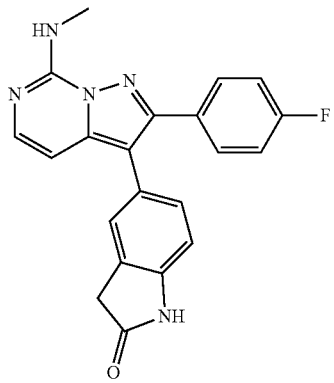 [SMILES: CNc1nccc2c(-c3ccc4c(c3)CC(=O)N4)c(-c3ccc(F)cc3)nn12]

The title compound was prepared in a manner analogous to Example 164. MS (ESI): mass calcd. for $C_{21}H_{16}FN_5O$, 373.1; m/z found, 374.0 [M+H]$^+$. $^1$H NMR (300 MHz, DMSO-d$_6$) δ 10.45 (s, 1H), 7.96-7.84 (m, 1H), 7.67-7.53 (m, 3H), 7.24 (t, J=8.9 Hz, 2H), 7.15 (s, 1H), 7.05 (d, J=8.0 Hz, 1H), 6.85 (d, J=8.0 Hz, 1H), 6.74 (d, J=6.2 Hz, 1H), 3.48 (s, 2H), 3.05 (d, J=4.5 Hz, 3H).

Example 172: 5-[7-(4-Acetylpiperazin-1-yl)-2-(4-fluorophenyl)pyrazolo[1,5-c]pyrimidin-3-yl]indolin-2-one

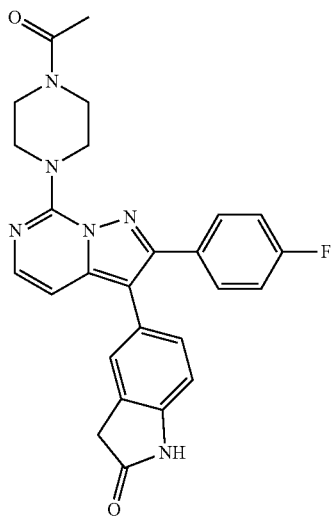 [SMILES: CC(=O)N1CCN(c2nccc3c(-c4ccc5c(c4)CC(=O)N5)c(-c4ccc(F)cc4)nn23)CC1]

The title compound was prepared in a manner analogous to Example 164. MS (ESI): mass calcd. for $C_{26}H_{23}FN_6O_2$, 470.2; m/z found, 471.0 [M+H]$^+$. $^1$H NMR (300 MHz, CDCl$_3$) δ 7.67-7.56 (m, 4H), 7.20-7.13 (m, 2H), 7.05 (t, J=8.7 Hz, 2H), 6.95 (d, J=6.3 Hz, 1H), 6.91 (d, J=8.4 Hz, 1H), 4.13-4.02 (m, 4H), 3.94-3.84 (m, 2H), 3.79-3.71 (m, 2H), 3.56 (s, 2H), 2.19 (s, 3H).

Example 173: 6-[2-(4-Fluorophenyl)-7-morpholinopyrazolo[1,5-c]pyrimidin-3-yl]-3H-1,3-benzoxazol-2-one

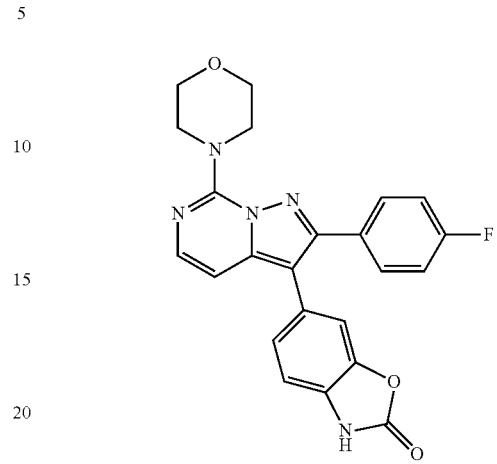

The title compound was prepared in a manner analogous to Example 164. MS (ESI): mass calcd. for $C_{23}H_{18}FN_5O_3$, 431.1; m/z found, 432.2 [M+H]$^+$. $^1$H NMR (300 MHz, CDCl$_3$) δ 8.55 (s, 1H), 7.63 (d, J=6.2 Hz, 1H), 7.56 (dd, J=8.6, 5.5 Hz, 2H), 7.18-6.99 (m, 5H), 6.94 (d, J=6.2 Hz, 1H), 4.11-4.03 (m, 4H), 4.00-3.87 (m, 4H).

Example 174: 5-[2-(4-Fluorophenyl)-7-(4-oxo-1-piperidyl)pyrazolo[1,5-c]pyrimidin-3-yl]indolin-2-one

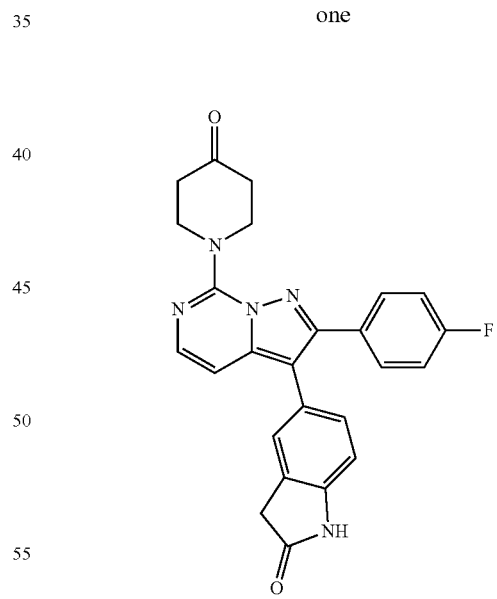

The title compound was prepared in a manner analogous to Example 164. MS (ESI): mass calcd. for $C_{25}H_{20}FN_5O_2$, 441.2; m/z found, 442.0 [M+H]$^+$. $^1$H NMR (300 MHz, CDCl$_3$) δ=8.00 (br s, 1H), 7.67-7.54 (m, 3H), 7.21-7.12 (m, 2H), 7.04 (t, J=8.6 Hz, 2H), 6.97 (d, J=6.0 Hz, 1H), 6.92 (d, J=8.4 Hz, 1H), 4.36 (t, J=5.8 Hz, 4H), 3.56 (s, 2H), 2.71 (t, J=5.8 Hz, 4H).

Example 175: 5-[2-(4-Fluorophenyl)pyrazolo[1,5-c]pyrimidin-3-yl]indolin-2-one

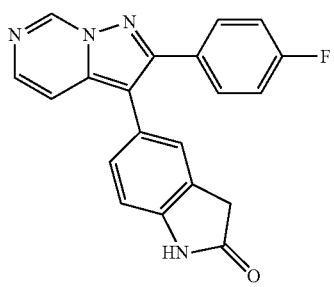 [SMILES: O=C1Cc2cc(-c3c(-c4ccc(F)cc4)nn4cnccc34)ccc2N1]

The title compound was prepared in a manner analogous to Example 164. MS (ESI): mass calcd. for $C_{20}H_{13}FN_4O$, 344.1; m/z found, 345.0 [M+H]$^+$. $^1$H NMR (300 MHz, DMSO-d$_6$) δ 10.49 (br s, 1H), 9.57 (s, 1H), 7.87 (d, J=6.3 Hz, 1H), 7.67-7.57 (m, 2H), 7.52 (d, J=5.8 Hz, 1H), 7.26 (t, J=8.7 Hz, 2H), 7.20 (br s, 1H), 7.09 (d, J=8.1 Hz, 1H), 6.88 (d, J=7.8 Hz, 1H), 3.50 (br s, 2H).

Example 176: 5-[7-(3,3-Difluoroazetidin-1-yl)-2-(4-fluorophenyl)pyrazolo[1,5-c]pyrimidin-3-yl]indolin-2-one

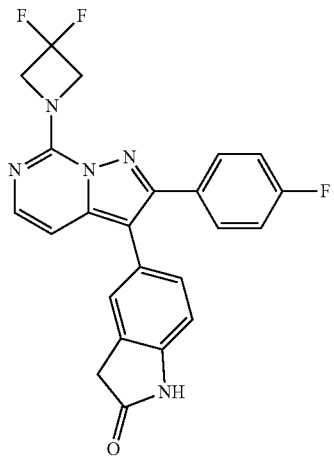 [SMILES: O=C1Cc2cc(-c3c(-c4ccc(F)cc4)nn4c(N5CC(F)(F)C5)nccc34)ccc2N1]

The title compound was prepared in a manner analogous to Example 164. MS (ESI): mass calcd. for $C_{23}H_{16}F_3N_5O$, 435.1; m/z found, 436.0 [M+H]$^+$. $^1$H NMR (300 MHz, DMSO-d$_6$) δ 10.47 (s, 1H), 7.68-7.55 (m, 3H), 7.23 (t, J=8.8 Hz, 2H), 7.15 (s, 1H), 7.05 (d, J=8.0 Hz, 1H), 6.96-6.81 (m, 2H), 4.91 (t, J=12.4 Hz, 4H), 3.49 (s, 2H)

Example 177: 5-[2-(4-Fluorophenyl)-7-(3-methylmorpholin-4-yl)pyrazolo[1,5-c]pyrimidin-3-yl]indolin-2-one

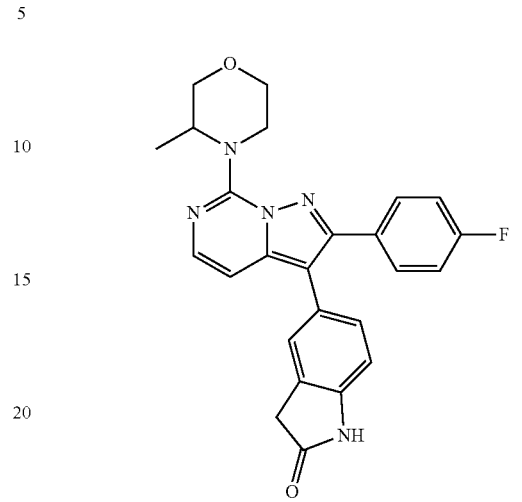

The title compound was prepared in a manner analogous to Example 164. MS (ESI): mass calcd. for $C_{25}H_{22}FN_5O_2$, 443.2; m/z found, 444.0 [M+H]$^+$. $^1$H NMR (300 MHz, CDCl$_3$) δ 7.67-7.54 (m, 3H), 7.20-7.12 (m, 2H), 7.04 (t, J=8.6 Hz, 2H), 6.93-6.86 (m, 2H), 5.38-5.27 (m, 1H), 4.38 (br. d, J=11.7 Hz, 1H), 4.10-3.94 (m, 3H), 3.91-3.67 (m, 3H), 3.55 (s, 2H), 1.45 (d, J=6.6 Hz, 3H).

Example 178: 5-[2-(4-Fluorophenyl)-7-morpholinopyrazolo[1,5-c]pyrimidin-3-yl]-1,3-dihydro-2,1-benzothiazole 2,2-dioxide

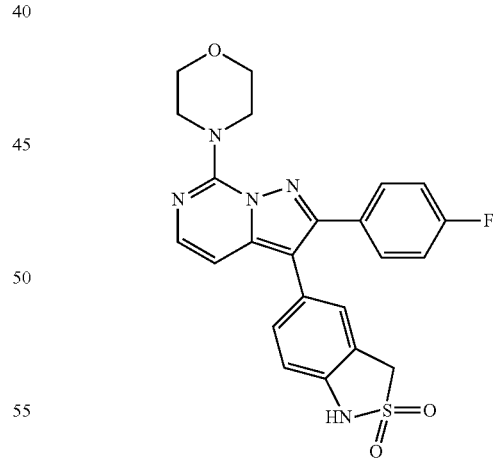

The title compound was prepared in a manner analogous to Example 164. MS (ESI): mass calcd. for $C_{23}H_{20}FN_5O_3S$, 465.1; m/z found, 466.0 [M+H]$^+$. $^1$H NMR (300 MHz, CDCl$_3$) δ 7.67-7.50 (m, 3H), 7.25-7.16 (m, 2H), 7.07 (t, J=8.5 Hz, 2H), 7.00-6.87 (m, 2H), 6.80 (br s, 1H), 4.40 (s, 2H), 4.12 (br s, 4H), 3.97 (br s, 4H).

Example 179: 5-[2-(4-Fluorophenyl)-7-(3-hydroxyazetidin-1-yl)pyrazolo[1,5-c]pyrimidin-3-yl]indolin-2-one

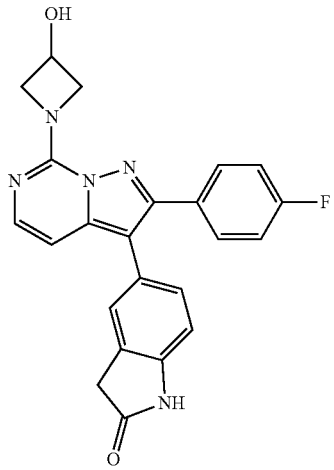 [SMILES: O=C1Cc2cc(-c3c(-c4ccc(F)cc4)nn4c(N5CC(O)C5)nccc34)ccc2N1]

MS (ESI): mass calcd. for $C_{23}H_{18}FN_5O_2$, 415.1; m/z found, 416.0 [M+H]$^+$. $^1$H NMR (300 MHz, DMSO-d$_6$) δ 10.44 (s, 1H), 7.65-7.56 (m, 2H), 7.51 (d, J=6.2 Hz, 1H), 7.22 (t, J=8.8 Hz, 2H), 7.14 (s, 1H), 7.04 (d, J=7.6 Hz, 1H), 6.86 (d, J=8.0 Hz, 1H), 6.74 (d, J=6.2 Hz, 1H), 5.75 (d, J=5.9 Hz, 1H), 4.83-4.51 (m, 3H), 4.34-4.12 (m, 2H), 3.49 (s, 2H).

Example 180: 5-[2-(4-Fluorophenyl)-7-[3-(hydroxymethyl)azetidin-1-yl]pyrazolo[1,5-c]pyrimidin-3-yl]indolin-2-one

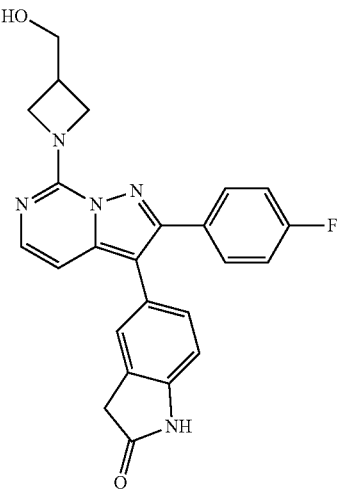 [SMILES: O=C1Cc2cc(-c3c(-c4ccc(F)cc4)nn4c(N5CC(CO)C5)nccc34)ccc2N1]

The title compound was prepared in a manner analogous to Example 164. MS (ESI): mass calcd. for $C_{24}H_{20}FN_5O_2$, 429.2; m/z found, 430.0 [M+H]$^+$. $^1$H NMR (300 MHz, DMSO-d$_6$) δ 10.44 (br s, 1H), 7.66-7.54 (m, 2H), 7.50 (br. d, J=5.5 Hz, 1H), 7.22 (br. t, J=8.1 Hz, 2H), 7.13 (br s, 1H), 7.04 (br. d, J=6.9 Hz, 1H), 6.86 (br. d, J=7.4 Hz, 1H), 6.71 (br. d, J=5.8 Hz, 1H), 4.84 (br s, 1H), 4.53 (br s, 2H), 4.27 (br s, 2H), 3.63 (br s, 2H), 3.48 (br s, 2H), 2.82 (br s, 1H).

Example 181: 5-[2-tert-Butyl-7-(4-hydroxy-1-piperidyl)pyrazolo[1,5-c]pyrimidin-3-yl]indolin-2-one

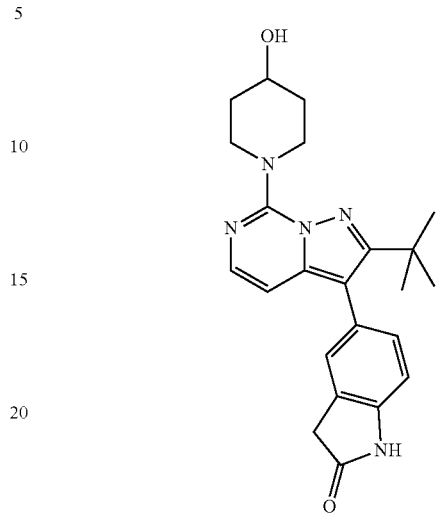

The title compound was prepared in a manner analogous to Example 164. MS (ESI): mass calcd. for $C_{23}H_{27}N_5O_2$, 405.2; m/z found, 406.2 [M+H]$^+$. $^1$H NMR (300 MHz, CDCl$_3$) δ 7.97 (br s, 1H), 7.44 (d, J=6.2 Hz, 1H), 7.20-7.12 (m, 2H), 6.91 (d, J=8.4 Hz, 1H), 6.47 (d, J=6.0 Hz, 1H), 4.65-4.49 (m, 2H), 4.10-3.96 (m, 1H), 3.62-3.59 (m, 2H), 3.62-3.47 (m, 2H), 2.19-2.05 (m, 2H), 1.90-1.73 (m, 2H), 1.33 (s, 9H), (OH was not observed).

Example 182: 5-(2-tert-Butyl-7-morpholino-pyrazolo[1,5-c]pyrimidin-3-yl)indolin-2-one

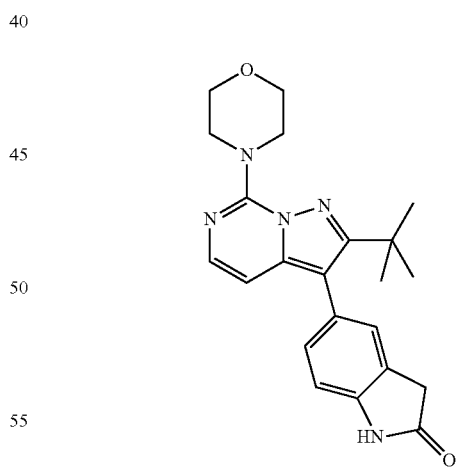

The title compound was prepared in a manner analogous to Example 164. MS (ESI): mass calcd. for $C_{22}H_{25}N_5O_2$, 391.2; m/z found, 392.0 [M+H]$^+$. $^1$H NMR (300 MHz, DMSO-d$_6$) δ 10.45 (s, 1H), 7.47 (d, J=6.2 Hz, 1H), 7.13 (s, 1H), 7.09 (d, J=8.0 Hz, 1H), 6.89 (d, J=7.8 Hz, 1H), 6.52 (d, J=6.2 Hz, 1H), 3.99-3.89 (m, 4H), 3.84-3.75 (m, 4H), 3.53 (s, 2H), 1.27 (s, 9H).

Example 183: 5-[2-tert-Butyl-7-(3,3-difluoroazetidin-1-yl)pyrazolo[1,5-c]pyrimidin-3-yl]indolin-2-one

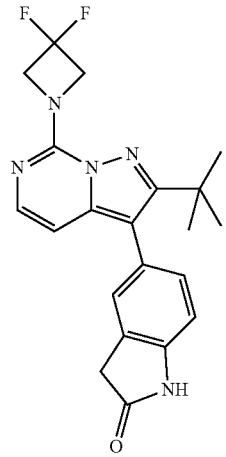 [SMILES: CC(C)(C)c1nn2c(N3CC(F)(F)C3)nccc2c1-c1ccc2c(c1)CC(=O)N2]

The title compound was prepared in a manner analogous to Example 164. MS (ESI): mass calcd. for $C_{21}H_{21}F_2N_5O$, 397.2; m/z found, 398.0 [M+H]+. 1H NMR (300 MHz, DMSO-$d_6$) δ 10.45 (s, 1H), 7.42 (d, J=6.2 Hz, 1H), 7.12 (s, 1H), 7.08 (d, J=8.2 Hz, 1H), 6.89 (d, J=7.8 Hz, 1H), 6.46 (d, J=6.3 Hz, 1H), 4.84 (t, J=12.4 Hz, 4H), 3.52 (s, 2H), 1.27 (s, 9H).

Example 184: 5-[2-(4-Fluorophenyl)-7-(3-hydroxy-3-methyl-azetidin-1-yl)pyrazolo[1,5-c]pyrimidin-3-yl]indolin-2-one

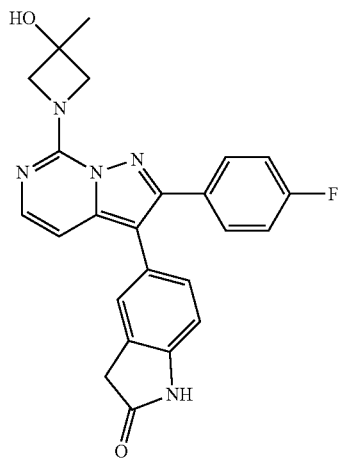 [SMILES: CC1(O)CN(c2nccc3c(-c4ccc5c(c4)CC(=O)N5)c(-c4ccc(F)cc4)nn23)C1]

The title compound was prepared in a manner analogous to Example 164. MS (ESI): mass calcd. for $C_{24}H_{20}FN_5O_2$, 429.2; m/z found, 430.0 [M+H]+. 1H NMR (300 MHz, DMSO-$d_6$) δ 10.45 (s, 1H), 7.65-7.55 (m, 2H), 7.51 (d, J=6.2 Hz, 1H), 7.22 (t, J=8.8 Hz, 2H), 7.14 (s, 1H), 7.04 (d, J=8.1 Hz, 1H), 6.86 (d, J=8.0 Hz, 1H), 6.74 (d, J=6.2 Hz, 1H), 5.68 (s, 1H), 4.52-4.21 (m, 4H), 3.49 (s, 2H), 1.49 (s, 3H).

Example 185: 5-(2-(4-Fluorophenyl)-8-(1,2,6-triazaspiro[2.5]oct-1-en-6-yl)imidazo[1,2-a]pyrazin-3-yl)indolin-2-one

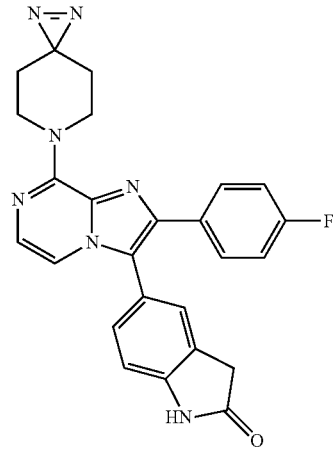 [SMILES: O=C1Cc2cc(-c3c(-c4ccc(F)cc4)nc4c(N5CCC6(CC5)N=N6)nccn34)ccc2N1]

The title compound was prepared in a manner analogous to Example 1, Steps A-D, substituting 1,2,6-triazaspiro[2.5]oct-1-ene for 1-boc-piperizine in Step C, (2-oxoindolin-5-yl)boronic acid for (4-hydroxyphenyl)boronic acid in Step D. The by-product of the reaction in Example 155. MS (ESI): mass calcd. for $C_{25}H_{20}FN_7O_7$, 453.5; m/z found, 454.2 [M+H]+. 1H NMR (500 MHz, CDCl$_3$) δ 1H NMR (500 MHz, CDCl$_3$) d 7.65 (s, 1H), 7.61 (dd, J=8.8, 5.5 Hz, 2H), 7.33 (d, J=4.6 Hz, 1H), 7.29 (s, 2H), 7.24 (d, J=4.6 Hz, 1H), 7.02 (d, J=7.9 Hz, 1H), 6.97 (t, J=8.7 Hz, 2H), 4.56 (t, J=5.9 Hz, 4H), 3.62 (s, 2H), 1.49 (t, J=5.9 Hz, 4H).

Example 186: 5-[2-(4-Fluorophenyl)-7-(4-hydroxy-4-methyl-1-piperidyl)pyrazolo[1,5-c]pyrimidin-3-yl]indolin-2-one

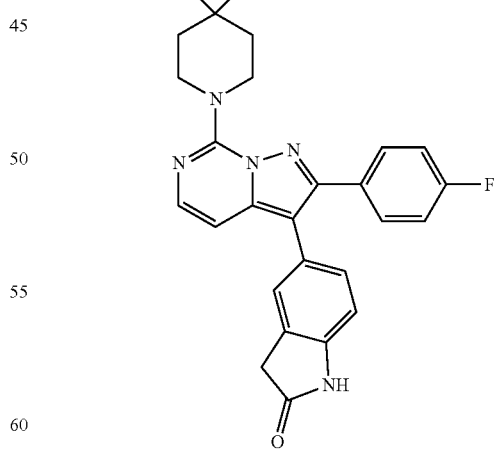

The title compound was prepared in a manner analogous to Example 164. MS (ESI): mass calcd. for $C_{26}H_{24}FN_5O_2$, 457.2; m/z found, 458.0 [M+H]+. 1H NMR (300 MHz, DMSO-$d_6$) δ 10.45 (s, 1H), 7.66-7.54 (m, 3H), 7.24 (t, J=8.9 Hz, 2H), 7.15 (s, 1H), 7.05 (d, J=8.0 Hz, 1H), 6.93-6.83 (m, 2H), 4.48-4.33 (m, 3H), 3.69-3.54 (m, 2H), 3.49 (s, 2H), 1.78-1.55 (m, 4H), 1.20 (s, 3H).

Example 187: 5-[7-(4-Hydroxy-1-piperidyl)-2-phenyl-pyrazolo[1,5-c]pyrimidin-3-yl]indolin-2-one

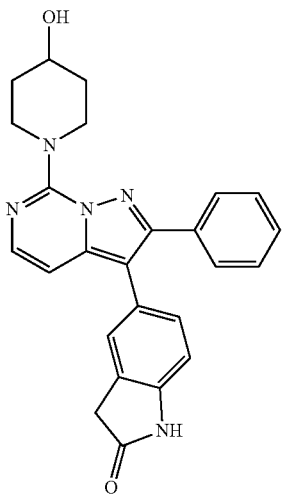 [SMILES: O=C1Cc2cc(-c3c(-c4ccccc4)nn4c(N5CCC(O)CC5)nccc34)ccc2N1]

The title compound was prepared in a manner analogous to Example 164. MS (ESI): mass calcd. for $C_{25}H_{23}N_5O_2$, 425.2; m/z found, 426.0 [M+H]$^+$. $^1$H NMR (300 MHz, DMSO-d$_6$) δ 10.44 (s, 1H), 7.64-7.53 (m, 3H), 7.45-7.33 (m, 3H), 7.15 (s, 1H), 7.05 (d, J=8.2 Hz, 1H), 6.92 (d, J=6.2 Hz, 1H), 6.85 (d, J=8.0 Hz, 1H), 4.77 (d, J=4.1 Hz, 1H), 4.54-4.36 (m, 2H), 3.86-3.73 (m, 1H), 3.57-3.43 (m, 4H), 1.97-1.82 (m, 2H), 1.65-1.48 (m, 2H).

Example 188: 5-[7-(4-Fluoro-1-piperidyl)-2-phenyl-pyrazolo[1,5-c]pyrimidin-3-yl]indolin-2-one

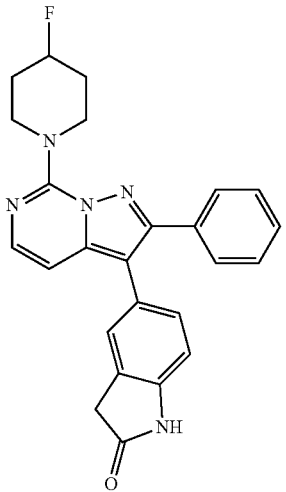 [SMILES: O=C1Cc2cc(-c3c(-c4ccccc4)nn4c(N5CCC(F)CC5)nccc34)ccc2N1]

The title compound was prepared in a manner analogous to Example 164. MS (ESI): mass calcd. for $C_{25}H_{22}FN_5O$, 427.2; m/z found, 428.0 [M+H]$^+$. $^1$H NMR (300 MHz, DMSO-d$_6$) δ 10.44 (s, 1H), 7.69-7.52 (m, 3H), 7.47-7.32 (m, 3H), 7.16 (s, 1H), 7.06 (d, J=7.8 Hz, 1H), 6.96 (d, J=6.2 Hz, 1H), 6.85 (d, J=8.0 Hz, 1H), 4.97 (sptd, J=3.3, 48.7 Hz, 2H), 4.19-3.89 (m, 4H), 3.49 (s, 2H), 2.21-1.98 (m, 2H), 1.97-1.79 (m, 2H).

Example 189: 5-[7-(4-Methoxy-1-piperidyl)-2-phenyl-pyrazolo[1,5-c]pyrimidin-3-yl]indolin-2-one

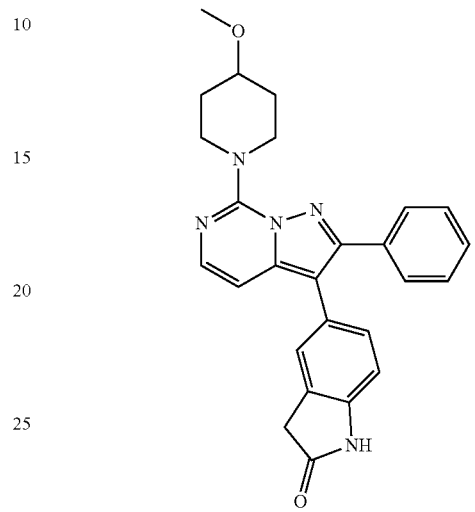

The title compound was prepared in a manner analogous to Example 164. MS (ESI): mass calcd. for $C_{26}H_{25}N_5O_2$, 439.2; m/z found, 440.0 [M+H]$^+$. $^1$H NMR (300 MHz, DMSO-d$_6$) δ 10.45 (s, 1H), 7.63-7.53 (m, 3H), 7.44-7.34 (m, 3H), 7.16 (s, 1H), 7.05 (d, J=8.0 Hz, 1H), 6.94 (d, J=6.3 Hz, 1H), 6.86 (d, J=7.8 Hz, 1H), 4.44-4.29 (m, 2H), 3.73-3.45 (m, 5H), 3.30 (s, 3H), 2.11-1.95 (m, 2H), 1.74-1.55 (m, 2H).

Example 190: 5-[2-(4-Fluorophenyl)-7-(4-fluoro-1-piperidyl)pyrazolo[1,5-c]pyrimidin-3-yl]indolin-2-one

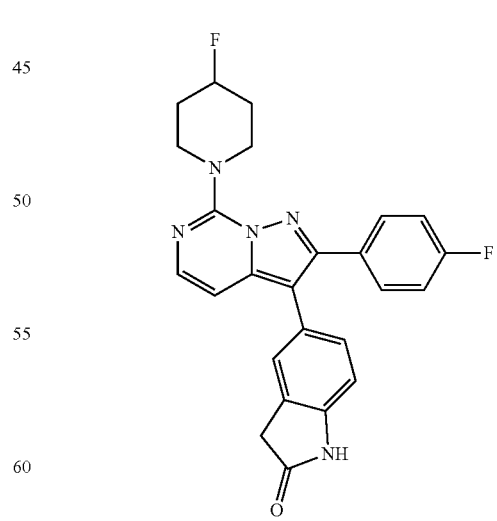

The title compound was prepared in a manner analogous to Example 164. MS (ESI): mass calcd. for $C_{25}H_{21}F_2N_5O$, 445.2; m/z found, 446.0 [M+H]$^+$. $^1$H NMR (300 MHz, DMSO-d$_6$) δ 10.46 (s, 1H), 7.68-7.54 (m, 3H), 7.24 (t, J=8.9

Hz, 2H), 7.16 (s, 1H), 7.06 (d, J=8.1 Hz, 1H), 6.96 (d, J=6.2 Hz, 1H), 6.87 (d, J=8.0 Hz, 1H), 5.12-4.84 (m, 1H), 4.19-3.88 (m, 4H), 3.49 (s, 2H), 2.22-1.98 (m, 2H), 1.97-1.78 (m, 2H).

Example 191: 5-[7-(3-Methoxyazetidin-1-yl)-2-phenyl-pyrazolo[1,5-c]pyrimidin-3-yl]indolin-2-one

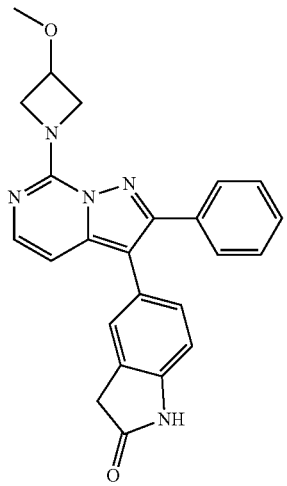 [SMILES: COC1CN(c2nccc3c(-c4ccc5c(c4)CC(=O)N5)c(-c4ccccc4)nn23)C1]

The title compound was prepared in a manner analogous to Example 164. MS (ESI): mass calcd. for $C_{24}H_{21}N_5O_2$, 411.2; m/z found, 412.0 [M+H]$^+$. $^1$H NMR (300 MHz, DMSO-d$_6$) δ 10.44 (s, 1H), 7.63-7.54 (m, 2H), 7.52 (d, J=6.2 Hz, 1H), 7.41-7.33 (m, 3H), 7.14 (s, 1H), 7.04 (d, J=8.0 Hz, 1H), 6.84 (d, J=7.8 Hz, 1H), 6.77 (d, J=6.2 Hz, 1H), 4.78-4.61 (m, 2H), 4.41-4.22 (m, 3H), 3.48 (s, 2H), 3.29 (s, 3H).

Example 192: 5-[7-(Cyclopentoxy)-2-phenyl-pyrazolo[1,5-c]pyrimidin-3-yl]indolin-2-one

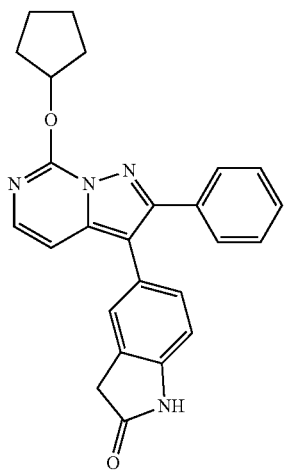 [SMILES: O=C1Cc2cc(-c3c(-c4ccccc4)nn4c(OC5CCCC5)nccc34)ccc2N1]

The title compound was prepared in a manner analogous to Example 164 using 3-bromo-7-(cyclopentyloxy)-2-phenylpyrazolo[1,5-c]pyrimidine (Intermediate 40) and 5-(4,4,5,5-tetramethyl-1,3,2-dioxaborolan-2-yl)indolin-2-one. MS (ESI): mass calcd. for $C_{25}H_{22}N_4O_2$, 410.2; m/z found, 411.0 [M+H]$^+$. $^1$H NMR (300 MHz, DMSO-d$_6$) δ 10.44 (s, 1H), 7.60 (d, J=6.3 Hz, 1H), 7.58-7.49 (m, 2H), 7.44-7.34 (m, 3H), 7.16 (s, 1H), 7.11 (d, J=6.3 Hz, 1H), 7.05 (d, J=8.0 Hz, 1H), 6.84 (d, J=8.0 Hz, 1H), 5.74-5.64 (m, 1H), 3.48 (s, 2H), 2.18-1.57 (m, 8H).

Example 193: trans-5-[7-(3-Fluoro-4-hydroxy-1-piperidyl)-2-phenyl-pyrazolo[1,5-c]pyrimidin-3-yl]indolin-2-one

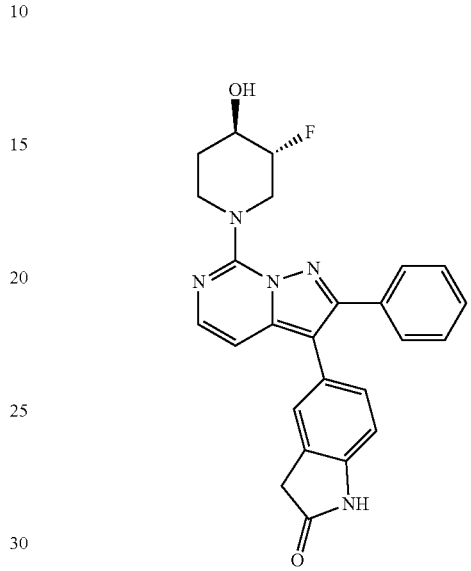

The title compound was prepared in a manner analogous to Example 164. MS (ESI): mass calcd. for $C_{25}H_{22}FN_5O_2$, 443.2; m/z found, 444.0 [M+H]$^+$. $^1$H NMR (300 MHz, DMSO-d$_6$) δ 10.45 (s, 1H), 7.66-7.52 (m, 3H), 7.46-7.34 (m, 3H), 7.16 (s, 1H), 7.06 (d, J=7.7 Hz, 1H), 6.96 (d, J=6.2 Hz, 1H), 6.86 (d, J=7.8 Hz, 1H), 5.38 (d, J=4.5 Hz, 1H), 4.66-4.39 (m, 2H), 4.36-4.21 (m, 1H), 4.08-3.90 (m, 1H), 3.89-3.76 (m, 1H), 3.73-3.56 (m, 1H), 3.49 (s, 2H), 2.19-2.03 (m, 1H), 1.69-1.52 (m, 1H).

Example 194: 5-(7-Isopropoxy-2-phenyl-pyrazolo[1,5-c]pyrimidin-3-yl)indolin-2-one

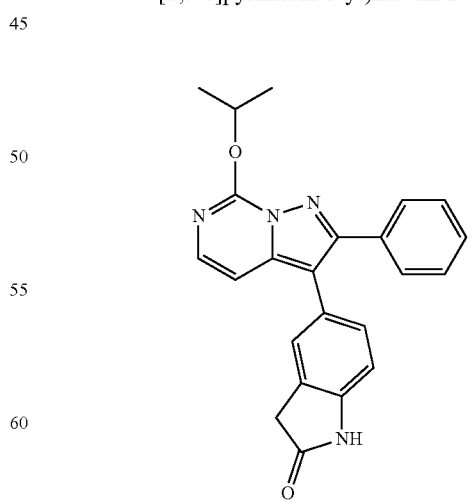

The title compound was prepared in a manner analogous to Example 164 using 3-bromo-7-isopropoxy-2-phenylpyrazolo[1,5-c]pyrimidine (Intermediate 41). MS (ESI): mass calcd. for $C_{23}H_{20}N_4O_2$, 384.2; m/z found, 385.0 [M+H]$^+$. $^1$H NMR (300 MHz, DMSO-d$_6$) δ 10.45 (s, 1H), 7.60 (d, J=6.3 Hz, 1H), 7.58-7.50 (m, 2H), 7.45-7.34 (m, 3H), 7.16 (s, 1H), 7.11 (d, J=6.3 Hz, 1H), 7.05 (d, J=8.0 Hz, 1H), 6.85 (d, J=8.0 Hz, 1H), 5.57 (spt, J=6.2 Hz, 1H), 3.48 (s, 2H), 1.48 (d, J=6.2 Hz, 6H).

Example 195: 5-[2-Cyclopentyl-7-(3-methoxyazetidin-1-yl)pyrazolo[1,5-c]pyrimidin-3-yl]indolin-2-one

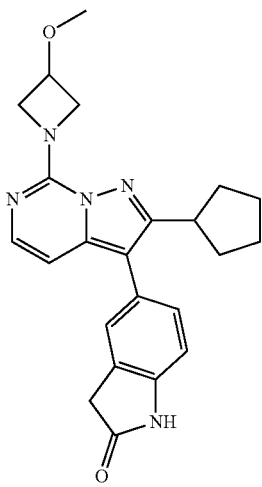 [SMILES: COC1CN(c2nccc3c(-c4ccc5c(c4)CC(=O)N5)c(C4CCCC4)nn23)C1]

The title compound was prepared in a manner analogous to Example 164. MS (ESI): mass calcd. for $C_{23}H_{25}N_5O_2$, 403.2; m/z found, 404.0 [M+H]$^+$. $^1$H NMR (300 MHz, CDCl$_3$) δ 7.61 (s, 1H), 7.44 (d, J=6.3 Hz, 1H), 7.25-7.18 (m, 2H), 6.92 (d, J=7.9 Hz, 1H), 6.65 (d, J=6.3 Hz, 1H), 4.85-4.66 (m, 2H), 4.50-4.27 (m, 3H), 3.60 (s, 2H), 3.38 (s, 3H), 3.35-3.22 (m, 1H), 2.02-1.75 (m, 6H), 1.73-1.59 (m, 2H).

Example 196: 5-[2-Cyclopentyl-7-(3-fluoroazetidin-1-yl)pyrazolo[1,5-c]pyrimidin-3-yl]indolin-2-one

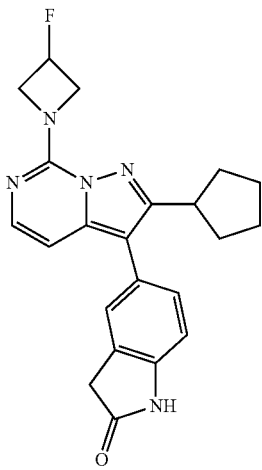 [SMILES: O=C1Cc2cc(-c3c(C4CCCC4)nn4c(N5CC(F)C5)nccc34)ccc2N1]

The title compound was prepared in a manner analogous to Example 164. MS (ESI): mass calcd. for $C_{22}H_{22}FN_5O$, 391.2; m/z found, 392.0 [M+H]$^+$. $^1$H NMR (300 MHz, DMSO-d$_6$) δ 10.42 (s, 1H), 7.46 (d, J=6.3 Hz, 1H), 7.22 (s, 1H), 7.18 (d, J=8.1 Hz, 1H), 6.91 (d, J=7.9 Hz, 1H), 6.77 (d, J=6.3 Hz, 1H), 5.50 (d, J=57.7 Hz, 1H), 4.88-4.63 (m, 2H), 4.58-4.34 (m, 2H), 3.53 (s, 2H), 3.44-3.37 (m, 1H), 2.02-1.52 (m, 8H).

Example 197: 5-[7-[(3S)-3-Methoxypyrrolidin-1-yl]-2-phenyl-pyrazolo[1,5-c]pyrimidin-3-yl]indolin-2-one

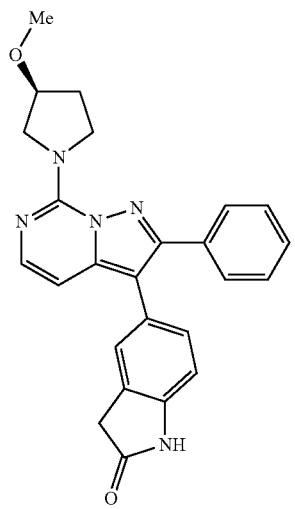 [SMILES: CO[C@H]1CCN(c2nccc3c(-c4ccc5c(c4)CC(=O)N5)c(-c4ccccc4)nn23)C1]

The title compound was prepared in a manner analogous to Example 164. MS (ESI): mass calcd. for $C_{25}H_{23}N_5O_2$, 425.2; m/z found, 426.0 [M+H]$^+$. $^1$H NMR (300 MHz, DMSO-d$_6$) δ 10.44 (s, 1H), 7.61-7.54 (m, 2H), 7.49 (d, J=6.2 Hz, 1H), 7.43-7.34 (m, 3H), 7.14 (s, 1H), 7.04 (d, J=8.1 Hz, 1H), 6.85 (d, J=8.0 Hz, 1H), 6.70 (d, J=6.2 Hz, 1H), 4.30-3.92 (m, 7H), 3.48 (s, 2H), 3.29 (s, 3H).

Example 198: 5-(5-Methyl-7-morpholino-2-phenyl-pyrazolo[1,5-c]pyrimidin-3-yl)indolin-2-one

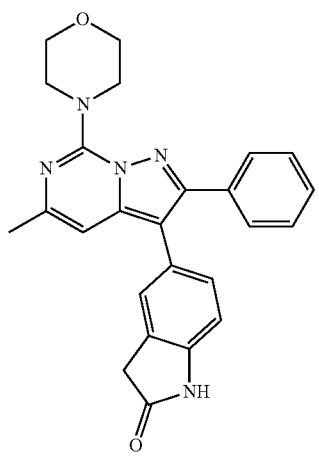 [SMILES: Cc1cc2c(-c3ccc4c(c3)CC(=O)N4)c(-c3ccccc3)nn2c(N2CCOCC2)n1]

The title compound was prepared in a manner analogous Example 164 using 4-(3-bromo-5-methyl-2-phenylpyrazolo

[1,5-c]pyrimidin-7-yl)morpholine (Intermediate 41). MS (ESI): mass calcd. for $C_{25}H_{23}N_5O_2$, 425.2; m/z found, 426.0 [M+H]$^+$. $^1$H NMR (300 MHz, DMSO-d$_6$) δ 10.43 (s, 1H), 7.59-7.51 (m, 2H), 7.41-7.32 (m, 3H), 7.14 (s, 1H), 7.03 (d, J=7.9 Hz, 1H), 6.85 (d, J=8.0 Hz, 1H), 6.81 (s, 1H), 4.02-3.91 (m, 4H), 3.86-3.74 (m, 4H), 3.48 (s, 2H), 2.31 (s, 3H).

Example 199: 5-[2-tert-Butyl-7-(6-oxa-2-azaspiro[3.3]heptan-2-yl)pyrazolo[1,5-c]pyrimidin-3-yl]indolin-2-one

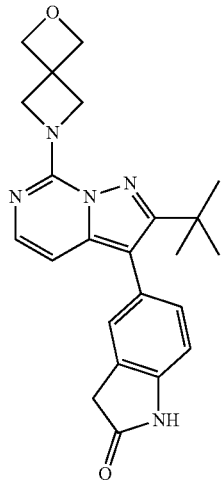 [SMILES: CC(C)(C)c1nn2c(N3CC4(COC4)C3)nccc2c1-c1ccc2c(c1)CC(=O)N2]

The title compound was prepared in a manner analogous to Example 164. MS (ESI): mass calcd. for $C_{23}H_{25}N_5O_2$, 403.5; m/z found, 404.2 [M+H]$^+$. $^1$H NMR (300 MHz, DMSO-d$_6$) δ=10.44 (br. s, 1H), 7.34 (d, J=6.2 Hz, 1H), 7.10 (s, 1H), 7.07 (d, J=8.4 Hz, 1H), 6.87 (d, J=7.8 Hz, 1H), 6.30 (d, J=6.3 Hz, 1H), 4.75 (s, 4H), 4.61 (br s, 4H), 3.52 (s, 2H), 1.27 (s, 9H).

Example 200: 5-[7-(3-Fluoroazetidin-1-yl)-2-phenyl-pyrazolo[1,5-c]pyrimidin-3-yl]indolin-2-one

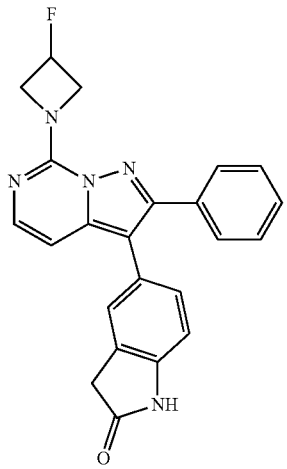 [SMILES: O=C1Cc2cc(-c3c(-c4ccccc4)nn4c(N5CC(F)C5)nccc34)ccc2N1]

The title compound was prepared in a manner analogous to Example 164. MS (ESI): mass calcd. for $C_{23}H_{18}FN_5O$, 399.4; m/z found, 400.2 [M+H]$^+$. $^1$H NMR (300 MHz, DMSO-d$_6$) δ=10.44 (br. s, 1H), 7.63-7.56 (m, 2H), 7.54 (d, J=6.3 Hz, 1H), 7.43-7.32 (m, 3H), 7.14 (s, 1H), 7.05 (d, J=8.1 Hz, 1H), 6.85 (d, J=8.2 Hz, 1H), 6.82 (d, J=6.3 Hz, 1H), 5.53 (br. d, J=58.0 Hz, 1H), 4.97-4.74 (m, 2H), 4.53 (dd, J=24.2, 11.4 Hz, 2H), 3.48 (s, 2H).

Example 201: 5-(7-Morpholino-2-phenyl-pyrazolo[1,5-c]pyrimidin-3-yl)indolin-2-one

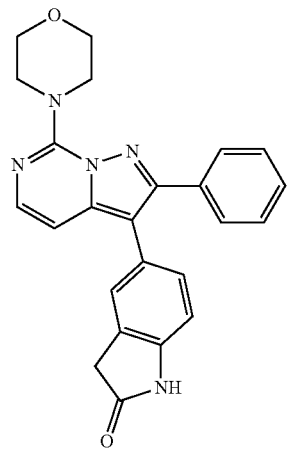 [SMILES: O=C1Cc2cc(-c3c(-c4ccccc4)nn4c(N5CCOCC5)nccc34)ccc2N1]

The title compound was prepared in a manner analogous to Example 164. MS (ESI): mass calcd. for $C_{24}H_{21}N_5O_2$, 411.5; m/z found, 412.0 [M+H]$^+$. $^1$H NMR (300 MHz, DMSO-d$_6$) δ=10.44 (br. s, 1H), 7.63 (d, J=6.2 Hz, 1H), 7.61-7.52 (m, 2H), 7.45-7.32 (m, 3H), 7.16 (s, 1H), 7.06 (d, J=8.0 Hz, 1H), 6.98 (d, J=6.2 Hz, 1H), 6.86 (d, J=8.0 Hz, 1H), 4.04-3.92 (m, 4H), 3.88-3.76 (m, 4H), 3.49 (s, 2H).

Example 202: 5-[7-[(3R)-3-Methoxypyrrolidin-1-yl]-2-phenyl-pyrazolo[1,5-c]pyrimidin-3-yl]indolin-2-one

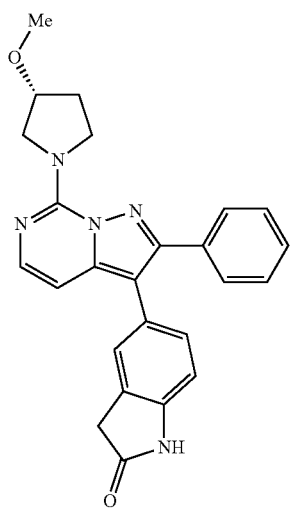 [SMILES: CO[C@@H]1CCN(c2nccc3c(-c4ccc5c(c4)CC(=O)N5)c(-c4ccccc4)nn23)C1]

The title compound was prepared in a manner analogous to Example 164. MS (ESI): mass calcd. for $C_{25}H_{23}N_5O_2$, 425.5; m/z found, 426.0 [M+H]⁺. ¹H NMR (300 MHz, DMSO-d₆) δ=10.43 (br. s, 1H), 7.63-7.53 (m, 2H), 7.49 (d, J=6.2 Hz, 1H), 7.42-7.31 (m, 3H), 7.14 (s, 1H), 7.04 (d, J=8.7 Hz, 1H), 6.85 (d, J=7.8 Hz, 1H), 6.70 (d, J=6.2 Hz, 1H), 4.27-3.93 (m, 5H), 3.48 (s, 2H), 3.29 (s, 3H), 2.18-1.95 (m, 2H).

Example 203: 5-(2-Cyclopentyl-7-morpholino-pyrazolo[1,5-c]pyrimidin-3-yl)indolin-2-one

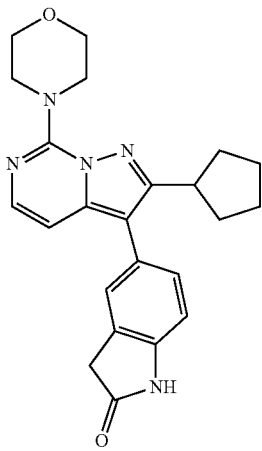 [SMILES: O=C1Cc2cc(-c3c(C4CCCC4)nn4c(N5CCOCC5)nccc34)ccc2N1]

The title compound was prepared in a manner analogous to Example 164. MS (ESI): mass calcd. for $C_{23}H_{25}N_5O_2$, 403.5; m/z found, 404.0 [M+H]⁺. ¹H NMR (300 MHz, CDCl₃) δ=7.70 (br s, 1H), 7.55 (d, J=6.2 Hz, 1H), 7.28-7.22 (m, 2H), 6.97 (d, J=7.8 Hz, 1H), 6.88 (d, J=6.2 Hz, 1H), 4.10-3.90 (m, 8H), 3.63 (s, 2H), 3.35 (quin, J=7.4 Hz, 1H), 2.11-1.77 (m, 6H), 1.77-1.63 (m, 2H).

Example 204: (cis)-5-[7-(3-Fluoro-4-hydroxy-1-piperidyl)-2-phenyl-pyrazolo[1,5-c]pyrimidin-3-yl]indolin-2-one

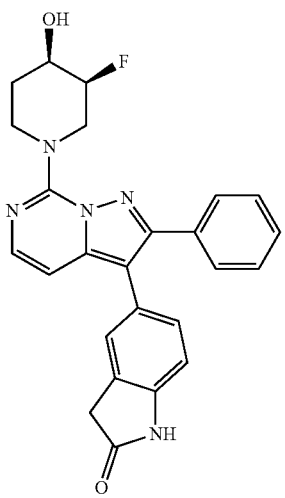 [SMILES: O=C1Cc2cc(-c3c(-c4ccccc4)nn4c(N5CC[C@@H](O)[C@@H](F)C5)nccc34)ccc2N1]

The title compound was prepared in a manner analogous to Example 164. MS (ESI): mass calcd. for $C_{25}H_{22}FN_5O_2$, 443.5; m/z found, 444.0 [M+H]⁺. ¹H NMR (300 MHz, DMSO-d₆) δ=10.44 (br s, 1H), 7.60 (br s, 3H), 7.39 (br s, 3H), 7.16 (s, 1H), 7.06 (d, J=6.9 Hz, 1H), 6.94 (d, J=5.1 Hz, 1H), 6.86 (d, J=7.1 Hz, 1H), 5.23-4.99 (m, 2H), 4.77 (br. d, J=49.4 Hz, 1H), 4.40 (br. d, J=11.5 Hz, 1H), 4.14-3.63 (m, 3H), 3.48 (s, 2H), 2.15-1.94 (m, 1H), 1.88-1.69 (m, 1H).

Example 205: 5-[2-Cyclopentyl-7-(3-hydroxyazetidin-1-yl)pyrazolo[1,5-c]pyrimidin-3-yl]indolin-2-one

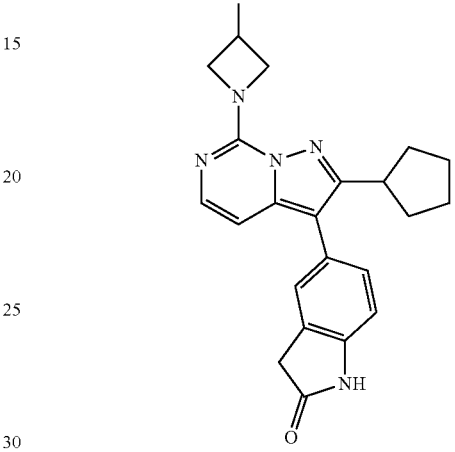

The title compound was prepared in a manner analogous to Example 164. MS (ESI): mass calcd. for $C_{22}H_{23}N_5O_2$, 389.5; m/z found, 390.0 [M+H]⁺. ¹H NMR (300 MHz, DMSO-d₆) δ=10.42 (br. s, 1H), 7.43 (d, J=6.3 Hz, 1H), 7.21 (s, 1H), 7.18 (d, J=8.7 Hz, 1H), 6.91 (d, J=8.0 Hz, 1H), 6.71 (d, J=6.2 Hz, 1H), 5.70 (d, J=6.0 Hz, 1H), 4.70-4.52 (m, 3H), 4.15 (br. d, J=6.2 Hz, 2H), 3.53 (s, 2H), 3.39-3.32 (m, 1H), 2.03-1.87 (m, 2H), 1.88-1.70 (m, 4H), 1.69-1.53 (m, 2H)

Example 206: 5-(7-Methoxy-2-phenyl-pyrazolo[1,5-c]pyrimidin-3-yl)indolin-2-one

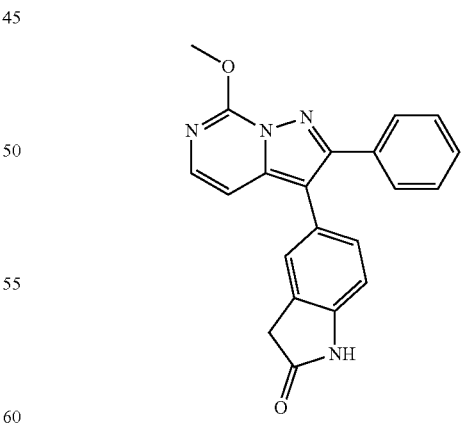

The title compound was prepared from 3-bromo-7-methoxy-2-phenylpyrazolo[1,5-c]pyrimidine (prepared in a manner analogous to Intermediate 28. MS (ESI): mass calcd. for $C_{21}H_{16}N_4O_2$, 356.4; m/z found, 357.0 [M+H]+, ¹H NMR (300 MHz, DMSO-d₆) δ=10.47 (s, 1H), 7.62 (d, J=6.3 Hz, 1H), 7.59-7.48 (m, 2H), 7.46-7.33 (m, 3H), 7.17 (s, 1H), 7.14 (d, J=6.3 Hz, 1H), 7.10-7.01 (m, 1H), 6.85 (d, J=8.0 Hz, 1H), 4.22 (s, 3H), 3.49 (s, 2H).

Example 207: 5-(4-Bromo-7-morpholino-2-phenyl-pyrazolo[1,5-c]pyrimidin-3-yl)indolin-2-one

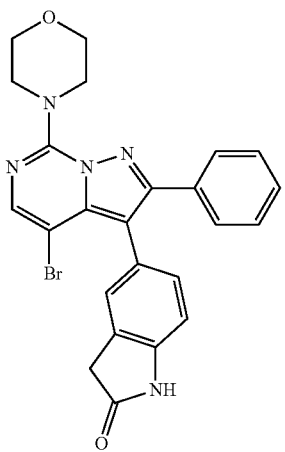 [SMILES: O=C1Cc2cc(-c3c(-c4ccccc4)nn4c(N5CCOCC5)ncc(Br)c34)ccc2N1]

To a cooled (0° C.) solution of 5-(7-morpholino-2-phenyl-pyrazolo[1,5-c]pyrimidin-3-yl)indolin-2-one (Example 201, 180 mg, 0.44 mmol) in CH$_3$CN (5 mL) was added NBS (86 mg, 0.48 mmol). The reaction mixture was stirred at 23° C. for 16 h. The mixture was diluted with NaHCO$_3$ and extracted with EtOAc. The combined organics were dried (MgSO$_4$), filtered, concentrated under reduced pressure. Purification (FCC, SiO$_2$, EtOAc/heptane gradient 0 to 50%) afforded the title compound (120 mg, 55%). MS (ESI): mass calcd. for C$_{24}$H$_{20}$BrN$_5$O$_2$, 489.1; m/z found, 490.0 [M+H]$^+$. $^1$H NMR (300 MHz, DMSO-d$_6$) δ 10.47 (s, 1H), 7.76 (s, 1H), 7.56-7.47 (m, 2H), 7.38-7.30 (m, 3H), 7.14 (s, 1H), 7.09 (d, J=8.0 Hz, 1H), 6.83 (d, J=7.8 Hz, 1H), 4.00-3.92 (m, 4H), 3.86-3.76 (m, 4H), 3.48 (s, 2H).

Example 208: 5-(4-Methyl-7-morpholino-2-phenyl-pyrazolo[1,5-c]pyrimidin-3-yl)indolin-2-one

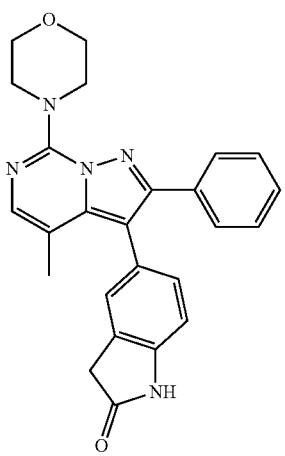

To a solution of 5-(4-bromo-7-morpholino-2-phenyl-pyrazolo[1,5-c]pyrimidin-3-yl)indolin-2-one (Example 207, 10 mg, 0.22 mmol), tetramethyltin (0.091 mL, 0.66 mmol), LiCl (190 mg, 0.44 mmol) in DMF was added Pd(PPh$_3$)$_2$Cl$_2$ (7.7 mg, 0.011 mmol). The reaction mixture was heated to 120° C. for 6 h. The mixture was diluted with water and extracted with EtOAc. The combined organics were dried (MgSO$_4$), filtered, concentrated under reduced pressure. Purification (FCC, SiO$_2$, MeOH/DCM gradient 0 to 4%) afforded the title compound (85 mg, 73%). MS (ESI): mass calcd. for C$_{25}$H$_{23}$N$_5$O$_2$, 425.2; m/z found, 426.0 [M+H]$^+$. $^1$H NMR (300 MHz, DMSO-d$_6$) δ 10.48 (s, 1H), 7.58-7.48 (m, 2H), 7.37 (s, 1H), 7.35-7.28 (m, 3H), 7.17 (s, 1H), 7.13 (d, J=8.0 Hz, 1H), 6.85 (d, J=8.0 Hz, 1H), 3.91-3.76 (m, 8H), 3.50 (s, 2H), 1.84 (s, 3H)

Example 209: 4-[3-(1H-Indazol-5-yl)-8-(3-oxopiperazin-1-yl)imidazo[1,2-a]pyrazin-2-yl]benzonitrile

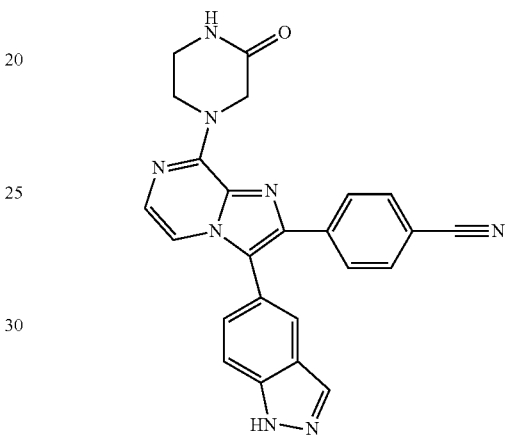

The title compound was prepared in a manner analogous to Example 164. MS (ESI): mass calcd. for C$_{24}$H$_{18}$N$_8$O, 434.2; m/z found, 450.2 [M+H]$^+$. $^1$H NMR (500 MHz, DMSO-d$_6$) δ 13.39 (br s, 1H), 8.20 (br s, 1H), 8.12 (br s, 1H), 7.97 (br s, 1H), 7.86-7.63 (m, 5H), 7.36 (br s, 3H), 4.74 (br s, 2H), 4.54 (br s, 2H), 3.41 (br s, 2H).

Example 210: 4-[3-(2-Oxoindolin-5-yl)-8-(3-oxopiperazin-1-yl)imidazo[1,2-a]pyrazin-2-yl]benzonitrile

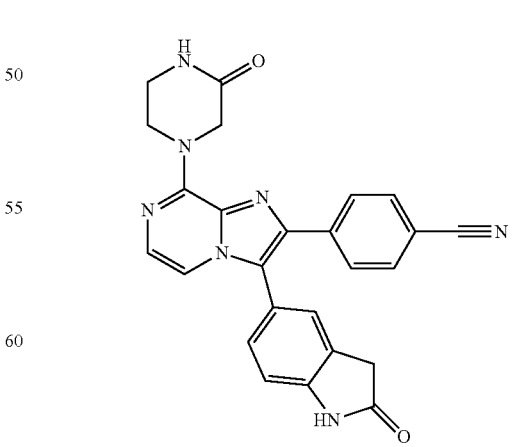

The title compound was prepared in a manner analogous to Example 164. MS (ESI): mass calcd. for C$_{25}$H$_{19}$N$_7$O$_2$, 449.2; m/z found, 450.2 [M+H]+. 1H NMR (500 MHz, DMSO-d6) δ 10.67 (s, 1H), 8.12 (br s, 1H), 7.81 (br. d, J=9.0 Hz, 2H), 7.77 (br. d, J=9.0 Hz, 2H), 7.38 (d, J=4.6 Hz, 1H), 7.35 (d, J=4.6 Hz, 1H), 7.34 (br s, 1H), 7.27 (d, J=7.5 Hz, 1H), 7.03 (d, J=8.1 Hz, 1H), 4.72 (s, 2H), 4.56-4.49 (m, 2H), 3.58 (s, 2H), 3.42-3.37 (m, 2H).

Example 211: 4-[3-(2-Oxo-1,3-dihydrobenzimidazol-5-yl)-8-(3-oxopiperazin-1-yl)imidazo[1,2-a]pyrazin-2-yl]benzonitrile

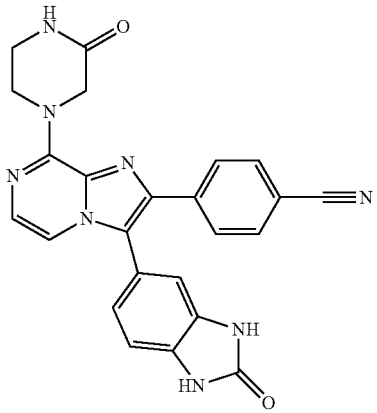 [SMILES: N#Cc1ccc(-c2nc3c(N4CCNC(=O)C4)nccn3c2-c2ccc3[nH]c(=O)[nH]c3c2)cc1]

The title compound was prepared in a manner analogous to Example 164. MS (ESI): mass calcd. for $C_{24}H_{18}N_8O_2$, 450.2; m/z found, 451.2 [M+H]+. 1H NMR (500 MHz, DMSO-d6) δ 10.81 (br s, 2H), 8.12 (br s, 1H), 7.79 (br. d, J=8.4 Hz, 2H), 7.75 (br. d, J=8.4 Hz, 2H), 7.36 (s, 2H), 7.15 (d, J=8.1 Hz, 1H), 7.03 (d, J=8.1 Hz, 1H), 7.00 (s, 1H), 4.72 (br s, 2H), 4.56-4.50 (m, 2H), 3.43-3.37 (m, 2H).

Example 212: 4-[3-(1H-Indazol-5-yl)-4-methyl-2-phenyl-pyrazolo[1,5-c]pyrimidin-7-yl]morpholine

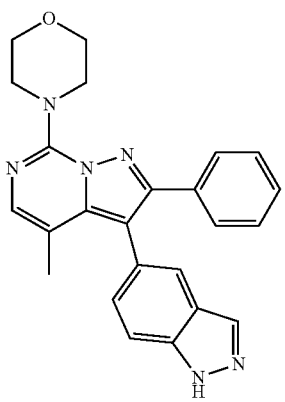 [SMILES: Cc1cnc(N2CCOCC2)n2nc(-c3ccccc3)c(-c3ccc4[nH]ncc4c3)c12]

Step A: 4-(2-Phenyl-3-(1-(tetrahydro-2H-pyran-2-yl)-1H-indazol-5-yl)pyrazolo[1,5-c]pyrimidin-7-yl)morpholine The title compound was prepared in a manner analogous to Example 164 using 4-(3-bromo-2-phenylpyrazolo[1,5-c]pyrimidin-7-yl)morpholine (Intermediate 22) and 1-(tetrahydro-2H-pyran-2-yl)-5-(4,4,5,5-tetramethyl-1,3,2-dioxaborolan-2-yl)-1H-indazole. MS (ESI): mass calcd. for $C_{28}H_{28}N_6O_2$, 480.6; m/z found, 481.0 [M+H]+.

Step B: 4-(4-Bromo-2-phenyl-3-(1-(tetrahydro-2H-pyran-2-yl)-1H-indazol-5-yl)pyrazolo[1,5-c]pyrimidin-7-yl)morpholine To a cooled (0° C.) solution of 4-(2-phenyl-3-(1-(tetrahydro-2H-pyran-2-yl)-1H-indazol-5-yl)pyrazolo[1,5-c]pyrimidin-7-yl)morpholine (230 mg, 0.47 mmol) in acetonitrile was added NBS (93 mg, 0.52 mmol). The mixture was stirred overnight at 23° C. To the reaction mixture was added sat. aq. NaHCO3 and EtOAc. The organics were separated, dried (MgSO4), filtered and concentrated under reduced pressure. Purification (FCC, SiO2, EtOAc in Heptane 0/100 to 70/30) afforded the title compound as a white foam (83 mg, 22% yield) which was used immediately in the next step.

Step C: 4-(4-Methyl-2-phenyl-3-(1-(tetrahydro-2H-pyran-2-yl)-1H-indazol-5-yl)pyrazolo[1,5-c]pyrimidin-7-yl)morpholine To a solution of 4-(4-bromo-2-phenyl-3-(1-(tetrahydro-2H-pyran-2-yl)-1H-indazol-5-yl)pyrazolo[1,5-c]pyrimidin-7-yl)morpholine (83 mg, 0.15 mmol), Pd(PPh3)4 (17 mg, 0.015 mmol) and Cs2CO3 (97 mg, 0.3 mmol) in 1,4-dioxane (1 mL) was added trimethylboroxine (0.025 mL, 0.18 mmol), while under N2. The reaction was stirred at 105° C. for 6 h. Water and EtOAc were added and the organics were separated. The organics were dried (MgSO4), filtered and concentrated under reduced pressure. Purification (FCC, SiO2, EtOAc in Heptane 0/100 to 35/65) afforded the title compound as a pale yellow foam (60 mg, 78%) which was used immediately in the next step.

Step D: 4-[3-(1H-Indazol-5-yl)-4-methyl-2-phenyl-pyrazolo[1,5-c]pyrimidin-7-yl]morpholine To a solution of 4-(4-methyl-2-phenyl-3-(1-(tetrahydro-2H-pyran-2-yl)-1H-indazol-5-yl)pyrazolo[1,5-c]pyrimidin-7-yl)morpholine (60 mg, 0.12 mmol) in EtOH (2 mL) was added 37% HCl (0.03 mL). The reaction mixture was heated at 70° C. in a sealed tube for 4 h. The reaction mixture was concentrated under reduced pressure and sat. aq. NaHCO3 and EtOAc were added. The organics were separated, dried (MgSO4), filtered and concentrated under reduced pressure. Purification (FCC, SiO2, EtOAc in Heptane 0/100 to 35/65) afforded the title compound which was crystallized with DIPE to afford the title compound as a white solid (6.2 mg, 12%). MS (ESI): mass calcd. for $C_{24}H_{22}N_6O$, 410.2; m/z found, 411 [M+H]+. 1H NMR (300 MHz, DMSO-d6) d 13.17 (s, 1H), 8.07 (s, 1H), 7.73 (s, 1H), 7.57 (d, J=8.5 Hz, 1H), 7.51-7.44 (m, 2H), 7.37 (s, 1H), 7.33-7.25 (m, 4H), 3.85 (d, J=6.3 Hz, 8H), 1.76 (s, 3H).

Example 213: 6-[7-(4-Methoxy-1-piperidyl)-2-phenyl-pyrazolo[1,5-c]pyrimidin-3-yl]-3H-1,3-benzothiazol-2-one

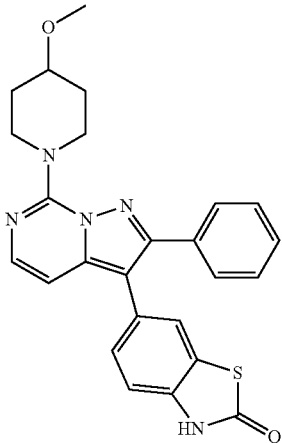 [SMILES: COC1CCN(c2nccc3c(-c4ccc5[nH]c(=O)sc5c4)c(-c4ccccc4)nn23)CC1]

Step A: 6-(7-(4-Methoxypiperidin-1-yl)-2-phenylpyrazolo[1,5-c]pyrimidin-3-yl)-34(2-(trimethylsilyl)ethoxy)methyl)benzo[d]thiazol-2(3H)-one The title compound was prepared in a manner analogous to Example 164 from 3-bromo-7-(4-methoxypiperidin-1-yl)-2-phenylpyrazolo[1,5-c]pyrimidine (Intermediate 23) and 6-(4,4,5,5-tetramethyl-1,3,2-dioxaborolan-2-yl)-3-((2(trimethylsilyl)ethoxy)methyl)benzo[d]thiazol-2(3H)-one (Intermediate 25). MS (ESI): mass calcd. for $C_{31}H_{37}N_5O_3SSi$, 587.8; m/z found, 588.0 [M+H]$^+$.

Step B: 6-[7-(4-Methoxy-1-piperidyl)-2-phenylpyrazolo[1,5-c]pyrimidin-3-yl]-3H-1,3-benzothiazol-2-one A solution of 6-(7-(4-methoxypiperidin-1-yl)-2-phenylpyrazolo[1,5-c]pyrimidin-3-yl)-3-((2-(trimethylsilyl)ethoxy)methyl)benzo[d]thiazol-2(3H)-one (79 mg, 0.15 mmol) in 4N HCl in dioxane (0.75 mL, 3.0 mmol) was stirred overnight at 23° C. The reaction mixture was cooled to 0° C. 6.0 N NaOH was added until pH=10. The reaction mixture was stirred for 4 h at 23° C. Saturated NH$_4$Cl was added and the reaction mixture was extracted with EtOAc. The organics were dried (MgSO$_4$), filtered, and concentrated under reduced pressure. Purification reverse phase HPLC [47% (25 mM NH$_4$HCO$_3$)-53% (MeCN:MeOH (1:1, v/v))] to [18% (25 mM NH$_4$HCO$_3$)-82% (MeCN:MeOH (1:1, v/v) afforded the title compound (6.7 mg, 23%). MS (ESI): mass calcd. for $C_{25}H_{23}N_5O_2S$, 457.2; m/z found, 458 [M+H]$^+$. $^1$H NMR (300 MHz, DMSO-d$_6$) d 11.94 (br s, 1H), 7.63 (d, J=6.1 Hz, 1H), 7.60-7.49 (m, 3H), 7.46-7.33 (m, 3H), 7.13 (s, 2H), 6.97 (d, J=6.1 Hz, 1H), 4.47-4.27 (m, 2H), 3.69-3.44 (m, 3H), 3.30 (s, 3H), 2.12-1.94 (m, 2H), 1.76-1.53 (m, 2H).

Example 214: N-Cyclohexyl-8-morpholino-3-(2-oxo-1,3-dihydrobenzimidazol-5-yl)imidazo[1,2-a]pyrazine-2-carboxamide

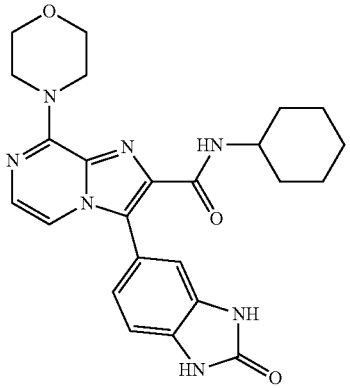 [SMILES: O=C(NC1CCCCC1)c1nc2c(N3CCOCC3)nccn2c1-c1ccc2[nH]c(=O)[nH]c2c1]

Step A. 3-Bromo-8-morpholinoimidazo[1,2-a]pyrazine-2-carboxylic acid

The title compound was prepared in a manner analogous to Example 137. MS (ESI): mass calcd. for $C_{11}H_{11}BrN_4O_3$, 327.1; m/z found, MH+=326.0 [M+H]$^+$.

Step B: 3-Bromo-N-cyclohexyl-8-morpholinoimidazo[1,2-a]pyrazine-2-carboxamide

To a solution of 3-bromo-8-morpholinoimidazo[1,2-a]pyrazine-2-carboxylic acid (250 mg, 0.764 mmol) in DMF (2 mL) was added cyclohexylamine (0.176 mL, 1.53 mmol), HATU (581 mg, 1.53 mmol) and DIPEA (0.263 mL, 1.53 mmol). The reaction mixture was stirred at 23° C. for 18 h. The solution was diluted with water and extracted with EtOAc. The combined organics were dried (Na$_2$SO$_4$), filtered and concentrated in vacuo. Purification (FCC, SiO$_2$; EtOAc in heptane 0/100 to 80/20) afforded the title compound as a brown oil (260 mg, 83%). MS (ESI): mass calcd. for $C_{17}H_{22}BrN_5O_2$, 408.3; m/z found, MH+=408.2 [M+H]$^+$.

Step C: N-Cyclohexyl-8-morpholino-3-(2-oxo-1,3-dihydrobenzimidazol-5-yl)imidazo[1,2-a]pyrazine-2-carboxamide To a solution of 3-bromo-N-cyclohexyl-8-morpholinoimidazo[1,2-a]pyrazine-2-carboxamide (150 mg, 0.37 mmol) and 5-(4,4,5,5-tetramethyl-1,3,2-dioxaborolan-2-yl)-1,3-dihydro-2H-benzo[d]imidazol-2-one (Intermediate 32, 239 mg, 0.92 mmol) in dioxane (2 mL) and saturated Na$_2$CO$_3$ (1 mL) was added Pd(PPh$_3$)$_4$ (21 mg, 0.018 mmol). The reaction mixture was stirred at 120° C. for 15 min under microwave irradiation, then more 5-(4,4,5,5-tetramethyl-1,3,2-dioxaborolan-2-yl)indolin-2-one (338 mg, 1.3 mmol) was added and the mixture was stirred at 120° C. for 15 min under microwave irradiation. The mixture was diluted with water and extracted with EtOAc. The combined organics were separated, dried (Na$_2$SO$_4$), filtered and concentrated in vacuo. Purification (FCC, SiO$_2$; 7M solution of ammonia in methanol in DCM 0/100 to 5/95)) afforded the title compound which was further purified (RP HPLC, Stationary phase: C18 XBridge 30×100 mm 5 um), Mobile phase: Gradient from 80% 0.1% NH$_4$CO$_3$H/NH$_4$OH pH 9 solution in water, 20% CH₃CN to 0% 0.1% NH₄CO₃H/NH₄OH pH 9 solution in water, 100% CH₃CN) to give the title compound (62 mg, 37%). MS (ESI): mass calcd. for C$_{24}$H$_{27}$N$_7$O$_3$, 461.2; m/z found, MH+=462.2 [M+H]⁺. ¹H NMR (500 MHz, DMSO-d$_6$) δ ppm 1.03-1.20 (m, 1H) 1.21-1.48 (m, 4H) 1.52-1.64 (m, 1H) 1.65-1.90 (m, 4H) 3.64-3.73 (m, 1H) 3.75-3.95 (m, 4H) 4.22 (br s, 4H) 6.96-7.23 (m, 3H) 7.36 (d, J=4.6 Hz, 1H) 7.45 (d, J=4.6 Hz, 1H) 7.82 (br d, J=8.4 Hz, 1H) 10.81 (br s, 2H).

Example 215: 5-[8-(4-Hydroxy-1-piperidyl)-2-(4-pyridyl)imidazo[1,2-a]pyrazin-3-yl]indolin-2-one

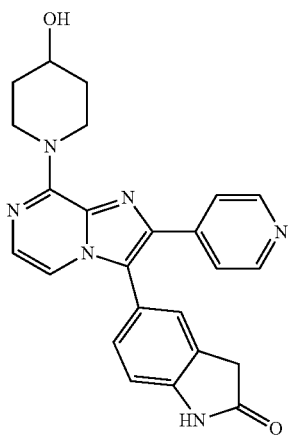 [SMILES: O=C1Cc2cc(-c3c(-c4ccncc4)nc4c(N5CCC(O)CC5)nccn34)ccc2N1]

Step A: 3-(Cyclohexyloxy)pyrazin-2-amine

To a stirred solution of cyclohexanol (14.8 mL, 140 mmol) in THF (126 mL) was added NaH (60% dispersion in mineral oil, 5.62 g, 140 mmol). The resulting mixture was stirred at 23° C. for 30 minutes. To the reaction mixture was added 3-chloropyrazin-2-amine (14 g, 108 mmol) and the resulting mixture was stirred at 130° C. for 16 h. The reaction mixture was filtered and washed with DCM. The filtrate was concentrated under reduced pressure and washed with water. The resulting suspension was filtered to afford the title compound as a yellow solid (16.8 g, 80.4%). MS (ESI): mass calcd. for C$_{10}$H$_{15}$N$_3$O, 193.2; m/z found, MH+=194.1 [M+H]⁺.

Step B: 8-(Cyclohexyloxy)imidazo[1,2-a]pyrazin-2-ol

To a solution of 3-(cyclohexyloxy)pyrazin-2-amine (13.2 g, 68.3 mmol) in DME (150 mL) was added ethyl bromoacetate (15.1 mL, 137 mmol). The reaction mixture was microwaved at 120° C. for 40 min. The reaction mixture was cooled to 23° C., and the resulting precipitate was filtered, washed with ether and dried in vacuo. The crude solid was suspended in MeOH (150 mL) was added triethylamine (14.3 mL, 102 mmol). The reaction mixture was microwaved at 100° C. for 15 minutes. The reaction mixture was concentrated in vacuo, diluted with water and extracted with DCM. The organic layer was separated, dried (Na$_2$SO$_4$), filtered and concentrated in vacuo to yield the title compound as a grey solid (9.0 g, 56%). MS (ESI): mass calcd. for C$_{12}$H$_{15}$N$_3$O$_2$, 233.2; m/z found, MH+=234.1 [M+H]⁺.

Step C: 8-(Cyclohexyloxy)imidazo[1,2-a]pyrazin-2-yl trifluoromethanesulfonate

To a solution of 8-(cyclohexyloxy)imidazo[1,2-a]pyrazin-2-ol (9.0 g, 38.6 mmol) and K$_2$CO$_3$ (16.0 g, 116 mmol) in THF (157 mL) was added N-phenyl-bis(trifluoromethanesulfonimide (15.2 g, 42.4 mmol). The reaction mixture was heated in the microwave at 120° C. for 10 minutes. The reaction mixture was filtered and concentrated in vacuo. Purification (FCC, SiO$_2$; EtOAc in heptane 0/100 to 50/50) afforded the title compound as a brown solid (1.4 g, 9.9%). MS (ESI): mass calcd. for C$_{13}$H$_{14}$F$_3$N$_3$O$_4$S, 365.3; m/z found, MH+=366.1 [M+H]⁺.

Step D: 8-(Cyclohexyloxy)-2-(pyridin-4-yl)imidazo[1,2-a]pyrazine

To a solution of 8-(cyclohexyloxy)imidazo[1,2-a]pyrazin-2-yl trifluoromethanesulfonate (1.35 g, 3.70 mmol), pyridin-4-ylboronic acid (681 mg, 5.54 mmol), K$_2$CO$_3$ (1.28 g, 9.24 mmol) in 1,4-dioxane (57 mL) and water (27 mL), was added PdCl$_2$(dppf) (270 mg, 370 mmol). The reaction mixture was heated at 80° C. for 5 h. The reaction mixture was cooled, and extracted with AcOH and water. The organics were separated, dried, filtered and concentrated in vacuo. Purification (FCC, SiO$_2$; 10% 2M NH$_3$MeOH in DCM/DCM 0/100 to 2/98) afforded the title compound as a brown solid (1.02 g, 69.4%). MS (ESI): mass calcd. for C$_{17}$H$_{18}$N$_4$O, 294.4; m/z found, MH+=295.2 [M+H]⁺.

Step E: 3-Bromo-8-(cyclohexyloxy)-2-(pyridin-4-yl)imidazo[1,2-a]pyrazine

To a solution of 8-(cyclohexyloxy)-2-(pyridin-4-yl)imidazo[1,2-a]pyrazine (1.02 g, 2.56 mmol) in DCM (12 mL) at 0° C. was added NBS (456 mg, 2.56 mmol). The reaction mixture was stirred at 0° C. for 1 h. The mixture was concentrated in vacuo, re-dissolved in EtOAc and basified with saturated NaHCO$_3$. The organic layer was separated, dried (Na$_2$SO$_4$), filtered and concentrated in vacuo. Purification (FCC, SiO$_2$; 7M NH$_3$ in MeOH/DCM 0/100 to 4/96) afforded the title compound as a black solid (610 mg, 49.1%). MS (ESI): mass calcd. for C$_{17}$H$_{17}$BrN$_4$O, 373.3; m/z found, MH+=375.1 [M+H]⁺.

Step F: 3-Bromo-2-(pyridin-4-yl)imidazo[1,2-a]pyrazin-8-ol

To a solution of 3-bromo-8-(cyclohexyloxy)-2-(pyridin-4-yl)imidazo[1,2-a]pyrazine (605 mg, 1.62 mmol) in MeOH (6.6 mL) was added HCl (6M in iPrOH, 0.81 mL, 4.9 mmol). The reaction mixture was stirred at 23° C. for 24 h. The reaction mixture was filtered, and the precipitate was washed with heptane, and dried in vacuo to afford the title compound as a brown solid (496 mg, 81.3%). ¹H NMR (500 MHz, DMSO-d$_6$) δ ppm 7.11 (t, J=5.78 Hz, 1H) 7.37-7.49 (m, 1H) 8.25 (d, J=6.94 Hz, 2H) 8.92-8.98 (m, 2H) 11.68 (d, J=5.20 Hz, 1H).

Step G: 1-(3-Bromo-2-(pyridin-4-yl)imidazo[1,2-a]pyrazin-8-yl(piperidin-4-ol

To a solution of 3-bromo-2-(pyridin-4-yl)imidazo[1,2-a]pyrazin-8-ol (100 mg, 0.247 mmol) and BOP (142 mg, 0.321 mmol) in MeCN (1.2 mL) were added DBU (0.11 mL, 0.742 mmol) and 4-hydroxypiperidine (30 mg, 0.30 mmol). The reaction mixture was stirred at 23° C. for 24 h. The mixture was extracted with EtOAc and water. The organic layer was separated, dried (MgSO$_4$), filtered and concentrated in vacuo. EtOAc and heptane were added to the crude product and the resulting precipitate was removed by filtration. The organic layer was concentrated once more in vacuo and the solid was triturated with Et$_2$O several times then dried in vacuo to afford the title compound as a white solid (80 mg, 75%). MS (ESI): mass calcd. for C$_{16}$H$_{16}$BrN$_5$O, 374.2; m/z found, MH+=376.1 [M+H]$^+$.

Step H: 5-[8-(4-Hydroxy-1-piperidyl)-2-(4-pyridyl)imidazo[1,2-a]pyrazin-3-yl]indolin-2-one To a solution of 1-(3-bromo-2-(pyridin-4-yl)imidazo[1,2-a]pyrazin-8-yl)piperidin-4-ol (85 mg, 0.28 mmol), 5(4,4,5,5-tetramethyl-1,3,2-dioxaborolan-2-yl)indolin-2-one (58.9 mg, 0.227 mmol), K$_3$PO$_4$ (121 mg, 0.568 mmol) in 1,4-dioxane (3.5 mL) and water (1.6 mL) was added PdCl$_2$(dtbpf) (14.8 mg, 22.7 mmol). The reaction mixture was stirred at 80° C. for 1 h. The solvents were removed under reduced pressure and the residue was extracted with EtOAc and water. The organic layer was separated, dried (MgSO$_4$), filtered and concentrated in vacuo. Purification (RP HPLC (Stationary phase: C18 XBridge 30×100 mm 5 um, Mobile phase: Gradient from 81% 10 mM NH$_4$CO$_3$H/NH$_4$OH pH 9 solution in water, 21% CH$_3$CN to 64% 10 mM NH$_4$CO$_3$H/NH$_4$OH pH 9 solution in water, 36% CH$_3$CN) afforded the title compound as a white solid (16 mg, 17%). MS (ESI): mass calcd. for C$_{24}$H$_{22}$N$_6$O$_2$, 426.2; m/z found, MH+=427.2 [M+H]$^+$. $^1$H NMR (400 MHz, DMSO-d$_6$) δ ppm 1.34-1.60 (m, 2H) 1.81-2.00 (m, 2H) 3.58 (s, 2H) 3.62-3.72 (m, 2H) 3.74-3.88 (m, 1H) 4.77 (d, J=4.4 Hz, 1H) 4.94 (br s, 2H) 7.03 (d, J=8.1 Hz, 1H) 7.21-7.31 (m, 2H) 7.32-7.40 (m, 2H) 7.46-7.59 (m, 2H) 8.43-8.55 (m, 2H) 10.68 (s, 1H).

Example 216: 6-[2-Cyclopropyl-6-(trifluoromethyl)imidazo[1,2-a]pyrazin-3-yl]-3H-1,3-benzothiazol-2-one

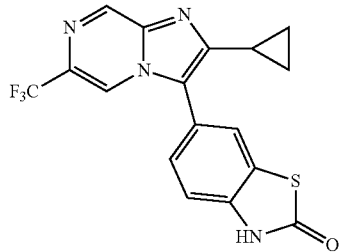 [SMILES: O=c1[nH]c2ccc(-c3c(C4CC4)nc4cnc(C(F)(F)F)cn34)cc2s1]

Step A. 3-Bromo-2-cyclopropyl-6-(trifluoromethyl)imidazo[1,2-a]pyrazine

The title compound was prepared in a manner analogous to Example 1. MS (ESI): mass calcd. for C$_{10}$H$_7$BrF$_3$N$_3$, 306.08; m/z found, MH+=306.0 [M+H]$^+$.

Step B: 6-(2-Cyclopropyl-6-(trifluoromethyl)imidazo[1,2-a]pyrazin-3-yl)-3-((2-(trimethylsilyl)ethoxy)methyl)benzo[d]thiazol-2(3H)-one To a solution of 3-bromo-2-cyclopropyl-6-(trifluoromethyl)imidazo[1,2-a]pyrazine (product from Step A, 120 mg, 0.392 mmol) and 6-(4,4,5,5-tetramethyl-1,3,2-dioxaborolan-2-yl)-3-((2-(trimethylsilyl)ethoxy)methyl)benzo[d]thiazol-2(3H)-one (Intermediate 30), 176 mg, 0.431 mmol) in dioxane (4 mL) and saturated Na$_2$CO$_3$ (1 mL) was added Pd(PPh$_3$)$_4$ (22.6 mg, 0.020 mmol) under N$_2$. The mixture was stirred at 90° C. for 4 h then mixture was cooled, diluted with water and extracted with EtOAc. The organic layer was separated, dried (MgSO$_4$), filtered and concentrated in vacuo. Purification (FCC, SiO$_2$; EtOAc/heptane 0/100 to 20/80) afforded the title compound as a white powder (144 mg, 72.5%). MS (ESI): mass calcd. for C$_{23}$H$_{25}$N$_4$O$_2$SSi, 506.6; m/z found, MH+=507.1 [M+H]$^+$. $^1$H NMR (500 MHz, CDCl$_3$) δ ppm 9.02 (s, 1H), 8.34 (s, 1H), 7.62 (t, J=1.0 Hz, 1H), 7.50 (s, 2H), 5.45 (s, 2H), 3.69 (dd, J=7.5, 8.7 Hz, 2H), 2.11-1.97 (m, 1H), 1.24-1.17 (m, 2H), 1.10-1.02 (m, 2H), 1.01-0.94 (m, 2H), 0.00 (s, 9H).

Step C: 6-[2-Cyclopropyl-6-(trifluoromethyl)imidazo[1,2-a]pyrazin-3-yl]-3H-1,3-benzothiazol-2-one A solution of 6-(2-cyclopropyl-6-(trifluoromethyl)imidazo[1,2-a]pyrazin-3-yl)-3-((2-(trimethylsilyl)ethoxy)methyl)benzo[d]thiazol-2(3H)-one (130 mg, 0.257 mmol) in HCl (6M in iPrOH, 0.855 mL) and iPrOH (10 mL) was stirred at 100° C. for 8 h. The mixture was cooled down, quenched with saturated NaHCO$_3$ solution (5 mL) and extracted with EtOAc (2×25 mL). The organic layer was washed with brine, dried (MgSO$_4$), filtered and concentrated in vacuo. Purification (FCC, SiO$_2$; EtOAc/heptane 0/100 to 50/50) afforded the title compound as a white solid (58 mg, 60%). MS (ESI): mass calcd. for C$_{17}$H$_{11}$F$_3$N$_4$OS, 376.1; m/z found, (M−H)−=375.0530 (0.2 mDa) [M+H]$^+$. $^1$H NMR (400 MHz, DMSO-d$_6$) δ=12.15 (s, 1H), 9.08 (d, J=0.7 Hz, 1H), 8.64 (s, 1H), 7.96 (d, J=1.8 Hz, 1H), 7.59 (dd, J=1.8, 8.1 Hz, 1H), 7.35 (d, J=8.3 Hz, 1H), 2.17-2.02 (m, 1H), 1.13-0.96 (m, 4H).

Example 217: 5-[2-Benzoyl-8-(methylamino)imidazo[1,2-a]pyrazin-3-yl]indolin-2-one

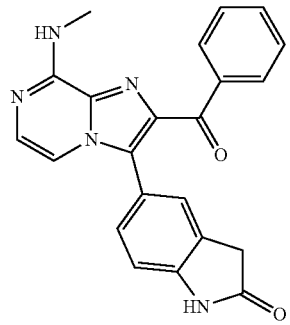 [SMILES: CNc1nccn2c(-c3ccc4c(c3)CC(=O)N4)c(C(=O)c3ccccc3)nc12]

Step A: Ethyl 8-hydroxyimidazo[1,2-a]pyrazine-2-carboxylate

A solution of ethyl 8-chloroimidazo[1,2-a]pyrazine-2-carboxylate (Intermediate 43, product from Step A, 20 g, 89 mmol) in EtOH (367 mL) was stirred at 90° C. for 2 h. The solid was filtered and washed with EtOH to afford the title compound as a white solid (8.5 g, 46%). MS (ESI): mass calcd. for C$_9$H$_9$N$_3$O$_3$ 207.1; m/z found, 208 [M+H]$^+$.

Step B: Ethyl 8-(methylthio)imidazo[1,2-a]pyrazine-2-carboxylate

To a suspension of ethyl 8-hydroxyimidazo[1,2-a]pyrazine-2-carboxylate (3.00 g, 14.5 mmol) and BOP (8.33 g, 18.8 mmol) in MeCN (72 mL) were added DBU (3.24 mL, 21.7 mmol) and MeSNa (1.22 g, 17.4 mmol). The reaction mixture was stirred at 23° C. for 1 h. The precipitate was filtered off and washed with MeCN (20 mL). The solvents were concentrated in vacuo and the residue was stirred in EtOAc. The precipitate was filtered and dried in vacuo to afford a white solid as the title compound. The mother liquor was concentrated in vacuo and the residue was purified (FCC, SiO$_2$; EtOAc/heptane 0/100 to 50/50) to afford the title compound as a white powder, both portions were combined to give the title compound (2.4 g, 70%). MS (ESI): mass calcd. for $C_{10}H_{11}N_3O_2S$, 237.1; m/z found, 238 [M+H]$^+$.

Step C: 8-(Methylthio)imidazo[1,2-a]pyrazine-2-carboxylic acid

To a suspension of ethyl 8-(methylthio)imidazo[1,2-a]pyrazine-2-carboxylate (2.4 g, 10 mmol) in THF (15 mL), MeOH (15 mL) and water (3 mL) was added LiOH (363 mg, 15.2 mmol). The reaction mixture was stirred at 23° C. for 1.5 h. Then the mixture was concentrated in vacuo and the residue was dissolved in water (5 mL). The resulting solution was acidified to pH 1 with 3M HCl (aqueous) to form a white solid. The solid was filtered, washed with water (10 mL) and ether (20 mL) then dried in vacuo to afford the title compound (1.8 g, 86%). $^1$H NMR (500 MHz, DMSO-d$_6$) δ 2.1 (s, 3H), 7.82 (d, J=4.62 Hz, 1H), 8.32 (d, J=4.62 Hz, 1H), 8.56 (s, 1H), 13.16 (br s, 1H).

Step D: 8-(Methylthio)imidazo[1,2-a]pyrazine-2-carbonyl chloride

To a suspension of 8-(methylthio)imidazo[1,2-a]pyrazine-2-carboxylic acid (1.79 g, 8.56 mmol) in DCM (10 mL) was added SOCl$_2$ (0.87 mL, 12 mmol). The reaction mixture was stirred at 45° C. for 2 h. The reaction mixture was concentrated in vacuo to afford a white solid which was used in the next step without further purification.

Step E: N-Methoxy-N-methyl-8-(methylthio)imidazo[1,2-a]pyrazine-2-carboxamide

To a solution of 8-(methylthio)imidazo[1,2-a]pyrazine-2-carbonyl chloride in DCM (10 mL) was added portion wise N,O-dimethylhydroxylamine HCl salt (1.0 g, 10 mmol) and DIPEA (4.4 mL, 26 mmol). The reaction mixture was stirred for 15 minutes. The reaction mixture was diluted with DCM (10 mL), washed with water and brine. The organic layer was dried (Na$_2$SO$_4$), filtered and concentrated in vacuo. Purification (FCC, SiO$_2$; 7M NH$_3$ in MeOH/DCM 0/100 to 3/97) afforded the title compound as a white solid (1.3 g, 61%). MS (ESI): mass calcd. for $C_{10}H_{12}N_4O_2S$, 252.0; m/z found, 253 [M+H]$^+$.

Step F: (8-(Methylthio)imidazo[1,2-a]pyrazin-2-yl)(phenyl)methanone

To a solution of N-methoxy-N-methyl-8-(methylthio)imidazo[1,2-a]pyrazine-2-carboxamide (1.2 g, 4.8 mmol) in THF (80 mL) at −78° C. was added phenylmagnesium bromide (3M, 5.6 mL, 17 mmol) slowly. The mixture was continued to stir at −78° C. for 1 h, then warmed to −40° C. and stirred for 4 h. Another portion of phenylmagnesium bromide (3M, 4.0 mL, 12 mmol) was added slowly and the mixture was stirred at −40° C. for another 3 h. The resulting mixture was quenched with aq. NH$_4$Cl (10 mL) and concentrated in vacuo. The residue was extracted with DCM/water. The organic layer was washed with brine, dried (MgSO$_4$), filtered and concentrated in vacuo. Purification (FCC, SiO$_2$; 7M NH$_3$ in MeOH/DCM 0/100 to 1/99) afforded the title compound a white solid (720 mg, 56.2%). MS (ESI): mass calcd. for $C_{14}H_{11}N_3OS$ 269; m/z found, 270 [M+H]$^+$.

Step G: (3-Bromo-8-(methylthio)imidazo[1,2-a]pyrazin-2-yl)(phenyl)methanone

To a solution of (8-(methylthio)imidazo[1,2-a]pyrazin-2-yl)(phenyl)methanone (1.0 g, 3.7 mmol) in DCM (28 mL) was added NBS (661 mg, 3.71 mmol) at 23° C. The reaction mixture was stirred for 6 h. The reaction mixture was diluted with water and the organic layer was washed with brine, dried (MgSO$_4$), filtered and concentrated in vacuo to afford the title compound as a cream solid (0.90 g, 69%). MS (ESI): mass calcd. for $C_{14}H_{10}BrN_3OS$ 347; m/z found, 348 [M+H]$^+$.

Step H: (3-Bromo-8-(methylsulfonyl)imidazo[1,2-a]pyrazin-2-yl)(phenyl)methanone

To a solution of (3-bromo-8-(methylthio)imidazo[1,2-a]pyrazin-2-yl)(phenyl)methanone (4.1 g, 12 mmol) in DCM at 0° C. was added mCPBA (4.1 g, 24 mmol). The reaction mixture was stirred at 0° C. for 3 h. To the reaction mixture was added mCPBA (4.1 g, 24 mmol) was added portion wise (1 g per hour). To the reaction mixture was added water followed by aqueous Na$_2$S$_2$O$_3$. The organic layer was washed with brine, dried (MgSO$_4$), filtered and concentrated in vacuo to afford the title compound as a yellow solid (4.45 g, 83.1%). MS (ESI): mass calcd. for $C_{14}H_{10}BrN_3O_3S$, 379; m/z found, 380 [M+H]$^+$.

Step I: (3-Bromo-8-(methylamino)imidazo[1,2-a]pyrazin-2-yl)(phenyl)methanone

A solution of (3-bromo-8-(methylsulfonyl)imidazo[1,2-a]pyrazin-2-yl)(phenyl)methanone (300 mg, 0.789 mmol) and methylamine (2M in THF, 0.79 mL, 1.6 mmol) in THF (3 mL) was stirred at 100° C. for 5 h. The resulting solution was concentrated in vacuo. Purification (FCC, SiO$_2$; EtOAc/heptane 0/100 to 60/40) afforded the title compound as a colorless oil (195 mg, 74.6%). MS (ESI): mass calcd. for $C_{14}H_{11}N_4O$, 330; m/z found, 331 [M+H]$^+$.

Step J: 5-[2-Benzoyl-8-(methylamino)imidazo[1,2-a]pyrazin-3-yl]indolin-2-one

To a stirred solution of (3-bromo-8-(methylamino)imidazo[1,2-a]pyrazin-2-yl)(phenyl)methanone (100 mg, 0.302 mmol), 5-(4,4,5,5-tetramethyl-1,3,2-dioxaborolan-2-yl)indolin-2-one (156 mg, 0.604 mmol) in dioxane (2 mL) and saturated Na$_2$CO$_3$ (0.5 mL) was added Pd(PPh$_3$)$_4$ (17 mg, 0.015 mmol) under N$_2$. The mixture was microwaved at 120° C. for 20 minutes then mixture was cooled, diluted with water, and extracted with EtOAc. The organic layer was separated, dried (Na₂SO₄), filtered and concentrated in vacuo. The residue was triturated with MeOH, filtered and the precipitate was treated with HCl in ether to afford the title compound as an HCl salt (48 mg, 38%). MS (ESI): mass calcd. for C$_{22}$H$_{17}$N$_5$O$_2$ 383.1; m/z found 384.2 [M+H]$^+$. $^1$H NMR (400 MHz, DMSO-d$_6$) δ 3.11 (br d, J=4.2 Hz, 3H) 3.55 (br s, 2H) 6.97 (d, J=8.1 Hz, 1H) 7.32 (d, J=5.5 Hz, 1H) 7.35 (br d, J=8.1 Hz, 1H) 7.38 (s, 1H) 7.48-7.55 (m, 3H) 7.61-7.68 (m, 1H) 8.00-8.11 (m, 2H) 9.41 (br s, 1H) 10.66 (s, 1H).

Example 218: 5-[2-Phenyl-6-(trifluoromethyl)imidazo[1,2-a]pyrazin-3-yl]indolin-2-one

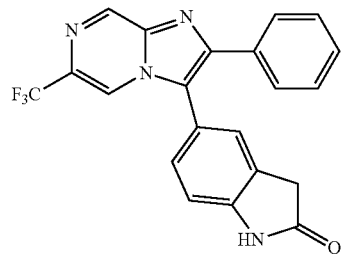 [SMILES: O=C1Cc2cc(-c3c(-c4ccccc4)nc4cnc(C(F)(F)F)cn34)ccc2N1]

The title compound was prepared in a manner analogous to Example 1 omitting steps C, E and F. MS (ESI): mass calcd. for C$_{21}$H$_{13}$F$_3$N$_4$O 394.1; m/z found, 395.1 [M+H]$^+$. $^1$H NMR (400 MHz, DMSO-d$_6$) δ10.68 (s, 1H), 9.28 (s, 1H), 8.41 (s, 1H), 7.69 (dd, J=1.6, 7.9 Hz, 2H), 7.44 (s, 1H), 7.42-7.29 (m, 4H), 7.04 (d, J=7.9 Hz, 1H), 3.59 (s, 2H).

Example 219: 5-[2-Cyclopropyl-6-(trifluoromethyl)imidazo[1,2-a]pyrazin-3-yl]indolin-2-one

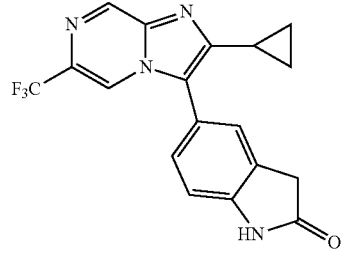 [SMILES: O=C1Cc2cc(-c3c(C4CC4)nc4cnc(C(F)(F)F)cn34)ccc2N1]

The title compound was prepared in a manner analogous to Example 1 omitting steps C, E and F. MS (ESI): mass calcd. for C$_{18}$H$_{13}$F$_3$N$_4$O 358.1; m/z found, 359.1 [M+H]$^+$. $^1$H NMR (500 MHz, DMSO-d$_6$) δ 10.70 (s, 1H), 9.13 (s, 1H), 8.60 (s, 1H), 7.80-7.38 (m, 2H), 7.13 (d, J=7.8 Hz, 1H), 3.67 (s, 2H), 2.25-2.07 (m, 1H), 1.27-0.86 (m, 4H).

Example 220: 5-[2-tert-Butyl-8-(4-oxo-1-piperidyl)imidazo[1,2-a]pyrazin-3-yl]indolin-2-one

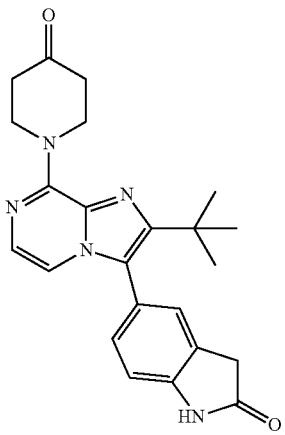 [SMILES: CC(C)(C)c1nc2c(N3CCC(=O)CC3)nccn2c1-c1ccc2c(c1)CC(=O)N2]

The title compound was prepared in a manner analogous to Example 109. MS (ESI): mass calcd. for C$_{23}$H$_{25}$N$_5$O$_2$ 403.2; m/z found 404.2 [M+H]$^+$. $^1$H NMR (500 MHz, DMSO-d$_6$) δ 1.20-1.28 (m, 9H) 2.59-2.69 (m, 4H) 3.60 (s, 2H) 4.53-4.66 (m, 4H) 7.00-7.06 (m, 1H) 7.07-7.12 (m, 1H) 7.17-7.30 (m, 3H) 10.52-10.90 (m, 1H).

Example 221: 8-Morpholino-3-(2-oxo-1,3-dihydrobenzimidazol-5-yl)-N-(2-pyridyl)imidazo[1,2-a]pyrazine-2-carboxamide

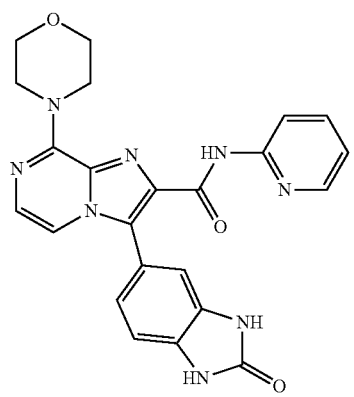 [SMILES: O=C(Nc1ccccn1)c1nc2c(N3CCOCC3)nccn2c1-c1ccc2[nH]c(=O)[nH]c2c1]

The title compound was prepared in a manner analogous to Example 137. MS (ESI): mass calcd. for C$_{23}$H$_{20}$N$_8$O$_3$ 456.2; m/z found 457.3 [M+H]$^+$. $^1$H NMR (500 MHz, DMSO-d$_6$) δ 3.68-3.95 (m, 4H) 4.27 (br s, 4H) 7.01-7.29 (m, 4H) 7.42 (d, J=4.6 Hz, 1H) 7.49 (d, J=4.6 Hz, 1H) 7.71-7.94 (m, 1H) 8.11 (br d, J=8.4 Hz, 1H) 8.27-8.45 (m, 1H) 9.95 (s, 1H) 10.81 (br s, 1H) 10.88 (br s, 1H).

Example 222: 5-[2-Phenyl-5-(trifluoromethyl)pyrazolo[1,5-c]pyrimidin-3-yl]indolin-2-one

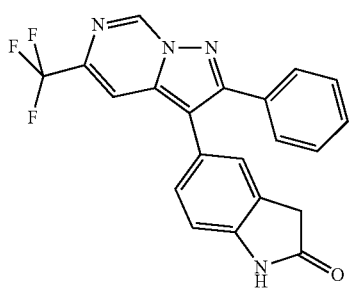 [SMILES: O=C1Cc2cc(-c3c(-c4ccccc4)nn4cnc(C(F)(F)F)cc34)ccc2N1]

The title compound was prepared in a manner analogous to Example 164 using 3-bromo-2-phenyl-5-(trifluoromethyl)pyrazolo[1,5-c]pyrimidine (Intermediate 17). MS (ESI): mass calcd. for $C_{21}H_{13}F_3N_4O$ 394.1; m/z found, 395 [M+H]$^+$. $^1$H NMR (300 MHz, DMSO-d$_6$) δ 10.44 (s, 1H), 9.70 (s, 1H), 7.87 (s, 1H), 7.63-7.46 (m, 2H), 7.37 (d, J=2.4 Hz, 3H), 7.21 (s, 1H), 7.06 (d, J=7.9 Hz, 1H), 6.82 (d, J=8.0 Hz, 1H), 3.45 (s, 2H).

Example 223: 6-[2-Phenyl-5-(trifluoromethyl)pyrazolo[1,5-c]pyrimidin-3-yl]-3H-1,3-benzoxazol-2-one

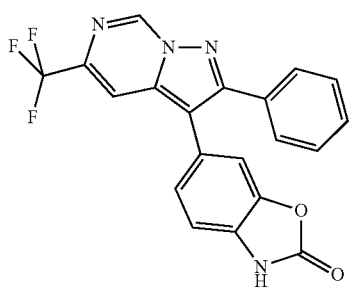 [SMILES: O=c1[nH]c2ccc(-c3c(-c4ccccc4)nn4cnc(C(F)(F)F)cc34)cc2o1]

The title compound was prepared in a manner analogous to Example 164 using 3-bromo-2-phenyl-5-(trifluoromethyl)pyrazolo[1,5-c]pyrimidine (Intermediate 17). MS (ESI): mass calcd. for $C_{20}H_{11}F_3N_4O_2$ 396.1; m/z found, 397 [M+H]$^+$. $^1$H NMR (300 MHz, DMSO-d$_6$) δ 11.72 (s, 1H), 9.73 (s, 1H), 7.95 (s, 1H), 7.59-7.47 (m, 2H), 7.44-7.32 (m, 3H), 7.29 (s, 1H), 7.10 (d, J=8.0 Hz, 1H), 7.05 (d, J=1.2 Hz, 1H).

Example 224: 6-[2-phenyl-5-(trifluoromethyl)pyrazolo[1,5-c]pyrimidin-3-yl]-3H-1,3-benzothiazol-2-one

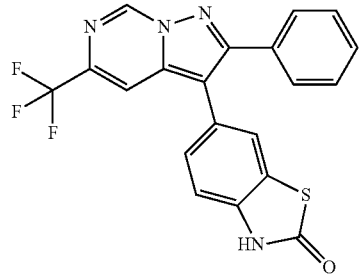 [SMILES: O=c1[nH]c2ccc(-c3c(-c4ccccc4)nn4cnc(C(F)(F)F)cc34)cc2s1]

The title compound was prepared in a manner analogous to Example 164 using 3-bromo-2-phenyl-5-(trifluoromethyl)pyrazolo[1,5-c]pyrimidine (Intermediate 17). MS (ESI): mass calcd. for $C_{20}H_{11}F_3N_4OS$ 412.1; m/z found, 413 [M+H]$^+$. $^1$H NMR (300 MHz, DMSO-d$_6$) δ 11.95 (s, 1H), 9.73 (s, 1H), 7.98 (s, 1H), 7.63 (s, 1H), 7.51 (d, J=3.6 Hz, 2H), 7.42-7.32 (m, 3H), 7.12 (d, J=1.8 Hz, 2H).

Example 225: 5-[2-tert-Butyl-5-(trifluoromethyl)pyrazolo[1,5-c]pyrimidin-3-yl]indolin-2-one

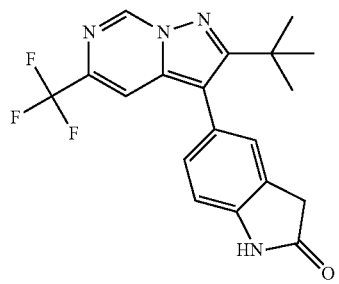 [SMILES: CC(C)(C)c1nn2cnc(C(F)(F)F)cc2c1-c1ccc2c(c1)CC(=O)N2]

The title compound was prepared in a manner analogous to Example 164 using 3-bromo-2-(tert-butyl)-5-(trifluoromethyl)pyrazolo[1,5-c]pyrimidine (Intermediate 11). MS (ESI): mass calcd. for $C_{19}H_{17}F_3N_4O$ 374.1; m/z found, 375 [M+H]$^+$. $^1$H NMR (300 MHz, CDCl$_3$) δ 9.22 (s, 1H), 8.01 (s, 1H), 7.37 (s, 1H), 7.20-7.10 (m, 2H), 6.96 (d, J=8.4 Hz, 1H), 3.63 (s, 2H), 1.34 (s, 9H).

Example 226: 5-[2-Cyclobutyl-5-(trifluoromethyl)pyrazolo[1,5-c]pyrimidin-3-yl]indolin-2-one

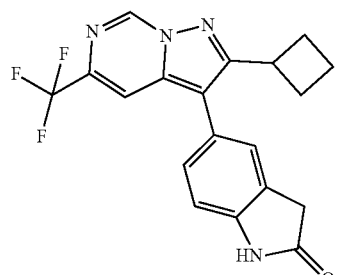

The title compound was prepared in a manner analogous to Example 164 using 3-bromo-2-cyclobutyl-5-(trifluoromethyl)pyrazolo[1,5-c]pyrimidine (Intermediate 12). MS (ESI): mass calcd. for $C_{19}H_{15}F_3N_4O$ 372.1; m/z found, 373 [M+H]$^+$. $^1$H NMR (300 MHz, CDCl$_3$) δ 9.29 (s, 1H), 8.12 (s, 1H), 7.73 (s, 1H), 7.22 (d, J=7.5 Hz, 2H), 7.03 (d, J=8.4 Hz, 1H), 3.82 (s, 1H), 2.65-2.47 (m, 2H), 2.38 (d, J=8.5 Hz, 2H), 2.28-1.90 (m, 2H).

Example 227: 5-[2-Isopropyl-5-(trifluoromethyl)pyrazolo[1,5-c]pyrimidin-3-yl]indolin-2-one

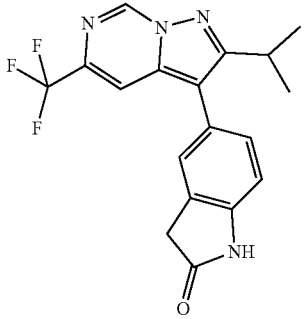 [SMILES: CC(C)c1nn2cnc(C(F)(F)F)cc2c1-c1ccc2c(c1)CC(=O)N2]

The title compound was prepared in a manner analogous to Example 164 using 3-bromo-2-isopropyl-5-(trifluoromethyl)pyrazolo[1,5-c]pyrimidine (Intermediate 13). MS (ESI): mass calcd. for $C_{18}H_{15}F_3N_4O$ 360.1; m/z found, 361 [M+H]$^+$. $^1$H NMR (300 MHz, CDCl$_3$) δ 9.27 (s, 1H), 8.04 (s, 1H), 7.69 (s, 1H), 7.27 (s, 2H), 7.05 (s, 1H), 3.67 (s, 2H), 3.34 (dq, J=13.9, 6.9 Hz, 1H), 1.38 (d, J=6.9 Hz, 6H).

Example 228: 5-[2-Cyclopropyl-5-(trifluoromethyl)pyrazolo[1,5-c]pyrimidin-3-yl]indolin-2-one

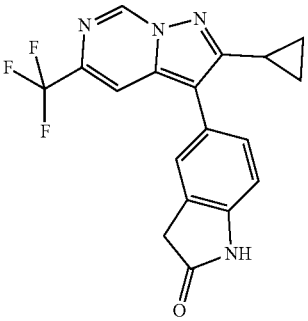 [SMILES: O=C1Cc2cc(-c3c(C4CC4)nn4cnc(C(F)(F)F)cc34)ccc2N1]

The title compound was prepared in a manner analogous to Example 164 using 3-bromo-2-cyclopropyl-5-(trifluoromethyl)pyrazolo[1,5-c]pyrimidine (Intermediate 15). MS (ESI). mass calcd. for $C_{18}H_{13}F_3N_4O$ 358.1; m/z found, 359 [M+H]$^+$. $^1$H NMR (300 MHz, DMSO-d$_6$) δ 10.44 (s, 1H), 9.49 (s, 1H), 7.85 (s, 1H), 7.55-7.20 (m, 2H), 6.92 (d, J=7.9 Hz, 1H), 3.51 (s, 2H), 2.30-1.97 (m, 1H), 1.22-0.85 (m, 4H).

Example 229: 6-[2-Cyclobutyl-5-(trifluoromethyl)pyrazolo[1,5-c]pyrimidin-3-yl]-3H-1,3-benzothiazol-2-one

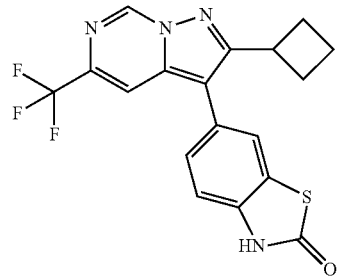 [SMILES: O=c1[nH]c2ccc(-c3c(C4CCC4)nn4cnc(C(F)(F)F)cc34)cc2s1]

The title compound was prepared in a manner analogous to Example 164 using 3-bromo-2-cyclobutyl-5-(trifluoromethyl)pyrazolo[1,5-c]pyrimidine (Intermediate 12). MS (ESI): mass calcd. for $C_{18}H_{13}F_3N_4OS$ 390.1; m/z found, 391 [M+H]$^+$. $^1$H NMR (300 MHz, DMSO-d$_6$) δ 11.99 (s, 1H), 9.71 (s, 1H), 8.03 (s, 1H), 7.71 (s, 1H), 7.34 (d, J=6.9 Hz, 1H), 7.26 (s, 1H), 4.00-3.76 (m, 1H), 2.38 (d, J=9.5 Hz, 3H), 2.19-1.78 (m, 2H).

Example 230: 6-[2-Cyclopropyl-5-(trifluoromethyl)pyrazolo[1,5-c]pyrimidin-3-yl]-3H-1,3-benzothiazol-2-one

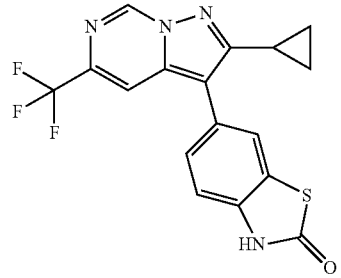 [SMILES: O=c1[nH]c2ccc(-c3c(C4CC4)nn4cnc(C(F)(F)F)cc34)cc2s1]

The title compound was prepared in a manner analogous to Example 164 using 3-bromo-2-cyclopropyl-5-(trifluoromethyl)pyrazolo[1,5-c]pyrimidine (Intermediate 15). MS (ESI): mass calcd. for $C_{17}H_{11}F_3N_4OS$ 376.1; m/z found, 377 [M+H]$^+$. $^1$H NMR (300 MHz, DMSO-d$_6$) δ 11.94 (s, 1H), 9.52 (s, 1H), 7.95 (s, 1H), 7.79 (d, J=1.4 Hz, 1H), 7.46 (dd, J=8.2, 1.6 Hz, 1H), 7.22 (s, 1H), 2.21-2.00 (m, 1H), 1.14-0.92 (m, 4H).

Example 231: 6-[2-Isopropyl-5-(trifluoromethyl)pyrazolo[1,5-c]pyrimidin-3-yl]-3H-1,3-benzothiazol-2-one

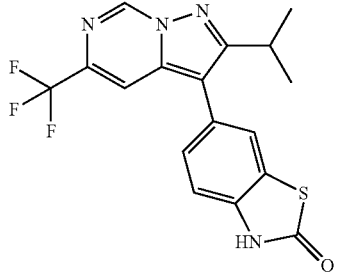

The title compound was prepared in a manner analogous to Example 164 using 3-bromo-2-isopropyl-5-(trifluoromethyl)pyrazolo[1,5-c]pyrimidine (Intermediate 13). MS (ESI): mass calcd. for $C_{17}H_{13}F_3N_4OS$ 378.1; m/z found, 379 [M+H]$^+$. $^1$H NMR (300 MHz, DMSO-d$_6$) δ 12.01 (s, 1H), 9.69 (s, 1H), 7.97 (s, 1H), 7.77 (s, 1H), 7.40 (d, J=8.2 Hz, 1H), 7.27 (d, J=8.2 Hz, 1H), 3.41 (s, 1H), 1.30 (d, J=6.8 Hz, 5H).

Example 232: 6-[2-tert-Butyl-5-(trifluoromethyl)pyrazolo[1,5-c]pyrimidin-3-yl]-3H-1,3-benzothiazol-2-one

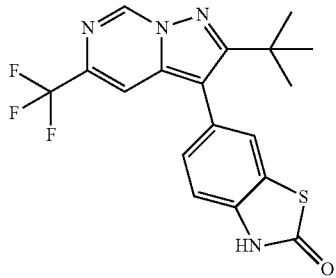 [SMILES: CC(C)(C)c1nn2cnc(C(F)(F)F)cc2c1-c1ccc2[nH]c(=O)sc2c1]

The title compound was prepared in a manner analogous to Example 164 using 3-bromo-2-(tert-butyl)-5-(trifluoromethyl)pyrazolo[1,5-c]pyrimidine (Intermediate 11). MS (ESI): mass calcd. for $C_{18}H_{15}F_3N_4OS$ 392.1; m/z found, 393 [M+H]$^+$. $^1$H NMR (300 MHz, DMSO-d$_6$) δ 9.66 (s, 1H), 7.60 (s, 2H), 7.23 (m, J=7.6 Hz, 2H), 1.30 (s, 9H).

Example 233: 4-[3-(1H-Indazol-5-yl)-2-phenyl-pyrazolo[1,5-c]pyrimidin-7-yl]morpholine

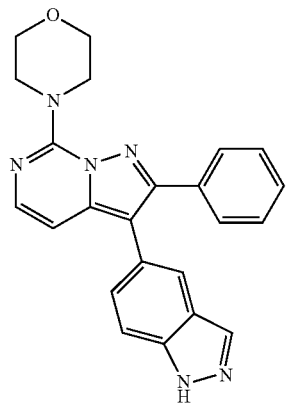 [SMILES: c1ccc(-c2nn3c(N4CCOCC4)nccc3c2-c2ccc3[nH]ncc3c2)cc1]

The title compound was prepared in a manner analogous to Example 164 using 4-(3-bromo-2-phenylpyrazolo[1,5-c]pyrimidin-7-yl)morpholine (Intermediate 22). MS (ESI): mass calcd. for $C_{23}H_{20}N_6O$ 396.2; m/z found, 397 [M+H]$^+$. $^1$H NMR (300 MHz, DMSO-d$_6$) δ 13.15 (br s, 1H), 8.08 (s, 1H), 7.73 (s, 1H), 7.64 (d, J=6.1 Hz, 1H), 7.60-7.50 (m, 3H), 7.40-7.31 (m, 3H), 7.19 (d, J=8.6 Hz, 1H), 7.02 (d, J=6.1 Hz, 1H), 4.05-3.93 (m, 4H), 3.87-3.76 (m, 4H).

Example 234: 3-(1H-Indazol-5-yl)-7-(4-methoxy-1-piperidyl)-2-phenyl-pyrazolo[1,5-c]pyrimidine

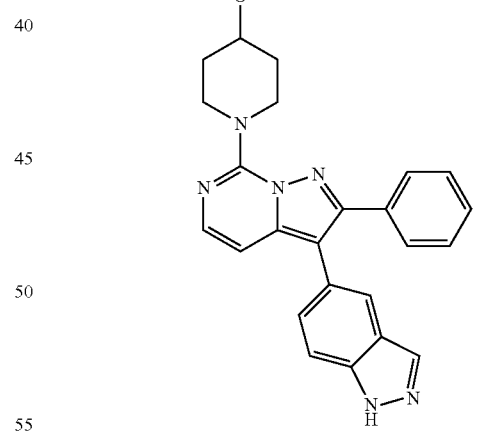

The title compound was prepared in a manner analogous to Example 164 using 3-bromo-7-(4-methoxypiperidin-1-yl)-2-phenylpyrazolo[1,5-c]pyrimidine (Intermediate 23). MS (ESI): mass calcd. for $C_{25}H_{24}N_6O$ 424.2; m/z found, 425 [M+H]$^+$. $^1$H NMR (300 MHz, DMSO-d$_6$) δ13.14 (s, 1H), 8.07 (s, 1H), 7.73 (s, 1H), 7.62 (d, J=6.2 Hz, 1H), 7.59-7.50 (m, J=9.0 Hz, 3H), 7.43-7.30 (m, 3H), 7.19 (d, J=8.6 Hz, 1H), 6.96 (d, J=6.1 Hz, 1H), 4.49-4.28 (m, 2H), 3.70-3.43 (m, 3H), 3.31 (s, 3H), 2.14-1.93 (m, 2H), 1.75-1.48 (m, 2H).

Example 235: 5-(4-Fluoro-2-isopropyl-7-morpholino-pyrazolo[1,5-c]pyrimidin-3-yl)indolin-2-one

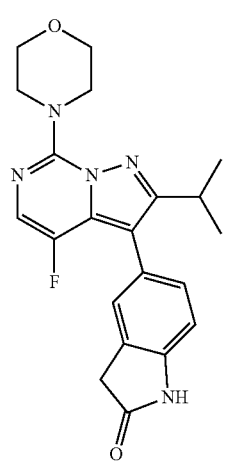 [SMILES: CC(C)c1nn2c(N3CCOCC3)ncc(F)c2c1-c1ccc2c(c1)CC(=O)N2]

The title compound was prepared in a manner analogous to Example 164 using 4-(3-bromo-4-fluoro-2-isopropylpyrazolo[1,5-c]pyrimidin-7-yl)morpholine (Intermediate 27). MS (ESI): mass calcd. for $C_{21}H_{22}FN_5O_2$ 395.4; m/z found, 395.0 [M+H]$^+$. $^1$H NMR (300 MHz, DMSO-d$_6$) δ 10.46 (br s, 1H), 7.59 (d, J=2.0 Hz, 1H), 7.22 (s, 1H), 7.19 (d, J=8.1 Hz, 1H), 6.89 (d, J=7.9 Hz, 1H), 3.80 (s, 8H), 3.53 (s, 2H), 3.24-3.11 (m, 1H), 1.24 (d, J=6.8 Hz, 6H).

Example 236: 4-[4-Fluoro-3-(1H-indazol-5-yl)-2-isopropyl-pyrazolo[1,5-c]pyrimidin-7-yl]morpholine

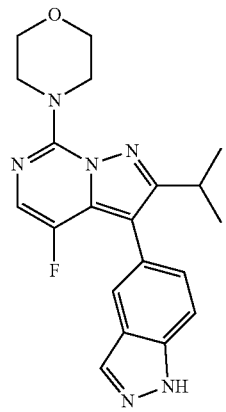 [SMILES: CC(C)c1nn2c(N3CCOCC3)ncc(F)c2c1-c1ccc2[nH]ncc2c1]

The title compound was prepared in a manner analogous to Example 164 using 4-(3-bromo-4-fluoro-2-isopropylpyrazolo[1,5-c]pyrimidin-7-yl)morpholine (Intermediate 27). MS (ESI): mass calcd. for $C_{20}H_{21}FN_6O$ 380.2; m/z found, 381 [M+H]$^+$. $^1$H NMR (300 MHz, DMSO-d$_6$) δ 13.16 (s, 1H), 8.11 (s, 1H), 7.78 (s, 1H), 7.71-7.54 (m, 2H), 7.37 (d, J=8.5 Hz, 1H), 3.81 (s, 8H), 3.27-3.12 (m, 1H), 1.24 (d, J=6.8 Hz, 6H).

Example 237: 3-(1H-indazol-5-yl)-2-isopropyl-7-(4-methoxy-1-piperidyl)pyrazolo[1,5-c]pyrimidine

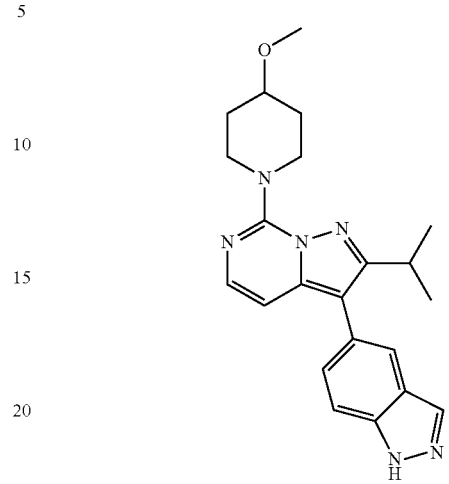

The title compound was prepared in a manner analogous to Example 164 using 3-bromo-2-isopropyl-7-(4-methoxypiperidin-1-yl)pyrazolo[1,5-c]pyrimidine (Intermediate 24). MS (ESI): mass calcd. for $C_{22}H_{26}N_6O$ 390.2; m/z found, 391 [M+H]$^+$. $^1$H NMR (300 MHz, DMSO-d$_6$) δ 13.13 (s, 1H), 8.11 (s, 1H), 7.76 (s, 1H), 7.64 (d, J=8.5 Hz, 1H), 7.54 (d, J=6.1 Hz, 1H), 7.37 (d, J=8.6 Hz, 1H), 6.89 (d, J=6.1 Hz, 1H), 4.35 (d, J=13.2 Hz, 2H), 3.69-3.41 (m, 4H), 3.30 (s, 3H), 2.00 (s, 2H), 1.61 (d, J=9.1 Hz, 2H), 1.27 (d, J=6.8 Hz, 6H).

Example 238: 4-[3-(1H-Indazol-5-yl)-2-isopropyl-pyrazolo[1,5-c]pyrimidin-7-yl]morpholine

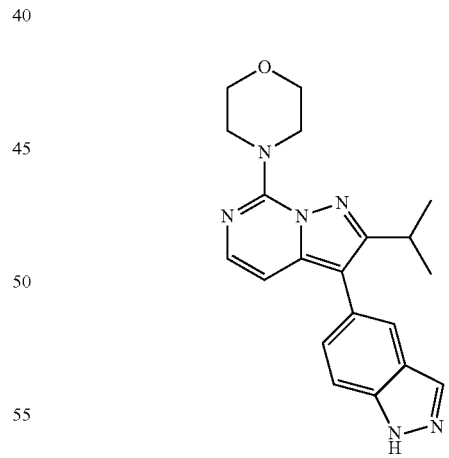

The title compound was prepared in a manner analogous to Example 164 using 4-(3-bromo-2-isopropylpyrazolo[1,5-c]pyrimidin-7-yl)morpholine (Intermediate 25). MS (ESI): mass calcd. for $C_{20}H_{22}N_6O$ 362.2; m/z found, 363 [M+H]$^+$. $^1$H NMR (300 MHz, DMSO-d$_6$) δ 13.14 (s, 1H), 8.11 (s, 1H), 7.76 (s, 1H), 7.65 (d, J=8.5 Hz, 1H), 7.57 (d, J=6.1 Hz, 1H), 7.37 (d, J=F8.7 Hz, 1H), 6.94 (d, J=6.2 Hz, 1H), 3.94 (d, J=4.4 Hz, 4H), 3.82 (d, J=4.4 Hz, 4H), 1.27 (d, J=6.8 Hz, 6H).

Example 239: 4-[3-(1H-Indazol-5-yl)-2-isopropyl-4-methyl-pyrazolo[1,5-c]pyrimidin-7-yl]morpholine

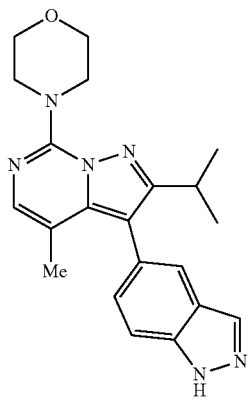 [SMILES: Cc1cnc(N2CCOCC2)n2nc(C(C)C)c(-c3ccc4[nH]ncc4c3)c12]

The title compound was prepared in a manner analogous to Example 212. MS (ESI): mass calcd. for $C_{21}H_{24}N_6O$ 376.2; m/z found, 377 [M+H]$^+$. $^1$H NMR (300 MHz, DMSO-d$_6$) δ 13.16 (br s, 1H), 8.09 (s, 1H), 7.71 (s, 1H), 7.58 (d, J=8.5 Hz, 1H), 7.34-7.25 (m, 2H), 3.81 (s, 8H), 3.07-2.89 (m, 1H), 1.76 (s, 3H), 1.28-1.09 (m, 6H).

Example 240-Example 244 were prepared in a manner analogous to Example 213.

Example 240: 6-(2-Isopropyl-7-morpholino-pyrazolo[1,5-c]pyrimidin-3-yl)-3H-1,3-benzothiazol-2-one

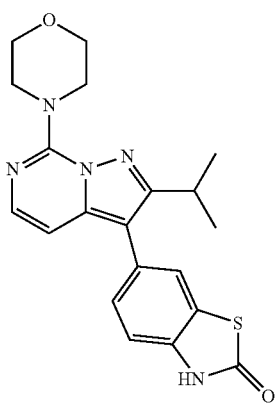 [SMILES: CC(C)c1nn2c(N3CCOCC3)nccc2c1-c1ccc2[nH]c(=O)sc2c1]

The title compound was prepared in a manner analogous to Example 213. MS (ESI): mass calcd. for $C_{20}H_{21}N_5O_2S$ 395.1; m/z found, 396 [M+H]$^+$. $^1$H NMR (300 MHz, DMSO-d$_6$) δ 11.94 (br s, 1H), 7.62 (br s, 1H), 7.58 (d, J=6.2 Hz, 1H), 7.29 (d, J=8.2 Hz, 1H), 7.21 (d, J=8.2 Hz, 1H), 6.96 (d, J=6.2 Hz, 1H), 3.96-3.88 (m, 4H), 3.82-3.76 (m, 4H), 3.27-3.19 (m, 1H), 1.26 (d, J=6.8 Hz, 6H).

Example 241: 6-[2-Isopropyl-7-(4-methoxy-1-piperidyl)pyrazolo[1,5-c]pyrimidin-3-yl]-3H-1,3-benzothiazol-2-one

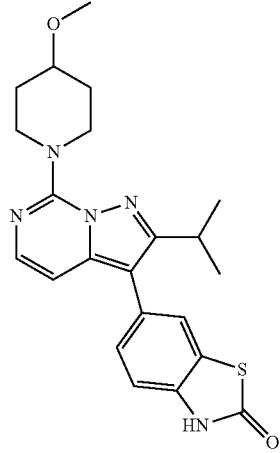 [SMILES: COC1CCN(c2nccc3c(-c4ccc5[nH]c(=O)sc5c4)c(C(C)C)nn23)CC1]

The title compound was prepared in a manner analogous to Example 213. MS (ESI): mass calcd. for $C_{22}H_{25}N_5O_2S$ 423.2; m/z found, 424 [M+H]$^+$. $^1$H NMR (300 MHz, DMSO-d$_6$) δ 11.92 (br s, 1H), 7.62 (s, 1H), 7.55 (d, J=6.2 Hz, 1H), 7.29 (d, J=8.2 Hz, 1H), 7.21 (d, J=8.2 Hz, 1H), 6.91 (d, J=6.2 Hz, 1H), 4.50-4.22 (m, 2H), 3.65-3.43 (m, 3H), 3.30 (s, 3H), 2.13-1.88 (m, 2H), 1.70-1.50 (m, 2H), 1.26 (d, J=6.8 Hz, 6H).

Example 242: 6-(7-Morpholino-2-phenyl-pyrazolo[1,5-c]pyrimidin-3-yl)-3H-1,3-benzothiazol-2-one

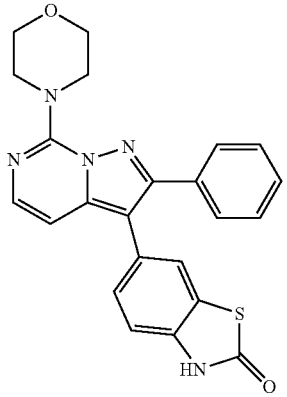 [SMILES: O=c1[nH]c2ccc(-c3c(-c4ccccc4)nn4c(N5CCOCC5)nccc34)cc2s1]

The title compound was prepared in a manner analogous to Example 213. MS (ESI): mass calcd. for $C_{23}H_{19}N_5O_2S$ 429.1; m/z found, 430 [M+H]$^+$. $^1$H NMR (300 MHz, DMSO-d$_6$) δ 11.96 (s, 1H), 7.66 (d, J=6.1 Hz, 1H), 7.55 (s, 3H), 7.44-7.36 (m, 3H), 7.14 (s, 2H), 7.03 (d, J=6.2 Hz, 1H), 3.97 (d, J=4.5 Hz, 4H), 3.82 (d, J=4.4 Hz, 4H).

Example 243: 6-(2-Isopropyl-4-methyl-7-morpholino-pyrazolo[1,5-c]pyrimidin-3-yl)-3H-1,3-benzothiazol-2-one

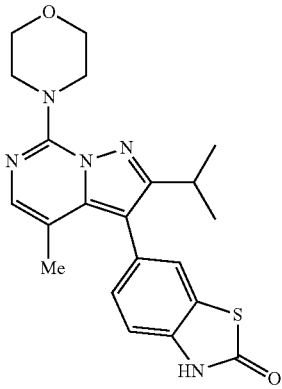 [SMILES: Cc1cnc(N2CCOCC2)n2nc(C(C)C)c(-c3ccc4[nH]c(=O)sc4c3)c12]

The title compound was prepared in a manner analogous to Example 213. MS (ESI): mass calcd. for $C_{21}H_{23}N_5O_2S$ 409.2; m/z found, 410 [M+H]$^+$. $^1$H NMR (300 MHz, DMSO-d$_6$) δ 11.76 (br s, 1H), 7.57 (s, 1H), 7.31 (s, 1H), 7.22 (d, J=8.0 Hz, 1H), 7.15 (d, J=8.1 Hz, 1H), 3.80 (s, 8H), 3.08-2.88 (m, 1H), 1.82 (s, 3H), 1.19 (d, J=6.6 Hz, 6H).

Example 244: 5-(2-Isopropyl-4-methyl-7-morpholino-pyrazolo[1,5-c]pyrimidin-3-yl)indolin-2-one

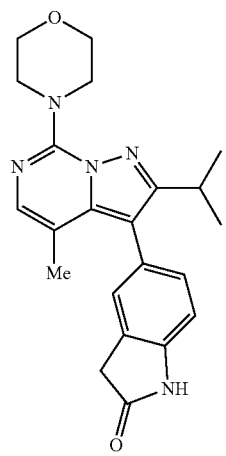 [SMILES: Cc1cnc(N2CCOCC2)n2nc(C(C)C)c(-c3ccc4c(c3)CC(=O)N4)c12]

The title compound was prepared in a manner analogous to Example 213. MS (ESI): mass calcd. for $C_{22}H_{25}N_5O_2$ 391.2; m/z found, 392 [M+H]$^+$. $^1$H NMR (300 MHz, DMSO-d$_6$) δ 10.45 (s, 1H), 7.29 (s, 1H), 7.16 (s, 1H), 7.12 (d, J=8.1 Hz, 1H), 6.86 (d, J=7.8 Hz, 1H), 3.80 (s, 8H), 3.53 (s, J=11.0 Hz, 2H), 3.07-2.86 (m, 1H), 1.82 (s, 3H), 1.19 (d, J=6.6 Hz, 6H).

Example 245: 6-[2-Phenyl-6-(trifluoromethyl)imidazo[1,2-a]pyrazin-3-yl]-3H-1,3-benzothiazol-2-one

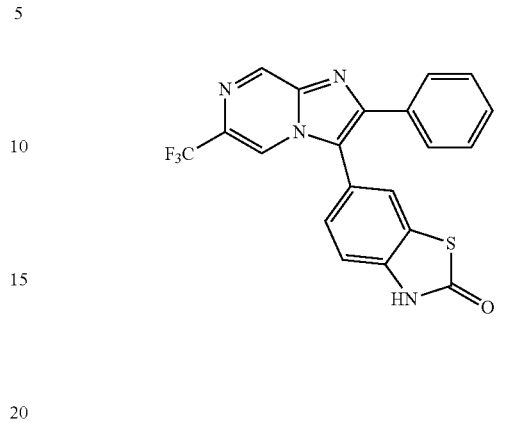

The title compound was prepared in a manner analogous to Example 216. MS (ESI): mass calcd. for $C_{20}H_{11}F_3N_4OS$ 412.1; m/z found, 411.1 [M+H]$^+$. $^1$H NMR (500 MHz, DMSO-d$_6$) δ 12.20 (s, 1H), 9.29 (s, 1H), 8.52 (s, 1H), 7.85 (d, J=1.4 Hz, 1H), 7.69-7.62 (m, 2H), 7.44 (dd, J=1.7, 8.1 Hz, 1H), 7.41-7.30 (m, 4H).

Example 246: 5-[2-Benzoyl-8-(3-oxopiperazin-1-yl)imidazo[1,2-a]pyrazin-3-yl]indolin-2-one

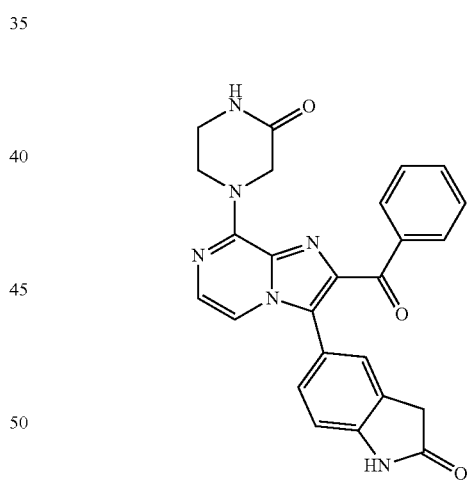

The title compound was prepared in a manner analogous to Example 217. MS (ESI): mass calcd. for $C_{25}H_{20}N_6O$ 452.2; m/z found, 453.1 [M+H]$^+$. $^1$H NMR (500 MHz, DMSO-d$_6$) δ 3.47 (m, 4H) 4.44 (br t, J=4.5 Hz, 2H) 4.67 (s, 2H) 6.97 (d, J=8.1 Hz, 1H) 7.33 (dd, J=8.1, 1.7 Hz, 1H) 7.36 (s, 1H) 7.44 (d, J=4.6 Hz, 1H) 7.51 (m, J=4.0, 4.0 Hz, 3H) 7.58-7.66 (m, 1H) 8.06 (dd, J=8.2, 1.3 Hz, 2H) 8.12 (br s, 1H) 10.67 (s, 1H).

Example 247: 5-[2-(4-Fluorophenyl)-8-methoxy-imidazo[1,2-a]pyrazin-3-yl]indolin-2-one

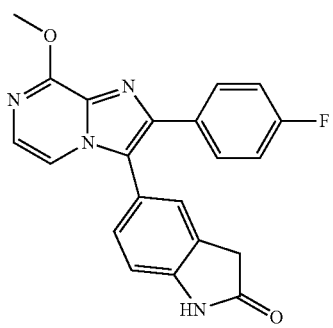 [SMILES: COc1nccn2c(-c3ccc4c(c3)CC(=O)N4)c(-c3ccc(F)cc3)nc12]

Step A: 3-Bromo-2-(4-fluorophenyl)-8-methoxy-imidazo[1,2-a]pyrazine

A suspension of 3-bromo-8-chloro-2-(4-fluorophenyl)imidazo[1,2-a]pyrazine (Intermediate 47; 500 mg, 1.53 mmol) in MeOH/DCM (1:1, 10 mL) was treated with sodium methoxide (414 mg, 7.66 mmol) in a sealed tube. The resulting mixture was stirred at 50° C. for 16 h. The reaction mixture was cooled to rt, diluted with water (30 mL), and extracted with DCM (3×30 mL). The combined organics were dried ($Na_2SO_4$), filtered and concentrated under reduced pressure to afford the title compound (472 mg, 96%). MS (APCI): mass calcd. for $C_{13}H_9BrFN_3O$ 321.0; m/z found, 321.9 [M+H]. $^1H$ NMR (400 MHz, $CDCl_3$) δ 4.04-4.34 (m, 3H) 7.12-7.21 (m, 2H) 7.53 (d, J=4.7 Hz, 1H) 7.77 (d, J=4.7 Hz, 1H) 8.06-8.20 (m, 2H)

Step B: 5-[2-(4-Fluorophenyl)-8-methoxy-imidazo[1,2-a]pyrazin-3-yl]indolin-2-one A suspension of 3-bromo-2-(4-fluorophenyl)-8-methoxy-imidazo[1,2-a]pyrazine (236 mg, 0.732 mmol), oxindole-5-boronic acid pinacol ester (247 mg, 0.952 mmol) in dioxane/ethanol (1:1, 13 mL) and 1M $Na_2CO_3$ (3.66 mL) inside a 20 mL microwave vial was treated with $PdCl_2(Ph_3P)_2$ (25.7 mg, 0.0366 mmol) and cyclohexyl JohnPhos (15.4 mg, 0.0440 mmol) and then the reaction mixture was purged with nitrogen then heated in microwave at 130° C. for 15 minutes. The reaction mixture was cooled and concentrated under reduced pressure. The crude product was adsorbed on $SiO_2$ and purified (FCC, $SiO_2$, 1 to 2% MeOH/DCM) to yield a solid (117 mg, 21%). MS (ESI): mass calcd. for $C_{21}H_{15}FN_4O_2$ 374.1; m/z found, 375.2 [M+H]$^+$. $^1H$ NMR (400 MHz, DMSO-$d_6$) δ 3.57 (s, 2H) 4.09 (s, 3H) 7.02 (d, J=7.9 Hz, 1H) 7.18 (t, J=8.9 Hz, 2H) 7.28 (dd, J=8.0, 1.7 Hz, 1H) 7.36 (d, J=1.2 Hz, 1H) 7.40 (d, J=4.6 Hz, 1H) 7.57-7.73 (m, 3H) 10.67 (s, 1H).

Example 248: 5-[8-Amino-2-(4-fluorophenyl)imidazo[1,2-a]pyrazin-3-yl]indolin-2-one

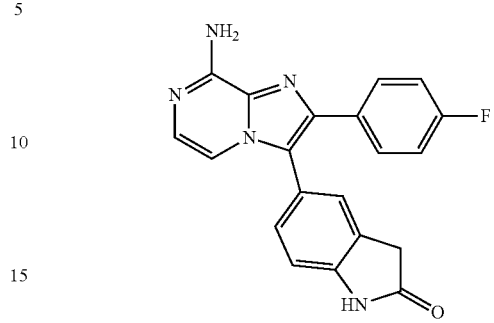

A suspension of 3-bromo-2-(4-fluorophenyl)imidazo[1,2-a]pyrazin-8-amine (Example 87, Step A; 250 mg, 0.814 mmol), oxindole-5-boronic acid pinacol ester (274 mg, 1.06 mmol) in dioxane/ethanol (1:1, 13 mL) and 1M $Na_2CO_3$ (4.1 mL) inside a 20 mL microwave vial was treated with $PdCl_2(Ph_3P)_2$ (28.6 mg, 0.041 mmol) and cyclohexyl JohnPhos (17.1 mg, 0.049 mmol) and then the reaction mixture was purged with nitrogen then heated in microwave at 130° C. for 15 minutes. The reaction mixture was cooled down and concentrated. The crude product was adsorbed on $SiO_2$ and purified (FCC, $SiO_2$, 2 to 5% MeOH/DCM) to yield a solid (50 mg, 17%). MS (ESI): mass calcd. for $C_{20}H_{14}FN_5O$ 359.1; m/z found, 360.2 [M+H]$^+$. $^1H$ NMR (500 MHz, DMSO-$d_6$) δ 3.57 (s, 2H) 6.94-7.03 (m, 3H) 7.14-7.22 (m, 3H) 7.25 (br d, J=4.9 Hz, 2H) 7.32 (s, 1H) 7.65 (dd, J=8.8, 5.6 Hz, 2H) 10.64 (br s, 1H).

Example 249: 5-[2-(4-Fluorophenyl)-8-hydroxy-imidazo[1,2-a]pyrazin-3-yl]-1,3-dihydrobenzimidazol-2-one

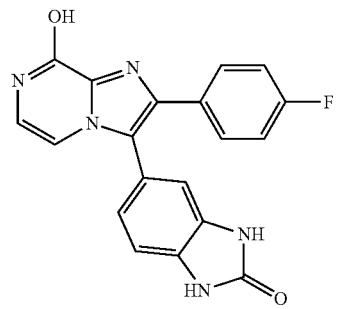 [SMILES: O=c1[nH]c2ccc(-c3c(-c4ccc(F)cc4)nc4c(O)nccn34)cc2[nH]1]

Step A: 5-[2-(4-Fluorophenyl)-8-methoxy-imidazo[1,2-a]pyrazin-3-yl]-1,3-dihydrobenzimidazol-2-one A suspension of 3-bromo-2-(4-fluorophenyl)-8-methoxy-imidazo[1,2-a]pyrazine (Example 247, Step B; 290 mg, 0.90 mmol), 2-hydroxybenzimidazole-5-boronic acid pinacol ester (281 mg, 1.08 mmol) and DIPEA (0.47 mL, 2.7 mmol) in dioxane/water (3:1, 8 mL) inside a 20 mL microwave vial was treated with $PdCl_2(dppf).CH_2Cl_2$ (37.0 mg, 0.045 mmol) and then the reaction mixture was purged with nitrogen then heated in microwave at 90° C. for 30 minutes. The reaction mixture was cooled down and concentrated.

The crude product was adsorbed on SiO$_2$ and purified (FCC, SiO$_2$, 2 to 6% MeOH/DCM) and repurified, by RP HPLC (Stationary phase: Eclipse XDB C18 150*4.6 mm 5 µm, Mobile phase: water/MeCN 65:35) to afford the title compound as a solid (117 mg, 21%). MS (ESI): mass calcd. for C$_{20}$H$_{14}$FN$_5$O$_2$ 375.1; m/z found, 376.0 [M+H]$^+$.

Step B: 5-[2-(4-Fluorophenyl)-8-hydroxy-imidazo[1,2-a]pyrazin-3-yl]-1,3-dihydrobenzimidazol-2-one A suspension of 5-[2-(4-fluorophenyl)-8-methoxy-imidazo[1,2-a]pyrazin-3-yl]indolin-2-one (82 mg, 0.218 mmol) in dioxane (2 mL) was treated with 6 M aq HCl (2 mL, 12.0 mmol) and the resulting mixture was refluxed for 1 h. Then it was cooled down to r.t., treated with 3.0 N NaOH (4.5 mL) until pH~10 and diluted with water (20 mL). The solid was filtered, washed with water (20 mL) and Et$_2$O (30 mL), and dried via vacuum to yield a solid (63 mg, 80%). MS (ESI): mass calcd. for C$_{19}$H$_{12}$FN$_5$O$_2$ 361.1; m/z found, 362.1 [M+H]$^+$. $^1$H NMR (500 MHz, DMSO-d$_6$) δ 3.60 (br s, 2H) 6.29-7.38 (m, 7H) 7.66 (br s, 2H).

Example 250: N-[(3R)-1-[2-(4-Fluorophenyl)-3-(2-oxoindolin-5-yl)imidazo[1,2-a]pyrazin-8-yl]pyrrolidin-3-yl]acetamide

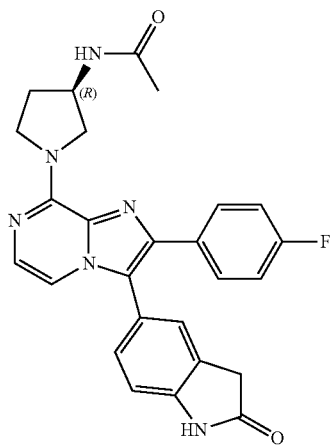

Step A: N-[(3R)-1-[3-bromo-2-(4-fluorophenyl)imidazo[1,2-a]pyrazin-8-yl]pyrrolidin-3-yl]acetamide A suspension of 3-bromo-8-chloro-2-(4-fluorophenyl)imidazo[1,2-a]pyrazine (Intermediate 47; 300 mg, 0.919 mmol) and DIPEA (0.32 mL, 1.84 mmol) in isopropanol (5 mL) was treated with (3R)-(+)-3-acetamidopyrrolidine (177 mg, 1.38 mmol) in a sealed tube. The resulting mixture was stirred at 90° C. for 16 h. Then it was cooled down to r.t., diluted with sat. NaHCO$_3$ (30 mL) and extracted with DCM (3×50 mL), dried (Na$_2$SO$_4$), filtered and concentrated. The crude product was triturated with Et$_2$O, filtered, washed with Et$_2$O (20 mL) and dried via vacuum to yield a solid (341 mg, 89%). $^1$H NMR (400 MHz, CDCl$_3$) δ 2.00-2.02 (m, 3H) 2.03-2.13 (m, 1H) 2.32 (td, J=13.5, 7.7 Hz, 1H) 4.03-4.40 (m, 4H) 4.61-4.77 (m, 1H) 5.75 (br d, J=7.4 Hz, 1H) 7.12-7.22 (m, 2H) 7.39-7.50 (m, 2H) 8.05-8.17 (m, 2H).

Step B: N-[(3R)-1-[2-(4-fluorophenyl)-3-(2-oxoindolin-5-yl)imidazo[1,2-a]pyrazin-8-yl]pyrrolidin-3-yl]acetamide A suspension of N-[(3R)-1-[3-bromo-2-(4-fluorophenyl)imidazo[1,2-a]pyrazin-8-yl]pyrrolidin-3-yl]acetamide (225 mg, 0.538 mmol), oxindole-5-boronic acid pinacol ester (181 mg, 0.699 mmol) in dioxane/ethanol (9 mL, 1:1) and 1M Na$_2$CO$_3$ (2.69 mL) inside a 20 mL microwave vial was treated with PdCl$_2$(Ph$_3$P)$_2$ (18.9 mg, 0.0269 mmol) and cyclohexyl JohnPhos (11.3 mg, 0.0323 mmol) and then the reaction mixture was purged with nitrogen then heated in microwave at 130° C. for 15 minutes. The reaction mixture was cooled down and concentrated. The crude product was adsorbed on SiO$_2$ and purified (FCC, SiO$_2$, 4 to 8% MeOH/DCM). Then, by RP HPLC (Stationary phase: Eclipse XDB C18 150*4.6 mm 5 µm, Mobile phase: water/MeCN 65:35) to yield a solid (60 mg, 25%). MS (ESI): mass calcd. for C$_{26}$H$_{23}$FN$_6$O$_2$ 470.2; m/z found, 471.3 [M+H]$^+$. $^1$H NMR (500 MHz, DMSO-d$_6$) δ 1.84 (s, 3H) 1.87-2.05 (m, 1H) 2.11-2.30 (m, 1H) 3.58 (s, 2H) 3.66-4.63 (m, 5H) 7.02 (d, J=7.8 Hz, 1H) 7.11-7.42 (m, 5H) 7.64 (dd, J=8.8, 5.6 Hz, 2H) 8.19 (br d, J=6.6 Hz, 1H) 10.64 (s, 1H).

Biological Assays

Calcium Flux Assay

This assay was used to test compounds for their ability to inhibit TARP γ8 dependent AMPA receptor activity. The AMPA receptor is a non-selective cation channel activated by glutamate. Ionotropic glutamate receptors normally desensitize too rapidly to allow detectable calcium influx in a FLIPR assay (Strange et al. (2006). "Functional characterisation of homomeric ionotropic glutamate receptors GluR1-GluR6 in a fluorescence-based high throughput screening assay." *Comb Chem High Throughput Screen* 9(2): 147-158). But, this desensitization is incomplete, and a substantial steady-state current remains in the sustained presence of glutamate (Cho et al. (2007). "Two families of TARP isoforms that have distinct effects on the kinetic properties of AMPA receptors and synaptic currents." *Neuron* 55(6): 890-904).

An in vitro assay was used to determine the potency of test compounds as inhibitors of the glutamate response of the channel formed by GluA1o-γ8. To ensure a 1:1 stoichiometry of GluA1O and γ8 subunits in the expressed channel, a fusion of the cDNAs for GRIA1o and CACNG8 was used. Following Shi et al (2009) "The stoichiometry of AMPA receptors and TARPs varies by neuronal cell type." *Neuron* 62(5): δ 33-640), the C-terminus of the cDNA for GRI1o was fused to the N-terminus of the cDNA for γ8. The linker sequence was QQQQQQQQQQEFAT. Channels expressed with this construct appear to have similar properties to channels formed by co-expression of GRI1o with an excess of CACNG8 (Shi et al. 2009). A clonal cell line in HEK293 cells stably expressing this construct, with a geneticin selection marker, was generated for use in this assay. Cell expressing the GRIA1o-CACNG8 fusion construct were grown in a monolayer in 96- or 384-well microtiter plates. They were washed with assay buffer (135 mM NaCl, 4 mM KCl, 3 mM CaCl$_2$, 1 mM MgCl$_2$, 5 mM glucose, 10 mM HEPES, pH 7.4, 300 mOs) using a Biotek EL405 plate washer. The cells were then loaded with a calcium-sensitive dye (Calcium-5 or Calcium-6, Molecular Devices) and the test compounds at a range of concentrations. Calcium flux following the addition of 15 µM glutamate was monitored using a Molecular Devices FLIPR Tetra.

The fluorescence in each well was normalized to the fluorescence of negative and positive control wells. The negative control wells had no added compounds, and the positive control wells had been incubated with 10 μM CP465022 (a non-subtype-selective AMPA receptor antagonist) (Lazzaro et al. (2002). "Functional characterization of CP-465,022, a selective, noncompetitive AMPA receptor antagonist." *Neuropharmacology* 42(2): 143-153). The responses to glutamate as functions of the test compound concentrations were fitted to a four-parameter logistic function. The fitted parameter corresponding to the midpoint was taken to be the potency of inhibition of the compound. The data in Table 3 below illustrates the observed potency for the compounds described herein. $pIC_{50}$ refers to the negative log of the $IC_{50}$ in molar.

Using a similar protocol, compounds were also tested for their ability to inhibit TARP γ2 dependent AMPA receptor activity. The compounds that were tested for TARP γ2 AMPA receptor activity had $pIC_{50}$ values less than 6.

TABLE 3

| Example # | Compound Name | GluR1-γ8 ($pIC_{50}$) |
|---|---|---|
| 1 | 1-[4-[2-(4-Fluorophenyl)-3-(4-hydroxyphenyl)imidazo[1,2-a]pyrazin-8-yl]piperazin-1-yl]ethanone; | 8.2 |
| 2 | 4-[2-(4-Fluorophenyl)-8-morpholino-imidazo[1,2-a]pyrazin-3-yl]-3-methyl-phenol; | 7.5 |
| 3 | tert-Butyl 4-[2-(4-fluorophenyl)-3-(4-hydroxyphenyl)imidazo[1,2-a]pyrazin-8-yl]piperazine-1-carboxylate; | 6.2 |
| 4 | 4-[2-(3-Fluorophenyl)-8-morpholino-imidazo[1,2-a]pyrazin-3-yl]phenol; | 7.2 |
| 5 | 4-[2-(4-Fluorophenyl)-8-piperazin-1-yl-imidazo[1,2-a]pyrazin-3-yl]phenol; | 5.9 |
| 6 | 4-[2-(4-Fluorophenyl)-8-(4-methylpiperazin-1-yl)imidazo[1,2-a]pyrazin-3-yl]phenol; | 6.3 |
| 7 | 4-[2-(4-Fluorophenyl)-8-(6-oxa-2-azaspiro[3.3]heptan-2-yl)imidazo[1,2-a]pyrazin-3-yl]phenol; | 7.3 |
| 8 | 5-[2-(4-Fluorophenyl)-8-morpholino-imidazo[1,2-a]pyrazin-3-yl]indolin-2-one; | 9.3 |
| 9 | 4-[2-(4-Fluorophenyl)-8-(1-piperidyl)imidazo[1,2-a]pyrazin-3-yl]phenol; | 6.7 |
| 10 | 4-[2-(4-Fluorophenyl)-3-(1H-indazol-5-yl)imidazo[1,2-a]pyrazin-8-yl]morpholine; | 9.2 |
| 11 | 5-[2-(4-Fluorophenyl)-8-morpholino-imidazo[1,2-a]pyrazin-3-yl]-1,3-dihydrobenzimidazol-2-one; | 9.4 |
| 12 | 5-[8-(4-Acetylpiperazin-1-yl)-2-(4-fluorophenyl)imidazo[1,2-a]pyrazin-3-yl]indolin-2-one; | 9.4 |
| 13 | 1-[4-[2-(4-Fluorophenyl)-3-(1H-indazol-5-yl)imidazo[1,2-a]pyrazin-8-yl]piperazin-1-yl]ethanone; | 9.7 |
| 14 | 5-[8-(4-Acetylpiperazin-1-yl)-2-(4-fluorophenyl)imidazo[1,2-a]pyrazin-3-yl]-1,3-dihydrobenzimidazol-2-one; | 8.8 |
| 15 | 4-(2-Benzyl-8-morpholino-imidazo[1,2-a]pyrazin-3-yl)phenol; | 7.6 |
| 16 | 4-[2-(4-Fluorophenyl)-3-(1H-indol-5-yl)imidazo[1,2-a]pyrazin-8-yl]morpholine; | 7.8 |
| 17 | 5-[8-(4-Acetylpiperazin-1-yl)-2-benzyl-imidazo[1,2-a]pyrazin-3-yl]indolin-2-one; | 8.9 |
| 18 | 1-[4-[2-Benzyl-3-(1H-indazol-5-yl)imidazo[1,2-a]pyrazin-8-yl]piperazin-1-yl]ethanone; | 9.1 |
| 19 | 5-[8-(4-Acetylpiperazin-1-yl)-2-benzyl-imidazo[1,2-a]pyrazin-3-yl]-1,3-dihydrobenzimidazol-2-one; | 8.4 |
| 20 | 5-(2-Benzyl-8-morpholino-imidazo[1,2-a]pyrazin-3-yl)indolin-2-one; | 9 |
| 21 | 4-[2-Benzyl-3-(1H-indazol-5-yl)imidazo[1,2-a]pyrazin-8-yl]morpholine; | 9 |
| 22 | 5-(2-Benzyl-8-morpholino-imidazo[1,2-a]pyrazin-3-yl)-1,3-dihydrobenzimidazol-2-one; | 8.8 |
| 23 | 1-[4-[2-Benzyl-3-(4-hydroxyphenyl)imidazo[1,2-a]pyrazin-8-yl]piperazin-1-yl]ethanone; | 7.6 |
| 24 | 5-[2-(4-Fluorophenyl)-8-(6-oxa-2-azaspiro[3.3]heptan-2-yl)imidazo[1,2-a]pyrazin-3-yl]indolin-2-one; | 8.3 |
| 25 | 2-[2-(4-Fluorophenyl)-3-(1H-indazol-5-yl)imidazo[1,2-a]pyrazin-8-yl]-6-oxa-2-azaspiro[3.3]heptane; | 8.1 |
| 26 | 5-[2-(4-Fluorophenyl)-8-(6-oxa-2-azaspiro[3.3]heptan-2-yl)imidazo[1,2-a]pyrazin-3-yl]-1,3-dihydrobenzimidazol-2-one; | 8.3 |
| 27 | 4-[2-(4-Fluorophenyl)-3-(4-hydroxyphenyl)imidazo[1,2-a]pyrazin-8-yl]piperazin-2-one; | 8.5 |
| 28 | 4-[8-(4,4-Difluoro-1-piperidyl)-2-(4-fluorophenyl)imidazo[1,2-a]pyrazin-3-yl]phenol; | 6.8 |
| 29 | 4-[8-(3,3-Difluoro-1-piperidyl)-2-(4-fluorophenyl)imidazo[1,2-a]pyrazin-3-yl]phenol; | 7.5 |
| 30 | 4-[3-(1H-Benzotriazol-5-yl)-2-(4-fluorophenyl)imidazo[1,2-a]pyrazin-8-yl]morpholine; | 7.1 |

TABLE 3-continued

| Example # | Compound Name | GluR1-γ8 (pIC$_{50}$) |
|---|---|---|
| 31 | 4-[3-(1H-Benzimidazol-5-yl)-2-(4-fluorophenyl)imidazo[1,2-a]pyrazin-8-yl]morpholine; | 6.2 |
| 32 | 5-[2-(4-Fluorophenyl)-8-(3-oxopiperazin-1-yl)imidazo[1,2-a]pyrazin-3-yl]indolin-2-one; | 9.3 |
| 33 | 4-[2-(4-Fluorophenyl)-3-(1H-indazol-5-yl)imidazo[1,2-a]pyrazin-8-yl]piperazin-2-one; | 9.7 |
| 34 | 5-[2-(4-Fluorophenyl)-8-(3-oxopiperazin-1-yl)imidazo[1,2-a]pyrazin-3-yl]-1,3-dihydrobenzimidazol-2-one; | 8.9 |
| 35 | 5-[2-(3,4-Difluorophenyl)-8-morpholino-imidazo[1,2-a]pyrazin-3-yl]indolin-2-one; | 9.3 |
| 36 | tert-Butyl 4-[2-benzyl-3-(2-oxoindolin-5-yl)imidazo[1,2-a]pyrazin-8-yl]piperazine-1-carboxylate; | 9.5 |
| 37 | 5-[2-(4-Fluorophenyl)-8-(4-hydroxy-1-piperidyl)imidazo[1,2-a]pyrazin-3-yl]indolin-2-one; | 9.5 |
| 38 | 5-[2-Benzyl-8-(3-oxopiperazin-1-yl)imidazo[1,2-a]pyrazin-3-yl]indolin-2-one; | 9 |
| 39 | 5-[2-(4-Fluorophenyl)-8-(3-methylmorpholin-4-yl)imidazo[1,2-a]pyrazin-3-yl]indolin-2-one; | 9.1 |
| 40 | 5-[2-(4-Fluorophenyl)-8-[(2-oxopyrrolidin-3-yl)amino]imidazo[1,2-a]pyrazin-3-yl]indolin-2-one; | 6.6 |
| 41 | 5-[2-(4-Fluorophenyl)-8-(3-hydroxypyrrolidin-1-yl)imidazo[1,2-a]pyrazin-3-yl]indolin-2-one; | 9.2 |
| 42 | 5-[2-(4-Fluorophenyl)-8-[2-(trifluoromethyl)morpholin-4-yl]imidazo[1,2-a]pyrazin-3-yl]indolin-2-one; | 8.1 |
| 43 | 5-[2-(4-Fluorophenyl)-8-[(3S)-3-methylmorpholin-4-yl]imidazo[1,2-a]pyrazin-3-yl]indolin-2-one; | 9.2 |
| 44 | 5-[2-(4-Fluorophenyl)-8-[(3R)-3-methylmorpholin-4-yl]imidazo[1,2-a]pyrazin-3-yl]indolin-2-one; | 8.1 |
| 45 | 5-[2-(4-Fluorophenyl)-8-pyrrolidin-1-yl-imidazo[1,2-a]pyrazin-3-yl]indolin-2-one; | 9 |
| 46 | 5-[8-[Cyclopropyl(methyl)amino]-2-(4-fluorophenyl)imidazo[1,2-a]pyrazin-3-yl]indolin-2-one; | 8.3 |
| 47 | 5-[8-(1,1-Dioxo-1,4-thiazinan-4-yl)-2-(4-fluorophenyl)imidazo[1,2-a]pyrazin-3-yl]indolin-2-one; | 9.4 |
| 48 | (R*)-5-[2-(4-Fluorophenyl)-8-[2-(trifluoromethyl)morpholin-4-yl]imidazo[1,2-a]pyrazin-3-yl]indolin-2-one; | 7.9 |
| 49 | (S*)-5-[2-(4-Fluorophenyl)-8-[2-(trifluoromethyl)morpholin-4-yl]imidazo[1,2-a]pyrazin-3-yl]indolin-2-one; | 8.1 |
| 50 | 5-[8-(3,3-Dimethylmorpholin-4-yl)-2-(4-fluorophenyl)imidazo[1,2-a]pyrazin-3-yl]indolin-2-one; | 7.5 |
| 51 | 5-[8-(Diethylamino)-2-(4-fluorophenyl)imidazo[1,2-a]pyrazin-3-yl]indolin-2-one; | 8.4 |
| 52 | (R*)-5-[2-(4-Fluorophenyl)-8-(3-hydroxypyrrolidin-1-yl)imidazo[1,2-a]pyrazin-3-yl]indolin-2-one; | 8.8 |
| 53 | (S*)-5-[2-(4-Fluorophenyl)-8-(3-hydroxypyrrolidin-1-yl)imidazo[1,2-a]pyrazin-3-yl]indolin-2-one; | 8.8 |
| 54 | 5-[2-(4-Fluorophenyl)-8-(3-hydroxy-1-piperidyl)imidazo[1,2-a]pyrazin-3-yl]indolin-2-one; | 9.5 |
| 55 | 5-[8-(1,4-Dioxa-8-azaspiro[4;5]decan-8-yl)-2-(4-fluorophenyl)imidazo[1,2-a]pyrazin-3-yl]indolin-2-one; | 9.7 |
| 56 | 5-(2-Cyclohexyl-8-morpholino-imidazo[1,2-a]pyrazin-3-yl)indolin-2-one; | 8.1 |
| 57 | 5-(2-Cyclopentyl-8-morpholino-imidazo[1,2-a]pyrazin-3-yl)indolin-2-one; | 7.8 |
| 58 | 5-[8-(Azetidin-1-yl)-2-(4-fluorophenyl)imidazo[1,2-a]pyrazin-3-yl]indolin-2-one; | 8.8 |
| 59 | 5-[8-(3-Fluoroazetidin-1-yl)-2-(4-fluorophenyl)imidazo[1,2-a]pyrazin-3-yl]indolin-2-one; | 9.3 |
| 60 | 5-[8-(3,3-Difluoroazetidin-1-yl)-2-(4-fluorophenyl)imidazo[1,2-a]pyrazin-3-yl]indolin-2-one; | 8.8 |
| 61 | 5-[8-(3-Chloroazetidin-1-yl)-2-(4-fluorophenyl)imidazo[1,2-a]pyrazin-3-yl]indolin-2-one; | 8.8 |
| 62 | 5-[2-(4-Fluorophenyl)-8-(3-methylsulfonylazetidin-1-yl)imidazo[1,2-a]pyrazin-3-yl]indolin-2-one; | 8 |
| 63 | 5-[2-(4-Fluorophenyl)-8-(2,2,3,3,5,5,6,6-octadeuteriomorpholin-4-yl)imidazo[1,2-a]pyrazin-3-yl]indolin-2-one; | 9.7 |
| 64 | 5-[2-(4-Fluorophenyl)-8-[3-(hydroxymethyl)azetidin-1-yl]imidazo[1,2-a]pyrazin-3-yl]indolin-2-one; | 9.1 |
| 65 | 5-(8-Morpholino-2-phenyl-imidazo[1,2-a]pyrazin-3-yl)indolin-2-one; | 9.8 |
| 66 | 1-[2-(4-Fluorophenyl)-3-(2-oxoindolin-5-yl)imidazo[1,2-a]pyrazin-8-yl]azetidine-3-carbonitrile; | 8.4 |

TABLE 3-continued

| Example # | Compound Name | GluR1-γ8 (pIC$_{50}$) |
|---|---|---|
| 67 | 5-[2-(4-Fluorophenyl)-8-(3-hydroxy-3-methyl-azetidin-1-yl)imidazo[1,2-a]pyrazin-3-yl]indolin-2-one; | 8.9 |
| 68 | 5-[2-(4-Fluorophenyl)-8-(4-hydroxy-4-methyl-1-piperidyl)imidazo[1,2-a]pyrazin-3-yl]indolin-2-one; | 10 |
| 69 | 5-[2-(4-Fluorophenyl)-8-[3-hydroxy-3-(trifluoromethyl)azetidin-1-yl]imidazo[1,2-a]pyrazin-3-yl]indolin-2-one; | 9 |
| 70 | (trans)-5-[8-(3-Fluoro-4-hydroxy-1-piperidyl)-2-(4-fluorophenyl)imidazo[1,2-a]pyrazin-3-yl]indolin-2-one; | 9.8 |
| 71 | 5-[8-(3,3-Difluoro-4-hydroxy-1-piperidyl)-2-(4-fluorophenyl)imidazo[1,2-a]pyrazin-3-yl]indolin-2-one; | 9.6 |
| 72 | 5-[2-(4-Fluorophenyl)-8-(4-methoxy-1-piperidyl)imidazo[1,2-a]pyrazin-3-yl]indolin-2-one; | 9.9 |
| 73 | (cis)-5-[8-(3-Fluoro-4-hydroxy-1-piperidyl)-2-(4-fluorophenyl)imidazo[1,2-a]pyrazin-3-yl]indolin-2-one; | 9.5 |
| 74 | 5-[2-(4-Fluorophenyl)-8-(4-fluoro-1-piperidyl)imidazo[1,2-a]pyrazin-3-yl]indolin-2-one; | 10.1 |
| 75 | 5-[8-(4-Fluoro-1-piperidyl)-2-phenyl-imidazo[1,2-a]pyrazin-3-yl]indolin-2-one; | 10.2 |
| 76 | 5-[8-[4-(Fluoromethyl)-1-piperidyl]-2-phenyl-imidazo[1,2-a]pyrazin-3-yl]indolin-2-one; | 9.6 |
| 77 | 5-[8-[4-(2-Fluoroethyl)-1-piperidyl]-2-phenyl-imidazo[1,2-a]pyrazin-3-yl]indolin-2-one; | 9.4 |
| 78 | 5-[8-(3-Methoxyazetidin-1-yl)-2-phenyl-imidazo[1,2-a]pyrazin-3-yl]indolin-2-one; | 8.7 |
| 79 | 5-[8-(6-Oxa-3-azabicyclo[3;1;1]heptan-3-yl)-2-phenyl-imidazo[1,2-a]pyrazin-3-yl]indolin-2-one; | 9.3 |
| 80 | 5-[8-(5-Azaspiro[2;3]hexan-5-yl)-2-phenyl-imidazo[1,2-a]pyrazin-3-yl]indolin-2-one; | 9.2 |
| 81 | 5-[8-(3-Fluoroazetidin-1-yl)-2-phenyl-imidazo[1,2-a]pyrazin-3-yl]indolin-2-one; | 9.4 |
| 82 | 5-[5-Chloro-2-(4-fluorophenyl)-8-morpholino-imidazo[1,2-a]pyrazin-3-yl]-1,3-dihydrobenzimidazol-2-one; | 9.5 |
| 83 | 4-[2-(4-Fluorophenyl)-8-morpholino-imidazo[1,2-a]pyrazin-3-yl]-phenol; | 7.9 |
| 84 | 4-[2-(2-Fluorophenyl)-8-morpholino-imidazo[1,2-a]pyrazin-3-yl]phenol; | 7.2 |
| 85 | 4-(2-Cyclohexyl-8-morpholino-imidazo[1,2-a]pyrazin-3-yl)phenol; | 6.7 |
| 86 | 5-(2-tert-Butyl-8-morpholino-imidazo[1,2-a]pyrazin-3-yl)indolin-2-one; | 6.8 |
| 87 | 5-[8-Amino-2-(4-fluorophenyl)imidazo[1,2-a]pyrazin-3-yl]-1,3-dihydrobenzimidazol-2-one; | 6.4 |
| 88 | 5-[2-tert-Butyl-8-(4-hydroxy-1-piperidyl)imidazo[1,2-a]pyrazin-3-yl]indolin-2-one; | 6.9 |
| 89 | 5-[8-(3-Fluoroazetidin-1-yl)-2-(4-pyridyl)imidazo[1,2-a]pyrazin-3-yl]indolin-2-one; | 6.7 |
| 90 | 5-(2-Cyclobutyl-8-morpholino-imidazo[1,2-a]pyrazin-3-yl)indolin-2-one; | 6.7 |
| 91 | 5-(2-Cyclopropyl-8-morpholino-imidazo[1,2-a]pyrazin-3-yl)indolin-2-one; | 6.3 |
| 92 | 1-[4-[2-(4-Chlorophenyl)-3-(4-hydroxyphenyl)imidazo[1,2-a]pyrazin-8-yl]-1,4-diazepan-1-yl]ethanone; | 7.6 |
| 93 | N-[1-[2-(4-Chlorophenyl)-3-(4-hydroxyphenyl)imidazo[1,2-a]pyrazin-8-yl]-4-piperidyl]acetamide; | 7.5 |
| 94 | 1-[4-[2-(4-Chlorophenyl)-3-(4-hydroxyphenyl)imidazo[1,2-a]pyrazin-8-yl]piperazin-1-yl]ethanone; | 8.5 |
| 95 | 4-[3-(4-Hydroxyphenyl)-8-morpholino-imidazo[1,2-a]pyrazin-2-yl]benzonitrile; | 7.5 |
| 96 | 4-[2-[(3-Fluorophenyl)methyl]-8-morpholino-imidazo[1,2-a]pyrazin-3-yl]phenol; | 7.7 |
| 97 | 4-[3-(1H-Indazol-5-yl)-8-morpholino-imidazo[1,2-a]pyrazin-2-yl]benzonitrile; | 8.4 |
| 98 | N-[(3S)-1-[2-(4-Fluorophenyl)-3-(2-oxo-1,3-dihydrobenzimidazol-5-yl)imidazo[1,2-a]pyrazin-8-yl]pyrrolidin-3-yl]acetamide; | 8.6 |
| 99 | 5-[2-(4-Fluorophenyl)-8-methoxy-imidazo[1,2-a]pyrazin-3-yl]-1,3-dihydrobenzimidazol-2-one; | 7.6 |
| 100 | N-[(3R)-1-[2-(4-Fluorophenyl)-3-(2-oxo-1,3-dihydrobenzimidazol-5-yl)imidazo[1,2-a]pyrazin-8-yl]pyrrolidin-3-yl]acetamide; | 7.9 |
| 101 | 5-[8-(Dimethylamino)-2-(4-fluorophenyl)imidazo[1,2-a]pyrazin-3-yl]-1,3-dihydrobenzimidazol-2-one; | 9.3 |

TABLE 3-continued

| Example # | Compound Name | GluR1-γ8 (pIC$_{50}$) |
|---|---|---|
| 102 | 4-[8-Morpholino-3-(2-oxoindolin-5-yl)imidazo[1,2-a]pyrazin-2-yl]benzonitrile; | 8.7 |
| 103 | 4-[8-(4-Acetylpiperazin-1-yl)-3-(1H-indazol-5-yl)imidazo[1,2-a]pyrazin-2-yl]benzonitrile; | 9.1 |
| 104 | 5-[2-(4-Fluorophenyl)-8-(methylamino)imidazo[1,2-a]pyrazin-3-yl]-1,3-dihydrobenzimidazol-2-one; | 8.2 |
| 105 | 4-[8-Morpholino-3-(2-oxo-1,3-dihydrobenzimidazol-5-yl)imidazo[1,2-a]pyrazin-2-yl]benzonitrile; | 8.9 |
| 106 | 4-[8-(4-Acetylpiperazin-1-yl)-3-(2-oxo-1,3-dihydrobenzimidazol-5-yl)imidazo[1,2-a]pyrazin-2-yl]benzonitrile; | 8.3 |
| 107 | 4-[8-(4-Acetylpiperazin-1-yl)-3-(2-oxoindolin-5-yl)imidazo[1,2-a]pyrazin-2-yl]benzonitrile; | 8.6 |
| 108 | 5-(2-(4-Fluorophenyl)-8-(2-oxa-6-azaspiro[3;3]heptan-6-yl)imidazo[1,2-a]pyrazin-3-yl)-1,3-dihydrobenzo[c]isothiazole 2,2-dioxide; | 7.8 |
| 109 | 5-(2-(4-Fluorophenyl)-8-(4-oxopiperidin-1-yl)imidazo[1,2-a]pyrazin-3-yl)indolin-2-one; | 10.2 |
| 110 | 5-(8-(4-Methyl-3-oxopiperazin-1-yl)-2-phenylimidazo[1,2-a]pyrazin-3-yl)indolin-2-one; | 8.9 |
| 111 | 5-(8-(2,4-Dimethyl-3-oxopiperazin-1-yl)-2-phenylimidazo[1,2-a]pyrazin-3-yl)indolin-2-one; | 8.8 |
| 112 | tert-Butyl 4-(2-benzyl-5-bromo-3-(2-oxoindolin-5-yl)imidazo[1,2-a]pyrazin-8-yl)piperazine-1-carboxylate; | 9.1 |
| 113 | 5-(8-(4-Acetylpiperazin-1-yl)-2-benzyl-5-bromoimidazo[1,2-a]pyrazin-3-yl)indolin-2-one; | 9.5 |
| 114 | 5-(8-(4-Acetylpiperazin-1-yl)-2-benzyl-5-methylimidazo[1,2-a]pyrazin-3-yl)indolin-2-one | 8.7 |
| 115 | 5-[8-(4-Acetylpiperazin-1-yl)-2-(4-fluorophenyl)imidazo[1,2-a]pyrazin-3-yl]indolin-2-one | |
| 116 | 6-(2-(4-Fluorophenyl)-8-morpholinoimidazo[1,2-a]pyrazin-3-yl)benzo[d]oxazol-2(3H)-one; | 8.5 |
| 117 | 5-[2-(4-Fluorophenyl)-8-morpholino-imidazo[1,2-a]pyrazin-3-yl]-1,3-dihydro-2,1-benzothiazole 2,2-dioxide; | 8.4 |
| 118 | 6-[2-(4-Fluorophenyl)-8-morpholino-imidazo[1,2-a]pyrazin-3-yl]-3H-1,3-benzothiazol-2-one; | 9.5 |
| 119 | 1-[3-(2,2-Dioxo-1,3-dihydro-2,1-benzothiazol-5-yl)-2-(4-fluorophenyl)imidazo[1,2-a]pyrazin-8-yl]piperidin-4-ol | 8.5 |
| 120 | 6-[2-(4-Fluorophenyl)-8-morpholino-imidazo[1,2-a]pyrazin-3-yl]-3,4-dihydro-1H-quinazolin-2-one; | 7 |
| 121 | 5-[2-(4-Fluorophenyl)-8-morpholino-imidazo[1,2-a]pyrazin-3-yl]-1H-benzimidazol-2-amine; | 6.2 |
| 122 | 3-Fluoro-5-[2-(4-fluorophenyl)-8-morpholino-imidazo[1,2-a]pyrazin-3-yl]indolin-2-one; | 8.5 |
| 123 | 4-[3-(3-Fluoro-1H-indol-5-yl)-2-(4-fluorophenyl)imidazo[1,2-a]pyrazin-8-yl]morpholine; | 6.9 |
| 124 | 6-[2-(4-Fluorophenyl)-8-morpholino-imidazo[1,2-a]pyrazin-3-yl]-1,4-dihydro-3,1-benzoxazin-2-one; | 8.1 |
| 125 | 6-[2-(4-Fluorophenyl)-8-morpholino-imidazo[1,2-a]pyrazin-3-yl]-1H-quinolin-2-one; | 7.4 |
| 126 | 4-[2-(4-Fluorophenyl)-8-pyrrolidin-1-yl-imidazo[1,2-a]pyrazin-3-yl]phenol; | 7.3 |
| 127 | 5-[2-(4-Fluorophenyl)-8-methylsulfonyl-imidazo[1,2-a]pyrazin-3-yl]indolin-2-one; | 6.4 |
| 128 | 5-[2-(4-Fluorophenyl)-8-methylsulfinyl-imidazo[1,2-a]pyrazin-3-yl]indolin-2-one; | 6.2 |
| 129 | 5-[2-(4-Fluorophenyl)-8-isopropoxy-imidazo[1,2-a]pyrazin-3-yl]indolin-2-one; | 7.7 |
| 130 | 1-[4-[2-(4-Fluorophenyl)-3-(4-hydroxyphenyl)imidazo[1,2-a]pyrazin-8-yl]-3,6-dihydro-2H-pyridin-1-yl]ethanone; | 6.8 |
| 131 | 5-(8-(3,6-Dihydro-2H-pyran-4-yl)-2-phenylimidazo[1,2-a]pyrazin-3-yl)indolin-2-one; | 8.1 |
| 132 | 5-[8-Fluoro-2-(4-fluorophenyl)imidazo[1,2-a]pyrazin-3-yl]indolin-2-one; | 6.2 |
| 133 | 5-[2-(4-Fluorophenyl)-8-methyl-imidazo[1,2-a]pyrazin-3-yl]indolin-2-one | 6.6 |
| 134 | 5-(2-Phenylimidazo[1,2-a]pyrazin-3-yl)indolin-2-one; | 6.8 |
| 135 | 5-(2-(4-Fluorophenyl)imidazo[1,2-a]pyrazin-3-yl)indolin-2-one; | 7 |
| 136 | 3,3-Difluoro-5-[2-(4-fluorophenyl)-8-morpholino-imidazo[1,2-a]pyrazin-3-yl]indolin-2-one; | 6.4 |
| 137 | 8-Morpholino-3-(2-oxoindolin-5-yl)-N-phenylimidazo[1,2-a]pyrazine-2-carboxamide; | 8.2 |
| 138 | 3-(4-Hydroxyphenyl)-8-morpholino-N-phenyl-imidazo[1,2-a]pyrazine-2-carboxamide; | 7.7 |

TABLE 3-continued

| Example # | Compound Name | GluR1-γ8 (pIC$_{50}$) |
|---|---|---|
| 139 | N-Benzyl-8-morpholino-3-(2-oxo-1,3-dihydrobenzimidazol-5-yl)imidazo[1,2-a]pyrazine-2-carboxamide; | 7.6 |
| 140 | 8-Morpholino-3-(2-oxo-1,3-dihydrobenzimidazol-5-yl)-N-phenyl-imidazo[1,2-a]pyrazine-2-carboxamide; | 7.7 |
| 141 | 5-[8-(Dimethylamino)-2-(4-fluorophenyl)imidazo[1,2-a]pyrazin-3-yl]indolin-2-one; | 9.1 |
| 142 | N-Benzyl-8-morpholino-3-(2-oxoindolin-5-yl)imidazo[1,2-a]pyrazine-2-carboxamide | 7.5 |
| 143 | 3-(2-Oxoindolin-5-yl)-8-(3-oxopiperazin-1-yl)-N-phenyl-imidazo[1,2-a]pyrazine-2-carboxamide; | 7.7 |
| 144 | 8-(Dimethylamino)-3-(2-oxoindolin-5-yl)-N-phenyl-imidazo[1,2-a]pyrazine-2-carboxamide; | 8.2 |
| 145 | N-Methyl-8-morpholino-3-(2-oxo-1,3-dihydrobenzimidazol-5-yl)-N-phenyl-imidazo[1,2-a]pyrazine-2-carboxamide; | 6.3 |
| 146 | N-Cyclopropyl-8-morpholino-3-(2-oxo-1,3-dihydrobenzimidazol-5-yl)imidazo[1,2-a]pyrazine-2-carboxamide; | 6.5 |
| 147 | 8-Morpholino-3-(2-oxo-1,3-dihydrobenzimidazol-5-yl)-N-(4-pyridyl)imidazo[1,2-a]pyrazine-2-carboxamide | 6.3 |
| 148 | 3-(4-Hydroxyphenyl)-8-morpholino-N-propyl-imidazo[1,2-a]pyrazine-2-carboxamide | 6.2 |
| 149 | 8-Morpholino-3-(2-oxoindolin-5-yl)-N-phenylimidazo[1,2-a]pyrazine-2-carboxamide; | 8.4 |
| 150 | N-[(3S)-1-[2-(4-Fluorophenyl)-3-(2-oxoindolin-5-yl)imidazo[1,2-a]pyrazin-8-yl]pyrrolidin-3-yl]acetamide; | 8.5 |
| 151 | [3-(4-Hydroxyphenyl)-8-morpholino-imidazo[1,2-a]pyrazin-2-yl]-phenyl-methanone; | 7.9 |
| 152 | 5-[2-Benzoyl-8-(dimethylamino)imidazo[1,2-a]pyrazin-3-yl]indolin-2-one; | 8.4 |
| 153 | 5-(2-Benzoyl-8-morpholino-imidazo[1,2-a]pyrazin-3-yl)indolin-2-one; | 9.5 |
| 154 | 5-[2-Benzoyl-8-(4-hydroxy-1-piperidyl)imidazo[1,2-a]pyrazin-3-yl]indolin-2-one; | 8.8 |
| 155 | 5-[2-(4-Fluorophenyl)-8-(4-hydroxylmino-1-piperidyl)imidazo[1,2-a]pyrazin-3-yl]indolin-2-one; | 7.1 |
| 156 | 6-(2-Benzoyl-8-morpholino-imidazo[1,2-a]pyrazin-3-yl)-3H-1,3-benzoxazol-2-one; | 8.9 |
| 157 | 5-[2-Benzoyl-8-(1,1-dioxo-1,4-thiazinan-4-yl)imidazo[1,2-a]pyrazin-3-yl]indolin-2-one; | 8.6 |
| 158 | 5-[8-(4-Acetylpiperazin-1-yl)-2-benzoyl-imidazo[1,2-a]pyrazin-3-yl]indolin-2-one; | 8.3 |
| 159 | [3-(2,2-Dioxo-1,3-dihydro-2,1-benzothiazol-5-yl)-8-morpholino-imidazo[1,2-a]pyrazin-2-yl]-phenyl-methanone; | 8.1 |
| 160 | 5[2-Benzoyl-8-(methylamino)imidazo[1,2-a]pyrazin-3-yl]indolin-2-one; | 7.5 |
| 161 | 5-(5-Fluoro-2-(4-fluorophenyl)-8-morpholinoimidazo[1,2-a]pyrazin-3-yl)indolin-2-one | 8.2 |
| 162 | 5-[5-Fluoro-2-(4-fluorophenyl)-8-morpholino-imidazo[1,2-a]pyrazin-3-yl]-1,3-dihydrobenzimidazol-2-one | 8.4 |
| 163 | 5-[5-Chloro-2-(4-fluorophenyl)-8-morpholino-imidazo[1,2-a]pyrazin-3-yl]indolin-2-one; | 9.9 |
| 164 | 5-[2-(4-Fluorophenyl)-7-morpholino-pyrazolo[1,5-c]pyrimidin-3-yl]indolin-2-one; | 9.3 |
| 165 | 5-(2-tert-Butylpyrazolo[1,5-c]pyrimidin-3-yl)indolin-2-one; | <5 |
| 166 | 5-[2-(4-Fluorophenyl)-7-(4-hydroxy-1-piperidyl)pyrazolo[1,5-c]pyrimidin-3-yl]indolin-2-one; | 9.7 |
| 167 | 5-[2-(4-Fluorophenyl)-8-(methylamino)imidazo[1,2-a]pyrazin-3-yl]indolin-2-one; | 7.6 |
| 168 | 5-[2-(4-Fluorophenyl)-7-(3-oxopiperazin-1-yl)pyrazolo[1,5-c]pyrimidin-3-yl]indolin-2-one; | 8.9 |
| 169 | 5-[7-(Dimethylamino)-2-(4-fluorophenyl)pyrazolo[1,5-c]pyrimidin-3-yl]indolin-2-one; | 8.8 |
| 170 | 5-[7-(1,1-Dioxo-1,4-thiazinan-4-yl)-2-(4-fluorophenyl)pyrazolo[1,5-c]pyrimidin-3-yl]indolin-2-one; | 9.2 |
| 171 | 5-[2-(4-Fluorophenyl)-7-(methylamino)pyrazolo[1,5-c]pyrimidin-3-yl]indolin-2-one; | 7.9 |
| 172 | 5-[7-(4-Acetylpiperazin-1-yl)-2-(4-fluorophenyl)pyrazolo[1,5-c]pyrimidin-3-yl]indolin-2-one; | 9.8 |
| 173 | 6-[2-(4-Fluorophenyl)-7-morpholino-pyrazolo[1,5-c]pyrimidin-3-yl]-3H-1,3-benzoxazol-2-one; | 8.9 |
| 174 | 5-[2-(4-Fluorophenyl)-7-(4-oxo-1-piperidyl)pyrazolo[1,5-c]pyrimidin-3-yl]indolin-2-one; | 10.1 |

TABLE 3-continued

| Example # | Compound Name | GluR1-γ8 (pIC$_{50}$) |
|---|---|---|
| 175 | 5-[2-(4-Fluorophenyl)pyrazolo[1,5-c]pyrimidin-3-yl]indolin-2-one; | 6.2 |
| 176 | 5-[7-(3,3-Difluoroazetidin-1-yl)-2-(4-fluorophenyl)pyrazolo[1,5-c]pyrimidin-3-yl]indolin-2-one; | 8.5 |
| 177 | 5-[2-(4-Fluorophenyl)-7-(3-methylmorpholin-4-yl)pyrazolo[1,5-c]pyrimidin-3-yl]indolin-2-one; | 9.7 |
| 178 | 5-[2-(4-Fluorophenyl)-7-morpholino-pyrazolo[1,5-c]pyrimidin-3-yl]-1,3-dihydro-2,1-benzothiazole 2,2-dioxide; | 8.7 |
| 179 | 5-[2-(4-Fluorophenyl)-7-(3-hydroxyazetidin-1-yl)pyrazolo[1,5-c]pyrimidin-3-yl]indolin-2-one; | 8.2 |
| 180 | 5-[2-(4-Fluorophenyl)-7-[3-(hydroxymethyl)azetidin-1-yl]pyrazolo[1,5-c]pyrimidin-3-yl]indolin-2-one; | 8.7 |
| 181 | 5-[2-tert-Butyl-7-(4-hydroxy-1-piperidyl)pyrazolo[1,5-c]pyrimidin-3-yl]indolin-2-one; | 6.7 |
| 182 | 5-(2-tert-Butyl-7-morpholino-pyrazolo[1,5-c]pyrimidin-3-yl)indolin-2-one; | 7.2 |
| 183 | 5-[2-tert-Butyl-7-(3,3-difluoroazetidin-1-yl)pyrazolo[1,5-c]pyrimidin-3-yl]indolin-2-one; | 7.2 |
| 184 | 5-[2-(4-Fluorophenyl)-7-(3-hydroxy-3-methyl-azetidin-1-yl)pyrazolo[1,5-c]pyrimidin-3-yl]indolin-2-one; | 8.5 |
| 185 | 5-[2-(4-Fluorophenyl)-8-(1,2,6-triazaspiro[2;5]oct-1-en-6-yl)imidazo[1,2-a]pyrazin-3-yl]indolin-2-one; | 9.8 |
| 186 | 5-[2-(4-Fluorophenyl)-7-(4-hydroxy-4-methyl-1-piperidyl)pyrazolo[1,5-c]pyrimidin-3-yl]indolin-2-one; | 9.7 |
| 187 | 5-[7-(4-Hydroxy-1-piperidyl)-2-phenyl-pyrazolo[1,5-c]pyrimidin-3-yl]indolin-2-one; | 9.8 |
| 188 | 5-[7-(4-Fluoro-1-piperidyl)-2-phenyl-pyrazolo[1,5-c]pyrimidin-3-yl]indolin-2-one; | 9.3 |
| 189 | 5-[7-(4-Methoxy-1-piperidyl)-2-phenyl-pyrazolo[1,5-c]pyrimidin-3-yl]indolin-2-one; | 9.8 |
| 190 | 5-[2-(4-Fluorophenyl)-7-(4-fluoro-1-piperidyl)pyrazolo[1,5-c]pyrimidin-3-yl]indolin-2-one; | 9.7 |
| 191 | 5-[7-(3-Methoxyazetidin-1-yl)-2-phenyl-pyrazolo[1,5-c]pyrimidin-3-yl]indolin-2-one; | 8.6 |
| 192 | 5-[7-(Cyclopentoxy)-2-phenyl-pyrazolo[1,5-c]pyrimidin-3-yl]indolin-2-one; | 8.1 |
| 193 | trans-5-[7-(3-Fluoro-4-hydroxy-1-piperidyl)-2-phenyl-pyrazolo[1,5-c]pyrimidin-3-yl]indolin-2-one; | 9.5 |
| 194 | 5-(7-Isopropoxy-2-phenyl-pyrazolo[1,5-c]pyrimidin-3-yl)indolin-2-one; | 7.5 |
| 195 | 5-[2-Cyclopentyl-7-(3-methoxyazetidin-1-yl)pyrazolo[1,5-c]pyrimidin-3-yl]indolin-2-one | 6.5 |
| 196 | 5-[2-Cyclopentyl-7-(3-fluoroazetidin-1-yl)pyrazolo[1,5-c]pyrimidin-3-yl]indolin-2-one; | 6.8 |
| 197 | 5-[7-[(3S)-3-Methoxypyrrolidin-1-yl]-2-phenyl-pyrazolo[1,5-c]pyrimidin-3-yl]indolin-2-one; | 8.9 |
| 198 | 5-(5-Methyl-7-morpholino-2-phenyl-pyrazolo[1,5-c]pyrimidin-3-yl)indolin-2-one; | 8.5 |
| 199 | 5-[2-tert-Butyl-7-(6-oxa-2-azaspiro[3;3]heptan-2-yl)pyrazolo[1,5-c]pyrimidin-3-yl]indolin-2-one; | 6.5 |
| 200 | 5-[7-(3-Fluoroazetidin-1-yl)-2-phenyl-pyrazolo[1,5-c]pyrimidin-3-yl]indolin-2-one; | 8.5 |
| 201 | 5-(7-Morpholino-2-phenyl-pyrazolo[1,5-c]pyrimidin-3-yl)indolin-2-one; | 9 |
| 202 | 5-[7-[(3R)-3-Methoxypyrrolidin-1-yl]-2-phenyl-pyrazolo[1,5-c]pyrimidin-3-yl]indolin-2-one; | 8.6 |
| 203 | 5-(2-Cyclopentyl-7-morpholino-pyrazolo[1,5-c]pyrimidin-3-yl)indolin-2-one; | 7.2 |
| 204 | (cis)-5-[7-(3-Fluoro-4-hydroxy-1-piperidyl)-2-phenyl-pyrazolo[1,5-c]pyrimidin-3-yl]indolin-2-one | 8.9 |
| 205 | 5-[2-Cyclopentyl-7-(3-hydroxyazetidin-1-yl)pyrazolo[1,5-c]pyrimidin-3-yl]indolin-2-one; | 6.2 |
| 206 | 5-(7-Methoxy-2-phenyl-pyrazolo[1,5-c]pyrimidin-3-yl)indolin-2-one; | 6.4 |
| 207 | 5-(4-Bromo-7-morpholino-2-phenyl-pyrazolo[1,5-c]pyrimidin-3-yl)indolin-2-one; | 9.4 |
| 208 | 5-(4-Methyl-7-morpholino-2-phenyl-pyrazolo[1,5-c]pyrimidin-3-yl)indolin-2-one; | 9.9 |
| 209 | 4-[3-(1H-Indazol-5-yl)-8-(3-oxopiperazin-1-yl)imidazo[1,2-a]pyrazin-2-yl]benzonitrile; | 8.7 |
| 210 | 4-[3-(2-Oxoindolin-5-yl)-8-(3-oxopiperazin-1-yl)imidazo[1,2-a]pyrazin-2-yl]benzonitrile; | 7.7 |
| 211 | 4-[3-(2-Oxo-1,3-dihydrobenzimidazol-5-yl)-8-(3-oxopiperazin-1-yl)imidazo[1,2-a]pyrazin-2-yl]benzonitrile; | 8.4 |

TABLE 3-continued

| Example # | Compound Name | GluR1-γ8 (pIC$_{50}$) |
|---|---|---|
| 212 | 4-[3-(1H-Indazol-5-yl)-4-methyl-2-phenyl-pyrazolo[1,5-c]pyrimidin-7-yl]morpholine; | 10.1 |
| 213 | 6-[7-(4-Methoxy-1-piperidyl)-2-phenyl-pyrazolo[1,5-c]pyrimidin-3-yl]-3H-1,3-benzothiazol-2-one; | 10.2 |
| 214 | N-Cyclohexyl-8-morpholino-3-(2-oxo-1,3-dihydrobenzimidazol-5-yl)imidazo[1,2-a]pyrazine-2-carboxamide; | 7.5 |
| 215 | 5-[8-(4-Hydroxy-1-piperidyl)-2-(4-pyridyl)imidazo[1,2-a]pyrazin-3-yl]indolin-2-one; | 7.4 |
| 216 | 6-[2-Cyclopropyl-6-(trifluoromethyl)imidazo[1,2-a]pyrazin-3-yl]-3H-1,3-benzothiazol-2-one; | 6.3 |
| 217 | 5-[2-Benzoyl-8-(methylamino)imidazo[1,2-a]pyrazin-3-yl]indolin-2-one; | 6.2 |
| 218 | 5-[2-Phenyl-6-(trifluoromethyl)imidazo[1,2-a]pyrazin-3-yl]indolin-2-one; | 7.0 |
| 219 | 5-[2-Cyclopropyl-6-(trifluoromethyl)imidazo[1,2-a]pyrazin-3-yl]indolin-2-one; | 5.2 |
| 220 | 5-[2-tert-Butyl-8-(4-oxo-1-piperidyl)imidazo[1,2-a]pyrazin-3-yl]indolin-2-one; | 7.2 |
| 221 | 8-Morpholino-3-(2-oxo-1,3-dihydrobenzimidazol-5-yl)-N-(2-pyridyl)imidazo[1,2-a]pyrazine-2-carboxamide; | 7.5 |
| 222 | 5-[2-Phenyl-5-(trifluoromethyl)pyrazolo[1,5-c]pyrimidin-3-yl]indolin-2-one; | 7.9 |
| 223 | 6-[2-Phenyl-5-(trifluoromethyl)pyrazolo[1,5-c]pyrimidin-3-yl]-3H-1,3-benzoxazol-2-one; | 6.3 |
| 224 | 6-[2-phenyl-5-(trifluoromethyl)pyrazolo[1,5-c]pyrimidin-3-yl]-3H-1,3-benzothiazol-2-one; | 7.7 |
| 225 | 5-[2-tert-Butyl-5-(trifluoromethyl)pyrazolo[1,5-c]pyrimidin-3-yl]indolin-2-one; | 6.3 |
| 226 | 5-[2-Cyclobutyl-5-(trifluoromethyl)pyrazolo[1,5-c]pyrimidin-3-yl]indolin-2-one; | 6.1 |
| 227 | 5-[2-Isopropyl-5-(trifluoromethyl)pyrazolo[1,5-c]pyrimidin-3-yl]indolin-2-one; | 5.8 |
| 228 | 5-[2-Cyclopropyl-5-(trifluoromethyl)pyrazolo[1,5-c]pyrimidin-3-yl]indolin-2-one; | 4.4 |
| 229 | 6-[2-Cyclobutyl-5-(trifluoromethyl)pyrazolo[1,5-c]pyrimidin-3-yl]-3H-1,3-benzothiazol-2-one; | 7.8 |
| 230 | 6-[2-Cyclopropyl-5-(trifluoromethyl)pyrazolo[1,5-c]pyrimidin-3-yl]-3H-1,3-benzothiazol-2-one; | 6.4 |
| 231 | 6-[2-Isopropyl-5-(trifluoromethyl)pyrazolo[1,5-c]pyrimidin-3-yl]-3H-1,3-benzothiazol-2-one; | 7.2 |
| 232 | 6-[2-tert-Butyl-5-(trifluoromethyl)pyrazolo[1,5-c]pyrimidin-3-yl]-3H-1,3-benzothiazol-2-one; | 6.5 |
| 233 | 4-[3-(1H-Indazol-5-yl)-2-phenyl-pyrazolo[1,5-c]pyrimidin-7-yl]morpholine; | 9.4 |
| 234 | 3-(1H-Indazol-5-yl)-7-(4-methoxy-1-piperidyl)-2-phenyl-pyrazolo[1,5-c]pyrimidine; | 9.2 |
| 235 | 5-(4-Fluoro-2-isopropyl-7-morpholino-pyrazolo[1,5-c]pyrimidin-3-yl)indolin-2-one; | 6.3 |
| 236 | 4-[4-Fluoro-3-(1H-indazol-5-yl)-2-isopropyl-pyrazolo[1,5-c]pyrimidin-7-yl]morpholine; | 6.8 |
| 237 | 3-(1H-indazol-5-yl)-2-isopropyl-7-(4-methoxy-1-piperidyl)pyrazolo[1,5-c]pyrimidine; | 6.9 |
| 238 | 4-[3-(1H-Indazol-5-yl)-2-isopropyl-pyrazolo[1,5-c]pyrimidin-7-yl]morpholine; | 6.4 |
| 239 | 4-[3-(1H-Indazol-5-yl)-2-isopropyl-4-methyl-pyrazolo[1,5-c]pyrimidin-7-yl]morpholine; | 7.4 |
| 240 | 6-(2-Isopropyl-7-morpholino-pyrazolo[1,5-c]pyrimidin-3-yl)-3H-1,3-benzothiazol-2-one; | 7.8 |
| 241 | 6-[2-Isopropyl-7-(4-methoxy-1-piperidyl)pyrazolo[1,5-c]pyrimidin-3-yl]-3H-1,3-benzothiazol-2-one; | 8.6 |
| 242 | 6-(7-Morpholino-2-phenyl-pyrazolo[1,5-c]pyrimidin-3-yl)-3H-1,3-benzothiazol-2-one; | 10.3 |
| 243 | 6-(2-Isopropyl-4-methyl-7-morpholino-pyrazolo[1,5-c]pyrimidin-3-yl)-3H-1,3-benzothiazol-2-one; | 8.4 |
| 244 | 5-(2-Isopropyl-4-methyl-7-morpholino-pyrazolo[1,5-c]pyrimidin-3-yl)indolin-2-one; | 7.1 |
| 245 | 6-[2-Phenyl-6-(trifluoromethyl)imidazo[1,2-a]pyrazin-3-yl]-3H-1,3-benzothiazol-2-one; | 7.9 |
| 246 | 5-[2-Benzoyl-8-(3-oxopiperazin-1-yl)imidazo[1,2-a]pyrazin-3-yl]indolin-2-one; | 7.5 |
| 247 | 5-[2-(4-Fluorophenyl)-8-methoxy-imidazo[1,2-a]pyrazin-3-yl]indolin-2-one; | 7.1 |
| 248 | 5-[8-Amino-2-(4-fluorophenyl)imidazo[1,2-a]pyrazin-3-yl]indolin-2-one; | 5.3 |
| 249 | 5-[2-(4-fluorophenyl)-8-hydroxy-imidazo[1,2-a]pyrazin-3-yl]-1,3-dihydrobenzimidazol-2-one; and | 5.8 |

TABLE 3-continued

| Example # | Compound Name | GluR1-γ8 (pIC$_{50}$) |
|---|---|---|
| 250 | N-[(3R)-1-[2-(4-fluorophenyl)-3-(2-oxoindolin-5-yl)imidazo[1,2-a]pyrazin-8-yl]pyrrolidin-3-yl]acetamide. | 7.4 |

NT means not tested

Electrophysiology Assay

The effects of selected compounds upon endogenous γ 8-containing AMPA receptor currents was evaluated using whole-cell electrophysiology on acutely-dissociated mouse hippocampal neurons. Hippocampus was chosen for this assay, since CACNG8 (the protein encoded by this gene is a type I transmembrane AMPA receptor regulatory protein i.e., TARP) is preferentially enriched in this brain region (Tomita et al. (2003). "Functional studies and distribution define a family of transmembrane AMPA receptor regulatory proteins." *J Cell Biol* 161(4): 805-816.2003).

Hippocampi were dissected from C57black6 mice at 4-12 weeks postnatal, following the protocol described by Brewer (Brewer, G. J. (1997). "Isolation and culture of adult rat hippocampal neurons." *Journal of Neuroscience Methods* 71(2): 143-155). The following is a brief summary of the procedure. Mice were asphyxiated with $CO_2$ then decapitated. The brain was rapidly removed, then placed into ice-cold HABG medium. The recipe for HABG medium was: HibernateA supplemented with 2% B27 and 0.5 mM Glutamax (all reagents from Life Technologies). Hippocampi were micro-dissected from the brains, then washed with HABG without calcium (Hibernate A minus Calcium, BrainBits; 2% B27, Life Technologies; 0.5 mM glutamax, Life Technologies).

The hippocampi were then transferred to HABG without calcium, supplemented with 2 mg/mL papain (Worthington Biochemical). They were incubated at 30° C. on a roller for 40 min, then gently triturated with a fire-polished glass pipette. The supernatant containing dissociated neurons was collected, then centrifuged for 2 min at 200 g. The cell pellet was collected, and then resuspended in 8 mL of HABG. Live cells were counted, then plated onto 12 mm glass coverslips in HABG (2 mL) in 24-well plates at a density of 50-100 cells per coverslip. These cells were maintained at room temperature until use.

Whole-cell electrophysiology was performed using 1.5 mm diameter glass capillary tubes (World Precision Instruments TW150-4), pulled to a fine tip with a Sutter P-97 micropipette puller. The intracellular buffer was 90 mM KF, 30 mM KCl, 10 mM HEPES, and 5 mM EGTA, pH 7.4, 290mOs. The extracellular buffer was 135 mM NaCl, 4 mM KCl, 2 mM $CaCl_2$, 1 mM $MgCl_2$, 5 mM glucose, 10 mM HEPES, pH 7.4, 300 mOs. The open-tip resistances of the micropipettes using these solutions were 2-4 MΩ. Whole-cell recordings of neuron cell bodies were performed in voltage-clamp mode using an Axon Axopatch 200B amplifier. Whole-cell current was measured holding the interior of the cell at −60 mV, using a 5 kHz lowpass filter. The cells were continuously perfused through 7 mm square glass barrels using a solenoid-controlled solution switching device (Warner Instruments, PF-77B). The peak current in response to a 500 ms exposure to 10 mM glutamate every 5 seconds was measured, before and after exposure to test compound.

For analysis, the mean peak current of 5 traces in the presence of test compound was divided by the mean peak current of 5 traces prior to the addition of test compound. Compounds were tested at concentrations at least ten times higher than their estimated potency in the calcium flux assay, in order to ensure near-saturating occupancy of the receptor.

TABLE 4

| Example No. | concentration (μM) | peak current (% control) | N |
|---|---|---|---|
| 7 | 10 | 55% | 6 |
| 10 | 0.1 | 64% | 10 |
| 37 | 0.1 | 66% | 6 |
| 107 | 0.1 | 67% | 7 |
| 17 | 0.1 | 68% | 6 |
| 12 | 0.1 | 69% | 9 |
| 10 | 1 | 74% | 3 |
| 83 | 10 | 78% | 4 |
| 1 | 10 | 81% | 5 |

All patents, patent applications, publications and presentations referred to herein are incorporated by reference in their entirety.

Any combination of the groups described above for the various variables is contemplated herein. Throughout the specification, groups and substituents thereof are chosen by one skilled in the field to provide stable moieties and compounds.

While the foregoing specification teaches the principles of the present invention, and specific embodiments of the invention have been described for the purposes of illustration, and examples have been provided for the purposes of illustration, it will be understood that various modifications may be made without deviating from the spirit and scope of the invention as come within the scope of the following claims and their equivalents.

What is claimed:

1. A compound of Formula (I), and pharmaceutically acceptable salts, N-oxides, or solvates thereof,

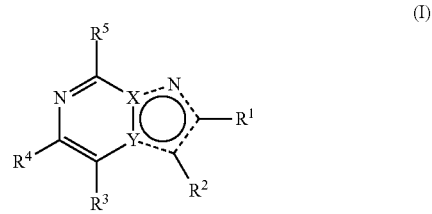

wherein
X is C or N;
Y is C or N; provided that X and Y cannot both be C, and X and Y cannot both be N;
the dotted line (- - - - -) indicates that the referenced bond is a single bond or a double bond;
$R^1$ is selected from the group consisting of: $C_{1-5}$alkyl; $C_{3-7}$cycloalkyl; phenyl optionally substituted with one, two or three members independently selected from halo and —CN; $CH_2$-phenyl optionally substituted with halo; C(=O)-phenyl, wherein said phenyl is optionally substituted with halo; C(=O)N(CH$_3$)-phenyl; C(=O)NH-phenyl; C(=O)NH—CH$_2$-phenyl; C(=O)NH-pyridinyl; C(=O)NH—C$_{3-7}$cycloalkyl; C(=O)NH—C$_{1-5}$alkyl; and pyridinyl;

R$^2$ is selected from the group consisting of:

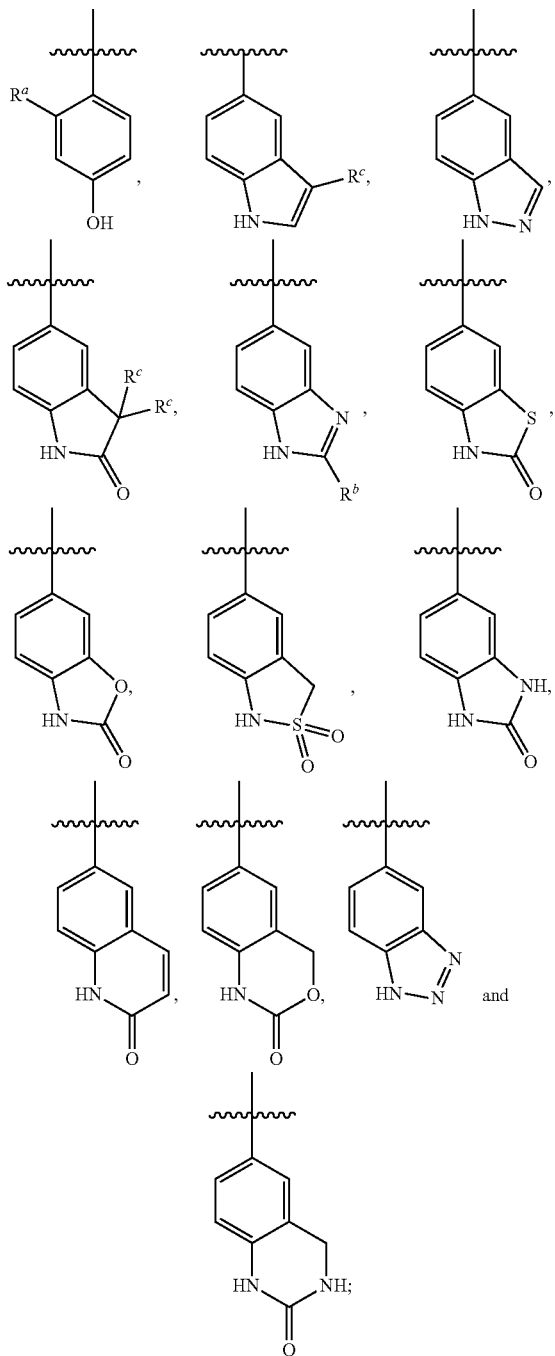

R$^a$ is H or —CH$_3$;
R$^b$ is H or —NH$_2$; and
R$^c$ is independently selected from: H and —F;
R$^3$ is selected from the group consisting of: H, $^3$H, —CH$_3$ and halo;

R$^4$ is H, —CH$_3$, or CF$_3$; and
R$^5$ is selected from the group consisting of:
H; halo; —C$_{1-5}$alkyl; —C$_{1-5}$alkoxy; —NH$_2$; —NH(C$_{1-5}$alkyl); —N(C$_{1-5}$alkyl)$_2$; —NH-2-oxopyrrolidin-3-yl; —N(CH$_3$)cyclopropyl; —N(C$_{1-5}$alkyl)$_2$; —SO$_2$CH$_3$; —(S=O)CH$_3$; —OH; —O-cyclopentyl; azetidinyl optionally independently substituted with one or two members selected from the group consisting of: halo, —CH$_3$, —CF$_3$, —OCH$_3$, —SO$_2$CH$_3$, —CH$_2$OH, —OH, and —CN; pyrrolidinyl optionally substituted with —OH, —OCH$_3$ or —NH—(C=O)CH$_3$; piperidine optionally independently substituted with one, two, or three members selected from the group consisting of: halo, —OH, —CH$_3$, —OCH$_3$, —CH$_2$F, —CH$_2$CH$_2$F, and —NH—(C=O)CH$_3$; piperazine optionally substituted with —CH$_3$, —(C=O)CH$_3$, or —CO$_2$tBu; morpholine optionally independently substituted with one or two —CH$_3$, or —CF$_3$; octadeuteriomorpholin-4-yl; 6-oxa-2-azaspiro[3.3]heptan-2-yl; 3-oxopiperazin-1-yl optionally substituted with one or two —CH$_3$; 1,1-dioxo-1,4-thiazinan-4-yl; 1,4-dioxa-8-azaspiro[4.5]decan-8-yl; 6-oxa-3-azabicyclo[3.1.1]heptan-3-yl; 5-azaspiro[2.3]hexan-5-yl; diazapanyl optionally substituted with —(C=O)CH$_3$; 4-oxopiperidin-1-yl; dihydro-2H-pyridinyl optionally substituted with —(C=O)CH$_3$; dihydro-2H-pyranyl; 4-hydroxyimino-1-piperidyl; and 1,2,6-triazaspiro[2.5]oct-1-en-6-yl.

2. A compound of claim 1, and pharmaceutically acceptable salts, N-oxides, or solvates thereof, wherein
X is C or N;
Y is C or N; provided that X and Y cannot both be C, and X and Y cannot both be N;
the dotted line (- - - - -) indicates that the referenced bond is a single bond or a double bond;
R$^1$ is selected from the group consisting of: C$_{1-5}$alkyl; C$_{3-7}$cycloalkyl; phenyl optionally substituted with one, two or three members independently selected from halo and —CN; CH$_2$-phenyl optionally substituted with halo; C(=O)-phenyl, wherein said phenyl is optionally substituted with halo; C(=O)N(CH$_3$)-phenyl; C(=O)NH-phenyl; C(=O)NH—CH$_2$-phenyl; C(=O)NH-pyridinyl; C(=O)NH—C$_{3-7}$cycloalkyl; C(=O)NH—C$_{1-5}$alkyl; and pyridinyl;
R$^2$ is selected from the group consisting of:

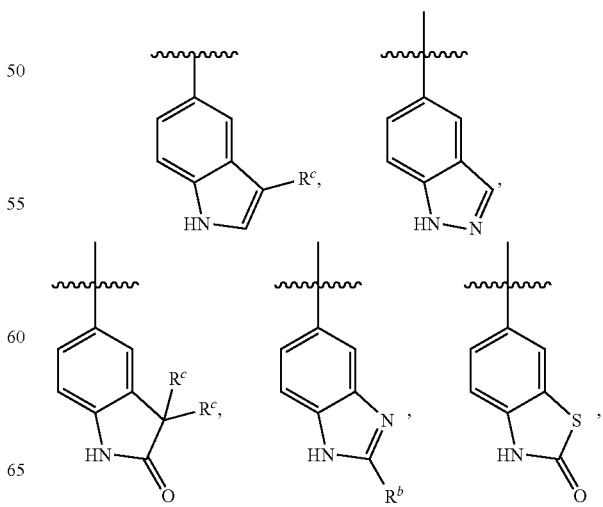

-continued

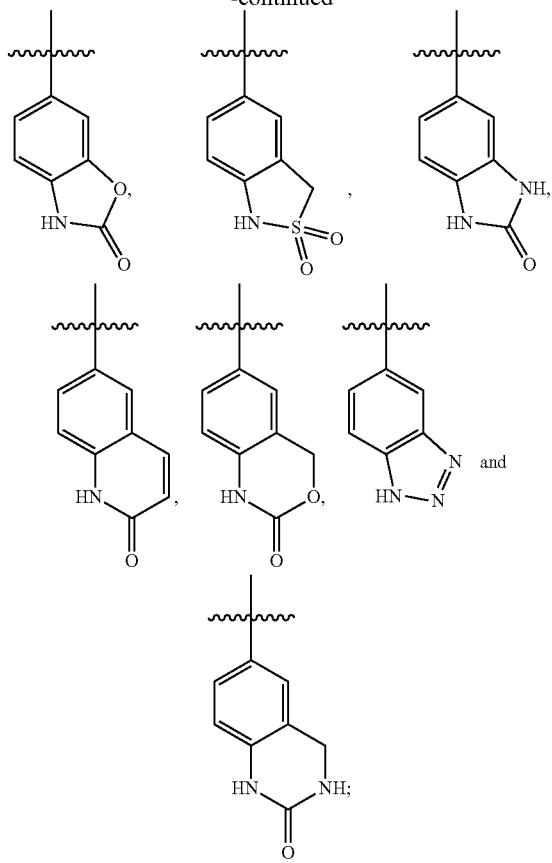

R^b is H or —NH$_2$; and
R^c is independently selected from: H and —F;
R$^3$ is selected from the group consisting of: H, $^3$H, —CH$_3$ and halo;
R$^4$ is H, —CH$_3$, or CF$_3$; and
R$^5$ is selected from the group consisting of:
 H; halo; —C$_{1-5}$alkyl; —C$_{1-5}$alkoxy; —NH$_2$; —NH (C$_{1-5}$alkyl); —N(C$_{1-5}$alkyl)$_2$; —NH-2-oxopyrrolidin-3-yl; —N(CH$_3$)cyclopropyl; —N(C$_{1-5}$alkyl)$_2$; —SO$_2$CH$_3$; —(S=O)CH$_3$; —OH; —O-cyclopentyl; azetidinyl optionally independently substituted with one or two members selected from the group consisting of: halo, —CH$_3$, —CF$_3$, —OCH$_3$, —SO$_2$CH$_3$, —CH$_2$OH, —OH, and —CN; pyrrolidinyl optionally substituted with —OH, —OCH$_3$ or —NH—(C=O)CH$_3$; piperidine optionally independently substituted with one, two, or three members selected from the group consisting of: halo, —OH, —CH$_3$, —OCH$_3$, —CH$_2$F, —CH$_2$CH$_2$F, and —NH—(C=O)CH$_3$; piperazine optionally substituted with —CH$_3$, —(C=O)CH$_3$, or —CO$_2$tBu; morpholine optionally independently substituted with one or two —CH$_3$, or —CF$_3$; octadeuteriomorpholin-4-yl; 6-oxa-2-azaspiro[3.3]heptan-2-yl; 3-oxopiperazin-1-yl optionally substituted with one or two —CH$_3$; 1,1-dioxo-1,4-thiazinan-4-yl; 1,4-dioxa-8-azaspiro[4.5]decan-8-yl; 6-oxa-3-azabicyclo[3.1.1]heptan-3-yl; 5-azaspiro[2.3]hexan-5-yl; diazapanyl optionally substituted with —(C=O)CH$_3$; 4-oxopiperidin-1-yl; dihydro-2H-pyridinyl optionally substituted with —(C=O)CH$_3$; dihydro-2H-pyranyl; 4-hydroxyimino-1-piperidyl; and 1,2,6-triazaspiro[2.5]oct-1-en-6-yl.

3. A compound of claim 1, and pharmaceutically acceptable salts, N-oxides, or solvates thereof, wherein X is C and Y is N, having the structure of Formula (II):

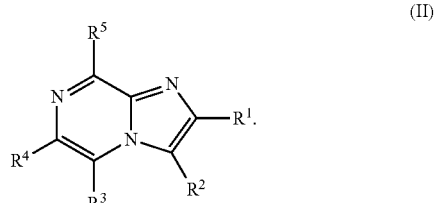

4. A compound of claim 1, and pharmaceutically acceptable salts, N-oxides, or solvates thereof, wherein X is C and Y is N, having the structure of Formula (III):

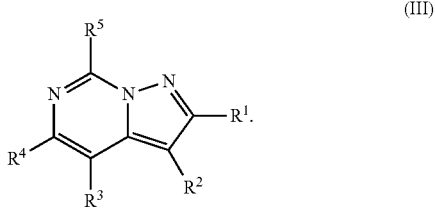

5. A compound of claim 1, wherein R$^1$ is —C$_{1-5}$alkyl; C$_{3-7}$cycloalkyl; phenyl optionally substituted with one, two, or three members independently selected from halo and —CN; CH$_2$-phenyl optionally substituted with halo; C(=O)-phenyl, wherein said phenyl is optionally substituted with halo; or pyridinyl.

6. A compound of claim 1, wherein R$^1$ is C(=O)N(CH$_3$)-phenyl; C(=O)NH-phenyl; C(=O)NH—CH$_2$-phenyl; C(=O)NH-pyridinyl; C(=O)NH—C$_{3-7}$cycloalkyl; or C(=O)NH—C$_{1-5}$alkyl.

7. A compound of claim 1, wherein R$^1$ is C$_{1-5}$alkyl, phenyl, or CH$_2$-phenyl, wherein the phenyl rings are independently optionally substituted with one or two substituents selected from halo or —CN.

8. A compound of claim 1, wherein R$^1$ is phenyl independently optionally substituted with one or two substituents selected from halo or —CN.

9. A compound of claim 1, wherein R$^2$ is selected from the group consisting of:

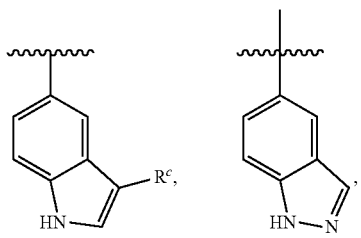

-continued

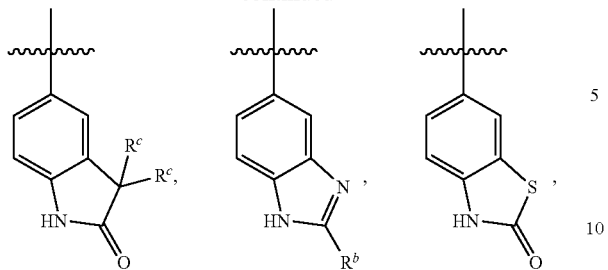

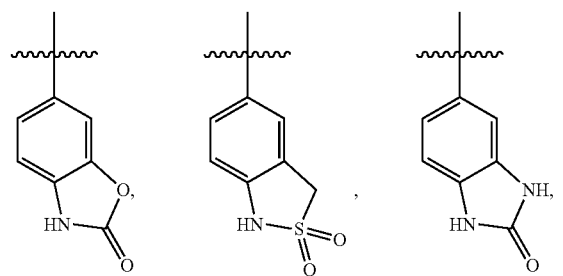

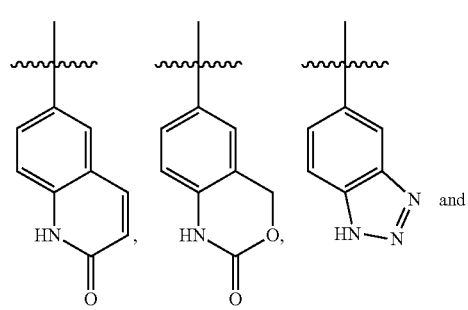

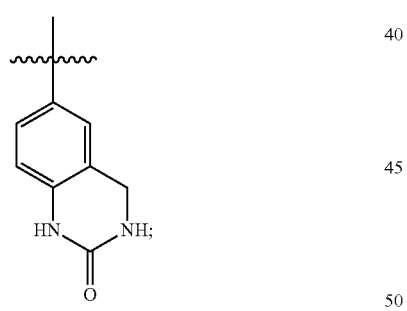

wherein $R^b$ and $R^c$ are as defined above in Formula (I).

10. A compound of claim 1, wherein $R^2$ is:

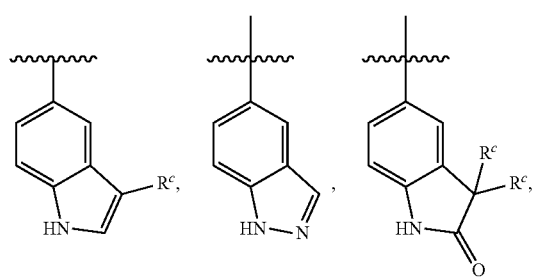

-continued

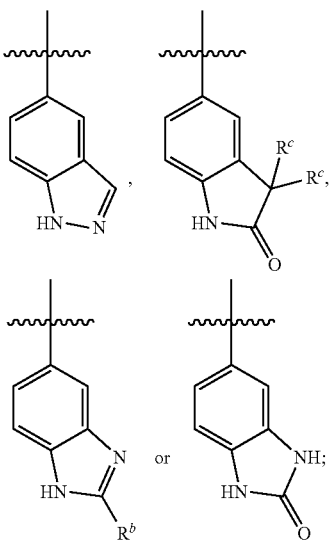

and $R^c$ is independently H or —F.

11. A compound of claim 1, wherein $R^2$ is:

and $R^c$ is independently H or —F.

12. A compound of claim 1, wherein $R^2$ is:

and $R^c$ is independently H or —F.

13. A compound of claim 1, wherein $R^3$ is H.
14. A compound of claim 1, wherein $R^3$ is H, $^3$H, —CH$_3$ or halo.
15. A compound of claim 1, wherein $R^3$ is —F, —Cl or —Br.
16. A compound of claim 1, wherein $R^3$ is —Br.
17. A compound of claim 1, wherein $R^3$ is —CH$_3$.
18. A compound of claim 1, wherein $R^3$ and $R^4$ are H.
19. A compound of claim 1, wherein $R^5$ is H; halo; —C$_{1-5}$alkyl; —C$_{1-5}$alkoxy; —NH$_2$; —NH(C$_{1-5}$alkyl); —N(C$_{1-5}$alkyl)$_2$; —NH-2-oxopyrrolidin-3-yl; —N(CH$_3$)cyclopropyl; —N(C$_{1-5}$alkyl)$_2$; —SO$_2$CH$_3$; —(S=O)CH$_3$; —OH; or —O-cyclopentyl.

20. A compound of claim 1, wherein $R^5$ is H; halo; —OH; —CH₃; —OCH₃; —OCH(CH₃)₂; —NH₂; —NH(CH₃); —N(CH₃)₂; —N(CH₂CH₃)₂; —N(CH₃)cyclopropyl; —SO₂CH₃; —(S=O)CH₃; or

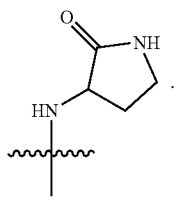 [SMILES: *NC1CCNC1=O]

21. A compound of claim 1, wherein $R^5$ is F, —CH₃, —(S=O)CH₃, —SO₂CH₃, —NH(CH₃), —N(CH₃)₂, or —OCH₃.

22. A compound of claim 1, wherein $R^5$ is H; —C₁₋₅alkoxy; —NH(C₁₋₅alkyl); —N(C₁₋₅alkyl)₂; and —O-cyclopentyl.

23. A compound of claim 1, wherein $R^5$ is: azetidinyl optionally independently substituted with one or two members selected from the group consisting of: halo, —CH₃, —CF₃, —OCH₃, —SO₂CH₃, —CH₂OH, —OH, and —CN; pyrrolidinyl optionally substituted with —OH, —OCH₃ or —NH—(C=O)CH₃; piperidine optionally independently substituted with one, two, or three members selected from the group consisting of: halo, —OH, —CH₃, —OCH₃, —CH₂F, —CH₂CH₂F, and —NH—(C=O)CH₃; piperazine optionally substituted with —CH₃, —(C=O)CH₃, or —CO₂tBu; morpholine optionally independently substituted with one or two —CH₃, or —CF₃; octadeuteriomorpholin-4-yl; 6-oxa-2-azaspiro[3.3]heptan-2-yl; 3-oxopiperazin-1-yl optionally substituted with one or two —CH₃; 1,1-dioxo-1,4-thiazinan-4-yl; 1,4-dioxa-8-azaspiro[4.5]decan-8-yl; 6-oxa-3-azabicyclo[3.1.1]heptan-3-yl; 5-azaspiro[2.3]hexan-5-yl; diazapanyl optionally substituted with —(C=O)CH₃; 4-oxopiperidin-1-yl; dihydro-2H-pyridinyl optionally substituted with —(C=O)CH₃; dihydro-2H-pyranyl; 4-hydroxyimino-1-piperidyl; or 1,2,6-triazaspiro[2.5]oct-1-en-6-yl.

24. A compound of claim 1, wherein $R^5$ is H.

25. A compound of claim 1, wherein $R^5$ is:

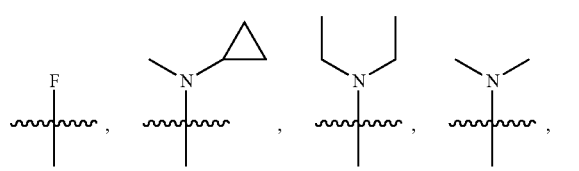

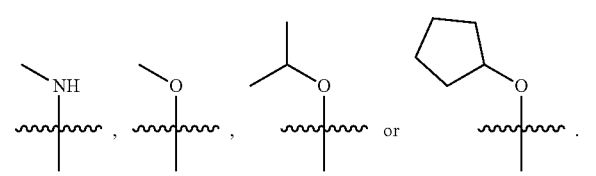

26. A compound of claim 1, wherein $R^5$ is

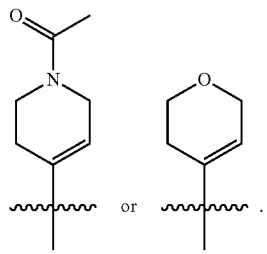

27. A compound of claim 1, wherein $R^5$ is:

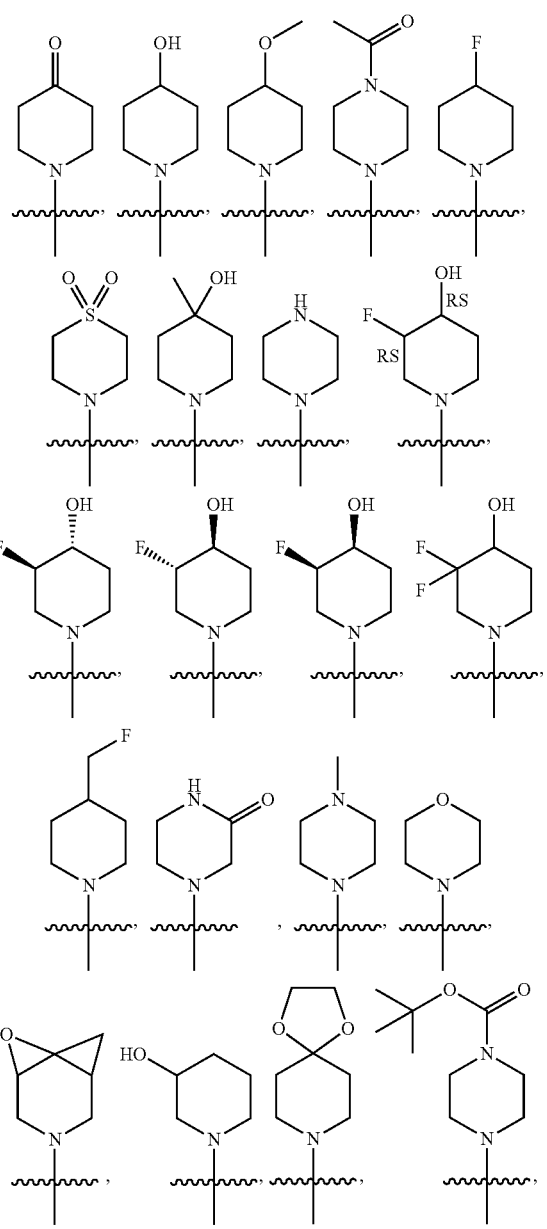

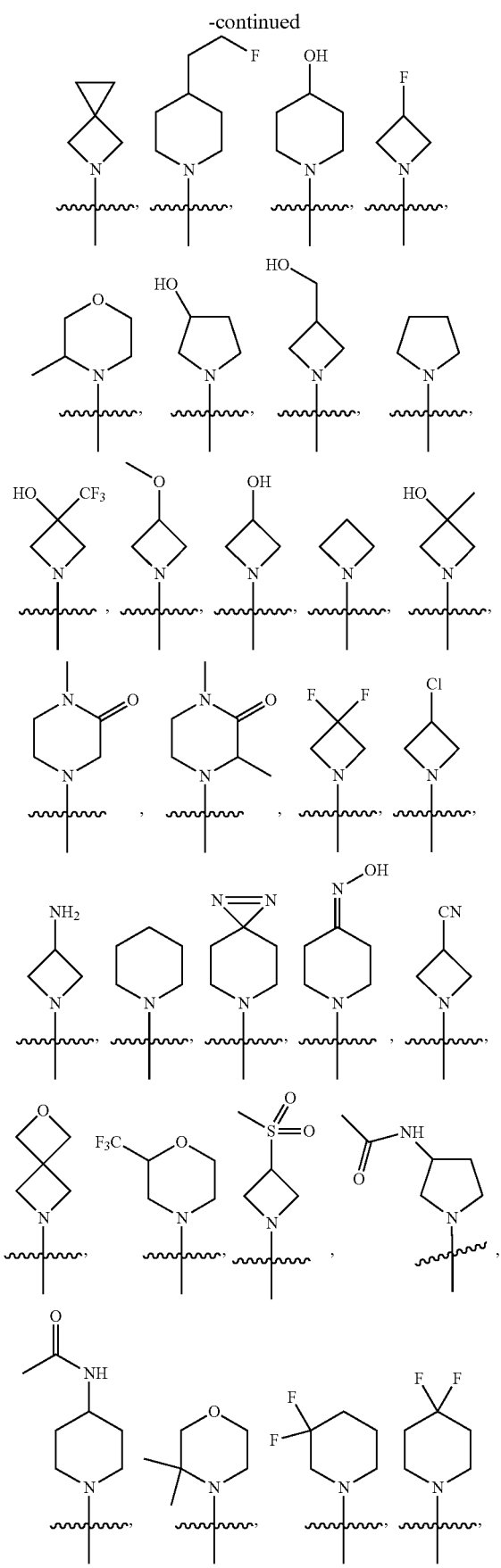
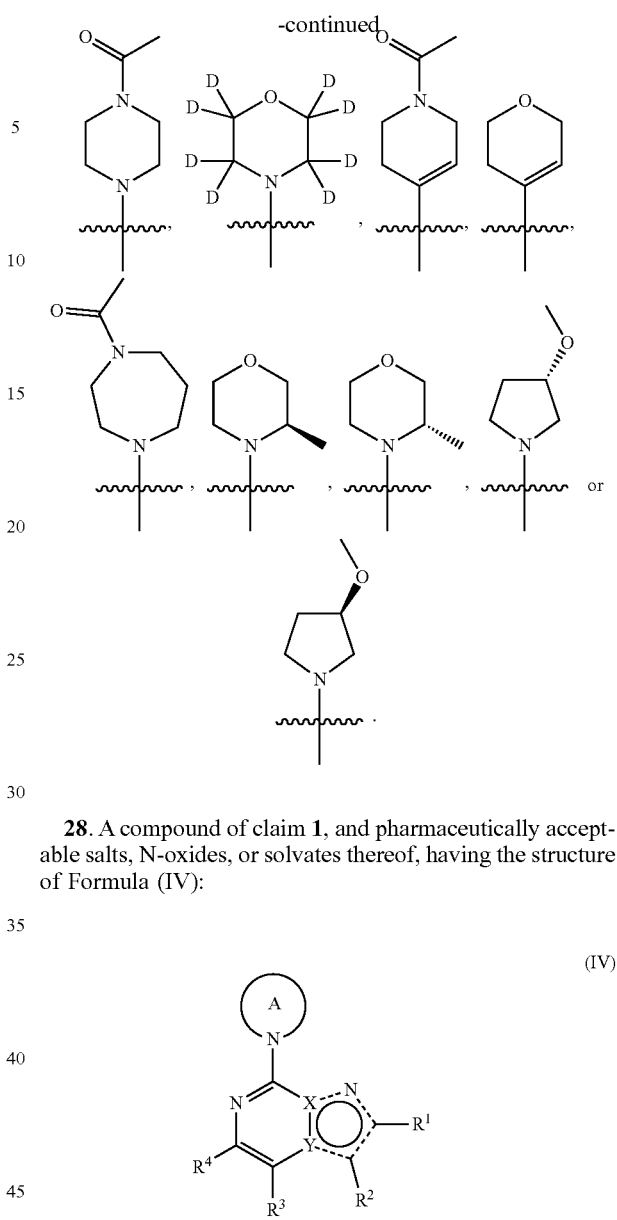

28. A compound of claim 1, and pharmaceutically acceptable salts, N-oxides, or solvates thereof, having the structure of Formula (IV):

$R^1$, $R^2$, $R^3$ and $R^4$ are as defined in claim 1; and
Ring A is azetidinyl optionally independently substituted with one or two members selected from the group consisting of: halo, —CH₃, —CF₃, —OCH₃, —SO₂CH₃, —CH₂OH, —OH, and —CN; pyrrolidinyl optionally substituted with —OH, —OCH₃ or —NH—(C═O)CH₃; piperidine optionally independently substituted with one, two, or three members selected from the group consisting of: halo, —OH, —CH₃, —OCH₃, —CH₂F, —CH₂CH₂F, and —NH—(C═O)CH₃; piperazine optionally substituted with —CH₃, —(C═O)CH₃, or —CO₂tBu; morpholine optionally independently substituted with one or two —CH₃, or —CF₃; octadeuteriomorpholin-4-yl; 6-oxa-2-azaspiro[3.3]heptan-2-yl; 3-oxopiperazin-1-yl optionally substituted with one or two —CH₃; 1,1-dioxo-1,4-thiazinan-4-yl; 1,4-dioxa-8-azaspiro[4.5]decan-8-yl; 6-oxa-3-azabicyclo[3.1.1]heptan-3-yl; 5-azaspiro[2.3]hexan-5-yl; diazapanyl optionally substituted with —(C═O)CH₃; 4-oxopiperidin-1-yl; dihydro-2H-pyridinyl optionally substituted with —(C=O)CH₃; 4-hydroxyimino-1-piperidyl; or 1,2,6-triazaspiro[2.5]oct-1-en-6-yl.
29. A compound of claim 28, wherein Ring A is:
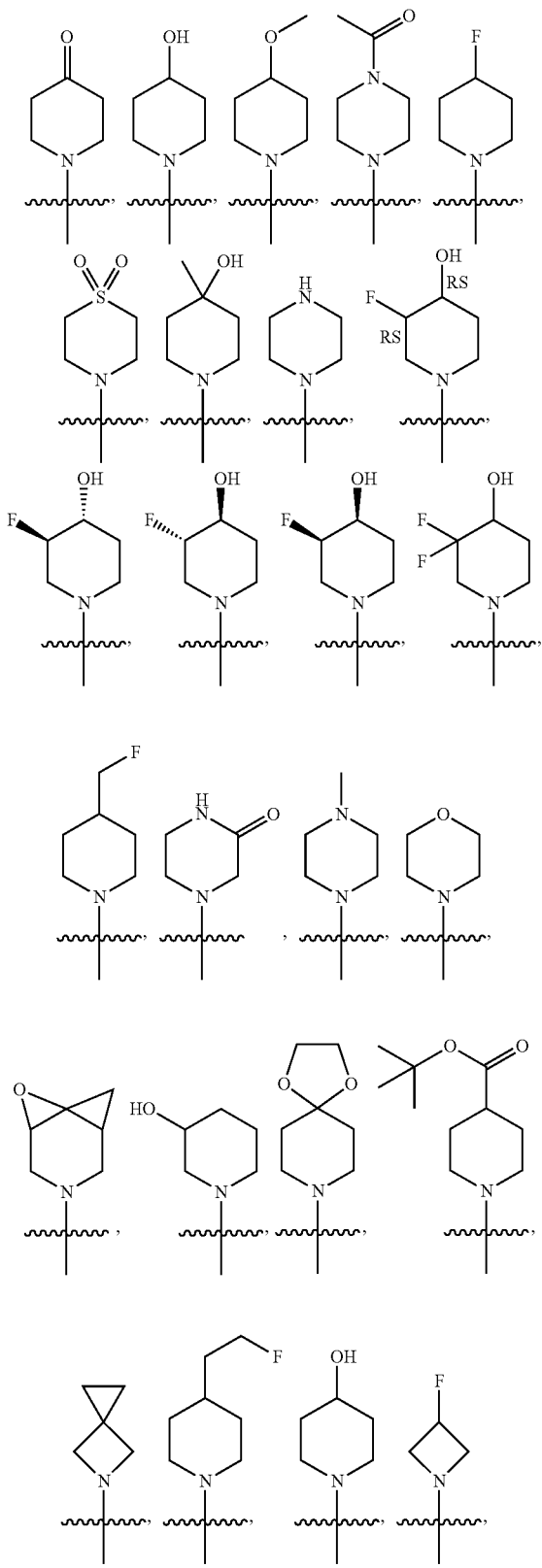
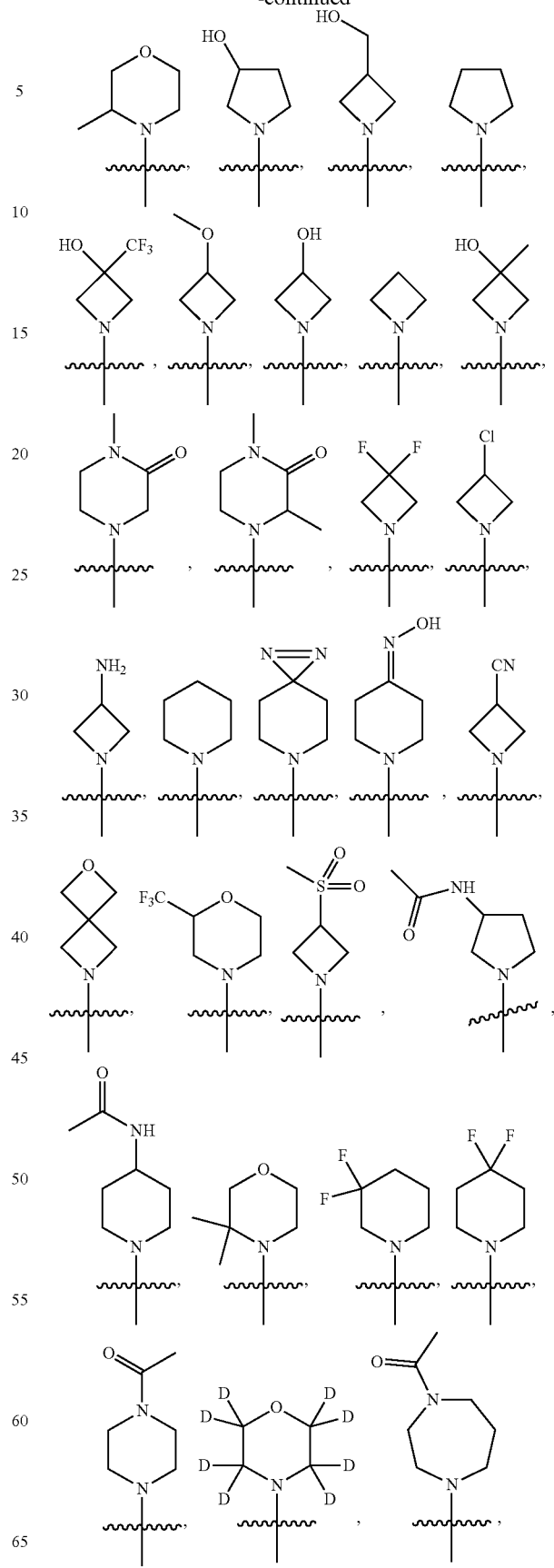

-continued

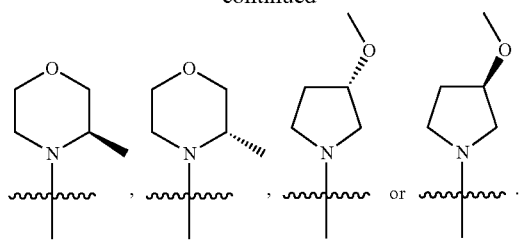

30. A compound of claim 28, wherein R² is:

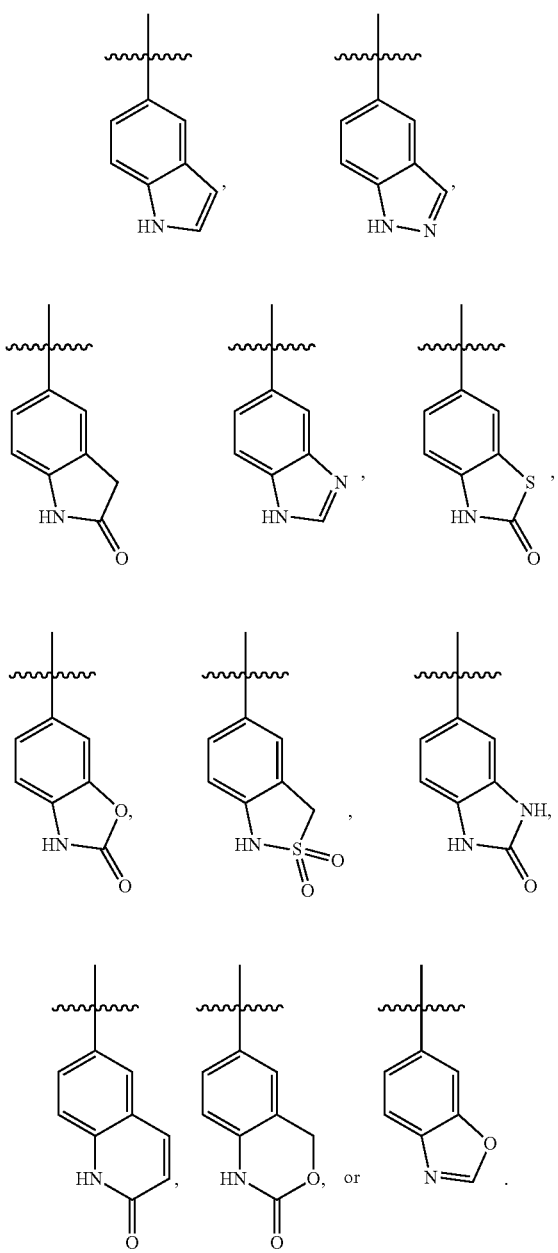

31. A compound of claim 1, and pharmaceutically acceptable salts, N-oxides, or solvates thereof, having the structure of Formula (IA):

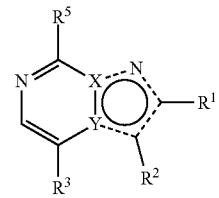

X is C and Y is N;
the dotted line (- - - - -) indicates that the referenced bond is a single bond or a double bond;
R¹ is selected from the group consisting of: —CH(CH₃)₂, —C(CH₃)₃, 4-fluorophenyl, 3-fluorophenyl, 2-fluorophenyl, 3,4-difluorophenyl, 4-chlorophenyl, 4-cyanophenyl, phenyl, benzyl, and (3-fluorophenyl)methyl;
R² is selected from the group consisting of:

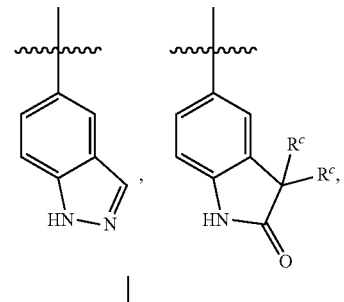

R³ is selected from the group consisting of: H, —CH₃ and halo; and
R⁵ is selected from the group consisting of:
H; halo; —C₁₋₅alkyl; —C₁₋₅alkoxy; —NH₂; —NH(C₁₋₅alkyl); —N(C₁₋₅alkyl)₂; —NH-2-oxopyrrolidin-3-yl; —N(CH₃)cyclopropyl; —N(C₁₋₅alkyl)₂; —SO₂CH₃; —(S=O)CH₃; —OH; —O— cyclopentyl; azetidinyl optionally independently substituted with one or two members selected from the group consisting of: halo, —CH₃, —CF₃, —OCH₃, —SO₂CH₃, —CH₂OH, —OH, and —CN; pyrrolidinyl optionally substituted with —OH, —OCH₃ or —NH—(C=O)CH₃; piperidine optionally independently substituted with one, two, or three members selected from the group consisting of: halo, —OH, —CH₃, —OCH₃, —CH₂F, —CH₂CH₂F, and —NH—(C=O)CH₃; piperazine optionally substituted with —CH₃, —(C=O)CH₃, or —CO₂tBu; morpholine optionally independently substituted with one or two —CH₃, or —CF₃; octadeuteriomorpholin-4-yl; 6-oxa-2-azaspiro[3.3]heptan-2-yl; 3-oxopiperazin-1-yl optionally substituted with one or two —CH₃; 1,1-dioxo-1,4-thiazinan-4-yl; 1,4-dioxa-8-azaspiro[4.5]decan-8-yl; 6-oxa-3-azabicyclo

[3.1.1]heptan-3-yl; 5-azaspiro[2.3]hexan-5-yl; diazapanyl optionally substituted with —(C═O)CH₃; 4-oxopiperidin-1-yl; dihydro-2H-pyridinyl optionally substituted with —(C═O)CH₃; dihydro-2H-pyranyl; 4-hydroxyimino-1-piperidyl; and 1,2,6-triazaspiro[2.5]oct-1-en-6-yl.

32. A compound of claim 31, and pharmaceutically acceptable salts, N-oxides, or solvates thereof, wherein X is N and Y is C, and having the structure of Formula (IIA):

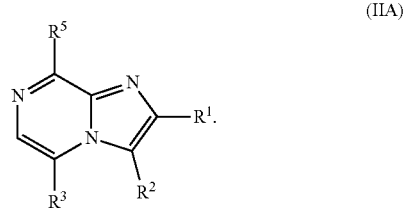

(IIA)

33. A compound of claim 31, and pharmaceutically acceptable salts, N-oxides, or solvates thereof, wherein X is N and Y is C, and having the structure of Formula (IIIA):

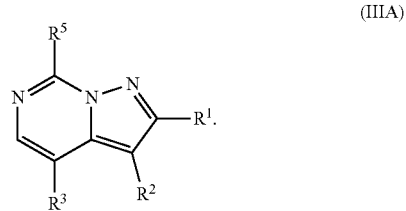

(IIIA)

34. A compound selected from the group consisting of:
1-[4-[2-(4-Fluorophenyl)-3-(4-hydroxyphenyl)imidazo[1,2-a]pyrazin-8-yl]piperazin-1-yl]ethanone;
4-[2-(4-Fluorophenyl)-8-morpholino-imidazo[1,2-a]pyrazin-3-yl]-3-methyl-phenol;
tert-Butyl 4-[2-(4-fluorophenyl)-3-(4-hydroxyphenyl)imidazo[1,2-a]pyrazin-8-yl]piperazine-1-carboxylate;
4-[2-(3-Fluorophenyl)-8-morpholino-imidazo[1,2-a]pyrazin-3-yl]phenol;
4-[2-(4-Fluorophenyl)-8-piperazin-1-yl-imidazo[1,2-a]pyrazin-3-yl]phenol;
4-[2-(4-Fluorophenyl)-8-(4-methylpiperazin-1-yl)imidazo[1,2-a]pyrazin-3-yl]phenol;
4-[2-(4-Fluorophenyl)-8-(6-oxa-2-azaspiro[3;3]heptan-2-yl)imidazo[1,2-a]pyrazin-3-yl]phenol;
5-[2-(4-Fluorophenyl)-8-morpholino-imidazo[1,2-a]pyrazin-3-yl]indolin-2-one;
4-[2-(4-Fluorophenyl)-8-(1-piperidyl)imidazo[1,2-a]pyrazin-3-yl]phenol;
4-[2-(4-Fluorophenyl)-3-(1H-indazol-5-yl)imidazo[1,2-a]pyrazin-8-yl]morpholine;
5-[2-(4-Fluorophenyl)-8-morpholino-imidazo[1,2-a]pyrazin-3-yl]-1,3-dihydrobenzimidazol-2-one;
5-[8-(4-Acetylpiperazin-1-yl)-2-(4-fluorophenyl)imidazo[1,2-a]pyrazin-3-yl]indolin-2-one;
1-[4-[2-(4-Fluorophenyl)-3-(1H-indazol-5-yl)imidazo[1,2-a]pyrazin-8-yl]piperazin-1-yl]ethanone;
5-[8-(4-Acetylpiperazin-1-yl)-2-(4-fluorophenyl)imidazo[1,2-a]pyrazin-3-yl]-1,3-dihydrobenzimidazol-2-one;
4-(2-Benzyl-8-morpholino-imidazo[1,2-a]pyrazin-3-yl)phenol;
4-[2-(4-Fluorophenyl)-3-(1H-indol-5-yl)imidazo[1,2-a]pyrazin-8-yl]morpholine;
5-[8-(4-Acetylpiperazin-1-yl)-2-benzyl-imidazo[1,2-a]pyrazin-3-yl]indolin-2-one;
1-[4-[2-Benzyl-3-(1H-indazol-5-yl)imidazo[1,2-a]pyrazin-8-yl]piperazin-1-yl]ethanone;
5-[8-(4-Acetylpiperazin-1-yl)-2-benzyl-imidazo[1,2-a]pyrazin-3-yl]-1,3-dihydrobenzimidazol-2-one;
5-(2-Benzyl-8-morpholino-imidazo[1,2-a]pyrazin-3-yl)indolin-2-one;
4-[2-Benzyl-3-(1H-indazol-5-yl)imidazo[1,2-a]pyrazin-8-yl]morpholine;
5-(2-Benzyl-8-morpholino-imidazo[1,2-a]pyrazin-3-yl)-1,3-dihydrobenzimidazol-2-one;
1-[4-[2-Benzyl-3-(4-hydroxyphenyl)imidazo[1,2-a]pyrazin-8-yl]piperazin-1-yl]ethanone;
5-[2-(4-Fluorophenyl)-8-(6-oxa-2-azaspiro[3;3]heptan-2-yl)imidazo[1,2-a]pyrazin-3-yl]indolin-2-one;
2-[2-(4-Fluorophenyl)-3-(1H-indazol-5-yl)imidazo[1,2-a]pyrazin-8-yl]-6-oxa-2-azaspiro[3;3]heptane;
5-[2-(4-Fluorophenyl)-8-(6-oxa-2-azaspiro[3; 3]heptan-2-yl)imidazo[1,2-a]pyrazin-3-yl]-1,3-dihydrobenzimidazol-2-one;
4-[2-(4-Fluorophenyl)-3-(4-hydroxyphenyl)imidazo[1,2-a]pyrazin-8-yl]piperazin-2-one;
4-[8-(4,4-Difluoro-1-piperidyl)-2-(4-fluorophenyl)imidazo[1,2-a]pyrazin-3-yl]phenol;
4-[8-(3,3-Difluoro-1-piperidyl)-2-(4-fluorophenyl)imidazo[1,2-a]pyrazin-3-yl]phenol;
4-[3-(1H-Benzotriazol-5-yl)-2-(4-fluorophenyl)imidazo[1,2-a]pyrazin-8-yl]morpholine;
4-[3-(1H-Benzimidazol-5-yl)-2-(4-fluorophenyl)imidazo[1,2-a]pyrazin-8-yl]morpholine;
5-[2-(4-Fluorophenyl)-8-(3-oxopiperazin-1-yl)imidazo[1,2-a]pyrazin-3-yl]indolin-2-one;
4-[2-(4-Fluorophenyl)-3-(1H-indazol-5-yl)imidazo[1,2-a]pyrazin-8-yl]piperazin-2-one;
5-[2-(4-Fluorophenyl)-8-(3-oxopiperazin-1-yl)imidazo[1,2-a]pyrazin-3-yl]-1,3-dihydrobenzimidazol-2-one;
5-[2-(3,4-Difluorophenyl)-8-morpholino-imidazo[1,2-a]pyrazin-3-yl]indolin-2-one;
tert-Butyl 4-[2-benzyl-3-(2-oxoindolin-5-yl)imidazo[1,2-a]pyrazin-8-yl]piperazine-1-carboxylate;
5-[2-(4-Fluorophenyl)-8-(4-hydroxy-1-piperidyl)imidazo[1,2-a]pyrazin-3-yl]indolin-2-one;
5-[2-Benzyl-8-(3-oxopiperazin-1-yl)imidazo[1,2-a]pyrazin-3-yl]indolin-2-one;
5-[2-(4-Fluorophenyl)-8-(3-methylmorpholin-4-yl)imidazo[1,2-a]pyrazin-3-yl]indolin-2-one;
5-[2-(4-Fluorophenyl)-8-[(2-oxopyrrolidin-3-yl)amino]imidazo[1,2-a]pyrazin-3-yl]indolin-2-one;
5-[2-(4-Fluorophenyl)-8-(3-hydroxypyrrolidin-1-yl)imidazo[1,2-a]pyrazin-3-yl]indolin-2-one;
5-[2-(4-Fluorophenyl)-8-[2-(trifluoromethyl)morpholin-4-yl]imidazo[1,2-a]pyrazin-3-yl]indolin-2-one;
5-[2-(4-Fluorophenyl)-8-[(3S)-3-methylmorpholin-4-yl]imidazo[1,2-a]pyrazin-3-yl]indolin-2-one;
5-[2-(4-Fluorophenyl)-8-[(3R)-3-methylmorpholin-4-yl]imidazo[1,2-a]pyrazin-3-yl]indolin-2-one;
5-[2-(4-Fluorophenyl)-8-pyrrolidin-1-yl-imidazo[1,2-a]pyrazin-3-yl]indolin-2-one;
5-[8-[Cyclopropyl(methyl)amino]-2-(4-fluorophenyl)imidazo[1,2-a]pyrazin-3-yl]indolin-2-one;
5-[8-(1,1-Dioxo-1,4-thiazinan-4-yl)-2-(4-fluorophenyl)imidazo[1,2-a]pyrazin-3-yl]indolin-2-one;
(R*)-5-[2-(4-Fluorophenyl)-8-[2-(trifluoromethyl)morpholin-4-yl]imidazo[1,2-a]pyrazin-3-yl]indolin-2-one;

(S*)-5-[2-(4-Fluorophenyl)-8-[2-(trifluoromethyl)morpholin-4-yl]imidazo[1,2-a]pyrazin-3-yl]indolin-2-one;
5-[8-(3,3-Dimethylmorpholin-4-yl)-2-(4-fluorophenyl)imidazo[1,2-a]pyrazin-3-yl]indolin-2-one;
5-[8-(Diethylamino)-2-(4-fluorophenyl)imidazo[1,2-a]pyrazin-3-yl]indolin-2-one;
(R*)-5-[2-(4-Fluorophenyl)-8-(3-hydroxypyrrolidin-1-yl)imidazo[1,2-a]pyrazin-3-yl]indolin-2-one;
(S*)-5-[2-(4-Fluorophenyl)-8-(3-hydroxypyrrolidin-1-yl)imidazo[1,2-a]pyrazin-3-yl]indolin-2-one;
5-[2-(4-Fluorophenyl)-8-(3-hydroxy-1-piperidyl)imidazo[1,2-a]pyrazin-3-yl]indolin-2-one;
5-[8-(1,4-Dioxa-8-azaspiro[4; 5]decan-8-yl)-2-(4-fluorophenyl)imidazo[1,2-a]pyrazin-3-yl]indolin-2-one;
5-(2-Cyclohexyl-8-morpholino-imidazo[1,2-a]pyrazin-3-yl)indolin-2-one;
5-(2-Cyclopentyl-8-morpholino-imidazo[1,2-a]pyrazin-3-yl)indolin-2-one;
5-[8-(Azetidin-1-yl)-2-(4-fluorophenyl)imidazo[1,2-a]pyrazin-3-yl]indolin-2-one;
5-[8-(3-Fluoroazetidin-1-yl)-2-(4-fluorophenyl)imidazo[1,2-a]pyrazin-3-yl]indolin-2-one;
5-[8-(3,3-Difluoroazetidin-1-yl)-2-(4-fluorophenyl)imidazo[1,2-a]pyrazin-3-yl]indolin-2-one;
5-[8-(3-Chloroazetidin-1-yl)-2-(4-fluorophenyl)imidazo[1,2-a]pyrazin-3-yl]indolin-2-one;
5-[2-(4-Fluorophenyl)-8-(3-methylsulfonylazetidin-1-yl)imidazo[1,2-a]pyrazin-3-yl]indolin-2-one;
5-[2-(4-Fluorophenyl)-8-(2,2,3,3,5,5,6,6-octadeuteriomorpholin-4-yl)imidazo[1,2-a]pyrazin-3-yl]indolin-2-one;
5-[2-(4-Fluorophenyl)-8-[3-(hydroxymethyl)azetidin-1-yl]imidazo[1,2-a]pyrazin-3-yl]indolin-2-one;
5-(8-Morpholino-2-phenyl-imidazo[1,2-a]pyrazin-3-yl)indolin-2-one;
1-[2-(4-Fluorophenyl)-3-(2-oxoindolin-5-yl)imidazo[1,2-a]pyrazin-8-yl]azetidine-3-carbonitrile;
5-[2-(4-Fluorophenyl)-8-(3-hydroxy-3-methyl-azetidin-1-yl)imidazo[1,2-a]pyrazin-3-yl]indolin-2-one;
5-[2-(4-Fluorophenyl)-8-(4-hydroxy-4-methyl-1-piperidyl)imidazo[1,2-a]pyrazin-3-yl]indolin-2-one;
5-[2-(4-Fluorophenyl)-8-[3-hydroxy-3-(trifluoromethyl)azetidin-1-yl]imidazo[1,2-a]pyrazin-3-yl]indolin-2-one;
(trans)-5-[8-(3-Fluoro-4-hydroxy-1-piperidyl)-2-(4-fluorophenyl)imidazo[1,2-a]pyrazin-3-yl]indolin-2-one;
5-[8-(3,3-Difluoro-4-hydroxy-1-piperidyl)-2-(4-fluorophenyl)imidazo[1,2-a]pyrazin-3-yl]indolin-2-one;
5-[2-(4-Fluorophenyl)-8-(4-methoxy-1-piperidyl)imidazo[1,2-a]pyrazin-3-yl]indolin-2-one;
(cis)-5-[8-(3-Fluoro-4-hydroxy-1-piperidyl)-2-(4-fluorophenyl)imidazo[1,2-a]pyrazin-3-yl]indolin-2-one;
5-[2-(4-Fluorophenyl)-8-(4-fluoro-1-piperidyl)imidazo[1,2-a]pyrazin-3-yl]indolin-2-one;
5-[8-(4-Fluoro-1-piperidyl)-2-phenyl-imidazo[1,2-a]pyrazin-3-yl]indolin-2-one;
5-[8-[4-(Fluoromethyl)-1-piperidyl]-2-phenyl-imidazo[1,2-a]pyrazin-3-yl]indolin-2-one;
5-[8-[4-(2-Fluoroethyl)-1-piperidyl]-2-phenyl-imidazo[1,2-a]pyrazin-3-yl]indolin-2-one;
5-[8-(3-Methoxyazetidin-1-yl)-2-phenyl-imidazo[1,2-a]pyrazin-3-yl]indolin-2-one;
5-[8-(6-Oxa-3-azabicyclo[3;1;1]heptan-3-yl)-2-phenyl-imidazo[1,2-a]pyrazin-3-yl]indolin-2-one;
5-[8-(5-Azaspiro[2;3]hexan-5-yl)-2-phenyl-imidazo[1,2-a]pyrazin-3-yl]indolin-2-one;
5-[8-(3-Fluoroazetidin-1-yl)-2-phenyl-imidazo[1,2-a]pyrazin-3-yl]indolin-2-one;
5-[5-Chloro-2-(4-fluorophenyl)-8-morpholino-imidazo[1,2-a]pyrazin-3-yl]-1,3-dihydrobenzimidazol-2-one;
4-[2-(4-Fluorophenyl)-8-morpholino-imidazo[1,2-a]pyrazin-3-yl]-phenol;
4-[2-(2-Fluorophenyl)-8-morpholino-imidazo[1,2-a]pyrazin-3-yl]phenol;
4-(2-Cyclohexyl-8-morpholino-imidazo[1,2-a]pyrazin-3-yl)phenol;
5-(2-tert-Butyl-8-morpholino-imidazo[1,2-a]pyrazin-3-yl)indolin-2-one;
5-[8-Amino-2-(4-fluorophenyl)imidazo[1,2-a]pyrazin-3-yl]-1,3-dihydrobenzimidazol-2-one;
5-[2-tert-Butyl-8-(4-hydroxy-1-piperidyl)imidazo[1,2-a]pyrazin-3-yl]indolin-2-one;
5-[8-(3-Fluoroazetidin-1-yl)-2-(4-pyridyl)imidazo[1,2-a]pyrazin-3-yl]indolin-2-one;
5-(2-Cyclobutyl-8-morpholino-imidazo[1,2-a]pyrazin-3-yl)indolin-2-one;
5-(2-Cyclopropyl-8-morpholino-imidazo[1,2-a]pyrazin-3-yl)indolin-2-one;
1-[4-[2-(4-Chlorophenyl)-3-(4-hydroxyphenyl)imidazo[1,2-a]pyrazin-8-yl]-1,4-diazepan-1-yl]ethanone;
N-[1-[2-(4-Chlorophenyl)-3-(4-hydroxyphenyl)imidazo[1,2-a]pyrazin-8-yl]-4-piperidyl]acetamide;
1-[4-[2-(4-Chlorophenyl)-3-(4-hydroxyphenyl)imidazo[1,2-a]pyrazin-8-yl]piperazin-1-yl]ethanone;
4-[3-(4-Hydroxyphenyl)-8-morpholino-imidazo[1,2-a]pyrazin-2-yl]benzonitrile;
4-[2-[(3-Fluorophenyl)methyl]-8-morpholino-imidazo[1,2-a]pyrazin-3-yl]phenol;
4-[3-(1H-Indazol-5-yl)-8-morpholino-imidazo[1,2-a]pyrazin-2-yl]benzonitrile;
N-[(3S)-1-[2-(4-Fluorophenyl)-3-(2-oxo-1,3-dihydrobenzimidazol-5-yl)imidazo[1,2-a]pyrazin-8-yl]pyrrolidin-3-yl]acetamide;
5-[2-(4-Fluorophenyl)-8-methoxy-imidazo[1,2-a]pyrazin-3-yl]-1,3-dihydrobenzimidazol-2-one;
N-[(3R)-1-[2-(4-Fluorophenyl)-3-(2-oxo-1,3-dihydrobenzimidazol-5-yl)imidazo[1,2-a]pyrazin-8-yl]pyrrolidin-3-yl]acetamide;
5-[8-(Dimethylamino)-2-(4-fluorophenyl)imidazo[1,2-a]pyrazin-3-yl]-1,3-dihydrobenzimidazol-2-one;
4-[8-Morpholino-3-(2-oxoindolin-5-yl)imidazo[1,2-a]pyrazin-2-yl]benzonitrile;
4-[8-(4-Acetylpiperazin-1-yl)-3-(1H-indazol-5-yl)imidazo[1,2-a]pyrazin-2-yl]benzonitrile;
5-[2-(4-Fluorophenyl)-8-(methylamino)imidazo[1,2-a]pyrazin-3-yl]-1,3-dihydrobenzimidazol-2-one;
4-[8-Morpholino-3-(2-oxo-1,3-dihydrobenzimidazol-5-yl)imidazo[1,2-a]pyrazin-2-yl]benzonitrile;
4-[8-(4-Acetylpiperazin-1-yl)-3-(2-oxo-1,3-dihydrobenzimidazol-5-yl)imidazo[1,2-a]pyrazin-2-yl]benzonitrile;
4-[8-(4-Acetylpiperazin-1-yl)-3-(2-oxoindolin-5-yl)imidazo[1,2-a]pyrazin-2-yl]benzonitrile;
5-(2-(4-Fluorophenyl)-8-(2-oxa-6-azaspiro[3; 3]heptan-6-yl)imidazo[1,2-a]pyrazin-3-yl)-1,3-dihydrobenzo[c]isothiazole 2,2-dioxide;
5-(2-(4-Fluorophenyl)-8-(4-oxopiperidin-1-yl)imidazo[1,2-a]pyrazin-3-yl)indolin-2-one;
5-(8-(4-Methyl-3-oxopiperazin-1-yl)-2-phenylimidazo[1,2-a]pyrazin-3-yl)indolin-2-one;
5-(8-(2,4-Dimethyl-3-oxopiperazin-1-yl)-2-phenylimidazo[1,2-a]pyrazin-3-yl)indolin-2-one;

tert-Butyl 4-(2-benzyl-5-bromo-3-(2-oxoindolin-5-yl)imidazo[1,2-a]pyrazin-8-yl)piperazine-1-carboxylate;
5-(8-(4-Acetylpiperazin-1-yl)-2-benzyl-5-bromoimidazo[1,2-a]pyrazin-3-yl)indolin-2-one;
5-(8-(4-Acetylpiperazin-1-yl)-2-benzyl-5-methylimidazo[1,2-a]pyrazin-3-yl)indolin-2-one
5-[8-(4-Acetylpiperazin-1-yl)-2-(4-fluorophenyl)imidazo[1,2-a]pyrazin-3-yl]indolin-2-one
6-(2-(4-Fluorophenyl)-8-morpholinoimidazo[1,2-a]pyrazin-3-yl)benzo[d]oxazol-2(3H)-one;
5-[2-(4-Fluorophenyl)-8-morpholino-imidazo[1,2-a]pyrazin-3-yl]-1,3-dihydro-2,1-benzothiazole 2,2-dioxide;
6-[2-(4-Fluorophenyl)-8-morpholino-imidazo[1,2-a]pyrazin-3-yl]-3H-1,3-benzothiazol-2-one;
1-[3-(2,2-Dioxo-1,3-dihydro-2,1-benzothiazol-5-yl)-2-(4-fluorophenyl)imidazo[1,2-a]pyrazin-8-yl]piperidin-4-ol
6-[2-(4-Fluorophenyl)-8-morpholino-imidazo[1,2-a]pyrazin-3-yl]-3,4-dihydro-1H-quinazolin-2-one;
5-[2-(4-Fluorophenyl)-8-morpholino-imidazo[1,2-a]pyrazin-3-yl]-1H-benzimidazol-2-amine;
3-Fluoro-5-[2-(4-fluorophenyl)-8-morpholino-imidazo[1,2-a]pyrazin-3-yl]indolin-2-one;
4-[3-(3-Fluoro-1H-indol-5-yl)-2-(4-fluorophenyl)imidazo[1,2-a]pyrazin-8-yl]morpholine;
6-[2-(4-Fluorophenyl)-8-morpholino-imidazo[1,2-a]pyrazin-3-yl]-1,4-dihydro-3,1-benzoxazin-2-one;
6-[2-(4-Fluorophenyl)-8-morpholino-imidazo[1,2-a]pyrazin-3-yl]-1H-quinolin-2-one;
4-[2-(4-Fluorophenyl)-8-pyrrolidin-1-yl-imidazo[1,2-a]pyrazin-3-yl]phenol;
5-[2-(4-Fluorophenyl)-8-methylsulfonyl-imidazo[1,2-a]pyrazin-3-yl]indolin-2-one;
5-[2-(4-Fluorophenyl)-8-methylsulfinyl-imidazo[1,2-a]pyrazin-3-yl]indolin-2-one;
5-[2-(4-Fluorophenyl)-8-isopropoxy-imidazo[1,2-a]pyrazin-3-yl]indolin-2-one;
1-[4-[2-(4-Fluorophenyl)-3-(4-hydroxyphenyl)imidazo[1,2-a]pyrazin-8-yl]-3,6-dihydro-2H-pyridin-1-yl]ethanone;
5-(8-(3,6-Dihydro-2H-pyran-4-yl)-2-phenylimidazo[1,2-a]pyrazin-3-yl)indolin-2-one;
5-[8-Fluoro-2-(4-fluorophenyl)imidazo[1,2-a]pyrazin-3-yl]indolin-2-one;
5-[2-(4-Fluorophenyl)-8-methyl-imidazo[1,2-a]pyrazin-3-yl]indolin-2-one
5-(2-Phenylimidazo[1,2-a]pyrazin-3-yl)indolin-2-one;
5-(2-(4-Fluorophenyl)imidazo[1,2-a]pyrazin-3-yl)indolin-2-one;
3,3-Difluoro-5-[2-(4-fluorophenyl)-8-morpholino-imidazo[1,2-a]pyrazin-3-yl]indolin-2-one;
8-Morpholino-3-(2-oxoindolin-5-yl)-N-phenylimidazo[1,2-a]pyrazine-2-carboxamide;
3-(4-Hydroxyphenyl)-8-morpholino-N-phenyl-imidazo[1,2-a]pyrazine-2-carboxamide;
N-Benzyl-8-morpholino-3-(2-oxo-1,3-dihydrobenzimidazol-5-yl)imidazo[1,2-a]pyrazine-2-carboxamide;
8-Morpholino-3-(2-oxo-1,3-dihydrobenzimidazol-5-yl)-N-phenyl-imidazo[1,2-a]pyrazine-2-carboxamide;
5-[8-(Dimethylamino)-2-(4-fluorophenyl)imidazo[1,2-a]pyrazin-3-yl]indolin-2-one;
N-Benzyl-8-morpholino-3-(2-oxoindolin-5-yl)imidazo[1,2-a]pyrazine-2-carboxamide
3-(2-Oxoindolin-5-yl)-8-(3-oxopiperazin-1-yl)-N-phenyl-imidazo[1,2-a]pyrazine-2-carboxamide;
8-(Dimethylamino)-3-(2-oxoindolin-5-yl)-N-phenyl-imidazo[1,2-a]pyrazine-2-carboxamide;
N-Methyl-8-morpholino-3-(2-oxo-1,3-dihydrobenzimidazol-5-yl)-N-phenyl-imidazo[1,2-a]pyrazine-2-carboxamide;
N-Cyclopropyl-8-morpholino-3-(2-oxo-1,3-dihydrobenzimidazol-5-yl)imidazo[1,2-a]pyrazine-2-carboxamide;
8-Morpholino-3-(2-oxo-1,3-dihydrobenzimidazol-5-yl)-N-(4-pyridyl)imidazo[1,2-a]pyrazine-2-carboxamide
3-(4-Hydroxyphenyl)-8-morpholino-N-propyl-imidazo[1,2-a]pyrazine-2-carboxamide
8-Morpholino-3-(2-oxoindolin-5-yl)-N-phenylimidazo[1,2-a]pyrazine-2-carboxamide;
N-[(3S)-1-[2-(4-Fluorophenyl)-3-(2-oxoindolin-5-yl)imidazo[1,2-a]pyrazin-8-yl]pyrrolidin-3-yl]acetamide;
[3-(4-Hydroxyphenyl)-8-morpholino-imidazo[1,2-a]pyrazin-2-yl]-phenyl-methanone;
5-[2-Benzoyl-8-(dimethylamino)imidazo[1,2-a]pyrazin-3-yl]indolin-2-one;
5-(2-Benzoyl-8-morpholino-imidazo[1,2-a]pyrazin-3-yl)indolin-2-one;
5-[2-Benzoyl-8-(4-hydroxy-1-piperidyl)imidazo[1,2-a]pyrazin-3-yl]indolin-2-one;
5-[2-(4-Fluorophenyl)-8-(4-hydroxyimino-1-piperidyl)imidazo[1,2-a]pyrazin-3-yl]indolin-2-one;
6-(2-Benzoyl-8-morpholino-imidazo[1,2-a]pyrazin-3-yl)-3H-1,3-benzoxazol-2-one;
5-[2-Benzoyl-8-(1,1-dioxo-1,4-thiazinan-4-yl)imidazo[1,2-a]pyrazin-3-yl]indolin-2-one;
5-[8-(4-Acetylpiperazin-1-yl)-2-benzoyl-imidazo[1,2-a]pyrazin-3-yl]indolin-2-one;
[3-(2,2-Dioxo-1,3-dihydro-2,1-benzothiazol-5-yl)-8-morpholino-imidazo[1,2-a]pyrazin-2-yl]-phenyl-methanone;
5-[2-Benzoyl-8-(methylamino)imidazo[1,2-a]pyrazin-3-yl]indolin-2-one;
5-(5-Fluoro-2-(4-fluorophenyl)-8-morpholinoimidazo[1,2-a]pyrazin-3-yl)indolin-2-one
5-[5-Fluoro-2-(4-fluorophenyl)-8-morpholino-imidazo[1,2-a]pyrazin-3-yl]-1,3-dihydrobenzimidazol-2-one
5-[5-Chloro-2-(4-fluorophenyl)-8-morpholino-imidazo[1,2-a]pyrazin-3-yl]indolin-2-one;
5-[2-(4-Fluorophenyl)-7-morpholino-pyrazolo[1,5-c]pyrimidin-3-yl]indolin-2-one;
5-(2-tert-Butylpyrazolo[1,5-c]pyrimidin-3-yl)indolin-2-one;
5-[2-(4-Fluorophenyl)-7-(4-hydroxy-1-piperidyl)pyrazolo[1,5-c]pyrimidin-3-yl]indolin-2-one;
5-[2-(4-Fluorophenyl)-8-(methylamino)imidazo[1,2-a]pyrazin-3-yl]indolin-2-one;
5-[2-(4-Fluorophenyl)-7-(3-oxopiperazin-1-yl)pyrazolo[1,5-c]pyrimidin-3-yl]indolin-2-one;
5-[7-(Dimethylamino)-2-(4-fluorophenyl)pyrazolo[1,5-c]pyrimidin-3-yl]indolin-2-one;
5-[7-(1,1-Dioxo-1,4-thiazinan-4-yl)-2-(4-fluorophenyl)pyrazolo[1,5-c]pyrimidin-3-yl]indolin-2-one;
5-[2-(4-Fluorophenyl)-7-(methylamino)pyrazolo[1,5-c]pyrimidin-3-yl]indolin-2-one;
5-[7-(4-Acetylpiperazin-1-yl)-2-(4-fluorophenyl)pyrazolo[1,5-c]pyrimidin-3-yl]indolin-2-one;
6-[2-(4-Fluorophenyl)-7-morpholino-pyrazolo[1,5-c]pyrimidin-3-yl]-3H-1,3-benzoxazol-2-one;
5-[2-(4-Fluorophenyl)-7-(4-oxo-1-piperidyl)pyrazolo[1,5-c]pyrimidin-3-yl]indolin-2-one;
5-[2-(4-Fluorophenyl)pyrazolo[1,5-c]pyrimidin-3-yl]indolin-2-one;

5-[7-(3,3-Difluoroazetidin-1-yl)-2-(4-fluorophenyl)pyrazolo[1,5-c]pyrimidin-3-yl]indolin-2-one;
5-[2-(4-Fluorophenyl)-7-(3-methylmorpholin-4-yl)pyrazolo[1,5-c]pyrimidin-3-yl]indolin-2-one;
5-[2-(4-Fluorophenyl)-7-morpholino-pyrazolo[1,5-c]pyrimidin-3-yl]-1,3-dihydro-2,1-benzothiazole 2,2-dioxide;
5-[2-(4-Fluorophenyl)-7-(3-hydroxyazetidin-1-yl)pyrazolo[1,5-c]pyrimidin-3-yl]indolin-2-one;
5-[2-(4-Fluorophenyl)-7-[3-(hydroxymethyl)azetidin-1-yl]pyrazolo[1,5-c]pyrimidin-3-yl]indolin-2-one;
5-[2-tert-Butyl-7-(4-hydroxy-1-piperidyl)pyrazolo[1,5-c]pyrimidin-3-yl]indolin-2-one;
5-(2-tert-Butyl-7-morpholino-pyrazolo[1,5-c]pyrimidin-3-yl)indolin-2-one;
5-[2-tert-Butyl-7-(3,3-difluoroazetidin-1-yl)pyrazolo[1,5-c]pyrimidin-3-yl]indolin-2-one;
5-[2-(4-Fluorophenyl)-7-(3-hydroxy-3-methyl-azetidin-1-yl)pyrazolo[1,5-c]pyrimidin-3-yl]indolin-2-one;
5-(2-(4-Fluorophenyl)-8-(1,2,6-triazaspiro[2;5]oct-1-en-6-yl)imidazo[1,2-a]pyrazin-3-yl)indolin-2-one;
5-[2-(4-Fluorophenyl)-7-(4-hydroxy-4-methyl-1-piperidyl)pyrazolo[1,5-c]pyrimidin-3-yl]indolin-2-one;
5-[7-(4-Hydroxy-1-piperidyl)-2-phenyl-pyrazolo[1,5-c]pyrimidin-3-yl]indolin-2-one;
5-[7-(4-Fluoro-1-piperidyl)-2-phenyl-pyrazolo[1,5-c]pyrimidin-3-yl]indolin-2-one;
5-[7-(4-Methoxy-1-piperidyl)-2-phenyl-pyrazolo[1,5-c]pyrimidin-3-yl]indolin-2-one;
5-[2-(4-Fluorophenyl)-7-(4-fluoro-1-piperidyl)pyrazolo[1,5-c]pyrimidin-3-yl]indolin-2-one;
5-[7-(3-Methoxyazetidin-1-yl)-2-phenyl-pyrazolo[1,5-c]pyrimidin-3-yl]indolin-2-one;
5-[7-(Cyclopentoxy)-2-phenyl-pyrazolo[1,5-c]pyrimidin-3-yl]indolin-2-one;
trans-5-[7-(3-Fluoro-4-hydroxy-1-piperidyl)-2-phenyl-pyrazolo[1,5-c]pyrimidin-3-yl]indolin-2-one;
5-(7-Isopropoxy-2-phenyl-pyrazolo[1,5-c]pyrimidin-3-yl)indolin-2-one;
5-[2-Cyclopentyl-7-(3-methoxyazetidin-1-yl)pyrazolo[1,5-c]pyrimidin-3-yl]indolin-2-one
5-[2-Cyclopentyl-7-(3-fluoroazetidin-1-yl)pyrazolo[1,5-c]pyrimidin-3-yl]indolin-2-one;
5-[7-[(3S)-3-Methoxypyrrolidin-1-yl]-2-phenyl-pyrazolo[1,5-c]pyrimidin-3-yl]indolin-2-one;
5-(5-Methyl-7-morpholino-2-phenyl-pyrazolo[1,5-c]pyrimidin-3-yl)indolin-2-one;
5-[2-tert-Butyl-7-(6-oxa-2-azaspiro[3;3]heptan-2-yl)pyrazolo[1,5-c]pyrimidin-3-yl]indolin-2-one;
5-[7-(3-Fluoroazetidin-1-yl)-2-phenyl-pyrazolo[1,5-c]pyrimidin-3-yl]indolin-2-one;
5-(7-Morpholino-2-phenyl-pyrazolo[1,5-c]pyrimidin-3-yl)indolin-2-one;
5-[7-[(3R)-3-Methoxypyrrolidin-1-yl]-2-phenyl-pyrazolo[1,5-c]pyrimidin-3-yl]indolin-2-one;
5-(2-Cyclopentyl-7-morpholino-pyrazolo[1,5-c]pyrimidin-3-yl)indolin-2-one;
(cis)-5-[7-(3-Fluoro-4-hydroxy-1-piperidyl)-2-phenyl-pyrazolo[1,5-c]pyrimidin-3-yl]indolin-2-one
5-[2-Cyclopentyl-7-(3-hydroxyazetidin-1-yl)pyrazolo[1,5-c]pyrimidin-3-yl]indolin-2-one;
5-(7-Methoxy-2-phenyl-pyrazolo[1,5-c]pyrimidin-3-yl)indolin-2-one;
5-(4-Bromo-7-morpholino-2-phenyl-pyrazolo[1,5-c]pyrimidin-3-yl)indolin-2-one;
5-(4-Methyl-7-morpholino-2-phenyl-pyrazolo[1,5-c]pyrimidin-3-yl)indolin-2-one;
4-[3-(1H-Indazol-5-yl)-8-(3-oxopiperazin-1-yl)imidazo[1,2-a]pyrazin-2-yl]benzonitrile;
4-[3-(2-Oxoindolin-5-yl)-8-(3-oxopiperazin-1-yl)imidazo[1,2-a]pyrazin-2-yl]benzonitrile;
4-[3-(2-Oxo-1,3-dihydrobenzimidazol-5-yl)-8-(3-oxopiperazin-1-yl)imidazo[1,2-a]pyrazin-2-yl]benzonitrile;
4-[3-(1H-Indazol-5-yl)-4-methyl-2-phenyl-pyrazolo[1,5-c]pyrimidin-7-yl]morpholine;
6-[7-(4-Methoxy-1-piperidyl)-2-phenyl-pyrazolo[1,5-c]pyrimidin-3-yl]-3H-1,3-benzothiazol-2-one;
N-Cyclohexyl-8-morpholino-3-(2-oxo-1,3-dihydrobenzimidazol-5-yl)imidazo[1,2-a]pyrazine-2-carboxamide;
5-[8-(4-Hydroxy-1-piperidyl)-2-(4-pyridyl)imidazo[1,2-a]pyrazin-3-yl]indolin-2-one;
6-[2-Cyclopropyl-6-(trifluoromethyl)imidazo[1,2-a]pyrazin-3-yl]-3H-1,3-benzothiazol-2-one;
5-[2-Benzoyl-8-(methylamino)imidazo[1,2-a]pyrazin-3-yl]indolin-2-one;
5-[2-Phenyl-6-(trifluoromethyl)imidazo[1,2-a]pyrazin-3-yl]indolin-2-one;
5-[2-Cyclopropyl-6-(trifluoromethyl)imidazo[1,2-a]pyrazin-3-yl]indolin-2-one;
5-[2-tert-Butyl-8-(4-oxo-1-piperidyl)imidazo[1,2-a]pyrazin-3-yl]indolin-2-one;
8-Morpholino-3-(2-oxo-1,3-dihydrobenzimidazol-5-yl)-N-(2-pyridyl)imidazo[1,2-a]pyrazine-2-carboxamide;
5-[2-Phenyl-5-(trifluoromethyl)pyrazolo[1,5-c]pyrimidin-3-yl]indolin-2-one;
6-[2-Phenyl-5-(trifluoromethyl)pyrazolo[1,5-c]pyrimidin-3-yl]-3H-1,3-benzoxazol-2-one;
6-[2-phenyl-5-(trifluoromethyl)pyrazolo[1,5-c]pyrimidin-3-yl]-3H-1,3-benzothiazol-2-one;
5-[2-tert-Butyl-5-(trifluoromethyl)pyrazolo[1,5-c]pyrimidin-3-yl]indolin-2-one;
5-[2-Cyclobutyl-5-(trifluoromethyl)pyrazolo[1,5-c]pyrimidin-3-yl]indolin-2-one;
5-[2-Isopropyl-5-(trifluoromethyl)pyrazolo[1,5-c]pyrimidin-3-yl]indolin-2-one;
5-[2-Cyclopropyl-5-(trifluoromethyl)pyrazolo[1,5-c]pyrimidin-3-yl]indolin-2-one;
6-[2-Cyclobutyl-5-(trifluoromethyl)pyrazolo[1,5-c]pyrimidin-3-yl]-3H-1,3-benzothiazol-2-one;
6-[2-Cyclopropyl-5-(trifluoromethyl)pyrazolo[1,5-c]pyrimidin-3-yl]-3H-1,3-benzothiazol-2-one;
6-[2-Isopropyl-5-(trifluoromethyl)pyrazolo[1,5-c]pyrimidin-3-yl]-3H-1,3-benzothiazol-2-one;
6-[2-tert-Butyl-5-(trifluoromethyl)pyrazolo[1,5-c]pyrimidin-3-yl]-3H-1,3-benzothiazol-2-one;
4-[3-(1H-Indazol-5-yl)-2-phenyl-pyrazolo[1,5-c]pyrimidin-7-yl]morpholine;
3-(1H-Indazol-5-yl)-7-(4-methoxy-1-piperidyl)-2-phenyl-pyrazolo[1,5-c]pyrimidine;
5-(4-Fluoro-2-isopropyl-7-morpholino-pyrazolo[1,5-c]pyrimidin-3-yl)indolin-2-one;
4-[4-Fluoro-3-(1H-indazol-5-yl)-2-isopropyl-pyrazolo[1,5-c]pyrimidin-7-yl]morpholine;
3-(1H-indazol-5-yl)-2-isopropyl-7-(4-methoxy-1-piperidyl)pyrazolo[1,5-c]pyrimidine;
4-[3-(1H-Indazol-5-yl)-2-isopropyl-pyrazolo[1,5-c]pyrimidin-7-yl]morpholine;
4-[3-(1H-Indazol-5-yl)-2-isopropyl-4-methyl-pyrazolo[1,5-c]pyrimidin-7-yl]morpholine;
6-(2-Isopropyl-7-morpholino-pyrazolo[1,5-c]pyrimidin-3-yl)-3H-1,3-benzothiazol-2-one;
6-[2-Isopropyl-7-(4-methoxy-1-piperidyl)pyrazolo[1,5-c]pyrimidin-3-yl]-3H-1,3-benzothiazol-2-one;

6-(7-Morpholino-2-phenyl-pyrazolo[1,5-c]pyrimidin-3-yl)-3H-1,3-benzothiazol-2-one;

6-(2-Isopropyl-4-methyl-7-morpholino-pyrazolo[1,5-c]pyrimidin-3-yl)-3H-1,3-benzothiazol-2-one;

5-(2-Isopropyl-4-methyl-7-morpholino-pyrazolo[1,5-c]pyrimidin-3-yl)indolin-2-one;

6-[2-Phenyl-6-(trifluoromethyl)imidazo[1,2-a]pyrazin-3-yl]-3H-1,3-benzothiazol-2-one;

5-[2-Benzoyl-8-(3-oxopiperazin-1-yl)imidazo[1,2-a]pyrazin-3-yl]indolin-2-one;

5-[2-(4-Fluorophenyl)-8-methoxy-imidazo[1,2-a]pyrazin-3-yl]indolin-2-one;

5-[8-Amino-2-(4-fluorophenyl)imidazo[1,2-a]pyrazin-3-yl]indolin-2-one;

5-[2-(4-fluorophenyl)-8-hydroxy-imidazo[1,2-a]pyrazin-3-yl]-1,3-dihydrobenzimidazol-2-one; and N-[(3R)-1-[2-(4-fluorophenyl)-3-(2-oxoindolin-5-yl)imidazo[1,2-a]pyrazin-8-yl]pyrrolidin-3-yl]acetamide;

and pharmaceutically acceptable salts, N-oxides or solvates thereof.

35. A pharmaceutical composition comprising:

(A) an effective amount of at least one compound of Formula (I):

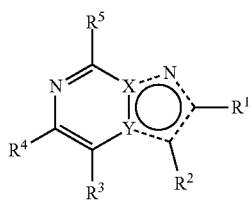

(I)

wherein

X is C or N;

Y is C or N; provided that X and Y cannot both be C, and X and Y cannot both be N;

the dotted line (- - - - -) indicates that the referenced bond is a single bond or a double bond;

$R^1$ is selected from the group consisting of: $C_{1-5}$alkyl; $C_{3-7}$cycloalkyl; phenyl optionally substituted with one, two or three members independently selected from halo and —CN; $CH_2$-phenyl optionally substituted with halo; C(=O)-phenyl, wherein said phenyl is optionally substituted with halo; C(=O)N(CH$_3$)-phenyl; C(=O)NH-phenyl; C(=O)NH—CH$_2$-phenyl; C(=O)NH-pyridinyl; C(=O)NH—C$_{3-7}$cycloalkyl; C(=O)NH—C$_{1-5}$alkyl; and pyridinyl;

$R^2$ is selected from the group consisting of:

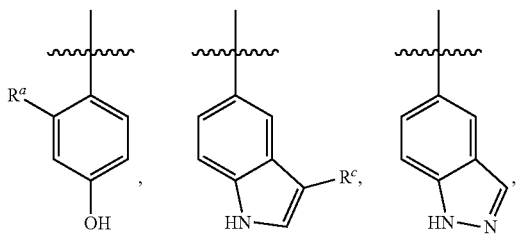

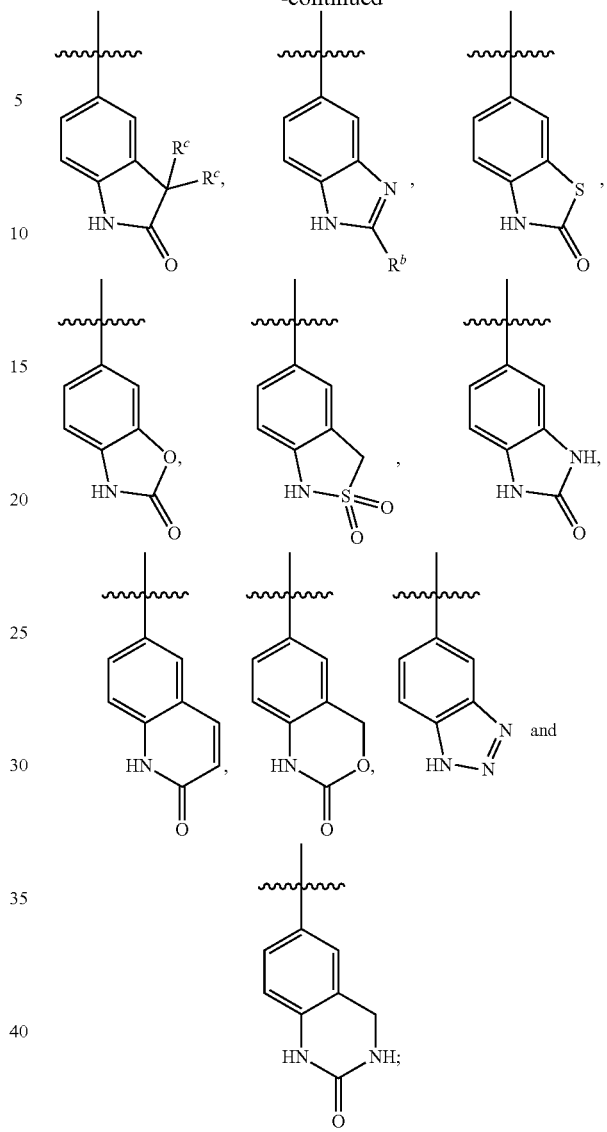

$R^a$ is H or —CH$_3$;

$R^b$ is H or —NH$_2$;

$R^c$ is independently selected from: H and —F;

$R^3$ is selected from the group consisting of: H, $^3$H, —CH$_3$ and halo;

$R^4$ is H, —CH$_3$, or CF$_3$; and $R^5$ is selected from the group consisting of:

H; halo; —C$_{1-5}$alkyl; —C$_{1-5}$alkoxy; —NH$_2$; —NH(C$_{1-5}$alkyl); —N(C$_{1-5}$alkyl)$_2$; —NH-2-oxopyrrolidin-3-yl; —N(CH$_3$)cyclopropyl; —N(C$_{1-5}$alkyl)$_2$; —SO$_2$CH$_3$; —(S=O)CH$_3$; —OH; —O-cyclopentyl; azetidinyl optionally independently substituted with one or two members selected from the group consisting of: halo, —CH$_3$, —CF$_3$, —OCH$_3$, —SO$_2$CH$_3$, —CH$_2$OH, —OH, and —CN; pyrrolidinyl optionally substituted with —OH, —OCH$_3$ or —NH—(C=O)CH$_3$; piperidine optionally independently substituted with one, two, or three members selected from the group consisting of: halo, —OH, —CH$_3$, —OCH$_3$, —CH$_2$F, —CH$_2$CH$_2$F, and —NH—(C=O)CH$_3$; piperazine optionally substituted with —CH$_3$, —(C=O)CH$_3$, or —CO$_2$tBu;

morpholine optionally independently substituted with one or two —CH₃, or —CF₃; octadeuteriomorpholin-4-yl; 6-oxa-2-azaspiro[3.3]heptan-2-yl; 3-oxopiperazin-1-yl optionally substituted with one or two —CH₃; 1,1-dioxo-1,4-thiazinan-4-yl; 1,4-dioxa-8-azaspiro[4.5]decan-8-yl; 6-oxa-3-azabicyclo[3.1.1]heptan-3-yl; 5-azaspiro[2.3]hexan-5-yl; diazapanyl optionally substituted with —(C=O)CH₃; 4-oxopiperidin-1-yl; dihydro-2H-pyridinyl optionally substituted with —(C=O)CH₃; dihydro-2H-pyranyl; 4-hydroxyimino-1-piperidyl; and 1,2,6-triazaspiro[2.5]oct-1-en-6-yl;

and pharmaceutically acceptable salts, N-oxides or solvates of compounds of Formula (I); and (B) at least one pharmaceutically acceptable excipient.

36. A pharmaceutical composition comprising an effective amount of at least one compound of claim 34 and at least one pharmaceutically acceptable excipient.

37. A method of treating a subject suffering from or diagnosed with a disease, disorder, or medical condition mediated by AMPA receptor activity selected from cerebral ischemia, head injury, spinal cord injury, Alzheimer's disease, Parkinson's disease, amyotrophic lateral sclerosis (ALS), Huntington's chorea, AIDS nervous disturbance, epilepsy, mobility disturbance, pain, spasticity, nervous disturbance by toxin in food, chronic pain, migraine, cancer pain, diabetic neuropathy, encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder (CNS lupus erythematodes, polyarteritis nodosa, Sjogren syndrome, sarcoidosis, isolated cerebral vasculitis), schizophrenia, prodromal schizophrenia, cognitive disorder, depression, anxiety disorders, anxious depression, bipolar disorder, depression, post traumatic stress disorder, epilepsy, schizophrenia, prodromal schizophrenia, or a cognitive disorder, comprising administering to a subject in need of such treatment an effective amount of at least one compound of Formula (I):

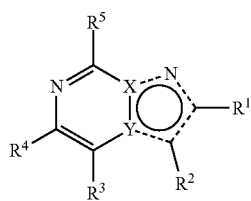

(I)

wherein
X is C or N;
Y is C or N; provided that X and Y cannot both be C, and X and Y cannot both be N;
the dotted line (- - - - -) indicates that the referenced bond is a single bond or a double bond;
$R^1$ is selected from the group consisting of: $C_{1-5}$alkyl; $C_{3-7}$cycloalkyl; phenyl optionally substituted with one, two or three members independently selected from halo and —CN; CH₂-phenyl optionally substituted with halo; C(=O)-phenyl, wherein said phenyl is optionally substituted with halo; C(=O)N(CH₃)-phenyl; C(=O)NH-phenyl; C(=O)NH—CH₂-phenyl; C(=O)NH-pyridinyl; C(=O)NH—$C_{3-7}$cycloalkyl; C(=O)NH—$C_{1-5}$alkyl; and pyridinyl;

$R^2$ is selected from the group consisting of:

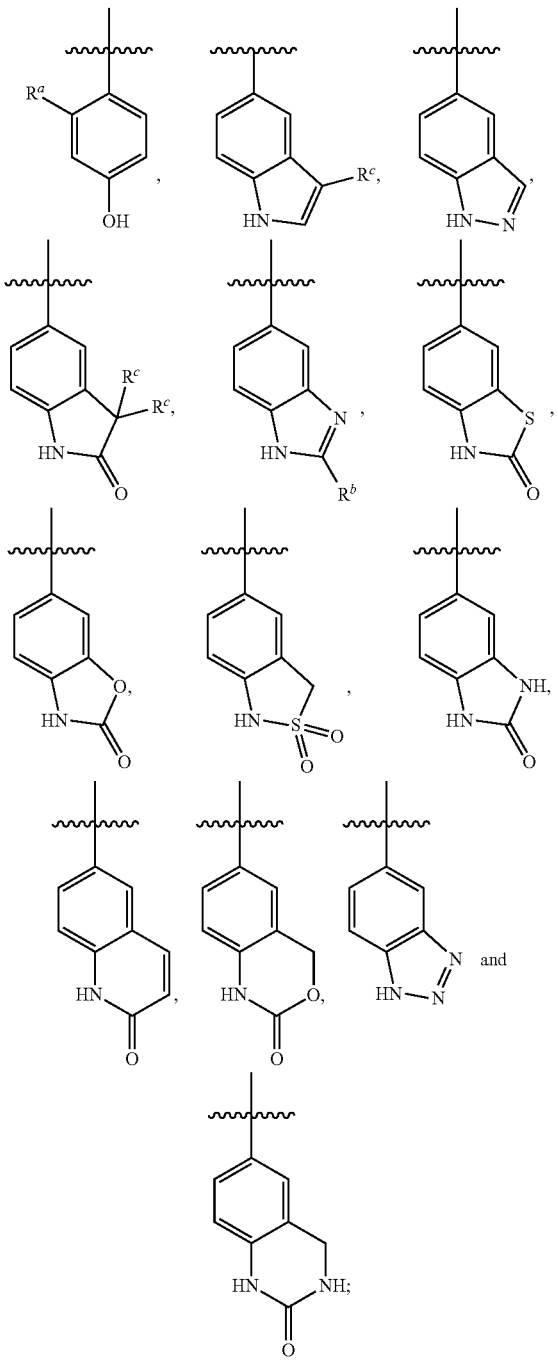

$R^a$ is H or —CH₃;
$R^b$ is H or —NH₂; and
$R^c$ is independently selected from: H and —F;
$R^3$ is selected from the group consisting of: H, ³H, —CH₃ and halo;
$R^4$ is H, —CH₃, or CF₃; and
$R^5$ is selected from the group consisting of:
 H; halo; —$C_{1-5}$alkyl; —$C_{1-5}$alkoxy; —NH₂; —NH($C_{1-5}$alkyl); —N($C_{1-5}$alkyl)₂; —NH-2-oxopyrrolidin-3-yl; —N(CH₃)cyclopropyl; —N(C₁₋₅alkyl)₂; —SO₂CH₃; —(S═O)CH₃; —OH; —O-cyclopentyl; azetidinyl optionally independently substituted with one or two members selected from the group consisting of: halo, —CH₃, —CF₃, —OCH₃, —SO₂CH₃, —CH₂OH, —OH, and —CN; pyrrolidinyl optionally substituted with —OH, —OCH₃ or —NH—(C═O)CH₃; piperidine optionally independently substituted with one, two, or three members selected from the group consisting of: halo, —OH, —CH₃, —OCH₃, —CH₂F, —CH₂CH₂F, and —NH—(C═O)CH₃; piperazine optionally substituted with —CH₃, —(C═O)CH₃, or —CO₂tBu; morpholine optionally independently substituted with one or two —CH₃, or —CF₃; octadeuteriomorpholin-4-yl; 6-oxa-2-azaspiro[3.3]heptan-2-yl; 3-oxopiperazin-1-yl optionally substituted with one or two —CH₃; 1,1-dioxo-1,4-thiazinan-4-yl; 1,4-dioxa-8-azaspiro[4.5]decan-8-yl; 6-oxa-3-azabicyclo[3.1.1]heptan-3-yl; 5-azaspiro[2.3]hexan-5-yl; diazapanyl optionally substituted with —(C═O)CH₃; 4-oxopiperidin-1-yl; dihydro-2H-pyridinyl optionally substituted with —(C═O)CH₃; dihydro-2H-pyranyl; 4-hydroxyimino-1-piperidyl; and 1,2,6-triazaspiro[2.5]oct-1-en-6-yl;

and pharmaceutically acceptable salts, N-oxides or solvates of compounds of Formula (I).

38. A compound of claim 1, and pharmaceutically acceptable salts, N-oxides, or solvates thereof, having the structure of Formula (IA):

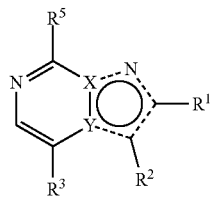

(IA)

X is N and Y is C;

the dotted line (- - - - -) indicates that the referenced bond is a single bond or a double bond;

R¹ is C₁₋₅alkyl; C₃₋₇cycloalkyl; phenyl optionally substituted with one or two halo;

R² is selected from the group consisting of:

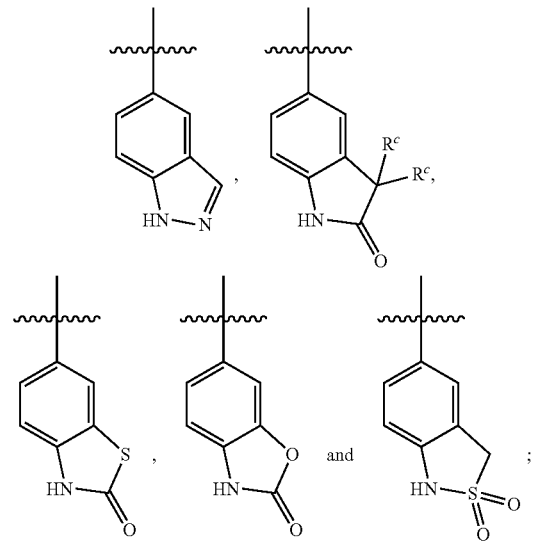

Rᶜ is H;

R³ is selected from the group consisting of: H, —CH₃ and halo; and

R⁵ is selected from the group consisting of:

H; —C₁₋₅alkoxy; —NH(C₁₋₅alkyl); —N(C₁₋₅alkyl)₂; —O-cyclopentyl; azetidinyl optionally independently substituted with one or two members selected from the group consisting of: halo, —CH₃, —OCH₃, —OH, and —CH₂OH; pyrrolidine optionally substituted with —OCH₃; piperidine optionally independently substituted with one or two members selected from halo, —OH, —CH₃, and —OCH₃; piperazine optionally substituted with —(C═O)CH₃; morpholine optionally substituted with —CH₃; 6-oxa-2-azaspiro[3.3]heptan-2-yl; 3-oxopiperazin-1-yl; 1,1-dioxo-1,4-thiazinan-4-yl; and 4-oxopiperidin-1-yl.

* * * * *